(12) United States Patent
Tackett et al.

(10) Patent No.: US 9,279,816 B2
(45) Date of Patent: Mar. 8, 2016

(54) METHODS AND KITS FOR ISOLATION AND ANALYSIS OF A CHROMATIN REGION

(71) Applicant: Board of Trustees of University of Arkansas, Little Rock, AR (US)

(72) Inventors: Alan J. Tackett, Little Rock, AR (US); Stephanie Byrum, Little Rock, AR (US); Sean Taverna, Little Rock, AR (US)

(73) Assignee: BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 14/081,812

(22) Filed: Nov. 15, 2013

(65) Prior Publication Data

US 2014/0154674 A1 Jun. 5, 2014

Related U.S. Application Data

(60) Provisional application No. 61/726,936, filed on Nov. 15, 2012, provisional application No. 61/875,969, filed on Sep. 10, 2013.

(51) Int. Cl.
G01N 33/68 (2006.01)

(52) U.S. Cl.
CPC .................................. *G01N 33/6875* (2013.01)

(58) Field of Classification Search
None
See application file for complete search history.

(56) References Cited

U.S. PATENT DOCUMENTS

| | | | |
|---|---|---|---|
| 6,453,242 | B1 | 9/2002 | Eisenberg et al. |
| 6,534,261 | B1 | 3/2003 | Cox, III et al. |
| 2011/0239315 | A1 | 9/2011 | Bonas et al. |
| 2011/0262908 | A1 | 10/2011 | Kingston et al. |
| 2012/0040857 | A1 | 2/2012 | Kingston et al. |
| 2012/0110685 | A1 | 5/2012 | Bonas et al. |
| 2012/0270273 | A1 | 10/2012 | Zhang et al. |

OTHER PUBLICATIONS

Rossant, "Stem Cells and Early Lineage Development", Cell, 2008, pp. 527-531, vol. 132.
Scholze et al., "TAL effector-DNA specificity", Virulence, 2010, pp. 428-432, vol. 1, No. 5.
Scholze et al., "TAL effectors are remote controls for gene activation", Current Opinion in Microbiology, 2011, pp. 47-53, vol. 14.
Shukla et al., "SAGA-associated Sgf73p facilitates formation of the preinitiation complex assembly at the promoters either in a HAT-dependent or independent manner in vivo", Nucleic Acids Research, 2006, pp. 6225-6232, vol. 34, No. 21.
Smart et al., "Mapping the local protein interactome of the NuA3 histone acetyltransferase", Protein Science, 2009, pp. 1987-1997, vol. 18.
Tackett et al., "I-DIRT, A General Method for Distinguishing between Specific and Nonspecific Protein Interactions", Journal of Proteome Research, 2005, pp. 1752-1756, vol. 4.
Tackett et al., "Proteomic and genomic characterization of chromatin complexes at a boundary", J. Cell Biol., 2005, pp. 35-47, vol. 169, No. 1.
Taverna et al., "Yng1 PHD Finger Binding to H3 Trimethylated at K4 Promotes NuA3 HAT Activity at K14 of H3 and Transcription at a Subset of Targeted ORFS", Molecular Cell, 2006, pp. 785-796, vol. 24.
Taverna et al., "Long-distance combinatorial linkage between methylation and acetylation on histone H3 N termini", Proc. Natl. Acad. Sci. USA, 2007, pp. 2086-2091, vol. 104, No. 7.
Unnikrishnan et al., "Dynamic changes in histone acetylation regulate origins of DNA replication", Nat. Struct. Mol. Biol., 2010, pp. 430-437, vol. 17, No. 4.
Zybailov et al., "Statistical Analysis of Membrane Proteome Expression Changes in *Saccharomyces cerevisiae*", Journal of Proteome Research, 2006, pp. 2339-2347, vol. 5, No. 9.
Agelopoulos et al., "Developmental regulation of chromatin conformation by Hox proteins in *Drosophila*", Cell Rep., 2012, pp. 350-359, vol. 1, No. 4.
Akiyoshi et al., "Quantitative proteomic analysis of purified yeast kinetochores identifies a PP1 regulatory subunit", Genes & Development, 2009, pp. 2887-2899, vol. 23.
Barski et al., "High-Resolution Profiling of Histone Methylations in the Human Genome", Cell, 2007, pp. 823-837, vol. 129.
Bock et al., "Detailed specificity analysis of antibodies binding to modified histone tails with peptide arrays", Epigenetics, 2011, pp. 256-263, vol. 6, No. 2.
Boffa et al., "Isolation of active genes containing CAG repeats by DNA strand invasion by a peptide nucleic acid", Proc. Natl. Acad. Sci. USA, 1995, pp. 1901-1905, vol. 92.
Byrum et al., "Quantitative analysis of histone exchange for transcriptionally active chromatin", Journal of Clinical Bioinformatics, 2011, 5 pgs., vol. 1.
Byrum et al., "Analysis of Histone Exchange during Chromatin Purification", J Integr OMICS, 2011, pp. 61-65, vol. 1, No. 1.
Byrum et al., "A Quantitative Proteomic Analysis of FFPE Melanoma", J. Culan. Pathol., 2011, pp. 933-936, vol. 38, No. 11.
Byrum et al., "Analysis of Stable and Transient Protein-Protein Interactions", Methods Mol. Biol., 2012, pp. 143-152, vol. 833.
Byrum et al., "ChAP-MS: A Method for Identification of Proteins and Histone Posttranslational Modifications at a Single Genomic Locus", Cell Rep., 2012, pp. 198-205, vol. 2, No. 1.
Byrum et al., "Purification of a specific native genomic locus for proteomic analysis", Nucleic Acids Research, 2013, e195, pp. 1-6, vol. 41, No. 20.
Byrum et al., "Quantitative Proteomics Identifies Activation of Hallmark Pathways of Cancer in Patient Melanoma", J Proteomics Bioinform., 2013, pp. 043-050, vol. 6, No. 3.
Cermak et al., "Efficient design and assembly of custom TALEN and other TAL effector-based constructs for DNA targeting", Nucleic Acids Research, 2011, e82, 11 pgs., vol. 39, No. 12.
Chait, "Mass spectrometry in the Postgenomic Era", Annu. Rev. Biochem., 2011, pp. 239-246, vol. 80.

(Continued)

*Primary Examiner* — Jacob Cheu
(74) *Attorney, Agent, or Firm* — Polsinelli PC

(57) ABSTRACT

The present invention encompasses methods of identifying proteins and protein modifications of proteins specifically associated with a chromatin.

11 Claims, 18 Drawing Sheets
(11 of 18 Drawing Sheet(s) Filed in Color)

(56) References Cited

OTHER PUBLICATIONS

Chi et al., "Covalent histone modifications—miswritten, misinterpreted, and miserased in human cancers", Nat. Rev. Cancer, 2010, pp. 457-469, vol. 10, No. 7.
Dai et al., "Global Epiproteomic Signatures Distinguish Embryonic Stem Cells from Differentiated Cells", Stem Cells, 2007, pp. 2567-2574, vol. 25.
Dedon et al., "Formaldehyde Cross-Linking and Immunoprecipitation Demonstrate Developmental Changes in H1 Association with Transcriptionally Active Genes", Molecular and Cellular Biology, 1991, pp. 1729-1733, vol. 11, No. 3.
DéJardin et al., "Purification of Proteins Associated with Specific Genomic Loci", Cell, 2009, pp. 175-186, vol. 136, No. 1.
DiCarlo et al., "Genome engineering in *Saccharomyces cerevisiae* using CRISPR-Cas systems", Nucleic Acids Research, 2013, pp. 4336-4343, vol. 41, No. 7.
Doyle et al., "TAL Effector-Nucleotide Targeter (TALE-NT) 2.0: tools for TAL effector design and target prediction", Nucleic Acids Research, 2012, pp. W117-W122, vol. 40.
Fu et al., "High frequency off-target mutagenesis induced by CRISPR-Cas nucleases in human cells", Nat Biotechnol., 2013, pp. 822-826, vol. 31, No. 9.
Fujita et al., "Efficient isolation of specific genomic regions and identification of associated proteins by engineered DNA-binding molecule-mediated chromatin immunoprecipitation (enChIP) using CRISPR", Biochemical and Biophysical Research Communications, 2013, pp. 132-136, vol. 439.
Geißler et al., "Transcriptional Activators of Human Genes with Programmable DNA-Specificity", PLoS One, 2011, e19509, vol. 6, No. 5.
Griesenbeck et al., "Affinity Purification of Specific Chromatin Segments from Chromosomal Loci in Yeast", Molecular and Cellular Biology, 2003, pp. 9275-9282, vol. 23, No. 24.
Hamperl et al., "Compositional and structural analysis of selected chromosomal domains from *Saccharomyces cerevisiae*", Nucleic Acids Research, 2014, e2, 20 pgs., vol. 42, No. 1.
Ho et al., "Chromatin remodelling during development", Nature, 2010, pp. 474-484, vol. 463.
Hoshino et al., "Insertional chromatin immunoprecipitation: A method for isolating specific genomic regions", Journal of Bioscience and Bioengineering, 2009, pp. 446-449, vol. 108, No. 5.
Houseley et al., "A ncRNA Modulates Histone Modification and mRNA Induction in the Yeast GAL Gene Cluster", Molecular Cell, 2008, pp. 685-695, vol. 32.
Jiang et al., "CRISPR—assisted editing of bacterial genomes", Nat Biotechnol., 2013, pp. 233-239, vol. 31, No. 3.
Johnson et al., "Genome-Wide Mapping of in Vivo Protein-DNA Interactions", Science, 2007, pp. 1497-1502, vol. 316.
Jones et al., "The Epigenomics of Cancer", Cell, 2007, pp. 683-692, vol. 128, No. 4.
Kouzarides, "Chromatin Modifications and Their Function", Cell, 2007, pp. 693-705, vol. 128.
Mali et al., "Cas9 as a versatile tool for engineering biology", Nat Methods, 2013, pp. 957-963, vol. 10, No. 10.
Martin, "Isolation of a pluripotent cell line from early mouse embryos cultured in medium conditioned by teratocarcinoma stem cells", Proc. Natl. Acad. Sci. USA, 1981, pp. 7634-7638, vol. 78, No. 12.
Mikkelsen et al., "Genome-wide maps of chromatin state in pluripotent and lineage-committed cells", Nature, 2007, pp. 553-560, vol. 448, No. 7153.
Miller et al., "A TALE nuclease architecture for efficient genome editing", Nature Biotechnology, 2011, pp. 143-148, vol. 29, No. 2.
Platt et al., "The yeast galactose genetic switch is mediated by the formation of a Gal4p-Gal80p-Gal3p complex", The EMBO Journal, 1998, pp. 4086-4091, vol. 17, No. 14.
Pokholok et al., "Genome-wide Map of Nucleosome Acetylation and Methylation in Yeast", Cell, 2005, pp. 517-527, vol. 122.
Ren et al., "Genome-Wide Location and Function of DNA Binding Proteins", Science, 2000, pp. 2306-2309, vol. 290.
Robertson et al., "Genome-wide profiles of STAT1 DNA association using chromatin immunoprecipitation and massively parallel sequencing", Nature Methods, 2007, pp. 651-657, vol. 4, No. 8.

SEQUENCE LISTING

<160> NUMBER OF SEQ ID NOS: 371

<210> SEQ ID NO 1
<211> LENGTH: 34
<212> TYPE: DNA
<213> ORGANISM: Artificial Sequence
<220> FEATURE:
<223> OTHER INFORMATION: SYNTHESIZED

<400> SEQUENCE: 1
cacttgatac tgtatgagca tacagtataa ttgc                              34

<210> SEQ ID NO 2
<211> LENGTH: 18
<212> TYPE: DNA
<213> ORGANISM: Saccharomyces cerevisiae

<400> SEQUENCE: 2
ggggtaatta atcagcga                                                18

<210> SEQ ID NO 3
<211> LENGTH: 9
<212> TYPE: PRT
<213> ORGANISM: Saccharomyces cerevisiae

<400> SEQUENCE: 3

Ala Asn Leu Asp Val Lys Asp Gln Lys
1               5

<210> SEQ ID NO 4
<211> LENGTH: 12
<212> TYPE: PRT
<213> ORGANISM: Saccharomyces cerevisiae

<400> SEQUENCE: 4

Tyr Asp Leu Asp Phe Lys Asn Pro Glu Ser Asp Lys
1               5                   10

<210> SEQ ID NO 5
<211> LENGTH: 15
<212> TYPE: PRT
<213> ORGANISM: Saccharomyces cerevisiae

<400> SEQUENCE: 5

Ala Val Asp Asp Phe Leu Leu Ser Leu Asp Gly Thr Ala Asn Lys
1               5                   10                  15

```
<210> SEQ ID NO 6
<211> LENGTH: 15
<212> TYPE: PRT
<213> ORGANISM: Saccharomyces cerevisiae

<400> SEQUENCE: 6

Asp Gly Lys Tyr Asp Leu Asp Phe Lys Asn Pro Glu Ser Asp Lys
1               5                   10                  15

<210> SEQ ID NO 7
<211> LENGTH: 19
<212> TYPE: PRT
<213> ORGANISM: Saccharomyces cerevisiae

<400> SEQUENCE: 7

Gly Val Met Asn Ala Val Asn Val Asn Asn Val Ile Ala Ala Ala
1               5                   10                  15

Phe Val Lys

<210> SEQ ID NO 8
<211> LENGTH: 23
<212> TYPE: PRT
<213> ORGANISM: Saccharomyces cerevisiae

<400> SEQUENCE: 8

Tyr Pro Ile Val Ser Ile Glu Asp Pro Phe Ala Glu Asp Asp Trp Glu
1               5                   10                  15

Ala Trp Ser His Phe Phe Lys
            20

<210> SEQ ID NO 9
<211> LENGTH: 24
<212> TYPE: PRT
<213> ORGANISM: Saccharomyces cerevisiae

<400> SEQUENCE: 9

Arg Tyr Pro Ile Val Ser Ile Glu Asp Pro Phe Ala Glu Asp Asp Trp
1               5                   10                  15

Glu Ala Trp Ser His Phe Phe Lys
            20

<210> SEQ ID NO 10
<211> LENGTH: 33
<212> TYPE: PRT
<213> ORGANISM: Saccharomyces cerevisiae

<400> SEQUENCE: 10

Tyr Gly Ala Ser Ala Gly Asn Val Gly Asp Glu Gly Gly Val Ala Pro
1               5                   10                  15

Asn Ile Gln Thr Ala Glu Glu Ala Leu Asp Leu Ile Val Asp Ala Ile
            20                  25                  30

Lys

<210> SEQ ID NO 11
<211> LENGTH: 9
<212> TYPE: PRT
<213> ORGANISM: Saccharomyces cerevisiae

<400> SEQUENCE: 11

Ala Asn Ile Asp Val Lys Asp Gln Lys
1               5
```

```
<210> SEQ ID NO 12
<211> LENGTH: 15
<212> TYPE: PRT
<213> ORGANISM: Saccharomyces cerevisiae

<400> SEQUENCE: 12

Ala Val Asp Asp Phe Leu Ile Ser Leu Asp Gly Thr Ala Asn Lys
1               5                   10                  15

<210> SEQ ID NO 13
<211> LENGTH: 22
<212> TYPE: PRT
<213> ORGANISM: Saccharomyces cerevisiae

<400> SEQUENCE: 13

Ile Glu Glu Glu Leu Gly Asp Asn Ala Val Phe Ala Gly Glu Asn Phe
1               5                   10                  15

His His Gly Asp Lys Leu
            20

<210> SEQ ID NO 14
<211> LENGTH: 9
<212> TYPE: PRT
<213> ORGANISM: Saccharomyces cerevisiae

<400> SEQUENCE: 14

Ile Thr Ile Thr Asn Asp Lys Gly Arg
1               5

<210> SEQ ID NO 15
<211> LENGTH: 12
<212> TYPE: PRT
<213> ORGANISM: Saccharomyces cerevisiae

<400> SEQUENCE: 15

Asn Phe Asn Asp Pro Glu Val Gln Gly Asp Met Lys
1               5                   10

<210> SEQ ID NO 16
<211> LENGTH: 11
<212> TYPE: PRT
<213> ORGANISM: Saccharomyces cerevisiae

<400> SEQUENCE: 16

Phe Lys Glu Glu Asp Glu Lys Glu Ser Gln Arg
1               5                   10

<210> SEQ ID NO 17
<211> LENGTH: 14
<212> TYPE: PRT
<213> ORGANISM: Saccharomyces cerevisiae

<400> SEQUENCE: 17

Asn Phe Thr Pro Glu Gln Ile Ser Ser Met Val Leu Gly Lys
1               5                   10

<210> SEQ ID NO 18
<211> LENGTH: 15
<212> TYPE: PRT
<213> ORGANISM: Saccharomyces cerevisiae

<400> SEQUENCE: 18

Leu Ile Asp Val Asp Gly Lys Pro Gln Ile Gln Val Glu Phe Lys
1               5                   10                  15
```

<210> SEQ ID NO 19
<211> LENGTH: 17
<212> TYPE: PRT
<213> ORGANISM: Saccharomyces cerevisiae

<400> SEQUENCE: 19

Ile Ile Asn Glu Pro Thr Ala Ala Ala Ile Ala Tyr Gly Leu Asp Lys
1               5                   10                  15

Lys

<210> SEQ ID NO 20
<211> LENGTH: 17
<212> TYPE: PRT
<213> ORGANISM: Saccharomyces cerevisiae

<400> SEQUENCE: 20

Leu Asp Lys Ser Gln Val Asp Glu Ile Val Leu Val Gly Gly Ser Thr
1               5                   10                  15

Arg

<210> SEQ ID NO 21
<211> LENGTH: 20
<212> TYPE: PRT
<213> ORGANISM: Saccharomyces cerevisiae

<400> SEQUENCE: 21

Asn Thr Ile Ser Glu Ala Gly Asp Lys Leu Glu Gln Ala Asp Lys Asp
1               5                   10                  15

Ala Val Thr Lys
            20

<210> SEQ ID NO 22
<211> LENGTH: 25
<212> TYPE: PRT
<213> ORGANISM: Saccharomyces cerevisiae

<400> SEQUENCE: 22

Thr Gln Asp Leu Leu Leu Leu Asp Val Ala Pro Leu Ser Leu Gly Ile
1               5                   10                  15

Glu Thr Ala Gly Gly Val Met Thr Lys
            20                  25

<210> SEQ ID NO 23
<211> LENGTH: 10
<212> TYPE: PRT
<213> ORGANISM: Saccharomyces cerevisiae

<400> SEQUENCE: 23

Asn Ala Thr Phe Pro Gly Val Gln Met Lys
1               5                   10

<210> SEQ ID NO 24
<211> LENGTH: 14
<212> TYPE: PRT
<213> ORGANISM: Saccharomyces cerevisiae

<400> SEQUENCE: 24

Val Ala Thr Thr Gly Glu Trp Asp Lys Leu Thr Gln Asp Lys
1               5                   10

<210> SEQ ID NO 25
<211> LENGTH: 19

```
<212> TYPE: PRT
<213> ORGANISM: Saccharomyces cerevisiae

<400> SEQUENCE: 25

Leu Leu Gln Thr Pro Ile Asp Met Ser Leu Lys Pro Asn Asp Ala Glu
1               5                   10                  15

Ser Glu Lys

<210> SEQ ID NO 26
<211> LENGTH: 20
<212> TYPE: PRT
<213> ORGANISM: Saccharomyces cerevisiae

<400> SEQUENCE: 26

Met Ile Glu Ile Met Leu Pro Val Phe Asp Ala Pro Gln Asn Leu Val
1               5                   10                  15

Glu Gln Ala Lys
            20

<210> SEQ ID NO 27
<211> LENGTH: 30
<212> TYPE: PRT
<213> ORGANISM: Saccharomyces cerevisiae

<400> SEQUENCE: 27

Leu Leu Gln Thr Pro Ile Asp Met Ser Leu Lys Pro Asn Asp Ala Glu
1               5                   10                  15

Ser Glu Lys Glu Val Ile Asp Thr Ile Leu Ala Leu Val Lys
            20                  25                  30

<210> SEQ ID NO 28
<211> LENGTH: 12
<212> TYPE: PRT
<213> ORGANISM: Saccharomyces cerevisiae

<400> SEQUENCE: 28

Asn Phe Asn Asp Pro Glu Val Gln Ala Asp Met Lys
1               5                   10

<210> SEQ ID NO 29
<211> LENGTH: 8
<212> TYPE: PRT
<213> ORGANISM: Saccharomyces cerevisiae

<400> SEQUENCE: 29

Ser Pro Phe Leu Asp Ala Leu Lys
1               5

<210> SEQ ID NO 30
<211> LENGTH: 12
<212> TYPE: PRT
<213> ORGANISM: Saccharomyces cerevisiae

<400> SEQUENCE: 30

Ala Leu Lys Asp Ile Leu Gly Asp Gln Val Glu Lys
1               5                   10

<210> SEQ ID NO 31
<211> LENGTH: 13
<212> TYPE: PRT
<213> ORGANISM: Saccharomyces cerevisiae

<400> SEQUENCE: 31
```

Val Lys Glu Glu Val Gln Glu Leu Glu Glu Leu Asn Lys
1               5                   10

<210> SEQ ID NO 32
<211> LENGTH: 14
<212> TYPE: PRT
<213> ORGANISM: Saccharomyces cerevisiae

<400> SEQUENCE: 32

Leu Glu Glu Val Asp Glu Glu Glu Glu Lys Lys Pro Lys
1               5                   10

<210> SEQ ID NO 33
<211> LENGTH: 14
<212> TYPE: PRT
<213> ORGANISM: Saccharomyces cerevisiae

<400> SEQUENCE: 33

Leu Phe Leu Lys Asp Asp Gln Leu Glu Tyr Leu Glu Glu Lys
1               5                   10

<210> SEQ ID NO 34
<211> LENGTH: 15
<212> TYPE: PRT
<213> ORGANISM: Saccharomyces cerevisiae

<400> SEQUENCE: 34

Leu Phe Leu Lys Asp Asp Gln Leu Glu Tyr Leu Glu Glu Lys Arg
1               5                   10                  15

<210> SEQ ID NO 35
<211> LENGTH: 18
<212> TYPE: PRT
<213> ORGANISM: Saccharomyces cerevisiae

<400> SEQUENCE: 35

Thr Leu Val Asp Ile Thr Lys Asp Phe Glu Leu Glu Glu Thr Asp Glu
1               5                   10                  15

Glu Lys

<210> SEQ ID NO 36
<211> LENGTH: 19
<212> TYPE: PRT
<213> ORGANISM: Saccharomyces cerevisiae

<400> SEQUENCE: 36

Val Phe Ile Thr Asp Glu Ala Glu Asp Leu Ile Pro Glu Trp Leu Ser
1               5                   10                  15

Phe Val Lys

<210> SEQ ID NO 37
<211> LENGTH: 20
<212> TYPE: PRT
<213> ORGANISM: Saccharomyces cerevisiae

<400> SEQUENCE: 37

Arg Val Phe Ile Thr Asp Glu Ala Glu Asp Leu Ile Pro Glu Trp Leu
1               5                   10                  15

Ser Phe Val Lys
            20

<210> SEQ ID NO 38
<211> LENGTH: 21

```
<212> TYPE: PRT
<213> ORGANISM: Saccharomyces cerevisiae

<400> SEQUENCE: 38

Thr Leu Val Asp Ile Thr Lys Asp Phe Glu Leu Glu Glu Thr Asp Glu
1               5                   10                  15

Glu Lys Ala Glu Arg
            20

<210> SEQ ID NO 39
<211> LENGTH: 11
<212> TYPE: PRT
<213> ORGANISM: Saccharomyces cerevisiae

<400> SEQUENCE: 39

Val Asp Phe Asn Val Pro Leu Asp Gly Lys Lys
1               5                   10

<210> SEQ ID NO 40
<211> LENGTH: 14
<212> TYPE: PRT
<213> ORGANISM: Saccharomyces cerevisiae

<400> SEQUENCE: 40

Val Leu Glu Asn Thr Glu Ile Gly Asp Ser Ile Phe Asp Lys
1               5                   10

<210> SEQ ID NO 41
<211> LENGTH: 20
<212> TYPE: PRT
<213> ORGANISM: Saccharomyces cerevisiae

<400> SEQUENCE: 41

Ser Ser Ala Ala Gly Asn Thr Val Ile Ile Gly Gly Gly Asp Thr Ala
1               5                   10                  15

Thr Val Ala Lys
            20

<210> SEQ ID NO 42
<211> LENGTH: 23
<212> TYPE: PRT
<213> ORGANISM: Saccharomyces cerevisiae

<400> SEQUENCE: 42

Gly Val Glu Val Val Leu Pro Val Asp Phe Ile Ile Ala Asp Ala Phe
1               5                   10                  15

Ser Ala Asp Ala Asn Thr Lys
            20

<210> SEQ ID NO 43
<211> LENGTH: 7
<212> TYPE: PRT
<213> ORGANISM: Saccharomyces cerevisiae

<400> SEQUENCE: 43

Glu Leu Asp Thr Ala Gln Lys
1               5

<210> SEQ ID NO 44
<211> LENGTH: 10
<212> TYPE: PRT
<213> ORGANISM: Saccharomyces cerevisiae

<400> SEQUENCE: 44
```

Val Val Asp Leu Val Glu His Val Ala Lys
1               5                  10

<210> SEQ ID NO 45
<211> LENGTH: 10
<212> TYPE: PRT
<213> ORGANISM: Saccharomyces cerevisiae

<400> SEQUENCE: 45

Tyr Ala Gly Glu Val Ser His Asp Asp Lys
1               5                  10

<210> SEQ ID NO 46
<211> LENGTH: 15
<212> TYPE: PRT
<213> ORGANISM: Saccharomyces cerevisiae

<400> SEQUENCE: 46

Thr Ala Ser Gly Asn Ile Ile Pro Ser Ser Thr Gly Ala Ala Lys
1               5                  10                  15

<210> SEQ ID NO 47
<211> LENGTH: 14
<212> TYPE: PRT
<213> ORGANISM: Saccharomyces cerevisiae

<400> SEQUENCE: 47

Val Pro Thr Val Asp Val Ser Val Val Asp Leu Thr Val Lys
1               5                  10

<210> SEQ ID NO 48
<211> LENGTH: 17
<212> TYPE: PRT
<213> ORGANISM: Saccharomyces cerevisiae

<400> SEQUENCE: 48

Tyr Ala Gly Glu Val Ser His Asp Asp Lys His Ile Ile Val Asp Gly
1               5                  10                  15

Lys

<210> SEQ ID NO 49
<211> LENGTH: 23
<212> TYPE: PRT
<213> ORGANISM: Saccharomyces cerevisiae

<400> SEQUENCE: 49

Asp Pro Ala Asn Leu Pro Trp Gly Ser Ser Asn Val Asp Ile Ala Ile
1               5                  10                  15

Asp Ser Thr Gly Val Phe Lys
            20

<210> SEQ ID NO 50
<211> LENGTH: 11
<212> TYPE: PRT
<213> ORGANISM: Saccharomyces cerevisiae

<400> SEQUENCE: 50

Lys Val Tyr Pro Asp Val Leu Tyr Thr Ser Lys
1               5                  10

<210> SEQ ID NO 51
<211> LENGTH: 11
<212> TYPE: PRT

-continued

```
<213> ORGANISM: Saccharomyces cerevisiae

<400> SEQUENCE: 51

Leu Leu Pro Tyr Trp Gln Asp Val Ile Ala Lys
1               5                   10

<210> SEQ ID NO 52
<211> LENGTH: 18
<212> TYPE: PRT
<213> ORGANISM: Saccharomyces cerevisiae

<400> SEQUENCE: 52

Ser Phe Asp Val Pro Pro Pro Ile Asp Ala Ser Ser Pro Phe Ser
1               5                   10                  15

Gln Lys

<210> SEQ ID NO 53
<211> LENGTH: 19
<212> TYPE: PRT
<213> ORGANISM: Saccharomyces cerevisiae

<400> SEQUENCE: 53

Arg Ser Phe Asp Val Pro Pro Pro Ile Asp Ala Ser Ser Pro Phe
1               5                   10                  15

Ser Gln Lys

<210> SEQ ID NO 54
<211> LENGTH: 14
<212> TYPE: PRT
<213> ORGANISM: Saccharomyces cerevisiae

<400> SEQUENCE: 54

Lys Pro Gln Val Thr Val Gly Ala Gln Asn Ala Tyr Leu Lys
1               5                   10

<210> SEQ ID NO 55
<211> LENGTH: 15
<212> TYPE: PRT
<213> ORGANISM: Saccharomyces cerevisiae

<400> SEQUENCE: 55

Ala Ser Gly Ala Phe Thr Gly Glu Asn Ser Val Asp Gln Ile Lys
1               5                   10                  15

<210> SEQ ID NO 56
<211> LENGTH: 13
<212> TYPE: PRT
<213> ORGANISM: Saccharomyces cerevisiae

<400> SEQUENCE: 56

Ser Tyr Phe His Glu Asp Asp Lys Phe Ile Ala Asp Lys
1               5                   10

<210> SEQ ID NO 57
<211> LENGTH: 20
<212> TYPE: PRT
<213> ORGANISM: Saccharomyces cerevisiae

<400> SEQUENCE: 57

Ala Ser Gly Ala Phe Thr Gly Glu Asn Ser Val Asp Gln Ile Lys Asp
1               5                   10                  15

Val Gly Ala Lys
            20
```

```
<210> SEQ ID NO 58
<211> LENGTH: 7
<212> TYPE: PRT
<213> ORGANISM: Saccharomyces cerevisiae

<400> SEQUENCE: 58

Leu Phe Ser Glu Tyr Gln Lys
1               5

<210> SEQ ID NO 59
<211> LENGTH: 9
<212> TYPE: PRT
<213> ORGANISM: Saccharomyces cerevisiae

<400> SEQUENCE: 59

Ile Leu Ala Val Asp Thr Val Ser Lys
1               5

<210> SEQ ID NO 60
<211> LENGTH: 11
<212> TYPE: PRT
<213> ORGANISM: Saccharomyces cerevisiae

<400> SEQUENCE: 60

Lys Phe Pro Glu Leu Gly Ala Glu Leu Ala Arg
1               5                   10

<210> SEQ ID NO 61
<211> LENGTH: 12
<212> TYPE: PRT
<213> ORGANISM: Saccharomyces cerevisiae

<400> SEQUENCE: 61

Leu Ser Gly Gln Leu Pro Ala Asn Trp Glu Ser Lys
1               5                   10

<210> SEQ ID NO 62
<211> LENGTH: 12
<212> TYPE: PRT
<213> ORGANISM: Saccharomyces cerevisiae

<400> SEQUENCE: 62

Val Val Ser Leu Pro Asp Phe Phe Thr Phe Asp Lys
1               5                   10

<210> SEQ ID NO 63
<211> LENGTH: 16
<212> TYPE: PRT
<213> ORGANISM: Saccharomyces cerevisiae

<400> SEQUENCE: 63

Gln Asn Leu Pro Gln Leu Glu Gly Ser Ser Ile Glu Ser Ala Ser Lys
1               5                   10                  15

<210> SEQ ID NO 64
<211> LENGTH: 14
<212> TYPE: PRT
<213> ORGANISM: Saccharomyces cerevisiae

<400> SEQUENCE: 64

Ser Phe Val Val Pro Gln Glu Val Tyr Asp His Tyr Gln Lys
1               5                   10
```

```
<210> SEQ ID NO 65
<211> LENGTH: 15
<212> TYPE: PRT
<213> ORGANISM: Saccharomyces cerevisiae

<400> SEQUENCE: 65

Thr Ala Val Val Asp Gly Val Phe Asp Glu Val Ser Leu Asp Lys
1               5                   10                  15

<210> SEQ ID NO 66
<211> LENGTH: 6
<212> TYPE: PRT
<213> ORGANISM: Saccharomyces cerevisiae

<400> SEQUENCE: 66

Phe Gln Glu Ile Val Lys
1               5

<210> SEQ ID NO 67
<211> LENGTH: 8
<212> TYPE: PRT
<213> ORGANISM: Saccharomyces cerevisiae

<400> SEQUENCE: 67

Leu Pro Leu Gln Asp Val Tyr Lys
1               5

<210> SEQ ID NO 68
<211> LENGTH: 15
<212> TYPE: PRT
<213> ORGANISM: Saccharomyces cerevisiae

<400> SEQUENCE: 68

Ser His Ile Asn Val Val Ile Gly His Val Asp Ser Gly Lys
1               5                   10                  15

<210> SEQ ID NO 69
<211> LENGTH: 21
<212> TYPE: PRT
<213> ORGANISM: Saccharomyces cerevisiae

<400> SEQUENCE: 69

Thr Leu Leu Glu Ala Ile Asp Ala Ile Glu Gln Pro Ser Arg Pro Thr
1               5                   10                  15

Asp Lys Pro Leu Arg
            20

<210> SEQ ID NO 70
<211> LENGTH: 23
<212> TYPE: PRT
<213> ORGANISM: Saccharomyces cerevisiae

<400> SEQUENCE: 70

Ser Val Glu Met His His Glu Gln Leu Glu Gln Gly Val Pro Gly Asp
1               5                   10                  15

Asn Val Gly Phe Asn Val Lys
            20

<210> SEQ ID NO 71
<211> LENGTH: 9
<212> TYPE: PRT
<213> ORGANISM: Saccharomyces cerevisiae

<400> SEQUENCE: 71
```

```
Leu Leu Ser Asp Phe Phe Asp Gly Lys
1               5
```

<210> SEQ ID NO 72
<211> LENGTH: 19
<212> TYPE: PRT
<213> ORGANISM: Saccharomyces cerevisiae

<400> SEQUENCE: 72

```
Val Ile Asp Val Asp Gly Asn Pro Val Ile Glu Val Gln Tyr Leu Glu
1               5                   10                  15

Glu Thr Lys
```

<210> SEQ ID NO 73
<211> LENGTH: 22
<212> TYPE: PRT
<213> ORGANISM: Saccharomyces cerevisiae

<400> SEQUENCE: 73

```
Ser Thr Ser Gly Asn Thr His Leu Gly Gly Gln Asp Phe Asp Thr Asn
1               5                   10                  15

Leu Leu Glu His Phe Lys
                20
```

<210> SEQ ID NO 74
<211> LENGTH: 12
<212> TYPE: PRT
<213> ORGANISM: Saccharomyces cerevisiae

<400> SEQUENCE: 74

```
Gln Ile Asn Glu Asn Asp Ala Glu Ala Met Asn Lys
1               5                   10
```

<210> SEQ ID NO 75
<211> LENGTH: 12
<212> TYPE: PRT
<213> ORGANISM: Saccharomyces cerevisiae

<400> SEQUENCE: 75

```
Ala Thr Glu Thr Val Asp Asn Lys Asp Ile Glu Arg
1               5                   10
```

<210> SEQ ID NO 76
<211> LENGTH: 14
<212> TYPE: PRT
<213> ORGANISM: Saccharomyces cerevisiae

<400> SEQUENCE: 76

```
Leu Val Glu Asp Pro Gln Val Ile Ala Pro Phe Leu Gly Lys
1               5                   10
```

<210> SEQ ID NO 77
<211> LENGTH: 17
<212> TYPE: PRT
<213> ORGANISM: Saccharomyces cerevisiae

<400> SEQUENCE: 77

```
Leu Leu Pro Trp Phe Asp Gly Met Leu Glu Ala Asp Glu Ala Tyr Phe
1               5                   10                  15

Lys
```

<210> SEQ ID NO 78
<211> LENGTH: 18

-continued

```
<212> TYPE: PRT
<213> ORGANISM: Saccharomyces cerevisiae

<400> SEQUENCE: 78

Lys Leu Leu Pro Trp Phe Asp Gly Met Leu Glu Ala Asp Glu Ala Tyr
1               5                   10                  15

Phe Lys

<210> SEQ ID NO 79
<211> LENGTH: 23
<212> TYPE: PRT
<213> ORGANISM: Saccharomyces cerevisiae

<400> SEQUENCE: 79

Ala Leu Pro Asp Ala Val Thr Ile Ile Glu Pro Lys Glu Glu Glu Pro
1               5                   10                  15

Ile Leu Ala Pro Ser Val Lys
            20

<210> SEQ ID NO 80
<211> LENGTH: 15
<212> TYPE: PRT
<213> ORGANISM: Saccharomyces cerevisiae

<400> SEQUENCE: 80

Glu Ala Val Leu Thr Val Pro Thr Asn Phe Ser Glu Glu Gln Lys
1               5                   10                  15

<210> SEQ ID NO 81
<211> LENGTH: 25
<212> TYPE: PRT
<213> ORGANISM: Saccharomyces cerevisiae

<400> SEQUENCE: 81

Leu Ile Ser Asp Tyr Asp Ala Asp Glu Leu Ala Glu Ala Leu Gln Pro
1               5                   10                  15

Val Ile Val Asn Thr Pro His Leu Lys
            20                  25

<210> SEQ ID NO 82
<211> LENGTH: 14
<212> TYPE: PRT
<213> ORGANISM: Saccharomyces cerevisiae

<400> SEQUENCE: 82

Thr Gly Thr Leu Thr Thr Ser Glu Thr Ala His Asn Met Lys
1               5                   10

<210> SEQ ID NO 83
<211> LENGTH: 14
<212> TYPE: PRT
<213> ORGANISM: Saccharomyces cerevisiae

<400> SEQUENCE: 83

Glu Thr Val Glu Ser Glu Ser Ser Gln Thr Ala Leu Ser Lys
1               5                   10

<210> SEQ ID NO 84
<211> LENGTH: 15
<212> TYPE: PRT
<213> ORGANISM: Saccharomyces cerevisiae

<400> SEQUENCE: 84
```

Trp Thr Asn Lys Asp Thr Asp Ala Glu Gly Lys Pro Leu Glu Arg
1               5                   10                  15

<210> SEQ ID NO 85
<211> LENGTH: 21
<212> TYPE: PRT
<213> ORGANISM: Saccharomyces cerevisiae

<400> SEQUENCE: 85

Gln Val Glu Asp Glu Asp His Met Glu Val Phe Pro Ala Gly Ser Ser
1               5                   10                  15

Phe Pro Ser Thr Lys
            20

<210> SEQ ID NO 86
<211> LENGTH: 23
<212> TYPE: PRT
<213> ORGANISM: Saccharomyces cerevisiae

<400> SEQUENCE: 86

Gln Ser Ile Ser Glu Ala Phe Gly Lys Pro Leu Ser Thr Thr Leu Asn
1               5                   10                  15

Gln Asp Glu Ala Ile Ala Lys
            20

<210> SEQ ID NO 87
<211> LENGTH: 13
<212> TYPE: PRT
<213> ORGANISM: Saccharomyces cerevisiae

<400> SEQUENCE: 87

Ser Ala His Leu Val Phe Asp Asp Ala Asn Ile Lys Lys
1               5                   10

<210> SEQ ID NO 88
<211> LENGTH: 15
<212> TYPE: PRT
<213> ORGANISM: Saccharomyces cerevisiae

<400> SEQUENCE: 88

Ile Val Lys Glu Glu Ile Phe Gly Pro Val Val Thr Val Ala Lys
1               5                   10                  15

<210> SEQ ID NO 89
<211> LENGTH: 18
<212> TYPE: PRT
<213> ORGANISM: Saccharomyces cerevisiae

<400> SEQUENCE: 89

Ile Ala Thr Tyr Gln Glu Arg Asp Pro Ala Asn Leu Pro Trp Gly Ser
1               5                   10                  15

Leu Lys

<210> SEQ ID NO 90
<211> LENGTH: 9
<212> TYPE: PRT
<213> ORGANISM: Saccharomyces cerevisiae

<400> SEQUENCE: 90

Val Ala Thr Ser Gly Val Ala Asn Lys
1               5

<210> SEQ ID NO 91

```
<211> LENGTH: 8
<212> TYPE: PRT
<213> ORGANISM: Saccharomyces cerevisiae

<400> SEQUENCE: 91

Ile Thr Val Asp Glu Leu Phe Lys
1               5

<210> SEQ ID NO 92
<211> LENGTH: 13
<212> TYPE: PRT
<213> ORGANISM: Saccharomyces cerevisiae

<400> SEQUENCE: 92

Ala Leu Asp Ala Asp Val Val Ser Ile Glu Phe Ser Lys
1               5                   10

<210> SEQ ID NO 93
<211> LENGTH: 15
<212> TYPE: PRT
<213> ORGANISM: Saccharomyces cerevisiae

<400> SEQUENCE: 93

Ala Pro Glu Gln Phe Asp Glu Val Val Ala Ala Ile Gly Asn Lys
1               5                   10                  15

<210> SEQ ID NO 94
<211> LENGTH: 9
<212> TYPE: PRT
<213> ORGANISM: Saccharomyces cerevisiae

<400> SEQUENCE: 94

Leu Asn Asp Ile Glu Asp Val Glu Lys
1               5

<210> SEQ ID NO 95
<211> LENGTH: 18
<212> TYPE: PRT
<213> ORGANISM: Saccharomyces cerevisiae

<400> SEQUENCE: 95

Leu Glu Ile Thr Lys Glu Glu Thr Leu Asn Pro Ile Ile Gln Asp Thr
1               5                   10                  15

Lys Lys

<210> SEQ ID NO 96
<211> LENGTH: 24
<212> TYPE: PRT
<213> ORGANISM: Saccharomyces cerevisiae

<400> SEQUENCE: 96

Ala Val Gly Asp Asn Asp Pro Ile Asp Val Leu Glu Ile Gly Glu Thr
1               5                   10                  15

Ile Ala Tyr Thr Gly Gln Val Lys
                20

<210> SEQ ID NO 97
<211> LENGTH: 10
<212> TYPE: PRT
<213> ORGANISM: Saccharomyces cerevisiae

<400> SEQUENCE: 97

Lys Asn Asp Asp Gly Ser Met Val Ala Lys
1               5                   10
```

-continued

<210> SEQ ID NO 98
<211> LENGTH: 19
<212> TYPE: PRT
<213> ORGANISM: Saccharomyces cerevisiae

<400> SEQUENCE: 98

Glu Lys Glu Glu Phe Gln Asp Ser Ile Leu Glu Asp Leu Asp Leu Leu
1               5                   10                  15

Gly Ile Lys

<210> SEQ ID NO 99
<211> LENGTH: 13
<212> TYPE: PRT
<213> ORGANISM: Saccharomyces cerevisiae

<400> SEQUENCE: 99

Met Ser Asn Ile Asp Phe Gln Tyr Asp Asp Ser Val Lys
1               5                   10

<210> SEQ ID NO 100
<211> LENGTH: 13
<212> TYPE: PRT
<213> ORGANISM: Saccharomyces cerevisiae

<400> SEQUENCE: 100

Ile Gln Asp Lys Glu Gly Ile Pro Pro Asp Gln Gln Arg
1               5                   10

<210> SEQ ID NO 101
<211> LENGTH: 9
<212> TYPE: PRT
<213> ORGANISM: Saccharomyces cerevisiae

<400> SEQUENCE: 101

Glu Leu Tyr Glu Val Asp Val Leu Lys
1               5

<210> SEQ ID NO 102
<211> LENGTH: 6
<212> TYPE: PRT
<213> ORGANISM: Saccharomyces cerevisiae

<400> SEQUENCE: 102

Asn Trp Phe Leu Ser Lys
1               5

<210> SEQ ID NO 103
<211> LENGTH: 15
<212> TYPE: PRT
<213> ORGANISM: Saccharomyces cerevisiae

<400> SEQUENCE: 103

Thr Phe Thr Thr Ala Glu Thr Ile Thr Asn Ala Asn Thr Ala Lys
1               5                   10                  15

<210> SEQ ID NO 104
<211> LENGTH: 16
<212> TYPE: PRT
<213> ORGANISM: Saccharomyces cerevisiae

<400> SEQUENCE: 104

Asn Leu Val Asn Asp Glu Ile Ile Ala Ala Leu Ile Glu Leu Ala Lys
1               5                   10                  15

<210> SEQ ID NO 105
<211> LENGTH: 21
<212> TYPE: PRT
<213> ORGANISM: Saccharomyces cerevisiae

<400> SEQUENCE: 105

Ala Asn Lys Pro Met Tyr Val Asp Gly Val Asn Val Ala Pro Glu Val
1               5                   10                  15

Asp Ser Val Leu Lys
            20

<210> SEQ ID NO 106
<211> LENGTH: 12
<212> TYPE: PRT
<213> ORGANISM: Saccharomyces cerevisiae

<400> SEQUENCE: 106

Thr Val Glu Gln Leu Gly Gln Glu Glu Tyr Glu Lys
1               5                   10

<210> SEQ ID NO 107
<211> LENGTH: 14
<212> TYPE: PRT
<213> ORGANISM: Saccharomyces cerevisiae

<400> SEQUENCE: 107

Ile Glu Gln Leu Tyr His Glu Tyr Glu Glu Ser Ile Ala Lys
1               5                   10

<210> SEQ ID NO 108
<211> LENGTH: 9
<212> TYPE: PRT
<213> ORGANISM: Saccharomyces cerevisiae

<400> SEQUENCE: 108

Ala Asn Glu Leu Leu Ile Asn Val Lys
1               5

<210> SEQ ID NO 109
<211> LENGTH: 13
<212> TYPE: PRT
<213> ORGANISM: Saccharomyces cerevisiae

<400> SEQUENCE: 109

Val Val Gly Leu Ser Thr Leu Pro Glu Ile Tyr Glu Lys
1               5                   10

<210> SEQ ID NO 110
<211> LENGTH: 15
<212> TYPE: PRT
<213> ORGANISM: Saccharomyces cerevisiae

<400> SEQUENCE: 110

Val Leu Gly Ile Asp Gly Gly Glu Gly Lys Glu Glu Leu Phe Arg
1               5                   10                  15

<210> SEQ ID NO 111
<211> LENGTH: 17
<212> TYPE: PRT
<213> ORGANISM: Saccharomyces cerevisiae

<400> SEQUENCE: 111

Val Thr Trp Glu Asn Asp Lys Gly Glu Gln Glu Val Ala Gln Gly Tyr

```
1               5                   10                  15

Arg

<210> SEQ ID NO 112
<211> LENGTH: 16
<212> TYPE: PRT
<213> ORGANISM: Saccharomyces cerevisiae

<400> SEQUENCE: 112

Ile Ser Val Gly Ile Glu Asp Thr Asp Asp Leu Leu Glu Asp Ile Lys
1               5                   10                  15

<210> SEQ ID NO 113
<211> LENGTH: 20
<212> TYPE: PRT
<213> ORGANISM: Saccharomyces cerevisiae

<400> SEQUENCE: 113

Ile Ser Val Gly Ile Glu Asp Thr Asp Asp Leu Leu Glu Asp Ile Lys
1               5                   10                  15

Gln Ala Leu Lys
            20

<210> SEQ ID NO 114
<211> LENGTH: 14
<212> TYPE: PRT
<213> ORGANISM: Saccharomyces cerevisiae

<400> SEQUENCE: 114

Thr Gly Gly Phe Leu Phe Pro Val Leu Ser Glu Ser Phe Lys
1               5                   10

<210> SEQ ID NO 115
<211> LENGTH: 23
<212> TYPE: PRT
<213> ORGANISM: Saccharomyces cerevisiae

<400> SEQUENCE: 115

Asp Val Pro Glu Pro Ile Thr Glu Phe Thr Ser Pro Pro Leu Asp Gly
1               5                   10                  15

Leu Leu Leu Glu Asn Ile Lys
            20

<210> SEQ ID NO 116
<211> LENGTH: 11
<212> TYPE: PRT
<213> ORGANISM: Saccharomyces cerevisiae

<400> SEQUENCE: 116

Glu Val Leu Gly Glu Gln Gly Lys Asp Val Lys
1               5                   10

<210> SEQ ID NO 117
<211> LENGTH: 12
<212> TYPE: PRT
<213> ORGANISM: Saccharomyces cerevisiae

<400> SEQUENCE: 117

Met Asn Phe Ser His Gly Ser Tyr Glu Tyr His Lys
1               5                   10

<210> SEQ ID NO 118
<211> LENGTH: 23
```

```
<212> TYPE: PRT
<213> ORGANISM: Saccharomyces cerevisiae

<400> SEQUENCE: 118

Gly Val Asn Leu Pro Gly Thr Asp Val Asp Leu Pro Ala Leu Ser Glu
1               5                   10                  15

Lys Asp Lys Glu Asp Leu Arg
            20

<210> SEQ ID NO 119
<211> LENGTH: 16
<212> TYPE: PRT
<213> ORGANISM: Saccharomyces cerevisiae

<400> SEQUENCE: 119

Leu Ala Glu Gln Ala Glu Arg Tyr Glu Glu Met Val Glu Asn Met Lys
1               5                   10                  15

<210> SEQ ID NO 120
<211> LENGTH: 19
<212> TYPE: PRT
<213> ORGANISM: Saccharomyces cerevisiae

<400> SEQUENCE: 120

Gln Ala Phe Asp Asp Ala Ile Ala Glu Leu Asp Thr Leu Ser Glu Glu
1               5                   10                  15

Ser Tyr Lys

<210> SEQ ID NO 121
<211> LENGTH: 23
<212> TYPE: PRT
<213> ORGANISM: Saccharomyces cerevisiae

<400> SEQUENCE: 121

Ile Ser Asp Asp Ile Leu Ser Val Leu Asp Ser His Leu Ile Pro Ser
1               5                   10                  15

Ala Thr Thr Gly Glu Ser Lys
            20

<210> SEQ ID NO 122
<211> LENGTH: 21
<212> TYPE: PRT
<213> ORGANISM: Saccharomyces cerevisiae

<400> SEQUENCE: 122

Ala Ile Met Pro Ile Ile Glu Gly His Asp Val Leu Ala Gln Ala Gln
1               5                   10                  15

Ser Gly Thr Gly Lys
            20

<210> SEQ ID NO 123
<211> LENGTH: 8
<212> TYPE: PRT
<213> ORGANISM: Saccharomyces cerevisiae

<400> SEQUENCE: 123

Val Gly Asp Ile Val Asp Ile Lys
1               5

<210> SEQ ID NO 124
<211> LENGTH: 19
<212> TYPE: PRT
<213> ORGANISM: Saccharomyces cerevisiae
```

<400> SEQUENCE: 124

Thr Val Glu Glu Asp His Pro Ile Pro Glu Asp Val His Glu Asn Tyr
1               5                   10                  15

Glu Asn Lys

<210> SEQ ID NO 125
<211> LENGTH: 16
<212> TYPE: PRT
<213> ORGANISM: Saccharomyces cerevisiae

<400> SEQUENCE: 125

Leu Leu Ala Gly Ala Leu Lys Pro Asp Glu Gly Gln Asp Ile Pro Lys
1               5                   10                  15

<210> SEQ ID NO 126
<211> LENGTH: 21
<212> TYPE: PRT
<213> ORGANISM: Saccharomyces cerevisiae

<400> SEQUENCE: 126

Val Val Pro Asn Glu Lys Ala Asp Asp Ser Val Thr Ile Ile Ser
1               5                   10                  15

Ala Gly Asn Asp Lys
            20

<210> SEQ ID NO 127
<211> LENGTH: 14
<212> TYPE: PRT
<213> ORGANISM: Saccharomyces cerevisiae

<400> SEQUENCE: 127

Glu Ile Tyr Tyr Thr Pro Asp Pro Ser Glu Leu Ala Ala Lys
1               5                   10

<210> SEQ ID NO 128
<211> LENGTH: 13
<212> TYPE: PRT
<213> ORGANISM: Saccharomyces cerevisiae

<400> SEQUENCE: 128

Phe Ala Pro Asp Phe Ala Asp Glu Glu Tyr Val Asn Lys
1               5                   10

<210> SEQ ID NO 129
<211> LENGTH: 21
<212> TYPE: PRT
<213> ORGANISM: Saccharomyces cerevisiae

<400> SEQUENCE: 129

Phe Ala Pro Asp Phe Ala Asp Glu Glu Tyr Val Asn Lys Leu Glu Gly
1               5                   10                  15

Glu Ile Pro Glu Lys
            20

<210> SEQ ID NO 130
<211> LENGTH: 22
<212> TYPE: PRT
<213> ORGANISM: Saccharomyces cerevisiae

<400> SEQUENCE: 130

Val Gly Glu Tyr Asn Ala Glu Thr Asp Glu Val Glu Leu Ile Phe Asp
1               5                   10                  15

Asp Tyr Leu Tyr Ala Lys
            20

<210> SEQ ID NO 131
<211> LENGTH: 10
<212> TYPE: PRT
<213> ORGANISM: Saccharomyces cerevisiae

<400> SEQUENCE: 131

Tyr Phe Thr Pro Asp Trp Leu Asp Glu Lys
1               5                   10

<210> SEQ ID NO 132
<211> LENGTH: 21
<212> TYPE: PRT
<213> ORGANISM: Saccharomyces cerevisiae

<400> SEQUENCE: 132

Ala Phe Asp Thr Thr Asp Glu Pro Asp Val Lys Pro Tyr Leu Pro Glu
1               5                   10                  15

Glu Ile Leu Trp Arg
            20

<210> SEQ ID NO 133
<211> LENGTH: 8
<212> TYPE: PRT
<213> ORGANISM: Saccharomyces cerevisiae

<400> SEQUENCE: 133

Ser Lys Glu Gly Ala Glu Pro Lys
1               5

<210> SEQ ID NO 134
<211> LENGTH: 11
<212> TYPE: PRT
<213> ORGANISM: Saccharomyces cerevisiae

<400> SEQUENCE: 134

Gly Tyr Trp Ile Glu Glu Asp Asp Ser Val Lys
1               5                   10

<210> SEQ ID NO 135
<211> LENGTH: 13
<212> TYPE: PRT
<213> ORGANISM: Saccharomyces cerevisiae

<400> SEQUENCE: 135

Asn Ser Gly Phe Glu Ile Ile Gln Gly Leu Leu Gly Lys
1               5                   10

<210> SEQ ID NO 136
<211> LENGTH: 12
<212> TYPE: PRT
<213> ORGANISM: Saccharomyces cerevisiae

<400> SEQUENCE: 136

Asn Val Leu Ile Glu Gln Pro Phe Gly Pro Pro Lys
1               5                   10

<210> SEQ ID NO 137
<211> LENGTH: 17
<212> TYPE: PRT
<213> ORGANISM: Saccharomyces cerevisiae

```
<400> SEQUENCE: 137

Ala Ala Val Glu Glu Gly Ile Leu Pro Gly Gly Gly Thr Ala Leu Val
1               5                   10                  15

Lys

<210> SEQ ID NO 138
<211> LENGTH: 20
<212> TYPE: PRT
<213> ORGANISM: Saccharomyces cerevisiae

<400> SEQUENCE: 138

Thr Thr Val Leu Leu Asp Tyr Thr Arg Pro Ile Ser Asp Asp Pro Glu
1               5                   10                  15

Val Ile Asn Lys
            20

<210> SEQ ID NO 139
<211> LENGTH: 9
<212> TYPE: PRT
<213> ORGANISM: Saccharomyces cerevisiae

<400> SEQUENCE: 139

Leu Leu Gly Ser Asp Val Ile Glu Lys
1               5

<210> SEQ ID NO 140
<211> LENGTH: 12
<212> TYPE: PRT
<213> ORGANISM: Saccharomyces cerevisiae

<400> SEQUENCE: 140

Trp Phe Asn Thr Val Ala Ala Ser Pro Ile Val Lys
1               5                   10

<210> SEQ ID NO 141
<211> LENGTH: 11
<212> TYPE: PRT
<213> ORGANISM: Saccharomyces cerevisiae

<400> SEQUENCE: 141

Tyr Val Asp Glu Gln Ser Lys Asn Glu Leu Lys
1               5                   10

<210> SEQ ID NO 142
<211> LENGTH: 12
<212> TYPE: PRT
<213> ORGANISM: Saccharomyces cerevisiae

<400> SEQUENCE: 142

Tyr Val Asp Glu Gln Ser Lys Asn Glu Leu Lys Lys
1               5                   10

<210> SEQ ID NO 143
<211> LENGTH: 17
<212> TYPE: PRT
<213> ORGANISM: Saccharomyces cerevisiae

<400> SEQUENCE: 143

Leu Gly Ser Leu Val Gly Gln Asp Ser Gly Tyr Val Gly Gly Leu Pro
1               5                   10                  15

Lys
```

```
<210> SEQ ID NO 144
<211> LENGTH: 18
<212> TYPE: PRT
<213> ORGANISM: Saccharomyces cerevisiae

<400> SEQUENCE: 144

Leu Ala Thr Gly Ala Asn Ile Val Gly Asn Ala Leu Ile Asp Pro Thr
1               5                   10                  15

Ala Lys

<210> SEQ ID NO 145
<211> LENGTH: 25
<212> TYPE: PRT
<213> ORGANISM: Saccharomyces cerevisiae

<400> SEQUENCE: 145

Ile Asn Ala Gly Leu Tyr Ile Leu Asn Pro Glu Val Ile Asp Leu Ile
1               5                   10                  15

Glu Met Lys Pro Thr Ser Ile Glu Lys
            20                  25

<210> SEQ ID NO 146
<211> LENGTH: 17
<212> TYPE: PRT
<213> ORGANISM: Saccharomyces cerevisiae

<400> SEQUENCE: 146

Ser Gly Val Ala Val Ala Asp Glu Ser Leu Thr Ala Phe Asn Asp Leu
1               5                   10                  15

Lys

<210> SEQ ID NO 147
<211> LENGTH: 16
<212> TYPE: PRT
<213> ORGANISM: Saccharomyces cerevisiae

<400> SEQUENCE: 147

Ser Val Gln Tyr Val Leu Glu Asp Pro Ile Ala Gly Pro Leu Val Lys
1               5                   10                  15

<210> SEQ ID NO 148
<211> LENGTH: 13
<212> TYPE: PRT
<213> ORGANISM: Saccharomyces cerevisiae

<400> SEQUENCE: 148

Ala Thr Asn Asp Val Glu Pro Ser Thr Tyr Asp Ser Lys
1               5                   10

<210> SEQ ID NO 149
<211> LENGTH: 13
<212> TYPE: PRT
<213> ORGANISM: Saccharomyces cerevisiae

<400> SEQUENCE: 149

Lys Val Glu Ser Leu Gly Ser Pro Ser Gly Ala Thr Lys
1               5                   10

<210> SEQ ID NO 150
<211> LENGTH: 14
<212> TYPE: PRT
<213> ORGANISM: Saccharomyces cerevisiae

<400> SEQUENCE: 150
```

Val Leu Glu Gln Leu Ser Gly Gln Thr Pro Val Gln Ser Lys
1               5                   10

<210> SEQ ID NO 151
<211> LENGTH: 17
<212> TYPE: PRT
<213> ORGANISM: Saccharomyces cerevisiae

<400> SEQUENCE: 151

Val Tyr Tyr Phe Gln Gly Gly Asn Asn Glu Leu Gly Thr Ala Val Gly
1               5                   10                  15
Lys

<210> SEQ ID NO 152
<211> LENGTH: 15
<212> TYPE: PRT
<213> ORGANISM: Saccharomyces cerevisiae

<400> SEQUENCE: 152

Thr Ala Glu Gln Leu Glu Asn Leu Asn Ile Gln Asp Asp Gln Lys
1               5                   10                  15

<210> SEQ ID NO 153
<211> LENGTH: 16
<212> TYPE: PRT
<213> ORGANISM: Saccharomyces cerevisiae

<400> SEQUENCE: 153

Val Thr Tyr Asp Ile Thr Ser Lys Pro Pro Ala Thr Val Glu Trp Glu
1               5                   10                  15

<210> SEQ ID NO 154
<211> LENGTH: 16
<212> TYPE: PRT
<213> ORGANISM: Saccharomyces cerevisiae

<400> SEQUENCE: 154

Ile Gly Ser Leu Asp Thr Leu Ile Val Glu Ser Glu Glu Leu Ser Lys
1               5                   10                  15

<210> SEQ ID NO 155
<211> LENGTH: 15
<212> TYPE: PRT
<213> ORGANISM: Saccharomyces cerevisiae

<400> SEQUENCE: 155

Thr Ile Ala Glu Thr Leu Ala Glu Glu Leu Ile Asn Ala Ala Lys
1               5                   10                  15

<210> SEQ ID NO 156
<211> LENGTH: 14
<212> TYPE: PRT
<213> ORGANISM: Saccharomyces cerevisiae

<400> SEQUENCE: 156

Phe Pro Thr Pro Val Ser His Asn Asp Asp Leu Tyr Gly Lys
1               5                   10

<210> SEQ ID NO 157
<211> LENGTH: 17
<212> TYPE: PRT
<213> ORGANISM: Saccharomyces cerevisiae

<400> SEQUENCE: 157

```
Ala Ala Ala Pro Thr Val Val Phe Leu Asp Glu Leu Asp Ser Ile Ala
1               5                   10                  15

Lys

<210> SEQ ID NO 158
<211> LENGTH: 14
<212> TYPE: PRT
<213> ORGANISM: Saccharomyces cerevisiae

<400> SEQUENCE: 158

Leu Gln Glu Thr Asn Pro Glu Glu Val Pro Lys Phe Glu Lys
1               5                   10

<210> SEQ ID NO 159
<211> LENGTH: 10
<212> TYPE: PRT
<213> ORGANISM: Saccharomyces cerevisiae

<400> SEQUENCE: 159

Phe Leu Asp Gly Ile Tyr Val Ser His Lys
1               5                   10

<210> SEQ ID NO 160
<211> LENGTH: 19
<212> TYPE: PRT
<213> ORGANISM: Saccharomyces cerevisiae

<400> SEQUENCE: 160

Tyr Ile Gln Thr Glu Gln Gln Ile Glu Val Pro Glu Gly Val Thr Val
1               5                   10                  15

Ser Ile Lys

<210> SEQ ID NO 161
<211> LENGTH: 23
<212> TYPE: PRT
<213> ORGANISM: Saccharomyces cerevisiae

<400> SEQUENCE: 161

Val Asp Phe Lys Asn Pro His Asp Ile Ile Glu Gly Ile Asn Ala Gly
1               5                   10                  15

Glu Ile Glu Ile Pro Glu Asn
            20

<210> SEQ ID NO 162
<211> LENGTH: 13
<212> TYPE: PRT
<213> ORGANISM: Saccharomyces cerevisiae

<400> SEQUENCE: 162

Thr Gly Val Phe Glu Pro Glu Phe Thr Ala Asp Gly Lys
1               5                   10

<210> SEQ ID NO 163
<211> LENGTH: 13
<212> TYPE: PRT
<213> ORGANISM: Saccharomyces cerevisiae

<400> SEQUENCE: 163

Leu Asn Thr Ala Ile Ser Asn Leu Glu Val Glu Asn Lys
1               5                   10

<210> SEQ ID NO 164
```

```
<211> LENGTH: 11
<212> TYPE: PRT
<213> ORGANISM: Saccharomyces cerevisiae

<400> SEQUENCE: 164

Thr Ala Ile Glu Gly Ser Tyr Ile Asp Lys Lys
1               5                   10

<210> SEQ ID NO 165
<211> LENGTH: 18
<212> TYPE: PRT
<213> ORGANISM: Saccharomyces cerevisiae

<400> SEQUENCE: 165

Ala Pro Thr Ala Ser Gln Leu Gln Asn Pro Pro Pro Pro Ser Thr
1               5                   10                  15

Thr Lys

<210> SEQ ID NO 166
<211> LENGTH: 17
<212> TYPE: PRT
<213> ORGANISM: Saccharomyces cerevisiae

<400> SEQUENCE: 166

Gly Lys Asp Asn Ala Glu Gly Gln Gly Glu Ser Leu Ala Asp Gln Ala
1               5                   10                  15

Arg

<210> SEQ ID NO 167
<211> LENGTH: 15
<212> TYPE: PRT
<213> ORGANISM: Saccharomyces cerevisiae

<400> SEQUENCE: 167

Thr Val Ser Gln Ala Asp Phe Pro Gly Leu Glu Gly Val Ala Lys
1               5                   10                  15

<210> SEQ ID NO 168
<211> LENGTH: 18
<212> TYPE: PRT
<213> ORGANISM: Saccharomyces cerevisiae

<400> SEQUENCE: 168

Lys Leu Glu Asp Leu Ser Pro Ser Thr His Asn Met Glu Val Pro Val
1               5                   10                  15

Val Lys

<210> SEQ ID NO 169
<211> LENGTH: 16
<212> TYPE: PRT
<213> ORGANISM: Saccharomyces cerevisiae

<400> SEQUENCE: 169

Ile Glu Gly Val Ala Thr Pro Gln Asp Ala Gln Phe Tyr Leu Gly Lys
1               5                   10                  15

<210> SEQ ID NO 170
<211> LENGTH: 21
<212> TYPE: PRT
<213> ORGANISM: Saccharomyces cerevisiae

<400> SEQUENCE: 170

Thr Lys Tyr Asp Ile Thr Ile Asp Glu Glu Ser Pro Arg Pro Gly Gln
```

```
1               5                   10                  15
Gln Thr Phe Glu Lys
            20

<210> SEQ ID NO 171
<211> LENGTH: 14
<212> TYPE: PRT
<213> ORGANISM: Saccharomyces cerevisiae

<400> SEQUENCE: 171

Ile Gly Ser Phe Gly Pro Gln Glu Asp Glu Phe Phe Asn Lys
1               5                   10

<210> SEQ ID NO 172
<211> LENGTH: 16
<212> TYPE: PRT
<213> ORGANISM: Saccharomyces cerevisiae

<400> SEQUENCE: 172

Gly Ser Lys Pro Gly Gln Gln Val Asp Leu Glu Glu Asn Glu Ile Arg
1               5                   10                  15

<210> SEQ ID NO 173
<211> LENGTH: 16
<212> TYPE: PRT
<213> ORGANISM: Saccharomyces cerevisiae

<400> SEQUENCE: 173

Lys Gly Glu Gln Glu Leu Glu Gly Leu Thr Asp Thr Thr Val Pro Lys
1               5                   10                  15

<210> SEQ ID NO 174
<211> LENGTH: 15
<212> TYPE: PRT
<213> ORGANISM: Saccharomyces cerevisiae

<400> SEQUENCE: 174

Ile Ile Lys Asp Phe Pro Glu Leu Asp Leu Gly Thr Ile Gly Lys
1               5                   10                  15

<210> SEQ ID NO 175
<211> LENGTH: 17
<212> TYPE: PRT
<213> ORGANISM: Saccharomyces cerevisiae

<400> SEQUENCE: 175

Ile Pro Glu Ile Pro Leu Val Val Ser Thr Asp Leu Glu Ser Ile Gln
1               5                   10                  15

Lys

<210> SEQ ID NO 176
<211> LENGTH: 20
<212> TYPE: PRT
<213> ORGANISM: Saccharomyces cerevisiae

<400> SEQUENCE: 176

Ile Ile Asn Ser Ser Glu Ile Gln Ser Ala Ile Arg Pro Ala Gly Gln
1               5                   10                  15

Ala Thr Gln Lys
            20

<210> SEQ ID NO 177
<211> LENGTH: 14
```

```
<212> TYPE: PRT
<213> ORGANISM: Saccharomyces cerevisiae

<400> SEQUENCE: 177

Gln Thr Glu Gln Asp Asn Val Glu Lys Glu Asn Gln Ile Lys
1               5                   10

<210> SEQ ID NO 178
<211> LENGTH: 16
<212> TYPE: PRT
<213> ORGANISM: Saccharomyces cerevisiae

<400> SEQUENCE: 178

Asn Lys Asp Leu Glu Gln Glu Asn Val Glu Lys Glu Asn Gln Ile Lys
1               5                   10                  15

<210> SEQ ID NO 179
<211> LENGTH: 20
<212> TYPE: PRT
<213> ORGANISM: Saccharomyces cerevisiae

<400> SEQUENCE: 179

Gln Asn Asp Ile Thr Asp Gly Lys Asp Tyr His Thr Leu Ala Asn Asn
1               5                   10                  15

Val Glu Ser Lys
            20

<210> SEQ ID NO 180
<211> LENGTH: 13
<212> TYPE: PRT
<213> ORGANISM: Saccharomyces cerevisiae

<400> SEQUENCE: 180

Asp Tyr Asp Glu Ser Leu Thr Asp Lys Asn Ile Glu Lys
1               5                   10

<210> SEQ ID NO 181
<211> LENGTH: 10
<212> TYPE: PRT
<213> ORGANISM: Saccharomyces cerevisiae

<400> SEQUENCE: 181

Gly Thr Ile Glu Ile Val Ser Asp Val Lys
1               5                   10

<210> SEQ ID NO 182
<211> LENGTH: 20
<212> TYPE: PRT
<213> ORGANISM: Saccharomyces cerevisiae

<400> SEQUENCE: 182

Asn Gln Ile Leu Val Ser Gly Glu Ile Pro Ser Thr Leu Asn Glu Glu
1               5                   10                  15

Ser Lys Asp Lys
            20

<210> SEQ ID NO 183
<211> LENGTH: 14
<212> TYPE: PRT
<213> ORGANISM: Saccharomyces cerevisiae

<400> SEQUENCE: 183

Leu Gly Asp Glu Ile Glu Ile Arg Pro Gly Ile Val Thr Lys
1               5                   10
```

<210> SEQ ID NO 184
<211> LENGTH: 17
<212> TYPE: PRT
<213> ORGANISM: Saccharomyces cerevisiae

<400> SEQUENCE: 184

Val Ala Phe Thr Gly Leu Glu Glu Asp Gly Glu Thr Glu Glu Glu Lys
1               5                   10                  15

Arg

<210> SEQ ID NO 185
<211> LENGTH: 16
<212> TYPE: PRT
<213> ORGANISM: Saccharomyces cerevisiae

<400> SEQUENCE: 185

Ile Glu Gly Val Ala Thr Pro Gln Glu Ala Gln Phe Tyr Leu Gly Lys
1               5                   10                  15

<210> SEQ ID NO 186
<211> LENGTH: 12
<212> TYPE: PRT
<213> ORGANISM: Saccharomyces cerevisiae

<400> SEQUENCE: 186

Val Ser Gly Phe Lys Asp Glu Val Leu Glu Thr Val
1               5                   10

<210> SEQ ID NO 187
<211> LENGTH: 14
<212> TYPE: PRT
<213> ORGANISM: Saccharomyces cerevisiae

<400> SEQUENCE: 187

Leu Lys Val Pro Ala Ile Asn Val Asn Asp Ser Val Thr Lys
1               5                   10

<210> SEQ ID NO 188
<211> LENGTH: 30
<212> TYPE: PRT
<213> ORGANISM: Saccharomyces cerevisiae

<400> SEQUENCE: 188

Ala Ser Leu Asn Val Gly Asn Val Leu Pro Leu Gly Ser Val Pro Glu
1               5                   10                  15

Gly Thr Ile Val Ser Asn Val Glu Glu Lys Pro Gly Asp Arg
                20                  25                  30

<210> SEQ ID NO 189
<211> LENGTH: 15
<212> TYPE: PRT
<213> ORGANISM: Saccharomyces cerevisiae

<400> SEQUENCE: 189

Ile Asn Glu Lys Pro Thr Val Val Asn Asp Tyr Glu Ala Ala Arg
1               5                   10                  15

<210> SEQ ID NO 190
<211> LENGTH: 14
<212> TYPE: PRT
<213> ORGANISM: Saccharomyces cerevisiae

<400> SEQUENCE: 190

```
Ile Pro Glu Ile Leu Glu Glu Met Gln Gly Asp Leu Phe Lys
1               5                   10
```

<210> SEQ ID NO 191
<211> LENGTH: 17
<212> TYPE: PRT
<213> ORGANISM: Saccharomyces cerevisiae

<400> SEQUENCE: 191

```
Phe His Glu Glu Tyr Leu Pro Leu Ile Ile Asp Ile Ile Asp Ser Ala
1               5                   10                  15

Lys
```

<210> SEQ ID NO 192
<211> LENGTH: 7
<212> TYPE: PRT
<213> ORGANISM: Saccharomyces cerevisiae

<400> SEQUENCE: 192

```
Ala Thr Leu Glu Leu Leu Lys
1               5
```

<210> SEQ ID NO 193
<211> LENGTH: 12
<212> TYPE: PRT
<213> ORGANISM: Saccharomyces cerevisiae

<400> SEQUENCE: 193

```
Thr Thr Pro Thr Leu Phe Glu Asn Asp Val Ile Lys
1               5                   10
```

<210> SEQ ID NO 194
<211> LENGTH: 14
<212> TYPE: PRT
<213> ORGANISM: Saccharomyces cerevisiae

<400> SEQUENCE: 194

```
Asp Tyr Lys Gly Glu Ala Asp Pro Gly Val Ile Ser Val Lys
1               5                   10
```

<210> SEQ ID NO 195
<211> LENGTH: 15
<212> TYPE: PRT
<213> ORGANISM: Saccharomyces cerevisiae

<400> SEQUENCE: 195

```
Asp Leu Ser Glu Ala Ser Val Tyr Pro Glu Tyr Ala Leu Pro Lys
1               5                   10                  15
```

<210> SEQ ID NO 196
<211> LENGTH: 24
<212> TYPE: PRT
<213> ORGANISM: Saccharomyces cerevisiae

<400> SEQUENCE: 196

```
Glu Phe Gln Ile Ile Asp Thr Leu Leu Pro Gly Leu Gln Asp Glu Val
1               5                   10                  15

Met Asn Ile Lys Pro Val Gln Lys
                20
```

<210> SEQ ID NO 197
<211> LENGTH: 6
<212> TYPE: PRT

```
<213> ORGANISM: Saccharomyces cerevisiae

<400> SEQUENCE: 197

Arg Glu Gln Leu Leu Lys
1               5

<210> SEQ ID NO 198
<211> LENGTH: 8
<212> TYPE: PRT
<213> ORGANISM: Saccharomyces cerevisiae

<400> SEQUENCE: 198

Asp Leu Thr Asp Tyr Leu Met Lys
1               5

<210> SEQ ID NO 199
<211> LENGTH: 13
<212> TYPE: PRT
<213> ORGANISM: Saccharomyces cerevisiae

<400> SEQUENCE: 199

Trp Gly Phe Thr Asn Leu Asp Arg Pro Glu Tyr Leu Lys
1               5                   10

<210> SEQ ID NO 200
<211> LENGTH: 16
<212> TYPE: PRT
<213> ORGANISM: Saccharomyces cerevisiae

<400> SEQUENCE: 200

Leu Ser Ser Glu Thr Pro Ala Leu Glu Ser Glu Gly Pro Gln Thr Lys
1               5                   10                  15

<210> SEQ ID NO 201
<211> LENGTH: 13
<212> TYPE: PRT
<213> ORGANISM: Saccharomyces cerevisiae

<400> SEQUENCE: 201

Ala Ile Lys Glu Glu Ser Gln Ser Ile Tyr Ile Pro Arg
1               5                   10

<210> SEQ ID NO 202
<211> LENGTH: 14
<212> TYPE: PRT
<213> ORGANISM: Saccharomyces cerevisiae

<400> SEQUENCE: 202

His Leu Glu Asp Asn Thr Leu Leu Val Thr Gly Pro Phe Lys
1               5                   10

<210> SEQ ID NO 203
<211> LENGTH: 9
<212> TYPE: PRT
<213> ORGANISM: Saccharomyces cerevisiae

<400> SEQUENCE: 203

Ile Asn Arg Ala Ser Gly Thr Thr Lys
1               5

<210> SEQ ID NO 204
<211> LENGTH: 6
<212> TYPE: PRT
<213> ORGANISM: Saccharomyces cerevisiae
```

```
<400> SEQUENCE: 204

Phe Gln Leu Val Glu Lys
1               5

<210> SEQ ID NO 205
<211> LENGTH: 7
<212> TYPE: PRT
<213> ORGANISM: Saccharomyces cerevisiae

<400> SEQUENCE: 205

Arg Ile Asp Ala Ala Ile Lys
1               5

<210> SEQ ID NO 206
<211> LENGTH: 14
<212> TYPE: PRT
<213> ORGANISM: Saccharomyces cerevisiae

<400> SEQUENCE: 206

Ile Ile Lys Ser Ala Asn Glu Leu Val Glu Thr Leu Ser Lys
1               5                   10

<210> SEQ ID NO 207
<211> LENGTH: 8
<212> TYPE: PRT
<213> ORGANISM: Saccharomyces cerevisiae

<400> SEQUENCE: 207

Met Asn Ser Pro Ile Leu Arg Lys
1               5

<210> SEQ ID NO 208
<211> LENGTH: 6
<212> TYPE: PRT
<213> ORGANISM: Saccharomyces cerevisiae

<400> SEQUENCE: 208

Gln Asn Glu Asn Gln Lys
1               5

<210> SEQ ID NO 209
<211> LENGTH: 12
<212> TYPE: PRT
<213> ORGANISM: Saccharomyces cerevisiae

<400> SEQUENCE: 209

Glu Tyr Phe Val Glu Pro Asn Ser Ala Glu Gly Lys
1               5                   10

<210> SEQ ID NO 210
<211> LENGTH: 16
<212> TYPE: PRT
<213> ORGANISM: Saccharomyces cerevisiae

<400> SEQUENCE: 210

Leu Asn Ala Ala Gly Leu Ile Gly Asp Ala Pro Lys Pro Val Val Lys
1               5                   10                  15

<210> SEQ ID NO 211
<211> LENGTH: 10
<212> TYPE: PRT
<213> ORGANISM: Saccharomyces cerevisiae

<400> SEQUENCE: 211
```

```
Ser Glu Gln Gly Ile Leu Asn Thr Pro Lys
1               5                  10
```

<210> SEQ ID NO 212
<211> LENGTH: 7
<212> TYPE: PRT
<213> ORGANISM: Saccharomyces cerevisiae

<400> SEQUENCE: 212

```
Ile Leu Asp Lys Ile Ile Arg
1               5
```

<210> SEQ ID NO 213
<211> LENGTH: 15
<212> TYPE: PRT
<213> ORGANISM: Saccharomyces cerevisiae

<400> SEQUENCE: 213

```
Ile Val Ala Gly Gln Val Asp Thr Asp Glu Ala Gly Tyr Ile Lys
1               5                  10                  15
```

<210> SEQ ID NO 214
<211> LENGTH: 6
<212> TYPE: PRT
<213> ORGANISM: Saccharomyces cerevisiae

<400> SEQUENCE: 214

```
Arg Gln Glu Leu Leu Lys
1               5
```

<210> SEQ ID NO 215
<211> LENGTH: 12
<212> TYPE: PRT
<213> ORGANISM: Saccharomyces cerevisiae

<400> SEQUENCE: 215

```
Val Phe Glu Asp Ile Pro Ile Glu Glu Ala Glu Lys
1               5                  10
```

<210> SEQ ID NO 216
<211> LENGTH: 8
<212> TYPE: PRT
<213> ORGANISM: Saccharomyces cerevisiae

<400> SEQUENCE: 216

```
Trp Glu Thr Thr Thr Gln Phe Lys
1               5
```

<210> SEQ ID NO 217
<211> LENGTH: 6
<212> TYPE: PRT
<213> ORGANISM: Saccharomyces cerevisiae

<400> SEQUENCE: 217

```
Glu Ile Lys Phe Ile Lys
1               5
```

<210> SEQ ID NO 218
<211> LENGTH: 13
<212> TYPE: PRT
<213> ORGANISM: Saccharomyces cerevisiae

<400> SEQUENCE: 218

```
Ile Lys Pro Phe Ile Glu Asn Leu Pro Gln Glu Phe Lys
1               5                  10
```

<210> SEQ ID NO 219
<211> LENGTH: 8
<212> TYPE: PRT
<213> ORGANISM: Saccharomyces cerevisiae

<400> SEQUENCE: 219

Leu Asn Glu Leu Phe Met Gly Lys
1               5

<210> SEQ ID NO 220
<211> LENGTH: 8
<212> TYPE: PRT
<213> ORGANISM: Saccharomyces cerevisiae

<400> SEQUENCE: 220

Ser Thr Thr Leu Ser Asp Ile Lys
1               5

<210> SEQ ID NO 221
<211> LENGTH: 7
<212> TYPE: PRT
<213> ORGANISM: Saccharomyces cerevisiae

<400> SEQUENCE: 221

Glu Arg Ala Leu Gly Ile Lys
1               5

<210> SEQ ID NO 222
<211> LENGTH: 7
<212> TYPE: PRT
<213> ORGANISM: Saccharomyces cerevisiae

<400> SEQUENCE: 222

Leu Thr Asn Ile Leu Leu Lys
1               5

<210> SEQ ID NO 223
<211> LENGTH: 12
<212> TYPE: PRT
<213> ORGANISM: Saccharomyces cerevisiae

<400> SEQUENCE: 223

Glu Thr Leu Ser Gly Leu Glu Phe Leu His Ser Lys
1               5                   10

<210> SEQ ID NO 224
<211> LENGTH: 6
<212> TYPE: PRT
<213> ORGANISM: Saccharomyces cerevisiae

<400> SEQUENCE: 224

Phe Ile Asn Leu Glu Lys
1               5

<210> SEQ ID NO 225
<211> LENGTH: 8
<212> TYPE: PRT
<213> ORGANISM: Saccharomyces cerevisiae

<400> SEQUENCE: 225

Leu Asp Tyr Val Leu Ala Leu Lys
1               5

-continued

```
<210> SEQ ID NO 226
<211> LENGTH: 21
<212> TYPE: PRT
<213> ORGANISM: Saccharomyces cerevisiae

<400> SEQUENCE: 226

Ser Ser Leu Gln Gly Gln Gly Lys Thr Gly Ile Cys Ser Ala Ile Asp
1               5                   10                  15

Pro Lys Ser Asp Lys
            20

<210> SEQ ID NO 227
<211> LENGTH: 8
<212> TYPE: PRT
<213> ORGANISM: Saccharomyces cerevisiae

<400> SEQUENCE: 227

Ile Asp Leu Val Ser Asn Asn Lys
1               5

<210> SEQ ID NO 228
<211> LENGTH: 8
<212> TYPE: PRT
<213> ORGANISM: Saccharomyces cerevisiae

<400> SEQUENCE: 228

Asp Val Asp Tyr Gln Thr Phe Lys
1               5

<210> SEQ ID NO 229
<211> LENGTH: 8
<212> TYPE: PRT
<213> ORGANISM: Saccharomyces cerevisiae

<400> SEQUENCE: 229

Phe Lys Ile Pro Gly Phe Gly Lys
1               5

<210> SEQ ID NO 230
<211> LENGTH: 10
<212> TYPE: PRT
<213> ORGANISM: Saccharomyces cerevisiae

<400> SEQUENCE: 230

Asp Ser Val Thr Tyr Thr Glu His Ala Lys
1               5                   10

<210> SEQ ID NO 231
<211> LENGTH: 11
<212> TYPE: PRT
<213> ORGANISM: Saccharomyces cerevisiae

<400> SEQUENCE: 231

Leu Asp Glu Leu Val Asn Leu Leu Val Phe Lys
1               5                   10

<210> SEQ ID NO 232
<211> LENGTH: 11
<212> TYPE: PRT
<213> ORGANISM: Saccharomyces cerevisiae

<400> SEQUENCE: 232

Ser Leu Leu Arg Lys Ser Lys Pro Leu Gln Ala
1               5                   10
```

<210> SEQ ID NO 233
<211> LENGTH: 18
<212> TYPE: PRT
<213> ORGANISM: Saccharomyces cerevisiae

<400> SEQUENCE: 233

Thr Ala Ser Ala Gln Leu Glu Gly Gly Val His Asn Leu His Ser Tyr
1               5                   10                  15

Glu Lys

<210> SEQ ID NO 234
<211> LENGTH: 8
<212> TYPE: PRT
<213> ORGANISM: Saccharomyces cerevisiae

<400> SEQUENCE: 234

Arg Leu Lys Glu Leu Glu Thr Lys
1               5

<210> SEQ ID NO 235
<211> LENGTH: 8
<212> TYPE: PRT
<213> ORGANISM: Saccharomyces cerevisiae

<400> SEQUENCE: 235

Thr Asn Leu Glu Thr Leu Glu Lys
1               5

<210> SEQ ID NO 236
<211> LENGTH: 19
<212> TYPE: PRT
<213> ORGANISM: Saccharomyces cerevisiae

<400> SEQUENCE: 236

Ile Asn Asn Leu Tyr Ala Ser Leu Lys Ala Glu Gly Leu Ile Tyr Thr
1               5                   10                  15

Pro Pro Lys

<210> SEQ ID NO 237
<211> LENGTH: 7
<212> TYPE: PRT
<213> ORGANISM: Saccharomyces cerevisiae

<400> SEQUENCE: 237

Gly Asn Lys Tyr Leu Ile Lys
1               5

<210> SEQ ID NO 238
<211> LENGTH: 9
<212> TYPE: PRT
<213> ORGANISM: Saccharomyces cerevisiae

<400> SEQUENCE: 238

Ile Pro Cys Asn Ser Ser Asp Ser Lys
1               5

<210> SEQ ID NO 239
<211> LENGTH: 17
<212> TYPE: PRT
<213> ORGANISM: Saccharomyces cerevisiae

<400> SEQUENCE: 239

Ile Asp Ile Leu Thr Lys Ile Gln Glu Asn Leu Leu Glu Glu Tyr Gln

<210> SEQ ID NO 240
<211> LENGTH: 7
<212> TYPE: PRT
<213> ORGANISM: Saccharomyces cerevisiae

<400> SEQUENCE: 240

Glu Ser Ile Pro Tyr Asp Lys
1               5

<210> SEQ ID NO 241
<211> LENGTH: 8
<212> TYPE: PRT
<213> ORGANISM: Saccharomyces cerevisiae

<400> SEQUENCE: 241

Arg Ile Ala Thr Ala Ile Glu Lys
1               5

<210> SEQ ID NO 242
<211> LENGTH: 12
<212> TYPE: PRT
<213> ORGANISM: Saccharomyces cerevisiae

<400> SEQUENCE: 242

Val Asn Gln Ile Gly Thr Leu Ser Glu Ser Ile Lys
1               5                   10

<210> SEQ ID NO 243
<211> LENGTH: 17
<212> TYPE: PRT
<213> ORGANISM: Saccharomyces cerevisiae

<400> SEQUENCE: 243

Thr Ala Gly Ile Gln Ile Val Ala Asp Asp Leu Thr Val Thr Asn Pro
1               5                   10                  15
Lys

<210> SEQ ID NO 244
<211> LENGTH: 21
<212> TYPE: PRT
<213> ORGANISM: Saccharomyces cerevisiae

<400> SEQUENCE: 244

Ile Glu Glu Glu Leu Gly Asp Asn Ala Val Phe Ala Gly Glu Asn Phe
1               5                   10                  15
His His Gly Asp Lys
            20

<210> SEQ ID NO 245
<211> LENGTH: 9
<212> TYPE: PRT
<213> ORGANISM: Saccharomyces cerevisiae

<400> SEQUENCE: 245

Glu Thr Thr Tyr Asp Glu Ile Lys Lys
1               5

<210> SEQ ID NO 246
<211> LENGTH: 12
<212> TYPE: PRT

<213> ORGANISM: Saccharomyces cerevisiae

<400> SEQUENCE: 246

Leu Asn Lys Glu Thr Thr Tyr Asp Glu Ile Lys Lys
1               5                   10

<210> SEQ ID NO 247
<211> LENGTH: 22
<212> TYPE: PRT
<213> ORGANISM: Saccharomyces cerevisiae

<400> SEQUENCE: 247

Lys Val Val Ile Thr Ala Pro Ser Ser Thr Ala Pro Met Phe Val Met
1               5                   10                  15

Gly Val Asn Glu Glu Lys
            20

<210> SEQ ID NO 248
<211> LENGTH: 24
<212> TYPE: PRT
<213> ORGANISM: Saccharomyces cerevisiae

<400> SEQUENCE: 248

Val Ile Asn Asp Ala Phe Gly Ile Glu Glu Gly Leu Met Thr Thr Val
1               5                   10                  15

His Ser Leu Thr Ala Thr Gln Lys
            20

<210> SEQ ID NO 249
<211> LENGTH: 7
<212> TYPE: PRT
<213> ORGANISM: Saccharomyces cerevisiae

<400> SEQUENCE: 249

Phe Asp Glu Leu Leu Glu Lys
1               5

<210> SEQ ID NO 250
<211> LENGTH: 24
<212> TYPE: PRT
<213> ORGANISM: Saccharomyces cerevisiae

<400> SEQUENCE: 250

Val Glu Thr Gly Val Ile Lys Pro Gly Met Val Val Thr Phe Ala Pro
1               5                   10                  15

Ala Gly Val Thr Thr Glu Val Lys
            20

<210> SEQ ID NO 251
<211> LENGTH: 12
<212> TYPE: PRT
<213> ORGANISM: Saccharomyces cerevisiae

<400> SEQUENCE: 251

Ser Val Ala Val Asp Ser Ser Glu Ser Asn Leu Lys
1               5                   10

<210> SEQ ID NO 252
<211> LENGTH: 13
<212> TYPE: PRT
<213> ORGANISM: Saccharomyces cerevisiae

<400> SEQUENCE: 252

Ser Val Ala Val Asp Ser Ser Glu Ser Asn Leu Lys Lys
1               5                   10

<210> SEQ ID NO 253
<211> LENGTH: 12
<212> TYPE: PRT
<213> ORGANISM: Saccharomyces cerevisiae

<400> SEQUENCE: 253

Met Lys Glu Thr Ala Glu Ser Tyr Leu Gly Ala Lys
1               5                   10

<210> SEQ ID NO 254
<211> LENGTH: 15
<212> TYPE: PRT
<213> ORGANISM: Saccharomyces cerevisiae

<400> SEQUENCE: 254

Asn Gln Ala Ala Met Asn Pro Ser Asn Thr Val Phe Asp Ala Lys
1               5                   10                  15

<210> SEQ ID NO 255
<211> LENGTH: 20
<212> TYPE: PRT
<213> ORGANISM: Saccharomyces cerevisiae

<400> SEQUENCE: 255

Asn Thr Ile Ser Glu Ala Gly Asp Lys Leu Glu Gln Ala Asp Lys Asp
1               5                   10                  15

Thr Val Thr Lys
            20

<210> SEQ ID NO 256
<211> LENGTH: 19
<212> TYPE: PRT
<213> ORGANISM: Saccharomyces cerevisiae

<400> SEQUENCE: 256

Asn Pro Val Thr Gly Ala Gln Gly Ile Thr Leu Ser Glu Gly Asn Glu
1               5                   10                  15

Ile Leu Lys

<210> SEQ ID NO 257
<211> LENGTH: 21
<212> TYPE: PRT
<213> ORGANISM: Saccharomyces cerevisiae

<400> SEQUENCE: 257

Tyr Phe Ser Glu Ser Asp Ser Val Leu Val Ala Gln Gly Val Ser Gly
1               5                   10                  15

Ala Val Val Asp Lys
            20

<210> SEQ ID NO 258
<211> LENGTH: 27
<212> TYPE: PRT
<213> ORGANISM: Saccharomyces cerevisiae

<400> SEQUENCE: 258

Gly Gly Leu Thr Tyr Asn Asp Phe Leu Val Leu Pro Gly Leu Val Asp
1               5                   10                  15

Phe Pro Ser Ser Glu Val Ser Leu Gln Thr Lys
            20                  25

<210> SEQ ID NO 259
<211> LENGTH: 16
<212> TYPE: PRT
<213> ORGANISM: Saccharomyces cerevisiae

<400> SEQUENCE: 259

Ser Thr Ala Thr Gly Pro Ser Glu Ala Val Trp Tyr Gly Pro Pro Lys
1               5                   10                  15

<210> SEQ ID NO 260
<211> LENGTH: 15
<212> TYPE: PRT
<213> ORGANISM: Saccharomyces cerevisiae

<400> SEQUENCE: 260

Tyr Gly Gly Val Tyr Val Gly Thr Leu Ser Lys Pro Glu Val Lys
1               5                   10                  15

<210> SEQ ID NO 261
<211> LENGTH: 7
<212> TYPE: PRT
<213> ORGANISM: Saccharomyces cerevisiae

<400> SEQUENCE: 261

Ala Ile Leu Phe Ile Pro Lys
1               5

<210> SEQ ID NO 262
<211> LENGTH: 10
<212> TYPE: PRT
<213> ORGANISM: Saccharomyces cerevisiae

<400> SEQUENCE: 262

Arg Val Asp Glu Gly Gly Ala Gln Asp Lys
1               5                   10

<210> SEQ ID NO 263
<211> LENGTH: 9
<212> TYPE: PRT
<213> ORGANISM: Saccharomyces cerevisiae

<400> SEQUENCE: 263

Lys Asp Glu Asp Asp Lys Lys Pro Lys
1               5

<210> SEQ ID NO 264
<211> LENGTH: 11
<212> TYPE: PRT
<213> ORGANISM: Saccharomyces cerevisiae

<400> SEQUENCE: 264

Ala Asn Phe Glu Ile Asp Leu Pro Asp Ala Lys
1               5                   10

<210> SEQ ID NO 265
<211> LENGTH: 13
<212> TYPE: PRT
<213> ORGANISM: Saccharomyces cerevisiae

<400> SEQUENCE: 265

Ile His Leu Glu Gly Ser Glu Ala Pro Gln Glu Pro Lys
1               5                   10

```
<210> SEQ ID NO 266
<211> LENGTH: 13
<212> TYPE: PRT
<213> ORGANISM: Saccharomyces cerevisiae

<400> SEQUENCE: 266

Glu Glu Leu Glu Glu Leu Val Lys Pro Leu Leu Glu Arg
1               5                   10

<210> SEQ ID NO 267
<211> LENGTH: 16
<212> TYPE: PRT
<213> ORGANISM: Saccharomyces cerevisiae

<400> SEQUENCE: 267

Gly Lys Leu Glu Glu Glu Tyr Ala Pro Phe Ala Ser Asp Ala Glu Lys
1               5                   10                  15

<210> SEQ ID NO 268
<211> LENGTH: 16
<212> TYPE: PRT
<213> ORGANISM: Saccharomyces cerevisiae

<400> SEQUENCE: 268

Ile Ile Gly Leu Asp Tyr His His Pro Asp Phe Glu Gln Glu Ser Lys
1               5                   10                  15

<210> SEQ ID NO 269
<211> LENGTH: 10
<212> TYPE: PRT
<213> ORGANISM: Saccharomyces cerevisiae

<400> SEQUENCE: 269

Val Asp Phe Asn Val Pro Leu Asp Gly Lys
1               5                   10

<210> SEQ ID NO 270
<211> LENGTH: 17
<212> TYPE: PRT
<213> ORGANISM: Saccharomyces cerevisiae

<400> SEQUENCE: 270

Gly Val Asn Leu Pro Gly Thr Asp Val Asp Leu Pro Ala Leu Ser Glu
1               5                   10                  15

Lys

<210> SEQ ID NO 271
<211> LENGTH: 17
<212> TYPE: PRT
<213> ORGANISM: Saccharomyces cerevisiae

<400> SEQUENCE: 271

Gly Asp Leu Gly Ile Glu Ile Pro Ala Pro Glu Val Leu Ala Val Gln
1               5                   10                  15

Lys

<210> SEQ ID NO 272
<211> LENGTH: 17
<212> TYPE: PRT
<213> ORGANISM: Saccharomyces cerevisiae

<400> SEQUENCE: 272

Ser Glu Glu Leu Tyr Pro Gly Arg Pro Leu Ala Ile Ala Leu Asp Thr
1               5                   10                  15
```

Lys

<210> SEQ ID NO 273
<211> LENGTH: 18
<212> TYPE: PRT
<213> ORGANISM: Saccharomyces cerevisiae

<400> SEQUENCE: 273

Lys Ser Glu Glu Leu Tyr Pro Gly Arg Pro Leu Ala Ile Ala Leu Asp
1               5                   10                  15

Thr Lys

<210> SEQ ID NO 274
<211> LENGTH: 14
<212> TYPE: PRT
<213> ORGANISM: Saccharomyces cerevisiae

<400> SEQUENCE: 274

Ser Ile Ile Gly Ala Thr Ser Ile Glu Asp Phe Ile Ser Lys
1               5                   10

<210> SEQ ID NO 275
<211> LENGTH: 15
<212> TYPE: PRT
<213> ORGANISM: Saccharomyces cerevisiae

<400> SEQUENCE: 275

Leu Gly Gly Phe Thr Asp Lys Glu Ile Ser Asp Val Phe Ala Lys
1               5                   10                  15

<210> SEQ ID NO 276
<211> LENGTH: 15
<212> TYPE: PRT
<213> ORGANISM: Saccharomyces cerevisiae

<400> SEQUENCE: 276

Ala Tyr Arg Glu Glu Pro Asp Leu Glu Asn Leu Leu Phe Asn Lys
1               5                   10                  15

<210> SEQ ID NO 277
<211> LENGTH: 18
<212> TYPE: PRT
<213> ORGANISM: Saccharomyces cerevisiae

<400> SEQUENCE: 277

Tyr Gly Pro Ser Leu Met Pro Gly Gly Ser Glu Glu Ala Trp Pro His
1               5                   10                  15

Ile Lys

<210> SEQ ID NO 278
<211> LENGTH: 12
<212> TYPE: PRT
<213> ORGANISM: Saccharomyces cerevisiae

<400> SEQUENCE: 278

Asn Pro Ser Ile Thr Leu Ile Asn Ala Asp Pro Lys
1               5                   10

<210> SEQ ID NO 279
<211> LENGTH: 13
<212> TYPE: PRT
<213> ORGANISM: Saccharomyces cerevisiae

<400> SEQUENCE: 279

Met Leu Val Leu Val Glu Glu Ser Leu Ala Asn Lys Lys
1               5                   10

<210> SEQ ID NO 280
<211> LENGTH: 16
<212> TYPE: PRT
<213> ORGANISM: Saccharomyces cerevisiae

<400> SEQUENCE: 280

Ser His Ser Glu Glu Val Ile Val Pro Glu Phe Asn Ser Ser Ala Lys
1               5                   10                  15

<210> SEQ ID NO 281
<211> LENGTH: 17
<212> TYPE: PRT
<213> ORGANISM: Saccharomyces cerevisiae

<400> SEQUENCE: 281

Val Leu Asn Glu Lys Asn Pro Ser Ile Thr Leu Ile Asn Ala Asp Pro
1               5                   10                  15

Lys

<210> SEQ ID NO 282
<211> LENGTH: 6
<212> TYPE: PRT
<213> ORGANISM: Saccharomyces cerevisiae

<400> SEQUENCE: 282

Leu Glu Val Leu Thr Lys
1               5

<210> SEQ ID NO 283
<211> LENGTH: 10
<212> TYPE: PRT
<213> ORGANISM: Saccharomyces cerevisiae

<400> SEQUENCE: 283

Asp Tyr Ile His Val Val Asp Leu Ala Lys
1               5                   10

<210> SEQ ID NO 284
<211> LENGTH: 13
<212> TYPE: PRT
<213> ORGANISM: Saccharomyces cerevisiae

<400> SEQUENCE: 284

Ala Gly Asp Val Leu Asn Leu Thr Ala Lys Pro Asp Arg
1               5                   10

<210> SEQ ID NO 285
<211> LENGTH: 16
<212> TYPE: PRT
<213> ORGANISM: Saccharomyces cerevisiae

<400> SEQUENCE: 285

Glu Ile Ala Thr Phe Asn Ser Thr Lys Pro Thr Val Leu Gly Pro Lys
1               5                   10                  15

<210> SEQ ID NO 286
<211> LENGTH: 15
<212> TYPE: PRT
<213> ORGANISM: Saccharomyces cerevisiae

```
<400> SEQUENCE: 286

Tyr Ala Ile Glu Asn Ile Leu Asn Asp Leu Tyr Asn Ser Asp Lys
1               5                   10                  15

<210> SEQ ID NO 287
<211> LENGTH: 17
<212> TYPE: PRT
<213> ORGANISM: Saccharomyces cerevisiae

<400> SEQUENCE: 287

Ser Val Asp Val Asp Lys Asn Met Ile Pro Thr Gly Asn Ile Val Asp
1               5                   10                  15

Arg

<210> SEQ ID NO 288
<211> LENGTH: 9
<212> TYPE: PRT
<213> ORGANISM: Saccharomyces cerevisiae

<400> SEQUENCE: 288

Arg Phe Asp Asp Glu Ser Val Gln Lys
1               5

<210> SEQ ID NO 289
<211> LENGTH: 11
<212> TYPE: PRT
<213> ORGANISM: Saccharomyces cerevisiae

<400> SEQUENCE: 289

Glu Asn Thr Leu Leu Gly Glu Phe Asp Leu Lys
1               5                   10

<210> SEQ ID NO 290
<211> LENGTH: 12
<212> TYPE: PRT
<213> ORGANISM: Saccharomyces cerevisiae

<400> SEQUENCE: 290

Glu His Asn Thr Asp Leu Phe Ala Asp Tyr Val Lys
1               5                   10

<210> SEQ ID NO 291
<211> LENGTH: 17
<212> TYPE: PRT
<213> ORGANISM: Saccharomyces cerevisiae

<400> SEQUENCE: 291

Leu Asp Gln Pro Ile Leu Pro Gln Asn Asp Ser Asn Glu Asp Asn Leu
1               5                   10                  15

Lys

<210> SEQ ID NO 292
<211> LENGTH: 21
<212> TYPE: PRT
<213> ORGANISM: Saccharomyces cerevisiae

<400> SEQUENCE: 292

Arg Pro Trp Leu Gly Gln Gln Glu Ala Ala Tyr Lys Pro Thr Ala Pro
1               5                   10                  15

Leu Tyr Asp Pro Lys
            20
```

```
<210> SEQ ID NO 293
<211> LENGTH: 17
<212> TYPE: PRT
<213> ORGANISM: Saccharomyces cerevisiae

<400> SEQUENCE: 293

Tyr Ile Pro Gly Glu Pro Glu Phe Leu Pro Phe Val Asn Glu Leu Pro
1               5                   10                  15

Lys

<210> SEQ ID NO 294
<211> LENGTH: 19
<212> TYPE: PRT
<213> ORGANISM: Saccharomyces cerevisiae

<400> SEQUENCE: 294

Asn Ala Ser Val Glu Ile Val Asp Glu Ile Ile Ser Asp Tyr Lys Asp
1               5                   10                  15

Trp Val Lys

<210> SEQ ID NO 295
<211> LENGTH: 18
<212> TYPE: PRT
<213> ORGANISM: Saccharomyces cerevisiae

<400> SEQUENCE: 295

Ile Glu Gln Phe Val Ile Thr Glu Pro Glu Lys Ser Trp Glu Glu Phe
1               5                   10                  15

Glu Lys

<210> SEQ ID NO 296
<211> LENGTH: 10
<212> TYPE: PRT
<213> ORGANISM: Saccharomyces cerevisiae

<400> SEQUENCE: 296

Ile Asp Asp Ser Gly Val Ser Ile Gly Lys
1               5                   10

<210> SEQ ID NO 297
<211> LENGTH: 15
<212> TYPE: PRT
<213> ORGANISM: Saccharomyces cerevisiae

<400> SEQUENCE: 297

Leu Asp Asp Asp Val Val Lys Glu Tyr Glu Glu Ile Leu Ala Lys
1               5                   10                  15

<210> SEQ ID NO 298
<211> LENGTH: 9
<212> TYPE: PRT
<213> ORGANISM: Saccharomyces cerevisiae

<400> SEQUENCE: 298

Glu Gly His Thr Leu Ala Ser Asp Lys
1               5

<210> SEQ ID NO 299
<211> LENGTH: 8
<212> TYPE: PRT
<213> ORGANISM: Saccharomyces cerevisiae

<400> SEQUENCE: 299
```

Tyr Asp Val Val Ile Asp Gln Lys
1               5

<210> SEQ ID NO 300
<211> LENGTH: 14
<212> TYPE: PRT
<213> ORGANISM: Saccharomyces cerevisiae

<400> SEQUENCE: 300

Thr Ala Glu Asp Gln Lys Asp Ser Ile Val Ser Leu Ile Lys
1               5                   10

<210> SEQ ID NO 301
<211> LENGTH: 16
<212> TYPE: PRT
<213> ORGANISM: Saccharomyces cerevisiae

<400> SEQUENCE: 301

Thr Gly Glu Val Ile Ile Asn Pro Leu Lys Glu Asp Gly Ser Pro Lys
1               5                   10                  15

<210> SEQ ID NO 302
<211> LENGTH: 20
<212> TYPE: PRT
<213> ORGANISM: Saccharomyces cerevisiae

<400> SEQUENCE: 302

Thr Ala Gln Leu Ser Leu Gln Asp Tyr Leu Asn Gln Gln Ala Asn Asn
1               5                   10                  15

Gln Phe Asn Lys
            20

<210> SEQ ID NO 303
<211> LENGTH: 24
<212> TYPE: PRT
<213> ORGANISM: Saccharomyces cerevisiae

<400> SEQUENCE: 303

Glu Ala Gln Ala Asp Ala Ala Glu Ile Ala Glu Asp Ala Ala Glu
1               5                   10                  15

Ala Glu Asp Ala Gly Lys Pro Lys
            20

<210> SEQ ID NO 304
<211> LENGTH: 12
<212> TYPE: PRT
<213> ORGANISM: Saccharomyces cerevisiae

<400> SEQUENCE: 304

Gly Ile Ser Asn Glu Gly Gln Asn Ala Ser Ile Lys
1               5                   10

<210> SEQ ID NO 305
<211> LENGTH: 14
<212> TYPE: PRT
<213> ORGANISM: Saccharomyces cerevisiae

<400> SEQUENCE: 305

Ser Ile Ser Gly Pro Val Ile Thr Asp Val Ala Ser Leu Lys
1               5                   10

<210> SEQ ID NO 306
<211> LENGTH: 7
<212> TYPE: PRT

<213> ORGANISM: Saccharomyces cerevisiae

<400> SEQUENCE: 306

Thr Gln Leu Arg Leu Lys Arg
1               5

<210> SEQ ID NO 307
<211> LENGTH: 13
<212> TYPE: PRT
<213> ORGANISM: Saccharomyces cerevisiae

<400> SEQUENCE: 307

Ala Tyr Glu Glu Leu Ser Asn Thr Asp Leu Glu Phe Lys
1               5                   10

<210> SEQ ID NO 308
<211> LENGTH: 24
<212> TYPE: PRT
<213> ORGANISM: Saccharomyces cerevisiae

<400> SEQUENCE: 308

Ala Tyr Glu Glu Leu Ser Asn Thr Asp Leu Glu Phe Lys Phe Pro Glu
1               5                   10                  15

Pro Gly Tyr Leu Glu Gly Val Lys
            20

<210> SEQ ID NO 309
<211> LENGTH: 17
<212> TYPE: PRT
<213> ORGANISM: Saccharomyces cerevisiae

<400> SEQUENCE: 309

Ala Val Ala Pro Ile Asp Thr Asp Val Leu Leu Gly Gln Tyr Gly
1               5                   10                  15

Lys

<210> SEQ ID NO 310
<211> LENGTH: 20
<212> TYPE: PRT
<213> ORGANISM: Saccharomyces cerevisiae

<400> SEQUENCE: 310

Ser Glu Asp Gly Ser Lys Pro Ala Tyr Val Asp Asp Thr Val Asp
1               5                   10                  15

Lys Asp Ser Lys
            20

<210> SEQ ID NO 311
<211> LENGTH: 12
<212> TYPE: PRT
<213> ORGANISM: Saccharomyces cerevisiae

<400> SEQUENCE: 311

Gly Asn Tyr Thr Asp Phe Glu Asn Thr Phe Gln Lys
1               5                   10

<210> SEQ ID NO 312
<211> LENGTH: 10
<212> TYPE: PRT
<213> ORGANISM: Saccharomyces cerevisiae

<400> SEQUENCE: 312

Leu Asp Ala Asp Ala Ala Glu Ile Glu Lys

```
1               5                   10
```

<210> SEQ ID NO 313
<211> LENGTH: 26
<212> TYPE: PRT
<213> ORGANISM: Saccharomyces cerevisiae

<400> SEQUENCE: 313

```
Ala Thr Thr Ile Asp Glu Gln Val Gly Leu Ile Val Asp Ser Leu Asn
1               5                   10                  15

Asp Glu Glu Leu Val Ser Thr Ala Asp Lys
            20                  25
```

<210> SEQ ID NO 314
<211> LENGTH: 13
<212> TYPE: PRT
<213> ORGANISM: Saccharomyces cerevisiae

<400> SEQUENCE: 314

```
Leu Ser Gly Asn His Thr Phe Asp Thr Thr Gln Ser Lys
1               5                   10
```

<210> SEQ ID NO 315
<211> LENGTH: 21
<212> TYPE: PRT
<213> ORGANISM: Saccharomyces cerevisiae

<400> SEQUENCE: 315

```
Thr Lys Tyr Asp Val Ala Val Asp Glu Gln Ser Pro Arg Pro Gly Gln
1               5                   10                  15

Gln Ala Phe Glu Lys
            20
```

<210> SEQ ID NO 316
<211> LENGTH: 27
<212> TYPE: PRT
<213> ORGANISM: Saccharomyces cerevisiae

<400> SEQUENCE: 316

```
Ala Leu Leu Glu Leu Leu Asp Asp Ser Pro Val Thr Pro Gly Glu Thr
1               5                   10                  15

Arg Pro Ala Tyr Asp Gly Tyr Glu Ala Ser Lys
            20                  25
```

<210> SEQ ID NO 317
<211> LENGTH: 17
<212> TYPE: PRT
<213> ORGANISM: Saccharomyces cerevisiae

<400> SEQUENCE: 317

```
Leu Glu Ile Thr Lys Glu Glu Thr Leu Asn Pro Ile Ile Gln Asp Thr
1               5                   10                  15

Lys
```

<210> SEQ ID NO 318
<211> LENGTH: 18
<212> TYPE: PRT
<213> ORGANISM: Saccharomyces cerevisiae

<400> SEQUENCE: 318

```
Gly Gln Val Val Ser Glu Glu Gln Arg Pro Gly Thr Pro Leu Phe Thr
1               5                   10                  15
```

Val Lys

<210> SEQ ID NO 319
<211> LENGTH: 14
<212> TYPE: PRT
<213> ORGANISM: Saccharomyces cerevisiae

<400> SEQUENCE: 319

Ser Asp Asp Ser Asn Ser Lys Pro Asn Val Asp Glu Tyr Lys
1               5                   10

<210> SEQ ID NO 320
<211> LENGTH: 15
<212> TYPE: PRT
<213> ORGANISM: Saccharomyces cerevisiae

<400> SEQUENCE: 320

Gln Phe Met Tyr Phe Asp Ser Leu Glu Ser Leu Pro Asp Pro Lys
1               5                   10                  15

<210> SEQ ID NO 321
<211> LENGTH: 15
<212> TYPE: PRT
<213> ORGANISM: Saccharomyces cerevisiae

<400> SEQUENCE: 321

Glu Lys Val Glu Glu Gln Glu Gln Gln Gln Gln Gln Ile Ile Lys
1               5                   10                  15

<210> SEQ ID NO 322
<211> LENGTH: 16
<212> TYPE: PRT
<213> ORGANISM: Saccharomyces cerevisiae

<400> SEQUENCE: 322

Asp Ile Phe Ser Asn Asp Glu Leu Leu Ser Asp Ala Tyr Asp Ala Lys
1               5                   10                  15

<210> SEQ ID NO 323
<211> LENGTH: 11
<212> TYPE: PRT
<213> ORGANISM: Saccharomyces cerevisiae

<400> SEQUENCE: 323

Phe Phe Leu Pro Leu Glu Gln Val Glu Phe Lys
1               5                   10

<210> SEQ ID NO 324
<211> LENGTH: 14
<212> TYPE: PRT
<213> ORGANISM: Saccharomyces cerevisiae

<400> SEQUENCE: 324

Lys Ala Gly Tyr Gln Asp Asp Pro Gln Tyr Ala Asp Phe Lys
1               5                   10

<210> SEQ ID NO 325
<211> LENGTH: 19
<212> TYPE: PRT
<213> ORGANISM: Saccharomyces cerevisiae

<400> SEQUENCE: 325

Asp Ala Asn Thr Gly Glu Glu Val Thr Glu Asp Phe Val Asn Asp Ile
1               5                   10                  15

Asn Val Lys

<210> SEQ ID NO 326
<211> LENGTH: 11
<212> TYPE: PRT
<213> ORGANISM: Saccharomyces cerevisiae

<400> SEQUENCE: 326

Glu Leu Met Gln Gln Ile Glu Asn Phe Glu Lys
1               5                   10

<210> SEQ ID NO 327
<211> LENGTH: 18
<212> TYPE: PRT
<213> ORGANISM: Saccharomyces cerevisiae

<400> SEQUENCE: 327

Gly Phe Asp Ile Pro Asn Ile Glu Asn His Asp Val Val Pro Met Leu
1               5                   10                  15

Gln Lys

<210> SEQ ID NO 328
<211> LENGTH: 15
<212> TYPE: PRT
<213> ORGANISM: Saccharomyces cerevisiae

<400> SEQUENCE: 328

Thr Lys Gly Glu Ala Gly Thr Gly Asp Val Ser Glu Ala Val Lys
1               5                   10                  15

<210> SEQ ID NO 329
<211> LENGTH: 15
<212> TYPE: PRT
<213> ORGANISM: Saccharomyces cerevisiae

<400> SEQUENCE: 329

Lys Asn Gln Gln Leu Glu Glu Asp Leu Glu Glu Ser Asp Thr Lys
1               5                   10                  15

<210> SEQ ID NO 330
<211> LENGTH: 13
<212> TYPE: PRT
<213> ORGANISM: Saccharomyces cerevisiae

<400> SEQUENCE: 330

Glu Phe Glu Tyr Lys Asp Gln Asp Gln Ser Ser Pro Lys
1               5                   10

<210> SEQ ID NO 331
<211> LENGTH: 19
<212> TYPE: PRT
<213> ORGANISM: Saccharomyces cerevisiae

<400> SEQUENCE: 331

Asp Asp Gln Gly Lys Asp Gln Glu Thr Asp Phe Val Leu Asn Val Glu
1               5                   10                  15

Pro Trp Arg

<210> SEQ ID NO 332
<211> LENGTH: 21
<212> TYPE: PRT
<213> ORGANISM: Saccharomyces cerevisiae

<400> SEQUENCE: 332

```
Gly Gln Asp Phe Ala Pro Ala Phe Asp Val Ala Pro Asp Trp Glu Ser
1               5                   10                  15

Tyr Glu Tyr Thr Lys
            20

<210> SEQ ID NO 333
<211> LENGTH: 18
<212> TYPE: PRT
<213> ORGANISM: Saccharomyces cerevisiae

<400> SEQUENCE: 333

Ser Ser Pro Asp Glu Asn Ser Thr Leu Leu Ser Asn Asp Ser Ile Ser
1               5                   10                  15

Leu Lys

<210> SEQ ID NO 334
<211> LENGTH: 23
<212> TYPE: PRT
<213> ORGANISM: Saccharomyces cerevisiae

<400> SEQUENCE: 334

Ala Ala Glu Glu Asn Phe Asn Ala Asp Asp Lys Thr Ile Ser Asp Thr
1               5                   10                  15

Ala Ala Val Val Gly Val Lys
            20

<210> SEQ ID NO 335
<211> LENGTH: 20
<212> TYPE: PRT
<213> ORGANISM: Saccharomyces cerevisiae

<400> SEQUENCE: 335

Ser Phe Leu Ser Pro Leu Glu Thr Asp Glu Glu Ile Glu Val Val Ile
1               5                   10                  15

Glu Gln Gly Lys
            20

<210> SEQ ID NO 336
<211> LENGTH: 28
<212> TYPE: PRT
<213> ORGANISM: Saccharomyces cerevisiae

<400> SEQUENCE: 336

Glu Val Phe Val Ser Asp Gly Glu Asn Val Asp Ser Ser Asp Leu Leu
1               5                   10                  15

Val Leu Leu Glu Asp Gln Val Pro Val Glu Thr Lys
            20                  25

<210> SEQ ID NO 337
<211> LENGTH: 9
<212> TYPE: PRT
<213> ORGANISM: Saccharomyces cerevisiae

<400> SEQUENCE: 337

Thr Gly Thr Glu Gly Ile Pro Met Lys
1               5

<210> SEQ ID NO 338
<211> LENGTH: 14
<212> TYPE: PRT
<213> ORGANISM: Saccharomyces cerevisiae
```

```
<400> SEQUENCE: 338

Asn Ala Pro Ser Gly Thr Leu Val Gly Asp Lys Glu Asp Arg
1               5                   10

<210> SEQ ID NO 339
<211> LENGTH: 23
<212> TYPE: PRT
<213> ORGANISM: Saccharomyces cerevisiae

<400> SEQUENCE: 339

Asp Phe Asp Tyr Ser Val Thr Pro Glu Glu Gly Ala Leu Val Pro Glu
1               5                   10                  15

Lys Asp Asp Thr Phe Leu Lys
            20

<210> SEQ ID NO 340
<211> LENGTH: 12
<212> TYPE: PRT
<213> ORGANISM: Saccharomyces cerevisiae

<400> SEQUENCE: 340

Thr Phe Ile Ala Val Lys Pro Asp Gly Val Gln Arg
1               5                   10

<210> SEQ ID NO 341
<211> LENGTH: 14
<212> TYPE: PRT
<213> ORGANISM: Saccharomyces cerevisiae

<400> SEQUENCE: 341

Glu Ile Gly Asp Phe Glu Asp Leu Ser Thr Glu Asn Glu Lys
1               5                   10

<210> SEQ ID NO 342
<211> LENGTH: 17
<212> TYPE: PRT
<213> ORGANISM: Saccharomyces cerevisiae

<400> SEQUENCE: 342

Asn Leu Ala Gly Val Asp Tyr Leu Thr Ile Ser Pro Ala Leu Leu Asp
1               5                   10                  15

Lys

<210> SEQ ID NO 343
<211> LENGTH: 12
<212> TYPE: PRT
<213> ORGANISM: Saccharomyces cerevisiae

<400> SEQUENCE: 343

Asp Ile Leu Ser Val Asp Tyr Thr Asp Ile Met Lys
1               5                   10

<210> SEQ ID NO 344
<211> LENGTH: 15
<212> TYPE: PRT
<213> ORGANISM: Saccharomyces cerevisiae

<400> SEQUENCE: 344

Glu Val His Thr Asn Gln Asp Pro Leu Asp Val Ser Ala Ser Lys
1               5                   10                  15

<210> SEQ ID NO 345
<211> LENGTH: 17
```

```
<212> TYPE: PRT
<213> ORGANISM: Saccharomyces cerevisiae

<400> SEQUENCE: 345

Lys Pro Glu Asn Ala Glu Thr Pro Ser Gln Thr Ser Gln Glu Ala Thr
1               5                   10                  15
Gln

<210> SEQ ID NO 346
<211> LENGTH: 17
<212> TYPE: PRT
<213> ORGANISM: Saccharomyces cerevisiae

<400> SEQUENCE: 346

Asn Ala Pro Ala Ile Ile Phe Ile Asp Glu Ile Asp Ser Ile Ala Pro
1               5                   10                  15
Lys

<210> SEQ ID NO 347
<211> LENGTH: 19
<212> TYPE: PRT
<213> ORGANISM: Saccharomyces cerevisiae

<400> SEQUENCE: 347

Glu Phe Glu Glu Gly Gly Gly Leu Pro Glu Gln Pro Leu Asn Pro Asp
1               5                   10                  15
Phe Ser Lys

<210> SEQ ID NO 348
<211> LENGTH: 18
<212> TYPE: PRT
<213> ORGANISM: Saccharomyces cerevisiae

<400> SEQUENCE: 348

Ala Pro Thr Ala Ala Glu Leu Gln Ala Pro Pro Pro Pro Ser Ser
1               5                   10                  15
Thr Lys

<210> SEQ ID NO 349
<211> LENGTH: 17
<212> TYPE: PRT
<213> ORGANISM: Saccharomyces cerevisiae

<400> SEQUENCE: 349

Gly Glu Ile Glu Glu Ala Ile Glu Asn Val Leu Pro Asn Val Glu Gly
1               5                   10                  15
Lys

<210> SEQ ID NO 350
<211> LENGTH: 9
<212> TYPE: PRT
<213> ORGANISM: Saccharomyces cerevisiae

<400> SEQUENCE: 350

Glu Ser Phe Leu Leu Glu Ser Ala Lys
1               5

<210> SEQ ID NO 351
<211> LENGTH: 7
<212> TYPE: PRT
<213> ORGANISM: Saccharomyces cerevisiae
```

```
<400> SEQUENCE: 351

Asn Gln Trp Phe Phe Ser Lys
1               5

<210> SEQ ID NO 352
<211> LENGTH: 9
<212> TYPE: PRT
<213> ORGANISM: Saccharomyces cerevisiae

<400> SEQUENCE: 352

Tyr Thr Leu Asp Val Glu Ala Phe Lys
1               5

<210> SEQ ID NO 353
<211> LENGTH: 14
<212> TYPE: PRT
<213> ORGANISM: Saccharomyces cerevisiae

<400> SEQUENCE: 353

Thr Met Tyr Ala Ala Asp Gly Asp Tyr Leu Glu Thr Tyr Lys
1               5                   10

<210> SEQ ID NO 354
<211> LENGTH: 15
<212> TYPE: PRT
<213> ORGANISM: Saccharomyces cerevisiae

<400> SEQUENCE: 354

Phe Leu Gln Asn Pro Leu Glu Ile Phe Val Asp Asp Glu Ala Lys
1               5                   10                  15

<210> SEQ ID NO 355
<211> LENGTH: 18
<212> TYPE: DNA
<213> ORGANISM: Saccharomyces cerevisiae

<400> SEQUENCE: 355
ggggtaatta atcatttt                                                18

<210> SEQ ID NO 356
<211> LENGTH: 18
<212> TYPE: DNA
<213> ORGANISM: Saccharomyces cerevisiae

<400> SEQUENCE: 356
ttatacatta atcagcga                                                18

<210> SEQ ID NO 357
<211> LENGTH: 18
<212> TYPE: DNA
<213> ORGANISM: Saccharomyces cerevisiae

<400> SEQUENCE: 357
ggggtaatta atgtaaat                                                18

<210> SEQ ID NO 358
<211> LENGTH: 18
<212> TYPE: DNA
<213> ORGANISM: Saccharomyces cerevisiae

<400> SEQUENCE: 358
aaattaatca gcggtgac                                                18
```

-continued

```
<210> SEQ ID NO 359
<211> LENGTH: 18
<212> TYPE: DNA
<213> ORGANISM: Saccharomyces cerevisiae

<400> SEQUENCE: 359
ggggtaatta aaatttct                                                      18

<210> SEQ ID NO 360
<211> LENGTH: 13
<212> TYPE: PRT
<213> ORGANISM: Saccharomyces cerevisiae
<220> FEATURE:
<221> NAME/KEY: MISC_FEATURE
<222> LOCATION: (1)..(1)
<223> OTHER INFORMATION: TRYPSIN CUT SITE
<220> FEATURE:
<221> NAME/KEY: MISC_FEATURE
<222> LOCATION: (8)..(8)
<223> OTHER INFORMATION: contains a post-translational modification
<220> FEATURE:
<221> NAME/KEY: MISC_FEATURE
<222> LOCATION: (13)..(13)
<223> OTHER INFORMATION: TRYPSIN CUT SITE

<400> SEQUENCE: 360

Arg Glu Ile Ala Gln Asp Phe Lys Thr Asp Leu Arg Phe
1               5                   10

<210> SEQ ID NO 361
<211> LENGTH: 12
<212> TYPE: PRT
<213> ORGANISM: Saccharomyces cerevisiae
<220> FEATURE:
<221> NAME/KEY: MISC_FEATURE
<222> LOCATION: (1)..(1)
<223> OTHER INFORMATION: trypsin cut site
<220> FEATURE:
<221> NAME/KEY: MISC_FEATURE
<222> LOCATION: (4)..(4)
<223> OTHER INFORMATION: contains a post-translational modification
<220> FEATURE:
<221> NAME/KEY: MISC_FEATURE
<222> LOCATION: (12)..(12)
<223> OTHER INFORMATION: trypsin cut site

<400> SEQUENCE: 361

Arg Phe Gln Lys Ser Thr Glu Leu Leu Ile Arg Lys
1               5                   10

<210> SEQ ID NO 362
<211> LENGTH: 11
<212> TYPE: PRT
<213> ORGANISM: Saccharomyces cerevisiae
<220> FEATURE:
<221> NAME/KEY: MISC_FEATURE
<222> LOCATION: (1)..(1)
<223> OTHER INFORMATION: trypsin cut site
<220> FEATURE:
<221> NAME/KEY: MISC_FEATURE
<222> LOCATION: (7)..(7)
<223> OTHER INFORMATION: contains a post-translational modification
<220> FEATURE:
<221> NAME/KEY: MISC_FEATURE
<222> LOCATION: (11)..(11)
<223> OTHER INFORMATION: trypsin cut site

<400> SEQUENCE: 362

Arg Lys Gln Leu Ala Ser Lys Ala Ala Arg Lys
1               5                   10
```

```
<210> SEQ ID NO 363
<211> LENGTH: 11
<212> TYPE: PRT
<213> ORGANISM: Saccharomyces cerevisiae
<220> FEATURE:
<221> NAME/KEY: MISC_FEATURE
<222> LOCATION: (1)..(1)
<223> OTHER INFORMATION: trypsin cut site
<220> FEATURE:
<221> NAME/KEY: MISC_FEATURE
<222> LOCATION: (2)..(2)
<223> OTHER INFORMATION: contains a post-translational modification
<220> FEATURE:
<221> NAME/KEY: MISC_FEATURE
<222> LOCATION: (7)..(7)
<223> OTHER INFORMATION: contains a post-translational modification
<220> FEATURE:
<221> NAME/KEY: MISC_FEATURE
<222> LOCATION: (11)..(11)
<223> OTHER INFORMATION: trypsin cut site

<400> SEQUENCE: 363

Arg Lys Gln Leu Ala Ser Lys Ala Ala Arg Lys
1               5                   10

<210> SEQ ID NO 364
<211> LENGTH: 11
<212> TYPE: PRT
<213> ORGANISM: Saccharomyces cerevisiae
<220> FEATURE:
<221> NAME/KEY: MISC_FEATURE
<222> LOCATION: (1)..(1)
<223> OTHER INFORMATION: trypsin cut site
<220> FEATURE:
<221> NAME/KEY: MISC_FEATURE
<222> LOCATION: (7)..(7)
<223> OTHER INFORMATION: contains a post-translational modification
<220> FEATURE:
<221> NAME/KEY: MISC_FEATURE
<222> LOCATION: (11)..(11)
<223> OTHER INFORMATION: trypsin cut site

<400> SEQUENCE: 364

Arg Lys Ser Thr Gly Gly Lys Ala Pro Arg Lys
1               5                   10

<210> SEQ ID NO 365
<211> LENGTH: 11
<212> TYPE: PRT
<213> ORGANISM: Saccharomyces cerevisiae
<220> FEATURE:
<221> NAME/KEY: MISC_FEATURE
<222> LOCATION: (1)..(1)
<223> OTHER INFORMATION: trypsin cut site
<220> FEATURE:
<221> NAME/KEY: MISC_FEATURE
<222> LOCATION: (2)..(2)
<223> OTHER INFORMATION: contains a post-translational modification
<220> FEATURE:
<221> NAME/KEY: MISC_FEATURE
<222> LOCATION: (7)..(7)
<223> OTHER INFORMATION: contains a post-translational modification
<220> FEATURE:
<221> NAME/KEY: MISC_FEATURE
<222> LOCATION: (11)..(11)
<223> OTHER INFORMATION: trypsin cut site

<400> SEQUENCE: 365

Arg Lys Ser Thr Gly Gly Lys Ala Pro Arg Lys
1               5                   10
```

```
<210> SEQ ID NO 366
<211> LENGTH: 15
<212> TYPE: PRT
<213> ORGANISM: Saccharomyces cerevisiae
<220> FEATURE:
<221> NAME/KEY: MISC_FEATURE
<222> LOCATION: (1)..(1)
<223> OTHER INFORMATION: trypsin cut site
<220> FEATURE:
<221> NAME/KEY: MISC_FEATURE
<222> LOCATION: (4)..(4)
<223> OTHER INFORMATION: contains a post-translational modification
<220> FEATURE:
<221> NAME/KEY: MISC_FEATURE
<222> LOCATION: (9)..(9)
<223> OTHER INFORMATION: contains a post-translational modification
<220> FEATURE:
<221> NAME/KEY: MISC_FEATURE
<222> LOCATION: (15)..(15)
<223> OTHER INFORMATION: trypsin cut site

<400> SEQUENCE: 366

Lys Ala Glu Lys Lys Pro Ala Ser Lys Ala Pro Ala Glu Lys Lys
1               5                   10                  15

<210> SEQ ID NO 367
<211> LENGTH: 17
<212> TYPE: PRT
<213> ORGANISM: Saccharomyces cerevisiae
<220> FEATURE:
<221> NAME/KEY: MISC_FEATURE
<222> LOCATION: (1)..(1)
<223> OTHER INFORMATION: trypsin cut site
<220> FEATURE:
<221> NAME/KEY: MISC_FEATURE
<222> LOCATION: (6)..(6)
<223> OTHER INFORMATION: contains a post-translational modification
<220> FEATURE:
<221> NAME/KEY: MISC_FEATURE
<222> LOCATION: (12)..(12)
<223> OTHER INFORMATION: contains a post-translational modification
<220> FEATURE:
<221> NAME/KEY: MISC_FEATURE
<222> LOCATION: (16)..(16)
<223> OTHER INFORMATION: trypsin cut site

<400> SEQUENCE: 367

Lys Lys Pro Ala Ser Lys Ala Pro Ala Glu Lys Lys Pro Ala Ala Lys
1               5                   10                  15

Lys

<210> SEQ ID NO 368
<211> LENGTH: 12
<212> TYPE: PRT
<213> ORGANISM: Saccharomyces cerevisiae
<220> FEATURE:
<221> NAME/KEY: MISC_FEATURE
<222> LOCATION: (1)..(1)
<223> OTHER INFORMATION: trypsin cut site
<220> FEATURE:
<221> NAME/KEY: MISC_FEATURE
<222> LOCATION: (7)..(7)
<223> OTHER INFORMATION: contains a post-translational modification
<220> FEATURE:
<221> NAME/KEY: MISC_FEATURE
<222> LOCATION: (12)..(12)
<223> OTHER INFORMATION: trypsin cut site

<400> SEQUENCE: 368

Lys Ala Pro Ala Glu Lys Lys Pro Ala Ala Lys Lys
1               5                   10
```

```
<210> SEQ ID NO 369
<211> LENGTH: 11
<212> TYPE: PRT
<213> ORGANISM: Saccharomyces cerevisiae
<220> FEATURE:
<221> NAME/KEY: MISC_FEATURE
<222> LOCATION: (1)..(1)
<223> OTHER INFORMATION: trypsin cut site
<220> FEATURE:
<221> NAME/KEY: MISC_FEATURE
<222> LOCATION: (4)..(4)
<223> OTHER INFORMATION: contains a post-translational modification
<220> FEATURE:
<221> NAME/KEY: MISC_FEATURE
<222> LOCATION: (11)..(11)
<223> OTHER INFORMATION: trypsin cut site

<400> SEQUENCE: 369

Lys Gly Gly Lys Ala Gly Ser Ala Ala Lys Ala
1               5                   10

<210> SEQ ID NO 370
<211> LENGTH: 10
<212> TYPE: PRT
<213> ORGANISM: Saccharomyces cerevisiae
<220> FEATURE:
<221> NAME/KEY: MISC_FEATURE
<222> LOCATION: (1)..(1)
<223> OTHER INFORMATION: trypsin cut site
<220> FEATURE:
<221> NAME/KEY: MISC_FEATURE
<222> LOCATION: (6)..(6)
<223> OTHER INFORMATION: contains a post-translational modification
<220> FEATURE:
<221> NAME/KEY: MISC_FEATURE
<222> LOCATION: (10)..(10)
<223> OTHER INFORMATION: trypsin cut site

<400> SEQUENCE: 370

Lys Ser Thr Gly Gly Lys Ala Pro Arg Lys
1               5                   10

<210> SEQ ID NO 371
<211> LENGTH: 9
<212> TYPE: PRT
<213> ORGANISM: Saccharomyces cerevisiae
<220> FEATURE:
<221> NAME/KEY: MISC_FEATURE
<222> LOCATION: (1)..(1)
<223> OTHER INFORMATION: trypsin cut site
<220> FEATURE:
<221> NAME/KEY: MISC_FEATURE
<222> LOCATION: (9)..(9)
<223> OTHER INFORMATION: trypsin cut site

<400> SEQUENCE: 371

Lys Ser Thr Glu Leu Leu Ile Arg Lys
1               5
```

METHODS AND KITS FOR ISOLATION AND ANALYSIS OF A CHROMATIN REGION

CROSS REFERENCE TO RELATED APPLICATIONS

This application is a US non-provisional that claims priority to U.S. provisional application 61/726,936 filed Nov. 15, 2012 and U.S. provisional application 61/875,969 filed Sep. 10, 2013, each of which is hereby incorporated by reference in its entirety.

GOVERNMENTAL RIGHTS

This invention was made with government support under R01DA025755, F32GM093614, P20RR015569, P20RR016460, U54RR020839, and UL1 TR000039 awarded by the National Institutes of Health. The government has certain rights in the invention.

FIELD OF THE INVENTION

The invention describes methods of identifying proteins and post-translational modification of proteins specifically associated with a chromatin region.

REFERENCE TO SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821(f).

BACKGROUND OF THE INVENTION

It has long been appreciated that chromatin-associated proteins and epigenetic factors play central roles in gene regulation. Mis-regulation of chromatin structure and post-translational modification of histones (PTMs) is linked to cancer and other epigenetic diseases. The field of epigenomics has been transformed by chromatin immunoprecipitation approaches that provide for the localization of a defined protein or post-translationally modified protein to specific chromosomal sites. However, the hierarchy of chromatin-templated events orchestrating the formation and inheritance of different epigenetic states remains poorly understood at a molecular level; there are no current methodologies that allow for determination of all proteins present at a defined, small region of chromatin. Chromatin immunoprecipitation (ChIP) assay shave allowed better understand genome-wide distribution of proteins and histone modifications within a genome at the nucleosome level. However, ChIP assays are largely confined to examining singular histone PTMs or proteins rather than simultaneous profiling of multiple targets, the inability to determine the co-occupancy of particular histone PTMs, and that ChIP is reliant on the previous identification of the molecular target. Other chromatin immunoprecipitation methodologies do not provide a mechanism for determining the specificity of protein interactions, or do not enrich for a small integrated genomic locus and cannot detect protein contamination in purified material. Therefore, there is a need for methods that allow for determination of all proteins and protein posttranslational modifications specifically associated at a defined, small region of chromatin.

Reference To Color Figures

The application file contains at least one photograph executed in color. Copies of this patent application publication with color photographs will be provided by the Office upon request and payment of the necessary fee.

DETAILED DESCRIPTION OF THE INVENTION

Figure 1A:
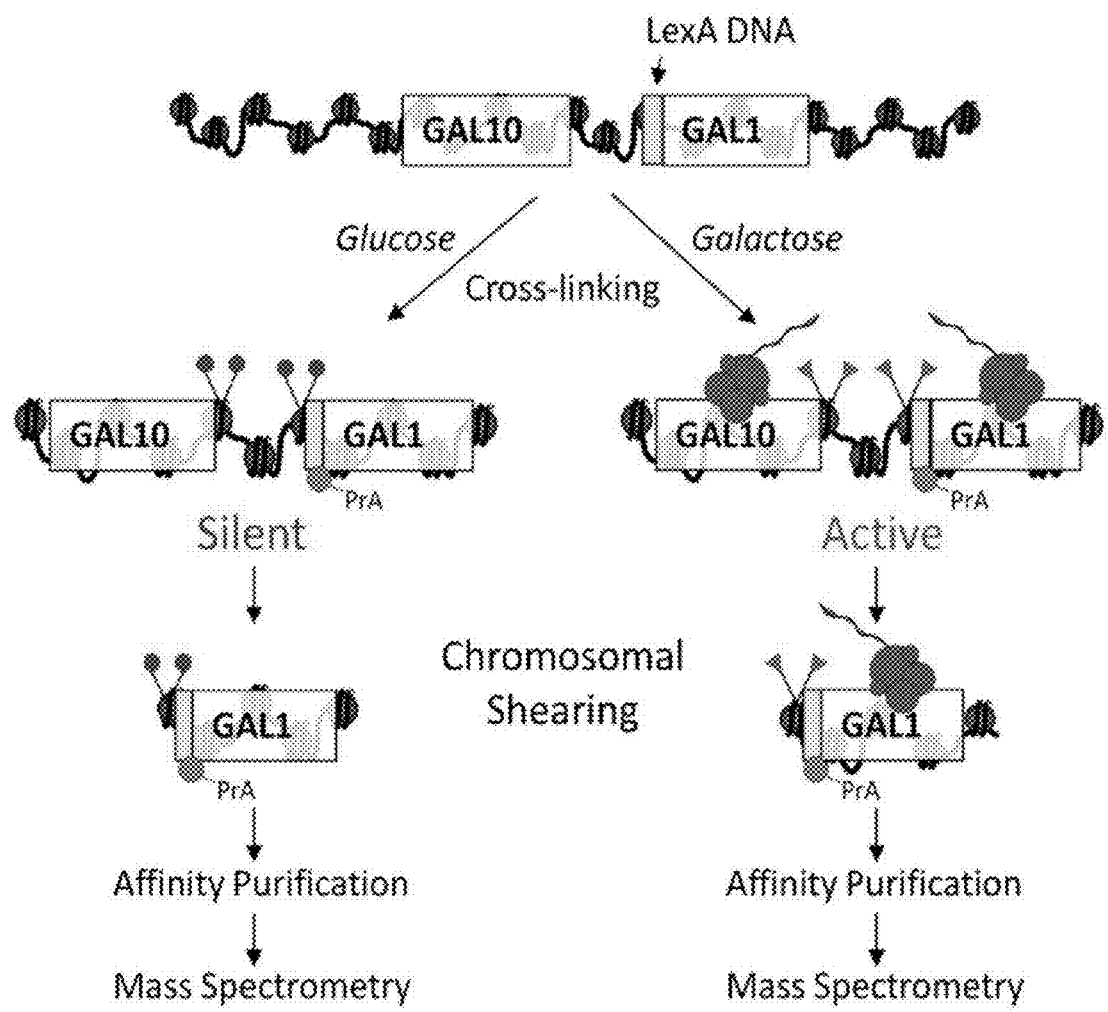
FIG. 1 graphically depicts the chromatin affinity purification with mass spectrometry method. (A) The chromatin affinity purification with mass spectrometry (ChAP-MS) approach provides for the specific enrichment of a given chromosome section and identification of specifically associated proteins and post-translational modifications. A LexA DNA affinity handle was engineered just upstream of the GAL1 start codon in S. cerevisiae. Strains containing the LexA DNA binding site and a plasmid expressing LexA-PrA protein affinity handle were cultured in glucose or galactose to provide transcriptional repression or activation, respectively, and subjected to in vivo chemical crosslinking to trap protein interactions. Following shearing of the chromatin to ~1,000 bp, LexA-PrA was affinity purified on IgG-coated Dynabeads and coenriched proteins/post-translational modifications were identified by high-resolution mass spectrometry. (B) To control for nonspecifically enriched proteins, a strain lacking the LexA DNA binding site, but containing the LexA-PrA plasmid, was cultured isotopically heavy ($^{13}C_6^{15}N_2$-lysine) in glucose or galactose and mixed equally with the corresponding isotopically light culture containing the LexA DNA binding site prior to cell lysis. Following affinity purification (AP) and mass spectrometric analysis, nonspecifically enriched proteins were identified as a 1:1 ratio of light to heavy lysine-containing peptides, while proteins specifically enriched with the chromosome section were identified with a higher level of isotopically light lysine-containing peptides.

A method of isolating and identifying proteins associated with a target region of chromatin in a cell has been discovered. The method may also be used to identify post-translational modifications (PTMs) of proteins associated with a target chromatin in a cell. Advantageously, the method may be used to determine whether the association of the identified proteins with a chromatin in a cell is specific or non-specific. As used herein, "specifically associated" or "specific association" of a protein with a target chromatin refers to any protein in a cell that normally associates with a chromatin in a cell. In addition, and as illustrated in the examples, the method may be used to determine the role of proteins and post-translational modifications (PTMs) of proteins in chromatin function, including regulatory mechanisms of transcription, and the role of epigenomic factors in controlling chromatin function.

I. Method of ChAP-MS

In some aspects, the invention provides methods of isolating and identifying proteins specifically associated with a target chromatin. As described in Example 1 and FIG. 1, a method of the invention comprises isolating a target chromatin from a cell. As used herein, a "target chromatin" refers to a specific chromatin or a chromatin fragment that may be used in an application of the invention. According to the method, isolating the target chromatin isolates nucleic acid sequences and proteins, including proteins comprising posttranslational modifications, associated with the target chromatin. The proteins and posttranslational modifications of proteins associated with the target chromatin may then be identified, and a determination of which of the identified proteins and post-translational modifications of proteins associated with a target chromatin isolated from a cell are specifically or non-specifically associated with the target chromatin is made.

To determine which of the identified proteins and post-translational modifications of proteins associated with a target chromatin isolated from a cell are specifically or non-specifically associated with the target chromatin, a method of the invention provides two cell samples, or lysates derived from two cell samples, comprising the target chromatin, wherein proteins in one cell sample, but not both of the cell samples are metabolically labeled. Typically, the two cell samples are grown identically. In addition, the target chromatin in one of the cell samples or an extract from one of the cell samples is tagged. The two cell samples, or lysates derived from the cell samples of the invention are combined. The tagged target chromatin is isolated in the presence of the other cell sample or an extract from the other cell sample. Therefore, if a target chromatin of the invention is tagged in the unlabeled cell sample, proteins specifically associated with the tagged chromatin are unlabeled, and will be isolated in the presence of labeled proteins from the labeled cell sample. Alternatively, if a target chromatin of the invention is tagged in the labeled cell sample, the proteins associated with the tagged chromatin are labeled, and will be isolated in the presence of unlabeled proteins from the unlabeled cell sample.

As such, determining if a certain identified protein associated with the target chromatin is labeled, unlabeled, or a combination of labeled and unlabeled may determine if the protein was specifically associated with a target chromatin of the invention. If an identified protein comprises a mixture of labeled and unlabeled proteins, then that protein became associated with a target chromatin during the chromatin isolation procedure, and association of that protein with the target chromatin is not specific. If a target chromatin of the invention is isolated from the unlabeled cell sample, only unlabeled identified proteins associated with the target chromatin are specifically associated with the target chromatin. Alternatively, if a target chromatin of the invention is isolated from the labeled cell sample, only labeled identified proteins associated with the target chromatin are specifically associated with the target chromatin.

In some embodiments, a tagged target chromatin of the invention is isolated from an unlabeled cell sample, and unlabeled proteins associated with the target chromatin are specifically associated with the target chromatin. In other embodiments, a tagged target chromatin of the invention is isolated from a labeled cell sample, and labeled proteins associated with the target chromatin are specifically associated with the target chromatin.

(a) Cells

A target nucleic acid sequence may be isolated from any cell comprising the target nucleic acid sequence of the invention. A cell may be an archaebacterium, a *eubacterium*, or a eukaryotic cell. For instance, a cell of the invention may be a methanogen, a halophile or a thermoacidophile archaeabacterium, a gram positive, a gram negative, a cyanobacterium, a spirochaete, or a firmicute bacterium, a fungal cell, a moss cell, a plant cell, an animal cell, or a protist cell.

In some embodiments, a cell of the invention is a cell from an animal. A cell from an animal cell may be a cell from an embryo, a juvenile, or an adult. Suitable animals include vertebrates such as mammals, birds, reptiles, amphibians, and fish. Examples of suitable mammals include without limit rodents, companion animals, livestock, and primates. Non-limiting examples of rodents include mice, rats, hamsters, gerbils, and guinea pigs. Suitable companion animals include but are not limited to cats, dogs, rabbits, hedgehogs, and ferrets. Non-limiting examples of livestock include horses, goats, sheep, swine, cattle, llamas, and alpacas. Suitable primates include but are not limited to humans, capuchin monkeys, chimpanzees, lemurs, macaques, marmosets, tamarins, spider monkeys, squirrel monkeys, and vervet monkeys. Non-limiting examples of birds include chickens, turkeys, ducks, and geese. In some embodiments, a cell is a cell from a human.

In some embodiments, a cell may be from a model organism commonly used in laboratory research. For instance, a cell of the invention may be an *E. coli*, a *Bacillus subtilis*, a *Caulobacter crescentus*, a *Mycoplasma genitalium*, an *Aliivibrio fischeri*, a *Synechocystis*, or a *Pseudomonas fluorescens* bacterial cell; a *Chlamydomonas reinhardtii*, a *Dictyostelium discoideum*, a *Tetrahymena thermophila*, an *Emiliania huxleyi*, or a *Thalassiosira pseudonana* protist cell; an *Ashbya gossypii*, an *Aspergillus nidulans*, a *Coprinus cinereus*, a *Cunninghamella elegans*, a *Neurospora crassa*, a *Saccharomyces cerevisiae*, a *Schizophyllum commune*, a *Schizosaccharomyces pombe*, or an *Ustilago maydis* fungal cell; an *Arabidopsis thaliana*, a *Selaginella moellendorffii*, a *Brachypodium distachyon*, a *Lotus japonicus*, a *Lemna gibba*, a *Zea mays*, a *Medicago truncatula*, a *Mimulus*, a tobacco, a rice, a *Populus*, or a *Nicotiana benthamiana* plant cell; a *Physcomitrella patens* moss; an *Amphimedon queenslandica* sponge, an *Arbacia punctulata* sea urchin, an *Aplysia* sea slug, a *Branchiostoma floridae* deuterostome, a *Caenorhabditis elegans* nematode, a *Ciona intestinalis* sea squirt, a *Daphnia* spp. crustacean, a *Drosophila* fruit fly, a *Euprymna scolopes* squid, a *Hydra* Cnidarian, a *Loligo pealei* squid, a *Macrostomum lignano* flatworm, a *Mnemiopsis leidyi* comb jelly, a *Nematostella vectensis* sea anemone, an *Oikopleura dioica* free-swimming tunicate, an *Oscarella carmela* sponge, a *Parhyale hawaiensis* crustacean, a *Platynereis dumerilii* marine polychaetous annelid, a *Pristionchus pacificus* roundworm, a *Schmidtea mediterranea* freshwater planarian, a *Stomatogastric ganglion* of various arthropod species, a *Strongylocentrotus purpuratus* sea urchin, a *Symsagittifera roscoffensis* flatworm, a *Tribolium castaneum* beetle, a *Trichoplax adhaerens* Placozoa, a *Tubifex tubifex* oligochaeta, a laboratory mouse, a Guinea pig, a Chicken, a Cat, a Dog, a Hamster, a Lamprey, a Medaka fish, a Rat, a Rhesus macaque, a Cotton rat, a Zebra finch, a Takifugu pufferfish, an African clawed frog, or a Zebrafish. In exemplary embodiments, a cell is a *Saccharomyces cerevisiae* yeast cell. In particularly exemplary embodiments, a cell is a *Saccharomyces cerevisiae* W303a yeast cell.

A cell of the invention may be derived from a tissue or from a cell line grown in tissue culture. A cell line may be adherent or non-adherent, or a cell line may be grown under conditions that encourage adherent, non-adherent or organotypic growth using standard techniques known to individuals skilled in the art. Cell lines and methods of culturing cell lines are known in the art. Non-limiting examples of cell lines commonly cultured in a laboratory may include HeLa, a cell line from the National Cancer Institute's 60 cancer cell lines, DU145 (prostate cancer), Lncap (prostate cancer), MCF-7 (breast cancer), MDA-MB-438 (breast cancer), PC3 (prostate cancer), T47D (breast cancer), THP-1 (acute myeloid leukemia), U87 (glioblastoma), SHSYSY Human neuroblastoma cells, Saos-2 cells (bone cancer), Vero, GH3 (pituitary tumor), PC12 (pheochromocytoma), MC3T3 (embryonic calvarium), Tobacco BY-2 cells, Zebrafish ZF4 and AB9 cells, Madin-Darby canine kidney (MDCK), or *Xenopus* A6 kidney epithelial cells.

As described in Section (I) above, two cell samples, or lysates derived from two cell samples are combined, and a tagged target chromatin of the invention is isolated from the combined cells or combined cell lysates. Typically, cells in two cell samples of the invention are from the same type of cells or they may be derived from the same type of cells. For instance, cells may comprise a heterologous nucleic acid in a target chromatin, and may also comprise a heterologous protein expressed in a cell of the invention. The heterologous nucleic acid in a target chromatin may be used for tagging a chromatin of the invention, and the heterologous protein expressed in a cell may be used for tagging a target chromatin as described in Section I(d). In some embodiments, cells in two cell samples of the invention are from the same type of cells. In other embodiments, cells in the first cell sample are derived from the same cell type as cells in the second cell sample.

Two cell samples of the invention may be from the same genus, species, variety or strain of cells. In preferred embodiments, two cell samples of the invention are *Saccharomyces cerevisiae* yeast cells or derivatives of *Saccharomyces cerevisiae* yeast cells. In exemplary embodiments, two cell samples of the invention are *Saccharomyces cerevisiae* W303a yeast cells or derivatives of *Saccharomyces cerevisiae* W303a yeast cells. In exemplary embodiments, two cell samples of the invention are derivatives of *Saccharomyces cerevisiae* W303a yeast cells comprising the lexA binding site upstream of the GAL1 transcription start site, wherein protein A is expressed in one of the cell samples of derived *Saccharomyces cerevisiae* W303a yeast cells.

According to the invention, a metabolically labeled cell sample and an unlabeled cell sample are combined to generate a combined cell sample, or lysates derived from the two cell samples are combined to generate a combined cell lysate. Cell samples may be combined in a weight to weight (w/w) ratio of about 1:100 to about 100:1, about 1:50 to about 50:1, about 1:25 to about 25:1, preferably about 1:10 to about 10:1, and more preferably about 1:5 to about 5:1. In preferred embodiments, cell samples are combined in a w/w ratio of about 1:5 to about 5:1, about 1:2 to about 2:1, about 1:1.5 to about 1.5:1, or about 1:1. In exemplary embodiments, cell samples are combined in a w/w ratio of about 1:1. If cell lysates derived from two cell samples of the invention are combined, lysates derived from cell ratios described herein are combined. Individuals of ordinary skill in the art will recognize that ratios of cell samples or lysates derived from cell samples described herein may be subject to statistical confidence limits of actual cell weight. For instance, the ratio may be based on 85, 90, 95% or more confidence limits on cell weight.

The number of cells in a cell sample can and will vary depending on the type of cells, the abundance of a target chromatin in a cell, and the method of protein identification used, among other variables. For instance, if a cell of the invention is *Saccharomyces cerevisiae*, about $5 \times 10^{11}$ to about $5 \times 10^{12}$, more preferably, about $1 \times 10^{11}$ to about $1 \times 10^{12}$ cells may be used in a cell sample. In some embodiments, about $1 \times 10^{11}$ to about $1 \times 10^{12}$ *Saccharomyces cerevisiae* cells are used in a cell sample.

Two cell samples of the invention are typically grown identically. Identically grown cell samples minimizes potential structural or functional differences at a target chromatin present in both cell samples. As used herein, "grown identically" refers to cultured cell samples grown using similar culture condition, or cells from a tissue harvested using identical harvesting techniques. As described below, the two cell samples of the invention are grown identically in a manner that allows the metabolic labeling of proteins in one of the cell samples. For instance, the two cell samples of the invention are grown identically, except that one of the cell samples may be grown in the presence of a labeled amino acid as described in the examples, to generate a cell sample with metabolically labeled proteins.

Proteins in a cell sample are metabolically labeled. Methods of metabolically labeling proteins in a cell are known in the art and may comprise culturing a cell in the presence of at least one labeled analogue of a biomolecule that is metabolized by a cell of the invention. When the labeled analog of a biomolecule is supplied to cells in culture instead of the unlabeled biomolecule, the labeled biomolecule is incorporated into all newly synthesized proteins. After a number of cell divisions, each instance of this particular labeled biomolecule will be replaced by its labeled analog. Since there is hardly any chemical difference between the labeled biomolecule and the unlabeled biomolecule, the cells behave exactly like the control cell population grown in the presence of unlabeled biomolecule. As such, up to 100% of the particular biomolecule in a cell may be labeled. In some embodiments, up to 10, 20, 30, 40, 50, 60, 70, 80, 90 or up to 100% of the particular biomolecule in a cell is labeled. In preferred embodiments, up to 50, 60, 70, 80, 90 or up to 100%, and more preferably up to 90 or up to 100% of the particular biomolecule in a cell is labeled. In preferred embodiments, up to 100% of the particular biomolecule in a cell is labeled.

A cell may be labeled by culturing a cell in the presence of one or more than one labeled biomolecule. For instance, a cell may be cultured in the presence of 1, 2, 3, 4, 5, 6, 7, 8, 9, 10 or more labeled biomolecules. In some embodiments, a cell may be cultured in the presence of 1, 2, 3, 4, or 5 labeled biomolecules. In other embodiments, a cell may be cultured in the presence of 5, 6, 7, 8, 9, or 10 labeled biomolecules. In preferred embodiments, a cell may be cultured in the presence of 1 or 2 labeled biomolecules.

Non-limiting examples of a biomolecule that may be labeled and is metabolized by a cell of the invention may include an amino acid, a nucleic acid, a carbohydrate or a labeled molecule that may be incorporated into an amino acid, a nucleic acid, or a carbohydrate. Non-limiting examples of a labeled molecule that may be incorporated into an amino acid, a nucleic acid, a carbohydrate may include labeled ammonium sulfate, and labeled ammonium chloride. A labeled biomolecule may be a component of a cell culture medium such as a food source, e.g., glucose, sera or cell extracts. In some embodiments, a labeled biomolecule that is metabolized by a cell of the invention is a labeled nucleic acid. In other embodiments, a labeled biomolecule that is metabolized by a cell of the invention is a labeled carbohydrate such as $[^{13}C]$glucose.

In preferred embodiments, a biomolecule that is metabolized by a cell of the invention is a labeled amino acid. In general, a labeled amino acid of the invention may be a labeled L-amino acid, a labeled D-amino acid or a mixture thereof. In preferred embodiments, a labeled amino acids is a labeled L-amino acids. A labeled amino acid may be a free amino acid or an amino acid salt. A labeled amino acid may also be in the form of intact protein or peptide, provided that the protein or peptide comprises a labeled amino acid of the invention. In some preferred embodiments, a labeled amino acid that may be used for metabolically labeling a cell of the invention may be a labeled L-Lysine, L-Arginine, L-Methionine, L-Tyrosine, or combinations thereof.

A labeled biomolecule may be labeled using a heavy isotope of one or more atoms of the biomolecule. Non limiting examples of a heavy isotope of one or more atoms of a biomolecule may include heavy hydrogen, carbon, nitrogen, phosphorous, oxygen, or sulfur. A labeled biomolecule may be about 1, 2, 3, 4, 5, 6, 7, 8, 9, 10, 11, 12, 13, 14, 15, 16, 17 18, 19 or 20Da or more heavier than an unlabeled biomolecule. In some embodiments, a labeled biomolecule is about 1, 2, 3, 4, or 5Da heavier than an unlabeled biomolecule. In other embodiments, a labeled biomolecule is about 5, 6, 7, 8, 9, or 10Da heavier than an unlabeled biomolecule. In yet other embodiments, a labeled biomolecule is about 10, 11, 12, 13, 14, or 15Da heavier than an unlabeled biomolecule. In additional embodiments, a labeled biomolecule is about 15, 16, 17 18, 19 or 20Da heavier than an unlabeled biomolecule. In preferred embodiments, a labeled biomolecule is about 4, 5, 6, 7, 8, 9, or 10Da heavier than an unlabeled biomolecule.

In preferred embodiments, a labeled biomolecule is a labeled amino acid that may be used for metabolically labeling a cell of the invention may be a heavy analog of L-Lysine, L-Arginine, L-Methionine, L-Tyrosine, or combinations thereof. Non limiting examples of heavy analogs of L-Lysine, L-Arginine, L-Methionine, L-Tyrosine may include, [$^{13}C_6$]-L-Lysine, [$^{13}C_6$, $^{15}N_2$]-L-Lysine, [$^{13}C_6$, $^{15}N_2$, D9]-L-Lysine, [$^{15}N_2$, D9]-L-Lysine, [4,4,5,5-D4]-L-Lysine, [$^{15}N_2$]-L-Lysine, [$^{13}C_6$, $^{15}N_2$]-L-Lysine, [$^{13}C_6$]-L-Arginine, [U-$^{13}C_6$, $^{15}N_4$]-L-Arginine, [U-$^{13}C_6$, $^{15}N_4$, D7]-L-Arginine, [$^{15}N_4$, D7]-L-Arginine, [$^{15}N_4$]-L-Arginine, [$^{13}C_6$, $^{15}N_4$]-L-Arginine, [1-13C, methyl-D3]-L-Methionine, [$^{13}C_9$; 9 Da]-L-Tyrosine, [$^{15}N$]-L-Tyrosine, and [$^{13}C_9$, $^{15}N$]-L-Tyrosine. In an exemplary embodiment, a labeled amino acid used to metabolically label a cell of the invention is [$^{13}C6$, $^{15}N4$]-L-Arginine.

(b) Chromatin

A method of the invention comprises identification of a protein and post-translational modification of a protein associated with a target chromatin. Generally, chromatin refers to the combination of nucleic acids and proteins in the nucleus of a eukaryotic cell. However, it is contemplated that the term "chromatin" may also refer to the combination of any nucleic acid sequence and proteins associated with the nucleic acid sequence in any cell.

A chromatin of the invention may comprise single stranded nucleic acid, double stranded nucleic acid, or a combination thereof. In some embodiments, a chromatin comprises single stranded nucleic acid. In other embodiments, a chromatin comprises a combination of single stranded and double stranded nucleic acids. In yet other embodiments, a chromatin comprises double stranded nucleic acid.

A chromatin of the invention may comprise a ribonucleic acid (RNA), a deoxyribonucleic acid (DNA), or a combination of RNA and DNA. In some embodiments, a chromatin of the invention comprises a combination of a RNA sequence and proteins associated with the RNA sequence in a cell. Non-limiting examples of RNA sequences may include mRNA, and non-coding RNA such as tRNA, rRNA, snoRNAs, microRNAs, siRNAs, piRNAs and the long noncoding RNA (lncRNA). In preferred embodiments, a chromatin of the invention comprises a combination of a DNA sequence and proteins associated with the DNA sequence in a cell. In other preferred embodiments, a chromatin of the invention comprises a combination of RNA and DNA sequences, and proteins associated with the RNA and DNA sequence in a cell. Non limiting examples of chromatin that may comprise a combination of RNA and DNA may include genomic DNA undergoing transcription, or genomic DNA comprising non-coding RNA such as lncRNA.

A chromatin of the invention may be genomic chromatin such as, chromatin from a chromosome of a cell, or chromatin from an organelle in the cell. Alternatively, a chromatin may be chromatin from an extrachromosomal nucleic acid sequence. In some embodiments, a chromatin of the invention is chromatin from an organelle in the cell. Non-limiting examples of a chromatin from an organelle may include mitochondrial nucleic acid sequence in plant and animal cells, and a chloroplast nucleic acid sequence in plant cells. In some embodiments, a nucleic acid sequence of the invention is a mitochondrial nucleic acid sequence. In other embodiments, a nucleic acid sequence of the invention is a chloroplast nucleic acid sequence.

In some embodiments, a chromatin of the invention is chromatin from an extrachromosomal nucleic acid sequence. The term "extrachromosomal," as used herein, refers to any nucleic acid sequence not contained within the cell's genomic nucleic acid sequence. An extrachromosomal nucleic acid sequence may comprise some sequences that are identical or similar to genomic sequences in the cell, however, an extrachromosomal nucleic acid sequence as used herein does not integrate with genomic sequences of the cell. Non-limiting examples of an extrachromosomal nucleic acid sequence may include a plasmid, a virus, a cosmid, a phasmid, and a plasmid.

In some preferred embodiments, a chromatin of the invention is genomic chromatin. In exemplary embodiments, a chromatin of the invention is genomic chromatin of a eukaryotic cell. A eukaryotic cell of the invention may be as described in Section I(a) above.

Primary functions of genomic chromatin of a eukaryotic cell may be DNA packaging into a smaller volume to fit in the cell, strengthening of the DNA to allow mitosis, prevent DNA damage, and to control gene expression and DNA replication. As described above, genomic chromatin of a eukaryotic cell may comprise DNA sequences and a plurality of DNA-binding proteins as well as certain RNA sequences, assembled into higher order structural or functional regions. As used herein, a "structural or functional feature of a chromatin", refers to a chromatin feature characterized by, or encoding, a function such as a regulatory function of a promoter, terminator, translation initiation, enhancer, etc., or a structural feature such as heterochromatin, euchromatin, a nucleosome, a telomere, or a centromere. A physical feature of a nucleic acid sequence may comprise a functional role and vice versa. As described below, a chromatin of the invention may be a chromatin fragment, and as such may comprise a fragment of a physical or functional feature of a chromatin, or no physical or functional features or known physical or functional features.

The primary protein components of genomic eukaryotic chromatin are histones that compact the DNA into a nucleosome. The nucleosome comprises an octet of histone proteins around which is wound a stretch of double stranded DNA sequence of about 150 to about 250 bp in length. Histones H2A, H2B, H3 and H4 are part of the nucleosome while histone H1 may act to link adjacent nucleosomes together into a higher order structure. Histones are subject to post translational which may affect their function in regulating chromatin function. Such modifications may include methylation, citrullination, acetylation, phosphorylation, SUMOylation, ubiquitination, and ADP-ribosylation.

Many further polypeptides and protein complexes interact with the nucleosome and the histones to regulate chromatin function. A "polypeptide complex" as used herein, is intended to describe proteins and polypeptides that assemble together to form a unitary association of factors. The members of a polypeptide complex may interact with each other via non-covalent or covalent bonds. Typically members of a polypeptide complex will cooperate to enable binding either to a nucleic acid sequence or to polypeptides and proteins already associated with or bound to a nucleic acid sequence in chromatin. Chromatin associated polypeptide complexes may comprise a plurality of proteins and/or polypeptides which each serve to interact with other polypeptides that may be permanently associated with the complex or which may associate transiently, dependent upon cellular conditions and position within the cell cycle. Hence, particular polypeptide complexes may vary in their constituent members at different stages of development, in response to varying physiological conditions or as a factor of the cell cycle. By way of example, in animals, polypeptide complexes with known chromatin remodelling activities include Polycomb group gene silencing complexes as well as Trithorax group gene activating complexes.

Additionally, a protein associated with a chromatin of the invention may be a protein normally expressed in a cell, or may be an exogenous heterologous protein expressed in a cell. In some embodiments, a protein associated with a chromatin of the invention is a protein normally expressed in a cell. In other embodiments, a protein associated with a chromatin of the invention is a protein normally expressed in a cell.

A chromatin of the invention may be an intact and complete chromatin from the cell, or may be a fragment of a chromatin in a cell. In some embodiments, a chromatin of the invention is an intact chromatin isolated from a cell. For instance, a chromatin of the invention may be a plasmid, a cosmid, or a phage chromatin or a complete organellar chromatin. In preferred embodiments, a chromatin of the invention is a fragment of a chromatin from a cell. In exemplary embodiments, a chromatin of the invention is a fragment of a genomic chromatin from a cell.

When a chromatin of the invention is a fragment of a chromatin in a cell, any method of fragmenting a chromatin known in the art may be used. Such methods may include physical methods of fragmenting a chromatin, or enzymatic digestion of a nucleic acid sequence of a chromatin. In some embodiments, a fragment of a chromatin may be generated using enzymatic digestion of a nucleic acid sequence in chromatin. Non-limiting examples of enzymatic digestion may include random or sequence specific enzymatic digestion using restriction enzymes, nucleases, combinations of restriction enzymes and nucleases, or combinations of nicking and other nucleases such as NEBNext™ fragmentase, which comprises a nicking enzyme that randomly generates nicks in double stranded DNA and another enzyme that cuts the strand opposite to the generated nicks.

In other embodiments, a fragment of a chromatin may be generated using a physical method of fragmenting a chromatin. Non-limiting examples of physical fragmenting methods that may be used to fragment a chromatin of the invention may include nebulization, sonication, and hydrodynamic shearing. In some embodiments, a fragment of a chromatin may be generated using nebulization. In other embodiments, a fragment of a chromatin may be generated using hydrodynamic shearing. In preferred embodiments, a fragment of a chromatin may be generated using sonication. During sonication, a sample comprising chromatin is subjected to ultrasonic waves, whose vibrations produce gaseous cavitations in the liquid that shear or break high molecular weight molecules such as chromatin through resonance vibration. Sonication methods that may be used to generate a chromatin of the invention are known in the art A fragment of a chromatin of the invention may comprise a nucleic acid sequence fragment and may be about 10, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 4000, 5000, 6000, 7000, 8000, 9000, or about 10000 bases long or more. In some embodiments, a chromatin of the invention may comprise a nucleic acid sequence fragment of about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or about 500 bases long. In other embodiments, a chromatin of the invention may comprise a nucleic acid sequence fragment of about 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or about 1000 bases long. In yet other embodiments, a chromatin of the invention may comprise a nucleic acid sequence fragment of about 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, or about 1500 bases long. In other embodiments, a chromatin of the invention may comprise a nucleic acid sequence fragment of about 1500, 1510, 1520, 1530, 1540, 1550, 1560, 1570, 1580, 1590, 1600, 1610, 1620, 1630, 1640, 1650, 1660, 1670, 1680, 1690, 1700, 1710, 1720, 1730, 1740, 1750, 1760, 1770, 1780, 1790, 1800, 1810, 1820, 1830, 1840, 1850, 1860, 1870, 1880, 1890, 1900, 1910, 1920, 1930, 1940, 1950, 1960, 1970, 1980, 1990, or about 2000 bases long. In additional embodiments, a chromatin of the invention may comprise a nucleic acid sequence fragment of about 2000, 2100, 2150, 2200, 2250, 2300, 2350, 2400, 2450, or about 2500 bases long. In other embodiments, a chromatin of the invention may comprise a nucleic acid sequence fragment of about 2000, 2050, 2100, 2150, 2200, 2250, 2300, 2350, 2400, 2450, or about 2500 bases long. In still other embodiments, a chromatin of the invention may comprise a nucleic acid sequence fragment of about 2500, 2550, 2600, 2650, 2700, 2750, 2800, 2850, 2900, 2950, 3000, 4000, 5000, 6000, 7000, 8000, 9000, or about 10000 bases long or more.

In some preferred embodiments, a chromatin fragment of the invention may comprise a nucleic acid sequence fragment of about 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, or about 1250 bases long. In a preferred embodiment, a chromatin of the invention may comprise a nucleic acid sequence fragment of about 750, 760, 770, 780, 790, 800, 810, 820, 830, 840, or about 850 bases long. In another preferred embodiment, a chromatin of the invention may comprise a nucleic acid sequence fragment of about 950, 960, 970, 980, 990, 1000, 1010, 1020, 1030, 1040, or about 1050 bases long.

In other preferred embodiments, a chromatin fragment of the invention may comprise a nucleic acid sequence fragment of about 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, or about 1500 bases long. In a preferred embodiment, a chromatin of the invention may comprise a nucleic acid sequence fragment of about 950, 960, 970, 980, 990, 1000, 1010, 1020, 1030, 1040, or about 1050 bases long. In another preferred embodiment, a chromatin of the invention may comprise a nucleic acid sequence fragment of about 1200, 1210, 1220, 1230, 1240, 1250, 1260, 1270, 1280, 1290, or about 1300 bases long.

As described in this section above, a chromatin of the invention may comprise one or more nucleosomes. As such, a chromatin fragment of the invention may comprise 1, 2, 3, 4, 5, 6, 7, 8, 9, 10, 11, 12, 13, 14, 15, 16, 17, 18, 19, or about 20 nucleosomes. In some embodiments, a chromatin fragment of the invention may comprise about 1, 2, 3, 4, or about 5 nucleosomes. In other embodiments, a chromatin fragment of the invention may comprise about 5, 6, 7, 8, 9, or about 10 nucleosomes. In yet other embodiments, a chromatin fragment of the invention may comprise about 10, 11, 12, 13, 14, or about 15 nucleosomes. In other embodiments, a chromatin fragment of the invention may comprise about 15, 16, 17, 18, 19, or about 20 nucleosomes. In preferred embodiments, a chromatin fragment of the invention may comprise about 4 nucleosomes. In other preferred embodiments, a chromatin fragment of the invention may comprise about 5 nucleosomes.

A target chromatin fragment of the invention may comprise a structural or a functional feature of chromatin as described above, a fragment of a physical or functional feature, or no physical or functional features or known physical or functional features. In some embodiments, a target chromatin fragment of the invention comprises a structural feature of chromatin. In other embodiments, a target chromatin fragment of the invention comprises no physical or functional features or known physical or functional features. In yet other embodiments, a target chromatin fragment of the invention comprises a functional feature of chromatin. In exemplary embodiments, a functional feature of chromatin is a promoter. In particularly exemplary embodiments, a functional feature of chromatin is a GAL1 promoter of *Saccharomyces cerevisiae*.

(c) Preparation of Cell Lysate

A target chromatin is isolated from a combined cell lysate. A combined cell lysate comprises a lysate of two combined cell samples, or a combination of two cell lysates derived from two cell samples, wherein a target chromatin is tagged in one of the cell samples. Irrespective of whether one cell sample or a combined cell sample is lysed, a skilled practitioner of the art will appreciate that structural and functional features of a target chromatin must be preserved during cell lysis and isolation of the target chromatin. The association of proteins with a target chromatin may be preserved during cell lysis and isolation of the target chromatin using methods known in the art for preserving a complex of proteins with a nucleic acid sequence. For instance, lysing of a cell and isolation of a target chromatin may be performed under refrigeration or using cryogenic methods and buffer conditions capable of preserving association of proteins and nucleic acid sequences. In addition, a complex of proteins with a nucleic acid may be preserved by crosslinking protein and nucleic acid complexes in a cell prior to lysing and isolating a chromatin. Crosslinking protein and nucleic acid complexes in a cell may also capture, or preserve, transient protein-protein and protein-nucleic acid interactions.

In some embodiments, a complex of proteins with a nucleic acid may be preserved by crosslinking protein and nucleic acid complexes in a chromatin prior to lysing a cell and isolating the chromatin. Crosslinking is the process of joining two or more molecules such as two proteins or a protein and a nucleic acid molecule, by a covalent bond. Molecules may be crosslinked by irradiation with ultraviolet light, or by using chemical crosslinking reagents. Chemical crosslinking reagents capable of crosslinking proteins and nucleic acids are known in the art and may include crosslinking reagents that target amines, sulfhydryls, carboxyls, carbonyls or hydroxyls; omobifunctional or heterobifunctional crosslinking reagent, variable spacer arm length or zero-length crosslinking reagents, cleavable or non-cleavable crosslinking reagents, and photoreactive crosslinking reagents. Non-limiting examples of crosslinking reagents that may be used to crosslink protein complexes and/or protein complexes and nucleic acids may include formaldehyde, glutaraldehyde, disuccinimidyl glutarate, disuccinimidyl suberate, a photoreactive amino acid such as photo-leucine or photo-methionine, and succinimidyl-diazirine. The degree of crosslinking can and will vary depending on the application of a method of the invention, and may be experimentally determined.

In a preferred embodiment, a complex of proteins with a nucleic acid in a chromatin of the invention may be preserved by crosslinking protein and nucleic acid complexes in a cell prior to lysing using formaldehyde. In an exemplary embodiment, a complex of proteins with a nucleic acid in a chromatin of the invention may be preserved by crosslinking protein and nucleic acid complexes in a cell prior to lysing using formaldehyde as described in the examples.

A skilled practitioner of the art will appreciate that protocols for lysing a cell can and will vary depending on the type of cell, the target chromatin of the invention, and the specific application of a method of the invention. Non limiting examples of methods that may be used to lyse a cell of the invention may include cell lysis using a detergent, an enzyme such as lysozyme, incubation in a hypotonic buffer which causes a cell to swell and burst, mechanical disruption such as liquid homogenization by forcing a cell through a narrow space, sonication, freeze/thaw, mortar and pestle, glass beads, and combinations thereof. In some embodiments, when a cell of the invention is a yeast cell, the cell may be cryogenically lysed under liquid nitrogen temperature with glass beads. In exemplary embodiments, when a cell of the invention is a yeast cell, the cell may be cryogenically lysed under liquid nitrogen temperature with glass beads as described in the examples.

Buffer conditions used during lysing and isolation of a chromatin of the invention can and will be altered to control stringent conditions during cell lysis and isolation to preserve association of proteins and nucleic acid sequences of a chromatin. "Stringent conditions" in the context of chromatin isolation are conditions capable of preserving specific association of proteins and nucleic acids of a chromatin, but minimizing non-specific association of proteins and nucleic acids. Stringent condition can and will vary depending on the application of a method of the invention, the target chromatin of the invention, the nucleic acid sequence in a target chromatin, the proteins or protein complexes associated with a target chromatin of the invention, whether or not proteins, protein complexes and nucleic acid sequences are crosslinked, and the conditions used for crosslinking proteins, protein complexes and nucleic acid sequences of a target chromatin. For instance, more stringent buffer conditions may be used in a method of the invention wherein proteins, protein-protein complexes, and protein-nucleic acid complexes are crosslinked compared to a method of the invention wherein proteins, protein-protein complexes, and protein-nucleic acid complexes are not crosslinked. As such, stringent buffer conditions used during cell lysis and isolation of a nucleic acid sequence of the invention may be experimentally determined for each application wherein a method of the invention is used. Buffer conditions that may alter stringent conditions during cell lysis and isolation may include pH and salt concentration. In preferred embodiments, proteins, protein-protein complexes, and protein-nucleic acid complexes of a target chromatin of the invention are crosslinked, and stringent buffer conditions are used during lysis and isolation of a chromatin of the invention. In exemplary embodiments, proteins, protein-protein complexes, and protein-nucleic acid complexes of a target chromatin of the invention are crosslinked, and stringent buffer conditions are used during lysis and isolation of a chromatin of the invention and are as described in the examples.

(d) Chromatin Isolation

According to the invention, a tagged target chromatin is isolated from a combined cell lysate. As described in Sections I(a) and I(c) above, a combined cell lysate comprises a lysate of two combined cell samples, or a combination of two cell lysates derived from two cell samples, wherein a target chromatin is tagged in one of the lysates, or one of the cell samples. As such, a target chromatin is isolated from a cell lysate comprising a combination of a tagged target chromatin and an untagged target chromatin. The ratio of tagged target chromatin to untagged target chromatin reflects the ratio at which the two cell samples or the lysates derived from the two cell sample are combined. In addition, proteins in one of the cell samples or lysate derived from one of the cell samples are metabolically labeled. Therefore, when a tagged target chromatin is from a cell sample wherein proteins are metabolically labeled, a cell lysate of the invention comprises a combination of a tagged target chromatin comprising metabolically labeled proteins, and an untagged target chromatin comprising unlabeled proteins. Conversely, when a tagged target chromatin is from a cell sample wherein proteins are unlabeled, a cell lysate of the invention comprises a combination of a tagged target chromatin comprising unlabeled proteins, and an untagged target chromatin comprising labeled proteins.

A target chromatin may be isolated from a mixture of chromatins or chromatin fragments in a cell lysate as described in this section. As used herein, a target nucleic acid sequence is said to be "isolated" or "purified" when it is substantially free of proteins not associated with the target chromatin, nucleic acid sequences other than the nucleic acid sequences associated with the target chromatin, and other cell debris and cell contents resulting from extraction and preparation of the target chromatin from a cell. A target chromatin of the present invention may be purified to homogeneity or other degrees of purity. In general, the level of purity of an isolated target chromatin can and will vary depending on the cell type, the specific chromatin to be isolated, and the intended use of a target chromatin of the invention. The level of purity of an isolated target chromatin may be determined using methods known in the art. For instance, the level of purity of an isolated target chromatin may be determined by determining the level of purity of a nucleic acid sequence associated with a target chromatin, by determining the level of purity of a protein associated with a target chromatin, or by determining the level of enrichment of a target chromatin, compared to a non-target chromatin in a cell. In preferred embodiments, the level of purity of an isolated target chromatin is determined by determining the level of enrichment of a target chromatin, compared to a non-target chromatin in a cell. Determining the level of enrichment of a target chromatin, compared to a non-target chromatin in a cell may be as described in this section below.

A target chromatin of the invention may be isolated using methods known in the art, such as electrophoresis, molecular, immunological and chromatographic techniques, ion exchange, hydrophobic, affinity, and reverse-phase HPLC chromatography, size exclusion chromatography, precipitation, dialysis, chromatofocusing, ultrafiltration and diafiltration techniques, and combinations thereof. For general guidance in suitable purification techniques, see Scopes, R., Protein Purification, Springer-Vertag, NY (1982).

In general, a method of the invention comprises isolating a target chromatin by affinity purification, or affinity purification in combination with other methods of isolating chromatin described above. In a preferred embodiment, a method of the invention comprises isolating a target chromatin by affinity purification. Non limiting examples of affinity purification techniques that may be used to isolate a target chromatin of the invention may include affinity chromatography, immunoaffinity chromatography, size exclusion chromatography, and combinations thereof. See, for example, Roe (ed), Protein Purification Techniques: A Practical Approach, Oxford University Press, 2nd edition, 2001.

In essence, affinity purification of a target chromatin may comprise tagging a target chromatin by contacting the target chromatin of the invention with a tag capable of specifically recognizing and binding one or more portions of a target chromatin. As described in Section (I), two cell samples, or lysates derived from the cell samples of the invention are combined, and a target chromatin in one of the cell samples or an extract from one of the cell samples is tagged. In addition, proteins in one cell sample, but not both of the cell samples are metabolically labeled. As such, a target chromatin may be tagged in a cell or an extract from a cell wherein proteins are metabolically labeled, and proteins specifically associated with an isolated target chromatin are metabolically labeled. Alternatively, a target chromatin may be tagged in a cell or an extract from a cell wherein proteins are not metabolically labeled, and proteins specifically associated with an isolated target chromatin are not metabolically labeled. In some embodiments, a target chromatin is tagged in a cell or an extract from a cell wherein proteins are metabolically labeled. In other embodiments, a target chromatin is tagged in a cell or an extract from a cell wherein proteins are metabolically labeled.

A tag may be capable of specifically recognizing and binding 1, 2, 3, 4, 5, 6, 7, 8, 9, or 10 components of a target chromatin. In preferred embodiments, a tag is capable of specifically recognizing and binding one component of a target chromatin.

A tag may be capable of specifically recognizing and binding a component in a target chromatin. A component in a target chromatin may be a nucleic acid sequence in a nucleic acid associated with a target chromatin, a protein associated with a target chromatin, or a chromatin structural or functional feature in a target chromatin. In some embodiments, a tag is capable of specifically recognizing and binding a protein associated with a target chromatin. In other embodiments, a tag is capable of specifically recognizing and binding a chromatin structural or functional feature in a target chromatin. In preferred embodiments, a tag is capable of specifically recognizing and binding a nucleic acid sequence associated with a target chromatin.

A nucleic acid sequence associated with a target chromatin that may be specifically recognized and bound by a tag of the invention may be a nucleic acid sequence normally found in a chromatin of a cell of the invention. Alternatively, a nucleic acid sequence associated with a target chromatin that may be specifically recognized and bound by a tag of the invention may be an exogenous nucleic acid sequence introduced into a cell to facilitate tagging a target chromatin of the invention. In some embodiments, a nucleic acid sequence that may be recognized and bound by a tag is a nucleic acid sequence normally found in a chromatin of a cell of the invention. In other embodiments, a nucleic acid sequence that may be recognized and bound by a tag of the invention is an exogenous nucleic acid sequence introduced into a cell of the invention to facilitate tagging a chromatin of the invention.

Non limiting examples of an exogenous nucleic acid sequence introduced into a cell to facilitate tagging a target chromatin of the invention may be the lexA binding sequence, and the Lac operator. In a preferred embodiment, a heterologous nucleic acid sequence introduced into a cell to facilitate tagging a target nucleic acid sequence of the invention is the lexA binding sequence. In an exemplary embodiment, a heterologous nucleic acid sequence introduced into a cell to facilitate tagging a target nucleic acid sequence of the invention is the lexA binding sequence immediately upstream of the transcription start site.

Individuals of ordinary skill in the art will recognize that an exogenous chromatin component introduced into a cell to facilitate tagging a target chromatin of the invention cannot and will not disrupt a target chromatin, or a structural or functional feature of a target chromatin. Methods of designing a chromatin component and a tag capable of binding the chromatin component that do not disrupt a chromatin of the invention may depend on the particular application of a method of the invention, and may be determined experimentally. For instance, if an application of a method of the invention comprises promoter function, a tag may be designed to bind anywhere adjacent to the promoter, but without disrupting the promoter.

A tag of the invention may further comprise one or more affinity handles. As used herein, the term "affinity handle" may refer to any handle that may be bound by a substrate for affinity purification, as described below. A tag may comprise one or more than one affinity handle. The inclusion of more than one affinity handle in a tag of the invention may significantly increase the efficiency of affinity purification for a low copy number chromatin target. As such, a tag may further comprise 1, 2, 3, 4, 5, 6, 7, 8, 9, 10 or more affinity handles. In a preferred embodiment, a tag of the invention comprises one affinity handle.

Affinity handles may include any affinity handle for which a cognate binding agent is readily available. An affinity handle may be an aptamer, an antibody, an antibody fragment, a double-stranded DNA sequence, modified nucleic acids and nucleic acid mimics such as peptide nucleic acids, locked nucleic acids, phosphorodiamidate morpholino oligomers (PMO), a ligand, a ligand fragment, a receptor, a receptor fragment, a polypeptide, a peptide, a coenzyme, a coregulator, an allosteric molecule, non-immunoglobulin scaffolds such as Affibodies, Anticalins, designed Ankyrin repeat proteins and others, an ion, or a small molecule for which a cognate binding agent is readily available. The term "aptamer" refers to a polypeptide or a polynucleotide capable of binding to a target molecule at a specific region. It is generally accepted that an aptamer, which is specific in its binding to any polypeptide, may be synthesized and/or identified by in vitro evolution methods. Non limiting examples of handles that may be suitable for isolating a chromatin may include biotin or a biotin analogue such as desthiobiotin, digoxigenin, dinitrophenol or fluorescein, a macromolecule that binds to a nucleic acid or a nucleic acid binding protein such as the Lac repressor, a zinc finger protein, a transcription activator protein capable of binding a nucleic acid, or a transcription activator-like (TAL) protein, antigenic polypeptides such as protein A, or peptide 'tags' such as polyhistidine, FLAG, HA and Myc tags. In preferred embodiments, a tag of the invention comprises an antigenic polypeptide. In exemplary embodiments, a tag of the invention comprises the protein A antigenic polypeptide, or derivatives thereof. Protein A is capable of binding the lexA binding site, and comprises an affinity handle capapble of binding IgG. As such, protein A may be used as an affinity purification tag for purifying a target chromatin comprising a lexA binding tag.

In some embodiments, a tag of the invention is a nucleic acid tag capable of binding a nucleic acid sequence component of a chromatin, wherein the nucleic acid sequence component of the chromatin is introduced into a cell of the invention. In some embodiments, a tag of the invention is a nucleic acid tag capable of binding a nucleic acid sequence component of a chromatin, wherein the nucleic acid sequence component of the chromatin is normally present in a cell of the invention. Non-limiting examples of nucleic acid tags capable of binding a nucleic acid sequence component of a chromatin include antisense RNA or DNA nucleic acid tags, and tags comprising modified nucleic acids and nucleic acid mimics such as peptide nucleic acids, locked nucleic acids, phosphorodiamidate morpholino oligomers (PMO). In some embodiments, a tag of the invention is a nucleic acid tag comprising locked nucleotides. For instance, a nucleic acid tag comprising locked nucleotides may be as described in US20110262908 or US20120040857, and a peptide nucleic acid tag may be as described in Boffa et al. 1995 PNAS 92:1901-1905, the disclosures of all of which are incorporated herein in their entirety.

In some preferred embodiments, a tag of the invention is a protein tag capable of binding a nucleic acid sequence component of a chromatin, wherein the nucleic acid sequence component of the chromatin is a nucleic acid sequence normally found in a chromatin of a cell of the invention. Non limiting examples of a protein tag capable of binding a nucleic acid sequence normally found in a chromatin of a cell may be a nucleic acid binding protein such as protein A, the Lac repressor, a zinc finger protein, a transcription activator protein capable of binding a nucleic acid, or a transcription activator-like (TAL) protein. In one embodiment, a tag of the invention is a transcription activator protein capable of binding a nucleic acid sequence normally found in a chromatin of a cell of the invention. In another embodiment, a tag of the invention is a zinc finger protein capable of binding a nucleic acid sequence normally found in a chromatin of a cell of the invention. In yet another embodiment, a tag of the invention is a transcription activator-like (TAL) protein capable of binding a nucleic acid sequence normally found in a chromatin of a cell of the invention.

A nucleic acid binding protein tag of the invention may be a wild type nucleic acid binding protein capable of binding a nucleic acid sequence normally found in a target chromatin. Alternatively, a nucleic acid binding protein tag of the invention may be engineered to have binding specificity for a nucleic acid sequence component normally found in a target chromatin of the invention. Individuals of ordinary skill in the art will recognize that nucleic acid binding proteins such as zinc finger proteins, transcription activator proteins, and transcription activator-like (TAL) proteins may be engineered to have novel nucleic acid binding specificity compared to naturally-occurring forms of the proteins. See, for example, U.S. Pat. Nos. 6,453,242 and 6,534,261, and U.S. Pate. Appl. Nos 20110239315, 20120110685, and 20120270273, the disclosures of which are incorporated by reference herein in their entireties. In some embodiments, a nucleic acid binding protein tag of the invention is a wild type nucleic acid binding protein capable of binding a nucleic acid sequence normally found in a target chromatin. In other embodiments, a nucleic acid binding protein tag of the invention is a nucleic acid binding protein engineered to have binding specificity for a nucleic acid sequence component of a target chromatin of the invention. In a preferred embodiment, a nucleic acid binding protein tag of the invention is a zinc finger protein engineered to have binding specificity for a nucleic acid sequence component of a target chromatin of the invention. In another preferred embodiment, a nucleic acid binding protein tag of the invention is a TAL protein engineered to have binding specificity for a nucleic acid sequence component of a target chromatin of the invention.

In other preferred embodiments, a tag of the invention is a protein tag capable of binding a nucleic acid sequence component of a chromatin, wherein the nucleic acid sequence component of the chromatin is an exogenous nucleic acid sequence introduced into a cell of the invention. In exemplary embodiments, a tag of the invention is a protein A tag capable of binding the lexA exogenous nucleic acid sequence introduced in a cell of the invention. In an exemplary embodiment, a tag of the invention is a protein A tag capable of binding the lexA exogenous nucleic acid sequence introduced upstream of the transcriptional start site of the GAL1 promoter of a *S. cereviseae* cell as described in the examples.

A target chromatin may be contacted with a tag at any time during a method of the invention leading to isolation of target chromatin. For instance, a target chromatin may be contacted with a protein tag during cell culture by expressing the protein tag in a cell of the invention. Alternatively, a target chromatin may be contacted with a tag after cell culture but before cell lysis, after cell lysis, or after fragmentation of chromatin to generate chromatin fragments comprising a target chromatin.

In some embodiments, a target chromatin is contacted with a tag after cell culture but before cell lysis. As such, a tag may be introduced into a cell before cell lysis. Methods of introducing a tag into a cell of the invention can and will vary depending on the type of cell, the tag, and the application of a method of the invention. For instance, a nucleic acid tag may be electroporated into a cell after culture. In other embodiments, a target chromatin is contacted with a tag after cell lysis. In yet other embodiments, a target chromatin is contacted with a tag after cell lysis and chromatin fragmentation. In preferred embodiments, a target chromatin is contacted with a tag during cell culture by expressing the tag in a cell of the invention during cell culture. In exemplary embodiments, a target chromatin comprises the lexA binding site, and the lexA binding site is contacted with a protein A tag during cell culture by expressing the protein A in a cell of the invention during cell culture. In an exemplary embodiment, a target chromatin comprises the lexA binding site, and the lexA binding site is contacted with a protein A tag during cell culture by expressing the protein A in a yeast cell of the invention during cell culture as described in the examples.

A target chromatin contacted and bound by a tag as described above may be isolated using an affinity handle of the tag. The term "isolated", may be used herein to describe a purified preparation of a target chromatin that is enriched for the target chromatin, but wherein the target chromatin is not necessarily in a pure form. That is, an isolated target chromatin is not necessarily 100% pure, but may be about 10%, 20%, 30%, 40%, 50%, 60%, 70%, 80% or 90% pure. An isolated target chromatin may be enriched for the target chromatin, relative to a chromatin in the lysed preparation that was not contacted by a tag of the invention. An isolated target chromatin may be enriched by 1, 2, 3, 4, 5, 6, 7, 8, 9, or 10 fold relative to a chromatin that is not contacted by a tag of the invention. In some embodiments, an isolated target chromatin is enriched by 2, 3, 4, or 5 fold relative to a chromatin that was not contacted by a tag of the invention. In other embodiments, an isolated target chromatin is enriched by 5, 6, 7, 8, 9, or 10 fold relative to a chromatin that was not contacted by a tag of the invention. In an exemplary embodiment, an isolated target chromatin is enriched 4, 5, or 6 fold relative to a chromatin that was not contacted by a tag of the invention.

A target chromatin contacted and bound by a tag as described above may be isolated using any affinity purification method known in the art. In short, a tagged target chromatin is bound to a substrate capable of binding the affinity handle. The substrate comprising a bound target chromatin may then be washed to remove non-target chromatin and other cell debris, and the target chromatin may be released from substrate. Methods of affinity purification of material comprising an affinity handle are known in the art and may include binding the affinity handle to a substrate capable of binding the affinity handle. The substrate may be a gel matrix such as gel beads, the surface of a container, or a chip. The tagged target chromatin bound to the substrate may then be purified. Methods of purifying tagged molecules are known in the art and will vary depending on the target molecule, the tag, and the substrate. For instance, if the tag is a protein A tag bound to a lexA binding site in a target chromatin, the target chromatin may be bound to a magnetic bead substrate comprising IgG, and purified using a magnet.

(e) Protein Extraction, Identification, and Determination of Labeling

Proteins and peptides associated with an isolated target chromatin are extracted from the isolated target chromatin. Methods of extracting proteins from chromatin are generally known in the art of protein biochemistry. Generally, any extraction protocol suitable for isolating proteins and known to those of skill in the art may be used. Extracted proteins may also be further purified before protein identification. For instance, protein extracts may be further purified by differential precipitation, differential solubilization, ultracentrifugation, using chromatographic methods such as size exclusion chromatography, hydrophobic interaction chromatography, ion exchange chromatography, affinity chromatography, metal binding, immunoaffinity chromatography, HPLC, or gel electrophoriesis such as SDS-PAGE and QPNC-PAGE. In a preferred embodiment, extracted proteins are further purified using SDS-PAGE.

Extracted and purified intact proteins and post-translational modification of proteins may then be identified. Alternatively, extracted and purified intact proteins may be further digested, and the resulting peptide fragments are identified. In some embodiments, intact extracted proteins are identified. In preferred embodiments, extracted proteins are further digested, and the resulting peptide fragments are identified. For instance, protein extracts may be fragmented by enzymatically digesting the proteins using a protease such as trypsin. In exemplary embodiments, extracted proteins are further digested as described in the examples.

Methods of identifying proteins or protein fragments are known in the art and may include mass spectrometry (MS) analysis, or a combination of mass spectrometry with a chromatographic technique. Non limiting examples of mass spectrometer techniques may include tandem mass spectrometry (MS/MS), matrix-assisted laser desorption/ionization source with a time-of-flight mass analyzer (MALDI-TOF), inductively coupled plasma-mass spectrometry (ICP-MS), accelerator mass spectrometry (AMS), thermal ionization-mass spectrometry (TIMS), isotope ratio mass spectrometry (IRMS), and spark source mass spectrometry (SSMS). Chromatographic techniques that may be used with MS may include gas chromatography, liquid chromatography, and ion mobility spectrometry. In a preferred embodiment, proteins may be identified using tandem mass spectrometry in combination with liquid chromatography (LC-MS/MS). In another preferred embodiment, post-translational modification of proteins may be identified using tandem mass spectrometry in combination with liquid chromatography (LC-MS/MS).

As described above, proteins isolated with a chromatin of the invention may be labeled, unlabeled or a combination of labeled and unlabeled proteins. As described in Section I(d), if a target chromatin is tagged in a cell or an extract from a cell wherein proteins are metabolically labeled, proteins specifically associated with an isolated target chromatin are metabolically labeled, whereas unlabeled proteins, or proteins comprising a combination of labeled and unlabeled proteins are not specifically associated with the target chromatin. Alternatively, if a target chromatin may be tagged in a cell or an extract from a cell wherein proteins are not metabolically labeled, proteins specifically associated with an isolated target chromatin are metabolically labeled, whereas unlabeled proteins, or proteins comprising a combination of labeled and unlabeled proteins are not specifically associated with the target chromatin.

When an isolated and identified protein is a combination of labeled and unlabeled protein, the ratio of labeled to unlabeled protein may reflect a ratio at which a metabolically labeled cell sample and an unlabeled cell sample are combined to generate a combined cell sample, or lysates derived from the two cell samples are combined to generate a combined cell lysate. For instance, if a metabolically labeled cell sample and an unlabeled cell sample, or lysates derived from the two cell samples, are combined at a ratio of 1:1, the ratio of labeled to unlabeled isolated protein may be 1:1.

However, since the ratio of labeled to unlabeled isolated protein depends on the rate of exchange of the identified protein during extraction and processing of a cell sample, a ratio of labeled to unlabeled isolated protein may differ from the ratio at which a metabolically labeled cell sample and an unlabeled cell sample are combined to generate a combined cell sample, or lysates derived from the two cell samples are combined to generate a combined cell lysate. For example, if a metabolically labeled cell sample and an unlabeled cell sample, or lysates derived from the two cell samples, are combined at a ratio of 1:1, a ratio of labeled to unlabeled isolated protein may deviate from a ratio of 1:1. As such, a ratio of labeled to unlabeled isolated protein may be compared to a baseline for non-specifically associated proteins. For instance, a baseline for non-specifically associated proteins may be a ratio of labeled to unlabeled of one or more proteins in a combined lysate, wherein the one or more proteins are not associated with a chromatin. Non-limiting examples of proteins not associated with a chromatin may include enzymes required for metabolism, receptors, and ribosomal proteins. In preferred embodiments, proteins not associated with a chromatin are ribosomal proteins, and a baseline for non-specifically associated proteins is a ratio of a labeled to unlabeled ribosomal protein, or an average of ratios of labeled to unlabeled ribosomal proteins. In a preferred embodiment, proteins not associated with a chromatin are 20 ribosomal proteins, and a baseline for non-specifically associated proteins is an average of ratios of the 20 labeled to unlabeled ribosomal proteins.

Isolated proteins with a ratio of labeled to unlabeled isolated protein may be specifically associated with a chromatin if the ratio of labeled to unlabeled isolated protein is significantly different from a baseline ratio. A significantly different ratio may be a ratio of labeled to unlabeled isolated protein greater than about 1, 2, 3, 4, 5, or more standard deviations than a baseline ratio. In some embodiments, a significantly different ratio is a ratio of labeled to unlabeled isolated protein greater than about 1, 1.5, 2, 2.5, 3, 3.5, 4, 4.5, or more standard deviations than a baseline ratio. In other embodiments, a significantly different ratio is a ratio of labeled to unlabeled isolated protein greater than about 1, 1.5, 2, or about 2.5 standard deviations than a baseline ratio. In preferred embodiments, a significantly different ratio is a ratio of labeled to unlabeled isolated protein greater than about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or about 3 standard deviations than a baseline ratio. In exemplary embodiments, a significantly different ratio is a ratio of labeled to unlabeled isolated protein greater than about 1.5, 1.6, 1.7, 1.8, 1.9, 2, 2.1, 2.2, 2.3, 2.4, or about 2.5 standard deviations than a baseline ratio.

Methods of determining if a protein or a protein fragment is labeled can and will vary depending on the type of label. For instance, if a protein is labeled using a tag, labeling may be determined using methods designed to detect the tag. For example, determining if a protein comprising a his-tag is tagged, untagged, or a combination of tagged and untagged may be by detecting the proteins comprising the his tag. If a protein is labeled using a radioactive isotope, labeling may be determined by determining the degree of radioactivity of isolated proteins or protein fragments. Alternatively, if a protein is labeled using a heavy isotope, MS analysis may be used to determine if a protein or a protein fragment is labeled or unlabeled. Advantageously, when a protein is labeled using a heavy isotope, MS analysis may be used to identify a protein or a protein fragment as described above, and to derive the MS data to determine if a protein or a protein fragment is labeled, unlabeled, or a combination of labeled and unlabeled protein or protein fragment.

In preferred embodiments, a protein is labeled using a heavy isotope, and MS analysis is used to identify a protein or a protein fragment, and to determine if a protein or a protein fragment is labeled, unlabeled, or a combination of labeled and unlabeled protein or protein fragment. Methods of deriving MS data to determine if a protein or a protein fragment is labeled, unlabeled, or a combination of labeled and unlabeled protein or protein fragment are known in the art, and may include using known computational techniques to distill MS data such as Mascot Distiller, Rosetta Elucidator, and MaxQuant. In some embodiments, MS data is derived using Rosetta Elucidator. In other embodiments, MS data is derived using MaxQuant. In preferred embodiments, MS data is derived using Mascot Distiller.

(f) Applications

A method of the invention may be used for any application wherein a determination of chromatin structure or function may be required. For instance, a method of the invention may be used to determine rearrangement in chromatin structure, genome metabolism, epigenetic regulatory mechanisms, transient association of proteins with chromatin, initiation or silencing of expression of a nucleic acid sequence, identify proteins transiently associated with a chromatin, or post-translational modification of proteins associated with a chromatin or chromatin rearrangement. An application of a method of the invention may include determining changes in chromatin function and structure in response to changing growth conditions, exposure to a drug or small molecule, or during stages of cell cycles.

In some embodiments, a method of the invention is used to determine differences in chromatin structure and function between a transcriptionally silent and a transcriptionally active state of a genomic locus. As such, proteins specifically associated with a genomic locus, and post-translational modifications of proteins associated with a chromatin comprising the genomic locus may be determined in cells comprising a transcriptionally silent state of a genomic locus, and in cells comprising a transcriptionally active state of a genomic locus. In preferred embodiments, a method of the invention is used to determine differences in chromatin structure and function between a transcriptionally silent and a transcriptionally active state of a *Saccharomyces cerevisiae* GAL1 genomic locus.

II. Method of TAL-ChAP-MS

Figure 7:
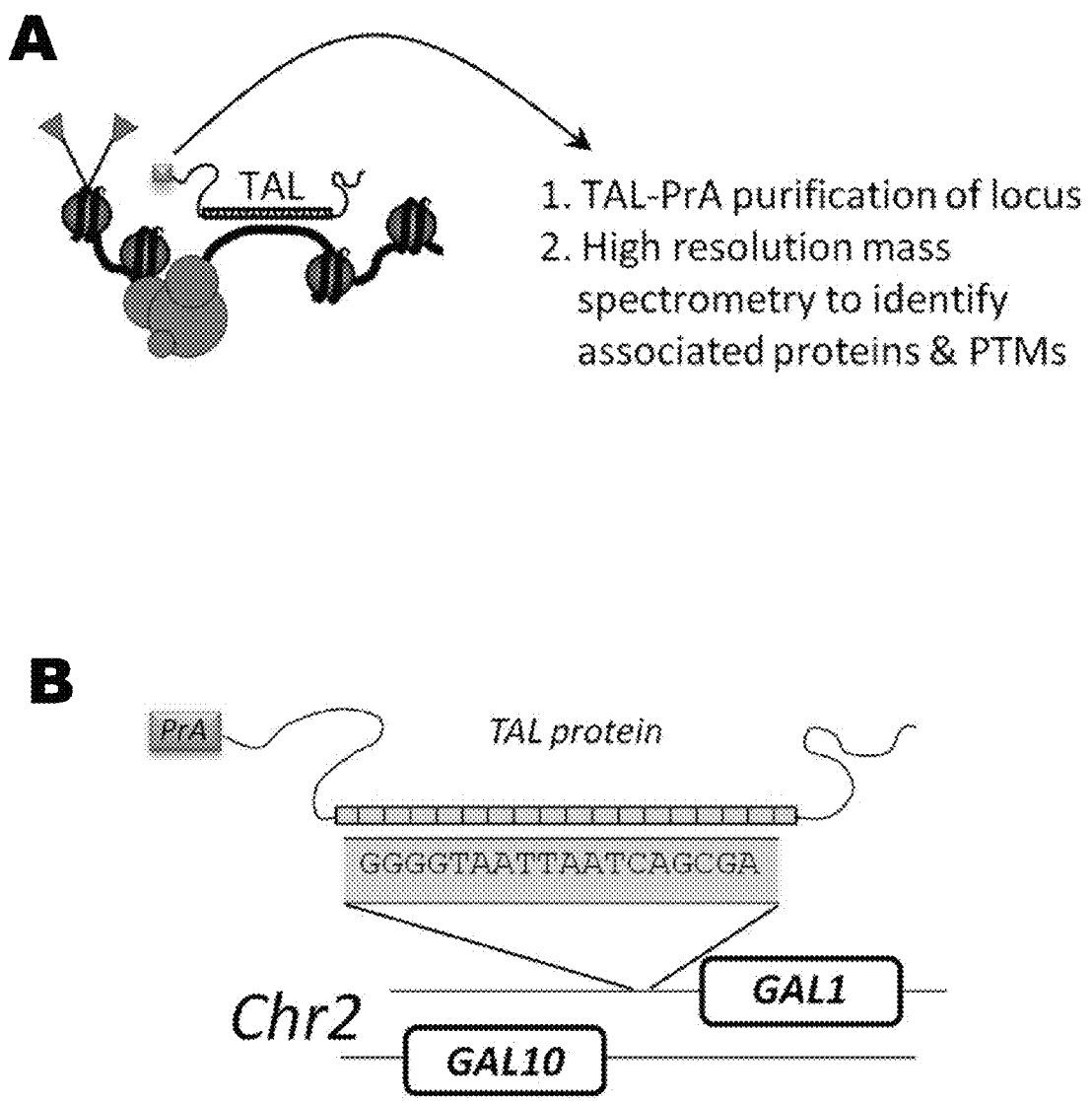
FIG. 7 depicts diagrams and graphs showing that TAL proteins can specifically enrich native chromatin sections. (A) Schematic overview of TAL-ChAP-MS technology. (B) A unique DNA sequence in the promoter region of GAL1 was used to design a specific binding TAL protein that contained a PrA affinity tag. (C) A pTAL-PrA plasmid was introduced into S. cerevisiae cells, and the constitutive expression of the TAL-PrA fusion protein was confirmed by western blotting for PrA. (D) Expression of TAL-PrA does not impede galactose-induced GAL1 transcription. cDNA from wild-type yeast and wild-type with a plasmid expressing PrA-tagged TAL (+pTAL-PrA) grown in glucose (Glu) or galactose (Gal) was used as a template for real time PCR analysis of GAL1 versus ACT1 gene transcription. Error bars are the standard deviation. (E-G) TAL-PrA specifically binds and enriches chromatin at the promoter of transcriptionally active GAL1. ChIP was performed to the PrA-tag in wild-type cells containing the TAL-PrA (+pTAL-PrA, light gray bars) and in wild-type control (dark gray bars). The efficiency of GAL1 enrichment relative to ACT1 was monitored by real-time PCR with primers targeted to the TAL binding site ('0') and to DNA sequences 2000 by up- and downstream (E). The standard deviation is indicated. (F) Under transcriptionally active conditions (galactose), TAL-PrA specifically enriched chromatin from the GAL1 promoter region relative to sequences 2 kb up- and downstream. (G) The TAL-PrA protein did not show enrichment of the GAL1 promter chromatin under transcriptionally repressive glucose growth conditions.
Figure 7:
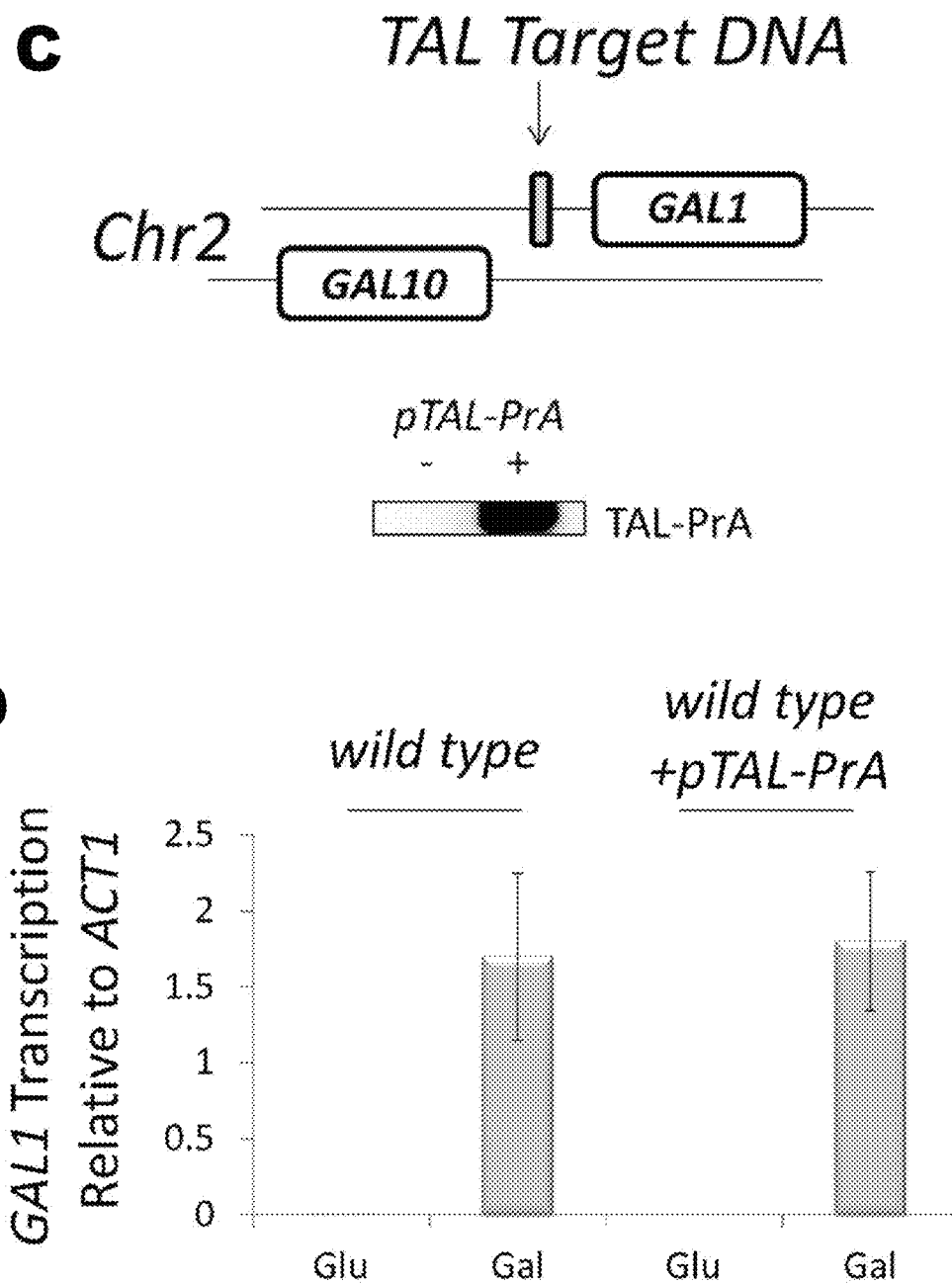
Figure 7:
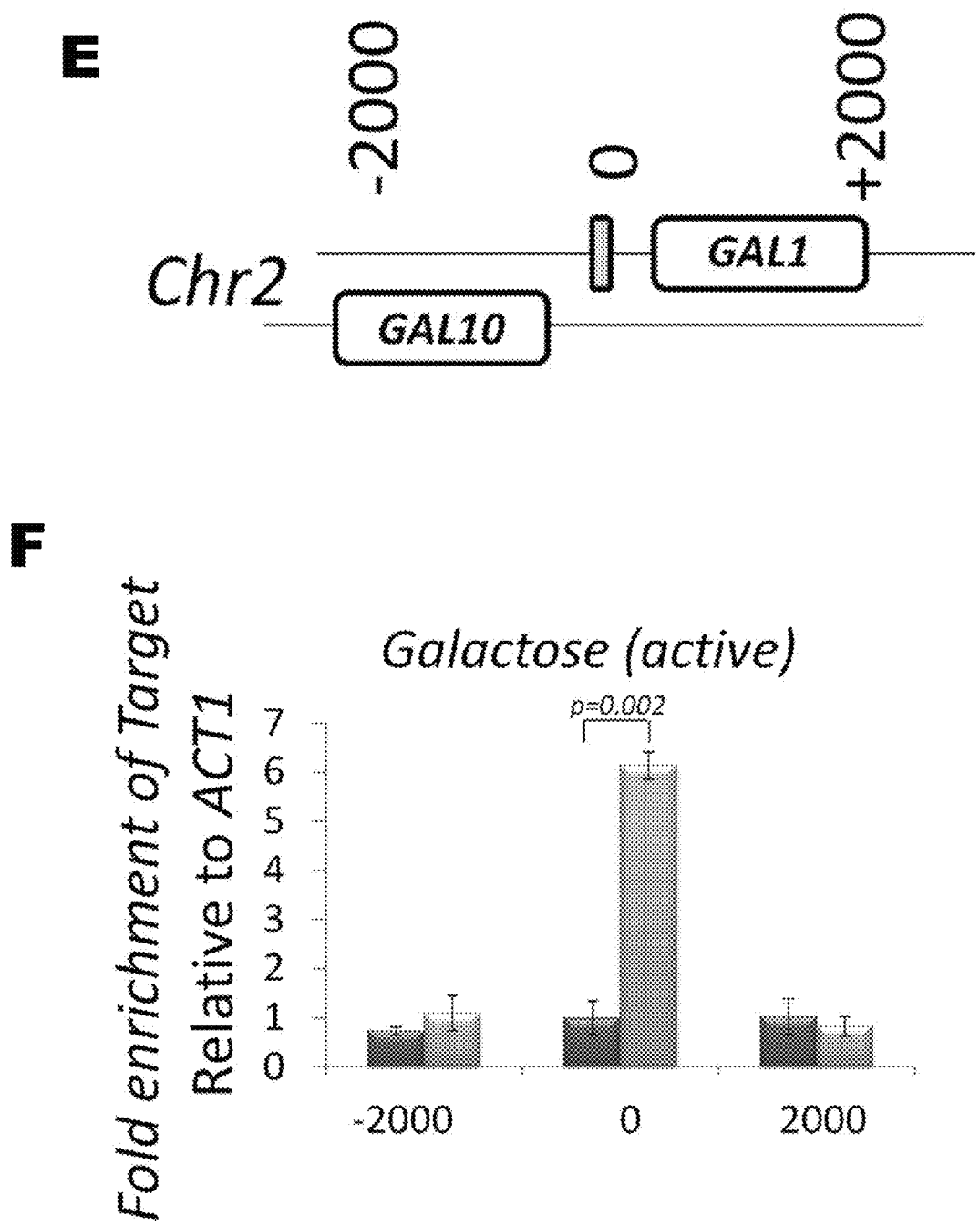

In some aspects, the invention provides methods of isolating and identifying proteins specifically associated with a target chromatin. As described in Example 4 and FIG. 7, a method of the invention comprises isolating a target chromatin from a cell. As used herein, a "target chromatin" refers to a specific chromatin or a chromatin fragment that may be used in an application of the invention. According to the method, isolating the target chromatin isolates nucleic acid sequences and proteins, including proteins comprising posttranslational modifications, associated with the target chromatin. The proteins and posttranslational modifications of proteins associated with the target chromatin may then be identified, and a determination of which of the identified proteins and posttranslational modifications of proteins associated with a target chromatin isolated from a cell are specifically or non-specifically associated with the target chromatin is made.

To determine which of the identified proteins and posttranslational modifications of proteins associated with a target chromatin isolated from a cell are specifically or non-specifically associated with the target chromatin, a method of high-resolution mass spectrometry coupled with label-free proteomics was used. One with skill in the art will appreciate that label-free quantitative proteomics methods include the following fundamental steps: (i) sample preparation including protein extraction, reduction, alkylation, and digestion; (ii) sample separation by liquid chromatography (LC or LC/LC) and analysis by MS/MS; (iii) data analysis including peptide/protein identification, quantification, and statistical analysis. A method of the invention provides two cell samples, or lysates derived from two cell samples, comprising the target chromatin, wherein the target chromatin in one cell sample, but not both of the cell samples is tagged. With label-free quantitiative methods, each sample is separately prepared, then subjected to individual LC-MS/MS or LC/LC-MS/MS runs. As reviewed in Zhu et al., J Biomed Biotechnol 2010, and incorporated by reference herein, protein quantification is generally based on two categories of measurements. In the first are the measurements of ion intensity changes such as peptide peak areas or peak heights in chromatography. The second is based on spectral counting of identified proteins after MS/MS analysis. Peptide peak intensity or spectral count is measured for individual LC-MS/MS or LC/LC-MS/MS runs and changes in protein abundance are calculated via a direct comparison between different analyses.

In the present invention, the method of spectral counting is used to categorize whether proteins enriched with a section of chromatin are specific or contaminant. As such, determining the abundance of an identified protein in a tagged chromatin sample compared to the same protein in an untagged chromatin sample, may determine if the protein was specifically associated with the target chromatin of the invention. If a protein associated with a target chromatin is enriched in a tagged chromatin sample compared to the same protein in an untagged chromatin sample, then the protein is specifically associated with the target chromatin. If an identified protein is not enriched in a tagged chromatin sample compared to an untagged chromatin sample, then association of that protein with the target chromatin is not specific.

In the present invention, to measure enrichment of a protein, the normalized spectral abundance factor (NSAF) is calculated for each protein in each lane of an SDS-PAGE gel by dividing the number of spectral counts (normalized for the size of the protein) of a given protein by the sum of all normalized spectral counts of all proteins in the gel lane. The enrichment level for each protein is identified by calculating the fold enrichment (tagged chromatin/untagged chromatin) using the NSAF values.

(a) Cells

A target nucleic acid sequence may be isolated from any cell comprising the target nucleic acid sequence of the invention. A cell may be an archaebacterium, a *eubacterium*, or a eukaryotic cell. For instance, a cell of the invention may be a methanogen, a halophile or a thermoacidophile archaeabacterium, a gram positive, a gram negative, a cyanobacterium, a spirochaete, or a firmicute bacterium, a fungal cell, a moss cell, a plant cell, an animal cell, or a protist cell.

In some embodiments, a cell of the invention is a cell from an animal. A cell from an animal cell may be a cell from an embryo, a juvenile, or an adult. Suitable animals include vertebrates such as mammals, birds, reptiles, amphibians, and fish. Examples of suitable mammals include without limit rodents, companion animals, livestock, and primates. Non-limiting examples of rodents include mice, rats, hamsters, gerbils, and guinea pigs. Suitable companion animals include but are not limited to cats, dogs, rabbits, hedgehogs, and ferrets. Non-limiting examples of livestock include horses, goats, sheep, swine, cattle, llamas, and alpacas. Suitable primates include but are not limited to humans, capuchin monkeys, chimpanzees, lemurs, macaques, marmosets, tamarins, spider monkeys, squirrel monkeys, and vervet monkeys. Non-limiting examples of birds include chickens, turkeys, ducks, and geese. In some embodiments, a cell is a cell from a human.

In some embodiments, a cell may be from a model organism commonly used in laboratory research. For instance, a cell of the invention may be an *E. coli*, a *Bacillus subtilis*, a *Caulobacter crescentus*, a *Mycoplasma genitalium*, an *Aliivibrio fischeri*, a *Synechocystis*, or a *Pseudomonas fluorescens* bacterial cell; a *Chlamydomonas reinhardtii*, a *Dictyostelium discoideum*, a *Tetrahymena thermophila*, an *Emiliania huxleyi*, or a *Thalassiosira pseudonana* protist cell; an *Ashbya gossypii*, an *Aspergillus nidulans*, a *Coprinus cinereus*, a *Cunninghamella elegans*, a *Neurospora crassa*, a *Saccharomyces cerevisiae*, a *Schizophyllum commune*, a *Schizosaccharomyces pombe*, or an *Ustilago maydis* fungal cell; an *Arabidopsis thaliana*, a *Selaginella moellendorffii*, a *Brachypodium distachyon*, a *Lotus japonicus*, a *Lemna gibba*, a *Zea mays*, a *Medicago truncatula*, a *Mimulus*, a tobacco, a rice, a *Populus*, or a *Nicotiana benthamiana* plant cell; a *Physcomitrella patens* moss; an *Amphimedon queenslandica* sponge, an *Arbacia punctulata* sea urchin, an *Aplysia* sea slug, a *Branchiostoma floridae* deuterostome, a *Caenorhabditis elegans* nematode, a *Ciona intestinalis* sea squirt, a *Daphnia* spp. crustacean, a *Drosophila* fruit fly, a *Euprymna scolopes* squid, a *Hydra* Cnidarian, a *Loligo pealei* squid, a *Macrostomum lignano* flatworm, a *Mnemiopsis leidyi* comb jelly, a *Nematostella vectensis* sea anemone, an *Oikopleura dioica* free-swimming tunicate, an *Oscarella carmela* sponge, a *Parhyale hawaiensis* crustacean, a *Platynereis dumerilii* marine polychaetous annelid, a *Pristionchus pacificus* roundworm, a *Schmidtea mediterranea* freshwater planarian, a *Stomatogastric* ganglion of various arthropod species, a *Strongylocentrotus purpuratus* sea urchin, a *Symsagittifera roscoffensis* flatworm, a *Tribolium castaneum* beetle, a *Trichoplax adhaerens* Placozoa, a *Tubifex tubifex* oligochaeta, a laboratory mouse, a Guinea pig, a Chicken, a Cat, a Dog, a Hamster, a Lamprey, a Medaka fish, a Rat, a Rhesus macaque, a Cotton rat, a Zebra finch, a Takifugu pufferfish, an African clawed frog, or a Zebrafish. In exemplary embodiments, a cell is a *Saccharomyces cerevisiae* yeast cell. In particularly exemplary embodiments, a cell is a *Saccharomyces cerevisiae* W303a yeast cell.

A cell of the invention may be derived from a tissue or from a cell line grown in tissue culture. A cell line may be adherent or non-adherent, or a cell line may be grown under conditions that encourage adherent, non-adherent or organotypic growth using standard techniques known to individuals skilled in the art. Cell lines and methods of culturing cell lines are known in the art. Non-limiting examples of cell lines commonly cultured in a laboratory may include HeLa, a cell line from the National Cancer Institute's 60 cancer cell lines, DU145 (prostate cancer), Lncap (prostate cancer), MCF-7 (breast cancer), MDA-MB-438 (breast cancer), PC3 (prostate cancer), T47D (breast cancer), THP-1 (acute myeloid leukemia), U87 (glioblastoma), SHSYSY Human neuroblastoma cells, Saos-2 cells (bone cancer), Vero, GH3 (pituitary tumor), PC12 (pheochromocytoma), MC3T3 (embryonic calvarium), Tobacco BY-2 cells, Zebrafish ZF4 and AB9 cells, Madin-Darby canine kidney (MDCK), or *Xenopus* A6 kidney epithelial cells.

As described in Section (II) above, two cell samples, or lysates derived from two cell samples may be subjected to mass-spectrometry coupled with label-free proteomics, one sample of which contains a tagged target chromatin of the invention. Typically, cells in two cell samples of the invention are from the same type of cells or they may be derived from the same type of cells. For instance, cells may comprise a heterologous protein expressed in a cell of the invention. The heterologous protein expressed in a cell may be used for tagging a target chromatin as described in Section II(d). In some embodiments, cells in two cell samples of the invention are from the same type of cells. In other embodiments, cells in the first cell sample are derived from the same cell type as cells in the second cell sample.

Two cell samples of the invention may be from the same genus, species, variety or strain of cells. In preferred embodiments, two cell samples of the invention are *Saccharomyces cerevisiae* yeast cells or derivatives of *Saccharomyces cerevisiae* yeast cells. In exemplary embodiments, two cell samples of the invention are *Saccharomyces cerevisiae* W303a yeast cells or derivatives of *Saccharomyces cerevisiae* W303a yeast cells. In exemplary embodiments, two cell samples of the invention are derivatives of *Saccharomyces cerevisiae* W303a yeast cells, wherein protein A tagged transcription activator-like (TAL) protein engineered to bind upstream of the GAL1 transcription start site is expressed in one of the cell samples of derived *Saccharomyces cerevisiae* W303a yeast cells.

The number of cells in a cell sample can and will vary depending on the type of cells, the abundance of a target chromatin in a cell, and the method of protein identification used, among other variables. For instance, if a cell of the invention is *Saccharomyces cerevisiae*, about $5 \times 10^{11}$ to about $5 \times 10^{12}$, more preferably, about $1 \times 10^{11}$ to about $1 \times 10^{12}$ cells may be used in a cell sample. In some embodiments, about $1 \times 10^{11}$ to about $1 \times 10^{12}$ *Saccharomyces cerevisiae* cells are used in a cell sample.

Two cell samples of the invention are typically grown identically. Identically grown cell samples minimizes potential structural or functional differences at a target chromatin present in both cell samples. As used herein, "grown identically" refers to cultured cell samples grown using similar culture condition, or cells from a tissue harvested using identical harvesting techniques.

(b) Chromatin

A method of the invention comprises identification of a protein and post-translational modification of a protein associated with a target chromatin. Generally, chromatin refers to the combination of nucleic acids and proteins in the nucleus of a eukaryotic cell. However, it is contemplated that the term "chromatin" may also refer to the combination of any nucleic acid sequence and proteins associated with the nucleic acid sequence in any cell.

Chromatin of the invention may be as described in Section I(b) above.

(c) Preparation of Cell Lysate

A target chromatin is isolated from a cell lysate derived from a cell sample, wherein a target chromatin is tagged in the cell sample. The method of isolating a target chromatin is also performed on a cell lysate derived from a cell sample, wherein a target chromatin is untagged in the cell sample. A skilled practitioner of the art will appreciate that structural and functional features of a target chromatin must be preserved during cell lysis and isolation of the target chromatin. The association of proteins with a target chromatin may be preserved during cell lysis and isolation of the target chromatin using methods known in the art for preserving a complex of proteins with a nucleic acid sequence. For instance, lysing of a cell and isolation of a target chromatin may be performed under refrigeration or using cryogenic methods and buffer conditions capable of preserving association of proteins and nucleic acid sequences. In addition, a complex of proteins with a nucleic acid may be preserved by crosslinking protein and nucleic acid complexes in a cell prior to lysing and isolating a chromatin. Crosslinking protein and nucleic acid complexes in a cell may also capture, or preserve, transient protein-protein and protein-nucleic acid interactions.

In some embodiments, a complex of proteins with a nucleic acid may be preserved by crosslinking protein and nucleic acid complexes in a chromatin prior to lysing a cell and isolating the chromatin. Crosslinking is the process of joining two or more molecules such as two proteins or a protein and a nucleic acid molecule, by a covalent bond. Molecules may be crosslinked by irradiation with ultraviolet light, or by using chemical crosslinking reagents. Chemical crosslinking reagents capable of crosslinking proteins and nucleic acids are known in the art and may include crosslinking reagents that target amines, sulfhydryls, carboxyls, carbonyls or hydroxyls; omobifunctional or heterobifunctional crosslinking reagent, variable spacer arm length or zero-length crosslinking reagents, cleavable or non-cleavable crosslinking reagents, and photoreactive crosslinking reagents. Non-limiting examples of crosslinking reagents that may be used to crosslink protein complexes and/or protein complexes and nucleic acids may include formaldehyde, glutaraldehyde, disuccinimidyl glutarate, disuccinimidyl suberate, a photoreactive amino acid such as photo-leucine or photo-methionine, and succinimidyl-diazirine. The degree of crosslinking can and will vary depending on the application of a method of the invention, and may be experimentally determined.

In a preferred embodiment, a complex of proteins with a nucleic acid in a chromatin of the invention may be preserved by crosslinking protein and nucleic acid complexes in a cell prior to lysing using formaldehyde. In an exemplary embodiment, a complex of proteins with a nucleic acid in a chromatin of the invention may be preserved by crosslinking protein and nucleic acid complexes in a cell prior to lysing using formaldehyde as described in the examples.

A skilled practitioner of the art will appreciate that protocols for lysing a cell can and will vary depending on the type of cell, the target chromatin of the invention, and the specific application of a method of the invention. Non limiting examples of methods that may be used to lyse a cell of the invention may include cell lysis using a detergent, an enzyme such as lysozyme, incubation in a hypotonic buffer which causes a cell to swell and burst, mechanical disruption such as liquid homogenization by forcing a cell through a narrow space, sonication, freeze/thaw, mortar and pestle, glass beads, and combinations thereof. In some embodiments, when a cell of the invention is a yeast cell, the cell may be cryogenically lysed under liquid nitrogen temperature with glass beads. In exemplary embodiments, when a cell of the invention is a yeast cell, the cell may be cryogenically lysed under liquid nitrogen temperature with glass beads as described in the examples.

Buffer conditions used during lysing and isolation of a chromatin of the invention can and will be altered to control stringent conditions during cell lysis and isolation to preserve association of proteins and nucleic acid sequences of a chromatin. "Stringent conditions" in the context of chromatin isolation are conditions capable of preserving specific association of proteins and nucleic acids of a chromatin, but minimizing non-specific association of proteins and nucleic acids. Stringent condition can and will vary depending on the application of a method of the invention, the target chromatin of the invention, the nucleic acid sequence in a target chromatin, the proteins or protein complexes associated with a target chromatin of the invention, whether or not proteins, protein complexes and nucleic acid sequences are crosslinked, and the conditions used for crosslinking proteins, protein complexes and nucleic acid sequences of a target chromatin. For instance, more stringent buffer conditions may be used in a method of the invention wherein proteins, protein-protein complexes, and protein-nucleic acid complexes are crosslinked compared to a method of the invention wherein proteins, protein-protein complexes, and protein-nucleic acid complexes are not crosslinked. As such, stringent buffer conditions used during cell lysis and isolation of a nucleic acid sequence of the invention may be experimentally determined for each application wherein a method of the invention is used. Buffer conditions that may alter stringent conditions during cell lysis and isolation may include pH and salt concentration. In preferred embodiments, proteins, protein-protein complexes, and protein-nucleic acid complexes of a target chromatin of the invention are crosslinked, and stringent buffer conditions are used during lysis and isolation of a chromatin of the invention. In exemplary embodiments, proteins, protein-protein complexes, and protein-nucleic acid complexes of a target chromatin of the invention are crosslinked, and stringent buffer conditions are used during lysis and isolation of a chromatin of the invention and are as described in the examples.

(d) Chromatin Isolation

According to the invention, the method of isolating a target chromatin is performed on cell lysates derived from cell samples, wherein one sample comprises a target chromatin that is tagged in the cell sample and one sample comprises a target chromatin that is untagged in the cell sample. As described in Sections II(a) and II(c) above, a cell lysate comprises a lysate of a cell sample, wherein a target chromatin is tagged in one of the lysates, or one of the cell samples. A cell lysate also comprises a lysate of a cell sample, wherein a target chromatin is not tagged in one of the lysates, or one of the cell samples.

A target chromatin may be isolated from a mixture of chromatins or chromatin fragments in a cell lysate as described in this section. As used herein, a target nucleic acid sequence is said to be "isolated" or "purified" when it is substantially free of proteins not associated with the target chromatin, nucleic acid sequences other than the nucleic acid sequences associated with the target chromatin, and other cell debris and cell contents resulting from extraction and preparation of the target chromatin from a cell. A target chromatin of the present invention may be purified to homogeneity or other degrees of purity. In general, the level of purity of an isolated target chromatin can and will vary depending on the cell type, the specific chromatin to be isolated, and the intended use of a target chromatin of the invention. The level of purity of an isolated target chromatin may be determined using methods known in the art. For instance, the level of purity of an isolated target chromatin may be determined by determining the level of purity of a nucleic acid sequence associated with a target chromatin, by determining the level of purity of a protein associated with a target chromatin, or by determining the level of enrichment of a target chromatin, compared to a non-target chromatin in a cell. In preferred embodiments, the level of purity of an isolated target chromatin is determined by determining the level of enrichment of a target chromatin, compared to a non-target chromatin in a cell. Determining the level of enrichment of a target chromatin, compared to a non-target chromatin in a cell may be as described in this section below.

A target chromatin of the invention may be isolated using methods known in the art, such as electrophoresis, molecular, immunological and chromatographic techniques, ion exchange, hydrophobic, affinity, and reverse-phase HPLC chromatography, size exclusion chromatography, precipitation, dialysis, chromatofocusing, ultrafiltration and diafiltration techniques, and combinations thereof. For general guidance in suitable purification techniques, see Scopes, R., Protein Purification, Springer-Vertag, NY (1982).

In general, a method of the invention comprises isolating a target chromatin by affinity purification, or affinity purification in combination with other methods of isolating chromatin described above. In a preferred embodiment, a method of the invention comprises isolating a target chromatin by affinity purification. Non limiting examples of affinity purification techniques that may be used to isolate a target chromatin of the invention may include affinity chromatography, immunoaffinity chromatography, size exclusion chromatography, and combinations thereof. See, for example, Roe (ed), Protein Purification Techniques: A Practical Approach, Oxford University Press, 2nd edition, 2001.

In essence, affinity purification of a target chromatin may comprise tagging a target chromatin by contacting the target chromatin of the invention with a tag capable of specifically recognizing and binding one or more portions of a target chromatin. As described in Section (II), a target chromatin from one cell sample, or lysate derived from the cell sample of the invention, but not both of the cell samples, is tagged.

A tag may be capable of specifically recognizing and binding 1, 2, 3, 4, 5, 6, 7, 8, 9, or 10 components of a target chromatin. In preferred embodiments, a tag is capable of specifically recognizing and binding one component of a target chromatin.

A tag may be capable of specifically recognizing and binding a component in a target chromatin. A component in a target chromatin may be a nucleic acid sequence in a nucleic acid associated with a target chromatin, a protein associated with a target chromatin, or a chromatin structural or functional feature in a target chromatin. In some embodiments, a tag is capable of specifically recognizing and binding a protein associated with a target chromatin. In other embodiments, a tag is capable of specifically recognizing and binding a chromatin structural or functional feature in a target chromatin. In preferred embodiments, a tag is capable of specifically recognizing and binding a nucleic acid sequence associated with a target chromatin.

A nucleic acid sequence associated with a target chromatin that may be specifically recognized and bound by a tag of the invention may be a nucleic acid sequence normally found in a chromatin of a cell of the invention. In some embodiments, a nucleic acid sequence that may be recognized and bound by a tag is a nucleic acid sequence normally found in a chromatin of a cell of the invention.

Individuals of ordinary skill in the art will recognize that an exogenous chromatin component introduced into a cell to facilitate tagging a target chromatin of the invention cannot and will not disrupt a target chromatin, or a structural or functional feature of a target chromatin. Methods of designing a chromatin component and a tag capable of binding the chromatin component that do not disrupt a chromatin of the invention may depend on the particular application of a method of the invention, and may be determined experimentally. For instance, if an application of a method of the invention comprises promoter function, a tag may be designed to bind anywhere adjacent to the promoter, but without disrupting the promoter.

A tag of the invention may further comprise one or more affinity handles. As used herein, the term "affinity handle" may refer to any handle that may be bound by a substrate for affinity purification, as described below. A tag may comprise one or more than one affinity handle. The inclusion of more than one affinity handle in a tag of the invention may significantly increase the efficiency of affinity purification for a low copy number chromatin target. As such, a tag may further comprise 1, 2, 3, 4, 5, 6, 7, 8, 9, 10 or more affinity handles. In a preferred embodiment, a tag of the invention comprises one affinity handle.

Affinity handles may include any affinity handle for which a cognate binding agent is readily available. An affinity handle may be an aptamer, an antibody, an antibody fragment, a double-stranded DNA sequence, modified nucleic acids and nucleic acid mimics such as peptide nucleic acids, locked nucleic acids, phosphorodiamidate morpholino oligomers (PMO), a ligand, a ligand fragment, a receptor, a receptor fragment, a polypeptide, a peptide, a coenzyme, a coregulator, an allosteric molecule, non-immunoglobulin scaffolds such as Affibodies, Anticalins, designed Ankyrin repeat proteins and others, an ion, or a small molecule for which a cognate binding agent is readily available. The term "aptamer" refers to a polypeptide or a polynucleotide capable of binding to a target molecule at a specific region. It is generally accepted that an aptamer, which is specific in its binding to any polypeptide, may be synthesized and/or identified by in vitro evolution methods. Non limiting examples of handles that may be suitable for isolating a chromatin may include biotin or a biotin analogue such as desthiobiotin, digoxigenin, dinitrophenol or fluorescein, a macromolecule that binds to a nucleic acid or a nucleic acid binding protein such as the Lac repressor, a zinc finger protein, a transcription activator protein capable of binding a nucleic acid, or a transcription activator-like (TAL) protein, antigenic polypeptides such as protein A, or peptide 'tags' such as polyhistidine, FLAG, HA and Myc tags. In preferred embodiments, a tag of the invention comprises an antigenic polypeptide. In other preferred embodiments, a tag of the invention comprises the protein A tagged TAL protein, or derivatives thereof. The TAL protein can be engineered to have binding specificity for a nucleic acid sequence component of a target chromatin of the invention. As such, TAL may be used as an affinity purification tag for purifying a target chromatin. Protein A comprises an affinity handle capable of binding IgG. In exemplary embodiments, a tag of the invention comprises the protein A tagged TAL protein engineered to bind upstream of the GAL1 transcription start site.

In some embodiments, a tag of the invention is a nucleic acid tag capable of binding a nucleic acid sequence component of a chromatin, wherein the nucleic acid sequence component of the chromatin is introduced into a cell of the invention. In some embodiments, a tag of the invention is a nucleic acid tag capable of binding a nucleic acid sequence component of a chromatin, wherein the nucleic acid sequence component of the chromatin is normally present in a cell of the invention. Non-limiting examples of nucleic acid tags capable of binding a nucleic acid sequence component of a chromatin include antisense RNA or DNA nucleic acid tags, and tags comprising modified nucleic acids and nucleic acid mimics such as peptide nucleic acids, locked nucleic acids, phosphorodiamidate morpholino oligomers (PMO). In some embodiments, a tag of the invention is a nucleic acid tag comprising locked nucleotides. For instance, a nucleic acid tag comprising locked nucleotides may be as described in US20110262908 or US20120040857, and a peptide nucleic acid tag may be as described in Boffa et al. 1995 PNAS 92:1901-1905, the disclosures of all of which are incorporated herein in their entirety.

In some preferred embodiments, a tag of the invention is a protein tag capable of binding a nucleic acid sequence component of a chromatin, wherein the nucleic acid sequence component of the chromatin is a nucleic acid sequence normally found in a chromatin of a cell of the invention. Non limiting examples of a protein tag capable of binding a nucleic acid sequence normally found in a chromatin of a cell may be a nucleic acid binding protein such as protein A, the Lac repressor, a zinc finger protein, a transcription activator protein capable of binding a nucleic acid, or a transcription activator-like (TAL) protein. In one embodiment, a tag of the invention is a transcription activator protein capable of binding a nucleic acid sequence normally found in a chromatin of a cell of the invention. In another embodiment, a tag of the invention is a zinc finger protein capable of binding a nucleic acid sequence normally found in a chromatin of a cell of the invention. In an exemplary embodiment, a tag of the invention is a protein A tagged transcription activator-like (TAL) protein capable of binding a nucleic acid sequence normally found in a chromatin of a cell of the invention.

A nucleic acid binding protein tag of the invention may be a wild type nucleic acid binding protein capable of binding a nucleic acid sequence normally found in a target chromatin. Alternatively, a nucleic acid binding protein tag of the invention may be engineered to have binding specificity for a nucleic acid sequence component normally found in a target chromatin of the invention. Individuals of ordinary skill in the art will recognize that nucleic acid binding proteins such as zinc finger proteins, transcription activator proteins, and transcription activator-like (TAL) proteins may be engineered to have novel nucleic acid binding specificity compared to naturally-occurring forms of the proteins. See, for example, U.S. Pat. Nos. 6,453,242 and 6,534,261, and U.S. Pate. Appl. Nos 20110239315, 20120110685, and 20120270273, the disclosures of which are incorporated by reference herein in their entireties. In some embodiments, a nucleic acid binding protein tag of the invention is a wild type nucleic acid binding protein capable of binding a nucleic acid sequence normally found in a target chromatin. In other embodiments, a nucleic acid binding protein tag of the invention is a nucleic acid binding protein engineered to have binding specificity for a nucleic acid sequence component of a target chromatin of the invention. In a preferred embodiment, a nucleic acid binding protein tag of the invention is a zinc finger protein engineered to have binding specificity for a nucleic acid sequence component of a target chromatin of the invention. In an exemplary embodiment, a nucleic acid binding protein tag of the invention is a TAL protein engineered to have binding specificity for a nucleic acid sequence component of a target chromatin of the invention.

In other preferred embodiments, a tag of the invention is a protein tag capable of binding a nucleic acid sequence component of a chromatin, wherein the nucleic acid sequence component of the chromatin is a nucleic acid sequence normally found in a cell of the invention. In exemplary embodiments, a tag of the invention is a protein A tagged TAL protein capable of binding a nucleic acid sequence normally found in a cell of the invention. In an exemplary embodiment, a tag of the invention is a protein A tagged TAL protein capable of binding a nucleic acid sequence normally found in a cell upstream of the transcriptional start site of the GAL1 promoter of a S. cereviseae cell as described in the examples.

A target chromatin may be contacted with a tag at any time during a method of the invention leading to isolation of target chromatin. For instance, a target chromatin may be contacted with a protein tag during cell culture by expressing the protein tag in a cell of the invention. Alternatively, a target chromatin may be contacted with a tag after cell culture but before cell lysis, after cell lysis, or after fragmentation of chromatin to generate chromatin fragments comprising a target chromatin.

In some embodiments, a target chromatin is contacted with a tag after cell culture but before cell lysis. As such, a tag may be introduced into a cell before cell lysis. Methods of introducing a tag into a cell of the invention can and will vary depending on the type of cell, the tag, and the application of a method of the invention. For instance, a nucleic acid tag may be electroporated into a cell after culture. In other embodiments, a target chromatin is contacted with a tag after cell lysis. In yet other embodiments, a target chromatin is contacted with a tag after cell lysis and chromatin fragmentation. In preferred embodiments, a target chromatin is contacted with a tag during cell culture by expressing the tag in a cell of the invention during cell culture. In exemplary embodiments, a target chromatin is contacted with a protein A tagged TAL protein during cell culture by expressing the protein A tagged TAL protein in a cell of the invention during cell culture. In an exemplary embodiment, a target chromatin is contacted with a protein A tagged TAL protein during cell culture by expressing the protein A tagged TAL protein in a yeast cell of the invention during cell culture as described in the examples.

A target chromatin contacted and bound by a tag as described above may be isolated using an affinity handle of the tag. The term "isolated", may be used herein to describe a purified preparation of a target chromatin that is enriched for the target chromatin, but wherein the target chromatin is not necessarily in a pure form. That is, an isolated target chromatin is not necessarily 100% pure, but may be about 10%, 20%, 30%, 40%, 50%, 60%, 70%, 80% or 90% pure. An isolated target chromatin may be enriched for the target chromatin, relative to a chromatin in the lysed preparation that was not contacted by a tag of the invention. An isolated target chromatin may be enriched by 1, 2, 3, 4, 5, 6, 7, 8, 9, or 10 fold relative to a chromatin that is not contacted by a tag of the invention. In some embodiments, an isolated target chromatin is enriched by 2, 3, 4, or 5 fold relative to a chromatin that was not contacted by a tag of the invention. In other embodiments, an isolated target chromatin is enriched by 5, 6, 7, 8, 9, or 10 fold relative to a chromatin that was not contacted by a tag of the invention. In an exemplary embodiment, an isolated target chromatin is enriched 4, 5, or 6 fold relative to a chromatin that was not contacted by a tag of the invention.

A target chromatin contacted and bound by a tag as described above may be isolated using any affinity purification method known in the art. In short, a tagged target chromatin is bound to a substrate capable of binding the affinity handle. The substrate comprising a bound target chromatin may then be washed to remove non-target chromatin and other cell debris, and the target chromatin may be released from substrate. Methods of affinity purification of material comprising an affinity handle are known in the art and may include binding the affinity handle to a substrate capable of binding the affinity handle. The substrate may be a gel matrix such as gel beads, the surface of a container, or a chip. The tagged target chromatin bound to the substrate may then be purified. Methods of purifying tagged molecules are known in the art and will vary depending on the target molecule, the tag, and the substrate. For instance, if the tag is a TAL-protein A tag bound to a site in a target chromatin, the target chromatin may be bound to a magnetic bead substrate comprising IgG, and purified using a magnet.

(e) Protein Extraction, Identification, and Determination of Labeling

Proteins and peptides associated with an isolated target chromatin are extracted from the isolated target chromatin. Methods of extracting proteins from chromatin are generally known in the art of protein biochemistry. Generally, any extraction protocol suitable for isolating proteins and known to those of skill in the art may be used. Extracted proteins may also be further purified before protein identification. For instance, protein extracts may be further purified by differential precipitation, differential solubilization, ultracentrifugation, using chromatographic methods such as size exclusion chromatography, hydrophobic interaction chromatography, ion exchange chromatography, affinity chromatography, metal binding, immunoaffinity chromatography, HPLC, or gel electrophoriesis such as SDS-PAGE and QPNC-PAGE. In a preferred embodiment, extracted proteins are further purified using SDS-PAGE.

Extracted and purified intact proteins and post-translational modification of proteins may then be identified. Alternatively, extracted and purified intact proteins may be further digested, and the resulting peptide fragments are identified. In some embodiments, intact extracted proteins are identified. In preferred embodiments, extracted proteins are further digested, and the resulting peptide fragments are identified. For instance, protein extracts may be fragmented by enzymatically digesting the proteins using a protease such as trypsin. In exemplary embodiments, extracted proteins are further digested as described in the examples.

Methods of identifying proteins or protein fragments are known in the art and may include mass spectrometry (MS) analysis, or a combination of mass spectrometry with a chromatographic technique. Non limiting examples of mass spectrometer techniques may include tandem mass spectrometry (MS/MS), matrix-assisted laser desorption/ionization source with a time-of-flight mass analyzer (MALDI-TOF), inductively coupled plasma-mass spectrometry (ICP-MS), accelerator mass spectrometry (AMS), thermal ionization-mass spectrometry (TIMS), isotope ratio mass spectrometry (IRMS), and spark source mass spectrometry (SSMS). Chromatographic techniques that may be used with MS may include gas chromatography, liquid chromatography, and ion mobility spectrometry. In a preferred embodiment, proteins may be identified using tandem mass spectrometry in combination with liquid chromatography (LC-MS/MS). In another preferred embodiment, post-translational modification of proteins may be identified using tandem mass spectrometry in combination with liquid chromatography (LC-MS/MS).

In the present invention, the method of label-free proteomics is used to categorize whether proteins enriched with a section of chromatin are specific or contaminant. Label-free methods of quantifying proteins or protein fragments are known in the art. In label-free quantitative proteomics, each sample is separately prepared, then subjected to individual methods of identifying proteins or protein fragments which may include LC-MS/MS or LC/LC-MS/MS. According to the invention, one sample comprises a target chromatin that is tagged in the cell sample and one sample comprises a target chromatin that is untagged in the cell sample. Label-free protein quantification is generally based on two categories of measurement. In the first are the measurements of ion intensity changes such as peptide peak areas or peak heights in chromatography. The second is based on the spectral counting of identified proteins after MS/MS analysis. Peptide peak intensity or spectral count is measured for individual LC-MS/MS or LC/LC-MS/MS runs and changes in protein abundance are calculated via a direct comparison between different analyses. In a preferred embodiment, the proteins identified using mass spectrometry are quantified and identified as enriched in the sample containing the tagged target chromatin compared to the sample containing the untagged target chromatin using label-free proteomics. In an exemplary embodiment, the proteins identified using mass spectrometry are quantified and identified as enriched in the sample containing the tagged target chromatin compared to the sample containing the untagged target chromatin using spectral counting.

The method of protein quantification by spectral count is known in the art and is reviewed in Zhu et al., J Biomed Biotechnol 2010, which is incorporated by reference herein. In spectral counting, relative protein quantification is achieved by comparing the number of identified MS/MS spectra from a protein of one sample to the same protein in the other sample. In the present invention, one sample comprises a target chromatin that is tagged and another sample comprises a target chromatin that is untagged. Protein quantification in spectral counting utilizes the fact that an increase in protein abundance typically results in an increase in the number of its proteolytic peptides, and vice versa. This increased number of (tryptic) digests then usually results in an increase in protein sequence coverage, the number of identified unique peptides, and the number of identified total MS/MS spectra (spectral count) for each protein.

As such, determining the abundance of an identified protein in a tagged chromatin sample compared to the same protein in an untagged chromatin sample, may determine if the protein was specifically associated with a target chromatin of the invention. If an identified protein associated with a target chromatin is in enriched in a tagged chromatin sample compared to the same protein in an untagged chromatin sample, then the protein was specifically associated with a target chromatin of the invention. If an identified protein is not enriched in a tagged chromatin sample compared to an untagged chromatin sample, then the protein is non-specifically associated with a target chromatin of the invention.

A skilled artisan in spectral counting will appreciate that normalization and statistical analysis of spectral counting datasets are necessary for accurate and reliable detection of protein changes. Since large proteins tend to contribute more peptide/spectra than small ones, a normalized spectral abundance factor (NSAF) is defined to account for the effect of protein length on spectral count. NSAF is calculated as the number of spectral counts (SpC) identifying a protein, divided by the protein's length (L), divided by the sum of SpC/L for all proteins in the experiment. NSAF allows the comparison of abundance of individual proteins in multiple independent samples and has been applied to quantify the expression changes in various complexes.

In the present invention, to measure enrichment of a protein, the normalized spectral abundance factor (NSAF) is calculated for each protein in each lane of an SDS-PAGE gel by dividing the number of spectral counts (normalized for the size of the protein) of a given protein by the sum of all normalized spectral counts of all proteins in the gel lane. The enrichment level for each protein is identified by calculating the fold enrichment (tagged chromatin/untagged chromatin) using the NSAF values. In an exemplary embodiment, proteins enriched in a sample containing a tagged target chromatin compared to a sample containing an untagged target chromatin are enriched by at least about 2 fold. In other embodiments, proteins enriched in a sample containing a tagged target chromatin compared to a sample containing the untagged target chromatin are enriched by at least about 1.5 fold. In other embodiments, proteins enriched in a sample containing a tagged target chromatin compared to a sample containing an untagged target chromatin are enriched by at least about 3 fold, about 4 fold, about 5 fold, about 6 fold, about 7 fold, about 8 fold, about 9 fold, about 10 fold, about 11 fold, about 12 fold, about 13 fold, about 14 fold, about 15 fold, about 16 fold, about 17 fold, about 18 fold, about 19 fold or about 20 fold. As such, a protein enriched by at least about 2 fold in a tagged chromatin sample compared to an untagged chromatin sample, is specifically associated with the chromatin. For instance, a baseline for non-specifically associated proteins may be proteins enriched by less than about 1.5 fold in a tagged chromatin sample compared to an untagged chromatin sample, wherein one or more proteins are not associated with chromatin. Non-limiting examples of proteins not associated with a chromatin may include enzymes required for metabolism, receptors, and ribosomal proteins. In preferred embodiments, proteins not associated with a chromatin are ribosomal proteins, and a baseline for non-specifically associated proteins is an enrichment less than about 1.5 fold in a tagged chromatin sampled compared to an untagged chromatin sample. In an exemplary embodiment, proteins or protein fragments enriched by at least 15 fold in a tagged chromatin sample compared to an untagged chromatin sample are specifically associated with a target chromatin.

In preferred embodiments, a target chromatin is tagged in one cell sample and a target chromatin is untagged in a second cell sample, and MS analysis is used to identify proteins or protein fragments isolated during affinity purification of each sample, and label-free proteomics is used to determine if a protein or a protein fragment is specifically or non-specifically associated with the target chromatin. Methods of deriving MS data to identify proteins or protein fragments are known in the art, and may include using known computational techniques to distill MS data such as Mascot Distiller, Rosetta Elucidator, and MaxQuant. In some embodiments, MS data is derived using Rosetta Elucidator. In other embodiments, MS data is derived using MaxQuant. In preferred embodiments, MS data is derived using Mascot Distiller.

(f) Applications

Applications of the invention may be as described in Section I(f) above.

III. Kits

In other aspects, the present invention provides kits for isolating and identifying proteins specifically associated with a chromatin. The kits may comprise, for example, a growth medium comprising a metabolic label, or a metabolic label that may be added to a growth medium, and cells comprising a tagged target chromatin, and instructions describing a method of the invention. A kit may further comprise material necessary for affinity purification of a tagged target chromatin, and a sample comprising metabolically labeled and unlabeled non-specifically associated proteins for determination of a baseline for non-specifically associated proteins. A kit my also comprise material necessary for affinity purification of a tagged target chromatin, and instructions describing a method of the invention.

Cells, and methods of the invention may be as described in Section I and Section II above.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Introduction for Examples 1-3

It has long been appreciated that chromatin-associated proteins and epigenetic factors play central roles in cell-fate reprogramming of genotypically identical stem cells through lineage-specific transcription or repression of precise genes and large chromosomal regions (Martin, 1981; Ho and Crabtree, 2010; Rossant, 2008). However, the hierarchy of chromatin-templated events orchestrating the formation and inheritance of different epigenetic states remains poorly understood at a molecular level. Since misregulation of chromatin structure and post-translational modification of histones (PTMs) is linked to cancer and other epigenetic diseases (Jones and Baylin, 2007; Chi et al., 2010), it is imperative to establish new methodologies that will allow comprehensive studies and unbiased screens for participants in epigenetic mechanisms. Unfortunately, defining how chromatin regulators collectively assemble and operate on a precise region of the genome is difficult to elucidate; there are no current methodologies that allow for determination of all proteins present at a defined, small region of chromatin.

Technical challenges have precluded the ability to determine positioning of chromatin factors along the chromosome. Chromatin immunoprecipitation (ChIP) assays have been used to better understand genome-wide distribution of proteins and histone modifications within a genome at the nucleosome level (Dedon at al., 1991; Ren et al., 2000; Pokholok et al., 2005; Robertson et al., 2007; Johnson et al., 2007; Barski at al., 2007; Mikkelsen et al., 2007). However, major drawbacks of ChIP-based chromatin enrichment methods include experiments that are largely confined to examining singular histone PTMs or proteins rather than simultaneous profiling of multiple targets, the inability to determine the co-occupancy of particular histone PTMs, and that ChIP is reliant on the previous identification of the molecular target. Affinity purification approaches have been devised for the isolation of a chromatin region (Griesenbeck et al., 2003; Agelopoulos et al., 2012); however, these approaches were not done at a level for proteomic analysis and they do not provide a mechanism for determining the specificity of protein interactions. More recently, groups biochemically enriching for intact chromatin have reported characterization of proteins associated with large chromatin structures such as telomeres (Dejardin and Kingston, 2009) and engineered plasmids (Akiyoshi et al., 2009; Unnikrishnan et al., 2010); however, these approaches do not enrich for a small integrated genomic locus and do not employ specialized mass spectrometric techniques to detect protein contamination in purified material.

We sought to compare differences in chromatin between the transcriptionally active and silent states of a single genomic locus, and developed a technology, called chromatin affinity purification with mass spectrometry (ChAP-MS). ChAP-MS provides for the site-specific enrichment of a given ~1,000 base pair section of a chromosome followed by unambiguous identification of both proteins and histone PTMs associated with this chromosome section using highly selective mass spectrometry. Using ChAP-MS, we were able to purify chromatin at the *Saccharomyces cerevisiae* GAL.1 locus in transcriptionally silent and active states. We identified proteins and combinatorial histone PTMs unique to each of these functional states and validated these findings with ChIP. The ChAP-MS technique will greatly improve the field of epigenomics as an unbiased approach to study regulatory mechanisms on chromatin.

Example 1

ChAP-MS Technology

Figure 1B:
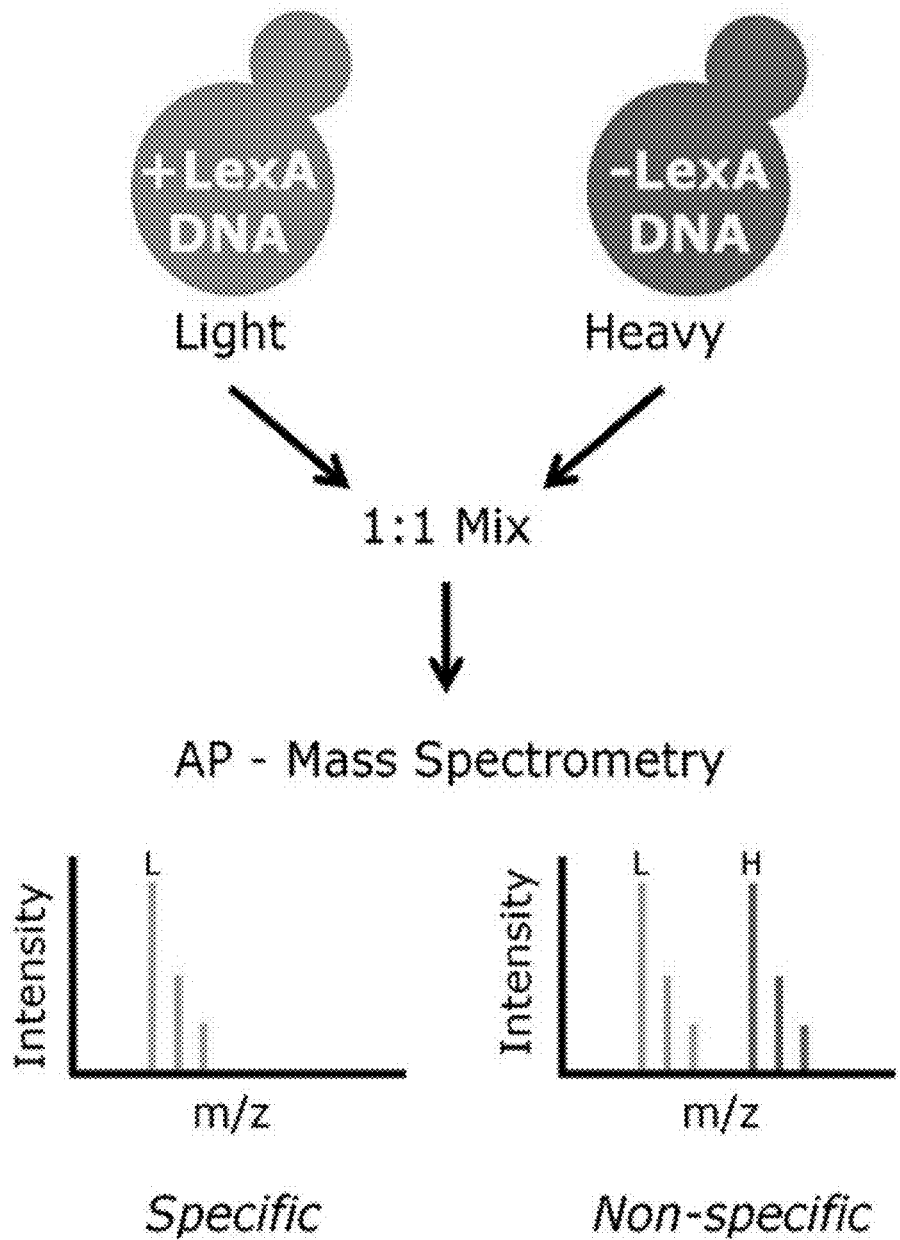

FIG. 1A provides an overview of the ChAP-MS approach that was used to screen for proteins and histone PTMs associated with a specific genomic locus in transcriptionally active or repressive states. A LexA DNA binding site was engineered immediately upstream of the GAL1 start codon in a *S. cerevisiae* strain constitutively expressing a LexA-Protein A (LexA-PrA) fusion protein. The LexA DNA binding site directs the localization of the LexA-PrA protein affinity "handle" to the GAL1 promoter in vivo. The positioning of the LexA DNA was designed to specifically enrich for chromatin-associated proteins and histone PTMs regulating gene expression near the transcriptional start site of GAL1. This strain was cultured in glucose to repress gene transcription, or galactose to activate gene transcription. Following in vivo chemical crosslinking to preserve the native protein-protein interactions at GAL1 promoter chromatin, the chromatin was sheared to ~1,000 base pair sections. The PrA moiety of the LexA-PrA fusion protein was then used to affinity purify the ~1,000 base pair section of chromatin at the 5' end of the GAL1 gene for high resolution mass spectrometric identification of proteins and histone PTMs. It was anticipated that culturing these cells in glucose would result in the isolation of proteins and PTMs correlated to silent chromatin, while culturing cells in the presence of galactose would purify histone PTMs and proteins, like RNA polymerase, that are involved with active gene transcription.

The GAL1 gene is present at one copy per haploid cell; due to the relative low abundance of the targeted chromatin region in cellular lysates, it was fully anticipated that proteins nonspecifically associating with GAL1 chromatin would complicate analysis of the resulting purified material. Copurification of nonspecifically associating proteins is one of the major complications of affinity purifications; however, isotopic labeling of media provides a means to gauge in vivo protein-protein interactions and quantitate differences in peptide abundance (Smart et al., 2009; Tackett et al., 2005a). The inventors had previously developed a variation of this labeling technique called iDIRT (isotopic differentiation of interactions as random or targeted) that provides a solution for determining which coenriched proteins are specifically or nonspecifically associated with a complex of proteins (Smart et al., 2009; Tackett et al., 2005a). The iDIRT technique was adapted (as described in FIG. 1B) to control for proteins nonspecifically enriching with LexA-PrA and the resin. By using this adaptation of iDIRT on chromatin enriched from active and repressed chromatin states, the proteins nonspecifically enriching with the isolated GAL1 chromatin section were identified. The strain containing the LexA DNA binding site and LexA-PrA fusion protein was cultured in isotopically light media, while a strain lacking the LexA DNA binding site (but still containing the LexA-PrA fusion protein) was cultured in isotopically heavy media ($^{13}C_6{}^{15}N_2$-lysine). N lysine). Following isolation of the cells, the light and heavy strains were mixed and colysed. The growth and mixing of light/heavy strains was performed separately under glucose and galactose growth conditions. The affinity purification of the GAL1 chromatin was performed from this mixture of light/heavy lysates. Proteins and histone PTMs specifically associated with the GAL1 chromatin containing the LexA DNA binding site were isotopically light as they arose from the cells grown in light media. Proteins that were nonspecific to the purification were a 1:1 mix of light and heavy as they were derived equally from the light and heavy lysates. Analysis of peptides from the enriched proteins with high-resolution mass spectrometry was used to determine the level of isotopically light and heavy proteins, thereby determining whether the detected protein was either a specific in vivo constituent of GAL1 chromatin or a nonspecific contaminant.

Example 2

Affinity Purification of a Specific Chromosome Section

Figure 2:
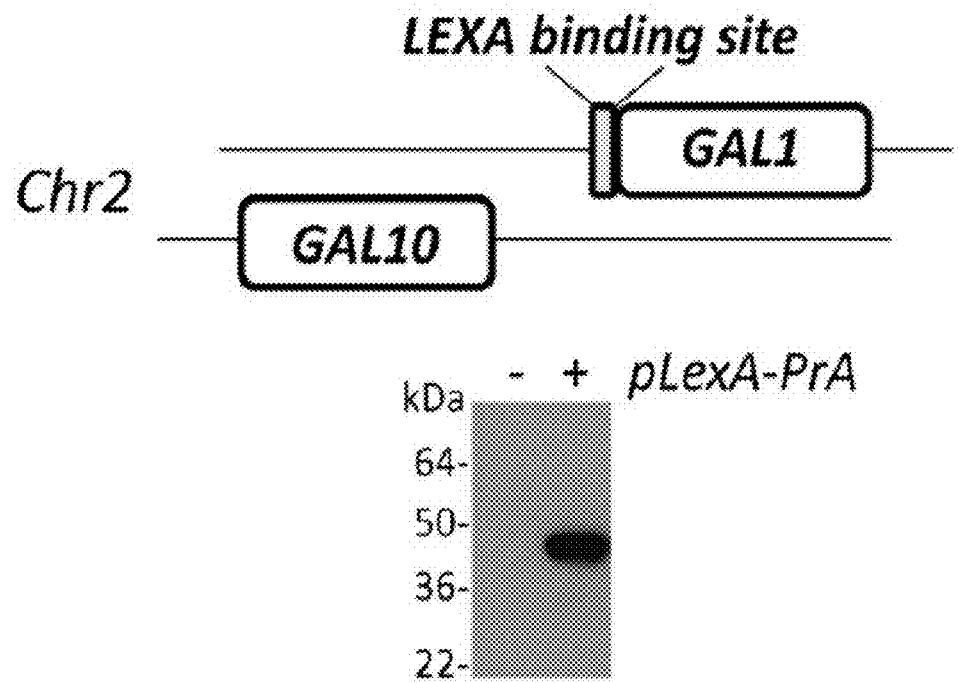
FIG. 2 depicts a plot, a Western blot image and a plot showing DNA affinity handle for purification of a specific chromosome section. (A) S. cerevisiae strain LEXA::GAL1 pLexA-PrA was created by insertion of a LEXA DNA binding site upstream of the GAL1 start codon via homologous recombination. The pLexA-PrA plasmid was introduced into this strain and the constitutive expression of the LexA-PrA fusion protein was confirmed by western blotting for PrA. (B) Introduction of the LEXA DNA binding site does not impede GAL1 transcription. cDNA from wild-type or LEXA::GAL1 pLexA-PrA strains grown in glucose or galactose was used as a template for real time PCR analysis of GAL1 versus ACT1 gene transcription. Error bars are the SE of triplicate analyses.
Figure 2:
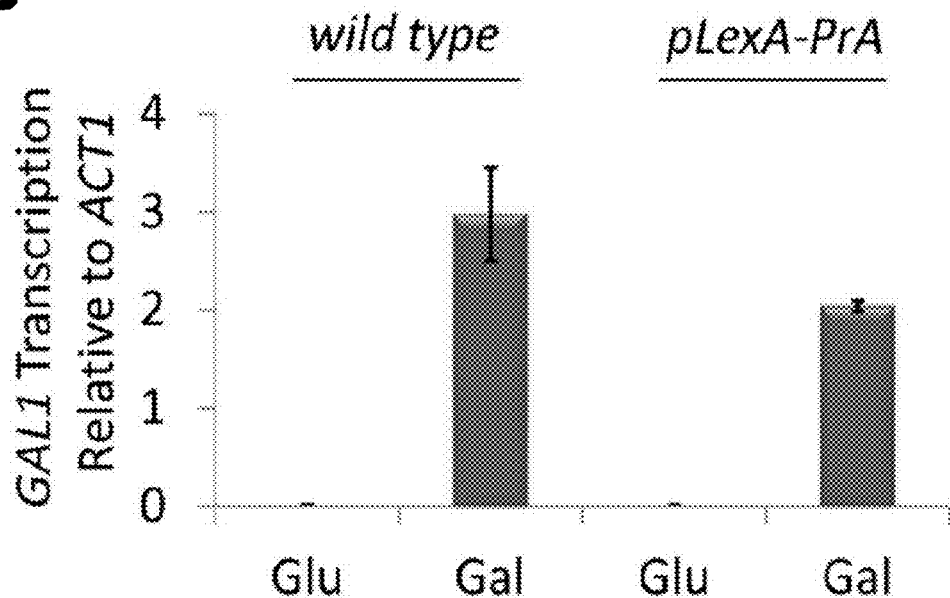

To provide for enrichment of a specific chromosome section, a DNA affinity handle was engineered at the GAL1 gene in S. cerevisiae (FIG. 2A). A LexA DNA binding site was inserted via homologous recombination just upstream of the GAL1 start codon to create strain LEXA::GAL1. To create this strain, GAL1 was genomically deleted with URA3 in the W303a background, and then the GAL1 gene was reinserted with the upstream LEXA DNA sequence by homologous recombination. A plasmid constitutively expressing LexA-PrA was introduced into the strain to create LEXA::GAL1 pLexA-PrA (FIG. 2A). This strain provides a DNA affinity handle at the GAL1 gene and a protein affinity handle for specific enrichment. To determine if insertion of this LexA DNA binding site at GAL1 affected gene transcription, LEXA::GAL1 pLexA-PrA was cultured in glucose to repress gene transcription at GAL1, and separately in galactose to activate transcription. From these growths, cDNA was prepared and real-time PCR was used to measure the activation of GAL1 transcription in the presence of galactose (FIG. 2B). Insertion of the LexA DNA binding site just upstream of the GAL1 start codon did not drastically affect the activation of gene transcription; thus, this strain was used for ChAP-MS purification of GAL1 chromatin in the transcriptionally active and silent states.

Figure 3A:
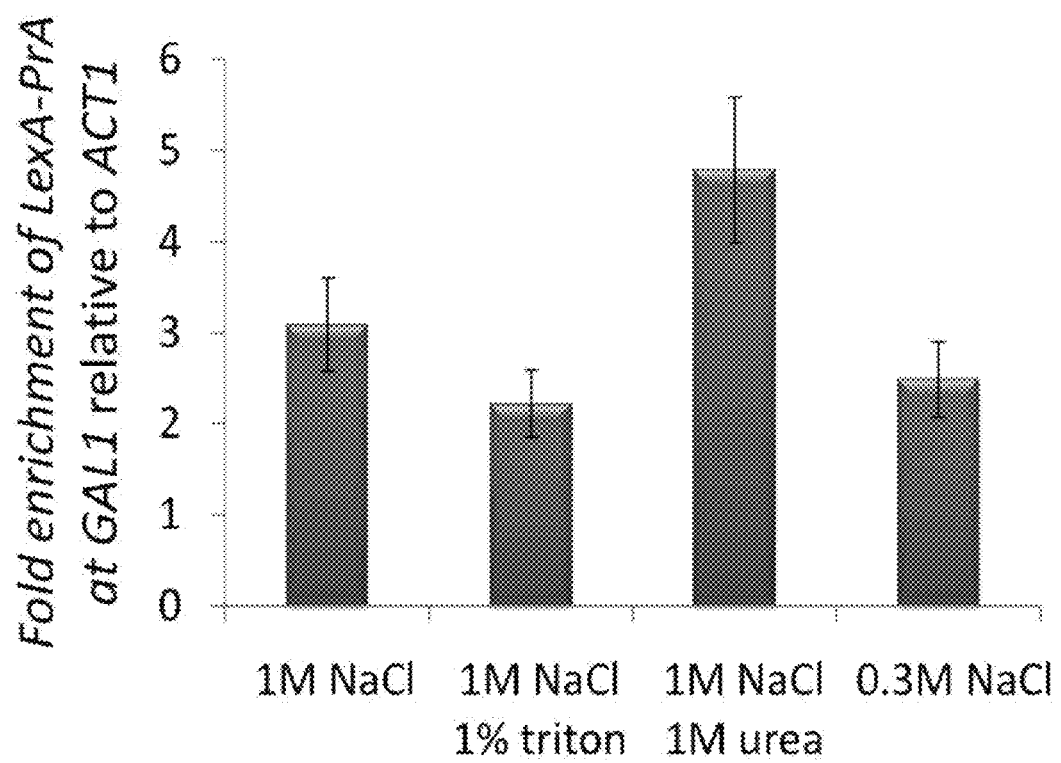
FIG. 3 depicts plots and a diagram showing efficiency of GAL1 chromatin purification. (A) The effect of buffer stringency on purification of LexA-PrA with associated chromatin was evaluated with ChIP. Strain LEXA::GAL1 pLexA-PrA was subjected to ChIP using the following buffer with the reagents indicated on the graph: 20 mM HEPES (pH 7.4), 0.1% Tween 20, and 2 mM MgCl$_2$. Enrichment of GAL1 DNA relative to ACT1 DNA was monitored by real-time PCR. (B) ChIP was used to measure the specificity of enrichment of LexA-PrA bound chromatin. Enrichment was monitored by real-time PCR with primer sets at the indicated chromosomal locations. (C) GAL1 chromatin is enriched in both glucose and galactose growth conditions. The relative efficiency of GAL1 enrichment was monitored by real-time PCR with primers targeted to the "0" position in panel (B) and to ACT1. The SE is indicated.
Figure 3B:
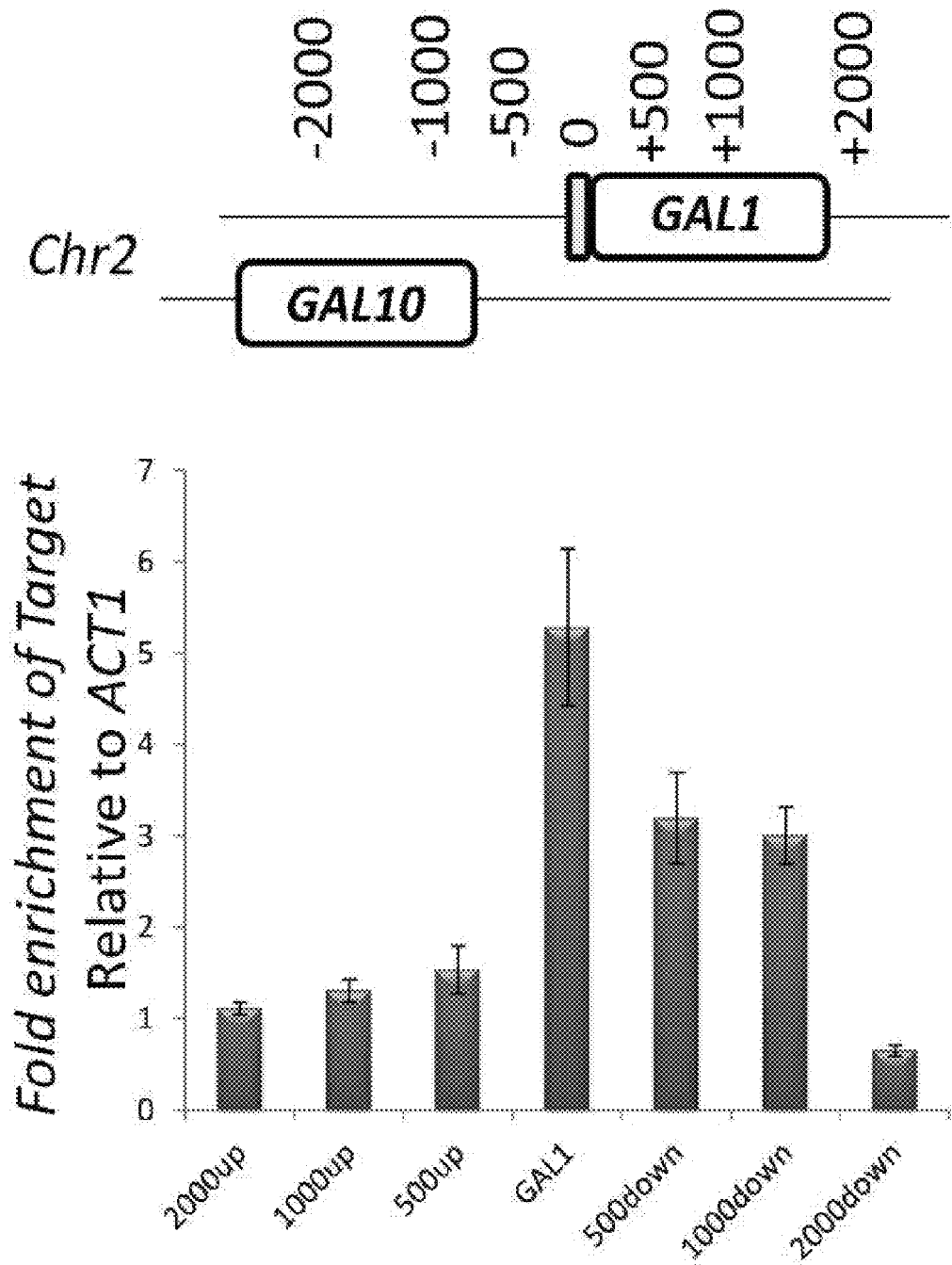
Figure 3C:
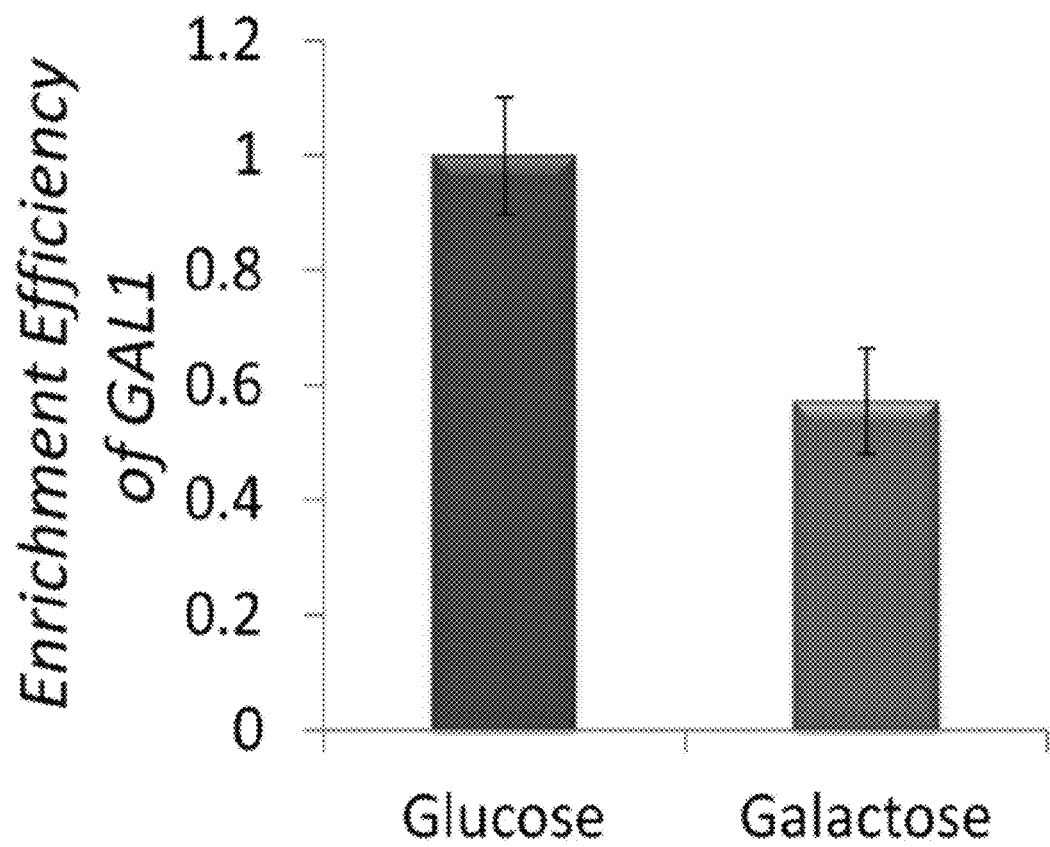

To determine the effectiveness of isolation of GAL1 chromatin, the stringency and specificity of different purification conditions was analyzed. Purification of protein complexes under increasing stringencies such as high salt levels provides for the isolation of fewer nonspecifically interacting proteins (Smart et al., 2009; Taverna et al., 2006). Since the proteins purified with GAL1 chromatin will be chemically crosslinked, the stringency of the purification can potentially be quite high. Indeed, ChIP-qPCR against GAL1 showed that the PrA-based purification can survive relatively stringent conditions (FIG. 3A). From these studies, 1M NaCl and 1M urea were selected for future purifications, as these conditions are quite stringent and provide for enrichment of the GAL1 chromatin. Using an identical ChIP approach, the specificity of the GAL1 chromatin enrichment was determined (FIG. 3B). Using primers targeted to the indicated regions of chromatin surrounding GAL1, it was detected that the first 1,000 base pair section of the GAL/gene was indeed enriched. Enrichment of GAL1 chromatin was observed at a similar level under glucose and galactose growth conditions (FIG. 3C). The slightly less efficient isolation under galactose growth conditions may reflect availability of the DNA affinity site due to alterations in chromatin structure.

Example 3

ChAP-MS Analysis of Transcriptionally Active Anti Silent GAL1 Chromatin

Figure 4A:
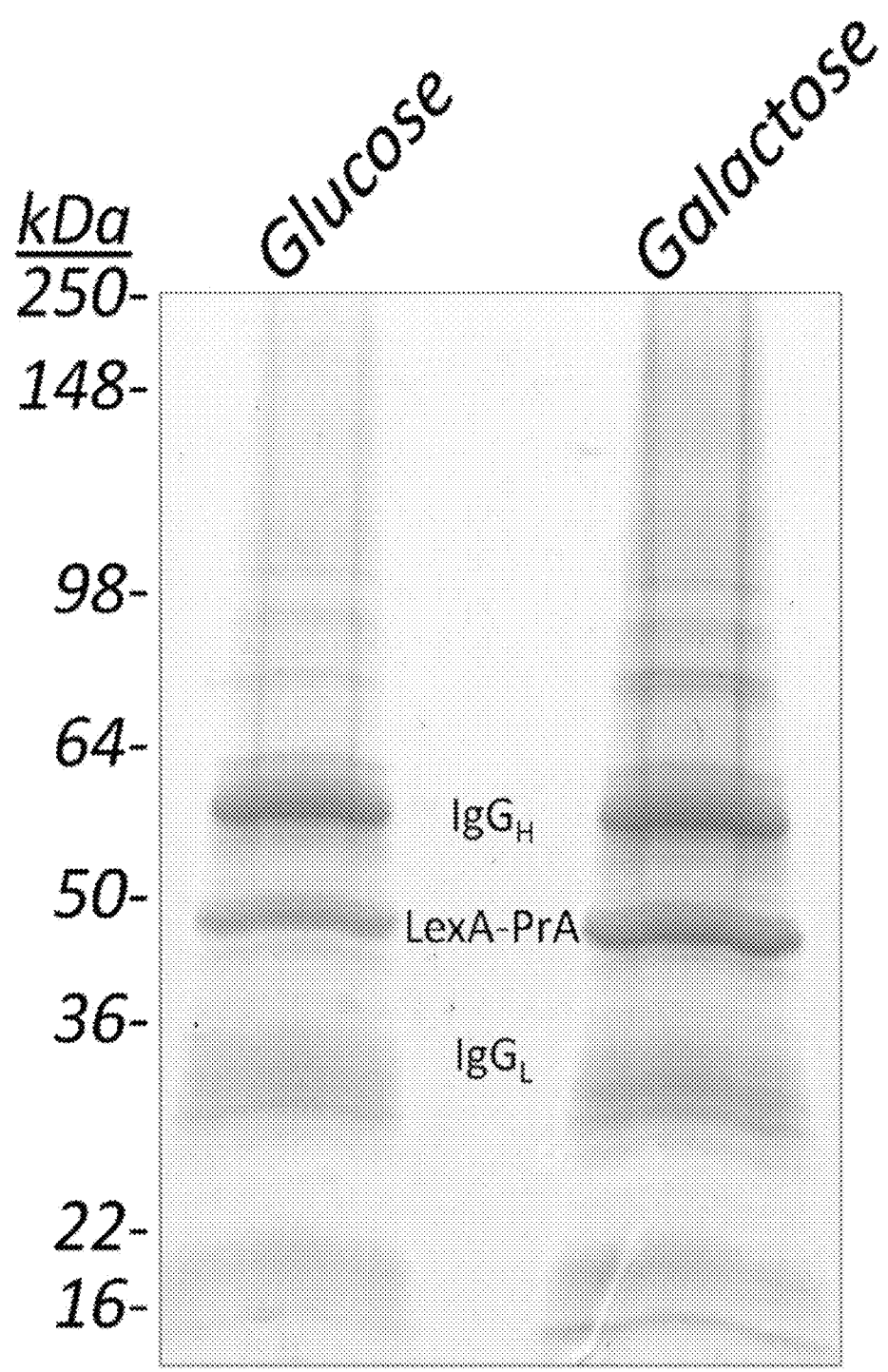
FIG. 4 depicts an image of an SDS-PAGE gel and mass spectra showing ChAP-MS analysis of GAL1 chromatin. (A) Enrichment of GAL1 chromatin under transcriptionally repressive glucose and active galactose growth conditions. Strain LEXA::GAL1 pLexA-PrA was grown in either glucose or galactose and subjected to affinity purification of GAL1 chromatin via LexA-PrA as detailed in FIG. 1. Addition of an equivalent amount of isotopically heavy ($^{13}C_6\ ^{15}N_2$-lysine) cells lacking the LexA DNA binding site provided for the identification of proteins specifically enriched with GAL1 chromatin. Proteins coenriching with LexA-PrA were resolved by SDS-PAGE and visualized by Coomassie-staining. Each gel lane was sliced into 2 mm sections. Gel slices were treated with trypsin and resulting peptides were analyzed by high-resolution mass spectrometry. (B-D) Representative high-resolution mass spectra from proteins and histone post-translational modifications identified from the purification of transcriptionally active GAL1 chromatin.
Figure 4B:
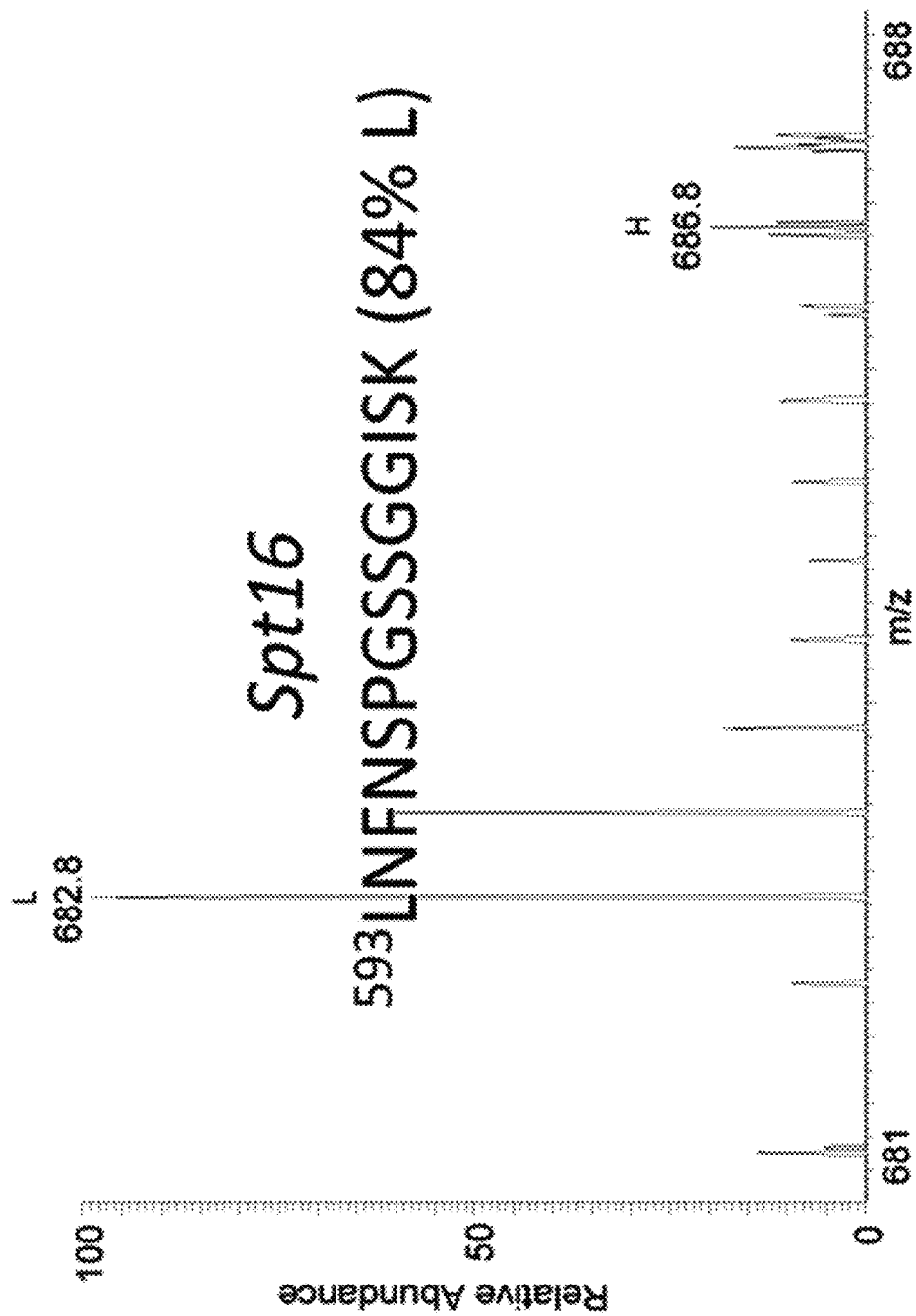
Figure 4C:
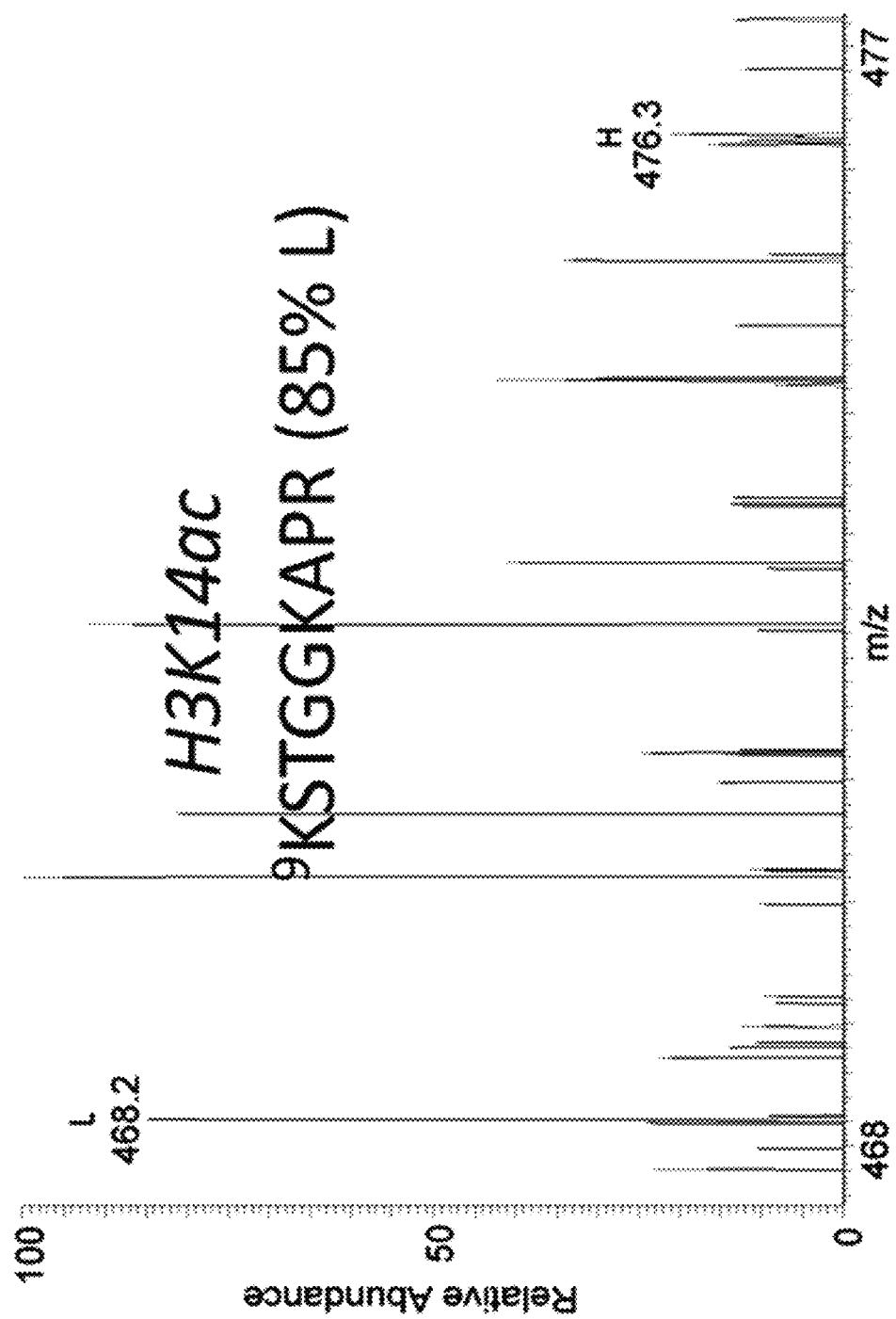
Figure 4D:
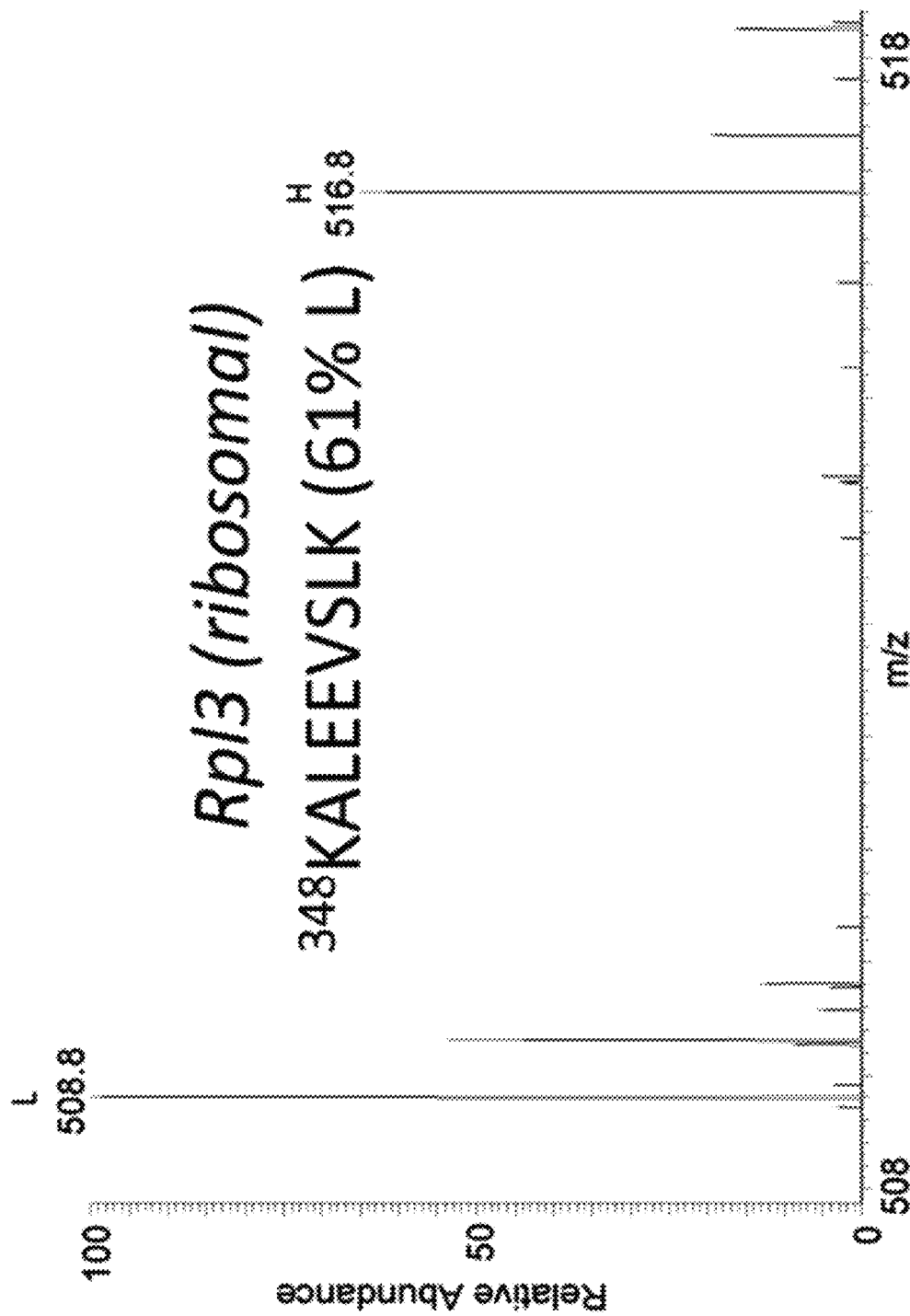

Strain LEXA::GAL1 pLexA-PrA was subjected to the ChAP-MS procedure as outlined in FIG. 1. Strain LEXA::GAL1 pLexA-PrA was grown in isotopically light media, while strain pLexA-PrA was grown in isotopically heavy media. Following growth of each strain to mid-log phase, the cells were treated with 1.25% formaldehyde to trap protein interactions on the chromosomes. A detailed analysis of the amount of formaldehyde crosslinking required to preserve the in vivo state of chromatin during affinity purifications was recently published by the inventors (Byrum et al., 2011a, 2011b). Approximately $2.5 \times 10^{11}$ LEXA::GAL1 pLexA-PrA cells were mixed with an equivalent amount of isotopically heavy pLexA-PrA cells (separately for media containing glucose and galactose) and then subjected to lysis under cryogenic conditions with a Retch MM301 ball mill (Tackett et al., 2005a). Lysates were suspended in 20 mM HEPES (pH 7.4), 0.1% Tween 20, 1 M NaCl, 1 M urea, and 2 mM $MgCl_2$. Lysates were then subjected to sonication and chromatin was sheared to sections of ~1,000 base pairs. LexA-PrA was collected on IgG-coated Dynabeads and coenriching proteins were resolved by SDS-PAGE and visualized by Coomassie staining (FIG. 4A). Gel lanes were sliced into 2 mm sections and subjected to in-gel trypsin digestion (Smart et al., 2009; Tackett et al., 2005a, 2005b). Peptides from proteins were identified by high-resolution mass spectrometry with a Thermo Velos Orbitrap mass spectrometer equipped with a Waters nanoACQUITY UPLC system. Proteins and PTM-containing peptides were identified and the level of isotopically light to heavy peptide was calculated with Mascot Distiller (Smart et al., 2009), Representative spectra are shown in FIG. 4B-D. Major bands observed in the gel lanes correspond to the affinity purification protein LexA-PrA and IgG chains as anticipated. Other proteins identified correspond to specifically and nonspecifically enriched proteins. Tables 1 and 2 list the proteins identified and percent isotopically light peptides (352 proteins from the glucose ChAP-MS and 399 proteins from the galactose ChAP-MS).

Figure 5:
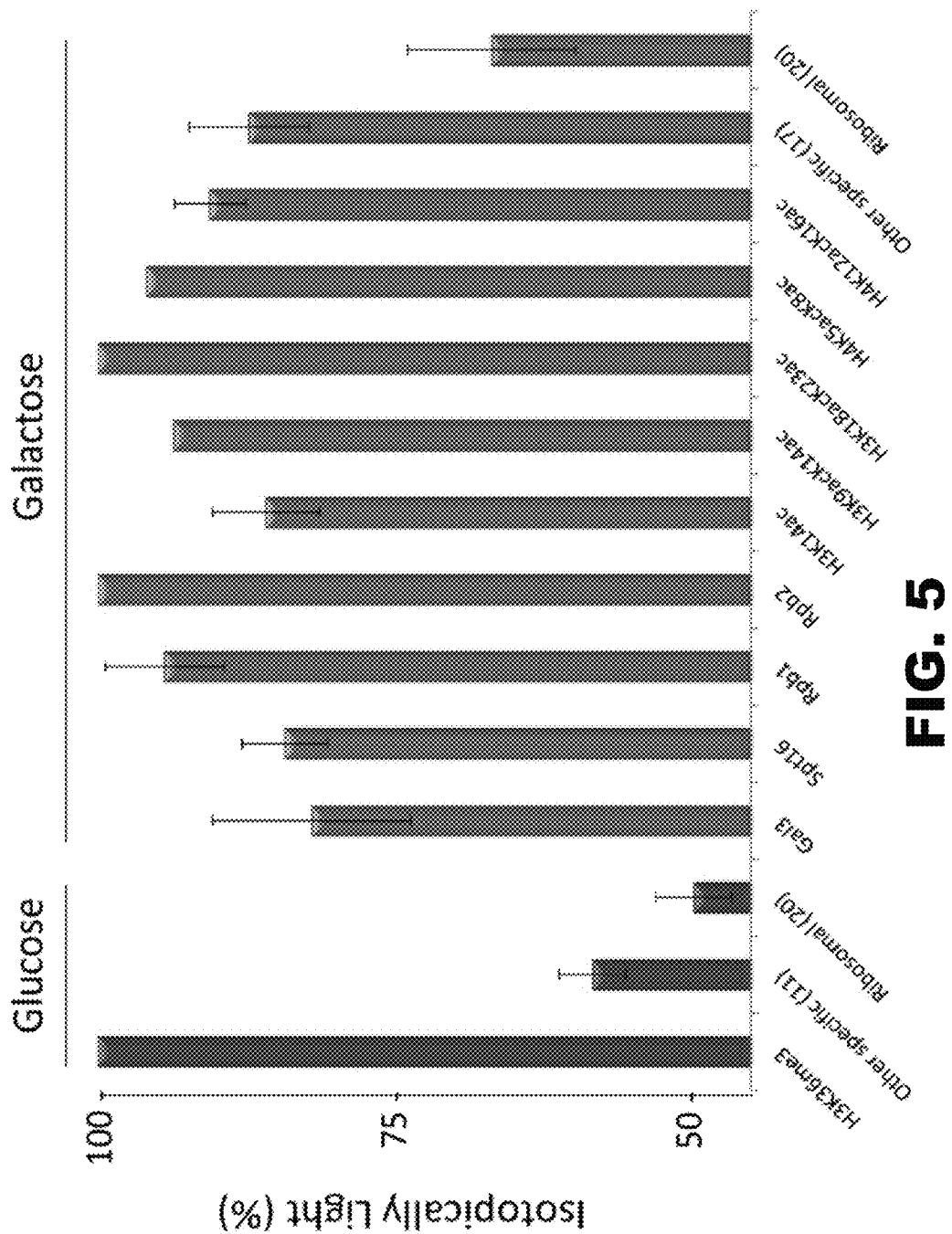
FIG. 5 depicts a plot showing proteins and histone post-translational modifications enriched with GAL1 chromatin. Proteins and histone post-translational modifications identified from the ChAP-MS analysis of GAL1 chromatin in the transcriptionally active galactose and repressive glucose growth conditions are listed in accordance to their percent isotopically light. Proteins or post-translational modifications were considered specifically enriched with GAL1 chromatin if the percent isotopically light was 2 SDs from the nonspecific baseline established by the average of contaminant ribosomal proteins. Other proteins shown to be specifically enriched, but not correlated to gene transcription, are averaged together and listed individually in Tables 4 and 5. The number of proteins averaged is shown in parentheses. The SD is indicated.

Once proteins were identified, a baseline was established for nonspecifically associated proteins in accordance to the iDIRT approach (Smart et al., 2009). Nonspecifically enriching ribosomal proteins were used to establish the nonspecifically associating baseline (Smart et al., 2009). The average percent isotopically light peptides from 20 ribosomal proteins from the glucose and galactose growth conditions were used to establish this nonspecifically associating baseline (Table 3). This resulted in a nonspecifically associating baseline of 49.93%±2.12% light for the glucose ChAP-MS and 66.8%±7.1% light for the galactose ChAP-MS (FIG. 5). Proteins were categorized as specifically associating with GAL1 chromatin if the percent light was greater than 2 SDs above the ribosomal level (Smart et al., 2009). FIG. 5 shows the proteins and histone PTMs specifically enriched with GAL1 chromatin under glucose and galactose growth conditions. Tables 4 and 5 list proteins that were identified as specifically enriched in both the glucose and galactose ChAP-MS analyses. Specifically enriched proteins or histone PTMs known to be involved in transcriptional regulation are listed in FIG. 5. For the glucose and galactose ChAP-MS analyses, 11 and 17 (respectively) additional proteins were detected as specifically enriched (FIG. 5, Tables 4 and 5). These additional proteins are abundant metabolic and heat shock proteins that are typical contaminants and false positives for this study. However, narrowing down 352 proteins identified from the glucose ChAP-MS and 399 proteins from the galactose ChAP-MS to 12 proteins and 27 proteins/PTMs specifically enriched produced a short list of candidates that was easily validated.

Figure 6:
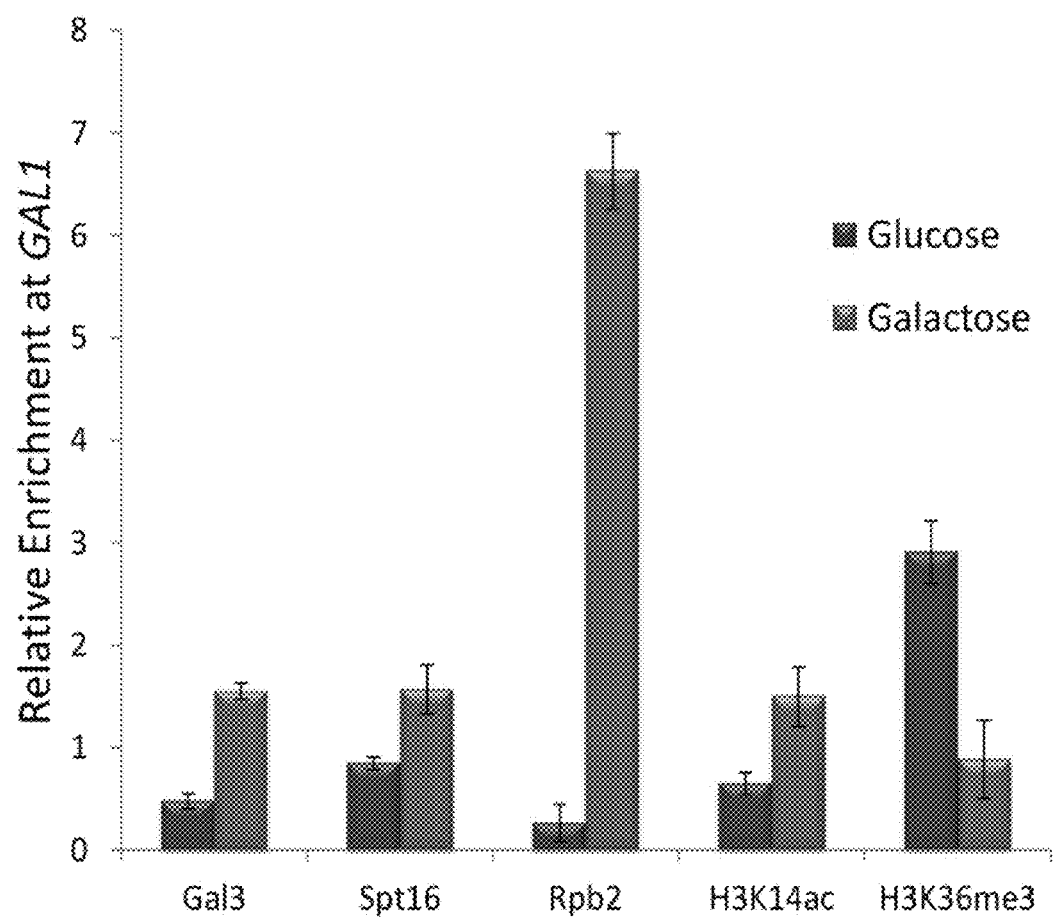
FIG. 6 depicts a plot showing the validation of proteins and histone post-translational modifications on GAL1 chromatin. ChIP was targeted to Gal3-TAP, Spt16-TAP, Rpb2-TAP, H3K14ac, and H3K36me3 under transcriptionally active galactose and repressive glucose growth conditions. ChIP to general H3 was used as a nucleosome occupancy control for each histone post-translational modification ChIP. Enrichment of the 5' end of GAL1 DNA relative to ACT1 DNA was monitored by real-time PCR. The SE is indicated.

The ChAP-MS analyses of GAL1 chromatin revealed association of Gal3, Spt16, Rpb1, Rpb2, H3K14ac, H3K9acK14ac, H3K18acK23ac, H4K5acK8ac, and H4K12acK16ac under transcriptionally active conditions, while transcriptionally repressive conditions showed the enrichment of H3K36me3. In order to validate the ChAP-MS approach, standard ChIP was performed to specific interactions detected in the transcriptionally active and silent chromatin state at GAL1 (FIG. 6). These ChIP experiments validated the proteins and PTMs found associated with the transcriptionally active and repressed states of GAL1 chromatin determined from the ChAP-MS approach.

Discussion for Examples 1-3

The chromatin biology and epigenomics research communities have been limited to biased technologies that restrict targeted genome localization studies to previously identified proteins or histone PTMs. Here, a newly developed technology, called ChAP-MS, is described that circumvents this limitation by providing for isolation of a ~1,000 base pair section of a chromosome for proteomic identification of specifically bound proteins and PTMs. In essence, the ChAP-MS approach allows one to take a "molecular snapshot" of chromatin dynamics at a specific genomic locus. Furthermore, employing this approach to target other chromatin regions will likely provide unprecedented insight on a variety of epigenetic regulatory mechanisms, chromatin structure, and genome metabolism.

Validation of the ChAP-MS Approach

The ChAP-MS approach was validated on the well-studied GAL1 locus in S. cerevisiae. The GAL1 gene is activated for gene transcription in the presence of galactose, while glucose represses transcription. Accordingly, it was rationalized that a purified ~1,000 base pair section of chromatin at the 5' end of the GAL1 gene from cells grown in galactose would contain histone PTMs correlated with active transcription and cellular machinery necessary for transcription, while the same chromatin section from cells grown in glucose would be enriched with histone PTMs associated with transcriptional repression. Prior publications have documented that H3 acetylation is enriched on the 5' end of the active galactose-induced GAL1 gene, while in the presence of glucose it contains H3K36me3 (Shukla et al., 2006; Houseley et al., 2008). Results presented in the Examples herein with ChAP-MS, support each of these prior findings (FIG. 5). Furthermore, the presence of doubly acetylated histones (H3K9acK14ac, H3K18acK23ac, H4K5acK8ac, H4K12acK16ac) during transcriptional activation was identified. This demonstrates how ChAP-MS may be used to study the combinatorial "code" of histone modifications at given chromosome regions without the need for prior identification of PTMs, PTM-specific antibodies, or sequential chromatin put-downs. Considering H4K12acK16ac for example, the identification of the double acetylation is unique to the ChAP-MS approach as antibodies to this double acetylation do not exist, thus one could not have performed a biased ChIP analysis. Additionally, it has been reported that commercially available antibodies to single acetylation at H4K12 or H4K16 are cross-reactive with other H4 acetylations and that double acetylation of H4K12K16 significantly alters the specificity of the antibody to the singly acetylated sites (Bock et al., 2011)—a limitation specific to antibodies used in biased ChIP studies and not to the unbiased ChAP-MS approach that uses quantitative mass spectrometric readout. The ChAP-MS approach simultaneously identified the presence of RNA polymerase (Rpb1, Rpb2) and FACT component Spt16 (which aids in reorganizing chromatin for RNA pol activity) under these transcriptionally active conditions. Also of interest was the identification of Gal3 at actively transcribing GAL1, which has previously been shown to inhibit the repressive activity of Gal80 at the GAL10/GAL1 locus (Platt and Reece, 1998). It was demonstrated how the ChAP-MS approach may be utilized to study chromatin dynamics at GAL1 under different states of gene transcription. Of particular interest for future functional studies may be the upstream activating sequence which binds the Gal4 actuator and Gal80 repressor which may allow better understand of the events surrounding the switch from repression to activation at GAL1 and GAL10, as well as the middle and 3' end of GAL1 to understand the processes of elongation and termination, respectively.

Utility of ChAP-IVIS as a General Tool for Studying Chromatin Biology

The ChAP-MS technology presented here demonstrates the ability to purify a unique chromosome section on the order of four to five nucleosomes in length from an in vivo source that can subsequently be subjected to sensitive proteomic studies. ChAP-MS has numerous advantages relative to traditional ChIP, including the ability to unbiasedly detect proteins/PTMs at a specific genomic locus and the identification of combinatorial histone modifications on a single histone molecule. Furthermore, ChAP-MS only requires approximately an order of magnitude more cells relative to biased ChIP studies, which is a huge advantage if doing more than ten blind ChIP studies at a given region is factored in (chances are many antibodies for many proteins would be heavily invested in, trying to guess a specifically bound protein/PTM). In this regard, ChAP-MS is a more cost-effective option for characterizing specifically bound proteins and histone PTMs relative to ChIP. Future derivations of this technology may employ targeted mass spectrometric approaches for better determination of combinatorial histone PTMs as well as identification of other regulatory PTMs on nonhistone proteins from these isolated sections (Taverna et al., 2007). Given the sensitivity of the mass spectrometry analysis employed and the relatively modest biological starting material, the findings presented in the Examples herein also establish a framework for applying ChAP-MS to profile across entire regions of chromosomes or investigate higher eukaryotic systems. Regardless, any advances that permit ChAP-MS analysis of in vivo untagged or unaltered samples, like tissues, will undoubtedly have valuable applications for investigating altered gene transcription mechanisms in human disease states, as this technique could provide a comprehensive way to intelligently identify targets for therapeutics.

Experimental Procedures for Examples 1-3

Construction of the LEXA::GAL1 pLexA-PrA Strain

The LEXA::GAL1 pLexA-PrA strain used to affinity enrich GAL1 chromatin was designed to have a LexA DNA binding site just upstream of the GAL1 start codon and contains a plasmid constitutively expressing a LexA-PrA fusion protein. In *S. cerevisiae* from the W303a background, the GAL1 gene was genomically replaced with URA3 using homologous recombination. Next, the GAL1 gene (+50 base pairs up- and downstream) was PCR amplified with primers that incorporated a LexA DNA binding site (5'-CACTTGATACTGTATGAGCATACAGTATAATTGC) immediately upstream of the GAL1 start codon. This LEXA::GAL1 cassette was transformed into the gal1::URA3 strain and selected for growth with 5-fluoroorotic acid, which is lethal in URA3 expressing cells. Positive transformants were sequenced to ensure homologous recombination of the cassette to create the LEXA::GAL1 strain. A plasmid that constitutively expresses LexA-PrA fusion protein with TRP selection was created by amplification of the PrA sequence from template pOM60 via PCR and subcloning into the Sac1/Sma1 ends of the expression plasmid pLexA-C. Transforming this plasmid into the LEXA:GAL1 strain gave rise to the LEXA:GAL1 pLexA-PrA strain. Additionally, a control used in these studies was W303a *S. cerevisiae* transformed only with pLexA-PrA.

Cell Culture

Strains LEXA:GAL1 pLexA-PrA and pLexA-PrA were grown in yeast synthetic media lacking tryptophan to mid-log phase at 30° C. LEXA:GAL1 pLexA-PrA strain growths were done with isotopically light lysine, while strain pLexA-PrA was cultured exclusively with isotopically heavy $^{13}C_6^{15}N_2$-lysine. For each strain, 12 l of media containing either 2% glucose or 3% galactose were grown to yield ~5×10$^{11}$ cells per growth condition. At mid-log phase, the cultures were crosslinked with 1.25% formaldehyde for 5 min at room temperature and then quenched with 125 mM glycine for 5 min at room temperature. Cells were harvested by centrifugation (2,500×g) and frozen in liquid nitrogen as pellets in suspension with 20 mM HEPES (pH 7.4), 1.2% polyvinylpyrrolidone (1 ml/10 g of cell pellet). Frozen cell pellets were mixed as follows at 1:1 cell weight ratios: (1) LEXA:GAL1 pLexA-PrA isotopically light in glucose plus pLexA-PrA isotopically heavy control in glucose (2) LEXA:GAL1 pLexA-PrA isotopically light in galactose plus pLexA-PrA isotopically heavy control in galactose. Cell mixtures were cryogenically lysed under liquid nitrogen temperature with a Retsch MM301 ball mill (Smart et al., 2009; Tackett et al., 2005a).

ChAP-MS Procedure

Each of the following two cell lysates were processed for purification of GAL1 chromatin: (1) LEXA:GAL1 pLexA-PrA isotopically light in glucose plus pLexA-PrA isotopically heavy control in glucose, referred to as the glucose ChAP-MS, and (2) LEXA:GAL1 pLexA-PrA isotopically light in galactose plus pLexA-PrA isotopically heavy control in galactose, referred to as the galactose ChAP-MS. Twenty grams of frozen cell lysate (~5×10$^{11}$ cells) was used for each of the glucose and galactose ChAP-MS analyses. ChAP-MS steps were performed at 4° C. unless otherwise noted. Lysates were resuspended in 20 mM HEPES (pH 7.4), 1 M NaCl, 2 mM MgCl$_2$, 1 M urea, 0.1% Tween 20, and 1% Sigma fungal protease inhibitor cocktail with 5 ml buffer per gram of frozen lysate. Lysates were subjected to sonication with a Diagenode Bioruptor UCD-200 (low setting, 30 s on/off cycle, 12 min total time) in 20 ml aliquots to yield ~1 kb chromatin fragments. Supernatants from sonicated lysates were collected by centrifugation at 2,000×g for 10 min. Dynabeads (80 mg) coated with rabbit IgG were added to the lysates and incubated for 4 hr with constant agitation (Byrum et al., 2012a). Dynabeads were collected with a magnet and washed 5 times with the purification buffer listed above and 3 times with 20 mM HEPES (pH 7.4), 2 mM MgCl$_2$, 10 mM NaCl, 0.1% Tween 20. Washed Dynabeads were treated with 0.5 N ammonium hydroxide/0.5 mM EDTA for 5 min at room temperature to elute proteins. Eluants were lyophilized with a Savant SpeedVac Concentrator. Lyophilized proteins were resuspended in Laemmli SDS-PAGE loading buffer, heated to 95° C. for 20 min, resolved with 4%-20% tris-glycine Invitrogen precast gels, and visualized by colloidal Coomassie staining.

High-Resolution Mass Spectrometry and Data Analysis

Gel lanes were sliced into 2 mm sections and subjected to in-gel trypsin digestion (Byrum et al., 2011a, Byrum et al., 2011b, Byrum et al., 2012a; Tackett et al., 2005b). Peptides were analyzed with a Thermo Velos Orbitrap mass spectrometer coupled to a Waters nanoACQUITY liquid chromatography system (Byrum et al., 2011b). Using a data-dependent mode, the most abundant 15 peaks were selected for MS$^2$ from a high-resolution MS scan. Proteins were identified and the ratio of isotopically light/heavy lysine-containing tryptic peptide intensity was determined with Mascot and Mascot Distiller. The search parameters included: precursor ion tolerance 10 ppm, fragment ion tolerance 0.65 Da, fixed modification of carbamidomethyl on cysteine, variable modification of oxidation on methionine, and two missed cleavages possible with trypsin. A threshold of 95% confidence for protein identification, 50% confidence for peptide identification and at least two identified peptides per protein was used, which gave a 2% peptide false discovery rate. All specifically associating protein identifications and ratios were manually validated.

A baseline was established for nonspecifically associated proteins with nonspecifically enriched ribosomal proteins (Smart et al., 2009). The average percent isotopically light peptides from 20 ribosomal proteins from the glucose and galactose growth condition were used to establish this nonspecifically associated baseline. This resulted in a nonspecifically associated baseline of 49.93%±2.12% light for the glucose ChAP-MS and 66.8%±7.1% light for the galactose CHAP-MS. Proteins were categorized as specifically associating if the percent light was greater than 2 SDs above the ribosomal level (Tables 4 and 5) (Smart et al., 2009). Duplicate ChAP-MS procedures showed Pearson and Spearman correlation coefficient p values of <0.001.

ChIP and Gene Transcription Assays

ChIP and gene transcription assays were performed as previously reported (Tackett et al., 2005b; Taverna et al., 2006). Assays were performed in triplicate and analyzed by real time PCR.

Introduction for Examples 4-5

One of the most compositionally diverse structures in a eukaryotic cell is a chromosome. A multitude of macromolecular protein interactions and epigenetic modifications must properly occur on chromatin to drive functional aspects of chromosome biology like gene transcription, DNA replication, recombination, repair and sister chromatid segregation. Analyzing how proteins interact in vivo with chromatin to direct these activities and how epigenetics factors into these mechanisms remains a significant challenge owing to the lack of technologies to comprehensively analyze protein associations and epigenetics at specific native chromosome sites. Chromatin immunoprecipitation (ChIP) assays have traditionally been used to better understand genome-wide distributions of chromatin-associated proteins and histone post-translational modifications (PTMs) at the nucleosome level (Cermak et al., 2011). However, major drawbacks of current ChIP-based methods include their confinement to examining singular histone PTMs or proteins rather than simultaneous profiling of multiple targets, the inability of ChIP to directly determine the co-occupancy of particular histone PTMs and that ChIP is reliant on the previous identification and development of affinity reagents against the molecular target. A more comprehensive and unbiased approach would be the biochemical isolation of a specific native genomic locus for proteomic identification of proteins-associated and histone PTMs. Similar approaches have been performed for large structures like telomeres, engineered plasmids or engineered loci (Griesenbeck et al., 2003; Dejardin and Kingston, 2009; Hoshino and Fuji, 2009; Akiyoshi et al., 2009; Unnikrishnan et al., 2010; Byrum et al., 2012b); however, the proteomic analysis of a small native genomic region without genomic engineering has yet to be performed. To work toward proteomic studies of native chromatin regions (i.e. sections of chromatin that are unaltered genetically and spatially the genome), we recently developed a technique termed Chromatin Affinity Purification with Mass Spectrometry (ChAP-MS) that provides for the enrichment of a native 1-kb section of a chromosome for site-specific identification of protein interactions and associated histone PTMs (Byrum et al., 2012b). This ChAP-MS approach uses the association of an ectopically expressed affinity-tagged LexA protein with a genomically incorporated LexA DNA binding site for site-specific chromatin enrichment. The ChAP-MS approach provides for the isolation of chromatin from the native site in the chromosome; however, one must genomically engineer a LexA DNA binding site, which could alter the native state of the chromatin and which requires a biological system readily amendable to genomic engineering.

To alleviate genomic engineering for affinity enrichment of chromatin sections, we report the use of modified transcription activator-like (TAL) effector proteins to site-specifically target a native section of a chromosome for purification and proteomic analysis. We term this approach TAL-ChAP-MS (FIG. 7A). TAL effector proteins are from *Xanthomonas*, which infects plants and translocates TAL effectors into cells where they serve as transcription activators (Scholze and Boch, 2010; Scholze and Boch, 2011; Doyle et al., 2012). TALs contain a central domain of 18 tandem repeats of 34 amino acids each, which direct sequence-specific DNA binding (Doyle et al., 2012; Cermak et al., 2011). Binding to a given nucleobase in DNA is determined by two adjacent amino acids (12 and 13) within each of the 18 repeats (Scholze and Boch, 2010). Thus, by mutating these amino acids in each of the 18 tandem repeats, one can 'program' binding to a given 18-nt region of DNA in vivo. TAL proteins have been validated in cell culture for targeting nucleases for genome editing and for targeting transcription activators (Miller et al., 2011; Geissler et al., 2011). To test the ability of a TAL protein to serve as an affinity enrichment reagent for native chromatin isolation, a TAL protein was designed that bound a unique 18-nt region of DNA in the promoter region of the GAL1 gene in *Saccharomyces cerevisiae* (FIG. 7B). We chose to analyze proteins and histone PTMs regulating the galactose-induced gene transcription of GAL1 because (1) this is a well-studied genomic locus, which will provide for proof-of-principle analysis, and (2) we previously used this locus to develop the ChAP-MS technique (Byrum et al., 2012b); thus, a comparison can be made to the new TAL-ChAP-MS approach.

One of the major complications for studying specific protein associations with purified protein complexes or with chromatin is the co-enrichment of non-specifically associating proteins. This particularly becomes an issue when studying low copy number entities such as a single genomic locus. With the advancement of high-resolution and sensitive mass spectrometry in recent years, it has been suggested that >$10^9$ cell equivalents are needed to study single genomic loci with proteomic approaches (Chait, 2011). In agreement, our ChAP-MS studies used $10^{11}$ cells for isolation of GAL1 promoter chromatin at levels sufficient for proteomic analysis (Byrum et al., 2012b). When scaling up purifications of low copy entities to meet the sensitivity necessary for high-resolution mass spectrometric analysis, the issue of co-purifying abundant non-specific proteins becomes a major challenge. In the ChAP-MS approach (Byrum et al., 2012b), we used an isotope-labeling strategy to categorize whether a protein co-enriching with a section of chromatin was specifically associated or a contaminant. Limitations for isotope-labeling approaches are cost and having biological systems of study that are amendable to stable isotope-labeling with amino acids. To circumvent the use of isotope-labeling, we now have incorporated label-free quantitative mass spectrometry in the TAL-ChAP-MS workflow. The described TAL-ChAP-MS approach can therefore provide for the purification of a native chromatin region for label-free quantitative proteomic analysis, which will greatly simplify studies of how proteins and combinatorial histone PTMs regulate chromosome metabolism.

Example 4

Development of TAL-ChAP-MS

A schematic of the TAL-ChAP-MS approach to purify native chromatin for proteomic analysis is shown in FIG. 7A. To demonstrate the utility of the TAL-ChAP-MS approach, we used a TAL protein to target the promoter chromatin region upstream of the galactose-inducible GAL1 gene in *S. cerevisiae* (FIG. 7B). Yeast cells were grown in the presence of galactose to induce transcription of the GAL1 gene, which will recruit proteins and histone PTMs that activate transcription. A wild-type culture and a culture of cells containing a plasmid that expressed a PrA-tagged TAL protein that bound the GAL1 promoter region were grown and subjected to in vivo formaldehyde cross-linking to preserve chromatin structure during purification (Byrum et al., 2011a; Byrum et al., 2011b). Following cryogenic cell lysis and sonication of chromatin sections to ~1 kb, each lysate was independently subjected to affinity enrichment of PrA with IgG-coated Dynabeads. Proteins co-enriching with TAL-PrA from the cells containing the pTAL-PrA plasmid and those enriching as contamination from the control cells with no plasmid were identified by high-resolution mass spectrometry. Using label-free quantitative analyses, the relative enrichment of proteins and histone PTMs specifically bound to the GAL1 promoter chromatin were identified.

*Saccharomyces cerevisiae* cells were transformed with pTAL-PrA, and protein expression was validated by western blotting (FIG. 7C). To evaluate whether TAL-PrA expression affected galactose-induced transcription of GAL 1, cDNA was prepared from wild-type and wild-type (+pTAL-PrA) cells under glucose (transcriptionally repressed GAL1) and galactose (transcriptionally active GAL1) growth conditions.

Figure 7G:
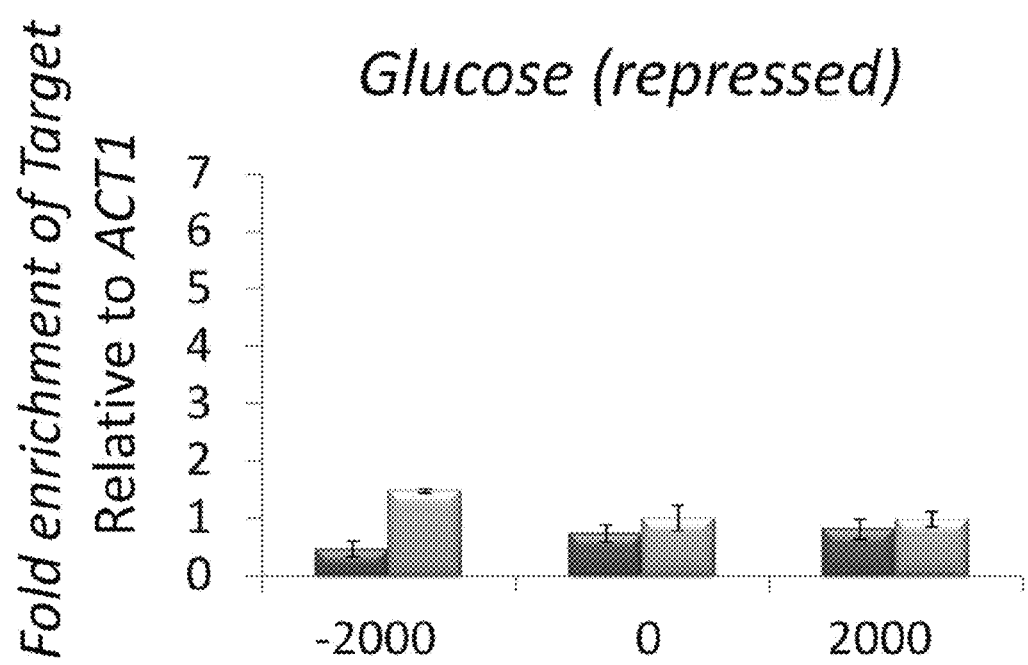

Quantitative rtPCR of this cDNA revealed that expression of TAL-PrA did not affect galactose-induced GAL1 transcription (FIG. 7D). To determine whether TAL-PrA enriched chromatin at the GAL1 promoter region, ChIP was performed to the PrA-tag in cells from glucose and galactose growths (FIG. 7E-G). Under transcriptionally active conditions, TAL-PrA specifically enriched chromatin from the GAL1 promoter region relative to sequences 2 kb up- and downstream (FIG. 7F). The level of chromatin enrichment by TAL-PrA under transcriptionally active conditions was similar to the level used for proteomic studies with LexA-PrA affinity enrichment in the ChAP-MS approach (Byrum et al., 2012b). Interestingly, the TAL-PrA protein did not show enrichment of the GAL1 promoter chromatin under transcriptionally repressive glucose growth conditions (FIG. 7G). One possibility of many is that the lack of enrichment could be due to inaccessibility of the TAL-PrA to the genomic target due to altered chromatin structure under transcriptionally repressive conditions—highlighting the importance for measuring specific chromatin enrichment of the TAL protein before using this approach for specific chromatin enrichment. In the previous publication of the ChAP approach (Byrum et al., 2012b), a LexA-PrA was targeted just upstream of the start codon of GAL1 for enrichment of chromatin, which showed enrichment under both glucose and galactose growth conditions. Importantly, the TAL used in the current study was targeted 193 by upstream of the target site of LexA, which suggests that proximal regions may be differentially accessible to DNA-binding affinity reagents under various transcriptional states. In addition to analyzing enrichment of GAL1 chromatin relative to proximal sequences (FIG. 7E-G), enrichment of GAL1 chromatin was measured relative to the five most homologous sequences in the genome (Table 6). The GAL1 target DNA showed 4.6-fold better enrichment relative to the next five most similar sites in the genome—demonstrating specificity of the TAL protein used in this study to the targeted sequence at the GAL1 promoter region. Collectively, the data in FIG. 7C-G and Table 6 demonstrate that the TAL-ChAP-MS approach can provide enriched chromatin from the GAL1 promoter under transcriptionally active conditions that would be suitable for proteomic studies.

Example 5

Using TAL-ChAP-MS to Identify Proteins and Histone PTMs at the GAL1 promoter

Figure 8:
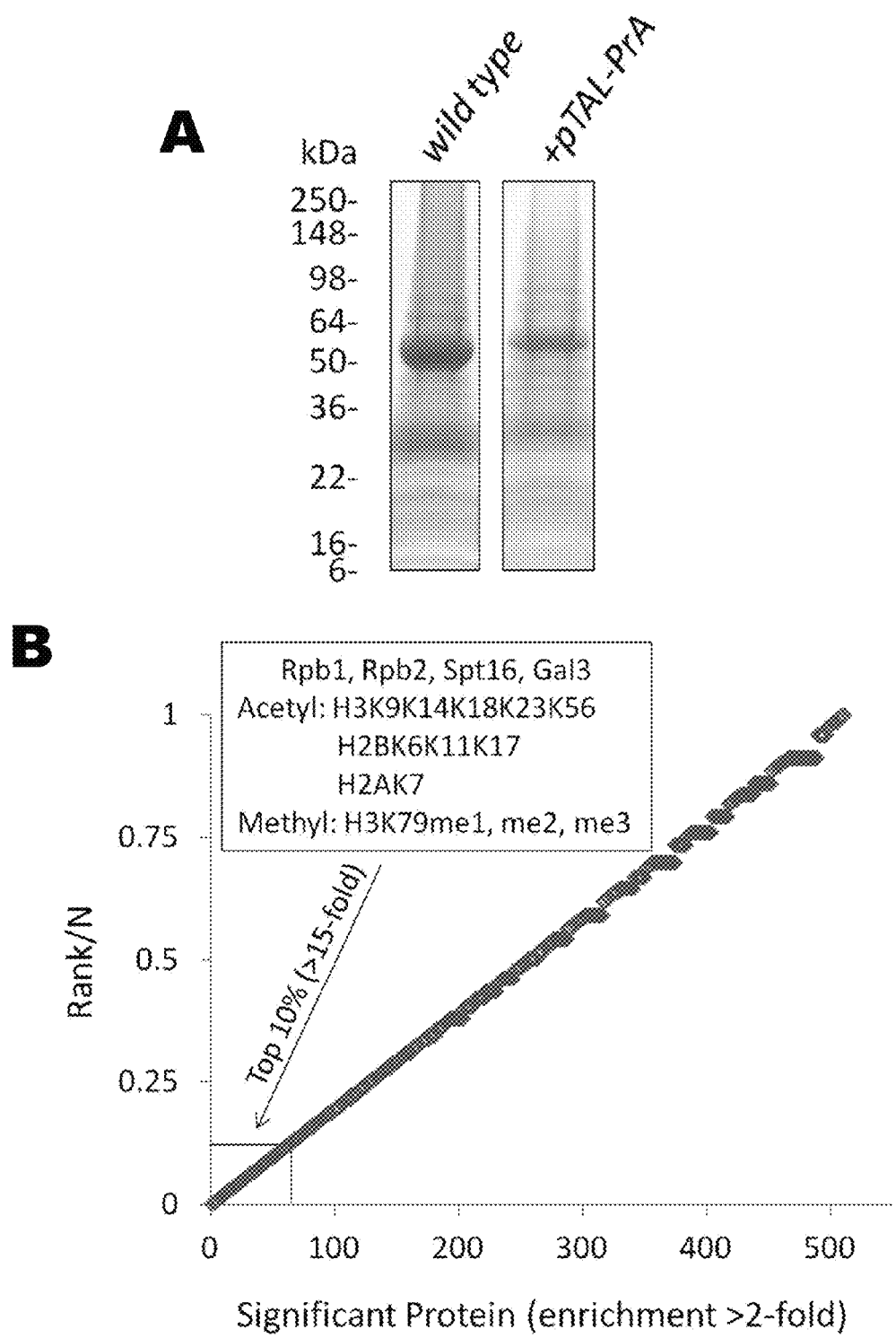
FIG. 8 depicts an image of an SDS-PAGE gel and graphs showing TAL-ChAP-MS analysis of GAL1 promoter chromatin from cells grown its galactose. (A) Proteins co-purifying with TAL-PrA targeted to the promoter region of GAL1 (+pTAL-PrA lane) and proteins non-specifically associating with the IgG-coated Dynabeads (wild-type lane) were resolved by SDS-PAGE/Coomassie-staining and identified by high-resolution mass spectrometry. (B) Proteins found by label-free proteomic analysis to be enriched by >2-fold with transcriptionally active GAL1 promoter chromatin are plotted in accordance to their ranked level of enrichment divided by the total number of enriched proteins (N). Highlighted are the top 10% of proteins (>15-fold enrichment) and histone PTMs enriched with GAL1 promoter chromatin. (C) ChIP was targeted to Spt16-TAP, Rpb2-TAP, Gal3-TAP and H3K14ac under transcriptionally active galactose (light gray bars) and repressive glucose (dark gray bars) growth conditions, ChIP to general H3 was used as a nucleosome occupancy control for H3K14ac ChIP. Enrichment adjacent to the TAL binding site in the promoter of GAL1 relative to ACT1 was monitored by real-time qPCR. The standard error is indicated.
Figure 8C:
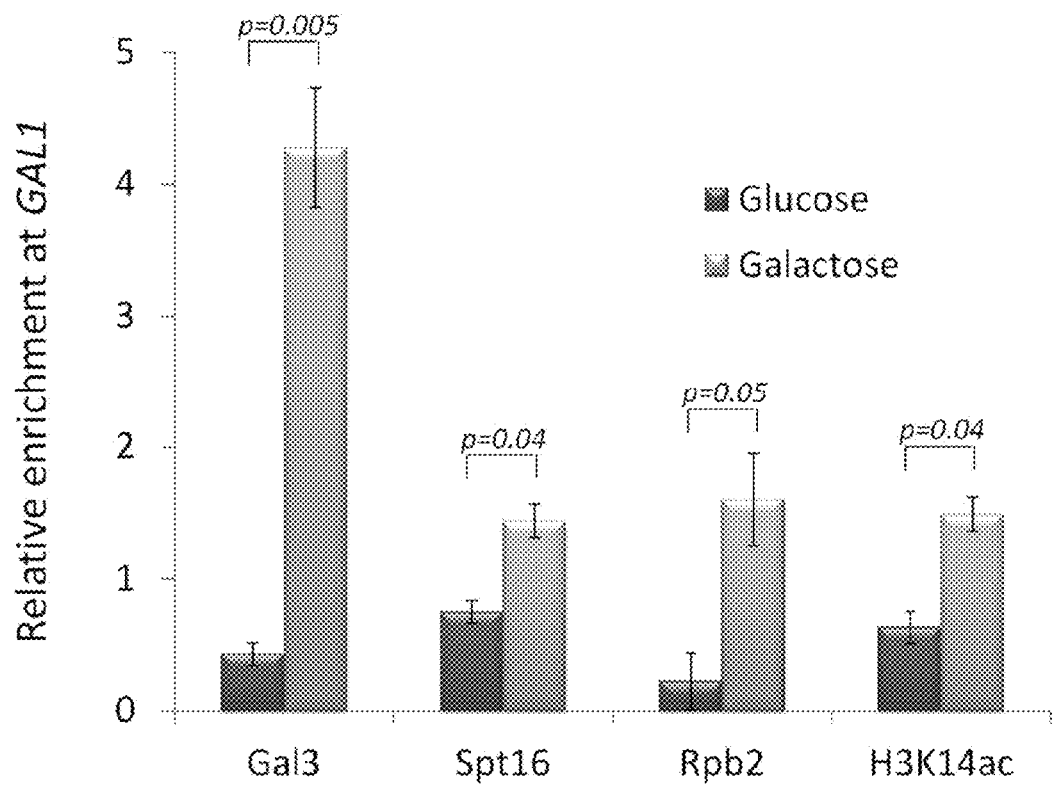

As detailed in the Experimental Procedures for Examples 4-5 section, chromatin from the transcriptionally active GAL1 promoter was enriched with TAL-PrA and resolved by SDS-PAGE (FIG. 8A). The similar Coomassie-stained protein pattern for the TAL-PrA and wild-type control samples in FIG. 8A demonstrates that the co-enrichment of contaminating proteins was a major issue for this approach. Accordingly, the label-free spectral counting approach described in the Experimental Procedures for Examples 4-5 section was used to identify proteins specifically enriched with the TAL-PrA. High-resolution mass spectrometry coupled with label-free proteomics was used to identify proteins and histone PTMs specifically enriched with the GAL1 promoter chromatin (FIG. 8B and Table 7). We focused our analysis on the top 10% of enriched proteins (54 proteins) that each showed >15-fold enrichment with the TAL-PrA (Table 7). Four of these 54 proteins (Rpb1, Rpb2, Spt16 and Gal3) are involved with active transcription of GAL1, and these are the same four proteins previously identified at the promoter of GAL1 with the ChAP approach (Byrum et al., 2012b). Rpb1 and Rpb2 are RNA polymerise components, and Spt16 is a subunit of yFACT that aids in re-organizing chromatin for RNA polymerase activity. Gal3 has previously been shown to inhibit the repressive activity of Gal80 at GAL1 locus (Platt and Reece, 1998). Rpb1, Rpb2, Spt16 and Gal3 were confirmed to be associated adjacent to the TAL-PrA genomic binding site with standard ChIP (FIG. 8C). Thus, the TAL-ChAP-MS approach identified precisely the same proteins as the published ChAP-MS approach during transcriptional activation at the promoter of GAL 1, thereby validating the TAL-ChAP-MS approach for studying the local proteome of small chromatin regions and the use of label-free proteomic approaches for quantifying such enrichments. Many of the other 50 proteins identified as >15-fold enriched with TAL-PrA are typical non-specific protein associations found in affinity purifications (e.g. highly abundant metabolic and ribosomal proteins).

In addition to protein associations with the GAL1 promoter, the following single histone PTMs were identified under transcriptionally active conditions: H3K14ac, H3K56ac, H3K79me1/me2/me3, $H_2$BK 17ac and H2AK7ac; and the following combinatorial histone PTMs: H3K9acK14ac, H3K18acK23ac, $H_2$BK6acK11ac and $H_2$BK11acK17ac (FIG. 8B and Table 8). The presence of H3K14ac was confirmed by standard ChIP (FIG. 8C). Previously using ChAP-MS and routine ChIPs (Byrum et al., 2012b), a similar profile of singly acetylated H3 lysine residues was identified at the GAL1 promoter region, thus confirming the utility of the TAL-ChAP-MS approach. In addition to the acetylations observed in the ChAP-MS study, the TAL-ChAP-MS approach additionally identified methylation of H3K79. As previously reported for the ChAP-MS approach, the TAL-ChAP-MS approach uncovered combinatorial sets (i.e. multiple PTMs on single peptides) of histone PTMs under transcriptionally active conditions at the promoter of GAL 1. The use of a technology like TAL-ChAP-MS to identify previously unknown combinatorial modifications is crucial to understand the epigenome, as specific antibodies to combinatorial histone PTMs are not usually available for standard approaches like ChIP. In general terms, acetylation of histone lysine residues and methylation of H3K79 correlate to transcriptional activation (Kouzarides, 2007); thus, the histone PTMs uncovered by TAL-ChAP-MS correlate to the active transcription state of GAL1 in the presence of galactose.

Discussion for Examples 4-5.

We describe a novel approach called TAL-ChAP-MS that provides for the biochemical isolation of 1-kb native chromatin sections for proteomic identification of specifically associated proteins and combinatorial histone PTMs. The described TAL-ChAP-MS approach overcomes limitations of the ChAP-MS approach (Byrum et al., 2012b), as genomic engineering is not necessary for TAL-based affinity enrichment and because protein enrichment with a given locus can now be determined with label-free proteomics. Even without genomic engineering of the DNA, the ChAP-MS approach does require targeting of a DNA-binding affinity enrichment reagent (i.e. the TAL protein), which has the potential to perturb the chromatin state. However, the data in FIG. 7D demonstrate that transcription of GAL1 is not altered on TAL targeting, which supports maintenance of the chromatin integrity for the studies reported here. Targeting TALs to different sequences in adjacent genomic regions that would provide for purification of overlapping chromatin sections is one possible way for investigators to overcome concerns of TAL binding (i.e. a tiling approach). The implications of the TAL-ChAP-MS approach are far-reaching as investigators can now begin to elucidate the dynamics of chromatin regulation in a site-specific and comprehensive manner. Researchers will now only need to 'reprogram' the DNA-binding specificity of the TAL protein to obtain a unique affinity purification reagent for their chromosome region of interest. Using the TAL-ChAP-MS approach brings researchers closer to being able to take molecular 'snapshots' of the assembly and disassembly of proteins on chromatin and how epigenetic states are modulated at small genomic loci.

Experimental Procedures for Examples 4-5 pTAL-PrA Plasmid, Real-Time rtPCR and ChIP

For affinity enrichment of chromatin from the promoter region of the GAL1 gene in S. cerevisiae, a TAL protein was designed (by the GeneArt Precision TAL services of Life Technologies) to bind a unique 18-nt sequence (GGGG-TAATTAATCAGCGA) 193 base pairs upstream of the GAL1 open-reading frame (FIG. 7B). The TAL protein was designed as a truncation that lacked the native N-terminal transcription activation domain, but it contained the site-specific DNA-binding region. To develop an affinity enrichment reagent, the LexA-coding region of pLexA-PrA [plasmid that constitutively expresses a PrA-tagged LexA protein under TRP selection; from (Byrum et al., 2012b)] was replaced with the TAL-coding region to generate pTAL-PrA. Real-time qPCR measurement of galactose-induced transcription of GAL1 and all ChIP studies were performed as reported in (Byrum et al., 2012b).

TAL-ChAP-MS

To test the TAL-ChAP-MS approach at the promoter region of GAL1, wild-type and wild-type (+pTAL-PrA) S. cerevisiae (W303 matA) cells were cultured to mid-log phase in 3% galactose-containing media, subjected to 1.25% formaldehyde cross-linking, cryogenically lysed and subjected to sonication to shear genomic DNA to ~1 kb [as detailed in (Byrum et al., 2012b; Byrum et al., 2011a; Byrum et al., 2011b)]. Immunoglobulin G (IgG)-coated Dynabeads were added to lyste from ~$10^{11}$ cells from each growth separately [as detailed in (Byrum et al., 2012b)]. Proteins co-enriching with the TAL-PrA (wild-type cells +pTAL-PrA lysate) or proteins non-specifically binding to the Dynabeads (wild-type cell lysate) were resolved by SDS-PAGE/Coomassie-staining (FIG. 8A), excised as 2-mm bands from the entire gel lane, digested in-gel with trypsin and subjected to high-resolution tandem mass spectrometric analysis with a Thermo Velos Orbitap mass spectrometer [as reported in (Byrum et al., 2012b)]. Proteins and typical histone PTMs (lysine acetylation and methylation) were identified using Mascot (Tables 7 and 8). To measure enrichment of a protein, the normalized spectral abundance factor (Zybailov et al., 2006) was calculated for each protein in each lane by dividing the number of spectral counts (normalized for the size of the protein) of a given protein by the sum of all normalized spectral counts of all proteins in the gel lane (Byrum et al., 2011c). The enrichment level for each protein was identified by calculating the fold enrichment (TAL-PrA/wild type) using the normalized spectral abundance factor values (Table 7). Proteins with a fold enrichment >2 (511 of 1459 proteins identified) were used to generate a quantile plot of fold enrichment with GAL1 promoter chromatin (FIG. 8B).

References

1. Agelopoulos, M., McKay, D. J., and Mann, R. S. (2012). Developmental regulation of chromatin conformation by Hox proteins in Drosophila. Cell Rep. 1, 350-359.
2. Akiyoshi, B., Nelson, C. R., Ranish, J. A., and Biggins, S. (2009). Quantitative proteomic analysis of purified yeast kinetochores identifies a PP1 regulatory subunit. Genes Dev. 23, 2887-2899.
3. Barski, A., Cuddapah, S., Cui, K., Roh, T. Y., Schones, D. E., Wang, Z., Wei, G., Chepelev, I., and Zhao, K. (2007). High-resolution profiling of histone methylations in the human genome. Cell 129, 823-837.
4. Bock, I., Dhayalan, A., Kudithipudi, S., Brandt, O., Rathert, P., and Jeltsch, A. (2011). Detailed specificity analysis of antibodies binding to modified histone tails with peptide arrays. Epigenetics 6, 256-263.
5. Boffa, L. C., Carpaneto, E. M., and Allfrey, V. G. (1995). Isolation of active genes containing CAG repeats by DNA strand invasion by a peptide nucleic acid. Proc. Natl. Acad. Sci. USA 92, 1901-1905.
6. Byrum, S. D., Taverna, S. D., and Tackett, A. J. (2011a). Quantitative analysis of histone exchange for transcriptionally active chromatin. J. Clin. Bioinforma 1, 17.
7. Byrum, S., Mackintosh, S. G., Edmondson, R. D., Cheung, W. L., Taverna, S. D., and Tackett, A. J. (2011b). Analysis of histone exchange during chromatin purification. J Integr OMICS 1, 61-65.
8. Byrum, S., Avaritt, N. L., Mackintosh, S. G., Munkberg, J. M., Badgwell, B. D., Cheung, W. L. and Tackett, A. J. (2011c) A quantitative proteomic analysis of FFPE melanoma. J. Culan. Pathol., 38, 933-936.
9. Byrum, S., Smart, S. K., Larson, S., and Tackett, A. J. (2012a). Analysis of stable and transient protein-protein interactions. Methods Mol. Biol. 833, 143-152.
10. Byrum, S., Raman, A., Taverna, S. D. and Tackett, A. J. (2012b) ChAP-MS: a method for identification of proteins and histone posttranslational modifications at a single genomic locus. Cell Rep., 2, 198-205.
11. Cermak, T., Doyle, E. L., Christian, M., Wang, L., Zhang, Y., Schmidt, D., Baller, J. A., Bogdanove, A. J. and Voytas, D. F. (2011) Efficient design and assembly of custom TALEN and other TAL effector-based constructs for DNA targeting. Nucleic Acids Res., 39, e82.
12. Chait, B. T. (2011) Mass spectrometry in the Postgenomic Era. Anna. Rev. Bioche., 80, 239-246.
13. Chi, P., Allis, C. D., and Wang, G. G. (2010). Covalent histone modifications—miswritten, misinterpreted and mis-erased in human cancers. Nat. Rev. Cancer 10, 457-469.
14. Dedon, P. C., Soults, J. A., Allis, C. D., and Gorovsky, M. A. (1991). Formaldehyde cross-linking and immunoprecipitation demonstrate developmental changes in H1 association with transcriptionally active genes. Mol. Cell. Biol. 11, 1729-1733.
15. Déjardin, J., and Kingston, R. E. (2009). Purification of proteins associated with specific genomic loci. Cell 136, 175-186.
16. Doyle, E. L., Booher, N. J., Standage, D. S., Voytas, D. F., Brendel, V. P., Vandyk, J. K. and Bogdanove, A. J. (2012) TAL Effector-Nucleotide Targeter (TALE-NT) 2.0: tools for TAL effector design and target prediction. Nucleic-Acids Res., 40, 117-122.
17. Geissler, R., Scholze, H., Hahn, S., Streubel, J., Bonas, U., Behrens, S. E. and Boch, J. (2011) Transcriptional activators of human genes with programmable DNA-specificity. PLoS One, 6, e19509.
18. Griesenbeck, J., Boeger, H., Strattan, J. S., and Kornberg, R. D. (2003). Affinity purification of specific chromatin segments from chromosomal loci in yeast. Mol. Cell. Biol. 23, 9275-9282.
19. Ho, L., and Crabtree, G. R. (2010). Chromatin remodelling during development. Nature 463, 474-484.
20. Hoshino, A. and Fujii, H. (2009) Insertional chromatin immunoprecipitation: a method for isolating specific genomic regions. J. Biosci. Bioeng., 108, 446-449.
21. Houseley, J., Rubbi, L., Grunstein, M., Tollervey, D., and Vogelauer, M. (2008). A ncRNA modulates histone modification and mRNA induction in the yeast GAL gene cluster. Mol. Cell. 32, 685-695.

22. Johnson, D. S., Mortazavi, A., Myers, R. M., and Wold, B. (2007). Genome-wide mapping of in vivo protein-DNA interactions. Science 316, 1497-1502.
23. Jones, P. A., and Baylin, S. B. (2007). The epigenomics of cancer. Cell 128, 683-692.
24. Kouzarides, T. (2007) Chromatin modifications and their function. Cell, 128, 693-705.
25. Martin, G. R. (1981). Isolation of a pluripotent cell line from early mouse embryos cultured in medium conditioned by teratocarcinoma stem cells. Proc. Natl. Acad. Sci. USA 78, 7634-7638.
26. Mikkelsen, T. S., Ku, M., Jaffe, D. B., Issac, B., Lieberman, E., Giannoukos, G., Alvarez, P., Brockman, W., Kim, T. K., Koche, R. P., et al. (2007). Genome-wide maps of chromatin state in pluripotent and lineage-committed cells. Nature 448, 553-560.
27. Miller, J. C., Tan, S., Qiao, G., Barlow, K. A., Wang, J., Xia, D. F., Meng, X., Paschon, D. E., Leung, E., Hinkley, S. J. et al. (2011) A TALE nuclease architecture for efficient genome editing. Not. Biotech., 29, 143-148.
28. Platt, A., and Reece, R. J. (1998). The yeast galactose genetic switch is mediated by the formation of a Gal4p-Gal80p-Gal3p complex. EMBO J. 17, 4086-4091.
29. Pokholok, D. K., Harbison, C. T., Levine, S., Cole, M., Hannett, N. M., Lee, T. I., Bell, G. W., Walker, K., Rolfe, P. A., Herbolsheimer, E., et al. (2005). Genomewide map of nucleosome acetylation and methylation in yeast. Cell 122, 517-527.
30. Ren, B., Robert, F., Wyrick, J. J., Aparicio, O., Jennings, E. G., Simon, I., Zeitlinger, J., Schreiber, J., Hannett, N., Kanin, E., et al. (2000). Genome-wide location and function of DNA binding proteins. Science 290, 2306-2309.
31. Robertson, G., Hirst, M., Bainbridge, M., Bilenky, M., Zhao, Y., Zeng, T., Euskirchen, G., Bernier, B., Varhol, R., Delaney, A., et al. (2007). Genome-wide profiles of STAT1 DNA association using chromatin immunoprecipitation and massively parallel sequencing. Nat. Methods 4, 651-657.
32. Rossant, J. (2008). Stem cells and early lineage development. Cell 132, 527-531.
33. Scholze, H. and Boch, J. (2010) TAL effector-DNA specificity. Virulence, 1, 428-432.
34. Scholze, H. and Boch, J. (2011) TAL effectors are remote controls for gene activation. Curr. Opin. Microbiol., 14, 47-53.
35. Shukla, A., Bajwa, P., and Bhaumik, S. R. (2006). SAGA-associated Sgf73p facilitates formation of the preinitiation complex assembly at the promoters either in a HAT-dependent or independent manner in vivo. Nucleic Acids Res. 34, 6225-6232.
36. Smart, S. K., Mackintosh, S. G., Edmondson, R. D., Taverna, S. D., and Tackett, A. J. (2009). Mapping the local protein interactome of the NuA3 histone acetyltransferase. Protein Sci. 18, 1987-1997.
37. Tackett, A. J., DeGrasse, J. A., Sekedat, M. D., Oeffinger, M., Rout, M. P., and Chait, B. T. (2005a). I-DIRT, a general method for distinguishing between specific and nonspecific protein interactions. J. Proteome Res. 4, 1752-1756.
38. Tackett, A. J., Dilworth, D. J., Davey, M. J., O'Donnell, M., Aitchison, J. D., Rout, M. P., and Chait, B. T. (2005b). Proteomic and genomic characterization of chromatin complexes at a boundary. J. Cell Biol. 169, 35-47.
39. Taverna, S. D., Ilin, S., Rogers, R. S., Tanny, J. C., Lavender, H., Li, H., Baker, L., Boyle, J., Blair, L. P., Chait, B. T., et al. (2006). Yng1 PHD finger binding to histone H3 trimethylated at lysine 4 promotes NuA3 HAT activity at lysine 14 of H3 and transcription at a subset of targeted ORFS. Mol. Cell. 24, 785-796.
40. Taverna, S. D., Ueberheide, B. M., Liu, Y., Tackett, A. J., Diaz, R. L., Shabanowitz, J., Chait, B. T., Hunt, D. F., and Allis, C. D. (2007). Long-distance combinatorial linkage between methylation and acetylation on histone $H_3N$ termini. Proc. Natl. Acad. Sci. USA 104, 2086-2091.
41. Unnikrishnan, A., Gafken, P. R., and Tsukiyama, T. (2010). Dynamic changes in histone acetylation regulate origins of DNA replication. Nat. Struct. Mol. Biol. 17, 430-437.
42. Zybailov, B., Mosley, A. L., Sardiu, M. E., Coleman, M. K., Florens, L. and Washburn, M. P. (2006) Statistical analysis of membrane proteome expression changes in *Saccharomyces cerevisiae*. J. Proteome Res., 5, 2339-2347.

TABLE 1

Proteins identified by Mascot Distiller from ChAP-MS analysis of GAL1 chromatin isolated from cells grown in glucose.
Mascot Distiller Quantitation Report Mascot search results: Glucose

| | Log ratio versus Intensity (all positive ratios) | Log ratio versus Intensity (selected ratios) |
|---|---|---|
| L/(L + H) | 0 | 0 |
| | 1.00e+7 | 5.00e+6 |
| | 2.00e+7 | 1.00e+7 |
| | 3.00e+7 | 1.50e+7 |
| | 4.00e+7 −4 −3 | 2.00e+7 −4 −3 |
| | −15 −10 −5 0 5 | −2 −1 0 1 |

| Hit | Accession | Score | Mass | L/(L + H) | SD(geo) | # |
|---|---|---|---|---|---|---|
| 1 | P00925 | 1180 | 46885 | 0.5797 | 1.009 | 7 |

ENO2_YEAST Enolase 2 OS = *Saccharomyces cerevisiae* GN = ENO2 PE = 1 SV = 2

| | z Sequence | Incl. L/(L + H) | Std. Err. | Fraction | Correlation | Intensity | Modifications |
|---|---|---|---|---|---|---|---|
| 1 | 2 ANLDVKDQK | 0.8222 | 0.03008 | 0.05098 | 0.4849 | 14020.00 | |
| 2 | 3 YDLDFKNPESDK | 0.4886 | 0.04889 | 0.1516 | 0.7 | 2.59E+05 | |

TABLE 1-continued

Proteins identified by Mascot Distiller from ChAP-MS analysis of GAL1 chromatin isolated from cells grown in glucose.
Mascot Distiller Quantitation Report

| | z | Sequence | Incl. | L/(L + H) | Std. Err. | Fraction | Correlation | Intensity | Modifications |
|---|---|---|---|---|---|---|---|---|---|
| 3 | 2 | YDLDFKNPESDK | X | 0.5785 | 0.01343 | 0.2062 | 0.9094 | 1.62E+05 | |
| 4 | 2 | AVDDFLLSLDGTANK | X | 0.5762 | 0.001 | 0.2292 | 0.9942 | 1.02E+07 | |
| 5 | 3 | AVDDFLLSLDGTANK | X | 0.5799 | 0.00158 | 0.6342 | 0.9975 | 8.26E+05 | |
| 6 | 2 | DGKYDLDFKNPESDK | X | 0.5622 | 0.00842 | 0.1735 | 0.989 | 1.71E+05 | |
| 7 | 2 | GVMNAVNNVNNVIAAAFVK | | 0.7536 | 0.05322 | 0.594 | 0.4909 | 2.12E+05 | |
| 8 | 3 | YPIVSIEDPFAEDDWEAWSHFFK | X | 0.5768 | 0 | 0.8459 | 0.9995 | 2.58E+06 | |
| 9 | 3 | RYPIVSIEDPFAEDDWEAWSHFFK | X | 0.5641 | 0.0183 | 0.5271 | 0.9778 | 1.27E+05 | |
| 10 | 3 | YGASAGNVGDEGGVAPNIQTAEEALDLIVDAIK | X | 0.5825 | 0 | 0.9229 | 0.9993 | 1.78E+07 | |

| Hit | Accession | Score | Mass | L/(L + H) | SD(geo) | # |
|---|---|---|---|---|---|---|
| 2 | P00924 | 1117 | 46773 | 0.5798 | 1.008 | 5 |

ENO1_YEAST Enolase 1 OS = *Saccharomyces cerevisiae* GN = ENO1 PE = 1 SV = 2

| | z | Sequence | Incl. | L/(L + H) | Std. Err. | Fraction | Correlation | Intensity | Modifications |
|---|---|---|---|---|---|---|---|---|---|
| 1 | 2 | ANIDVKDQK | | 0.8222 | 0.03008 | 0.05098 | 0.4849 | 1.40E+04 | |
| 2 | 2 | AVDDFLISLDGTANK | X | 0.5762 | 0.001 | 0.2292 | 0.9942 | 1.02E+07 | |
| 3 | 3 | AVDDFLISLDGTANK | X | 0.5799 | 0.00158 | 0.6342 | 0.9975 | 8.26E+05 | |
| 4 | 3 | IEEELGDNAVFAGENFHHGDKL | X | 0.6064 | 0.00518 | 0.5017 | 0.978 | 3.82E+05 | |
| 5 | 3 | YPIVSIEDPFAEDDWEAWSHFFK | X | 0.5768 | 0 | 0.8459 | 0.9995 | 2.58E+06 | |
| 6 | 3 | RYPIVSIEDPFAEDDWEAWSHFFK | X | 0.5641 | 0.0183 | 0.5271 | 0.9778 | 1.27E+05 | |
| 7 | 3 | YGASAGNVGDEGGVAPNIQTAEEALDLIVDAIK | X | 0.5825 | 0 | 0.9229 | 0.9993 | 1.78E+07 | |

| Hit | Accession | Score | Mass | L/(L + H) | SD(geo) | # |
|---|---|---|---|---|---|---|
| 3 | P10592 | 565 | 69844 | 0.5495 | | 10 |

HSP72_YEAST Heat shock protein SSA2 OS = *Saccharomyces cerevisiae* GN = SSA2 PE = 1 SV = 3

| | z | Sequence | Incl. | L/(L + H) | Std. Err. | Fraction | Correlation | Intensity | Modifications |
|---|---|---|---|---|---|---|---|---|---|
| 1 | 2 | ITITNDKGR | X | 0.9873 | 0.0152 | 0.06237 | 0.9611 | 4.21E+04 | |
| 2 | 2 | NFNDPEVQGDMK | X | 0.554 | 0.0076 | 0.3809 | 0.9603 | 8.52E+05 | |
| 3 | 2 | FKEEDEKESQR | X | 0.5702 | 0.0088 | 0.0696 | 0.9865 | 9.27E+04 | |
| 4 | 2 | NFTPEQISSMVLGK | X | 0.5605 | 0.00872 | 0.1288 | 0.9508 | 5.66E+05 | |
| 5 | 2 | LIDVDGKPQIQVEFK | X | 0.5488 | 0.00255 | 0.256 | 0.9909 | 4.00E+05 | |
| 6 | 3 | LIDVDGKPQIQVEFK | X | 0.5555 | 0.00158 | 0.624 | 0.9945 | 2.37E+06 | |
| 7 | 3 | IINEPTAAAIAYGLDKK | X | 0.5399 | 0.00584 | 0.05784 | 0.938 | 3.22E+05 | |
| 8 | 3 | LDKSQVDEIVLVGGSTR | X | 0.528 | 0.02077 | 0.3666 | 0.7616 | 7.53E+05 | |
| 9 | 3 | NTISEAGDKLEQADKDAVTK | X | 0.5444 | 0.00255 | 0.3405 | 0.9868 | 2.60E+06 | |
| 10 | 3 | TQDLLLLDVAPLSLGIETAGGVMTK | X | 0.5041 | 0.07248 | 0.196 | 0.9741 | 1.75E+05 | |

TABLE 1-continued

Proteins identified by Mascot Distiller from ChAP-MS analysis of GAL1 chromatin isolated from cells grown in glucose.
Mascot Distiller Quantitation Report

| Hit | Accession | Score | Mass | L/(L + H) | SD(geo) | # |
|---|---|---|---|---|---|---|
| 4 | P06169 | 555 | 61737 | 0.5581 | 1.008 | 5 |

PDC1_YEAST Pyruvate decarboxylase isozyme 1 OS = Saccharomyces cerevisiae GN = PDC1 PE = 1 SV = 7

| | z | Sequence | Incl. | L/(L + H) | Std. Err. | Fraction | Correlation | Intensity | Modifications |
|---|---|---|---|---|---|---|---|---|---|
| 1 | 2 | NATFPGVQMK | X | 0.5499 | 0.00466 | 0.3978 | 0.9842 | 1.13E+06 | |
| 2 | 3 | VATTGEWDKLTQDK | X | 0.5476 | 0.00455 | 0.265 | 0.9899 | 1.17E+06 | |
| 3 | 3 | LLQTPIDMSLKPNDAESEK | X | 0.5635 | 0.00264 | 0.4617 | 0.9956 | 2.39E+05 | |
| 4 | 2 | MIEIMLPVFDAPQNLVEQAK | X | 0.5603 | 0.0038 | 0.7877 | 0.9907 | 7.07E+06 | |
| 5 | 3 | LLQTPIDMSLKPNDAESEKEVIDTILALVK | X | 0.56 | 0.00158 | 0.5686 | 0.9967 | 2.71E+06 | |

| Hit | Accession | Score | Mass | L/(L + H) | SD(geo) | # |
|---|---|---|---|---|---|---|
| 5 | P10591 | 551 | 70039 | 0.5549 | | 9 |

HSP71_YEAST Heat shock protein SSA1 OS = Saccharomyces cerevisiae GN = SSA1 PE = 1 SV = 4

| | z | Sequence | Incl. | L/(L + H) | Std. Err. | Fraction | Correlation | Intensity | Modifications |
|---|---|---|---|---|---|---|---|---|---|
| 1 | 2 | ITITNDKGR | X | 0.9873 | 0.0152 | 0.06237 | 0.9611 | 4.21E+04 | |
| 2 | 2 | NFNDPEVQADMK | X | 0.595 | 0.00755 | 0.1662 | 0.9451 | 4.27E+05 | |
| 3 | 2 | FKEEDEKESQR | X | 0.5702 | 0.0088 | 0.0696 | 0.9865 | 9.27E+04 | |
| 4 | 2 | NFTPEQISSMVLGK | X | 0.5605 | 0.00872 | 0.1288 | 0.9508 | 5.66E+05 | |
| 5 | 2 | LIDVDGKPQIQVEFK | X | 0.5488 | 0.00255 | 0.256 | 0.9909 | 4.00E+05 | |
| 6 | 3 | LIDVDGKPQIQVEFK | X | 0.5555 | 0.00158 | 0.624 | 0.9945 | 2.37E+06 | |
| 7 | 3 | IINEPTAAAIAYGLDKK | X | 0.5399 | 0.00584 | 0.05784 | 0.938 | 3.22E+05 | |
| 8 | 3 | LDKSQVDEIVLVGGSTR | X | 0.528 | 0.02077 | 0.3666 | 0.7616 | 7.53E+05 | |
| 9 | 3 | TQDLLLLDVAPLSLGIETAGGVMTK | X | 0.5041 | 0.07248 | 0.196 | 0.9741 | 1.75E+05 | |

| Hit | Accession | Score | Mass | L/(L + H) | SD(geo) | # |
|---|---|---|---|---|---|---|
| 6 | P15108 | 548 | 80850 | 0.4277 | | 10 |

HSC82_YEAST ATP-dependent molecular chaperone HSC82 OS = Saccharomyces cerevisiae GN = HSC82 PE = 1 SV = 4

| | z | Sequence | Incl. | L/(L + H) | Std. Err. | Fraction | Correlation | Intensity | Modifications |
|---|---|---|---|---|---|---|---|---|---|
| 1 | 2 | SPFLDALK | X | 0.594 | 0.00899 | 0.5359 | 0.9605 | 4.97E+05 | |
| 2 | 3 | ALKDILGDQVEK | X | 0.5513 | 0.02217 | 0.189 | 0.9214 | 5.90E+04 | |
| 3 | 3 | VKEEVQELEELNK | X | 0.5794 | 0.01043 | 0.07342 | 0.9201 | 7.47E+04 | |
| 4 | 2 | LEEVDEEEEKKPK | | 0.1049 | 999 | 0.1111 | 0.1643 | 2.69E+04 | |
| 5 | 2 | LFLKDDQLEYLEEK | X | 0.5684 | 0.02513 | 0.191 | 0.9399 | 5.88E+05 | |
| 6 | 3 | LFLKDDQLEYLEEKR | X | 0.4997 | 0.04689 | 0.1356 | 0.8192 | 3.36E+05 | |
| 7 | 3 | TLVDITKDFELEETDEEK | X | 0.4212 | 0.04847 | 0.09843 | 0.7318 | 2.17E+05 | |
| 8 | 2 | VFITDEAEDLIPEWLSFVK | X | 0.5569 | 0.00991 | 0.227 | 0.9585 | 1.35E+06 | |
| 9 | 3 | VFITDEAEDLIPEWLSFVK | X | 0.5764 | 0.00772 | 0.5192 | 0.9965 | 3.80E+05 | |
| 10 | 3 | RVFITDEAEDLIPEWLSFVK | X | 0.5766 | 0.02142 | 0.2893 | 0.9293 | 1.19E+05 | |
| 11 | 3 | TLVDITKDFELEETDEEKAER | X | 0.216 | 0.1336 | 0.2606 | 0.801 | 1.35E+06 | |

TABLE 1-continued

Proteins identified by Mascot Distiller from ChAP-MS analysis of GAL1 chromatin isolated from cells grown in glucose.
Mascot Distiller Quantitation Report

| Hit | Accession | Score | Mass | L/(L + H) | SD(geo) | # |
|---|---|---|---|---|---|---|
| 7 | P00560 | 506 | 44711 | 0.5584 | | 4 |

PGK_YEAST Phosphoglycerate kinase OS = *Saccharomyces cerevisiae*
GN = PGK1 PE = 1 SV = 2

| | z Sequence | Incl. | L/(L + H) | Std. Err. | Fraction | Correlation | Intensity | Modifications |
|---|---|---|---|---|---|---|---|---|
| 1 | 3 VDFNVPLDGKK | X | 0.3003 | 0.01134 | 0.1059 | 0.8842 | 3.08E+05 | |
| 2 | 2 VLENTEIGDSIFDK | | 0.9928 | 0.00158 | 0.8106 | 0.3129 | 3.18E+07 | |
| 3 | 2 SSAAGNTVIIGGGDTATVAK | X | 0.577 | 0.00158 | 0.6503 | 0.9976 | 1.77E+06 | |
| 4 | 3 GVEVVLPVDFIIADAFSADANTK | X | 0.6021 | 0.00634 | 0.4734 | 0.9828 | 1.32E+06 | |
| 5 | 2 GVEVVLPVDFIIADAFSADANTK | X | 0.5722 | 0.00525 | 0.5529 | 0.9973 | 1.42E+06 | |

| Hit | Accession | Score | Mass | L/(L + H) | SD(geo) | # |
|---|---|---|---|---|---|---|
| 8 | P00359 | 492 | 35724 | 0.5592 | 1.017 | 5 |

G3P3_YEAST Glyceraldehyde-3-phosphate dehydrogenase 3
OS = *Saccharomyces cerevisiae* GN = TDH3 PE = 1 SV = 3

| | z Sequence | Incl. | L/(L + H) | Std. Err. | Fraction | Correlation | Intensity | Modifications |
|---|---|---|---|---|---|---|---|---|
| 1 | 2 ELDTAQK | X | 0.5482 | 0.00832 | 0.1767 | 0.9264 | 2.25E+04 | |
| 2 | 2 VVDLVEHVAK | X | 0.5557 | 0.001 | 0.6963 | 0.9976 | 2.33E+06 | |
| 3 | 2 YAGEVSHDDK | | 0.7269 | 0.01789 | 0.2422 | 0.6988 | 8.10E+04 | |
| 4 | 2 TASGNIIPSSTGAAK | X | 0.5621 | 0.00158 | 0.7985 | 0.9966 | 9.13E+06 | |
| 5 | 3 VPTVDVSVVDLTVK | X | 0.5299 | 0.00836 | 0.3828 | 0.9782 | 2.33E+05 | |
| 6 | 3 YAGEVSHDDKHIIVDGK | | 0.4138 | 0.03022 | 0.1569 | 0.4338 | 1.27E+06 | |
| 7 | 2 YAGEVSHDDKHIIVDGK | | 0.4604 | 0.01421 | 0.386 | 0.4585 | 4.81E+05 | |
| 8 | 2 DPANLPWGSNVDIAIDSTGVFK | X | 0.5497 | 0.00466 | 0.5417 | 0.9953 | 1.10E+06 | |

| Hit | Accession | Score | Mass | L/(L + H) | SD(geo) | # |
|---|---|---|---|---|---|---|
| 9 | P00950 | 289 | 27592 | 0.5753 | 1.028 | 4 |

PMG1_YEAST Phosphoglycerate mutase 1 OS = *Saccharomyces cerevisiae*
GN = GPM1 PE = 1 SV = 3

| | z Sequence | Incl. | L/(L + H) | Std. Err. | Fraction | Correlation | Intensity | Modifications |
|---|---|---|---|---|---|---|---|---|
| 1 | 3 KVYPDVLYTSK | X | 0.6133 | 0.00839 | 0.05839 | 0.9039 | 9.79E+04 | |
| 2 | 2 LLPYWQDVIAK | X | 0.5686 | 0.001 | 0.6124 | 0.9984 | 3.23E+06 | |
| 3 | 2 SFDVPPPPIDASSPFSQK | X | 0.579 | 0.00467 | 0.7461 | 0.9747 | 5.95E+06 | |
| 4 | 3 RSFDVPPPPIDASSPFSQK | X | 0.5607 | 0.0055 | 0.1214 | 0.9811 | 2.74E+05 | |

| Hit | Accession | Score | Mass | L/(L + H) | SD(geo) | # |
|---|---|---|---|---|---|---|
| 10 | P00942 | 273 | 26779 | 0.8938 | 1.241 | 4 |

TPIS_YEAST Triosephosphate isomerase OS = *Saccharomyces cerevisiae*
GN = TPI1 PE = 1 SV = 2

| | z Sequence | Incl. | L/(L + H) | Std. Err. | Fraction | Correlation | Intensity | Modifications |
|---|---|---|---|---|---|---|---|---|
| 1 | 3 KPQVTVGAQNAYLK | X | 1 | 0 | 0.6505 | 0.7407 | 2.01E+06 | |
| 2 | 2 ASGAFTGENSVDQIK | X | 0.8721 | 0.00784 | 0.8579 | 0.9988 | 1.90E+06 | |
| 3 | 3 SYFHEDDKFIADK | X | 0.5635 | 0.00564 | 0.2565 | 0.9791 | 2.28E+05 | |

TABLE 1-continued

Proteins identified by Mascot Distiller from ChAP-MS analysis of GAL1 chromatin isolated from cells grown in glucose.
Mascot Distiller Quantitation Report

| | z | Sequence | Incl. | L/(L + H) | Std. Err. | Fraction | Correlation | Intensity | Modifications |
|---|---|---|---|---|---|---|---|---|---|
| 4 | 2 | ASGAFTGENSVDQIKDVGAK | X | 0.5037 | 0.05902 | 0.5738 | 0.8696 | 1.28E+05 | |

| Hit | Accession | Score | Mass | L/(L + H) | SD(geo) | # |
|---|---|---|---|---|---|---|
| 11 | P23254 | 258 | 74104 | 0.5924 | 1.089 | 4 |

TKT1_YEAST Transketolase 1 OS = *Saccharomyces cerevisiae* GN = TKL1
PE = 1 SV = 4

| | z | Sequence | Incl. | L/(L + H) | Std. Err. | Fraction | Correlation | Intensity | Modifications |
|---|---|---|---|---|---|---|---|---|---|
| 1 | 2 | LFSEYQK | | 0.7783 | 0.02398 | 0.136 | 0.6468 | 1.69E+05 | |
| 2 | 2 | ILAVDTVSK | X | 0.6661 | 0.02039 | 0.1191 | 0.8514 | 6.18E+05 | |
| 3 | 3 | KFPELGAELAR | X | 0.4889 | 0.01828 | 0.08146 | 0.9458 | 3.41E+04 | |
| 4 | 2 | LSGQLPANWESK | | 0.9991 | 0.00158 | 0.5921 | 0.6509 | 1.69E+06 | |
| 5 | 2 | VVSLPDFFTFDK | X | 0.5277 | 0.01746 | 0.3974 | 0.82 | 4.93E+05 | |
| 6 | 2 | QNLPQLEGSSIESASK | X | 0.5395 | 0.00842 | 0.1282 | 0.9767 | 9.63E+04 | |
| 7 | 2 | SFVVPQEVYDHYQK | | 0.4152 | 0.04681 | 0.3912 | 0.41 | 1.50E+05 | |

| Hit | Accession | Score | Mass | L/(L + H) | SD(geo) | # |
|---|---|---|---|---|---|---|
| 12 | P34760 | 251 | 21688 | 0.5583 | | 1 |

TSA1_YEAST Peroxiredoxin TSA1 OS = *Saccharomyces cerevisiae*
GN = TSA1 PE = 1 SV = 3

| | z | Sequence | Incl. | L/(L + H) | Std. Err. | Fraction | Correlation | Intensity | Modifications |
|---|---|---|---|---|---|---|---|---|---|
| 1 | 2 | TAVVDGVFDEVSLDK | X | 0.5583 | 0.01341 | 0.4102 | 0.9415 | 7.29E+05 | |

| Hit | Accession | Score | Mass | L/(L + H) | SD(geo) | # |
|---|---|---|---|---|---|---|
| 13 | P02994 | 242 | 50001 | 0.5996 | | 5 |

EF1A_YEAST Elongation factor 1-alpha OS = *Saccharomyces cerevisiae*
GN = TEF1 PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 2 | FQEIVK | X | 0.9909 | 0.00329 | 0.1232 | 0.9948 | 5.97E+05 | |
| 2 | 2 | LPLQDVYK | X | 0.5266 | 0.002 | 0.5985 | 0.9845 | 4.55E+06 | |
| 3 | 3 | SHINVVIGHVDSGK | X | 0.5427 | 0.01093 | 0.07069 | 0.9813 | 4.33E+04 | |
| 4 | 3 | TLLEAIDAIEQPSRPTDKPLR | X | 0.6222 | 0.01 | 0.3809 | 0.7963 | 1.58E+07 | |
| 5 | 3 | SVEMHHEQLEQGVPGDNVGFNVK | X | 0.5271 | 0.00255 | 0.8205 | 0.9972 | 2.24E+06 | |

| Hit | Accession | Score | Mass | L/(L + H) | SD(geo) | # |
|---|---|---|---|---|---|---|
| 14 | P11484 | 235 | 66937 | 0.5697 | 1.042 | 3 |

HSP75_YEAST Heat shock protein SSB1 OS = *Saccharomyces cerevisiae*
GN = SSB1 PE = 1 SV = 3

| | z | Sequence | Incl. | L/(L + H) | Std. Err. | Fraction | Correlation | Intensity | Modifications |
|---|---|---|---|---|---|---|---|---|---|
| 1 | 2 | LLSDFFDGK | X | 0.5313 | 0.004 | 0.3939 | 0.9936 | 1.18E+06 | |
| 2 | 2 | VIDVDGNPVIEVQYLEETK | X | 0.5573 | 0.03139 | 0.2885 | 0.9312 | 2.81E+05 | |
| 3 | 3 | STSGNTHLGGQDFDTNLLEHFK | X | 0.6018 | 0.01912 | 0.5754 | 0.975 | 1.64E+06 | |

TABLE 1-continued

Proteins identified by Mascot Distiller from ChAP-MS analysis of GAL1 chromatin isolated from cells grown in glucose.
Mascot Distiller Quantitation Report

| Hit | Accession | Score | Mass | L/(L + H) | SD(geo) | # |
|---|---|---|---|---|---|---|
| 15 | P16521 | 220 | 115920 | 0.4751 | 1.086 | 3 |

EF3A_YEAST Elongation factor 3A OS = *Saccharomyces cerevisiae*
GN = YEF3 PE = 1 SV = 3

| | z | Sequence | Incl. | L/(L + H) | Std. Err. | Fraction | Correlation | Intensity | Modifications |
|---|---|---|---|---|---|---|---|---|---|
| 1 | 2 | QINENDAEAMNK | X | 0.502 | 0.03789 | 0.1931 | 0.9204 | 1.87E+05 | |
| 2 | 2 | ATETVDNKDIER | X | 0.5572 | 0.01016 | 0.3336 | 0.9535 | 2.92E+05 | |
| 3 | 2 | LVEDPQVIAPFLGK | X | 0.4314 | 0.01731 | 0.1193 | 0.9722 | 5.89E+05 | |

| Hit | Accession | Score | Mass | L/(L + H) | SD(geo) | # |
|---|---|---|---|---|---|---|
| 16 | P14540 | 217 | 39812 | 0.5455 | 1.017 | 4 |

ALF_YEAST Fructose-bisphosphate aldolase OS = *Saccharomyces cerevisiae* GN = FBA1 PE = 1 SV = 3

| | z | Sequence | Incl. | L/(L + H) | Std. Err. | Fraction | Correlation | Intensity | Modifications |
|---|---|---|---|---|---|---|---|---|---|
| 1 | 2 | LLPWFDGMLEADEAYFK | X | 0.5387 | 0.01791 | 0.6343 | 0.9901 | 2.73E+06 | |
| 2 | 3 | LLPWFDGMLEADEAYFK | X | 0.5693 | 0.00324 | 0.7442 | 0.9942 | 4.58E+05 | |
| 3 | 2 | KLLPWFDGMLEADEAYFK | X | 0.5497 | 0.02627 | 0.3049 | 0.8469 | 4.81E+04 | |
| 4 | 3 | KLLPWFDGMLEADEAYFK | X | 0.5579 | 0.00588 | 0.6699 | 0.9919 | 6.41E+05 | |

| Hit | Accession | Score | Mass | L/(L + H) | SD(geo) | # |
|---|---|---|---|---|---|---|
| 17 | P05750 | 214 | 26630 | 0.5144 | | 1 |

RS3_YEAST 40S ribosomal protein S3 OS = *Saccharomyces cerevisiae*
GN = RPS3 PE = 1 SV = 5

| | z | Sequence | Incl. | L/(L + H) | Std. Err. | Fraction | Correlation | Intensity | Modifications |
|---|---|---|---|---|---|---|---|---|---|
| 1 | 3 | ALPDAVTIIEPKEEEPILAPSVK | X | 0.5144 | 0.00787 | 0.0782 | 0.9853 | 1.22E+06 | |

| Hit | Accession | Score | Mass | L/(L + H) | SD(geo) | # |
|---|---|---|---|---|---|---|
| 18 | P38788 | 196 | 58515 | 0.5268 | 1.003 | 2 |

SSZ1_YEAST Ribosome-associated complex subunit SSZ1
OS = *Saccharomyces cerevisiae* GN = SSZ1 PE = 1 SV = 2

| | z | Sequence | Incl. | L/(L + H) | Std. Err. | Fraction | Correlation | Intensity | Modifications |
|---|---|---|---|---|---|---|---|---|---|
| 1 | 2 | EAVLTVPTNFSEEQK | X | 0.5251 | 0.00574 | 0.2728 | 0.9966 | 3.66E+05 | |
| 2 | 3 | LISDYDADELAEALQPVIVNTPHLK | X | 0.5276 | 0.00557 | 0.6012 | 0.9986 | 7.77E+05 | |

| Hit | Accession | Score | Mass | L/(L + H) | SD(geo) | # |
|---|---|---|---|---|---|---|
| 19 | P40150 | 195 | 66930 | 0.5697 | 1.042 | 3 |

HSP76_YEAST Heat shock protein SSB2 OS = *Saccharomyces cerevisiae*
GN = SSB2 PE = 1 SV = 2

| | z | Sequence | Incl. | L/(L + H) | Std. Err. | Fraction | Correlation | Intensity | Modifications |
|---|---|---|---|---|---|---|---|---|---|
| 1 | 2 | LLSDFFDGK | X | 0.5313 | 0.004 | 0.3939 | 0.9936 | 1.18E+06 | |
| 2 | 2 | VIDVDGNPVIEVQYLEETK | X | 0.5573 | 0.03139 | 0.2885 | 0.9312 | 2.81E+05 | |
| 3 | 3 | STSGNTHLGGQDFDTNLLEHFK | X | 0.6018 | 0.01912 | 0.5754 | 0.975 | 1.64E+06 | |

TABLE 1-continued

Proteins identified by Mascot Distiller from ChAP-MS analysis of GAL1 chromatin isolated from cells grown in glucose.
Mascot Distiller Quantitation Report

| Hit | Accession | Score | Mass | L/(L + H) | SD(geo) | # |
|---|---|---|---|---|---|---|
| 20 | P32324 | 189 | 93719 | 0.4948 | 1.141 | 4 |

EF2_YEAST Elongation factor 2 OS = *Saccharomyces cerevisiae* GN = EFT1 PE = 1 SV = 1

| | z Sequence | Incl. | L/(L + H) | Std. Err. | Fraction | Correlation | Intensity | Modifications |
|---|---|---|---|---|---|---|---|---|
| 1 | 2 TGTLTTSETAHNMK | X | 0.5494 | 0.05488 | 0.2574 | 0.9685 | 3.09E+04 | |
| 2 | 2 ETVESESSQTALSK | X | 0.4964 | 0.00945 | 0.5999 | 0.989 | 1.00E+06 | |
| 3 | 3 WTNKDTDAEGKPLER | X | 0.4881 | 0.01896 | 0.04008 | 0.9109 | 1.19E+05 | |
| 4 | 2 WTNKDTDAEGKPLER | X | 0.383 | 0.06499 | 0.03736 | 0.93 | 1.87E+04 | |

| Hit | Accession | Score | Mass | L/(L + H) | SD(geo) | # |
|---|---|---|---|---|---|---|
| 21 | P32589 | 184 | 77318 | | | 0 |

HSP7F_YEAST Heat shock protein homolog SSE1 OS = *Saccharomyces cerevisiae* GN = SSE1 PE = 1 SV = 4

| | z Sequence | Incl. | L/(L + H) | Std. Err. | Fraction | Correlation | Intensity | Modifications |
|---|---|---|---|---|---|---|---|---|
| 1 | 3 QVEDEDHMEVFPAGSSFPSTK | | 0.6809 | 0.02791 | 0.3031 | 0.3098 | 9.21E+05 | |
| 2 | 3 QSISEAFGKPLSTTLNQDEAIAK | | 0.5365 | 0.06281 | 0.4112 | 0.2745 | 3.29E+05 | |

| Hit | Accession | Score | Mass | L/(L + H) | SD(geo) | # |
|---|---|---|---|---|---|---|
| 22 | P54115 | 183 | 54380 | 0.6157 | | 1 |

ALDH6_YEAST Magnesium-activated aldehyde dehydrogenase, cytosolic OS = *Saccharomyces cerevisiae* GN = ALD6 PE = 1 SV = 4

| | z Sequence | Incl. | L/(L + H) | Std. Err. | Fraction | Correlation | Intensity | Modifications |
|---|---|---|---|---|---|---|---|---|
| 1 | 2 SAHLVFDDANIKK | X | 0.6157 | 0.0168 | 0.06354 | 0.9683 | 1.83E+04 | |
| 2 | 3 IVKEEIFGPVVTVAK | | −0.01367 | 0.6603 | 0.692 | 0.03687 | 2.37E+06 | |

| Hit | Accession | Score | Mass | L/(L + H) | SD(geo) | # |
|---|---|---|---|---|---|---|
| 23 | P00360 | 179 | 35728 | 0.5624 | 1.059 | 4 |

G3P1_YEAST Glyceraldehyde-3-phosphate dehydrogenase 1 OS = *Saccharomyces cerevisiae* GN = TDH1 PE = 1 SV = 3

| | z Sequence | Incl. | L/(L + H) | Std. Err. | Fraction | Correlation | Intensity | Modifications |
|---|---|---|---|---|---|---|---|---|
| 1 | 2 ELDTAQK | X | 0.5482 | 0.00832 | 0.1767 | 0.9264 | 2.25E+04 | |
| 2 | 2 TASGNIIPSSTGAAK | X | 0.5621 | 0.00158 | 0.7985 | 0.9966 | 9.13E+06 | |
| 3 | 3 VPTVDVSVVDLTVK | X | 0.5299 | 0.00836 | 0.3828 | 0.9782 | 2.33E+05 | |
| 4 | 3 IATYQERDPANLPWGSLK | X | 0.6109 | 0.00894 | 0.4762 | 0.9875 | 2.36E+05 | |

| Hit | Accession | Score | Mass | L/(L + H) | SD(geo) | # |
|---|---|---|---|---|---|---|
| 24 | P05694 | 159 | 86296 | 0.5474 | 1.143 | 4 |

METE_YEAST 5-methyltetrahydropteroyltriglutamate--homocysteine methyltransferase OS = *Saccharomyces cerevisiae* GN = MET6 PE = 1 SV = 4

| | z Sequence | Incl. | L/(L + H) | Std. Err. | Fraction | Correlation | Intensity | Modifications |
|---|---|---|---|---|---|---|---|---|
| 1 | 2 VATSGVANK | X | 0.4292 | 0.05981 | 0.2367 | 0.7626 | 5.78E+05 | |
| 2 | 2 ITVDELFK | X | 0.7613 | 0.02167 | 0.4122 | 0.9349 | 3.00E+05 | |
| 3 | 2 ALDADVVSIEFSK | X | 0.5995 | 0.00506 | 0.3617 | 0.9908 | 4.15E+05 | |

TABLE 1-continued

Proteins identified by Mascot Distiller from ChAP-MS analysis of GAL1 chromatin isolated from cells grown in glucose.
Mascot Distiller Quantitation Report

| | | | | | | | |
|---|---|---|---|---|---|---|---|
| 4 | 3 APEQFDEVVA AIGNK | X | 0.5769 | 0.02178 | 0.2145 | 0.9228 | 7.39E+04 |

| Hit | Accession | Score | Mass | L/(L + H) | SD(geo) | # |
|---|---|---|---|---|---|---|
| 25 | P00817 | 159 | 32280 | 0.3148 | 1.707 | 2 |

IPYR_YEAST Inorganic pyrophosphatase OS = *Saccharomyces cerevisiae* GN = IPP1 PE = 1 SV = 4

| | z Sequence | Incl. | L/(L + H) | Std. Err. | Fraction | Correlation | Intensity | Modifications |
|---|---|---|---|---|---|---|---|---|
| 1 | 2 LNDIEDVEK | X | 0.1915 | 0.08967 | 0.192 | 0.967 | 2.15E+05 | |
| 2 | 3 LEITKEETLNP IIQDTKK | | 0.5691 | 0.01513 | 0.1321 | 0.6614 | 3.55E+04 | |
| 3 | 3 AVGDNDPID VLEIGETIAYT GQVK | X | 0.5565 | 0.00915 | 0.5386 | 0.9951 | 1.89E+05 | |

| Hit | Accession | Score | Mass | L/(L + H) | SD(geo) | # |
|---|---|---|---|---|---|---|
| 26 | P46655 | 156 | 81369 | 0.4215 | 1.269 | 2 |

SYEC_YEAST Glutamyl-tRNA synthetase cytoplasmic OS = *Saccharomyces cerevisiae* GN = GUS1 PE = 1 SV = 3

| | z Sequence | Incl. | L/(L + H) | Std. Err. | Fraction | Correlation | Intensity | Modifications |
|---|---|---|---|---|---|---|---|---|
| 1 | 2 KNDDGSMVAK | X | 0.5902 | 0.05607 | 0.0228 | 0.8152 | 515.7 | |
| 2 | 3 EKEEFQDSIL EDLDLLGIK | X | 0.4214 | 0.04183 | 0.2818 | 0.7588 | 6.23E+05 | |

| Hit | Accession | Score | Mass | L/(L + H) | SD(geo) | # |
|---|---|---|---|---|---|---|
| 27 | P09436 | 156 | 123651 | 0.9973 | | 1 |

SYIC_YEAST Isoleucyl-tRNA synthetase, cytoplasmic OS = *Saccharomyces cerevisiae* GN = ILS1 PE = 1 SV = 1

| | z Sequence | Incl. | L/(L + H) | Std. Err. | Fraction | Correlation | Intensity | Modifications |
|---|---|---|---|---|---|---|---|---|
| 1 | 2 MSNIDFQYD DSVK | X | 0.9973 | 0.00158 | 0.6248 | 0.961 | 3.01E+06 | |

| Hit | Accession | Score | Mass | L/(L + H) | SD(geo) | # |
|---|---|---|---|---|---|---|
| 28 | P61864 | 148 | 8552 | 0.8538 | | 1 |

UBIQ_YEAST Ubiquitin OS = *Saccharomyces cerevisiae* GN = UBI1 PE = 1 SV = 1

| | z Sequence | Incl. | L/(L + H) | Std. Err. | Fraction | Correlation | Intensity | Modifications |
|---|---|---|---|---|---|---|---|---|
| 1 | 2 IQDKEGIPPD QQR | X | 0.8538 | 0.01276 | 0.1534 | 0.8756 | 1.67E+05 | |

| Hit | Accession | Score | Mass | L/(L + H) | SD(geo) | # |
|---|---|---|---|---|---|---|
| 29 | P04456 | 146 | 15748 | 0.5126 | | 1 |

RL25_YEAST 60S ribosomal protein L25 OS = *Saccharomyces cerevisiae* GN = RPL25 PE = 1 SV = 4

| | z Sequence | Incl. | L/(L + H) | Std. Err. | Fraction | Correlation | Intensity | Modifications |
|---|---|---|---|---|---|---|---|---|
| 1 | 2 ELYEVDVLK | X | 0.5126 | 0.00785 | 0.1734 | 0.9804 | 4.97E+05 | |

| Hit | Accession | Score | Mass | L/(L + H) | SD(geo) | # |
|---|---|---|---|---|---|---|
| 30 | P12709 | 146 | 61261 | 0.5947 | | 3 |

G6PI_YEAST Glucose-6-phosphate isomerase OS = *Saccharomyces cerevisiae* GN = PGI1 PE = 1 SV = 3

| | z Sequence | Incl. | L/(L + H) | Std. Err. | Fraction | Correlation | Intensity | Modifications |
|---|---|---|---|---|---|---|---|---|
| 1 | 2 NWFLSK | X | 0.5893 | 0.01445 | 0.08506 | 0.8965 | 1.22E+04 | |
| 2 | 2 TFTTAETITN ANTAK | | 0.7863 | 0.02669 | 0.2797 | 0.4859 | 1.42E+05 | |
| 3 | 2 NLVNDEIIAA LIELAK | X | 0.7445 | 0.01763 | 0.05341 | 0.9308 | 1.58E+04 | |

TABLE 1-continued

Proteins identified by Mascot Distiller from ChAP-MS analysis of GAL1 chromatin isolated from cells grown in glucose.
Mascot Distiller Quantitation Report

| | z | Sequence | Incl. | L/(L + H) | Std. Err. | Fraction | Correlation | Intensity | Modifications |
|---|---|---|---|---|---|---|---|---|---|
| 4 | 3 | ANKPMYVDGVNVAPEVDSVLK | X | 0.5898 | 0.03119 | 0.315 | 0.7014 | 4.18E+05 | |

| Hit | Accession | Score | Mass | L/(L + H) | SD(geo) | # |
|---|---|---|---|---|---|---|
| 31 | P08524 | 145 | 40738 | 0.5181 | | 1 |

FPPS_YEAST Farnesyl pyrophosphate synthase OS = *Saccharomyces cerevisiae* GN = FPP1 PE = 1 SV = 2

| | z | Sequence | Incl. | L/(L + H) | Std. Err. | Fraction | Correlation | Intensity | Modifications |
|---|---|---|---|---|---|---|---|---|---|
| 1 | 2 | TVEQLGQEEYEK | X | 0.5181 | 0.00585 | 0.1843 | 0.9906 | 4.80E+05 | |
| 2 | 2 | IEQLYHEYEESIAK | | 0.3587 | 0.08308 | 0.1586 | 0.6297 | 6.38E+04 | |

| Hit | Accession | Score | Mass | L/(L + H) | SD(geo) | # |
|---|---|---|---|---|---|---|
| 32 | P00330 | 142 | 36800 | 0.5295 | 1.039 | 3 |

ADH1_YEAST Alcohol dehydrogenase 1 OS = *Saccharomyces cerevisiae* GN = ADH1 PE = 1 SV = 4

| | z | Sequence | Incl. | L/(L + H) | Std. Err. | Fraction | Correlation | Intensity | Modifications |
|---|---|---|---|---|---|---|---|---|---|
| 1 | 2 | ANELLINVK | X | 0.5781 | 0.01445 | 0.406 | 0.9865 | 4.01E+05 | |
| 2 | 2 | VVGLSTLPEIYEK | X | 0.518 | 0.001 | 0.6074 | 0.9963 | 5.17E+06 | |
| 3 | 3 | VLGIDGGEGKEELFR | X | 0.5414 | 0.00403 | 0.7131 | 0.9802 | 3.52E+06 | |

| Hit | Accession | Score | Mass | L/(L + H) | SD(geo) | # |
|---|---|---|---|---|---|---|
| 33 | P07262 | 138 | 49763 | 0.2171 | | 1 |

DHE4_YEAST NADP-specific glutamate dehydrogenase 1 OS = *Saccharomyces cerevisiae* GN = GDH1 PE = 1 SV = 2

| | z | Sequence | Incl. | L/(L + H) | Std. Err. | Fraction | Correlation | Intensity | Modifications |
|---|---|---|---|---|---|---|---|---|---|
| 1 | 3 | VTWENDKGEQEVAQGYR | X | 0.2171 | 0.1184 | 0.5086 | 0.7666 | 6.81E+05 | |

| Hit | Accession | Score | Mass | L/(L + H) | SD(geo) | # |
|---|---|---|---|---|---|---|
| 34 | P31373 | 138 | 42692 | 0.6023 | 1.05 | 2 |

CYS3_YEAST Cystathionine gamma-lyase OS = *Saccharomyces cerevisiae* GN = CYS3 PE = 1 SV = 2

| | z | Sequence | Incl. | L/(L + H) | Std. Err. | Fraction | Correlation | Intensity | Modifications |
|---|---|---|---|---|---|---|---|---|---|
| 1 | 2 | ISVGIEDTDDLLEDIK | X | 0.613 | 0.00887 | 0.1862 | 0.967 | 6.82E+05 | |
| 2 | 3 | ISVGIEDTDDLLEDIKQALK | X | 0.5634 | 0.01345 | 0.3481 | 0.9112 | 1.80E+05 | |

| Hit | Accession | Score | Mass | L/(L + H) | SD(geo) | # |
|---|---|---|---|---|---|---|
| 35 | P22202 | 137 | 70009 | 0.5832 | 1.457 | 2 |

HSP74_YEAST Heat shock protein SSA4 OS = *Saccharomyces cerevisiae* GN = SSA4 PE = 1 SV = 3

| | z | Sequence | Incl. | L/(L + H) | Std. Err. | Fraction | Correlation | Intensity | Modifications |
|---|---|---|---|---|---|---|---|---|---|
| 1 | 2 | ITITNDKGR | X | 0.9873 | 0.0152 | 0.06237 | 0.9611 | 4.21E+04 | |
| 2 | 3 | IINEPTAAAIAYGLDKK | X | 0.5399 | 0.00584 | 0.05784 | 0.938 | 3.22E+05 | |

TABLE 1-continued

Proteins identified by Mascot Distiller from ChAP-MS analysis of GAL1 chromatin isolated from cells grown in glucose.
Mascot Distiller Quantitation Report

| Hit | Accession | Score | Mass | L/(L + H) | SD(geo) | # |
|---|---|---|---|---|---|---|
| 36 | A6ZP47 | 134 | 65697 | 0.3172 | | 1 |

DED1_YEAS7 ATP-dependent RNA helicase DED1 OS = *Saccharomyces cerevisiae* (strain YJM789) GN = DED1 PE = 3 SV = 1

| | z | Sequence | Incl. | L/(L + H) | Std. Err. | Fraction | Correlation | Intensity | Modifications |
|---|---|---|---|---|---|---|---|---|---|
| 1 | 2 | TGGFLFPVLSESFK | X | 0.3172 | 0.03297 | 0.08265 | 0.8019 | 3.08E+05 | |
| 2 | 3 | DVPEPITEFTSPPLDGLLLENIK | | 0.00052 | 7.122 | 0.6671 | 0.1659 | 1.16E+06 | |

| Hit | Accession | Score | Mass | L/(L + H) | SD(geo) | # |
|---|---|---|---|---|---|---|
| 37 | P00549 | 134 | 54510 | 0.5402 | 2.375 | 2 |

KPYK1_YEAST Pyruvate kinase 1 OS = *Saccharomyces cerevisiae* GN = PYK1 PE = 1 SV = 2

| | z | Sequence | Incl. | L/(L + H) | Std. Err. | Fraction | Correlation | Intensity | Modifications |
|---|---|---|---|---|---|---|---|---|---|
| 1 | 2 | EVLGEQGKDVK | | 0.8211 | 0.01418 | 0.5587 | 0.4163 | 9.19E+05 | |
| 2 | 3 | MNFSHGSYEYHK | X | 0.159 | 0.3656 | 0.233 | 0.8491 | 3.57E+04 | |
| 3 | 3 | GVNLPGTDVDLPALSEKDKEDLR | X | 0.5499 | 0.00705 | 0.3217 | 0.9634 | 2.45E+06 | |

| Hit | Accession | Score | Mass | L/(L + H) | SD(geo) | # |
|---|---|---|---|---|---|---|
| 38 | P29311 | 134 | 30073 | 0.5686 | 1.063 | 3 |

BMH1_YEAST Protein BMH1 OS = *Saccharomyces cerevisiae* GN = BMH1 PE = 1 SV = 4

| | z | Sequence | Incl. | L/(L + H) | Std. Err. | Fraction | Correlation | Intensity | Modifications |
|---|---|---|---|---|---|---|---|---|---|
| 1 | 3 | LAEQAERYEEMVENMK | X | 0.6493 | 0.01923 | 0.1302 | 0.8619 | 2.33E+04 | |
| 2 | 3 | QAFDDAIAELDTLSEESYK | X | 0.5798 | 0.00382 | 0.3875 | 0.9933 | 2.42E+05 | |
| 3 | 3 | ISDDILSVLDSHLIPSATTGESK | X | 0.5643 | 0.01199 | 0.1289 | 0.8075 | 1.04E+06 | |

| Hit | Accession | Score | Mass | L/(L + H) | SD(geo) | # |
|---|---|---|---|---|---|---|
| 39 | P26321 | 133 | 33890 | | | 0 |

RL5_YEAST 60S ribosomal protein L5 OS = *Saccharomyces cerevisiae* GN = RPL5 PE = 1 SV = 3

| | z | Sequence | Incl. | L/(L + H) | Std. Err. | Fraction | Correlation | Intensity | Modifications |
|---|---|---|---|---|---|---|---|---|---|

| Hit | Accession | Score | Mass | L/(L + H) | SD(geo) | # |
|---|---|---|---|---|---|---|
| 40 | P26263 | 130 | 61542 | | | 0 |

PDC6_YEAST Pyruvate decarboxylase isozyme 3 OS = *Saccharomyces cerevisiae* GN = PDC6 PE = 1 SV = 3

| | z | Sequence | Incl. | L/(L + H) | Std. Err. | Fraction | Correlation | Intensity | Modifications |
|---|---|---|---|---|---|---|---|---|---|

| Hit | Accession | Score | Mass | L/(L + H) | SD(geo) | # |
|---|---|---|---|---|---|---|
| 41 | A6ZQJ1 | 121 | 44837 | 0.5295 | | 1 |

IF4A_YEAS7 ATP-dependent RNA helicase eIF4A OS = *Saccharomyces cerevisiae* (strain YJM789) GN = TIF1 PE = 3 SV = 1

| | z | Sequence | Incl. | L/(L + H) | Std. Err. | Fraction | Correlation | Intensity | Modifications |
|---|---|---|---|---|---|---|---|---|---|
| 1 | 3 | AIMPIIEGHDVLAQAQSGTGK | X | 0.5295 | 0.00498 | 0.5721 | 0.9845 | 4.30E+05 | |

TABLE 1-continued

Proteins identified by Mascot Distiller from ChAP-MS analysis of GAL1 chromatin isolated from cells grown in glucose.
Mascot Distiller Quantitation Report

| Hit | Accession | Score | Mass | L/(L + H) | SD(geo) | # |
|---|---|---|---|---|---|---|
| 42 | Q02753 | 119 | 18231 | 0.4842 | | 1 |

RL21A_YEAST 60S ribosomal protein L21-A OS = *Saccharomyces cerevisiae* GN = RPL21A PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 2 | VGDIVDIK | X | 0.4842 | 0.00614 | 0.01566 | 0.9582 | 1.27E+05 | |

| Hit | Accession | Score | Mass | L/(L + H) | SD(geo) | # |
|---|---|---|---|---|---|---|
| 43 | P05030 | 119 | 99941 | 0.5928 | | 1 |

PMA1_YEAST Plasma membrane ATPase 1 OS = *Saccharomyces cerevisiae* GN = PMA1 PE = 1 SV = 2

| | z | Sequence | Incl. | L/(L + H) | Std. Err. | Fraction | Correlation | Intensity | Modifications |
|---|---|---|---|---|---|---|---|---|---|
| 1 | 3 | TVEEDHPIPEDVHENYENK | X | 0.5928 | 0.02245 | 0.3764 | 0.8651 | 3.27E+05 | |

| Hit | Accession | Score | Mass | L/(L + H) | SD(geo) | # |
|---|---|---|---|---|---|---|
| 44 | Q03195 | 119 | 68297 | | | 0 |

RLI1_YEAST Translation initiation factor RLI1 OS = *Saccharomyces cerevisiae* GN = RLI1 PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 3 | LLAGALKPDEGQDIPK | | 0.1154 | 0.2281 | 0.1563 | 0.679 | 1.09E+05 | |

| Hit | Accession | Score | Mass | L/(L + H) | SD(geo) | # |
|---|---|---|---|---|---|---|
| 45 | P38011 | 119 | 34936 | 0.4788 | | 1 |

GBLP_YEAST Guanine nucleotide-binding protein subunit beta-like protein OS = *Saccharomyces cerevisiae* GN = ASC1 PE = 1 SV = 4

| | z | Sequence | Incl. | L/(L + H) | Std. Err. | Fraction | Correlation | Intensity | Modifications |
|---|---|---|---|---|---|---|---|---|---|
| 1 | 3 | VVPNEKADDDSVTIISAGNDK | X | 0.4788 | 0.00934 | 0.03497 | 0.9434 | 2.43E+05 | |

| Hit | Accession | Score | Mass | L/(L + H) | SD(geo) | # |
|---|---|---|---|---|---|---|
| 46 | P19097 | 117 | 206818 | 0.6972 | | 1 |

FAS2_YEAST Fatty acid synthase subunit alpha OS = *Saccharomyces cerevisiae* GN = FAS2 PE = 1 SV = 2

| | z | Sequence | Incl. | L/(L + H) | Std. Err. | Fraction | Correlation | Intensity | Modifications |
|---|---|---|---|---|---|---|---|---|---|
| 1 | 2 | EIYYTPDPSELAAK | X | 0.6972 | 0.02896 | 0.2436 | 0.8764 | 4.39E+05 | |

| Hit | Accession | Score | Mass | L/(L + H) | SD(geo) | # |
|---|---|---|---|---|---|---|
| 47 | P22768 | 116 | 47175 | | | 0 |

ASSY_YEAST Argininosuccinate synthase OS = *Saccharomyces cerevisiae* GN = ARG1 PE = 1 SV = 2

| | z | Sequence | Incl. | L/(L + H) | Std. Err. | Fraction | Correlation | Intensity | Modifications |
|---|---|---|---|---|---|---|---|---|---|

| Hit | Accession | Score | Mass | L/(L + H) | SD(geo) | # |
|---|---|---|---|---|---|---|
| 48 | P41277 | 112 | 28138 | 0.5193 | 1.003 | 2 |

GPP1_YEAST (DL)-glycerol-3-phosphatase 1 OS = *Saccharomyces cerevisiae* GN = GPP1 PE = 1 SV = 3

| | z | Sequence | Incl. | L/(L + H) | Std. Err. | Fraction | Correlation | Intensity | Modifications |
|---|---|---|---|---|---|---|---|---|---|
| 1 | 2 | FAPDFADEEYVNK | | 0.2622 | 0.08634 | 0.2384 | 0.6536 | 3.56E+05 | |
| 2 | 3 | FAPDFADEEYVNKLEGEIPEK | X | 0.5189 | 0.00547 | 0.2526 | 0.9631 | 1.44E+06 | |

TABLE 1-continued

Proteins identified by Mascot Distiller from ChAP-MS analysis of GAL1 chromatin isolated from cells grown in glucose.
Mascot Distiller Quantitation Report

| | z | Sequence | Incl. | L/(L + H) | Std. Err. | Fraction | Correlation | Intensity | Modifications |
|---|---|---|---|---|---|---|---|---|---|
| 3 | 2 | VGEYNAETDE VELIFDDYLY AK | X | 0.5217 | 0.01439 | 0.5462 | 0.9935 | 2.38E+05 | |

| Hit | Accession | Score | Mass | L/(L + H) | SD(geo) | # |
|---|---|---|---|---|---|---|
| 49 | P49090 | 110 | 64857 | 0.5527 | 1.053 | 2 |

ASNS2_YEAST Asparagine synthetase [glutamine-hydrolyzing] 2
OS = *Saccharomyces cerevisiae* GN = ASN2 PE = 1 SV = 2

| | z | Sequence | Incl. | L/(L + H) | Std. Err. | Fraction | Correlation | Intensity | Modifications |
|---|---|---|---|---|---|---|---|---|---|
| 1 | 2 | YFTPDWLDEK | X | 0.5819 | 0.02038 | 0.1065 | 0.9343 | 3.09E+05 | |
| 2 | 3 | AFDTTDEPDV KPYLPEEILWR | X | 0.5251 | 0.03417 | 0.2562 | 0.9393 | 3.11E+05 | |

| Hit | Accession | Score | Mass | L/(L + H) | SD(geo) | # |
|---|---|---|---|---|---|---|
| 50 | P15624 | 110 | 67691 | 0.9837 | 1.076 | 3 |

SYFB_YEAST Phenylalanyl-tRNA synthetase beta chain
OS = *Saccharomyces cerevisiae* GN = FRS1 PE = 1 SV = 3

| | z | Sequence | Incl. | L/(L + H) | Std. Err. | Fraction | Correlation | Intensity | Modifications |
|---|---|---|---|---|---|---|---|---|---|
| 1 | 2 | SKEGAEPK | X | 0.9916 | 0.00141 | 0.07152 | 0.9856 | 1.79E+06 | |
| 2 | 2 | GYWIEEDDS VK | X | 0.8641 | 0.05554 | 0.05094 | 0.8192 | 3.24E+04 | |
| 3 | 2 | NSGFEIIQGL LGK | X | 0.8704 | 0.03036 | 0.142 | 0.8105 | 8.54E+04 | |

| Hit | Accession | Score | Mass | L/(L + H) | SD(geo) | # |
|---|---|---|---|---|---|---|
| 51 | P19882 | 109 | 60714 | 0.4595 | | 1 |

HSP60_YEAST Heat shock protein 60, mitochondrial OS = *Saccharomyces cerevisiae* GN = HSP60 PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 2 | NVLIEQPFGP PK | | 0.3833 | 0.07553 | 0.1289 | 0.6499 | 8.66E+04 | |
| 2 | 2 | AAVEEGILPG GGTALVK | X | 0.4595 | 0.03115 | 0.1117 | 0.9559 | 1.38E+05 | |

| Hit | Accession | Score | Mass | L/(L + H) | SD(geo) | # |
|---|---|---|---|---|---|---|
| 52 | P38088 | 109 | 75845 | | | 0 |

SYG_YEAST Glycyl-tRNA synthetase 1 OS = *Saccharomyces cerevisiae* GN = GRS1 PE = 1 SV = 1

| | z | Sequence | Incl. | L/(L + H) | Std. Err. | Fraction | Correlation | Intensity | Modifications |
|---|---|---|---|---|---|---|---|---|---|

| Hit | Accession | Score | Mass | L/(L + H) | SD(geo) | # |
|---|---|---|---|---|---|---|
| 53 | P07284 | 105 | 53276 | | | 0 |

SYSC_YEAST Seryl-tRNA synthetase, cytoplasmic OS = *Saccharomyces cerevisiae* GN = SES1 PE = 1 SV = 2

| | z | Sequence | Incl. | L/(L + H) | Std. Err. | Fraction | Correlation | Intensity | Modifications |
|---|---|---|---|---|---|---|---|---|---|

| Hit | Accession | Score | Mass | L/(L + H) | SD(geo) | # |
|---|---|---|---|---|---|---|
| 54 | P53184 | 99 | 24978 | 0.4323 | | 1 |

PNC1_YEAST Nicotinamidase OS = *Saccharomyces cerevisiae* GN = PNC1 PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 3 | TTVLLDYTRPI SDDPEVINK | X | 0.4323 | 0.02539 | 0.2814 | 0.7218 | 1.46E+06 | |

TABLE 1-continued

Proteins identified by Mascot Distiller from ChAP-MS analysis of GAL1 chromatin isolated from cells grown in glucose.
Mascot Distiller Quantitation Report

| Hit | Accession | Score | Mass | L/(L + H) | SD(geo) | # |
|---|---|---|---|---|---|---|
| 55 | P36008 | 99 | 46827 | 0.8918 | 1.457 | 2 |

EF1G2_YEAST Elongation factor 1-gamma 2 OS = *Saccharomyces cerevisiae* GN = TEF4 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 LLGSDVIEK | X | 0.9663 | 0.00996 | 0.4982 | 0.9961 | 1.44E+06 | |
| 2 | 2 WFNTVAASPIVK | X | 0.527 | 0.01203 | 0.07669 | 0.8876 | 2.21E+05 | |

| Hit | Accession | Score | Mass | L/(L + H) | SD(geo) | # |
|---|---|---|---|---|---|---|
| 56 | Q01560 | 95 | 45444 | | | 0 |

NOP3_YEAST Nucleolar protein 3 OS = *Saccharomyces cerevisiae* GN = NPL3 PE = 1 SV = 1

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 57 | P40213 | 94 | 15974 | | | 0 |

RS16_YEAST 40S ribosomal protein S16 OS = *Saccharomyces cerevisiae* GN = RPS16A PE = 1 SV = 2

| z | Sequence | Incl. | L/(L + H) | Std. Err. | Fraction | Correlation | Intensity | Modifications |
|---|---|---|---|---|---|---|---|---|
| 1 | 2 YVDEQSKNELK | | 0.9917 | 0.00434 | 0.3579 | 0.08027 | 4.77E+05 | |
| 2 | 2 YVDEQSKNELKK | | 0.9999 | 0.00574 | 0.1204 | 0.1164 | 4.58E+05 | |

| Hit | Accession | Score | Mass | L/(L + H) | SD(geo) | # |
|---|---|---|---|---|---|---|
| 58 | P16140 | 94 | 57922 | | | 0 |

VATB_YEAST V-type proton ATPase subunit B OS = *Saccharomyces cerevisiae* GN = VMA2 PE = 1 SV = 2

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 59 | P25293 | 93 | 47855 | 0.5024 | | 1 |

NAP1_YEAST Nucleosome assembly protein OS = *Saccharomyces cerevisiae* GN = NAP1 PE = 1 SV = 2

| z | Sequence | Incl. | L/(L + H) | Std. Err. | Fraction | Correlation | Intensity | Modifications |
|---|---|---|---|---|---|---|---|---|
| 1 | 2 LGSLVGQDSGYVGGLPK | X | 0.5024 | 0.03188 | 0.08129 | 0.758 | 2.53E+04 | |

| Hit | Accession | Score | Mass | L/(L + H) | SD(geo) | # |
|---|---|---|---|---|---|---|
| 60 | P41940 | 93 | 39781 | 0.5624 | 1.009 | 2 |

MPG1_YEAST Mannose-1-phosphate guanyltransferase OS = *Saccharomyces cerevisiae* GN = MPG1 PE = 1 SV = 2

| z | Sequence | Incl. | L/(L + H) | Std. Err. | Fraction | Correlation | Intensity | Modifications |
|---|---|---|---|---|---|---|---|---|
| 1 | 2 LATGANIVGNALIDPTAK | X | 0.5695 | 0.00687 | 0.05507 | 0.9887 | 2.54E+04 | |
| 2 | 3 INAGLYILNPEVIDLIEMKPTSIEK | X | 0.562 | 0.00414 | 0.5133 | 0.9966 | 4.50E+05 | |

TABLE 1-continued

Proteins identified by Mascot Distiller from ChAP-MS analysis of GAL1 chromatin isolated from cells grown in glucose.
Mascot Distiller Quantitation Report

| Hit | Accession | Score | Mass | L/(L + H) | SD(geo) | # |
|---|---|---|---|---|---|---|
| 61 | P15705 | 93 | 66705 | | | 0 |

STI1_YEAST Heat shock protein STI1 OS = Saccharomyces cerevisiae GN = STI1 PE = 1 SV = 1 z Sequence   Incl.  L/(L + H)  Std. Err.  Fraction Correlation  Intensity  Modifications

| Hit | Accession | Score | Mass | L/(L + H) | SD(geo) | # |
|---|---|---|---|---|---|---|
| 62 | Q03048 | 91 | 15979 | | | 0 |

COFI_YEAST Cofilin OS = Saccharomyces cerevisiae GN = COF1 PE = 1 SV = 1 z Sequence   Incl.  L/(L + H)  Std. Err.  Fraction Correlation  Intensity  Modifications

| | z | Sequence | Incl. | L/(L + H) | Std. Err. | Fraction | Correlation | Intensity | Modifications |
|---|---|---|---|---|---|---|---|---|---|
| 1 | 2 | SGVAVADES LTAFNDLK | | 0.2984 | 0.1196 | 0.0948 | 0.4874 | 1.00E+05 | |

| Hit | Accession | Score | Mass | L/(L + H) | SD(geo) | # |
|---|---|---|---|---|---|---|
| 63 | P38707 | 90 | 62168 | 0.6442 | | 1 |

SYNC_YEAST Asparaginyl-tRNA synthetase, cytoplasmic OS = Saccharomyces cerevisiae GN = DED81 PE = 1 SV = 1 z Sequence   Incl.  L/(L + H)  Std. Err.  Fraction Correlation  Intensity  Modifications

| | z | Sequence | Incl. | L/(L + H) | Std. Err. | Fraction | Correlation | Intensity | Modifications |
|---|---|---|---|---|---|---|---|---|---|
| 1 | 2 | SVQYVLEDPI AGPLVK | X | 0.6442 | 0.02511 | 0.182 | 0.8768 | 2.97E+05 | |

| Hit | Accession | Score | Mass | L/(L + H) | SD(geo) | # |
|---|---|---|---|---|---|---|
| 64 | P49089 | 89 | 64734 | 0.4454 | 1.252 | 2 |

ASNS1_YEAST Asparagine synthetase [glutamine-hydrolyzing] 1 OS = Saccharomyces cerevisiae GN = ASN1 PE = 1 SV = 2 z Sequence   Incl.  L/(L + H)  Std. Err.  Fraction Correlation  Intensity  Modifications

| | z | Sequence | Incl. | L/(L + H) | Std. Err. | Fraction | Correlation | Intensity | Modifications |
|---|---|---|---|---|---|---|---|---|---|
| 1 | 2 | YFTPDWLDEK | X | 0.5819 | 0.02038 | 0.1065 | 0.9343 | 3.09E+05 | |
| 2 | 2 | ATNDVEPSTY DSK | X | 0.375 | 0.01032 | 0.3126 | 0.9726 | 4.80E+05 | |

| Hit | Accession | Score | Mass | L/(L + H) | SD(geo) | # |
|---|---|---|---|---|---|---|
| 65 | P14832 | 88 | 17380 | | | 0 |

CYPH_YEAST Peptidyl-prolyl cis-trans isomerase OS = Saccharomyces cerevisiae GN = CPR1 PE = 1 SV = 3 z Sequence   Incl.  L/(L + H)  Std. Err.  Fraction Correlation  Intensity  Modifications

| | z | Sequence | Incl. | L/(L + H) | Std. Err. | Fraction | Correlation | Intensity | Modifications |
|---|---|---|---|---|---|---|---|---|---|
| 1 | 2 | KVESLGSPSG ATK | | 0.5598 | 0.00415 | 0.2553 | 0.5249 | 4.83E+05 | |

| Hit | Accession | Score | Mass | L/(L + H) | SD(geo) | # |
|---|---|---|---|---|---|---|
| 66 | P0C0W9 | 86 | 19844 | 0.3135 | | 1 |

RL11A_YEAST 60S ribosomal protein L11-A OS = Saccharomyces cerevisiae GN = RPL11A PE = 1 SV = 2 z Sequence   Incl.  L/(L + H)  Std. Err.  Fraction Correlation  Intensity  Modifications

| | z | Sequence | Incl. | L/(L + H) | Std. Err. | Fraction | Correlation | Intensity | Modifications |
|---|---|---|---|---|---|---|---|---|---|
| 1 | 2 | VLEQLSGQTP VQSK | | 0.000776 | 0.4364 | 0.8707 | 0.2733 | 1.50E+07 | |
| 2 | 3 | VLEQLSGQTP VQSK | X | 0.3135 | 0.169 | 0.1611 | 0.8233 | 1.39E+04 | |

TABLE 1-continued

Proteins identified by Mascot Distiller from ChAP-MS analysis of GAL1 chromatin isolated from cells grown in glucose.
Mascot Distiller Quantitation Report

| Hit | Accession | Score | Mass | L/(L + H) | SD(geo) | # |
|---|---|---|---|---|---|---|
| 67 | P14120 | 84 | 11504 | 0.5841 | | 1 |

RL30_YEAST 60S ribosomal protein L30 OS = Saccharomyces cerevisiae
GN = RPL30 PE = 1 SV = 3

| | z | Sequence | Incl. | L/(L + H) | Std. Err. | Fraction | Correlation | Intensity | Modifications |
|---|---|---|---|---|---|---|---|---|---|
| 1 | 2 | VYYFQGGNN ELGTAVGK | X | 0.5841 | 0.02582 | 0.205 | 0.8988 | 9.20E+04 | |

| Hit | Accession | Score | Mass | L/(L + H) | SD(geo) | # |
|---|---|---|---|---|---|---|
| 68 | P26755 | 84 | 13863 | | | 0 |

RFA3_YEAST Replication factor A protein 3 OS = Saccharomyces cerevisiae GN = RFA3 PE = 1 SV = 1

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 69 | P04147 | 83 | 64304 | | | 0 |

PABP_YEAST Polyadenylate-binding protein, cytoplasmic and nuclear
OS = Saccharomyces cerevisiae GN = PAB1 PE = 1 SV = 4

| | z | Sequence | Incl. | L/(L + H) | Std. Err. | Fraction | Correlation | Intensity | Modifications |
|---|---|---|---|---|---|---|---|---|---|
| 1 | 2 | TAEQLENLNI QDDQK | | 0.001099 | 1.859 | 0.4682 | 0.9671 | 3.84E+05 | |

| Hit | Accession | Score | Mass | L/(L + H) | SD(geo) | # |
|---|---|---|---|---|---|---|
| 70 | P32527 | 82 | 49439 | | | 0 |

ZUO1_YEAST Zuotin OS = Saccharomyces cerevisiae GN = ZUO1 PE = 1 SV = 1

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 71 | P38625 | 82 | 58750 | 0.5454 | | 1 |

GUAA_YEAST GMP synthase [glutamine-hydrolyzing]
OS = Saccharomyces cerevisiae GN = GUA1 PE = 1 SV = 4

| | z | Sequence | Incl. | L/(L + H) | Std. Err. | Fraction | Correlation | Intensity | Modifications |
|---|---|---|---|---|---|---|---|---|---|
| 1 | 2 | VTYDITSKPP ATVEWE | X | 0.5454 | 0.01078 | 0.239 | 0.9456 | 3.32E+05 | |

| Hit | Accession | Score | Mass | L/(L + H) | SD(geo) | # |
|---|---|---|---|---|---|---|
| 72 | P31412 | 80 | 44434 | 0.6452 | | 1 |

VATC_YEAST V-type proton ATPase subunit C OS = Saccharomyces cerevisiae GN = VMA5 PE = 1 SV = 4

| | z | Sequence | Incl. | L/(L + H) | Std. Err. | Fraction | Correlation | Intensity | Modifications |
|---|---|---|---|---|---|---|---|---|---|
| 1 | 2 | IGSLDTLIVE SEELSK | X | 0.6452 | 0.01519 | 0.07177 | 0.9753 | 2.77E+04 | |

| Hit | Accession | Score | Mass | L/(L + H) | SD(geo) | # |
|---|---|---|---|---|---|---|
| 73 | P05753 | 80 | 29608 | | | 0 |

RS4_YEAST 40S ribosomal protein S4 OS = Saccharomyces cerevisiae
GN = RPS4A PE = 1 SV = 3

| z | Sequence | Incl. | L/(L + H) | Std. Err. | Fraction | Correlation | Intensity | Modifications |
|---|---|---|---|---|---|---|---|---|

TABLE 1-continued

Proteins identified by Mascot Distiller from ChAP-MS analysis of GAL1 chromatin isolated from cells grown in glucose.
Mascot Distiller Quantitation Report

| Hit | Accession | Score | Mass | L/(L + H) | SD(geo) | # |
|---|---|---|---|---|---|---|
| 74 | P26783 | 79 | 25023 | 0.4952 | | 1 |

RS5_YEAST 40S ribosomal protein S5 OS = *Saccharomyces cerevisiae*
GN = RPS5 PE = 1 SV = 3

| z | Sequence | Incl. | L/(L + H) | Std. Err. | Fraction | Correlation | Intensity | Modifications |
|---|---|---|---|---|---|---|---|---|
| 1 | 3 TIAETLAEELI NAAK | X | 0.4952 | 0.0071 | 0.5691 | 0.9574 | 1.53E+05 | |

| Hit | Accession | Score | Mass | L/(L + H) | SD(geo) | # |
|---|---|---|---|---|---|---|
| 75 | P17076 | 76 | 28396 | | | 0 |

RL8A_YEAST 60S ribosomal protein L8-A OS = *Saccharomyces cerevisiae*
GN = RPL8A PE = 1 SV = 4 z Sequence   Incl. L/(L + H) Std. Err. Fraction Correlation Intensity Modifications

| Hit | Accession | Score | Mass | L/(L + H) | SD(geo) | # |
|---|---|---|---|---|---|---|
| 76 | P53030 | 76 | 24470 | 0.5139 | | 1 |

RL1_YEAST 60S ribosomal protein L1 OS = *Saccharomyces cerevisiae*
GN = RPL1A PE = 1 SV = 1

| z | Sequence | Incl. | L/(L + H) | Std. Err. | Fraction | Correlation | Intensity | Modifications |
|---|---|---|---|---|---|---|---|---|
| 1 | 2 FPTPVSHND DLYGK | X | 0.5139 | 0.02598 | 0.07442 | 0.8939 | 3.55E+05 | |

| Hit | Accession | Score | Mass | L/(L + H) | SD(geo) | # |
|---|---|---|---|---|---|---|
| 77 | P25694 | 74 | 92331 | 0.5765 | | 1 |

CDC48_YEAST Cell division control protein 48 OS = *Saccharomyces cerevisiae* GN = CDC48 PE = 1 SV = 3

| z | Sequence | Incl. | L/(L + H) | Std. Err. | Fraction | Correlation | Intensity | Modifications |
|---|---|---|---|---|---|---|---|---|
| 1 | 2 AAAPTVVFLD ELDSIAK | X | 0.5765 | 0.01988 | 0.2107 | 0.9888 | 1.27E+05 | |

| Hit | Accession | Score | Mass | L/(L + H) | SD(geo) | # |
|---|---|---|---|---|---|---|
| 78 | P40303 | 73 | 28574 | | | 0 |

PSA7_YEAST Proteasome component PRE6 OS = *Saccharomyces cerevisiae* GN = PRE6 PE = 1 SV = 1 z Sequence   Incl. L/(L + H) Std. Err. Fraction Correlation Intensity Modifications

| Hit | Accession | Score | Mass | L/(L + H) | SD(geo) | # |
|---|---|---|---|---|---|---|
| 79 | P16861 | 73 | 108408 | | | 0 |

K6PF1_YEAST 6-phosphofructokinase subunit alpha OS = *Saccharomyces cerevisiae* GN = PFK1 PE = 1 SV = 1 z Sequence   Incl. L/(L + H) Std. Err. Fraction Correlation Intensity Modifications

| Hit | Accession | Score | Mass | L/(L + H) | SD(geo) | # |
|---|---|---|---|---|---|---|
| 80 | P35691 | 73 | 18729 | | | 0 |

TCTP_YEAST Translationally-controlled tumor protein homolog OS = *Saccharomyces cerevisiae* GN = TMA19 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 LQETNPEEVP KFEK | | | 0.01574 | 0.05686 | 0.3046 | 0.3037 | 2.21E+06 |

TABLE 1-continued

Proteins identified by Mascot Distiller from ChAP-MS analysis of GAL1 chromatin isolated from cells grown in glucose.
Mascot Distiller Quantitation Report

| Hit | Accession | Score | Mass | L/(L + H) | SD(geo) | # |
|---|---|---|---|---|---|---|
| 81 | P05738 | 72 | 21556 | 0.6443 | | 1 |

RL9A_YEAST 60S ribosomal protein L9-A OS = *Saccharomyces cerevisiae*
GN = RPL9A PE = 1 SV = 2

| | z | Sequence | Incl. | L/(L + H) | Std. Err. | Fraction | Correlation | Intensity | Modifications |
|---|---|---|---|---|---|---|---|---|---|
| 1 | 3 | FLDGIYVSHK | X | 0.6443 | 0.01495 | 0.1913 | 0.8882 | 2.99E+04 | |
| 2 | 3 | YIQTEQQIEV PEGVTVSIK | | 0.008727 | 0.6329 | 0.355 | 0.4397 | 1.88E+06 | |

| Hit | Accession | Score | Mass | L/(L + H) | SD(geo) | # |
|---|---|---|---|---|---|---|
| 82 | P00899 | 71 | 56732 | | | 0 |

TRPE_YEAST Anthranilate synthase component 1 OS = *Saccharomyces cerevisiae* GN = TRP2 PE = 1 SV = 4 z Sequence Incl. L/(L + H) Std. Err. Fraction Correlation Intensity Modifications

| Hit | Accession | Score | Mass | L/(L + H) | SD(geo) | # |
|---|---|---|---|---|---|---|
| 83 | P17079 | 71 | 17956 | 0.5847 | | 1 |

RL12_YEAST 60S ribosomal protein L12 OS = *Saccharomyces cerevisiae*
GN = RPL12A PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 3 | VDFKNPHDII EGINAGEIEIP EN | X | 0.5847 | 0.02535 | 0.1429 | 0.8697 | 3.12E+05 | |

| Hit | Accession | Score | Mass | L/(L + H) | SD(geo) | # |
|---|---|---|---|---|---|---|
| 84 | P07806 | 70 | 126596 | 0.4001 | 1.235 | 2 |

SYV_YEAST Valyl-tRNA synthetase, mitochondrial OS = *Saccharomyces cerevisiae* GN = VAS1 PE = 1 SV = 2

| | z | Sequence | Incl. | L/(L + H) | Std. Err. | Fraction | Correlation | Intensity | Modifications |
|---|---|---|---|---|---|---|---|---|---|
| 1 | 2 | TGVFEPEFTA DGK | X | 0.365 | 0.03845 | 0.2789 | 0.8561 | 4.52E+05 | |
| 2 | 2 | LNTAISNLEV ENK | X | 0.5312 | 0.02003 | 0.0767 | 0.9905 | 1.46E+05 | |

| Hit | Accession | Score | Mass | L/(L + H) | SD(geo) | # |
|---|---|---|---|---|---|---|
| 85 | P26781 | 70 | 17898 | 0.4992 | | 1 |

RS11_YEAST 40S ribosomal protein S11 OS = *Saccharomyces cerevisiae*
GN = RPS11A PE = 1 SV = 3

| | z | Sequence | Incl. | L/(L + H) | Std. Err. | Fraction | Correlation | Intensity | Modifications |
|---|---|---|---|---|---|---|---|---|---|
| 1 | 2 | TAIEGSYIDKK | X | 0.4992 | 0.0041 | 0.1365 | 0.9905 | 1.73E+05 | |

| Hit | Accession | Score | Mass | L/(L + H) | SD(geo) | # |
|---|---|---|---|---|---|---|
| 86 | P53252 | 70 | 38326 | 0.5822 | | 1 |

PIL1_YEAST Sphingolipid long chain base-responsive protein PIL1 OS = *Saccharomyces cerevisiae* GN = PIL1 PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 2 | APTASQLQNP PPPPSTTK | X | 0.5822 | 0.02737 | 0.2412 | 0.8526 | 1.83E+04 | |

TABLE 1-continued

Proteins identified by Mascot Distiller from ChAP-MS analysis of GAL1 chromatin isolated from cells grown in glucose.
Mascot Distiller Quantitation Report

| Hit | Accession | Score | Mass | L/(L + H) | SD(geo) | # |
|---|---|---|---|---|---|---|
| 87 | P22943 | 68 | 11686 | | | 0 |

HSP12_YEAST 12 kDa heat shock protein OS = *Saccharomyces cerevisiae* GN = HSP12 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 GKDNAEGQG ESLADQAR | | 0.01324 | 0.7291 | 0.2434 | 0.4791 | 3.47E+04 | |

| Hit | Accession | Score | Mass | L/(L + H) | SD(geo) | # |
|---|---|---|---|---|---|---|
| 88 | P02407 | 67 | 15891 | | | 0 |

RS17A_YEAST 40S ribosomal protein S17-A OS = *Saccharomyces cerevisiae* GN = RPS17A PE = 1 SV = 1

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 89 | P04801 | 66 | 84467 | | | 0 |

SYTC_YEAST Threonyl-tRNA synthetase, cytoplasmic OS = *Saccharomyces cerevisiae* GN = THS1 PE = 1 SV = 2

| z | Sequence | Incl. | L/(L + H) | Std. Err. | Fraction | Correlation | Intensity | Modifications |
|---|---|---|---|---|---|---|---|---|
| 1 | 2 TVSQADFPGL EGVAK | | 0.9625 | 0.01322 | 0.639 | 0.3281 | 3.05E+05 | |

| Hit | Accession | Score | Mass | L/(L + H) | SD(geo) | # |
|---|---|---|---|---|---|---|
| 90 | P09733 | 63 | 49945 | | | 0 |

TBA1_YEAST Tubulin alpha-1 chain OS = *Saccharomyces cerevisiae* GN = TUB1 PE = 1 SV = 2

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 91 | P33204 | 62 | 19959 | | | 0 |

ARPC4_YEAST Actin-related protein 2/3 complex subunit 4 OS = *Saccharomyces cerevisiae* GN = ARC19 PE = 1 SV = 2

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 92 | P23301 | 62 | 17208 | 0.4447 | | 1 |

IF5A2_YEAST Eukaryotic translation initiation factor 5A-2 OS = *Saccharomyces cerevisiae* GN = HYP2 PE = 1 SV = 3

| z | Sequence | Incl. | L/(L + H) | Std. Err. | Fraction | Correlation | Intensity | Modifications |
|---|---|---|---|---|---|---|---|---|
| 1 | 3 KLEDLSPSTH NMEVPVVK | X | 0.4447 | 0.02507 | 0.3275 | 0.7978 | 8.63E+05 | |

| Hit | Accession | Score | Mass | L/(L + H) | SD(geo) | # |
|---|---|---|---|---|---|---|
| 93 | P06168 | 61 | 44565 | | | 0 |

ILV5_YEAST Ketol-acid reductoisomerase, mitochondrial OS = *Saccharomyces cerevisiae* GN = ILV5 PE = 1 SV = 1

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 94 | P05744 | 59 | 12219 | 0.6527 | | 1 |

RL33A_YEAST 60S ribosomal protein L33-A OS = *Saccharomyces cerevisiae* GN = RPL33A PE = 1 SV = 3

| z | Sequence | Incl. | L/(L + H) | Std. Err. | Fraction | Correlation | Intensity | Modifications |
|---|---|---|---|---|---|---|---|---|
| 1 | 2 IEGVATPQDA QFYLGK | X | 0.6527 | 0.01745 | 0.2096 | 0.9659 | 1.36E+05 | |

TABLE 1-continued

Proteins identified by Mascot Distiller from ChAP-MS analysis of GAL1 chromatin isolated from cells grown in glucose.
Mascot Distiller Quantitation Report

| Hit | Accession | Score | Mass | L/(L + H) | SD(geo) | # |
|---|---|---|---|---|---|---|
| 95 | P04807 | 58 | 53908 | 0.6227 | | 1 |

HXKB_YEAST Hexokinase-2 OS = *Saccharomyces cerevisiae* GN = HXK2 PE = 1 SV = 4

| z | Sequence | Incl. | L/(L + H) | Std. Err. | Fraction | Correlation | Intensity | Modifications |
|---|---|---|---|---|---|---|---|---|
| 1 | 3 TKYDITIDEE SPRPGQQTFEK | X | 0.6227 | 0.02524 | 0.2555 | 0.8918 | 7.65E+04 | |

| Hit | Accession | Score | Mass | L/(L + H) | SD(geo) | # |
|---|---|---|---|---|---|---|
| 96 | P03965 | 58 | 124439 | | | 0 |

CARB_YEAST Carbamoyl-phosphate synthase arginine-specific large chain OS = *Saccharomyces cerevisiae* GN = CPA2 PE = 1 SV = 1

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 97 | Q00955 | 58 | 250197 | | | 0 |

ACAC_YEAST Acetyl-CoA carboxylase OS = *Saccharomyces cerevisiae* GN = FAS3 PE = 1 SV = 2

| z | Sequence | Incl. | L/(L + H) | Std. Err. | Fraction | Correlation | Intensity | Modifications |
|---|---|---|---|---|---|---|---|---|
| 1 | 2 IGSFGPQEDE FFNK | | 0.8663 | 0.02199 | 0.1144 | 0.6383 | 4.24E+05 | |

| Hit | Accession | Score | Mass | L/(L + H) | SD(geo) | # |
|---|---|---|---|---|---|---|
| 98 | P32598 | 58 | 35884 | 0.499 | | 1 |

PP12_YEAST Serine/threonine-protein phosphatase PP1-2 OS = *Saccharomyces cerevisiae* GN = GLC7 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 GSKPGQQVD LEENEIR | X | 0.499 | 0.03409 | 0.1183 | 0.9862 | 2959 | |

| Hit | Accession | Score | Mass | L/(L + H) | SD(geo) | # |
|---|---|---|---|---|---|---|
| 99 | P02365 | 58 | 27204 | 0.4787 | | 1 |

RS6_YEAST 40S ribosomal protein S6 OS = *Saccharomyces cerevisiae* GN = RPS6A PE = 1 SV = 1

| z | Sequence | Incl. | L/(L + H) | Std. Err. | Fraction | Correlation | Intensity | Modifications |
|---|---|---|---|---|---|---|---|---|
| 1 | 2 KGEQELEGLT DTTVPK | X | 0.4787 | 0.01467 | 0.0397 | 0.9854 | 2.01E+04 | |

| Hit | Accession | Score | Mass | L/(L + H) | SD(geo) | # |
|---|---|---|---|---|---|---|
| 100 | P37012 | 57 | 63049 | | | 0 |

PGM2_YEAST Phosphoglucomutase-2 OS = *Saccharomyces cerevisiae* GN = PGM2 PE = 1 SV = 1

| z | Sequence | Incl. | L/(L + H) | Std. Err. | Fraction | Correlation | Intensity | Modifications |
|---|---|---|---|---|---|---|---|---|
| 1 | 3 IIKDFPELDLG TIGK | | 0.6291 | 0.02728 | 0.1059 | 0.6921 | 5.18E+04 | |

| Hit | Accession | Score | Mass | L/(L + H) | SD(geo) | # |
|---|---|---|---|---|---|---|
| 101 | P10664 | 57 | 39325 | 0.482 | 1.07 | 2 |

RL4A_YEAST 60S ribosomal protein L4-A OS = *Saccharomyces cerevisiae* GN = RPL4A PE = 1 SV = 4

| z | Sequence | Incl. | L/(L + H) | Std. Err. | Fraction | Correlation | Intensity | Modifications |
|---|---|---|---|---|---|---|---|---|
| 1 | 2 IPEIPLVVSTD LESIQK | X | 0.4871 | 0.01446 | 0.3459 | 0.9946 | 8.51E+05 | |
| 2 | 3 IINSSEIQSAI RPAGQATQK | X | 0.4381 | 0.02184 | 0.2528 | 0.953 | 9.33E+04 | |

TABLE 1-continued

Proteins identified by Mascot Distiller from ChAP-MS analysis of GAL1 chromatin isolated from cells grown in glucose.
Mascot Distiller Quantitation Report

| Hit | Accession | Score | Mass | L/(L + H) | SD(geo) | # |
|---|---|---|---|---|---|---|
| 102 | P17536 | 55 | 23527 | | | 0 |

TPM1_YEAST Tropomyosin-1 OS = *Saccharomyces cerevisiae* GN = TPM1
PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 2 | QTEQDNVEK ENQIK | | 0.4204 | 0.1271 | 0.03615 | 0.4953 | 1.04E+04 | |
| 2 | 3 | NKDLEQENV EKENQIK | | 0.438 | 0.04989 | 0.1615 | 0.6221 | 6.92E+04 | |

| Hit | Accession | Score | Mass | L/(L + H) | SD(geo) | # |
|---|---|---|---|---|---|---|
| 103 | P32469 | 55 | 33970 | | | 0 |

DPH5_YEAST Diphthine synthase OS = *Saccharomyces cerevisiae*
GN = DPH5 PE = 1 SV = 1 z Sequence    Incl. L/(L + H) Std. Err. Fraction Correlation Intensity Modifications

| Hit | Accession | Score | Mass | L/(L + H) | SD(geo) | # |
|---|---|---|---|---|---|---|
| 104 | P35271 | 54 | 17115 | 0.5135 | | 1 |

RS18_YEAST 40S ribosomal protein S18 OS = *Saccharomyces cerevisiae*
GN = RPS18A PE = 1 SV = 4

| | z | Sequence | Incl. | L/(L + H) | Std. Err. | Fraction | Correlation | Intensity | Modifications |
|---|---|---|---|---|---|---|---|---|---|
| 1 | 3 | QNDITDGKD YHTLANNVESK | X | 0.5135 | 0.01629 | 0.07641 | 0.9441 | 5.50E+04 | |

| Hit | Accession | Score | Mass | L/(L + H) | SD(geo) | # |
|---|---|---|---|---|---|---|
| 105 | P13663 | 54 | 39735 | | | 0 |

DHAS_YEAST Aspartate-semialdehyde dehydrogenase
OS = *Saccharomyces cerevisiae* GN = HOM2 PE = 1 SV = 1 z Sequence    Incl. L/(L + H) Std. Err. Fraction Correlation Intensity Modifications

| Hit | Accession | Score | Mass | L/(L + H) | SD(geo) | # |
|---|---|---|---|---|---|---|
| 106 | P54839 | 53 | 54979 | | | 0 |

HMCS_YEAST Hydroxymethylglutaryl-CoA synthase OS = *Saccharomyces cerevisiae* GN = ERG13 PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 2 | DYDESLTDK NIEK | | 0.1337 | 0.1737 | 0.3775 | 0.4027 | 2.38E+05 | |

| Hit | Accession | Score | Mass | L/(L + H) | SD(geo) | # |
|---|---|---|---|---|---|---|
| 107 | P40016 | 53 | 60385 | | | 0 |

RPN3_YEAST 26S proteasome regulatory subunit RPN3
OS = *Saccharomyces cerevisiae* GN = RPN3 PE = 1 SV = 4 z Sequence    Incl. L/(L + H) Std. Err. Fraction Correlation Intensity Modifications

| Hit | Accession | Score | Mass | L/(L + H) | SD(geo) | # |
|---|---|---|---|---|---|---|
| 108 | P05317 | 52 | 33866 | 0.5164 | | 1 |

RLA0_YEAST 60S acidic ribosomal protein P0 OS = *Saccharomyces cerevisiae* GN = RPP0 PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 2 | GTIEIVSDVK | X | 0.5164 | 0.00778 | 0.1538 | 0.9872 | 4.30E+05 | |

TABLE 1-continued

Proteins identified by Mascot Distiller from ChAP-MS analysis of GAL1 chromatin isolated from cells grown in glucose.
Mascot Distiller Quantitation Report

| Hit | Accession | Score | Mass | L/(L + H) | SD(geo) | # |
|---|---|---|---|---|---|---|
| 109 | P15992 | 51 | 23865 | | | 0 |

HSP26_YEAST Heat shock protein 26 OS = *Saccharomyces cerevisiae* GN = HSP26 PE = 1 SV = 3

| z | Sequence | Incl. | L/(L + H) | Std. Err. | Fraction | Correlation | Intensity | Modifications |
|---|---|---|---|---|---|---|---|---|
| 1 | 3 NQILVSGEIP STLNEESKDK | | 0.6438 | 0.03278 | 0.3187 | 0.6599 | 2.01E+05 | |

| Hit | Accession | Score | Mass | L/(L + H) | SD(geo) | # |
|---|---|---|---|---|---|---|
| 110 | P32481 | 50 | 57829 | | | 0 |

IF2G_YEAST Eukaryotic translation initiation factor 2 subunit gamma OS = *Saccharomyces cerevisiae* GN = GCD11 PE = 1 SV = 1

| z | Sequence | Incl. | L/(L + H) | Std. Err. | Fraction | Correlation | Intensity | Modifications |
|---|---|---|---|---|---|---|---|---|
| 1 | 3 LGDEIEIRPGI VTK | | 0.6051 | 0.09736 | 0.2626 | 0.3614 | 1.13E+05 | |
| 2 | 3 VAFTGLEEDG ETEEEKR | | 0.3223 | 0.05784 | 0.09351 | 0.5764 | 1.71E+05 | |

| Hit | Accession | Score | Mass | L/(L + H) | SD(geo) | # |
|---|---|---|---|---|---|---|
| 111 | P41056 | 49 | 12233 | | | 0 |

RL33B_YEAST 60S ribosomal protein L33-B OS = *Saccharomyces cerevisiae* GN = RPL33B PE = 1 SV = 2

| z | Sequence | Incl. | L/(L + H) | Std. Err. | Fraction | Correlation | Intensity | Modifications |
|---|---|---|---|---|---|---|---|---|
| 1 | 2 IEGVATPQEA QFYLGK | | 0.000032 | 376.9 | 0.3763 | 0.1226 | 1.13E+05 | |

| Hit | Accession | Score | Mass | L/(L + H) | SD(geo) | # |
|---|---|---|---|---|---|---|
| 112 | P14126 | 49 | 44075 | | | 0 |

RL3_YEAST 60S ribosomal protein L3 OS = *Saccharomyces cerevisiae* GN = RPL3 PE = 1 SV = 4

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 113 | B3LLJ2 | 49 | 29059 | 0.5829 | | 1 |

RS3A2_YEAS1 40S ribosomal protein S1-B OS = *Saccharomyces cerevisiae* (strain RM11-1a) GN = RPS1B PE = 3 SV = 1

| z | Sequence | Incl. | L/(L + H) | Std. Err. | Fraction | Correlation | Intensity | Modifications |
|---|---|---|---|---|---|---|---|---|
| 1 | 2 VSGFKDEVLE TV | X | 0.5829 | 0.0184 | 0.1617 | 0.9565 | 4.47E+05 | |

| Hit | Accession | Score | Mass | L/(L + H) | SD(geo) | # |
|---|---|---|---|---|---|---|
| 114 | P35997 | 49 | 8930 | | | 0 |

RS27A_YEAST 40S ribosomal protein S27-A OS = *Saccharomyces cerevisiae* GN = RPS27A PE = 1 SV = 1

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 115 | P39954 | 48 | 49094 | 0.1786 | | 1 |

SAHH_YEAST Adenosylhomocysteinase OS = *Saccharomyces cerevisiae* GN = SAH1 PE = 1 SV = 1

| z | Sequence | Incl. | L/(L + H) | Std. Err. | Fraction | Correlation | Intensity | Modifications |
|---|---|---|---|---|---|---|---|---|
| 1 | 3 LKVPAINVND SVTK | X | 0.1786 | 0.1265 | 0.1537 | 0.7426 | 1.16E+06 | |

TABLE 1-continued

Proteins identified by Mascot Distiller from ChAP-MS analysis of GAL1 chromatin isolated from cells grown in glucose.
Mascot Distiller Quantitation Report

| Hit | Accession | Score | Mass | L/(L + H) | SD(geo) | # |
|---|---|---|---|---|---|---|
| 116 | P05736 | 48 | 27392 | 0.5256 |  | 1 |

RL2_YEAST 60S ribosomal protein L2 OS = *Saccharomyces cerevisiae*
GN = RPL2A PE = 1 SV = 3

| z | Sequence | Incl. | L/(L + H) | Std. Err. | Fraction | Correlation | Intensity | Modifications |
|---|---|---|---|---|---|---|---|---|
| 1 | 3 ASLNVGNVLP LGSVPEGTIV SNVEEKPGDR | X | 0.5256 | 0.00852 | 0.3563 | 0.9201 | 1.23E+06 | |

| Hit | Accession | Score | Mass | L/(L + H) | SD(geo) | # |
|---|---|---|---|---|---|---|
| 117 | Q12306 | 47 | 11662 | | | 0 |

SMT3_YEAST Ubiquitin-like protein SMT3 OS = *Saccharomyces cerevisiae*
GN = SMT3 PE = 1 SV = 1 z Sequence  Incl. L/(L + H) Std. Err. Fraction Correlation Intensity Modifications

| Hit | Accession | Score | Mass | L/(L + H) | SD(geo) | # |
|---|---|---|---|---|---|---|
| 118 | O14467 | 47 | 16394 | 0.7594 | | 1 |

MBF1_YEAST Multiprotein-bridging factor 1 OS = *Saccharomyces cerevisiae* GN = MBF1 PE = 1 SV = 2

| z | Sequence | Incl. | L/(L + H) | Std. Err. | Fraction | Correlation | Intensity | Modifications |
|---|---|---|---|---|---|---|---|---|
| 1 | 2 INEKPTVVND YEAAR | X | 0.7594 | 0.04153 | 0.08694 | 0.7815 | 1.61E+04 | |

| Hit | Accession | Score | Mass | L/(L + H) | SD(geo) | # |
|---|---|---|---|---|---|---|
| 119 | Q08438 | 46 | 73997 | | | 0 |

VHS3_YEAST Protein VHS3 OS = *Saccharomyces cerevisiae* GN = VHS3
PE = 1 SV = 1 z Sequence  Incl. L/(L + H) Std. Err. Fraction Correlation Intensity Modifications

| Hit | Accession | Score | Mass | L/(L + H) | SD(geo) | # |
|---|---|---|---|---|---|---|
| 120 | P38708 | 46 | 77337 | 0.3265 | | 1 |

YHI0_YEAST Putative prolyl-tRNA synthetase YHR020W
OS = *Saccharomyces cerevisiae* GN = YHR020W PE = 1 SV = 1

| z | Sequence | Incl. | L/(L + H) | Std. Err. | Fraction | Correlation | Intensity | Modifications |
|---|---|---|---|---|---|---|---|---|
| 1 | 2 IPEILEEMQG DLFK | X | 0.3265 | 0.09196 | 0.1283 | 0.9662 | 6.43E+04 | |

| Hit | Accession | Score | Mass | L/(L + H) | SD(geo) | # |
|---|---|---|---|---|---|---|
| 121 | P40069 | 44 | 122981 | 0.8151 | | 1 |

IMB4_YEAST Importin subunit beta-4 OS = *Saccharomyces cerevisiae*
GN = KAP123 PE = 1 SV = 1

| z | Sequence | Incl. | L/(L + H) | Std. Err. | Fraction | Correlation | Intensity | Modifications |
|---|---|---|---|---|---|---|---|---|
| 1 | 3 FHEEYLPLIID IIDSAK | X | 0.8151 | 0.02809 | 0.2967 | 0.9444 | 3.29E+04 | |

| Hit | Accession | Score | Mass | L/(L + H) | SD(geo) | # |
|---|---|---|---|---|---|---|
| 122 | P05737 | 42 | 27621 | 0.5221 | | 1 |

RL7A_YEAST 60S ribosomal protein L7-A OS = *Saccharomyces cerevisiae*
GN = RPL7A PE = 1 SV = 3

| z | Sequence | Incl. | L/(L + H) | Std. Err. | Fraction | Correlation | Intensity | Modifications |
|---|---|---|---|---|---|---|---|---|
| 1 | 2 ATLELLK | X | 0.5221 | 0.00509 | 0.1793 | 0.9871 | 8.87E+04 | |

TABLE 1-continued

Proteins identified by Mascot Distiller from ChAP-MS analysis of GAL1 chromatin isolated from cells grown in glucose.
Mascot Distiller Quantitation Report

| Hit | Accession | Score | Mass | L/(L + H) | SD(geo) | # |
|---|---|---|---|---|---|---|
| 123 | P38715 | 42 | 37095 | 0.03996 | | 1 |

GRE3_YEAST NADPH-dependent aldose reductase GRE3
OS = Saccharomyces cerevisiae GN = GRE3 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 TTPTLFENDVIK | X | 0.03996 | 0.4915 | 0.0985 | 0.8748 | 1.48E+05 | |

| Hit | Accession | Score | Mass | L/(L + H) | SD(geo) | # |
|---|---|---|---|---|---|---|
| 124 | P15019 | 40 | 37302 | 0.5972 | | 1 |

TAL1_YEAST Transaldolase OS = Saccharomyces cerevisiae GN = TAL1 PE = 1 SV = 4

| z | Sequence | Incl. | L/(L + H) | Std. Err. | Fraction | Correlation | Intensity | Modifications |
|---|---|---|---|---|---|---|---|---|
| 1 | 3 DYKGEADPGVISVK | X | 0.5972 | 0.01513 | 0.05713 | 0.9284 | 1.93E+04 | |

| Hit | Accession | Score | Mass | L/(L + H) | SD(geo) | # |
|---|---|---|---|---|---|---|
| 125 | P39939 | 40 | 13438 | | | 0 |

RS26B_YEAST 40S ribosomal protein S26-B OS = Saccharomyces cerevisiae GN = RPS26B PE = 1 SV = 1

| z | Sequence | Incl. | L/(L + H) | Std. Err. | Fraction | Correlation | Intensity | Modifications |
|---|---|---|---|---|---|---|---|---|
| 1 | 2 DLSEASVYPEYALPK | | 0.4244 | 0.02522 | 0.09777 | 0.5891 | 8.08E+05 | |

| Hit | Accession | Score | Mass | L/(L + H) | SD(geo) | # |
|---|---|---|---|---|---|---|
| 126 | P25443 | 40 | 27433 | 0.4963 | | 1 |

RS2_YEAST 40S ribosomal protein S2 OS = Saccharomyces cerevisiae GN = RPS2 PE = 1 SV = 3

| z | Sequence | Incl. | L/(L + H) | Std. Err. | Fraction | Correlation | Intensity | Modifications |
|---|---|---|---|---|---|---|---|---|
| 1 | 3 EFQIIDTLLPGLQDEVMNIKPVQK | X | 0.4963 | 0.00439 | 0.4363 | 0.9932 | 1.18E+06 | |

| Hit | Accession | Score | Mass | L/(L + H) | SD(geo) | # |
|---|---|---|---|---|---|---|
| 127 | P43620 | 39 | 75867 | 0.5908 | | 1 |

RMD8_YEAST Sporulation protein RMD8 OS = Saccharomyces cerevisiae GN = RMD8 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 REQLLK | X | 0.5908 | 0.00487 | 0.1874 | 0.9696 | 5.33E+05 | |

| Hit | Accession | Score | Mass | L/(L + H) | SD(geo) | # |
|---|---|---|---|---|---|---|
| 128 | P52910 | 39 | 75765 | | | 0 |

ACS2_YEAST Acetyl-coenzyme A synthetase 2 OS = Saccharomyces cerevisiae GN = ACS2 PE = 1 SV = 1

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 129 | P60010 | 38 | 41663 | | | 0 |

ACT_YEAST Actin OS = Saccharomyces cerevisiae GN = ACT1 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 DLTDYLMK | | 0.8897 | 0.01324 | 0.1224 | 0.6466 | 4.23E+05 | |

TABLE 1-continued

Proteins identified by Mascot Distiller from ChAP-MS analysis of GAL1 chromatin isolated from cells grown in glucose.
Mascot Distiller Quantitation Report

| Hit | Accession | Score | Mass | L/(L + H) | SD(geo) | # |
|---|---|---|---|---|---|---|
| 130 | P41805 | 37 | 25522 | 0.7348 | | 1 |

RL10_YEAST 60S ribosomal protein L10 OS = *Saccharomyces cerevisiae*
GN = RPL10 PE = 1 SV = 1

| z | Sequence | Incl. | L/(L + H) | Std. Err. | Fraction | Correlation | Intensity | Modifications |
|---|---|---|---|---|---|---|---|---|
| 1 | 3 WGFTNLDRP EYLK | X | 0.7348 | 0.02758 | 0.107 | 0.8056 | 2.97E+05 | |

| Hit | Accession | Score | Mass | L/(L + H) | SD(geo) | # |
|---|---|---|---|---|---|---|
| 131 | Q86ZR7 | 37 | 26338 | | | 0 |

YKD3A_YEAST Putative uncharacterized hydrolase YKL033W-A
OS = *Saccharomyces cerevisiae* GN = YKL033W-A PE = 1 SV = 2 z Sequence    Incl. L/(L + H) Std. Err. Fraction Correlation Intensity Modifications

| Hit | Accession | Score | Mass | L/(L + H) | SD(geo) | # |
|---|---|---|---|---|---|---|
| 132 | P38205 | 35 | 77830 | | | 0 |

NCL1_YEAST tRNA (cytosine-5-)-methyltransferase NCL1
OS = *Saccharomyces cerevisiae* GN = NCL1 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 LSSETPALES EGPQTK | | 0.3404 | 0.01969 | 0.1416 | 0.3584 | 2.22E+04 | |

| Hit | Accession | Score | Mass | L/(L + H) | SD(geo) | # |
|---|---|---|---|---|---|---|
| 133 | P17255 | 35 | 118562 | | | 0 |

VATA_YEAST V-type proton ATPase cataytic subunit A
OS = *Saccharomyces cerevisiae* GN = TFP1 PE = 1 SV = 3

| z | Sequence | Incl. | L/(L + H) | Std. Err. | Fraction | Correlation | Intensity | Modifications |
|---|---|---|---|---|---|---|---|---|
| 1 | 3 AIKEESQSIYI PR | | 0.2979 | 0.2188 | 0.09557 | 0.4074 | 1.46E+05 | |

| Hit | Accession | Score | Mass | L/(L + H) | SD(geo) | # |
|---|---|---|---|---|---|---|
| 134 | P05739 | 35 | 20183 | 0.5423 | | 1 |

RL6B_YEAST 60S ribosomal protein L6-B OS = *Saccharomyces cerevisiae*
GN = RPL6B PE = 1 SV = 4

| z | Sequence | Incl. | L/(L + H) | Std. Err. | Fraction | Correlation | Intensity | Modifications |
|---|---|---|---|---|---|---|---|---|
| 1 | 3 HLEDNTLLVT GPFK | X | 0.5423 | 0.02668 | 0.2265 | 0.9184 | 1.35E+05 | |

| Hit | Accession | Score | Mass | L/(L + H) | SD(geo) | # |
|---|---|---|---|---|---|---|
| 135 | Q07530 | 35 | 34457 | 0.9709 | | 1 |

YD114_YEAST Uncharacterized oxidoreductase YDL114W
OS = *Saccharomyces cerevisiae* GN = YDL114W PE = 2 SV = 1

| z | Sequence | Incl. | L/(L + H) | Std. Err. | Fraction | Correlation | Intensity | Modifications |
|---|---|---|---|---|---|---|---|---|
| 1 | 2 INRASGTTK | X | 0.9709 | 0.00996 | 0.1262 | 0.9924 | 1.27E+05 | |

| Hit | Accession | Score | Mass | L/(L + H) | SD(geo) | # |
|---|---|---|---|---|---|---|
| 136 | P15625 | 34 | 57804 | | | 0 |

SYFA_YEAST Phenylalanyl-tRNA synthetase alpha chain
OS = *Saccharomyces cerevisiae* GN = FRS2 PE = 1 SV = 3 z Sequence    Incl. L/(L + H) Std. Err. Fraction Correlation Intensity Modifications TABLE 1-continued Proteins identified by Mascot Distiller from ChAP-MS analysis of GAL1 chromatin isolated from cells grown in glucose.
Mascot Distiller Quantitation Report

| Hit | Accession | Score | Mass | L/(L + H) | SD(geo) | # |
|---|---|---|---|---|---|---|
| 137 | Q02209 | 33 | 41274 | 0.9909 | | 1 |

YKZ1_YEAST Uncharacterized protein YKR011C OS = *Saccharomyces cerevisiae* GN = YKR011C PE = 1 SV = 2

| z | Sequence | Incl. | L/(L + H) | Std. Err. | Fraction | Correlation | Intensity | Modifications |
|---|---|---|---|---|---|---|---|---|
| 1 | 2 FQLVEK | X | 0.9909 | 0.00329 | 0.1232 | 0.9948 | 5.97E+05 | |

| Hit | Accession | Score | Mass | L/(L + H) | SD(geo) | # |
|---|---|---|---|---|---|---|
| 138 | A6ZZJ1 | 32 | 86 | 0.5908 | | 1 |

MYO3_YEAS7 Myosin-3 OS = *Saccharomyces cerevisiae* (strain YJM789) GN = MYO3 PE = 3 SV = 1

| z | Sequence | Incl. | L/(L + H) | Std. Err. | Fraction | Correlation | Intensity | Modifications |
|---|---|---|---|---|---|---|---|---|
| 1 | 2 RIDAAIK | X | 0.5908 | 0.00487 | 0.1874 | 0.9696 | 5.33E+05 | |
| 2 | 3 IIKSANELVETLSK | | 0.5256 | 0.06512 | 0.2213 | 0.1936 | 2.39E+05 | |

| Hit | Accession | Score | Mass | L/(L + H) | SD(geo) | # |
|---|---|---|---|---|---|---|
| 139 | P40077 | 32 | 64327 | | | 0 |

DSE1_YEAST Protein DSE1 OS = *Saccharomyces cerevisiae* GN = DSE1 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 MNSPILRK | | 0.003135 | 3.635 | 0.06896 | 0.9784 | 7203 | |

| Hit | Accession | Score | Mass | L/(L + H) | SD(geo) | # |
|---|---|---|---|---|---|---|
| 140 | A7A1S5 | 31 | 76547 | | | 0 |

DUS3_YEAS7 tRNA-dihydrouridine synthase 3 OS = *Saccharomyces cerevisiae* (strain YJM789) GN = DUS3 PE = 3 SV = 1

| z | Sequence | Incl. | L/(L + H) | Std. Err. | Fraction | Correlation | Intensity | Modifications |
|---|---|---|---|---|---|---|---|---|
| 1 | 2 QNENQK | | 0.4468 | 0.05701 | 0.00365 | 0.6454 | 6837 | |

| Hit | Accession | Score | Mass | L/(L + H) | SD(geo) | # |
|---|---|---|---|---|---|---|
| 141 | P02557 | 31 | 51011 | | | 0 |

TBB_YEAST Tubulin beta chain OS = *Saccharomyces cerevisiae* GN = TUB2 PE = 1 SV = 2

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 142 | P17423 | 31 | 38792 | | | 0 |

KHSE_YEAST Homoserine kinase OS = *Saccharomyces cerevisiae* GN = THR1 PE = 1 SV = 4

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 143 | P04076 | 30 | 52173 | | | 0 |

ARLY_YEAST Argininosuccinate lyase OS = *Saccharomyces cerevisiae* GN = ARG4 PE = 1 SV = 2

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 144 | A6ZWD3 | 29 | 68204 | | | 0 |

DBP1_YEAS7 ATP-dependent RNA helicase DBP1 OS = *Saccharomyces cerevisiae* (strain YJM789) GN = DBP1 PE = 3 SV = 1

| z | Sequence | Incl. | L/(L + H) | Std. Err. | Fraction | Correlation | Intensity | Modifications |
|---|---|---|---|---|---|---|---|---|

TABLE 1-continued

Proteins identified by Mascot Distiller from ChAP-MS analysis of GAL1 chromatin isolated from cells grown in glucose.
Mascot Distiller Quantitation Report

| Hit | Accession | Score | Mass | L/(L + H) | SD(geo) | # |
|---|---|---|---|---|---|---|
| 145 | P07702 | 29 | 155248 | | | 0 |

LYS2_YEAST L-aminoadipate-semialdehyde dehydrogenase
OS = *Saccharomyces cerevisiae* GN = LYS2 PE = 1 SV = 2

| z | Sequence | Incl. | L/(L + H) | Std. Err. | Fraction | Correlation | Intensity | Modifications |
|---|---|---|---|---|---|---|---|---|
| 1 | 2 EYFVEPNSAE GK | | 0.0214 | 0.957 | 0.3831 | 0.02822 | 9.46E+05 | |

| Hit | Accession | Score | Mass | L/(L + H) | SD(geo) | # |
|---|---|---|---|---|---|---|
| 146 | P39976 | 27 | 55190 | | | 0 |

DLD3_YEAST D-lactate dehydrogenase [cytochrome] 3
OS = *Saccharomyces cerevisiae* GN = DLD3 PE = 1 SV = 1

| z | Sequence | Incl. | L/(L + H) | Std. Err. | Fraction | Correlation | Intensity | Modifications |
|---|---|---|---|---|---|---|---|---|
| 1 | 3 LNAAGLIGDA PKPVVK | | 1 | 0.00277 | 0.1741 | 0.2978 | 8.97E+04 | |

| Hit | Accession | Score | Mass | L/(L + H) | SD(geo) | # |
|---|---|---|---|---|---|---|
| 147 | P53953 | 27 | 98881 | 0.4536 | | 1 |

SFB2_YEAST SED5-binding protein 2 OS = *Saccharomyces cerevisiae*
GN = SFB2 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 SEQGILNTPK | X | 0.4536 | 0.03249 | 0.3059 | 0.9489 | 4.80E+05 | |

| Hit | Accession | Score | Mass | L/(L + H) | SD(geo) | # |
|---|---|---|---|---|---|---|
| 148 | Q08647 | 27 | 77419 | | | 0 |

PUS7_YEAST Multisubstrate pseudouridine synthase 7
OS = *Saccharomyces cerevisiae* GN = PUS7 PE = 1 SV = 1

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 149 | Q07798 | 26 | 102104 | 0.9876 | | 1 |

SPO75_YEAST Sporulation-specific protein 75 OS = *Saccharomyces cerevisiae* GN = SPO75 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 ILDKIIR | X | 0.9876 | 0.00489 | 0.02083 | 0.9895 | 5.42E+04 | |

| Hit | Accession | Score | Mass | L/(L + H) | SD(geo) | # |
|---|---|---|---|---|---|---|
| 150 | P29509 | 26 | 34409 | 0.3208 | | 1 |

TRXB1_YEAST Thioredoxin reductase 1 OS = *Saccharomyces cerevisiae*
GN = TRR1 PE = 1 SV = 3

| z | Sequence | Incl. | L/(L + H) | Std. Err. | Fraction | Correlation | Intensity | Modifications |
|---|---|---|---|---|---|---|---|---|
| 1 | 2 IVAGQVDTD EAGYIK | X | 0.3208 | 0.06408 | 0.4281 | 0.9649 | 5.48E+05 | |

| Hit | Accession | Score | Mass | L/(L + H) | SD(geo) | # |
|---|---|---|---|---|---|---|
| 151 | P38720 | 26 | 53774 | | | 0 |

6PGD1_YEAST 6-phosphogluconate dehydrogenase, decarboxylating 1
OS = *Saccharomyces cerevisiae* GN = GND1 PE = 1 SV = 1

| z | Sequence | Incl. | L/(L + H) | Std. Err. | Fraction | Correlation | Intensity | Modifications |
|---|---|---|---|---|---|---|---|---|

TABLE 1-continued

Proteins identified by Mascot Distiller from ChAP-MS analysis of GAL1 chromatin isolated from cells grown in glucose.
Mascot Distiller Quantitation Report

| Hit | Accession | Score | Mass | L/(L + H) | SD(geo) | # |
|---|---|---|---|---|---|---|
| 152 | P26785 | 26 | 22444 | | | 0 |

RL16B_YEAST 60S ribosomal protein L16-B OS = *Saccharomyces cerevisiae* GN = RPL16B PE = 1 SV = 3
  z Sequence     Incl. L/(L + H) Std. Err. Fraction Correlation Intensity Modifications

| Hit | Accession | Score | Mass | L/(L + H) | SD(geo) | # |
|---|---|---|---|---|---|---|
| 153 | P06843 | 25 | 38928 | 0.5908 | | 1 |

SPT2_YEAST Protein SPT2 OS = *Saccharomyces cerevisiae* GN = SPT2 PE = 1 SV = 1
  z Sequence     Incl. L/(L + H) Std. Err. Fraction Correlation Intensity Modifications

| | | | | | | |
|---|---|---|---|---|---|---|
| 1 | 2 RQELLK | X | 0.5908 | 0.00487 | 0.1874 | 0.9696 5.33E+05 |

| Hit | Accession | Score | Mass | L/(L + H) | SD(geo) | # |
|---|---|---|---|---|---|---|
| 154 | P06101 | 25 | 58845 | 0.9702 | | 1 |

CDC37_YEAST Hsp90 co-chaperone Cdc37 OS = *Saccharomyces cerevisiae* GN = CDC37 PE = 1 SV = 2
  z Sequence     Incl. L/(L + H) Std. Err. Fraction Correlation Intensity Modifications

| | | | | | | |
|---|---|---|---|---|---|---|
| 1 | 2 VFEDIPIEEAEK | X | 0.9702 | 0.01138 | 0.1397 | 0.737 1.27E+05 |

| Hit | Accession | Score | Mass | L/(L + H) | SD(geo) | # |
|---|---|---|---|---|---|---|
| 155 | P07149 | 25 | 228547 | | | 0 |

FAS1_YEAST Fatty acid synthase subunit beta OS = *Saccharomyces cerevisiae* GN = FAS1 PE = 1 SV = 2
  z Sequence     Incl. L/(L + H) Std. Err. Fraction Correlation Intensity Modifications

| | | | | | | |
|---|---|---|---|---|---|---|
| 1 | 2 WETTTQFK | | 0.3417 | 0.07701 | 0.06965 | 0.6964 5.87E+04 |

| Hit | Accession | Score | Mass | L/(L + H) | SD(geo) | # |
|---|---|---|---|---|---|---|
| 156 | P35169 | 24 | 280962 | 1.001 | | 1 |

TOR1_YEAST Serine/threonine-protein kinase TOR1 OS = *Saccharomyces cerevisiae* GN = TOR1 PE = 1 SV = 3
  z Sequence     Incl. L/(L + H) Std. Err. Fraction Correlation Intensity Modifications

| | | | | | | |
|---|---|---|---|---|---|---|
| 1 | 2 EIKFIK | X | 1.001 | 0 | 0.1891 | 0.9934 1.08E+05 |

| Hit | Accession | Score | Mass | L/(L + H) | SD(geo) | # |
|---|---|---|---|---|---|---|
| 157 | Q05016 | 24 | 29301 | | | 0 |

YM71_YEAST Uncharacterized oxidoreductase YMR226C OS = *Saccharomyces cerevisiae* GN = YMR226C PE = 1 SV = 1
  z Sequence     Incl. L/(L + H) Std. Err. Fraction Correlation Intensity Modifications

| | | | | | | |
|---|---|---|---|---|---|---|
| 1 | 3 IKPFIENLPQEFK | | 0.4711 | 0.02328 | 0.1926 | 0.2766 5.31E+04 |

| Hit | Accession | Score | Mass | L/(L + H) | SD(geo) | # |
|---|---|---|---|---|---|---|
| 158 | P23796 | 24 | 59181 | | | 0 |

RIT1_YEAST tRNA A64-2'-O-ribosylphosphate transferase OS = *Saccharomyces cerevisiae* GN = RIT1 PE = 1 SV = 3
  z Sequence     Incl. L/(L + H) Std. Err. Fraction Correlation Intensity Modifications

| | | | | | | |
|---|---|---|---|---|---|---|
| 1 | 2 LNELFMGK | | 0.173 | 0.1599 | 0.1023 | 0.6886 5.41E+04 |

TABLE 1-continued

Proteins identified by Mascot Distiller from ChAP-MS analysis of GAL1 chromatin isolated from cells grown in glucose.
Mascot Distiller Quantitation Report

| Hit | Accession | Score | Mass | L/(L + H) | SD(geo) | # |
|---|---|---|---|---|---|---|
| 159 | Q12734 | 23 | 124772 | 0.9979 | | 1 |

CSR2_YEAST Transcription factor CSR2 OS = *Saccharomyces cerevisiae*
GN = CSR2 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 STTLSDIK | X | 0.9979 | 0 | 0.5316 | 0.9992 | 3.05E+06 | |

| Hit | Accession | Score | Mass | L/(L + H) | SD(geo) | # |
|---|---|---|---|---|---|---|
| 160 | P24384 | 23 | 130674 | 0.5908 | | 1 |

PRP22_YEAST Pre-mRNA-splicing factor ATP-dependent RNA helicase
PRP22 OS = *Saccharomyces cerevisiae* GN = PRP22 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 ERALGIK | X | 0.5908 | 0.00487 | 0.1874 | 0.9696 | 5.33E+05 | |

| Hit | Accession | Score | Mass | L/(L + H) | SD(geo) | # |
|---|---|---|---|---|---|---|
| 161 | Q04412 | 23 | 54780 | 0.9523 | | 1 |

AGE1_YEAST ADP-ribosylation factor GTPase-activating protein effector
protein 1 OS = *Saccharomyces cerevisiae* GN = AGE1 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 LTNILLK | X | 0.9523 | 0.00751 | 0.01207 | 0.9072 | 1.83E+05 | |

| Hit | Accession | Score | Mass | L/(L + H) | SD(geo) | # |
|---|---|---|---|---|---|---|
| 162 | P53191 | 22 | 70950 | | | 0 |

PIB2_YEAST Phosphatidylinositol-3-phosphate-binding protein 2
OS = *Saccharomyces cerevisiae* GN = PIB2 PE = 1 SV = 1

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 163 | Q03497 | 22 | 102940 | 1 | | 1 |

STE20_YEAST Serine/threonine-protein kinase STE20
OS = *Saccharomyces cerevisiae* GN = STE20 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 ETLSGLEFLH SK | X | 1 | 0.00609 | 0.6136 | 0.9975 | 1.27E+06 | |

| Hit | Accession | Score | Mass | L/(L + H) | SD(geo) | # |
|---|---|---|---|---|---|---|
| 164 | P40462 | 22 | 107655 | 0.9911 | | 1 |

TM108_YEAST Protein TMA108 OS = *Saccharomyces cerevisiae*
GN = TMA108 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 FINLEK | X | 0.9911 | 0.00377 | 0.122 | 0.9964 | 5.91E+05 | |

| Hit | Accession | Score | Mass | L/(L + H) | SD(geo) | # |
|---|---|---|---|---|---|---|
| 165 | P05755 | 22 | 22285 | | | 0 |

RS9B_YEAST 40S ribosomal protein S9-B OS = *Saccharomyces cerevisiae*
GN = RPS9B PE = 1 SV = 4

| z | Sequence | Incl. | L/(L + H) | Std. Err. | Fraction | Correlation | Intensity | Modifications |
|---|---|---|---|---|---|---|---|---|
| 1 | 2 LDYVLALK | | 0.005702 | 1.64 | 0.079 | 0.8879 | 9978 | |

TABLE 1-continued

Proteins identified by Mascot Distiller from ChAP-MS analysis of GAL1 chromatin isolated from cells grown in glucose.
Mascot Distiller Quantitation Report

| Hit | Accession | Score | Mass | L/(L + H) | SD(geo) | # |
|---|---|---|---|---|---|---|
| 166 | P46679 | 22 | 97766 | | | 0 |

STB2_YEAST Protein STB2 OS = *Saccharomyces cerevisiae* GN = STB2 PE = 1 SV = 2

| z | Sequence | Incl. | L/(L + H) | Std. Err. | Fraction | Correlation | Intensity | Modifications |
|---|---|---|---|---|---|---|---|---|
| 1 | 3 SSLQGQGKT GICSAIDPKS DK | | 0.9544 | 0.00932 | 0.1894 | 0.3151 | 7.47E+05 | |

| Hit | Accession | Score | Mass | L/(L + H) | SD(geo) | # |
|---|---|---|---|---|---|---|
| 167 | P0C0W1 | 22 | 14705 | | | 0 |

RS22A_YEAST 40S ribosomal protein S22-A OS = *Saccharomyces cerevisiae* GN = RPS22A PE = 1 SV = 2

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 168 | P36096 | 22 | 88064 | 0.9908 | | 1 |

TUL1_YEAST Transmembrane E3 ubiquitin-protein ligase 1 OS = *Saccharomyces cerevisiae* GN = TUL1 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 IDLVSNNK | X | 0.9908 | 0.00823 | 0.03719 | 0.9728 | 1.54E+05 | |

| Hit | Accession | Score | Mass | L/(L + H) | SD(geo) | # |
|---|---|---|---|---|---|---|
| 169 | P38967 | 21 | 65362 | | | 0 |

TAT2_YEAST Tryptophan permease OS = *Saccharomyces cerevisiae* GN = TAT2 PE = 1 SV = 1

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 170 | Q05955 | 21 | 57795 | 0.8578 | | 1 |

ADY4_YEAST Accumulates dyads protein 4 OS = *Saccharomyces cerevisiae* GN = ADY4 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 DVDYQTFK | X | 0.8578 | 0.03111 | 0.08023 | 0.9212 | 1.78E+05 | |

| Hit | Accession | Score | Mass | L/(L + H) | SD(geo) | # |
|---|---|---|---|---|---|---|
| 171 | P26786 | 21 | 21761 | | | 0 |

RS7A_YEAST 40S ribosomal protein S7-A OS = *Saccharomyces cerevisiae* GN = RPS7A PE = 1 SV = 4

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 172 | P18759 | 21 | 84004 | 1 | | 1 |

SEC18_YEAST Vesicular-fusion protein SEC18 OS = *Saccharomyces cerevisiae* GN = SEC18 PE = 1 SV = 2

| z | Sequence | Incl. | L/(L + H) | Std. Err. | Fraction | Correlation | Intensity | Modifications |
|---|---|---|---|---|---|---|---|---|
| 1 | 2 FKIPGFGK | X | 1 | 0.00372 | 0.3628 | 0.9814 | 2.01E+05 | |

| Hit | Accession | Score | Mass | L/(L + H) | SD(geo) | # |
|---|---|---|---|---|---|---|
| 173 | P02309 | 21 | 11361 | 0.4287 | | 1 |

H4_YEAST Histone H4 OS = *Saccharomyces cerevisiae* GN = HHF1 PE = 1 SV = 2

| z | Sequence | Incl. | L/(L + H) | Std. Err. | Fraction | Correlation | Intensity | Modifications |
|---|---|---|---|---|---|---|---|---|
| 1 | 2 DSVTYTEHAK | X | 0.4287 | 0.05722 | 0.06178 | 0.844 | 1.78E+04 | |

TABLE 1-continued

Proteins identified by Mascot Distiller from ChAP-MS analysis of GAL1 chromatin isolated from cells grown in glucose.
Mascot Distiller Quantitation Report

| Hit | Accession | Score | Mass | L/(L + H) | SD(geo) | # |
|---|---|---|---|---|---|---|
| 174 | P36139 | 20 | 31428 | | | 0 |

PET10_YEAST Protein PET10 OS = *Saccharomyces cerevisiae* GN = PET10 PE = 1 SV = 3

| z | Sequence | Incl. | L/(L + H) | Std. Err. | Fraction | Correlation | Intensity | Modifications |
|---|---|---|---|---|---|---|---|---|
| 1 | 2 LDELVNLLVFK | | −0.001257 | 0.6587 | 0.7685 | 0.9993 | 1.17E+06 | |

| Hit | Accession | Score | Mass | L/(L + H) | SD(geo) | # |
|---|---|---|---|---|---|---|
| 175 | Q02773 | 20 | 140029 | | | 1 |

RPM2_YEAST Ribonuclease P protein component, mitochondrial
OS = *Saccharomyces cerevisiae* GN = RPM2 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 SLLRKSKPLQA | X | 0 | 999 | 0.00047 | 0.8095 | 271.1 | |

| Hit | Accession | Score | Mass | L/(L + H) | SD(geo) | # |
|---|---|---|---|---|---|---|
| 176 | P38697 | 20 | 56494 | 0.3128 | | 1 |

IMDH2_YEAST Inosine-5'-monophosphate dehydrogenase IMD2
OS = *Saccharomyces cerevisiae* GN = IMD2 PE = 1 SV = 1

| z | Sequence | Incl. | L/(L + H) | Std. Err. | Fraction | Correlation | Intensity | Modifications |
|---|---|---|---|---|---|---|---|---|
| 1 | 3 TASAQLEGGVHNLHSYEK | X | 0.3128 | 0.09825 | 0.218 | 0.8306 | 1.40E+04 | |

| Hit | Accession | Score | Mass | L/(L + H) | SD(geo) | # |
|---|---|---|---|---|---|---|
| 177 | P41832 | 20 | 221017 | 0.02392 | | 1 |

BNI1_YEAST Protein BNI1 OS = *Saccharomyces cerevisiae* GN = BNI1 PE = 1 SV = 2

| z | Sequence | Incl. | L/(L + H) | Std. Err. | Fraction | Correlation | Intensity | Modifications |
|---|---|---|---|---|---|---|---|---|
| 1 | 2 RLKELETK | X | 0.02392 | 0.2888 | 0.00547 | 0.8577 | 1621 | |

| Hit | Accession | Score | Mass | L/(L + H) | SD(geo) | # |
|---|---|---|---|---|---|---|
| 178 | P17119 | 20 | 83952 | 0.09389 | | 1 |

KAR3_YEAST Kinesin-like protein KAR3 OS = *Saccharomyces cerevisiae* GN = KAR3 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 TNLETLEK | X | 0.09389 | 0.2254 | 0.0084 | 0.9135 | 5.14E+04 | |

| Hit | Accession | Score | Mass | L/(L + H) | SD(geo) | # |
|---|---|---|---|---|---|---|
| 179 | P15303 | 20 | 85579 | | | 0 |

SEC23_YEAST Protein transport protein SEC23 OS = *Saccharomyces cerevisiae* GN = SEC23 PE = 1 SV = 1

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 180 | P32565 | 20 | 104768 | | | 0 |

RPN2_YEAST 26S proteasome regulatory subunit RPN2
OS = *Saccharomyces cerevisiae* GN = RPN2 PE = 1 SV = 4

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 181 | Q03660 | 20 | 128787 | | | 0 |

TR130_YEAST Transport protein particle 130 kDa subunit
OS = *Saccharomyces cerevisiae* GN = TRS130 PE = 1 SV = 1

| z | Sequence | Incl. | L/(L + H) | Std. Err. | Fraction | Correlation | Intensity | Modifications |
|---|---|---|---|---|---|---|---|---|

TABLE 1-continued

Proteins identified by Mascot Distiller from ChAP-MS analysis of GAL1 chromatin isolated from cells grown in glucose.
Mascot Distiller Quantitation Report

| Hit | Accession | Score | Mass | L/(L + H) | SD(geo) | # |
|---|---|---|---|---|---|---|
| 182 | P39081 | 19 | 71853 | | | 0 |

PCF11_YEAST Protein PCF11 OS = *Saccharomyces cerevisiae* GN = PCF11 PE = 1 SV = 2

| z Sequence | Incl. | L/(L + H) | Std. Err. | Fraction | Correlation | Intensity | Modifications |
|---|---|---|---|---|---|---|---|
| 1  3 INNLYASLKA EGLIYTPPK | | 0.9323 | 0.01402 | 0.3541 | 0.6434 | 6.37E+04 | |

| Hit | Accession | Score | Mass | L/(L + H) | SD(geo) | # |
|---|---|---|---|---|---|---|
| 183 | B3LRC2 | 19 | 36810 | | | 0 |

UTH1_YEAS1 Protein UTH1 OS = *Saccharomyces cerevisiae* (strain RM11-1a) GN = UTH1 PE = 3 SV = 1

| z Sequence | Incl. | L/(L + H) | Std. Err. | Fraction | Correlation | Intensity | Modifications |
|---|---|---|---|---|---|---|---|

| Hit | Accession | Score | Mass | L/(L + H) | SD(geo) | # |
|---|---|---|---|---|---|---|
| 184 | P07259 | 19 | 244972 | | | 0 |

PYR1_YEAST Protein URA1 OS = *Saccharomyces cerevisiae* GN = URA2 PE = 1 SV = 4

| z Sequence | Incl. | L/(L + H) | Std. Err. | Fraction | Correlation | Intensity | Modifications |
|---|---|---|---|---|---|---|---|

| Hit | Accession | Score | Mass | L/(L + H) | SD(geo) | # |
|---|---|---|---|---|---|---|
| 185 | P18963 | 19 | 350758 | 0.9999 | | 1 |

IRA1_YEAST Inhibitory regulator protein IRA1 OS = *Saccharomyces cerevisiae* GN = IRA1 PE = 1 SV = 2

| z Sequence | Incl. | L/(L + H) | Std. Err. | Fraction | Correlation | Intensity | Modifications |
|---|---|---|---|---|---|---|---|
| 1  2 GNKYLIK | X | 0.9999 | 0.00158 | 0.0893 | 0.9713 | 3.78E+04 | |

| Hit | Accession | Score | Mass | L/(L + H) | SD(geo) | # |
|---|---|---|---|---|---|---|
| 186 | P38850 | 18 | 123854 | | | 0 |

RTT107_YEAST Regulator of Ty1 transposition protein 107 OS = *Saccharomyces cerevisiae* GN = RTT107 PE = 1 SV = 1

| z Sequence | Incl. | L/(L + H) | Std. Err. | Fraction | Correlation | Intensity | Modifications |
|---|---|---|---|---|---|---|---|

| Hit | Accession | Score | Mass | L/(L + H) | SD(geo) | # |
|---|---|---|---|---|---|---|
| 187 | Q04199 | 18 | 51420 | | | 0 |

CAC2_YEAST Chromatin assembly factor 1 subunit p60 OS = *Saccharomyces cerevisiae* GN = CAC2 PE = 1 SV = 1

| z Sequence | Incl. | L/(L + H) | Std. Err. | Fraction | Correlation | Intensity | Modifications |
|---|---|---|---|---|---|---|---|
| 1  2 IPCNSSDSK | | 0.9943 | 0.00328 | 0.1865 | 0.52 | 1.44E+06 | |

| Hit | Accession | Score | Mass | L/(L + H) | SD(geo) | # |
|---|---|---|---|---|---|---|
| 188 | Q12345 | 17 | 28402 | | | 0 |

IES3_YEAST Ino eighty subunit 3 OS = *Saccharomyces cerevisiae* GN = IES3 PE = 1 SV = 1

| z Sequence | Incl. | L/(L + H) | Std. Err. | Fraction | Correlation | Intensity | Modifications |
|---|---|---|---|---|---|---|---|
| 1  3 IDILTKIQENL LEEYQK | | 0.04155 | 1.417 | 0.06472 | 0.5595 | 1068 | |

| Hit | Accession | Score | Mass | L/(L + H) | SD(geo) | # |
|---|---|---|---|---|---|---|
| 189 | P53598 | 17 | 35010 | 1.001 | | 1 |

SUCA_YEAST Succinyl-CoA ligase [ADP-forming] subunit alpha mitochondrial OS = *Saccharomyces cerevisiae* GN = LSC1 PE = 1 SV = 1

| z Sequence | Incl. | L/(L + H) | Std. Err. | Fraction | Correlation | Intensity | Modifications |
|---|---|---|---|---|---|---|---|
| 1  2 ESIPYDK | X | 1.001 | 0.001 | 0.6215 | 0.9959 | 3.11E+06 | |

TABLE 2

Proteins identified by Mascot Distiller from ChAP-MS analysis of GAL1 chromatin isolated from cells grown in galactose.
Mascot Distiller
Quantitation Report Mascot search results: Galactose

| | | | | Log ratio versus Intensity (all positive ratios) | | Log ratio versus Intensity (selected ratios) | |
|---|---|---|---|---|---|---|---|
| L/(L + H) | | | | 0<br>2.00e+7<br>4.00e+7<br>6.00e+7<br>-15 -10<br>-5 0 5 | | 0<br>5.00e+6<br>1.00e+7<br>1.50e+7 -6<br>-4 -2 0 2 | |

| Hit | Accession | Score | Mass | L/(L + H) | SD(geo) | # |
|---|---|---|---|---|---|---|
| 1 | P00924 | 952 | 46773 | 0.727 | 1.077 | 10 |

ENO1_YEAST Enolase 1 OS = *Saccharomyces cerevisiae* GN = ENO1 PE = 1 SV = 2

| | z Sequence | Incl. | L/(L + H) | Std. Err. | Fraction | Correlation | Intensity | Modifications |
|---|---|---|---|---|---|---|---|---|
| 1 | 2 RIATAIEK | X | 0.9922 | 0.001 | 0.0623 | 0.9937 | 78080.00 | |
| 2 | 2 VNQIGTLSESIK | X | 0.7237 | 0.001 | 0.6107 | 0.9971 | 1.48E+06 | |
| 3 | 3 AVDDFLISLDGTANK | X | 0.6953 | 0.00258 | 0.5605 | 0.9825 | 2.57E+05 | |
| 4 | 2 AVDDFLISLDGTANK | X | 0.678 | 0.00158 | 0.1606 | 0.9839 | 3.20E+06 | |
| 5 | 2 TAGIQIVADDLTVTNPK | X | 0.8499 | 0 | 0.4502 | 0.9983 | 8.74E+05 | |
| 6 | 3 IEEELGDNAVFAGENFHHGDK | X | 0.7139 | 0.01531 | 0.04418 | 0.7314 | 3.10E+04 | |
| 7 | 2 IEEELGDNAVFAGENFHHGDKL | X | 0.8709 | 0.00321 | 0.8165 | 0.9933 | 1.28E+05 | |
| 8 | 3 IEEELGDNAVFAGENFHHGDKL | X | 0.8482 | 0.00579 | 0.7751 | 0.9956 | 5.69E+05 | |
| 9 | 3 YPIVSIEDPFAEDDWEAWSHFFK | X | 0.743 | 0.001 | 0.7934 | 0.9984 | 1.74E+06 | |
| 10 | 3 RYPIVSIEDPFAEDDWEAWSHFFK | | 0.2589 | 0.1734 | 0.2248 | 0.5408 | 1353 | |
| 11 | 3 YGASAGNVGDEGGVAPNIQTAEEALDLIVDAIK | X | 0.7223 | 0.00158 | 0.9201 | 0.9993 | 1.05E+07 | |

| Hit | Accession | Score | Mass | L/(L + H) | SD(geo) | # |
|---|---|---|---|---|---|---|
| 2 | P00925 | 827 | 46885 | 0.7156 | 1.024 | 5 |

ENO2_YEAST Enolase 2 OS = *Saccharomyces cerevisiae* GN = ENO2 PE = 1 SV = 2

| | z Sequence | Incl. | L/(L + H) | Std. Err. | Fraction | Correlation | Intensity | Modifications |
|---|---|---|---|---|---|---|---|---|
| 1 | 2 VNQIGTLSESIK | X | 0.7237 | 0.001 | 0.6107 | 0.9971 | 1.48E+06 | |
| 2 | 3 AVDDFLLSLDGTANK | X | 0.6953 | 0.00258 | 0.5605 | 0.9825 | 2.57E+05 | |
| 3 | 2 AVDDFLLSLDGTANK | X | 0.678 | 0.00158 | 0.1606 | 0.9839 | 3.20E+06 | |
| 4 | 2 DGKYDLDFKNPESDK | | 0.593 | 0.03836 | 0.2515 | 0.6481 | 3.31E+05 | |
| 5 | 3 DGKYDLDFKNPESDK | | 0.2183 | 0.1283 | 0.2233 | 0.1889 | 8.04E+05 | |
| 6 | 3 YPIVSIEDPFAEDDWEAWSHFFK | X | 0.743 | 0.001 | 0.7934 | 0.9984 | 1.74E+06 | |

TABLE 2-continued

Proteins identified by Mascot Distiller from ChAP-MS analysis of GAL1 chromatin isolated from cells grown in galactose.
Mascot Distiller
Quantitation Report

|  | z | Sequence | Incl. | L/(L + H) | Std. Err. | Fraction | Correlation | Intensity | Modifications |
|---|---|---|---|---|---|---|---|---|---|
| 7 | 3 | RYPIVSIEDPFAEDDWEAWSHFFK |  | 0.2589 | 0.1734 | 0.2248 | 0.5408 | 1353 |  |
| 8 | 3 | YGASAGNVGDEGGVAPNIQTAEEALDLIVDAIK | X | 0.7223 | 0.00158 | 0.9201 | 0.9993 | 1.05E+07 |  |

| Hit | Accession | Score | Mass | L/(L + H) | SD(geo) | # |
|---|---|---|---|---|---|---|
| 3 | P00359 | 773 | 35724 | 0.6771 | 1.019 | 7 |

G3P3_YEAST Glyceraldehyde-3-phosphate dehydrogenase 3 OS = *Saccharomyces cerevisiae* GN = TDH3 PE = 1 SV = 3

|  | z | Sequence | Incl. | L/(L + H) | Std. Err. | Fraction | Correlation | Intensity | Modifications |
|---|---|---|---|---|---|---|---|---|---|
| 1 | 3 | ETTYDEIKK | X | 0.6838 | 0.00472 | 0.3538 | 0.9553 | 3.68E+05 |  |
| 2 | 2 | TASGNIIPSSTGAAK | X | 0.6648 | 0.00158 | 0.6513 | 0.9983 | 3.86E+06 |  |
| 3 | 2 | VPTVDVSVVDLTVK | X | 0.7282 | 0.0064 | 0.2127 | 0.8286 | 6.60E+05 |  |
| 4 | 3 | LNKETTYDEIKK |  | 0.7548 | 0.04527 | 0.0313 | 0.2068 | 5.04E+04 |  |
| 5 | 3 | YAGEVSHDDKHIIVDGK |  | 0.688 | 0.0049 | 0.1652 | 0.6807 | 4.07E+06 |  |
| 6 | 2 | YAGEVSHDDKHIIVDGK | X | 0.6826 | 0.00224 | 0.3878 | 0.8652 | 2.07E+06 |  |
| 7 | 3 | KVVITAPSSTAPMFVMGVNEEK | X | 0.7193 | 0.00631 | 0.1023 | 0.9512 | 2.42E+05 |  |
| 8 | 2 | DPANLPWGSSNVDIAIDSTGVFK | X | 0.6776 | 0.00494 | 0.5179 | 0.9695 | 1.47E+06 |  |
| 9 | 3 | DPANLPWGSSNVDIAIDSTGVFK |  | 0.6946 | 0.02605 | 0.3559 | 0.4268 | 1.47E+06 |  |
| 10 | 3 | VINDAFGIEEGLMTTVHSLTATQK | X | 0.6612 | 0.0114 | 0.3918 | 0.9512 | 5.69E+05 |  |

| Hit | Accession | Score | Mass | L/(L + H) | SD(geo) | # |
|---|---|---|---|---|---|---|
| 4 | P02994 | 662 | 50394 | 0.8504 | 1.012 | 7 |

EF1A_YEAST Elongation factor 1-alpha OS = *Saccharomyces cerevisiae* GN = TEF1 PE = 1 SV = 1

|  | z | Sequence | Incl. | L/(L + H) | Std. Err. | Fraction | Correlation | Intensity | Modifications |
|---|---|---|---|---|---|---|---|---|---|
| 1 | 2 | FDELLEK | X | 0.826 | 0.00158 | 0.3074 | 0.9923 | 4.71E+06 |  |
| 2 | 3 | SHINVVVIGHVDSGK |  | 0.8651 | 0.00919 | 0.1342 | 0.4249 | 1.91E+05 |  |
| 3 | 2 | TLLEAIDAIEQPSRPTDKPLR | X | 0.8558 | 0 | 0.7243 | 0.9974 | 1.11E+06 |  |
| 4 | 3 | TLLEAIDAIEQPSRPTDKPLR | X | 0.8371 | 0.00322 | 0.6393 | 0.9893 | 8.82E+06 |  |
| 5 | 3 | VETGVIKPGMVVTFAPAGVTTEVK | X | 0.8774 | 0.001 | 0.7139 | 0.9992 | 6.53E+06 |  |
| 6 | 2 | VETGVIKPGMVVTFAPAGVTTEVK | X | 0.8911 | 0 | 0.7784 | 0.9982 | 2.27E+06 |  |
| 7 | 3 | SVEMHHEQLEQGVPGDNVGFNVK | X | 0.8474 | 0.00071 | 0.7764 | 0.9988 | 1.10E+07 |  |
| 8 | 2 | SVEMHHEQLEQGVPGDNVGFNVK | X | 0.8482 | 0.001 | 0.8709 | 0.999 | 1.09E+06 |  |

TABLE 2-continued

Proteins identified by Mascot Distiller from ChAP-MS analysis of GAL1 chromatin isolated from cells grown in galactose.
Mascot Distiller
Quantitation Report

| Hit | Accession | Score | Mass | L/(L + H) | SD(geo) | # |
|---|---|---|---|---|---|---|
| 5 | P54115 | 486 | 54380 | 0.6881 | 1.024 | 5 |

ALDH6_YEAST Magnesium-activated aldehyde dehydrogenase, cytosolic OS = *Saccharomyces cerevisiae* GN = ALD6 PE = 1 SV = 4

| | z | Sequence | Incl. | L/(L + H) | Std. Err. | Fraction | Correlation | Intensity | Modifications |
|---|---|---|---|---|---|---|---|---|---|
| 1 | 2 | SVAVDSSESNLK | X | 0.7081 | 0.0109 | 0.05156 | 0.971 | 5.45E+05 | |
| 2 | 3 | SVAVDSSESNLKK | X | 0.6272 | 0.01694 | 0.1014 | 0.9286 | 2.04E+05 | |
| 3 | 2 | SVAVDSSESNLKK | X | 0.6886 | 0.00158 | 0.2331 | 0.997 | 7.45E+05 | |
| 4 | 3 | SAHLVFDDANIKK | X | 0.6792 | 0.004 | 0.1402 | 0.9596 | 2.03E+05 | |
| 5 | 3 | IVKEEIFGPVVTVAK | | 0.2547 | 0.07849 | 0.4923 | 0.06903 | 3.53E+06 | |
| 6 | 2 | IVKEEIFGPVVTVAK | X | 0.6996 | 0.00158 | 0.1833 | 0.9947 | 3.23E+05 | |

| Hit | Accession | Score | Mass | L/(L + H) | SD(geo) | # |
|---|---|---|---|---|---|---|
| 6 | P10591 | 482 | 70039 | 0.8188 | 1.018 | 4 |

HSP71_YEAST Heat shock protein SSA1 OS = *Saccharomyces cerevisiae* GN = SSA1 PE = 1 SV = 4

| | z | Sequence | Incl. | L/(L + H) | Std. Err. | Fraction | Correlation | Intensity | Modifications |
|---|---|---|---|---|---|---|---|---|---|
| 1 | 2 | MKETAESYLGAK | X | 0.7735 | 0.00986 | 0.2692 | 0.9866 | 2.32E+05 | |
| 2 | 2 | NFNDPEVQADMK | X | 0.8218 | 0.00856 | 0.2133 | 0.9657 | 9.80E+05 | |
| 3 | 2 | NQAAMNPSNTVFDAK | X | 0.8186 | 0.0035 | 0.4594 | 0.9975 | 1.37E+06 | |
| 4 | 3 | NTISEAGDKLEQADKDTVTK | | 0.3583 | 0.06491 | 0.4424 | 0.4808 | 1.01E+07 | |
| 5 | 2 | NTISEAGDKLEQADKDTVTK | X | 0.8301 | 0.00158 | 0.6157 | 0.995 | 7.24E+05 | |

| Hit | Accession | Score | Mass | L/(L + H) | SD(geo) | # |
|---|---|---|---|---|---|---|
| 7 | P50095 | 425 | 56813 | 0.9382 | 1.024 | 5 |

IMDH3_YEAST Probable inosine-5'-monophosphate dehydrogenase IMD3 OS = *Saccharomyces cerevisiae* GN = IMD3 PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 3 | TASAQLEGGVHNLHSYEK | | 0.4222 | 0.1268 | 0.5294 | 0.3116 | 7.78E+05 | |
| 2 | 2 | TASAQLEGGVHNLHSYEK | X | 0.893 | 0.02366 | 0.2283 | 0.9113 | 2.44E+05 | |
| 3 | 2 | NPVTGAQGITLSEGNEILK | X | 0.9433 | 0.00754 | 0.3647 | 0.9924 | 1.01E+06 | |
| 4 | 3 | NPVTGAQGITLSEGNEILK | X | 0.9335 | 0.00158 | 0.3228 | 0.9933 | 3.39E+05 | |
| 5 | 2 | YFSESDSVLVAQGVSGAVVDK | X | 1 | 0.001 | 0.4121 | 0.9864 | 7.24E+04 | |
| 6 | 2 | GGLTYNDFLVLPGLVDFPSSEVSLQTK | X | 0.9534 | 0 | 0.8179 | 0.9932 | 2.35E+05 | |

TABLE 2-continued

Proteins identified by Mascot Distiller from ChAP-MS analysis of GAL1 chromatin isolated from cells grown in galactose.
Mascot Distiller
Quantitation Report

| Hit | Accession | Score | Mass | L/(L + H) | SD(geo) | # |
|---|---|---|---|---|---|---|
| 8 | P07262 | 383 | 49539 | 0.5666 | 1.061 | 3 |

DHE4_YEAST NADP-specific glutamate dehydrogenase 1
OS = *Saccharomyces cerevisiae* GN = GDH1 PE = 1 SV = 2

| | z | Sequence | Incl. | L/(L + H) | Std. Err. | Fraction | Correlation | Intensity | Modifications |
|---|---|---|---|---|---|---|---|---|---|
| 1 | 2 | STATGPSE AVWYGPPK | X | 0.6132 | 0.00959 | 0.3565 | 0.9733 | 2.44E+05 | |
| 2 | 3 | VTWENDK GEQEVAQG YR | X | 0.535 | 0.02836 | 0.5322 | 0.8087 | 5.75E+05 | |
| 3 | 2 | VTWENDK GEQEVAQG YR | X | 0.6306 | 0.00328 | 0.4773 | 0.9937 | 1.29E+05 | |

| Hit | Accession | Score | Mass | L/(L + H) | SD(geo) | # |
|---|---|---|---|---|---|---|
| 9 | P06169 | 369 | 61737 | 0.5627 | | 5 |

PDC1_YEAST Pyruvate decarboxylase isozyme 1 OS = *Saccharomyces cerevisiae* GN = PDC1 PE = 1 SV = 7

| | z | Sequence | Incl. | L/(L + H) | Std. Err. | Fraction | Correlation | Intensity | Modifications |
|---|---|---|---|---|---|---|---|---|---|
| 1 | 2 | VATTGEWD KLTQDK | X | 0.5604 | 0.00308 | 0.3782 | 0.9946 | 8.35E+05 | |
| 2 | 3 | YGGVYVGT LSKPEVK | X | 0.5512 | 0.00325 | 0.3138 | 0.9816 | 4.29E+05 | |
| 3 | 2 | YGGVYVGT LSKPEVK | X | 0.5578 | 0.001 | 0.3925 | 0.9961 | 8.00E+05 | |
| 4 | 3 | LLQTPIDM SLKPNDAE SEK | X | 0.6389 | 0.08423 | 0.3737 | 0.9119 | 2000 | |
| 5 | 2 | MIEIMLPVF DAPQNLVE QAK | X | 0.6331 | 0.00453 | 0.5965 | 0.979 | 1.63E+05 | |

| Hit | Accession | Score | Mass | L/(L + H) | SD(geo) | # |
|---|---|---|---|---|---|---|
| 10 | P29311 | 363 | 30209 | 0.7744 | 1.108 | 3 |

BMH1_YEAST Protein BMH1 OS = *Saccharomyces cerevisiae* GN = BMH1 PE = 1 SV = 4

| | z | Sequence | Incl. | L/(L + H) | Std. Err. | Fraction | Correlation | Intensity | Modifications |
|---|---|---|---|---|---|---|---|---|---|
| 1 | 3 | QAFDDAIA ELDTLSEES YK | X | 0.7998 | 0.00255 | 0.5395 | 0.9946 | 4.35E+05 | |
| 2 | 2 | ISDDILSVL DSHLIPSAT TGESK | X | 0.625 | 0.01278 | 0.271 | 0.7283 | 1.76E+05 | |
| 3 | 3 | ISDDILSVL DSHLIPSAT TGESK | X | 0.7868 | 0.00158 | 0.1746 | 0.9972 | 1.49E+06 | |

| Hit | Accession | Score | Mass | L/(L + H) | SD(geo) | # |
|---|---|---|---|---|---|---|
| 11 | P15108 | 361 | 81435 | 0.007455 | | 6 |

HSC82_YEAST ATP-dependent molecular chaperone HSC82
OS = *Saccharomyces cerevisiae* GN = HSC82 PE = 1 SV = 4

| | z | Sequence | Incl. | L/(L + H) | Std. Err. | Fraction | Correlation | Intensity | Modifications |
|---|---|---|---|---|---|---|---|---|---|
| 1 | 2 | AILFIPK | X | 0.7304 | 0.00664 | 0.3427 | 0.9954 | 5.12E+04 | |
| 2 | 2 | RVDEGGA QDK | X | 0.734 | 0.007 | 0.04224 | 0.965 | 9084 | |
| 3 | 2 | KDEDDKKPK | | 0.4443 | 0.1702 | 0.04474 | 0.339 | 2202 | |
| 4 | 2 | ALKDILGD QVEK | X | 0.7398 | 0.01231 | 0.03927 | 0.8976 | 8.40E+04 | |
| 5 | 3 | VKEEVQEL EELNK | X | 0.711 | 0.00306 | 0.1697 | 0.9942 | 2.85E+05 | |
| 6 | 2 | LEEVDEEE EEKKPK | X | 0.6241 | 0.03842 | 0.06528 | 0.873 | 2.25E+05 | |

TABLE 2-continued

Proteins identified by Mascot Distiller from ChAP-MS analysis of GAL1 chromatin isolated from cells grown in galactose.
Mascot Distiller
Quantitation Report

| | z | Sequence | Incl. | L/(L + H) | Std. Err. | Fraction | Correlation | Intensity | Modifications |
|---|---|---|---|---|---|---|---|---|---|
| 7 | 3 | TLVDITKDFELEETDEEKAER | X | 0.005607 | 0.09361 | 0.4759 | 0.9104 | 1.04E+07 | |

| Hit | Accession | Score | Mass | L/(L + H) | SD(geo) | # |
|---|---|---|---|---|---|---|
| 12 | P46655 | 353 | 81369 | 0.8084 | | 4 |

SYEC_YEAST Glutamyl-tRNA synthetase, cytoplasmic
OS = *Saccharomyces cerevisiae* GN = GUS1 PE = 1 SV = 3

| | z | Sequence | Incl. | L/(L + H) | Std. Err. | Fraction | Correlation | Intensity | Modifications |
|---|---|---|---|---|---|---|---|---|---|
| 1 | 2 | ANFEIDLPDAK | X | 0.8028 | 0.00578 | 0.1682 | 0.9743 | 6.26E+05 | |
| 2 | 2 | IHLEGSEAPQEPK | X | 0.8001 | 0.01046 | 0.2506 | 0.9636 | 5.39E+05 | |
| 3 | 3 | EKEEFQDSILEDLDLLGIK | X | 0.8258 | 0.00576 | 0.2679 | 0.9657 | 5.87E+05 | |
| 4 | 2 | EKEEFQDSILEDLDLLGIK | X | 0.7985 | 0.00441 | 0.3707 | 0.9948 | 1.96E+05 | |

| Hit | Accession | Score | Mass | L/(L + H) | SD(geo) | # |
|---|---|---|---|---|---|---|
| 13 | P32589 | 346 | 77318 | 0.7318 | 1.014 | 3 |

HSP7F_YEAST Heat shock protein homolog SSE1 OS = *Saccharomyces cerevisiae* GN = SSE1 PE = 1 SV = 4

| | z | Sequence | Incl. | L/(L + H) | Std. Err. | Fraction | Correlation | Intensity | Modifications |
|---|---|---|---|---|---|---|---|---|---|
| 1 | 2 | EELEELVKPLLER | X | 0.7536 | 0.03052 | 0.07918 | 0.8999 | 7.17E+04 | |
| 2 | 2 | GKLEEEYAPFASDAEK | | 0.6193 | 0.01623 | 0.1684 | 0.5929 | 1.11E+06 | |
| 3 | 2 | IIGLDYHHPDFEQESK | X | 0.7328 | 0.01091 | 0.08547 | 0.9763 | 8.03E+04 | |
| 4 | 3 | QVEDEDHMEVFPAGSSFPSTK | X | 0.7218 | 0.01002 | 0.3701 | 0.8889 | 1.59E+05 | |

| Hit | Accession | Score | Mass | L/(L + H) | SD(geo) | # |
|---|---|---|---|---|---|---|
| 14 | P00560 | 322 | 44711 | 0.5639 | 1.448 | 3 |

PGK_YEAST Phosphoglycerate kinase OS = *Saccharomyces cerevisiae* GN = PGK1 PE = 1 SV = 2

| | z | Sequence | Incl. | L/(L + H) | Std. Err. | Fraction | Correlation | Intensity | Modifications |
|---|---|---|---|---|---|---|---|---|---|
| 1 | 2 | VDFNVPLDGK | X | 0.272 | 0.04331 | 0.3024 | 0.8665 | 1.97E+06 | |
| 2 | 2 | VLENTEIGDSIFDK | | 0.9987 | 0 | 0.8558 | 0.2984 | 5.35E+07 | |
| 3 | 2 | SSAAGNTVIIGGGDTATVAK | X | 0.7606 | 0.00838 | 0.6009 | 0.9775 | 2.98E+06 | |
| 4 | 2 | GVEVVLPVDFIIADAFSADANTK | X | 0.8169 | 0.00271 | 0.6174 | 0.9986 | 1.47E+06 | |

| Hit | Accession | Score | Mass | L/(L + H) | SD(geo) | # |
|---|---|---|---|---|---|---|
| 15 | P00549 | 296 | 54807 | 0.7976 | 1.025 | 5 |

KPYK1_YEAST Pyruvate kinase 1 OS = *Saccharomyces cerevisiae* GN = PYK1 PE = 1 SV = 2

| | z | Sequence | Incl. | L/(L + H) | Std. Err. | Fraction | Correlation | Intensity | Modifications |
|---|---|---|---|---|---|---|---|---|---|
| 1 | 3 | MNFSHGSYEYHK | X | 0.7461 | 0.02847 | 0.1614 | 0.8404 | 2.71E+05 | |
| 2 | 2 | MNFSHGSYEYHK | X | 0.8117 | 0.00999 | 0.1068 | 0.9731 | 4.19E+05 | |
| 3 | 2 | GVNLPGTDVDLPALSEK | X | 0.8043 | 0.00272 | 0.5459 | 0.9882 | 6.30E+06 | |

TABLE 2-continued

Proteins identified by Mascot Distiller from ChAP-MS analysis of GAL1 chromatin isolated from cells grown in galactose.
Mascot Distiller
Quantitation Report

| | | | | | | | |
|---|---|---|---|---|---|---|---|
| 4 | 2 GDLGIEIPA PEVLAVQK | X | 0.7994 | 0.001 | 0.5602 | 0.9987 | 7.61E+06 |
| 5 | 2 SEELYPGRP LAIALDTK | | 0.002097 | 3.304 | 0.1291 | 0.6758 | 1.89E+05 |
| 6 | 3 KSEELYPG RPLAIALDTK | X | 0.7575 | 0.00877 | 0.1331 | 0.7972 | 1.12E+06 |

| Hit | Accession | Score | Mass | L/(L + H) | SD(geo) | # |
|---|---|---|---|---|---|---|
| 16 | P38720 | 295 | 53509 | 0.9328 | 1.029 | 4 |

6PGD1_YEAST 6-phosphogluconate dehydrogenase, decarboxylating 1
OS = Saccharomyces cerevisiae GN = GND1 PE = 1 SV = 1

| | z Sequence | Incl. | L/(L + H) | Std. Err. | Fraction | Correlation | Intensity | Modifications |
|---|---|---|---|---|---|---|---|---|
| 1 | 2 SIIGATSIE DFISK | X | 0.9129 | 0.001 | 0.1873 | 0.9973 | 1.68E+05 | |
| 2 | 3 LGGFTDKE ISDVFAK | X | 0.949 | 0.00158 | 0.2086 | 0.9846 | 6.26E+05 | |
| 3 | 2 AYREEPDL ENLLFNK | X | 0.936 | 0.00484 | 0.3345 | 0.723 | 3.06E+06 | |
| 4 | 3 YGPSLMPG GSEEAWPH IK | X | 0.8712 | 0.00561 | 0.3785 | 0.9595 | 2.62E+05 | |

| Hit | Accession | Score | Mass | L/(L + H) | SD(geo) | # |
|---|---|---|---|---|---|---|
| 17 | P04385 | 290 | 57907 | 0.6139 | 1.13 | 4 |

GAL1_YEAST Galactokinase OS = Saccharomyces cerevisiae GN = GAL1
PE = 1 SV = 4

| | z Sequence | Incl. | L/(L + H) | Std. Err. | Fraction | Correlation | Intensity | Modifications |
|---|---|---|---|---|---|---|---|---|
| 1 | 2 NPSITLINA DPK | X | 0.7365 | 0.001 | 0.5381 | 0.9953 | 2.36E+06 | |
| 2 | 3 MLVLVEES LANKK | X | 0.7882 | 0.0105 | 0.2982 | 0.9203 | 2.53E+05 | |
| 3 | 2 SHSEEVIVP EFNSSAK | X | 0.5377 | 0.04126 | 0.3609 | 0.9033 | 3.79E+06 | |
| 4 | 2 VLNEKNPSI TLINADPK | X | 0.7577 | 0.00342 | 0.1352 | 0.9951 | 4.28E+04 | |

| Hit | Accession | Score | Mass | L/(L + H) | SD(geo) | # |
|---|---|---|---|---|---|---|
| 18 | P04397 | 264 | 78146 | 0.6778 | | 7 |

GAL10_YEAST Bifunctional protein GAL10 OS = Saccharomyces cerevisiae GN = GAL10 PE = 1 SV = 2

| | z Sequence | Incl. | L/(L + H) | Std. Err. | Fraction | Correlation | Intensity | Modifications |
|---|---|---|---|---|---|---|---|---|
| 1 | 1 LEVLTK | X | 0.8734 | 0.001 | 0.01287 | 0.9936 | 9.32E+04 | |
| 2 | 2 DYIHVVDL AK | X | 0.8614 | 0.00158 | 0.2342 | 0.9952 | 1.38E+06 | |
| 3 | 3 DYIHVVDL AK | X | 0.9574 | 0 | 0.4691 | 0.9578 | 4.66E+05 | |
| 4 | 2 AGDVLNLT AKPDR | X | 0.8088 | 0.00531 | 0.07739 | 0.9941 | 4.67E+05 | |
| 5 | 2 EIATFNSTK PTVLGPK | X | 1.003 | 0.01104 | 0.02312 | 0.9843 | 1.39E+04 | |
| 6 | 2 YAIENILND LYNSDK | X | 0.5331 | 0.02963 | 0.3656 | 0.7372 | 2.83E+06 | |
| 7 | 2 SVDVDKN MIPTGNIV DR | X | 0.8696 | 0.00158 | 0.2804 | 0.9956 | 3.03E+05 | |

| Hit | Accession | Score | Mass | L/(L + H) | SD(geo) | # |
|---|---|---|---|---|---|---|
| 19 | P11484 | 262 | 66561 | 0.8176 | 1.003 | 3 |

HSP75_YEAST Heat shock protein SSB1 OS = Saccharomyces cerevisiae GN = SSB1 PE = 1 SV = 3

| | z Sequence | Incl. | L/(L + H) | Std. Err. | Fraction | Correlation | Intensity | Modifications |
|---|---|---|---|---|---|---|---|---|
| 1 | 2 LLSDFFDGK | X | 0.8188 | 0.001 | 0.534 | 0.998 | 9.62E+05 | |
| 2 | 2 RFDDESVQK | X | 0.8212 | 0.00341 | 0.3458 | 0.9841 | 1.10E+06 | |

TABLE 2-continued

Proteins identified by Mascot Distiller from ChAP-MS analysis of GAL1 chromatin isolated from cells grown in galactose.
Mascot Distiller
Quantitation Report

| | z | Sequence | Incl. | L/(L + H) | Std. Err. | Fraction | Correlation | Intensity | Modifications |
|---|---|---|---|---|---|---|---|---|---|
| 3 | 2 | ENTLLGEFDLK | X | 0.8144 | 0.00158 | 0.4074 | 0.9981 | 1.59E+06 | |

| Hit | Accession | Score | Mass | L/(L + H) | SD(geo) | # |
|---|---|---|---|---|---|---|
| 20 | P08431 | 261 | 42358 | 0.6343 | 8.653 | 3 |

GAL7_YEAST Galactose-1-phosphate uridylyltransferase
OS = *Saccharomyces cerevisiae* GN = GAL7 PE = 1 SV = 4

| | z | Sequence | Incl. | L/(L + H) | Std. Err. | Fraction | Correlation | Intensity | Modifications |
|---|---|---|---|---|---|---|---|---|---|
| 1 | 3 | EHNTDLFADYVK | X | 0.01158 | 0.4988 | 0.2836 | 0.9602 | 5.87E+05 | |
| 2 | 2 | LDQPILPQNDSNEDNLK | X | 0.918 | 0 | 0.8548 | 0.9997 | 6.17E+06 | |
| 3 | 3 | RPWLGQQEAAYKPTAPLYDPK | X | 0.7836 | 0.01208 | 0.1133 | 0.9209 | 3.76E+05 | |

| Hit | Accession | Score | Mass | L/(L + H) | SD(geo) | # |
|---|---|---|---|---|---|---|
| 21 | Q01560 | 247 | 45444 | | | 0 |

NOP3_YEAST Nucleolar protein 3 OS = *Saccharomyces cerevisiae*
GN = NPL3 PE = 1 SV = 1

| | z | Sequence | Incl. | L/(L + H) | Std. Err. | Fraction | Correlation | Intensity | Modifications |
|---|---|---|---|---|---|---|---|---|---|

| Hit | Accession | Score | Mass | L/(L + H) | SD(geo) | # |
|---|---|---|---|---|---|---|
| 22 | P07284 | 238 | 53677 | 0.2383 | | 4 |

SYSC_YEAST Seryl-tRNA synthetase, cytoplasmic OS = *Saccharomyces cerevisiae* GN = SES1 PE = 1 SV = 2

| | z | Sequence | Incl. | L/(L + H) | Std. Err. | Fraction | Correlation | Intensity | Modifications |
|---|---|---|---|---|---|---|---|---|---|
| 1 | 2 | YIPGEPEFLPFVNELPK | X | 0.8227 | 0.00158 | 0.4653 | 0.9473 | 1.11E+05 | |
| 2 | 3 | NASVEIVDEIISDYKDWVK | X | 0.7951 | 0.00573 | 0.4831 | 0.9887 | 3.44E+05 | |
| 3 | 2 | NASVEIVDEIISDYKDWVK | X | 0.7696 | 0.01392 | 0.1984 | 0.9426 | 6.67E+04 | |
| 4 | 3 | IEQFVITEPEKSWEEFEK | X | 0.114 | 0.1522 | 0.1374 | 0.9075 | 8.56E+05 | |

| Hit | Accession | Score | Mass | L/(L + H) | SD(geo) | # |
|---|---|---|---|---|---|---|
| 23 | P38088 | 234 | 75364 | 0.8224 | 1.006 | 2 |

SYG_YEAST Glycyl-tRNA synthetase 1 OS = *Saccharomyces cerevisiae*
GN = GRS1 PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 2 | IDDSGVSIGK | X | 0.8259 | 0.01171 | 0.1781 | 0.9752 | 4.43E+05 | |
| 2 | 2 | LDDDVVKEYEEILAK | X | 0.8161 | 0.01051 | 0.07847 | 0.9658 | 2.44E+05 | |

| Hit | Accession | Score | Mass | L/(L + H) | SD(geo) | # |
|---|---|---|---|---|---|---|
| 24 | P17709 | 225 | 55342 | 0.1024 | 15.72 | 2 |

HXKG_YEAST Glucokinase-1 OS = *Saccharomyces cerevisiae* GN = GLK1
PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 2 | EGHTLASDK | X | 0.003844 | 0.1695 | 0.7656 | 0.9015 | 6.01E+05 | |
| 2 | 2 | YDVVIDQK | X | 0.836 | 0.0107 | 0.2711 | 0.9649 | 9.39E+05 | |

TABLE 2-continued

Proteins identified by Mascot Distiller from ChAP-MS analysis of GAL1 chromatin isolated from cells grown in galactose.
Mascot Distiller
Quantitation Report

| Hit | Accession | Score | Mass | L/(L + H) | SD(geo) | # |
|---|---|---|---|---|---|---|
| 25 | P10592 | 223 | 69844 | 0.6324 | 1.099 | 3 |

HSP72_YEAST Heat shock protein SSA2 OS = *Saccharomyces cerevisiae* GN = SSA2 PE = 1 SV = 3

| | z | Sequence | Incl. | L/(L + H) | Std. Err. | Fraction | Correlation | Intensity | Modifications |
|---|---|---|---|---|---|---|---|---|---|
| 1 | 2 | MKETAESYLGAK | X | 0.7735 | 0.00986 | 0.2692 | 0.9866 | 2.32E+05 | |
| 2 | 2 | NFNDPEVQGDMK | X | 0.5921 | 0.01773 | 0.3417 | 0.9151 | 3.96E+05 | |
| 3 | 3 | NTISEAGDKLEQADKDAVTK | X | 0.6179 | 0.00324 | 0.3113 | 0.9818 | 8.87E+05 | |

| Hit | Accession | Score | Mass | L/(L + H) | SD(geo) | # |
|---|---|---|---|---|---|---|
| 26 | P34760 | 203 | 21688 | 0.8525 | | 1 |

TSA1_YEAST Peroxiredoxin TSA1 OS = *Saccharomyces cerevisiae* GN = TSA1 PE = 1 SV = 3

| | z | Sequence | Incl. | L/(L + H) | Std. Err. | Fraction | Correlation | Intensity | Modifications |
|---|---|---|---|---|---|---|---|---|---|
| 1 | 2 | TAVVDGVFDEVSLDK | X | 0.8525 | 0.003 | 0.2304 | 0.9765 | 1.37E+06 | |

| Hit | Accession | Score | Mass | L/(L + H) | SD(geo) | # |
|---|---|---|---|---|---|---|
| 27 | P07806 | 202 | 126596 | 0.902 | 1.08 | 2 |

SYV_YEAST Valyl-tRNA synthetase, mitochondrial OS = *Saccharomyces cerevisiae* GN = VAS1 PE = 1 SV = 2

| | z | Sequence | Incl. | L/(L + H) | Std. Err. | Fraction | Correlation | Intensity | Modifications |
|---|---|---|---|---|---|---|---|---|---|
| 1 | 2 | TAEDQKDSIVSLIK | X | 0.8245 | 0.0142 | 0.06813 | 0.9834 | 6.02E+04 | |
| 2 | 2 | TGEVIINPLKEDGSPK | X | 0.9585 | 0.02748 | 0.09926 | 0.894 | 8.93E+04 | |

| Hit | Accession | Score | Mass | L/(L + H) | SD(geo) | # |
|---|---|---|---|---|---|---|
| 28 | P39015 | 200 | 29977 | 0.8734 | 1.037 | 2 |

STM1_YEAST Suppressor protein STM1 OS = *Saccharomyces cerevisiae* GN = STM1 PE = 1 SV = 3

| | z | Sequence | Incl. | L/(L + H) | Std. Err. | Fraction | Correlation | Intensity | Modifications |
|---|---|---|---|---|---|---|---|---|---|
| 1 | 3 | TAQLSLQDYLNQQANNQFNK | X | 0.9037 | 0.0159 | 0.345 | 0.8549 | 1.14E+05 | |
| 2 | 2 | EAQADAAAEIAEDAAEAEDAGKPK | X | 0.8405 | 0.03245 | 0.2666 | 0.956 | 1.01E+05 | |

| Hit | Accession | Score | Mass | L/(L + H) | SD(geo) | # |
|---|---|---|---|---|---|---|
| 29 | P14540 | 196 | 39596 | 0.7378 | 1.02 | 2 |

ALF_YEAST Fructose-bisphosphate aldolase OS = *Saccharomyces cerevisiae* GN = FBA1 PE = 1 SV = 3

| | z | Sequence | Incl. | L/(L + H) | Std. Err. | Fraction | Correlation | Intensity | Modifications |
|---|---|---|---|---|---|---|---|---|---|
| 1 | 2 | GISNEGQNASIK | X | 0.7232 | 0.00563 | 0.2971 | 0.9957 | 2.70E+06 | |
| 2 | 2 | LLPWFDGMLEADEAYFK | X | 0.7527 | 0.00701 | 0.6657 | 0.9971 | 2.69E+06 | |

TABLE 2-continued

Proteins identified by Mascot Distiller from ChAP-MS analysis of GAL1 chromatin isolated from cells grown in galactose.
Mascot Distiller
Quantitation Report

| Hit | Accession | Score | Mass | L/(L + H) | SD(geo) | # |
|---|---|---|---|---|---|---|
| 30 | P07259 | 183 | 245990 | 0.6064 | | 1 |

PYR1_YEAST Protein URA1 OS = *Saccharomyces cerevisiae* GN = URA2
PE = 1 SV = 4

| | z | Sequence | Incl. | L/(L + H) | Std. Err. | Fraction | Correlation | Intensity | Modifications |
|---|---|---|---|---|---|---|---|---|---|
| 1 | 2 | SISGPVITDVASLK | X | 0.6064 | 0.03681 | 0.07372 | 0.792 | 2.43E+05 | |

| Hit | Accession | Score | Mass | L/(L + H) | SD(geo) | # |
|---|---|---|---|---|---|---|
| 31 | P16521 | 177 | 115920 | 0.7059 | 1.311 | 3 |

EF3A_YEAST Elongation factor 3A OS = *Saccharomyces cerevisiae*
GN = YEF3 PE = 1 SV = 3

| | z | Sequence | Incl. | L/(L + H) | Std. Err. | Fraction | Correlation | Intensity | Modifications |
|---|---|---|---|---|---|---|---|---|---|
| 1 | 2 | TQLRLKR | X | 0.9013 | 0.00444 | 0.3845 | 0.99 | 2.38E+06 | |
| 2 | 2 | AYEELSNTDLEFK | X | 0.7997 | 0.02628 | 0.5649 | 0.9771 | 1.97E+06 | |
| 3 | 3 | AYEELSNTDLEFKFPEPGYLEGVK | X | 0.3863 | 0.03175 | 0.257 | 0.8484 | 1.37E+06 | |

| Hit | Accession | Score | Mass | L/(L + H) | SD(geo) | # |
|---|---|---|---|---|---|---|
| 32 | P11412 | 168 | 57830 | 0.5867 | 1.242 | 2 |

G6PD_YEAST Glucose-6-phosphate 1-dehydrogenase
OS = *Saccharomyces cerevisiae* GN = ZWF1 PE = 1 SV = 4

| | z | Sequence | Incl. | L/(L + H) | Std. Err. | Fraction | Correlation | Intensity | Modifications |
|---|---|---|---|---|---|---|---|---|---|
| 1 | 2 | AVAPIDTDDVLLGQYGK | X | 0.5629 | 0.04227 | 0.2849 | 0.9375 | 7.08E+05 | |
| 2 | 3 | SEDGSKPAYVDDDTVDKDSK | X | 0.7949 | 0.00856 | 0.1299 | 0.9748 | 9.45E+04 | |

| Hit | Accession | Score | Mass | L/(L + H) | SD(geo) | # |
|---|---|---|---|---|---|---|
| 33 | P07149 | 160 | 228547 | 0.8094 | | 1 |

FAS1_YEAST Fatty acid synthase subunit beta OS = *Saccharomyces cerevisiae* GN = FAS1 PE = 1 SV = 2

| | z | Sequence | Incl. | L/(L + H) | Std. Err. | Fraction | Correlation | Intensity | Modifications |
|---|---|---|---|---|---|---|---|---|---|
| 1 | 2 | GNYTDFENTFQK | X | 0.8094 | 0.01799 | 0.0845 | 0.9521 | 3.39E+05 | |

| Hit | Accession | Score | Mass | L/(L + H) | SD(geo) | # |
|---|---|---|---|---|---|---|
| 34 | P28240 | 159 | 62369 | 0.3227 | | 1 |

ACEA_YEAST Isocitrate lyase OS = *Saccharomyces cerevisiae* GN = ICL1
PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 2 | LDADAAEIEK | X | 0.3227 | 0.07711 | 0.202 | 0.9617 | 8.83E+05 | |

| Hit | Accession | Score | Mass | L/(L + H) | SD(geo) | # |
|---|---|---|---|---|---|---|
| 35 | P00330 | 155 | 36800 | 0.8664 | 1.009 | 3 |

ADH1_YEAST Alcohol dehydrogenase 1 OS = *Saccharomyces cerevisiae*
GN = ADH1 PE = 1 SV = 4

| | z | Sequence | Incl. | L/(L + H) | Std. Err. | Fraction | Correlation | Intensity | Modifications |
|---|---|---|---|---|---|---|---|---|---|
| 1 | 2 | VVGLSTLPEIYEK | X | 0.8678 | 0.00158 | 0.5758 | 0.9962 | 2.12E+06 | |
| 2 | 2 | VLGIDGGEGKEELFR | X | 0.8513 | 0.00158 | 0.397 | 0.9977 | 2.05E+06 | |

TABLE 2-continued

Proteins identified by Mascot Distiller from ChAP-MS analysis of GAL1 chromatin isolated from cells grown in galactose.
Mascot Distiller
Quantitation Report

| | z | Sequence | Incl. | L/(L + H) | Std. Err. | Fraction | Correlation | Intensity | Modifications |
|---|---|---|---|---|---|---|---|---|---|
| 3 | 3 | VLGIDGGEGKEELFR | X | 0.8778 | 0.00344 | 0.5496 | 0.9935 | 2.51E+06 | |

| Hit | Accession | Score | Mass | L/(L + H) | SD(geo) | # |
|---|---|---|---|---|---|---|
| 36 | P32527 | 155 | 48990 | 0.8655 | | 1 |

ZUO1_YEAST Zuotin OS = *Saccharomyces cerevisiae* GN = ZUO1 PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 3 | ATTIDEQVGLIVDSLNDEELVSTADK | X | 0.8655 | 0.00448 | 0.4525 | 0.9613 | 2.75E+05 | |

| Hit | Accession | Score | Mass | L/(L + H) | SD(geo) | # |
|---|---|---|---|---|---|---|
| 37 | P04806 | 155 | 53705 | 0.8304 | | 1 |

HXKA_YEAST Hexokinase-1 OS = *Saccharomyces cerevisiae* GN = HXK1 PE = 1 SV = 2

| | z | Sequence | Incl. | L/(L + H) | Std. Err. | Fraction | Correlation | Intensity | Modifications |
|---|---|---|---|---|---|---|---|---|---|
| 1 | 2 | LSGNHTFDTTQSK | | 0.1191 | 0.209 | 0.1488 | 0.6634 | 3.26E+05 | |
| 2 | 3 | TKYDVAVDEQSPRPGQQAFEK | X | 0.8304 | 0.01169 | 0.1392 | 0.9589 | 2.37E+04 | |

| Hit | Accession | Score | Mass | L/(L + H) | SD(geo) | # |
|---|---|---|---|---|---|---|
| 38 | P05750 | 153 | 26486 | 0.7359 | | 1 |

RS3_YEAST 40S ribosomal protein S3 OS = *Saccharomyces cerevisiae* GN = RPS3 PE = 1 SV = 5

| | z | Sequence | Incl. | L/(L + H) | Std. Err. | Fraction | Correlation | Intensity | Modifications |
|---|---|---|---|---|---|---|---|---|---|
| 1 | 3 | ALPDAVTIIEPKEEEPILAPSVK | X | 0.7359 | 0.01251 | 0.06703 | 0.9895 | 3.55E+05 | |

| Hit | Accession | Score | Mass | L/(L + H) | SD(geo) | # |
|---|---|---|---|---|---|---|
| 39 | P53252 | 152 | 38486 | 0.8196 | | 1 |

PIL1_YEAST Sphingolipid long chain base-responsive protein PIL1 OS = *Saccharomyces cerevisiae* GN = PIL1 PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 2 | APTASQLQNPPPPPSTTK | X | 0.8196 | 0.01915 | 0.2011 | 0.9301 | 1.74E+05 | |
| 2 | 3 | ALLELLDDSPVTPGETRPAYDGYEASK | | 0.6536 | 0.03193 | 0.2367 | 0.6395 | 5.49E+05 | |

| Hit | Accession | Score | Mass | L/(L + H) | SD(geo) | # |
|---|---|---|---|---|---|---|
| 40 | P00817 | 151 | 32280 | 0.467 | | 4 |

IPYR_YEAST Inorganic pyrophosphatase OS = *Saccharomyces cerevisiae* GN = IPP1 PE = 1 SV = 4

| | z | Sequence | Incl. | L/(L + H) | Std. Err. | Fraction | Correlation | Intensity | Modifications |
|---|---|---|---|---|---|---|---|---|---|
| 1 | 2 | LNDIEDVEK | X | 0.3227 | 0.07711 | 0.202 | 0.9617 | 8.83E+05 | |
| 2 | 3 | LEITKEETLNPIIQDTK | X | 0.736 | 0.01106 | 0.2893 | 0.9314 | 4.97E+05 | |
| 3 | 3 | AVGDNDPIDVLEIGETIAYTGQVK | X | 0.7062 | 0.00365 | 0.6552 | 0.992 | 1.59E+05 | |
| 4 | 2 | AVGDNDPIDVLEIGETIAYTGQVK | X | 0.741 | 0.002 | 0.7827 | 0.9921 | 7.42E+04 | |

TABLE 2-continued

Proteins identified by Mascot Distiller from ChAP-MS analysis of GAL1 chromatin isolated from cells grown in galactose.
Mascot Distiller Quantitation Report

| Hit | Accession | Score | Mass | L/(L + H) | SD(geo) | # |
|---|---|---|---|---|---|---|
| 41 | Q03048 | 144 | 15891 | | | 0 |

COFI_YEAST Cofilin OS = *Saccharomyces cerevisiae* GN = COF1 PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 2 | SGVAVADE SLTAFNDLK | | 0.519 | 0.05769 | 0.1215 | 0.5982 | 3.04E+05 | |

| Hit | Accession | Score | Mass | L/(L + H) | SD(geo) | # |
|---|---|---|---|---|---|---|
| 42 | P32324 | 142 | 93230 | 0.7058 | | 3 |

EF2_YEAST Elongation factor 2 OS = *Saccharomyces cerevisiae* GN = EFT1 PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 3 | WTNKDTD AEGKPLER | X | 0.7908 | 0.00868 | 0.07043 | 0.8558 | 2.83E+05 | |
| 2 | 2 | WTNKDTD AEGKPLER | X | 0.1675 | 0.2545 | 0.2121 | 0.7622 | 2.57E+05 | |
| 3 | 3 | GQVVSEEQ RPGTPLFTVK | X | 0.8025 | 0.001 | 0.5728 | 0.9927 | 2.98E+06 | |

| Hit | Accession | Score | Mass | L/(L + H) | SD(geo) | # |
|---|---|---|---|---|---|---|
| 43 | A6ZP47 | 141 | 65697 | | | 0 |

DED1_YEAS7 ATP-dependent RNA helicase DED1 OS = *Saccharomyces cerevisiae* (strain YJM789) GN = DED1 PE = 3 SV = 1

| | z | Sequence | Incl. | L/(L + H) | Std. Err. | Fraction | Correlation | Intensity | Modifications |
|---|---|---|---|---|---|---|---|---|---|
| 1 | 2 | DVPEPITEF TSPPLDGLL LENIK | | −0.00021 | 5.488 | 0.7663 | 0.08765 | 2.92E+06 | |

| Hit | Accession | Score | Mass | L/(L + H) | SD(geo) | # |
|---|---|---|---|---|---|---|
| 44 | P22515 | 139 | 114195 | 0.756 | | 1 |

UBA1_YEAST Ubiquitin-activating enzyme E1 1 OS = *Saccharomyces cerevisiae* GN = UBA1 PE = 1 SV = 2

| | z | Sequence | Incl. | L/(L + H) | Std. Err. | Fraction | Correlation | Intensity | Modifications |
|---|---|---|---|---|---|---|---|---|---|
| 1 | 2 | SDDSNSKP NVDEYK | X | 0.756 | 0.02454 | 0.07431 | 0.9725 | 4.83E+04 | |
| 2 | 2 | QFMYFDSL ESLPDPK | | 0.000528 | 7.296 | 0.0675 | 0.6501 | 1.43E+06 | |

| Hit | Accession | Score | Mass | L/(L + H) | SD(geo) | # |
|---|---|---|---|---|---|---|
| 45 | P38701 | 137 | 14011 | 0.6173 | | 1 |

RS20_YEAST 40S ribosomal protein S20 OS = *Saccharomyces cerevisiae* GN = RPS20 PE = 1 SV = 3

| | z | Sequence | Incl. | L/(L + H) | Std. Err. | Fraction | Correlation | Intensity | Modifications |
|---|---|---|---|---|---|---|---|---|---|
| 1 | 2 | EKVEEQEQ QQQQIIK | X | 0.6173 | 0.00734 | 0.2134 | 0.9546 | 6.58E+05 | |

| Hit | Accession | Score | Mass | L/(L + H) | SD(geo) | # |
|---|---|---|---|---|---|---|
| 46 | P14742 | 133 | 80357 | | | 0 |

GFA1_YEAST Glucosamine--fructose-6-phosphate aminotransferase [isomerizing] OS = *Saccharomyces cerevisiae* GN = GFA1 PE = 1 SV = 4

| | z | Sequence | Incl. | L/(L + H) | Std. Err. | Fraction | Correlation | Intensity | Modifications |
|---|---|---|---|---|---|---|---|---|---|

TABLE 2-continued

Proteins identified by Mascot Distiller from ChAP-MS analysis of GAL1 chromatin isolated from cells grown in galactose.
Mascot Distiller
Quantitation Report

| Hit | Accession | Score | Mass | L/(L + H) | SD(geo) | # |
|---|---|---|---|---|---|---|
| 47 | P22768 | 133 | 47175 | | | 0 |

ASSY_YEAST Argininosuccinate synthase OS = *Saccharomyces cerevisiae* GN = ARG1 PE = 1 SV = 2 z Sequence   Incl. L/(L + H) Std. Err. Fraction Correlation Intensity Modifications

| Hit | Accession | Score | Mass | L/(L + H) | SD(geo) | # |
|---|---|---|---|---|---|---|
| 48 | P10664 | 131 | 39325 | 0.7018 | 1.054 | 3 |

RL4A_YEAST 60S ribosomal protein L4-A OS = *Saccharomyces cerevisiae* GN = RPL4A PE = 1 SV = 4

| | z | Sequence | Incl. | L/(L + H) | Std. Err. | Fraction | Correlation | Intensity | Modifications |
|---|---|---|---|---|---|---|---|---|---|
| 1 | 3 | IPEIPLVVSTDLESIQK | X | 0.7524 | 0.00693 | 0.3528 | 0.9385 | 3.17E+05 | |
| 2 | 2 | IPEIPLVVSTDLESIQK | X | 0.6885 | 0.00408 | 0.4963 | 0.9979 | 7.46E+05 | |
| 3 | 3 | IINSSEIQSAIRPAGQATQK | X | 0.6478 | 0.00324 | 0.4073 | 0.9947 | 9.65E+04 | |

| Hit | Accession | Score | Mass | L/(L + H) | SD(geo) | # |
|---|---|---|---|---|---|---|
| 49 | P35691 | 128 | 18849 | 0.8547 | | 1 |

TCTP_YEAST Translationally-controlled tumor protein homolog OS = *Saccharomyces cerevisiae* GN = TMA19 PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 2 | DIFSNDELLSDAYDAK | X | 0.8547 | 0.00941 | 0.2439 | 0.9901 | 9.80E+05 | |

| Hit | Accession | Score | Mass | L/(L + H) | SD(geo) | # |
|---|---|---|---|---|---|---|
| 50 | P15303 | 127 | 85331 | | | 0 |

SEC23_YEAST Protein transport protein SEC23 OS = *Saccharomyces cerevisiae* GN = SEC23 PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 2 | FFLPLEQVEFK | | 0.7553 | 0.01157 | 0.2147 | 0.5191 | 1.45E+05 | |
| 2 | 2 | KAGYQDDPQYADFK | | 0.9927 | 0.02465 | 0.1877 | 0.3964 | 5.07E+04 | |

| Hit | Accession | Score | Mass | L/(L + H) | SD(geo) | # |
|---|---|---|---|---|---|---|
| 51 | Q03690 | 124 | 145076 | 0.5813 | | 1 |

TIF31_YEAST Protein TIF31 OS = *Saccharomyces cerevisiae* GN = TIF31 PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 2 | DANTGEEVTEDFVNDINVK | X | 0.5813 | 0.0468 | 0.1058 | 0.8113 | 3.64E+05 | |

| Hit | Accession | Score | Mass | L/(L + H) | SD(geo) | # |
|---|---|---|---|---|---|---|
| 52 | P04807 | 117 | 54189 | 0.7785 | 1.004 | 2 |

HXKB_YEAST Hexokinase-2 OS = *Saccharomyces cerevisiae* GN = HXK2 PE = 1 SV = 4

| | z | Sequence | Incl. | L/(L + H) | Std. Err. | Fraction | Correlation | Intensity | Modifications |
|---|---|---|---|---|---|---|---|---|---|
| 1 | 2 | ELMQQIENFEK | X | 0.7802 | 0.01438 | 0.2465 | 0.9009 | 7.27E+05 | |
| 2 | 3 | GFDIPNIENHDVVPMLQK | X | 0.7742 | 0.01687 | 0.1579 | 0.835 | 2.97E+05 | |

TABLE 2-continued

Proteins identified by Mascot Distiller from ChAP-MS analysis of GAL1 chromatin isolated from cells grown in galactose.
Mascot Distiller
Quantitation Report

| Hit | Accession | Score | Mass | L/(L + H) | SD(geo) | # |
|---|---|---|---|---|---|---|
| 53 | P43545 | 115 | 31998 | 0.06161 | | 1 |

SNZ3_YEAST Probable pyridoxine biosynthesis protein SNZ3
OS = *Saccharomyces cerevisiae* GN = SNZ3 PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 2 | TKGEAGTG DVSEAVK | X | 0.06161 | 0.5232 | 0.2013 | 0.789 | 4.12E+05 | |

| Hit | Accession | Score | Mass | L/(L + H) | SD(geo) | # |
|---|---|---|---|---|---|---|
| 54 | P17536 | 115 | 23527 | 0.3192 | | 1 |

TPM1_YEAST Tropomyosin-1 OS = *Saccharomyces cerevisiae* GN = TPM1 PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 2 | KNQQLEED LEESDTK | X | 0.3192 | 0.1604 | 0.08858 | 0.7363 | 1.43E+04 | |

| Hit | Accession | Score | Mass | L/(L + H) | SD(geo) | # |
|---|---|---|---|---|---|---|
| 55 | P07264 | 112 | 85741 | | | 0 |

LEUC_YEAST 3-isopropylmalate dehydratase OS = *Saccharomyces cerevisiae* GN = LEU1 PE = 1 SV = 3

| | z | Sequence | Incl. | L/(L + H) | Std. Err. | Fraction | Correlation | Intensity | Modifications |
|---|---|---|---|---|---|---|---|---|---|
| 1 | 2 | EFEYKDQD QSSPK | | 0.302 | 0.09083 | 0.02215 | 0.6239 | 1.86E+05 | |
| 2 | 3 | DDQGKDQ ETDFVLNV EPWR | | 0.5589 | 0.01861 | 0.2447 | 0.6753 | 2.83E+06 | |
| 3 | 2 | DDQGKDQ ETDFVLNV EPWR | | 0.8426 | 0.002 | 0.7265 | 0.4088 | 5.60E+05 | |

| Hit | Accession | Score | Mass | L/(L + H) | SD(geo) | # |
|---|---|---|---|---|---|---|
| 56 | P05744 | 110 | 12219 | 0.6213 | | 1 |

RL33A_YEAST 60S ribosomal protein L33-A OS = *Saccharomyces cerevisiae* GN = RPL33A PE = 1 SV = 3

| | z | Sequence | Incl. | L/(L + H) | Std. Err. | Fraction | Correlation | Intensity | Modifications |
|---|---|---|---|---|---|---|---|---|---|
| 1 | 2 | IEGVATPQ DAQFYLGK | X | 0.6213 | 0.0083 | 0.1734 | 0.995 | 1.38E+05 | |

| Hit | Accession | Score | Mass | L/(L + H) | SD(geo) | # |
|---|---|---|---|---|---|---|
| 57 | P36008 | 110 | 46491 | 0.8109 | | 1 |

EF1G2_YEAST Elongation factor 1-gamma 2 OS = *Saccharomyces cerevisiae* GN = TEF4 PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 2 | GQDFAPAF DVAPDWE SYEYTK | X | 0.8109 | 0.01799 | 0.3455 | 0.9756 | 2.24E+05 | |

| Hit | Accession | Score | Mass | L/(L + H) | SD(geo) | # |
|---|---|---|---|---|---|---|
| 58 | P16862 | 108 | 104953 | 0.8294 | 1.029 | 2 |

K6PF2_YEAST 6-phosphofructokinase subunit beta
OS = *Saccharomyces cerevisiae* GN = PFK2 PE = 1 SV = 4

| | z | Sequence | Incl. | L/(L + H) | Std. Err. | Fraction | Correlation | Intensity | Modifications |
|---|---|---|---|---|---|---|---|---|---|
| 1 | 2 | SSPDENST LLSNDSISLK | X | 0.8127 | 0.01294 | 0.187 | 0.9353 | 1.95E+05 | |

TABLE 2-continued

Proteins identified by Mascot Distiller from ChAP-MS analysis of GAL1 chromatin isolated from cells grown in galactose.
Mascot Distiller
Quantitation Report

| | z | Sequence | Incl. | L/(L + H) | Std. Err. | Fraction | Correlation | Intensity | Modifications |
|---|---|---|---|---|---|---|---|---|---|
| 2 | 3 | AAEENFNADDKTISDTAAVVGVK | X | 0.8594 | 0.01841 | 0.2622 | 0.9073 | 1.12E+05 | |

| Hit | Accession | Score | Mass | L/(L + H) | SD(geo) | # |
|---|---|---|---|---|---|---|
| 59 | P11154 | 107 | 130539 | 0.9707 | | 1 |

PYC1_YEAST Pyruvate carboxylase 1 OS = *Saccharomyces cerevisiae* GN = PYC1 PE = 1 SV = 2

| | z | Sequence | Incl. | L/(L + H) | Std. Err. | Fraction | Correlation | Intensity | Modifications |
|---|---|---|---|---|---|---|---|---|---|
| 1 | 2 | SFLSPLETDEEIEVVIEQGK | X | 0.9707 | 0.00158 | 0.4859 | 0.886 | 1.52E+06 | |
| 2 | 3 | EVFVSDGENVDSSDLLVLLEDQVPVETK | | 0.5025 | 0.07115 | 0.1391 | 0.5886 | 1.13E+05 | |

| Hit | Accession | Score | Mass | L/(L + H) | SD(geo) | # |
|---|---|---|---|---|---|---|
| 60 | P52910 | 106 | 75765 | | | 0 |

ACS2_YEAST Acetyl-coenzyme A synthetase 2 OS = *Saccharomyces cerevisiae* GN = ACS2 PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 2 | TGTEGIPMK | | 0.6962 | 0.01855 | 0.4457 | 0.1173 | 7.72E+06 | |

| Hit | Accession | Score | Mass | L/(L + H) | SD(geo) | # |
|---|---|---|---|---|---|---|
| 61 | P35844 | 106 | 49461 | 0.7224 | | 1 |

KES1_YEAST Protein KES1 OS = *Saccharomyces cerevisiae* GN = KES1 PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 2 | NAPSGTLVGDKEDR | X | 0.7224 | 0.06623 | 0.06821 | 0.8339 | 1.10E+05 | |
| 2 | 3 | DFDYSVTPEEGALVPEKDDTFLK | | 0.6484 | 0.09516 | 0.283 | 0.6012 | 1.42E+05 | |

| Hit | Accession | Score | Mass | L/(L + H) | SD(geo) | # |
|---|---|---|---|---|---|---|
| 62 | P36010 | 105 | 17268 | | | 0 |

NDK_YEAST Nucleoside diphosphate kinase OS = *Saccharomyces cerevisiae* GN = YNK1 PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 2 | TFIAVKPDGVQR | | 0.03719 | 0.7149 | 0.1927 | 0.2162 | 1.95E+05 | |

| Hit | Accession | Score | Mass | L/(L + H) | SD(geo) | # |
|---|---|---|---|---|---|---|
| 63 | P04802 | 104 | 63861 | 0.8286 | | 1 |

SYDC_YEAST Aspartyl-tRNA synthetase, cytoplasmic OS = *Saccharomyces cerevisiae* GN = DPS1 PE = 1 SV = 3

| | z | Sequence | Incl. | L/(L + H) | Std. Err. | Fraction | Correlation | Intensity | Modifications |
|---|---|---|---|---|---|---|---|---|---|
| 1 | 2 | EIGDFEDLSTENEK | X | 0.8286 | 0.00835 | 0.2225 | 0.9736 | 4.26E+05 | |

TABLE 2-continued

Proteins identified by Mascot Distiller from ChAP-MS analysis of GAL1 chromatin isolated from cells grown in galactose.
Mascot Distiller
Quantitation Report

| Hit | Accession | Score | Mass | L/(L + H) | SD(geo) | # |
|---|---|---|---|---|---|---|
| 64 | P12709 | 104 | 61582 | 0.7709 | 1.002 | 2 |

G6PI_YEAST Glucose-6-phosphate isomerase OS = *Saccharomyces cerevisiae* GN = PGI1 PE = 1 SV = 3

| | z | Sequence | Incl. | L/(L + H) | Std. Err. | Fraction | Correlation | Intensity | Modifications |
|---|---|---|---|---|---|---|---|---|---|
| 1 | 3 | ANKPMYVDGVNVAPEVDSVLK | X | 0.7705 | 0.01145 | 0.2097 | 0.7988 | 5.44E+05 | |
| 2 | 2 | ANKPMYVDGVNVAPEVDSVLK | X | 0.7726 | 0.02338 | 0.1041 | 0.9243 | 1.51E+05 | |

| Hit | Accession | Score | Mass | L/(L + H) | SD(geo) | # |
|---|---|---|---|---|---|---|
| 65 | P15019 | 104 | 37302 | 0.8418 | 1.446 | 2 |

TAL1_YEAST Transaldolase OS = *Saccharomyces cerevisiae* GN = TAL1 PE = 1 SV = 4

| | z | Sequence | Incl. | L/(L + H) | Std. Err. | Fraction | Correlation | Intensity | Modifications |
|---|---|---|---|---|---|---|---|---|---|
| 1 | 2 | DYKGEADPGVISVK | X | 0.9932 | 0.01166 | 0.08304 | 0.9874 | 3.01E+05 | |
| 2 | 2 | NLAGVDYLTISPALLDK | X | 0.5131 | 0.1041 | 0.121 | 0.9331 | 6.69E+04 | |

| Hit | Accession | Score | Mass | L/(L + H) | SD(geo) | # |
|---|---|---|---|---|---|---|
| 66 | P14120 | 103 | 11504 | 0.6528 | | 1 |

RL30_YEAST 60S ribosomal protein L30 OS = *Saccharomyces cerevisiae* GN = RPL30 PE = 1 SV = 3

| | z | Sequence | Incl. | L/(L + H) | Std. Err. | Fraction | Correlation | Intensity | Modifications |
|---|---|---|---|---|---|---|---|---|---|
| 1 | 2 | VYYFQGGNNELGTAVGK | X | 0.6528 | 0.01167 | 0.1559 | 0.9767 | 1.26E+05 | |

| Hit | Accession | Score | Mass | L/(L + H) | SD(geo) | # |
|---|---|---|---|---|---|---|
| 67 | P22943 | 102 | 11806 | | | 0 |

HSP12_YEAST 12 kDa heat shock protein OS = *Saccharomyces cerevisiae* GN = HSP12 PE = 1 SV = 1

| | z | Sequence | Incl. | L/(L + H) | Std. Err. | Fraction | Correlation | Intensity | Modifications |
|---|---|---|---|---|---|---|---|---|---|

| Hit | Accession | Score | Mass | L/(L + H) | SD(geo) | # |
|---|---|---|---|---|---|---|
| 68 | P0C217 | 101 | 199542 | 0.8624 | 1.013 | 2 |

YL14B_YEAST Transposon Ty1-LR4 Gag-Pol polyprotein OS = *Saccharomyces cerevisiae* GN = TY1B-LR4 PE = 3 SV = 1

| | z | Sequence | Incl. | L/(L + H) | Std. Err. | Fraction | Correlation | Intensity | Modifications |
|---|---|---|---|---|---|---|---|---|---|
| 1 | 2 | DILSVDYTDIMK | X | 0.8498 | 0.02246 | 0.04882 | 0.8124 | 1.27E+05 | |
| 2 | 2 | EVHTNQDPLDVSASK | X | 0.8722 | 0.01118 | 0.2043 | 0.9837 | 1.65E+05 | |

| Hit | Accession | Score | Mass | L/(L + H) | SD(geo) | # |
|---|---|---|---|---|---|---|
| 69 | P0C215 | 101 | 198422 | 0.8624 | 1.013 | 2 |

YL12B_YEAST Transposon Ty1-LR2 Gag-Pol polyprotein OS = *Saccharomyces cerevisiae* GN = TY1B-LR2 PE = 3 SV = 1

| | z | Sequence | Incl. | L/(L + H) | Std. Err. | Fraction | Correlation | Intensity | Modifications |
|---|---|---|---|---|---|---|---|---|---|
| 1 | 2 | DILSVDYTDIMK | X | 0.8498 | 0.02246 | 0.04882 | 0.8124 | 1.27E+05 | |
| 2 | 2 | EVHTNQDPLDVSASK | X | 0.8722 | 0.01118 | 0.2043 | 0.9837 | 1.65E+05 | |

TABLE 2-continued

Proteins identified by Mascot Distiller from ChAP-MS analysis of GAL1 chromatin isolated from cells grown in galactose.
Mascot Distiller
Quantitation Report

| Hit | Accession | Score | Mass | L(L + H) | SD(geo) | # |
|---|---|---|---|---|---|---|
| 70 | P32598 | 101 | 35884 | 0.8363 | | 1 |

PP12_YEAST Serine/threonine-protein phosphatase PP1-2 OS = *Saccharomyces cerevisiae* GN = GLC7 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 GSKPGQQVDLEENEIR | X | 0.8363 | 0.01279 | 0.1472 | 0.9874 | 4.79E+04 | |

| Hit | Accession | Score | Mass | L/(L + H) | SD(geo) | # |
|---|---|---|---|---|---|---|
| 71 | P25087 | 99 | 43403 | 0.8036 | | 1 |

ERG6_YEAST Sterol 24-C-methyltransferase OS = *Saccharomyces cerevisiae* GN = ERG6 PE = 1 SV = 4

| z | Sequence | Incl. | L/(L + H) | Std. Err. | Fraction | Correlation | Intensity | Modifications |
|---|---|---|---|---|---|---|---|---|
| 1 | 2 KPENAETPSQTSQEATQ | X | 0.8036 | 0.04785 | 0.08929 | 0.8981 | 4.04E+04 | |

| Hit | Accession | Score | Mass | L/(L + H) | SD(geo) | # |
|---|---|---|---|---|---|---|
| 72 | P08524 | 98 | 40458 | | | 0 |

FPPS_YEAST Farnesyl pyrophosphate synthase OS = *Saccharomyces cerevisiae* GN = FPP1 PE = 1 SV = 2

| z | Sequence | Incl. | L/(L + H) | Std. Err. | Fraction | Correlation | Intensity | Modifications |
|---|---|---|---|---|---|---|---|---|
| 1 | 2 IEQLYHEYEESIAK | | 0.3329 | 0.09842 | 0.4172 | 0.2092 | 1.03E+06 | |

| Hit | Accession | Score | Mass | L/(L + H) | SD(geo) | # |
|---|---|---|---|---|---|---|
| 73 | P15705 | 97 | 66224 | | | 0 |

STI1_YEAST Heat shock protein STI1 OS = *Saccharomyces cerevisiae* GN = STI1 PE = 1 SV = 1

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 74 | P25694 | 97 | 92331 | 0.8407 | | 1 |

CDC48_YEAST Cell division control protein 48 OS = *Saccharomyces cerevisiae* GN = CDC48 PE = 1 SV = 3

| z | Sequence | Incl. | L/(L + H) | Std. Err. | Fraction | Correlation | Intensity | Modifications |
|---|---|---|---|---|---|---|---|---|
| 1 | 2 NAPAIIFIDEIDSIAPK | X | 0.8407 | 0.0034 | 0.1098 | 0.9968 | 8.16E+04 | |

| Hit | Accession | Score | Mass | L/(L + H) | SD(geo) | # |
|---|---|---|---|---|---|---|
| 75 | P00942 | 96 | 26947 | 0.9321 | | 1 |

TPIS_YEAST Triosephosphate isomerase OS = *Saccharomyces cerevisiae* GN = TPI1 PE = 1 SV = 2

| z | Sequence | Incl. | L/(L + H) | Std. Err. | Fraction | Correlation | Intensity | Modifications |
|---|---|---|---|---|---|---|---|---|
| 1 | 2 ASGAFTGENSVDQIK | X | 0.9321 | 0.00579 | 0.6559 | 0.9989 | 1.71E+06 | |

| Hit | Accession | Score | Mass | L/(L + H) | SD(geo) | # |
|---|---|---|---|---|---|---|
| 76 | P02400 | 95 | 11099 | | | 0 |

RLA4_YEAST 60S acidic ribosomal protein P2-beta OS = *Saccharomyces cerevisiae* GN = RPP2B PE = 1 SV = 2

| z | Sequence | Incl. | L/(L + H) | Std. Err. | Fraction | Correlation | Intensity | Modifications |
|---|---|---|---|---|---|---|---|---|

TABLE 2-continued

Proteins identified by Mascot Distiller from ChAP-MS analysis of GAL1 chromatin isolated from cells grown in galactose.
Mascot Distiller
Quantitation Report

| Hit | Accession | Score | Mass | L/(L + H) | SD(geo) | # |
|---|---|---|---|---|---|---|
| 77 | P40069 | 94 | 122525 | | | 0 |

IMB4_YEAST Importin subunit beta-4 OS = *Saccharomyces cerevisiae*
GN = KAP123 PE = 1 SV = 1
   z Sequence  Incl. L/(L + H) Std. Err. Fraction Correlation Intensity Modifications

| Hit | Accession | Score | Mass | L/(L + H) | SD(geo) | # |
|---|---|---|---|---|---|---|
| 78 | P32481 | 93 | 57829 | 0.8691 | 1.017 | 2 |

IF2G_YEAST Eukaryotic translation initiation factor 2 subunit gamma
OS = *Saccharomyces cerevisiae* GN = GCD11 PE = 1 SV = 1
   z Sequence  Incl. L/(L + H) Std. Err. Fraction Correlation Intensity Modifications

| | z | Sequence | Incl. | L/(L + H) | Std. Err. | Fraction | Correlation | Intensity | Modifications |
|---|---|---|---|---|---|---|---|---|---|
| 1 | 3 | LGDEIEIRPGIVTK | | 0.9246 | 0.04186 | 0.2121 | 0.3448 | 9.63E+04 | |
| 2 | 3 | VAFTGLEEDGETEEEKR | X | 0.888 | 0.00751 | 0.1402 | 0.8705 | 2.90E+05 | |
| 3 | 2 | EFEEGGGLPEQPLNPDFSK | X | 0.8595 | 0.00652 | 0.4126 | 0.9885 | 5.61E+05 | |

| Hit | Accession | Score | Mass | L/(L + H) | SD(geo) | # |
|---|---|---|---|---|---|---|
| 79 | Q12230 | 92 | 38048 | 0.8619 | | 1 |

LSP1_YEAST Sphingolipid long chain base-responsive protein LSP1
OS = *Saccharomyces cerevisiae* GN = LSP1 PE = 1 SV = 1
   z Sequence  Incl. L/(L + H) Std. Err. Fraction Correlation Intensity Modifications

| | z | Sequence | Incl. | L/(L + H) | Std. Err. | Fraction | Correlation | Intensity | Modifications |
|---|---|---|---|---|---|---|---|---|---|
| 1 | 2 | APTAAELQAPPPPPSSTK | X | 0.8619 | 0.03102 | 0.1585 | 0.8149 | 4.28E+04 | |

| Hit | Accession | Score | Mass | L/(L + H) | SD(geo) | # |
|---|---|---|---|---|---|---|
| 80 | P0C0W9 | 90 | 19707 | | | 0 |

RL11A_YEAST 60S ribosomal protein L11-A OS = *Saccharomyces cerevisiae* GN = RPL11A PE = 1 SV = 2
   z Sequence  Incl. L/(L + H) Std. Err. Fraction Correlation Intensity Modifications

| | z | Sequence | Incl. | L/(L + H) | Std. Err. | Fraction | Correlation | Intensity | Modifications |
|---|---|---|---|---|---|---|---|---|---|
| 1 | 2 | VLEQLSGQTPVQSK | | 0.007131 | 0.04219 | 0.7402 | 0.3062 | 5.33E+06 | |

| Hit | Accession | Score | Mass | L/(L + H) | SD(geo) | # |
|---|---|---|---|---|---|---|
| 81 | P38788 | 86 | 58515 | | | 0 |

SSZ1_YEAST Ribosome-associated complex subunit SSZ1
OS = *Saccharomyces cerevisiae* GN = SSZ1 PE = 1 SV = 2
   z Sequence  Incl. L/(L + H) Std. Err. Fraction Correlation Intensity Modifications

| Hit | Accession | Score | Mass | L/(L + H) | SD(geo) | # |
|---|---|---|---|---|---|---|
| 82 | P41811 | 85 | 99383 | | | 0 |

COPB2_YEAST Coatomer subunit beta' OS = *Saccharomyces cerevisiae*
GN = SEC27 PE = 1 SV = 1
   z Sequence  Incl. L/(L + H) Std. Err. Fraction Correlation Intensity Modifications

| | z | Sequence | Incl. | L/(L + H) | Std. Err. | Fraction | Correlation | Intensity | Modifications |
|---|---|---|---|---|---|---|---|---|---|
| 1 | 2 | GEIEEAIENVLPNVEGK | | 0.473 | 0.09943 | 0.113 | 0.5911 | 1.71E+05 | |

TABLE 2-continued

Proteins identified by Mascot Distiller from ChAP-MS analysis of GAL1 chromatin isolated from cells grown in galactose.

Mascot Distiller Quantitation Report

| Hit | Accession | Score | Mass | L/(L + H) | SD(geo) | # |
|---|---|---|---|---|---|---|
| 83 | P38707 | 85 | 62168 | | | 0 |

SYNC_YEAST Asparaginyl-tRNA synthetase, cytoplasmic OS = *Saccharomyces cerevisiae* GN = DED81 PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 2 | SVQYVLEDPIAGPLVK | | 0.5764 | 0.02059 | 0.2109 | 0.4796 | 4.80E+05 | |

| Hit | Accession | Score | Mass | L/(L + H) | SD(geo) | # |
|---|---|---|---|---|---|---|
| 84 | P00899 | 85 | 56732 | | | 0 |

TRPE_YEAST Anthranilate synthase component 1 OS = *Saccharomyces cerevisiae* GN = TRP2 PE = 1 SV = 4

| | z | Sequence | Incl. | L/(L + H) | Std. Err. | Fraction | Correlation | Intensity | Modifications |
|---|---|---|---|---|---|---|---|---|---|
| 1 | 2 | ESFLLESAK | | 0.9519 | 0.00995 | 0.2493 | 0.2379 | 2.91E+05 | |

| Hit | Accession | Score | Mass | L/(L + H) | SD(geo) | # |
|---|---|---|---|---|---|---|
| 85 | P0C2H6 | 83 | 15522 | 0.6874 | | 1 |

RL27A_YEAST 60S ribosomal protein L27-A OS = *Saccharomyces cerevisiae* GN = RPL27A PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 2 | NQWFFSK | | 0.618 | 0.04071 | 0.1012 | 0.5142 | 1.00E+05 | |
| 2 | 2 | YTLDVEAFK | X | 0.6874 | 0.04111 | 0.01567 | 0.7996 | 2.90E+05 | |

| Hit | Accession | Score | Mass | L/(L + H) | SD(geo) | # |
|---|---|---|---|---|---|---|
| 86 | P26321 | 83 | 33890 | | | 0 |

RL5_YEAST 60S ribosomal protein L5 OS = *Saccharomyces cerevisiae* GN = RPL5 PE = 1 SV = 3

| | z | Sequence | Incl. | L/(L + H) | Std. Err. | Fraction | Correlation | Intensity | Modifications |
|---|---|---|---|---|---|---|---|---|---|

| Hit | Accession | Score | Mass | L/(L + H) | SD(geo) | # |
|---|---|---|---|---|---|---|
| 87 | P38115 | 83 | 38859 | 0.118 | | 1 |

ARA1_YEAST D-arabinose dehydrogenase [NAD(P)+] heavy chain OS = *Saccharomyces cerevisiae* GN = ARA1 PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 2 | TMYAADGDYLETYK | X | 0.118 | 0.1798 | 0.2653 | 0.8455 | 1.50E+05 | |

| Hit | Accession | Score | Mass | L/(L + H) | SD(geo) | # |
|---|---|---|---|---|---|---|
| 88 | P32599 | 82 | 72057 | | | 0 |

FIMB_YEAST Fimbrin OS = *Saccharomyces cerevisiae* GN = SAC6 PE = 1 SV = 1

| | z | Sequence | Incl. | L/(L + H) | Std. Err. | Fraction | Correlation | Intensity | Modifications |
|---|---|---|---|---|---|---|---|---|---|

| Hit | Accession | Score | Mass | L/(L + H) | SD(geo) | # |
|---|---|---|---|---|---|---|
| 89 | A6ZXP4 | 81 | 50248 | 0.3547 | | 1 |

SUB2_YEAS7 ATP-dependent RNA helicase SUB2 OS = *Saccharomyces cerevisiae* (strain YJM789) GN = SUB2 PE = 3 SV = 1

| | z | Sequence | Incl. | L/(L + H) | Std. Err. | Fraction | Correlation | Intensity | Modifications |
|---|---|---|---|---|---|---|---|---|---|
| 1 | 2 | FLQNPLEIFVDDEAK | X | 0.3547 | 0.08683 | 0.2049 | 0.8314 | 2.82E+04 | |

TABLE 2-continued

Proteins identified by Mascot Distiller from ChAP-MS analysis of GAL1 chromatin isolated from cells grown in galactose.

Mascot Distiller Quantitation Report

| Hit | Accession | Score | Mass | L/(L + H) | SD(geo) | # |
|---|---|---|---|---|---|---|
| 90 | P28273 | 80 | 140340 | | | 0 |

YKV5_YEAST Uncharacterized protein YKL215C OS = Saccharomyces cerevisiae GN = YKL215C PE = 1 SV = 2
    z Sequence  Incl.  L/(L + H)  Std. Err.  Fraction Correlation Intensity Modifications

| Hit | Accession | Score | Mass | L/(L + H) | SD(geo) | # |
|---|---|---|---|---|---|---|
| 91 | P15625 | 80 | 57804 | 0.7091 | | 1 |

SYFA_YEAST Phenylalanyl-tRNA synthetase alpha chain OS = accharomyces cerevisiae
GN = FRS2
PE = 1 SV = 3

| z | Sequence | Incl. | L/(L + H) | Std. Err. | Fraction | Correlation | Intensity | Modifications |
|---|---|---|---|---|---|---|---|---|
| 1 | 3 DLQDTFYIKDPLTADLPDDK | X | 0.7091 | 0.04609 | 0.1531 | 0.7641 | 1.01E+05 | |

| Hit | Accession | Score | Mass | L/(L + H) | SD(geo) | # |
|---|---|---|---|---|---|---|
| 92 | P38934 | 80 | 54606 | 0.2713 | | 1 |

BFR1_YEAST Nuclear segregation protein BFR1 OS = Saccharomyces cerevisiae GN = BFR1 PE = 1 SV = 1

| z | Sequence | Incl. | L/(L + H) | Std. Err. | Fraction | Correlation | Intensity | Modifications |
|---|---|---|---|---|---|---|---|---|
| 1 | 3 INEIEESIASGDLSLVQEK | X | 0.2713 | 0.04844 | 0.1734 | 0.8316 | 7.51E+05 | |

| Hit | Accession | Score | Mass | L/(L + H) | SD(geo) | # |
|---|---|---|---|---|---|---|
| 93 | P05317 | 78 | 33866 | 0.9997 | | 1 |

RLA0_YEAST 60S acidic ribosomal protein P0 OS = Saccharomyces cerevisiae GN = RPP0 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 GTIEIVSDVK | X | 0.9997 | 0 | 0.5768 | 0.9991 | 4.62E+06 | |

| Hit | Accession | Score | Mass | L/(L + H) | SD(geo) | # |
|---|---|---|---|---|---|---|
| 94 | P07257 | 78 | 40702 | | | 0 |

QCR2_YEAST Cytochrome b-c1 complex subunit 2, mitochondrial OS = Saccharomyces cerevisiae GN = QCR2 PE = 1 SV = 1
    z Sequence  Incl.  L/(L + H)  Std. Err.  Fraction Correlation Intensity Modifications

| Hit | Accession | Score | Mass | L/(L + H) | SD(geo) | # |
|---|---|---|---|---|---|---|
| 95 | P46367 | 77 | 56688 | 0.916 | | 1 |

ALDH4_YEAST Potassium-activated aldehyde dehydrogenase, mitochondrial OS = Saccharomyces cerevisiae GN = ALD4 PE = 1 SV = 2

| z | Sequence | Incl. | L/(L + H) | Std. Err. | Fraction | Correlation | Intensity | Modifications |
|---|---|---|---|---|---|---|---|---|
| 1 | 2 IAPALVTGNTVVLK | X | 0.916 | 0.00158 | 0.04226 | 0.9968 | 5.28E+04 | |

| Hit | Accession | Score | Mass | L/(L + H) | SD(geo) | # |
|---|---|---|---|---|---|---|
| 96 | P16140 | 77 | 57713 | 0.5186 | | 1 |

VATB_YEAST V-type proton ATPase subunit B OS = Saccharomyces cerevisiae GN = VMA2 PE = 1 SV = 2

| z | Sequence | Incl. | L/(L + H) | Std. Err. | Fraction | Correlation | Intensity | Modifications |
|---|---|---|---|---|---|---|---|---|
| 1 | 2 AIVQVFEGTSGIDVK | X | 0.5186 | 0.06922 | 0.03856 | 0.8934 | 1.27E+04 | |

TABLE 2-continued

Proteins identified by Mascot Distiller from ChAP-MS analysis of GAL1 chromatin isolated from cells grown in galactose.
Mascot Distiller
Quantitation Report

| Hit | Accession | Score | Mass | L/(L + H) | SD(geo) | # |
|---|---|---|---|---|---|---|
| 97 | P39708 | 74 | 49596 | 0.9962 | | 1 |

DHE5_YEAST NADP-specific glutamate dehydrogenase 2
OS = *Saccharomyces cerevisiae* GN = GDH3 PE = 1 SV = 1

| z | Sequence | Incl. | L/(L + H) | Std. Err. | Fraction | Correlation | Intensity | Modifications |
|---|---|---|---|---|---|---|---|---|
| 1 | 3 HIGKDTDVPAGDIGVGGR | X | 0.9962 | 0.0039 | 0.09871 | 0.9621 | 8.21E+05 | |

| Hit | Accession | Score | Mass | L/(L + H) | SD(geo) | # |
|---|---|---|---|---|---|---|
| 98 | P15992 | 74 | 23865 | | | 0 |

HSP26_YEAST Heat shock protein 26 OS = *Saccharomyces cerevisiae* GN = HSP26 PE = 1 SV = 3

| z | Sequence | Incl. | L/(L + H) | Std. Err. | Fraction | Correlation | Intensity | Modifications |
|---|---|---|---|---|---|---|---|---|
| 1 | 2 VITLPDYPGVDADNIK | | 0.1164 | 0.2258 | 0.295 | 0.3292 | 2.05E+05 | |

| Hit | Accession | Score | Mass | L/(L + H) | SD(geo) | # |
|---|---|---|---|---|---|---|
| 99 | B3LP78 | 73 | 55768 | | | 0 |

BLH1_YEAS1 Cysteine proteinase 1, mitochondrial
OS = *Saccharomyces cerevisiae* (strain RM11-1a) GN = LAP3 PE = 3 SV = 2

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 100 | P32327 | 73 | 130638 | 0.6239 | 3.892 | 2 |

PYC2_YEAST Pyruvate carboxylase 2 OS = *Saccharomyces cerevisiae* GN = PYC2 PE = 1 SV = 2

| z | Sequence | Incl. | L/(L + H) | Std. Err. | Fraction | Correlation | Intensity | Modifications |
|---|---|---|---|---|---|---|---|---|
| 1 | 2 NFLAPAEPDEEIEVTIEQGK | X | 0.894 | 0.01442 | 0.2074 | 0.9142 | 9.25E+05 | |
| 2 | 3 DGESVDASDLLVVLEEETLPPSQK | X | 0.09446 | 0.1607 | 0.3531 | 0.8345 | 1.76E+05 | |

| Hit | Accession | Score | Mass | L/(L + H) | SD(geo) | # |
|---|---|---|---|---|---|---|
| 101 | P37291 | 73 | 52186 | | | 0 |

GLYC_YEAST Serine hydroxymethyltransferase, cytosolic
OS = *Saccharomyces cerevisiae* GN = SHM2 PE = 1 SV = 2

| z | Sequence | Incl. | L/(L + H) | Std. Err. | Fraction | Correlation | Intensity | Modifications |
|---|---|---|---|---|---|---|---|---|
| 1 | 3 LITSHLVDTDPEVDSIIKDEIER | | 0.6945 | 0.07766 | 0.1892 | 0.388 | 1.35E+05 | |

| Hit | Accession | Score | Mass | L/(L + H) | SD(geo) | # |
|---|---|---|---|---|---|---|
| 102 | P60010 | 73 | 41663 | 0.8046 | | 1 |

ACT_YEAST Actin OS = *Saccharomyces cerevisiae* GN = ACT1 PE = 1 SV = 1

| z | Sequence | Incl. | L/(L + H) | Std. Err. | Fraction | Correlation | Intensity | Modifications |
|---|---|---|---|---|---|---|---|---|
| 1 | 3 QEYDESGPSIVHHK | | 0.674 | 0.07934 | 0.1333 | 0.5876 | 6.38E+04 | |
| 2 | 2 QEYDESGPSIVHHK | X | 0.8046 | 0.02603 | 0.1087 | 0.8907 | 1.96E+05 | |

TABLE 2-continued

Proteins identified by Mascot Distiller from ChAP-MS analysis of GAL1 chromatin isolated from cells grown in galactose.
Mascot Distiller
Quantitation Report

| Hit | Accession | Score | Mass | L/(L + H) | SD(geo) | # |
|---|---|---|---|---|---|---|
| 103 | P32582 | 72 | 56396 | | | 0 |

CBS_YEAST Cystathionine beta-synthase OS = *Saccharomyces cerevisiae* GN = CYS4 PE = 1 SV = 1
　z Sequence　Incl.　L/(L + H)　Std. Err.　Fraction Correlation　Intensity　Modifications

| Hit | Accession | Score | Mass | L/(L + H) | SD(geo) | # |
|---|---|---|---|---|---|---|
| 104 | P01095 | 71 | 8585 | | | 0 |

IPB2_YEAST Protease B inhibitors 2 and 1 OS = *Saccharomyces cerevisiae* GN = PBI2 PE = 1 SV = 3
　z Sequence　Incl.　L/(L + H)　Std. Err.　Fraction Correlation　Intensity　Modifications

| 1 | 3 HNDVIENV EEDKEVHTN | | 0.7575 | 0.01705 | 0.129 | 0.6437 | 5.58E+05 | |

| Hit | Accession | Score | Mass | L/(L + H) | SD(geo) | # |
|---|---|---|---|---|---|---|
| 105 | Q00955 | 71 | 250197 | 0.8507 | | 1 |

ACAC_YEAST Acetyl-CoA carboxylase OS = *Saccharomyces cerevisiae* GN = FAS3 PE = 1 SV = 2
　z Sequence　Incl.　L/(L + H)　Std. Err.　Fraction Correlation　Intensity　Modifications

| 1 | 2 QLSDGGLL IAIGGK | X | 0.8507 | 0.01702 | 0.06509 | 0.973 | 1.45E+05 | |

| Hit | Accession | Score | Mass | L/(L + H) | SD(geo) | # |
|---|---|---|---|---|---|---|
| 106 | P22203 | 70 | 26455 | | | 0 |

VATE_YEAST V-type proton ATPase subunit E OS = *Saccharomyces cerevisiae* GN = VMA4 PE = 1 SV = 4
　z Sequence　Incl.　L/(L + H)　Std. Err.　Fraction Correlation　Intensity　Modifications

| 1 | 2 EQSLDGIF EETK | | 0.3294 | 0.1126 | 0.06772 | 0.6913 | 3.41E+04 | |

| Hit | Accession | Score | Mass | L/(L + H) | SD(geo) | # |
|---|---|---|---|---|---|---|
| 107 | P38249 | 70 | 110276 | 0.9265 | | 1 |

EIF3A_YEAST Eukaryotic translation initiation factor 3 subunit A OS = *Saccharomyces cerevisiae* GN = TIF32 PE = 1 SV = 1
　z Sequence　Incl.　L/(L + H)　Std. Err.　Fraction Correlation　Intensity　Modifications

| 1 | 2 TAGGSSPA TPATPATPA TPTPSSGPK | X | 0.9265 | 0.00916 | 0.2441 | 0.9925 | 7.88E+04 | |

| Hit | Accession | Score | Mass | L/(L + H) | SD(geo) | # |
|---|---|---|---|---|---|---|
| 108 | P09435 | 69 | 70504 | | | 0 |

HSP73_YEAST Heat shock protein SSA3 OS = *Saccharomyces cerevisiae* GN = SSA3 PE = 1 SV = 3
　z Sequence　Incl.　L/(L + H)　Std. Err.　Fraction Correlation　Intensity　Modifications

| Hit | Accession | Score | Mass | L/(L + H) | SD(geo) | # |
|---|---|---|---|---|---|---|
| 109 | P32588 | 69 | 50758 | | | 0 |

PUB1_YEAST Nuclear and cytoplasmic polyadenylated RNA-binding protein PUB1 OS = *Saccharomyces cerevisiae* GN = PUB1 PE = 1 SV = 3
　z Sequence　Incl.　L/(L + H)　Std. Err.　Fraction Correlation　Intensity　Modifications

| 1 | 2 QYFQVGGP IANIK | | 0.9947 | 0.002 | 0.3581 | 0.3382 | 2.32E+05 | |

TABLE 2-continued

Proteins identified by Mascot Distiller from ChAP-MS analysis of GAL1 chromatin isolated from cells grown in galactose.
Mascot Distiller
Quantitation Report

| Hit | Accession | Score | Mass | L/(L + H) | SD(geo) | # |
|---|---|---|---|---|---|---|
| 110 | P53900 | 68 | 15171 | 0.05129 | | 1 |

PFD4_YEAST Prefoldin subunit 4 OS = *Saccharomyces cerevisiae* GN = GIM3 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 NNTQVTFE DQQK | X | 0.05129 | 0.3627 | 0.09004 | 0.7859 | 1.49E+05 | |

| Hit | Accession | Score | Mass | L/(L + H) | SD(geo) | # |
|---|---|---|---|---|---|---|
| 111 | P40825 | 68 | 107940 | | | 0 |

SYAC_YEAST Alanyl-tRNA synthetase cytoplasmic OS = *Saccharomyces cerevisiae* GN = ALA1 PE = 1 SV = 2

| z | Sequence | Incl. | L/(L + H) | Std. Err. | Fraction | Correlation | Intensity | Modifications |
|---|---|---|---|---|---|---|---|---|
| 1 | 2 TFFETNEN APYLVK | | 0.9828 | 0.00532 | 0.346 | 0.5419 | 8.94E+04 | |

| Hit | Accession | Score | Mass | L/(L + H) | SD(geo) | # |
|---|---|---|---|---|---|---|
| 112 | P38631 | 68 | 214712 | | | 0 |

FKS1_YEAST 1,3-beta-glucan synthase component FKS1 OS = *Saccharomyces cerevisiae* GN = FKS1 PE = 1 SV = 2

| z | Sequence | Incl. | L/(L + H) | Std. Err. | Fraction | Correlation | Intensity | Modifications |
|---|---|---|---|---|---|---|---|---|
| 1 | 3 ILAEETAAY EGNENEAE KEDALK | | 0.01026 | 1.465 | 0.2542 | 0.6992 | 1.23E+05 | |

| Hit | Accession | Score | Mass | L/(L + H) | SD(geo) | # |
|---|---|---|---|---|---|---|
| 113 | P47079 | 67 | 61952 | | | 0 |

TCPQ_YEAST T-complex protein 1 subunit theta OS = *Saccharomyces cerevisiae* GN = CCT8 PE = 1 SV = 1

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 114 | P38205 | 66 | 78319 | | | 0 |

NCL1_YEAST tRNA (cytosine-5-)-methyltransferase NCL1 OS = *Saccharomyces cerevisiae* GN = NCL1 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 LSSETPALE SEGPQTK | | 0.5913 | 0.04967 | 0.1079 | 0.3943 | 3.39E+05 | |

| Hit | Accession | Score | Mass | L/(L + H) | SD(geo) | # |
|---|---|---|---|---|---|---|
| 115 | P39939 | 65 | 13438 | | | 0 |

RS26B_YEAST 40S ribosomal protein S26-B OS = *Saccharomyces cerevisiae* GN = RPS26B PE = 1 SV = 1

| z | Sequence | Incl. | L/(L + H) | Std. Err. | Fraction | Correlation | Intensity | Modifications |
|---|---|---|---|---|---|---|---|---|
| 1 | 2 DLSEASVY PEYALPK | | 0.3176 | 0.05414 | 0.1397 | 0.3309 | 6.58E+05 | |

| Hit | Accession | Score | Mass | L/(L + H) | SD(geo) | # |
|---|---|---|---|---|---|---|
| 116 | P35189 | 64 | 27423 | 0.8078 | | 1 |

TAF14_YEAST Transcription initiation factor TFIID subunit 14 OS = *Saccharomyces cerevisiae* GN = TAF14 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 SGSTEETT ANTGTIGK | X | 0.8078 | 0.02101 | 0.0963 | 0.9487 | 1.58E+04 | |

TABLE 2-continued

Proteins identified by Mascot Distiller from ChAP-MS analysis of GAL1 chromatin isolated from cells grown in galactose.
Mascot Distiller
Quantitation Report

| Hit | Accession | Score | Mass | L/(L + H) | SD(geo) | # |
|---|---|---|---|---|---|---|
| 117 | Q08972 | 64 | 134247 | | | 0 |

NEW1_YEAST [NU+] prion formation protein 1 OS = *Saccharomyces cerevisiae* GN = NEW1 PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 3 | ASNLAKPS VDDDDSPA NIK | | 0.3162 | 0.05206 | 0.143 | 0.3829 | 2.23E+05 | |

| Hit | Accession | Score | Mass | L/(L + H) | SD(geo) | # |
|---|---|---|---|---|---|---|
| 118 | P05736 | 63 | 27392 | 0.622 | 1.054 | 2 |

RL2_YEAST 60S ribosomal protein L2 OS = *Saccharomyces cerevisiae* GN = RPL2A PE = 1 SV = 3

| | z | Sequence | Incl. | L/(L + H) | Std. Err. | Fraction | Correlation | Intensity | Modifications |
|---|---|---|---|---|---|---|---|---|---|
| 1 | 2 | KVISSDAR | X | 0.5777 | 0.00446 | 0.06036 | 0.9809 | 2.68E+04 | |
| 2 | 3 | ASLNVGNV LPLGSVPE GTIVSNVE EKPGDR | X | 0.624 | 0.00764 | 0.308 | 0.9797 | 6.09E+05 | |

| Hit | Accession | Score | Mass | L/(L + H) | SD(geo) | # |
|---|---|---|---|---|---|---|
| 119 | P06367 | 61 | 14600 | | | 0 |

RS14A_YEAST 40S ribosomal protein S14-A OS = *Saccharomyces cerevisiae* GN = RPS14A PE = 1 SV = 5

| | z | Sequence | Incl. | L/(L + H) | Std. Err. | Fraction | Correlation | Intensity | Modifications |
|---|---|---|---|---|---|---|---|---|---|

| Hit | Accession | Score | Mass | L/(L + H) | SD(geo) | # |
|---|---|---|---|---|---|---|
| 120 | Q03195 | 60 | 68297 | 0.3246 | | 1 |

RLI1_YEAST Translation initiation factor RLI1 OS = *Saccharomyces cerevisiae* GN = RLI1 PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 2 | FDDPPEWQ EIIK | X | 0.3246 | 0.05303 | 0.04664 | 0.8258 | 2.37E+05 | |

| Hit | Accession | Score | Mass | L/(L + H) | SD(geo) | # |
|---|---|---|---|---|---|---|
| 121 | P23638 | 60 | 28697 | | | 0 |

PSA4_YEAST Proteasome component Y13 OS = *Saccharomyces cerevisiae* GN = PRE9 PE = 1 SV = 1

| | z | Sequence | Incl. | L/(L + H) | Std. Err. | Fraction | Correlation | Intensity | Modifications |
|---|---|---|---|---|---|---|---|---|---|

| Hit | Accession | Score | Mass | L/(L + H) | SD(geo) | # |
|---|---|---|---|---|---|---|
| 122 | P33327 | 60 | 124254 | 0.9911 | 1.026 | 2 |

DHE2_YEAST NAD-specific glutamate dehydrogenase OS = *Saccharomyces cerevisiae* GN = GDH2 PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 2 | GDIESISDK | X | 1.001 | 0.00158 | 0.3693 | 0.9924 | 5.15E+05 | |
| 2 | 2 | LVSFWAPE SELK | X | 0.957 | 0.01189 | 0.05111 | 0.9876 | 1.49E+05 | |

TABLE 2-continued

Proteins identified by Mascot Distiller from ChAP-MS analysis of GAL1 chromatin isolated from cells grown in galactose.
Mascot Distiller Quantitation Report

| | | | | | | | |
|---|---|---|---|---|---|---|---|
| 3 | 3 RNDTTLLEIVENLK | 0.1906 | 0.2454 | 0.2091 | 0.5903 | 2.89E+04 | |

| Hit | Accession | Score | Mass | L/(L + H) | SD(geo) | # |
|---|---|---|---|---|---|---|
| 123 | P17076 | 59 | 28107 | 0.7946 | | 1 |

RL8A_YEAST 60S ribosomal protein L8-A OS = *Saccharomyces cerevisiae* GN = RPL8A PE = 1 SV = 4

| | z | Sequence | Incl. | L/(L + H) | Std. Err. | Fraction | Correlation | Intensity | Modifications |
|---|---|---|---|---|---|---|---|---|---|
| 1 | 2 | YRPETAAEK | X | 0.7946 | 0.00569 | 0.2624 | 0.987 | 1.02E+05 | |
| 2 | 3 | SKQDASPKPYAVK | | -0.000859 | 3.397 | 0.2839 | 0.2521 | 2.27E+05 | |

| Hit | Accession | Score | Mass | L/(L + H) | SD(geo) | # |
|---|---|---|---|---|---|---|
| 124 | P00815 | 58 | 87666 | | | 0 |

HIS2_YEAST Histidine biosynthesis trifunctional protein OS = *Saccharomyces cerevisiae* GN = HIS4 PE = 1 SV = 3

| | z | Sequence | Incl. | L/(L + H) | Std. Err. | Fraction | Correlation | Intensity | Modifications |
|---|---|---|---|---|---|---|---|---|---|
| 1 | 2 | IKEEAEELTEAK | | 0.1694 | 0.3439 | 0.09508 | 0.2327 | 1.01E+05 | |

| Hit | Accession | Score | Mass | L/(L + H) | SD(geo) | # |
|---|---|---|---|---|---|---|
| 125 | P02309 | 57 | 11361 | | | 0 |

H4_YEAST Histone H4 OS = *Saccharomyces cerevisiae* GN = HHF1 PE = 1 SV = 2

| | z | Sequence | Incl. | L/(L + H) | Std. Err. | Fraction | Correlation | Intensity | Modifications |
|---|---|---|---|---|---|---|---|---|---|
| 1 | 2 | DSVTYTEHAK | | 0.3491 | 0.08223 | 0.2286 | 0.1483 | 5.70E+05 | |

| Hit | Accession | Score | Mass | L/(L + H) | SD(geo) | # |
|---|---|---|---|---|---|---|
| 126 | P37299 | 57 | 8587 | 0.04592 | | 1 |

QCR10_YEAST Cytochrome b-c1 complex subunit 10 OS = *Saccharomyces cerevisiae* GN = QCR10 PE = 1 SV = 2

| | z | Sequence | Incl. | L/(L + H) | Std. Err. | Fraction | Correlation | Intensity | Modifications |
|---|---|---|---|---|---|---|---|---|---|
| 1 | 3 | IPLLGPTLEDHTPPEDKPN | X | 0.04592 | 0.3578 | 0.08934 | 0.7487 | 1.68E+05 | |

| Hit | Accession | Score | Mass | L/(L + H) | SD(geo) | # |
|---|---|---|---|---|---|---|
| 127 | P23287 | 55 | 63355 | 1 | | 1 |

PP2B1_YEAST Serine/threonine-protein phosphatase 2B catalytic subunit A1 OS = *Saccharomyces cerevisiae* GN = CNA1 PE = 1 SV = 2

| | z | Sequence | Incl. | L/(L + H) | Std. Err. | Fraction | Correlation | Intensity | Modifications |
|---|---|---|---|---|---|---|---|---|---|
| 1 | 3 | ILNMSTVALSKEPNLLKLK | X | 1 | 0.001 | 0.05272 | 0.9692 | 2.68E+05 | |

| Hit | Accession | Score | Mass | L/(L + H) | SD(geo) | # |
|---|---|---|---|---|---|---|
| 128 | P38011 | 54 | 34784 | 0.7242 | | 1 |

GBLP_YEAST Guanine nucleotide-binding protein subunit beta-like protein OS = *Saccharomyces cerevisiae* GN = ASC1 PE = 1 SV = 4

| | z | Sequence | Incl. | L/(L + H) | Std. Err. | Fraction | Correlation | Intensity | Modifications |
|---|---|---|---|---|---|---|---|---|---|
| 1 | 3 | VFSLDPQYLVDDLRPEFAGYSK | X | 0.7242 | 0.00801 | 0.4127 | 0.9795 | 8.90E+05 | |

TABLE 2-continued

Proteins identified by Mascot Distiller from ChAP-MS analysis of GAL1 chromatin isolated from cells grown in galactose.
Mascot Distiller
Quantitation Report

| Hit | Accession | Score | Mass | L/(L + H) | SD(geo) | # |
|---|---|---|---|---|---|---|
| 129 | P53200 | 54 | 28564 | 0.5579 | | 1 |

AML1_YEAST N(6)-adenine-specific DNA methyltransferase-like 1
OS = Saccharomyces cerevisiae GN = AML1 PE = 1 SV = 2

| z | Sequence | Incl. | L/(L + H) | Std. Err. | Fraction | Correlation | Intensity | Modifications |
|---|---|---|---|---|---|---|---|---|
| 1 | 2 EEQQHQEAFQK | X | 0.5579 | 0.1156 | 0.04329 | 0.7172 | 6.21E+04 | |

| Hit | Accession | Score | Mass | L/(L + H) | SD(geo) | # |
|---|---|---|---|---|---|---|
| 130 | P32190 | 52 | 80158 | | | 0 |

GLPK_YEAST Glycerol kinase OS = Saccharomyces cerevisiae GN = GUT1 PE = 1 SV = 1

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 131 | P19358 | 51 | 42470 | 0.9999 | | 1 |

METK2_YEAST S-adenosylmethionine synthase 2 OS = Saccharomyces cerevisiae GN = SAM2 PE = 1 SV = 3

| z | Sequence | Incl. | L/(L + H) | Std. Err. | Fraction | Correlation | Intensity | Modifications |
|---|---|---|---|---|---|---|---|---|
| 1 | 3 TQLQKDIVEK | X | 0.9999 | 0.00317 | 0.04256 | 0.7785 | 2.46E+05 | |

| Hit | Accession | Score | Mass | L/(L + H) | SD(geo) | # |
|---|---|---|---|---|---|---|
| 132 | Q12363 | 50 | 48353 | 0.7508 | | 1 |

WTM1_YEAST Transcriptional modulator WTM1 OS = Saccharomyces cerevisiae GN = WTM1 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 YNPDDTIAPPQDATEESQTK | X | 0.7508 | 0.002 | 0.7573 | 0.9978 | 2.44E+05 | |

| Hit | Accession | Score | Mass | L/(L + H) | SD(geo) | # |
|---|---|---|---|---|---|---|
| 133 | P31539 | 47 | 102533 | 0.8569 | | 1 |

HS104_YEAST Heat shock protein 104 OS = Saccharomyces cerevisiae GN = HSP104 PE = 1 SV = 2

| z | Sequence | Incl. | L/(L + H) | Std. Err. | Fraction | Correlation | Intensity | Modifications |
|---|---|---|---|---|---|---|---|---|
| 1 | 2 GADTNTPLEYLSK | X | 0.8569 | 0.01624 | 0.2723 | 0.9822 | 3.21E+05 | |

| Hit | Accession | Score | Mass | L/(L + H) | SD(geo) | # |
|---|---|---|---|---|---|---|
| 134 | P39935 | 46 | 107036 | 0.815 | | 1 |

IF4F1_YEAST Eukaryotic initiation factor 4F subunit p150
OS = Saccharomyces cerevisiae GN = TIF4631 PE = 1 SV = 2

| z | Sequence | Incl. | L/(L + H) | Std. Err. | Fraction | Correlation | Intensity | Modifications |
|---|---|---|---|---|---|---|---|---|
| 1 | 3 LKETSDSTSTSTPTPTPSTNDSK | X | 0.815 | 0.05328 | 0.1577 | 0.8433 | 8.82E+04 | |

TABLE 2-continued

Proteins identified by Mascot Distiller from ChAP-MS analysis of GAL1 chromatin isolated from cells grown in galactose.
Mascot Distiller
Quantitation Report

| Hit | Accession | Score | Mass | L/(L + H) | SD(geo) | # |
|---|---|---|---|---|---|---|
| 135 | P35732 | 46 | 83923 | 0.9125 | | 1 |

YKF4_YEAST Uncharacterized protein YKL054C OS = *Saccharomyces cerevisiae* GN = YKL054C PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 3 | EQVKEEEQ TAEELEQE QDNVAAPE EEVTVVEEK | X | 0.9125 | 0.02943 | 0.623 | 0.9847 | 1.75E+05 | |

| Hit | Accession | Score | Mass | L/(L + H) | SD(geo) | # |
|---|---|---|---|---|---|---|
| 136 | P17255 | 45 | 119131 | | | 0 |

VATA_YEAST V-type proton ATPase catalytic subunit A
OS = *Saccharomyces cerevisiae* GN = TFP1 PE = 1 SV = 3

| | z | Sequence | Incl. | L/(L + H) | Std. Err. | Fraction | Correlation | Intensity | Modifications |
|---|---|---|---|---|---|---|---|---|---|

| Hit | Accession | Score | Mass | L/(L + H) | SD(geo) | # |
|---|---|---|---|---|---|---|
| 137 | P02294 | 45 | 14229 | 0.8421 | | 1 |

H2B2_YEAST Histone H2B.2 OS = *Saccharomyces cerevisiae* GN = HTB2 PE = 1 SV = 2

| | z | Sequence | Incl. | L/(L + H) | Std. Err. | Fraction | Correlation | Intensity | Modifications |
|---|---|---|---|---|---|---|---|---|---|
| 1 | 2 | QTHPDTGI SQK | X | 0.8421 | 0.00914 | 0.1463 | 0.9218 | 1.30E+05 | |

| Hit | Accession | Score | Mass | L/(L + H) | SD(geo) | # |
|---|---|---|---|---|---|---|
| 138 | P02293 | 45 | 14244 | 0.8421 | | 1 |

H2B1_YEAST Histone H2B.1 OS = *Saccharomyces cerevisiae* GN = HTB1 PE = 1 SV = 2

| | z | Sequence | Incl. | L/(L + H) | Std. Err. | Fraction | Correlation | Intensity | Modifications |
|---|---|---|---|---|---|---|---|---|---|
| 1 | 2 | QTHPDTGI SQK | X | 0.8421 | 0.00914 | 0.1463 | 0.9218 | 1.30E+05 | |

| Hit | Accession | Score | Mass | L/(L + H) | SD(geo) | # |
|---|---|---|---|---|---|---|
| 139 | P05749 | 43 | 13789 | | | 0 |

RL22A_YEAST 60S ribosomal protein L22-A OS = *Saccharomyces cerevisiae* GN = RPL22A PE = 1 SV = 3

| | z | Sequence | Incl. | L/(L + H) | Std. Err. | Fraction | Correlation | Intensity | Modifications |
|---|---|---|---|---|---|---|---|---|---|

| Hit | Accession | Score | Mass | L/(L + H) | SD(geo) | # |
|---|---|---|---|---|---|---|
| 140 | P40204 | 43 | 8477 | 1 | | 1 |

RUXG_YEAST Small nuclear ribonucleoprotein G OS = *Saccharomyces cerevisiae* GN = SMX2 PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 2 | KVAGILR | X | 1 | 0 | 0.07689 | 0.9937 | 4.35E+05 | |

| Hit | Accession | Score | Mass | L/(L + H) | SD(geo) | # |
|---|---|---|---|---|---|---|
| 141 | P08518 | 43 | 139256 | | | 0 |

RPB2_YEAST DNA-directed RNA polymerase II subunit RPB2
OS = *Saccharomyces cerevisiae* GN = RPB2 PE = 1 SV = 2

| | z | Sequence | Incl. | L/(L + H) | Std. Err. | Fraction | Correlation | Intensity | Modifications |
|---|---|---|---|---|---|---|---|---|---|

TABLE 2-continued

Proteins identified by Mascot Distiller from ChAP-MS analysis of GAL1 chromatin isolated from cells grown in galactose.
Mascot Distiller
Quantitation Report

| Hit | Accession | Score | Mass | L/(L + H) | SD(geo) | # |
|---|---|---|---|---|---|---|
| 142 | P05755 | 43 | 22421 | | | 0 |

RS9B_YEAST 40S ribosomal protein S9-B OS = *Saccharomyces cerevisiae* GN = RPS9B PE = 1 SV = 4
    z Sequence   Incl.  L/(L + H)  Std. Err.  Fraction Correlation  Intensity Modifications

| Hit | Accession | Score | Mass | L/(L + H) | SD(geo) | # |
|---|---|---|---|---|---|---|
| 143 | Q01855 | 43 | 15992 | | | 0 |

RS15_YEAST 40S ribosomal protein S15 OS = *Saccharomyces cerevisiae* GN = RPS15 PE = 1 SV = 1
    z Sequence   Incl.  L/(L + H)  Std. Err.  Fraction Correlation  Intensity Modifications 1  2 LLEMSTED           0.384      0.05738    0.2239    0.6167      5.45E+05
    FVK

| Hit | Accession | Score | Mass | L/(L + H) | SD(geo) | # |
|---|---|---|---|---|---|---|
| 144 | P26781 | 42 | 17898 | 1 | | 1 |

RS11_YEAST 40S ribosomal protein S11 OS = *Saccharomyces cerevisiae* GN = RPS11A PE = 1 SV = 3
    z Sequence   Incl.  L/(L + H)  Std. Err.  Fraction Correlation  Intensity Modifications 1  1 NAGLGFK      X         1           0         0.701     0.9998      2.17E+06

| Hit | Accession | Score | Mass | L/(L + H) | SD(geo) | # |
|---|---|---|---|---|---|---|
| 145 | P00950 | 42 | 27784 | | | 0 |

PMG1_YEAST Phosphoglycerate mutase 1 OS = *Saccharomyces cerevisiae* GN = GPM1 PE = 1 SV = 3
    z Sequence   Incl.  L/(L + H)  Std. Err.  Fraction Correlation  Intensity Modifications

| Hit | Accession | Score | Mass | L/(L + H) | SD(geo) | # |
|---|---|---|---|---|---|---|
| 146 | P32380 | 41 | 112692 | 0.9554 | | 1 |

NUF1_YEAST Protein NUF1 OS = *Saccharomyces cerevisiae* GN = NUF1 PE = 1 SV = 1
    z Sequence   Incl.  L/(L + H)  Std. Err.  Fraction Correlation  Intensity Modifications 1  2 IIDLQKK             0.9984     0.00413    0.00899   0.6498      1.06E+04
2  2 IEIENWK     X       0.9554     0.01028    0.1168    0.9842      1.57E+05

| Hit | Accession | Score | Mass | L/(L + H) | SD(geo) | # |
|---|---|---|---|---|---|---|
| 147 | P16120 | 41 | 57439 | | | 0 |

THRC_YEAST Threonine synthase OS = *Saccharomyces cerevisiae* GN = THR4 PE = 1 SV = 1
    z Sequence   Incl.  L/(L + H)  Std. Err.  Fraction Correlation  Intensity Modifications 1  3 LYIAQEEIP           0.04854    0.3108     0.1234    0.3822      1.17E+06
    DADLKDLIK

| Hit | Accession | Score | Mass | L/(L + H) | SD(geo) | # |
|---|---|---|---|---|---|---|
| 148 | P43616 | 41 | 52838 | 0.6185 | | 1 |

DUG1_YEAST Cys-Gly metallodipeptidase DUG1 OS = *Saccharomyces cerevisiae* GN = DUG1 PE = 1 SV = 1
    z Sequence   Incl.  L/(L + H)  Std. Err.  Fraction Correlation  Intensity Modifications 1  2 ILIDGIDEM   X       0.6185     0.00821    0.1115    0.9559      3.58E+04
    VAPLTEK TABLE 2-continued Proteins identified by Mascot Distiller from ChAP-MS analysis of GAL1 chromatin isolated from cells grown in galactose.
Mascot Distiller
Quantitation Report

| Hit | Accession | Score | Mass | L/(L + H) | SD(geo) | # |
|---|---|---|---|---|---|---|
| 149 | P25294 | 38 | 37567 | 0.5309 | | 1 |

SIS1_YEAST Protein SIS1 OS = *Saccharomyces cerevisiae* GN = SIS1 PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 2 | YHPDKPTGDTEK | X | 0.5309 | 0.05698 | 0.03541 | 0.7338 | 2.13E+05 | |

| Hit | Accession | Score | Mass | L/(L + H) | SD(geo) | # |
|---|---|---|---|---|---|---|
| 150 | P0C0T4 | 37 | 12002 | 0.8113 | | 1 |

RS25B_YEAST 40S ribosomal protein S25-B OS = *Saccharomyces cerevisiae* GN = RPS25B PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 3 | AQHAVILDQEK | X | 0.8113 | 0.04438 | 0.03423 | 0.7174 | 2.04E+04 | |
| 2 | 3 | AQHAVILDQEKYDR | | 0.1884 | 0.06967 | 0.3797 | 0.1743 | 2.54E+06 | |

| Hit | Accession | Score | Mass | L/(L + H) | SD(geo) | # |
|---|---|---|---|---|---|---|
| 151 | Q08438 | 37 | 73997 | | | 0 |

VHS3_YEAST Protein VHS3 OS = *Saccharomyces cerevisiae* GN = VHS3 PE = 1 SV = 1 z Sequence  Incl.  L/(L + H)  Std. Err.  Fraction Correlation Intensity Modifications

| Hit | Accession | Score | Mass | L/(L + H) | SD(geo) | # |
|---|---|---|---|---|---|---|
| 152 | Q0550 | 36 | 69890 | | | 0 |

SYRC_YEAST Arginyl-tRNA synthetase, cytoplasmic OS = *Saccharomyces cerevisiae* GN = YDR341C PE = 1 SV = 1

| | z | Sequence | Incl. | L/(L + H) | Std. Err. | Fraction | Correlation | Intensity | Modifications |
|---|---|---|---|---|---|---|---|---|---|
| 1 | 2 | YGNEEALVK | | 0.1829 | 0.1367 | 0.1933 | 0.1382 | 3.93E+05 | |

| Hit | Accession | Score | Mass | L/(L + H) | SD(geo) | # |
|---|---|---|---|---|---|---|
| 153 | P06168 | 36 | 44565 | | | 0 |

ILV5_YEAST Ketol-acid reductoisomerase, mitochondrial OS = *Saccharomyces cerevisiae* GN = ILV5 PE = 1 SV = 1 z Sequence  Incl.  L/(L + H)  Std. Err.  Fraction Correlation Intensity Modifications

| Hit | Accession | Score | Mass | L/(L + H) | SD(geo) | # |
|---|---|---|---|---|---|---|
| 154 | P38167 | 36 | 123534 | 0.5931 | | 1 |

ECM21_YEAST Protein ECM21 OS = *Saccharomyces cerevisiae* GN = ECM21 PE = 1 SV = 2

| | z | Sequence | Incl. | L/(L + H) | Std. Err. | Fraction | Correlation | Intensity | Modifications |
|---|---|---|---|---|---|---|---|---|---|
| 1 | 2 | SRFNNLDK | X | 0.5931 | 0.03207 | 0.03169 | 0.8355 | 1.66E+05 | |

| Hit | Accession | Score | Mass | L/(L + H) | SD(geo) | # |
|---|---|---|---|---|---|---|
| 155 | P04076 | 34 | 52173 | | | 0 |

ARLY_YEAST Argininosuccinate lyase OS = *Saccharomyces cerevisiae* GN = ARG4 PE = 1 SV = 2 z Sequence  Incl.  L/(L + H)  Std. Err.  Fraction Correlation Intensity Modifications

TABLE 2-continued

Proteins identified by Mascot Distiller from ChAP-MS analysis of GAL1 chromatin isolated from cells grown in galactose.
Mascot Distiller
Quantitation Report

| Hit | Accession | Score | Mass | L/(L + H) | SD(geo) | # |
|---|---|---|---|---|---|---|
| 156 | P61864 | 33 | 8552 | 0.8436 | | 1 |

UBIQ_YEAST Ubiquitin OS = *Saccharomyces cerevisiae* GN = UBI1 PE = 1 SV = 1

| | z | Sequence | Incl. | L/(L + H) | Std. Err. | Fraction Correlation | Intensity | Modifications |
|---|---|---|---|---|---|---|---|---|
| 1 | 2 | IQDKEGIPP DQQR | X | 0.8436 | 0.00578 | 0.2069 | 0.9679 | 1.11E+06 |

| Hit | Accession | Score | Mass | L/(L + H) | SD(geo) | # |
|---|---|---|---|---|---|---|
| 157 | P54839 | 33 | 55324 | | | 0 |

HMCS_YEAST Hydroxymethylglutaryl-CoA synthase
OS = *Saccharomyces cerevisiae* GN = ERG13 PE = 1 SV = 1
   z Sequence   Incl.  L/(L + H)  Std. Err.  Fraction Correlation  Intensity  Modifications

| Hit | Accession | Score | Mass | L/(L + H) | SD(geo) | # |
|---|---|---|---|---|---|---|
| 158 | P40482 | 33 | 103842 | | | 0 |

SEC24_YEAST Protein transport protein SEC24 OS = *Saccharomyces cerevisiae* GN = SEC24 PE = 1 SV = 1
   z Sequence   Incl.  L/(L + H)  Std. Err.  Fraction Correlation  Intensity  Modifications

| Hit | Accession | Score | Mass | L/(L + H) | SD(geo) | # |
|---|---|---|---|---|---|---|
| 159 | P05694 | 31 | 85807 | | | 0 |

METE_YEAST 5-methyltetrahydropteroyltriglutamate--homocysteine methyltransferase OS = *Saccharomyces cerevisiae* GN = MET6 PE = 1 SV = 4

| | z | Sequence | Incl. | L/(L + H) | Std. Err. | Fraction Correlation | Intensity | Modifications |
|---|---|---|---|---|---|---|---|---|
| 1 | 3 | APEQFDEV VAAIGNK | | 0.8993 | 0.03287 | 0.3114 | 0.6099 | 7.32E+05 |

| Hit | Accession | Score | Mass | L/(L + H) | SD(geo) | # |
|---|---|---|---|---|---|---|
| 160 | P0C0W1 | 31 | 14705 | | | 0 |

RS22A_YEAST 40S ribosomal protein S22-A OS = *Saccharomyces cerevisiae* GN = RPS22A PE = 1 SV = 2
   z Sequence   Incl.  L/(L + H)  Std. Err.  Fraction Correlation  Intensity  Modifications

| Hit | Accession | Score | Mass | L/(L + H) | SD(geo) | # |
|---|---|---|---|---|---|---|
| 161 | P06105 | 30 | 135689 | | | 0 |

SC160_YEAST Protein SCP160 OS = *Saccharomyces cerevisiae* GN = SCP160 PE = 1 SV = 3

| | z | Sequence | Incl. | L/(L + H) | Std. Err. | Fraction Correlation | Intensity | Modifications |
|---|---|---|---|---|---|---|---|---|
| 1 | 3 | FQFLIDAEE LKEK | | 0.2574 | 0.1495 | 0.03011 | 0.4086 | 8.22E+300 | 4 |

| Hit | Accession | Score | Mass | L/(L + H) | SD(geo) | # |
|---|---|---|---|---|---|---|
| 162 | P14065 | 30 | 35057 | 0.8654 | | 1 |

GCY_YEAST Protein GCY OS = *Saccharomyces cerevisiae* GN = GCY1 PE = 1 SV = 1

| | z | Sequence | Incl. | L/(L + H) | Std. Err. | Fraction Correlation | Intensity | Modifications |
|---|---|---|---|---|---|---|---|---|
| 1 | 2 | GYVVLPK | X | 0.8654 | 0.0811 | 0.06444 | 0.8822 | 3.00E+04 |

TABLE 2-continued

Proteins identified by Mascot Distiller from ChAP-MS analysis of GAL1 chromatin isolated from cells grown in galactose.
Mascot Distiller
Quantitation Report

| Hit | Accession | Score | Mass | L/(L + H) | SD(geo) | # |
|---|---|---|---|---|---|---|
| 163 | P52490 | 29 | 17561 | | | 0 |

UBC13_YEAST Ubiquitin-conjugating enzyme E2 13
OS = *Saccharomyces cerevisiae* GN = UBC13 PE = 1 SV = 1
z Sequence  Incl. L/(L + H) Std. Err. Fraction Correlation Intensity Modifications

| Hit | Accession | Score | Mass | L/(L + H) | SD(geo) | # |
|---|---|---|---|---|---|---|
| 164 | P38994 | 28 | 89754 | | | 0 |

MSS4_YEAST Probable phosphatidylinositol-4-phosphate 5-kinase
MSS4 OS = *Saccharomyces cerevisiae* GN = MSS4 PE = 1 SV = 2
z Sequence  Incl. L/(L + H) Std. Err. Fraction Correlation Intensity Modifications

| z | Sequence | Incl. | L/(L + H) | Std. Err. | Fraction | Correlation | Intensity | Modifications |
|---|---|---|---|---|---|---|---|---|
| 1 | 2 ISAVTATSTTIK | | −0.000063 | 7.067 | 0.305 | 0.9995 | 4.66E+05 | |

| Hit | Accession | Score | Mass | L/(L + H) | SD(geo) | # |
|---|---|---|---|---|---|---|
| 165 | P32893 | 28 | 63328 | | | 0 |

KRE11_YEAST Beta-glucan synthesis-associated protein KRE11
OS = *Saccharomyces cerevisiae* GN = KRE11 PE = 1 SV = 1
z Sequence  Incl. L/(L + H) Std. Err. Fraction Correlation Intensity Modifications

| z | Sequence | Incl. | L/(L + H) | Std. Err. | Fraction | Correlation | Intensity | Modifications |
|---|---|---|---|---|---|---|---|---|
| 1 | 2 ASEQLTKK | | 0.3303 | 0.2361 | 0.02043 | 0.1669 | 9586 | |

| Hit | Accession | Score | Mass | L/(L + H) | SD(geo) | # |
|---|---|---|---|---|---|---|
| 166 | A6ZPZ1 | 28 | 95169 | 0.999 | | 1 |

YJ00_YEAS7 UPF0508 protein SCY_2952 OS = *Saccharomyces cerevisiae* (strain YJM789) GN = SCY_2952 PE = 3 SV = 1
z Sequence  Incl. L/(L + H) Std. Err. Fraction Correlation Intensity Modifications

| z | Sequence | Incl. | L/(L + H) | Std. Err. | Fraction | Correlation | Intensity | Modifications |
|---|---|---|---|---|---|---|---|---|
| 1 | 2 SIQVPLSPK | X | 0.999 | 0.00323 | 0.07993 | 0.9881 | 3.06E+05 | |

| Hit | Accession | Score | Mass | L/(L + H) | SD(geo) | # |
|---|---|---|---|---|---|---|
| 167 | P15891 | 28 | 65536 | | | 0 |

ABP1_YEAST Actin-binding protein OS = *Saccharomyces cerevisiae*
GN = ABP1 PE = 1 SV = 4
z Sequence  Incl. L/(L + H) Std. Err. Fraction Correlation Intensity Modifications

| z | Sequence | Incl. | L/(L + H) | Std. Err. | Fraction | Correlation | Intensity | Modifications |
|---|---|---|---|---|---|---|---|---|
| 1 | 3 AEAPKPEVPEDEPEGEPDVK | | 0.2106 | 0.08472 | 0.3799 | 0.4288 | 9.13E+05 | |

| Hit | Accession | Score | Mass | L/(L + H) | SD(geo) | # |
|---|---|---|---|---|---|---|
| 168 | P32074 | 27 | 105239 | 0.8225 | | 1 |

COPG_YEAST Coatomer subunit gamma OS = *Saccharomyces cerevisiae* GN = SEC21 PE = 1 SV = 2
z Sequence  Incl. L/(L + H) Std. Err. Fraction Correlation Intensity Modifications

| z | Sequence | Incl. | L/(L + H) | Std. Err. | Fraction | Correlation | Intensity | Modifications |
|---|---|---|---|---|---|---|---|---|
| 1 | 3 SETTLDTTPEAESVPEKR | X | 0.8225 | 0.02368 | 0.1323 | 0.7806 | 1.44E+05 | |

| Hit | Accession | Score | Mass | L/(L + H) | SD(geo) | # |
|---|---|---|---|---|---|---|
| 169 | P04801 | 27 | 84987 | | | 0 |

SYTC_YEAST Threonyl-tRNA synthetase, cytoplasmic
OS = *Saccharomyces cerevisiae* GN = THS1 PE = 1 SV = 2
z Sequence  Incl. L/(L + H) Std. Err. Fraction Correlation Intensity Modifications

TABLE 2-continued

Proteins identified by Mascot Distiller from ChAP-MS analysis of GAL1 chromatin isolated from cells grown in galactose.
Mascot Distiller
Quantitation Report

| Hit | Accession | Score | Mass | L/(L + H) | SD(geo) | # |
|---|---|---|---|---|---|---|
| 170 | B3RHV0 | 27 | 28726 | 0.954 | | 1 |

RS3A1_YEAS1 40S ribosomal protein S1-A OS = *Saccharomyces cerevisiae* (strain RM11-1a) GN = RPS1A PE = 3 SV = 1

| z | Sequence | Incl. | L/(L + H) | Std. Err. | Fraction | Correlation | Intensity | Modifications |
|---|---|---|---|---|---|---|---|---|
| 1 | 2 LRVDEVQGK | X | 0.954 | 0.00845 | 0.1571 | 0.9013 | 1.03E+06 | |

| Hit | Accession | Score | Mass | L/(L + H) | SD(geo) | # |
|---|---|---|---|---|---|---|
| 171 | Q01217 | 27 | 95307 | | | 0 |

ARG56_YEAST Protein ARG5,6, mitochondrial OS = *Saccharomyces cerevisiae* GN = ARG5, 6 PE = 1 SV = 1

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 172 | P32861 | 27 | 56234 | 0.7068 | | 1 |

UGPA1_YEAST UTP--glucose-1-phosphate uridylyltransferase OS = *Saccharomyces cerevisiae* GN = UGP1 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 YEIISQQPENVSNLSK | X | 0.7068 | 0.00158 | 0.1676 | 0.9848 | 2.66E+05 | |

| Hit | Accession | Score | Mass | L/(L + H) | SD(geo) | # |
|---|---|---|---|---|---|---|
| 173 | Q12462 | 27 | 26995 | | | 0 |

PEX11_YEAST Peroxisomal membrane protein PMP27 OS = *Saccharomyces cerevisiae* GN = PEX11 PE = 1 SV = 2

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 174 | P53583 | 27 | 61628 | 0.9997 | | 1 |

MPA43_YEAST Protein MPA43 OS = *Saccharomyces cerevisiae* GN = MPA43 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 ALQKCLQKLNIR | X | 0.9997 | 0 | 0.5408 | 0.9792 | 4.03E+05 | |

| Hit | Accession | Score | Mass | L/(L + H) | SD(geo) | # |
|---|---|---|---|---|---|---|
| 175 | P38737 | 26 | 211316 | 1 | | 1 |

ECM29_YEAST Proteasome component ECM29 OS = *Saccharomyces cerevisiae* GN = ECM29 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 LKNLLR | X | 1 | 0 | 0.07689 | 0.9937 | 4.35E+05 | |

| Hit | Accession | Score | Mass | L/(L + H) | SD(geo) | # |
|---|---|---|---|---|---|---|
| 176 | P40494 | 26 | 90976 | 1 | | 1 |

PRK1_YEAST Actin-regulating kinase PRK1 OS = *Saccharomyces cerevisiae* GN = PRK1 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 LKNLIR | X | 1 | 0 | 0.07689 | 0.9937 | 4.35E+05 | |

TABLE 2-continued

Proteins identified by Mascot Distiller from ChAP-MS analysis of GAL1 chromatin isolated from cells grown in galactose.
Mascot Distiller
Quantitation Report

| Hit | Accession | Score | Mass | L/(L + H) | SD(geo) | # |
|---|---|---|---|---|---|---|
| 177 | P36048 | 26 | 114578 | 1 | | 1 |

SN114_YEAST 114 kDa U5 small nuclear ribonucleoprotein component
OS = *Saccharomyces cerevisiae* GN = SNU114 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 LKNLLR | X | 1 | 0 | 0.07689 | 0.9937 | 4.35E+05 | |

| Hit | Accession | Score | Mass | L/(L + H) | SD(geo) | # |
|---|---|---|---|---|---|---|
| 178 | Q01846 | 26 | 130637 | 0.08842 | | 1 |

MDM1_YEAST Structural protein MDM1 OS = *Saccharomyces cerevisiae*
GN = MDM1 PE = 1 SV = 3

| z | Sequence | Incl. | L/(L + H) | Std. Err. | Fraction | Correlation | Intensity | Modifications |
|---|---|---|---|---|---|---|---|---|
| 1 | 2 TKIYIR | X | 0.08842 | 0.1027 | 0.1197 | 0.9815 | 7.92E+04 | |

| Hit | Accession | Score | Mass | L/(L + H) | SD(geo) | # |
|---|---|---|---|---|---|---|
| 179 | P04456 | 26 | 15924 | | | 0 |

RL25_YEAST 60S ribosomal protein L25 OS = *Saccharomyces cerevisiae* GN = RPL25 PE = 1 SV = 4

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 180 | Q99186 | 24 | 55352 | 1.007 | | 1 |

AP2M_YEAST AP-2 complex subunit mu OS = *Saccharomyces cerevisiae*
GN = APM4 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 HSGSDFGNK | X | 1.007 | 0.00775 | 0.03715 | 0.9671 | 4599 | |

| Hit | Accession | Score | Mass | L/(L + H) | SD(geo) | # |
|---|---|---|---|---|---|---|
| 181 | Q04922 | 23 | 53135 | 0.9994 | | 1 |

MFB1_YEAST Mitochondrial F-box protein MFB1 OS = *Saccharomyces cerevisiae* GN = MFB1 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 KDNPRLK | X | 0.9994 | 0.00158 | 0.4699 | 0.9983 | 3.45E+06 | |

| Hit | Accession | Score | Mass | L/(L + H) | SD(geo) | # |
|---|---|---|---|---|---|---|
| 182 | Q03786 | 23 | 22353 | | | 0 |

GNTK_YEAST Probable gluconokinase OS = *Saccharomyces cerevisiae*
GN = YDR248C PE = 1 SV = 1

| z | Sequence | Incl. | L/(L + H) | Std. Err. | Fraction | Correlation | Intensity | Modifications |
|---|---|---|---|---|---|---|---|---|
| 1 | 2 KYRDLIR | | 0.000004 | 1211 | 0.06617 | 0.9937 | 3.09E+04 | |

| Hit | Accession | Score | Mass | L/(L + H) | SD(geo) | # |
|---|---|---|---|---|---|---|
| 183 | P04147 | 23 | 64304 | | | 0 |

PABP_YEAST Polyadenylate-binding protein, cytoplasmic and nuclear
OS = *Saccharomyces cerevisiae* GN = PAB1 PE = 1 SV = 4

| z | Sequence | Incl. | L/(L + H) | Std. Err. | Fraction | Correlation | Intensity | Modifications |
|---|---|---|---|---|---|---|---|---|
| 1 | 2 YQGVNLFVK | | 0.6493 | 0.04431 | 0.1257 | 0.2785 | 2.62E+05 | |

TABLE 2-continued

Proteins identified by Mascot Distiller from ChAP-MS analysis of GAL1 chromatin isolated from cells grown in galactose.
Mascot Distiller
Quantitation Report

| Hit | Accession | Score | Mass | L/(L + H) | SD(geo) | # |
|---|---|---|---|---|---|---|
| 184 | P13663 | 23 | 39519 | | | 0 |

DHAS_YEAST Aspartate-semialdehyde dehydrogenase
OS = *Saccharomyces cerevisiae* GN = HOM2 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 IREDPLLDFK | | 0.18 | 0.182 | 0.08109 | 0.1847 | 7.16E+04 | |

| Hit | Accession | Score | Mass | L/(L + H) | SD(geo) | # |
|---|---|---|---|---|---|---|
| 185 | P19097 | 23 | 207964 | | | 0 |

FAS2_YEAST Fatty acid synthase subunit alpha OS = *Saccharomyces cerevisiae* GN = FAS2 PE = 1 SV = 2

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD(geo) | # |
|---|---|---|---|---|---|---|
| 186 | P38264 | 23 | 21123 | | | 0 |

PHO88_YEAST Inorganic phosphate transport protein PHO88
OS = *Saccharomyces cerevisiae* GN = PHO88 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 SALEHNEVK | | 0.942 | 0.01455 | 0.09329 | 0.575 | 5.32E+04 | |

| Hit | Accession | Score | Mass | L/(L + H) | SD(geo) | # |
|---|---|---|---|---|---|---|
| 187 | P33203 | 23 | 69023 | 0.9927 | | 1 |

PRP40_YEAST Pre-mRNA-processing protein PRP40
OS = *Saccharomyces cerevisiae* GN = PRP40 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 YLSNRSADQLLK | X | 0.9927 | 0.00412 | 0.2098 | 0.996 | 4.72E+04 | |

| Hit | Accession | Score | Mass | L/(L + H) | SD(geo) | # |
|---|---|---|---|---|---|---|
| 188 | P32386 | 22 | 189043 | | | 0 |

YBT1_YEAST ATP-dependent bile acid permease OS = *Saccharomyces cerevisiae* GN = YBT1 PE = 1 SV = 2

| z | Sequence | Incl. | L/(L + H) | Std. Err. | Fraction | Correlation | Intensity | Modifications |
|---|---|---|---|---|---|---|---|---|
| 1 | 2 IFNMILNK | | 0.004101 | 0.9579 | 0.2443 | 0.5181 | 1.15E+06 | |

| Hit | Accession | Score | Mass | L/(L + H) | SD(geo) | # |
|---|---|---|---|---|---|---|
| 189 | P40075 | 22 | 26909 | | | 0 |

SCS2_YEAST Vesicle-associated membrane protein-associated protein SCS2 OS = *Saccharomyces cerevisiae* GN = SCS2 PE = 1 SV = 3

| z | Sequence | Incl. | L/(L + H) | Std. Err. | Fraction | Correlation | Intensity | Modifications |
|---|---|---|---|---|---|---|---|---|
| 1 | 3 YLISPDVHPAQNQNIQENK | | 0.6453 | 0.1021 | 0.2303 | 0.4558 | 6.49E+04 | |

| Hit | Accession | Score | Mass | L/(L + H) | SD(geo) | # |
|---|---|---|---|---|---|---|
| 190 | Q06685 | 22 | 129674 | 1.008 | | 1 |

VIP1_YEAST Inositol hexakisphosphate and diphosphoinositol-pentakisphosphate kinase OS = *Saccharomyces cerevisiae* GN = VIP1 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 SSTSHPKPR | X | 1.008 | 0.02117 | 0.06128 | 0.7799 | 7778 | |

TABLE 2-continued

Proteins identified by Mascot Distiller from ChAP-MS analysis of GAL1 chromatin isolated from cells grown in galactose.
Mascot Distiller
Quantitation Report

| Hit | Accession | Score | Mass | L/(L + H) | SD(geo) | # |
|---|---|---|---|---|---|---|
| 191 | P46962 | 21 | 38057 | | | 0 |

CTK2_YEAST CTD kinase subunit beta OS = *Saccharomyces cerevisiae* GN = CTK2 PE = 1 SV = 1
   z Sequence   Incl.  L/(L + H)  Std. Err.  Fraction  Correlation  Intensity  Modifications

| Hit | Accession | Score | Mass | L/(L + H) | SD(geo) | # |
|---|---|---|---|---|---|---|
| 192 | P13188 | 21 | 93075 | 0.9115 | | 1 |

SYQ_YEAST Glutaminyl-tRNA synthetase OS = *Saccharomyces cerevisiae* GN = GLN4 PE = 1 SV = 2
   z Sequence   Incl.  L/(L + H)  Std. Err.  Fraction  Correlation  Intensity  Modifications

| | | | | | | | |
|---|---|---|---|---|---|---|---|
| 1 | 2 | SDFSENVDDKEFFR | X | 0.9115 | 0.00801 | 0.1843 | 0.8822 | 6.60E+05 |

| Hit | Accession | Score | Mass | L/(L + H) | SD(geo) | # |
|---|---|---|---|---|---|---|
| 193 | Q02208 | 21 | 86313 | 0.9576 | | 1 |

TOF2_YEAST Topoisomerase 1-associated factor 2 OS = *Saccharomyces cerevisiae* GN = TOF2 PE = 1 SV = 1
   z Sequence   Incl.  L/(L + H)  Std. Err.  Fraction  Correlation  Intensity  Modifications

| | | | | | | | |
|---|---|---|---|---|---|---|---|
| 1 | 2 | AESKDLDLLR | X | 0.9576 | 0.00992 | 0.5313 | 0.8332 | 4.35E+06 |

| Hit | Accession | Score | Mass | L/(L + H) | SD(geo) | # |
|---|---|---|---|---|---|---|
| 194 | P43544 | 21 | 25116 | 0.9621 | | 1 |

SNO3_YEAST Probable glutamine amidotransferase SNO3 OS = *Saccharomyces cerevisiae* GN = SNO3 PE = 1 SV = 1
   z Sequence   Incl.  L/(L + H)  Std. Err.  Fraction  Correlation  Intensity  Modifications

| | | | | | | | |
|---|---|---|---|---|---|---|---|
| 1 | 2 | LDGKDNGGQELIVAAK | X | 0.9621 | 0.00918 | 0.1046 | 0.9559 | 1.74E+05 |

| Hit | Accession | Score | Mass | L/(L + H) | SD(geo) | # |
|---|---|---|---|---|---|---|
| 195 | P53254 | 21 | 141262 | | | 0 |

UTP22_YEAST U3 small nucleolar RNA-associated protein 22 OS = *Saccharomyces cerevisiae* GN = UTP22 PE = 1 SV = 1
   z Sequence   Incl.  L/(L + H)  Std. Err.  Fraction  Correlation  Intensity  Modifications

| | | | | | | | |
|---|---|---|---|---|---|---|---|
| 1 | 2 | LSERLTLAQYK | | 0.002931 | 1.18 | 0.313 | 0.9968 | 1.09E+06 |

| Hit | Accession | Score | Mass | L/(L + H) | SD(geo) | # |
|---|---|---|---|---|---|---|
| 196 | Q12507 | 21 | 38997 | 0.9995 | | 1 |

SFG1_YEAST Superficial pseudohyphal growth protein 1 OS = *Saccharomyces cerevisiae* GN = SFG1 PE = 1 SV = 1
   z Sequence   Incl.  L/(L + H)  Std. Err.  Fraction  Correlation  Intensity  Modifications

| | | | | | | | |
|---|---|---|---|---|---|---|---|
| 1 | 2 | TSSKNVK | X | 0.9995 | 0.00158 | 0.4979 | 0.9993 | 2.25E+06 |

| Hit | Accession | Score | Mass | L/(L + H) | SD(geo) | # |
|---|---|---|---|---|---|---|
| 197 | Q06625 | 20 | 175551 | | | 0 |

GDE_YEAST Glycogen debranching enzyme OS = *Saccharomyces cerevisiae* GN = GDB1 PE = 1 SV = 1
   z Sequence   Incl.  L/(L + H)  Std. Err.  Fraction  Correlation  Intensity  Modifications TABLE 2-continued Proteins identified by Mascot Distiller from ChAP-MS analysis of GAL1 chromatin isolated from cells grown in galactose.
Mascot Distiller
Quantitation Report

| Hit | Accession | Score | Mass | L/(L + H) | SD(geo) | # |
|---|---|---|---|---|---|---|
| 198 | P17555 | 20 | 57486 | 0.7116 | | 1 |

CAP_YEAST Adenylyl cyclase-associated protein OS = *Saccharomyces cerevisiae* GN = SRV2 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 SDGGNIYLSK | X | 0.7116 | 0.00648 | 0.07351 | 0.9734 | 7.93E+04 | |

| Hit | Accession | Score | Mass | L/(L + H) | SD(geo) | # |
|---|---|---|---|---|---|---|
| 199 | Q12345 | 20 | 28402 | | | 0 |

IES3_YEAST Ino eighty subunit 3 OS = *Saccharomyces cerevisiae* GN = IES3 PE = 1 SV = 1

| z | Sequence | Incl. | L/(L + H) | Std. Err. | Fraction | Correlation | Intensity | Modifications |
|---|---|---|---|---|---|---|---|---|
| 1 | 3 IDILTKIQENLLEEYQK | | 0.7775 | 0.1023 | 0.03577 | 0.4115 | 952.5 | |

| Hit | Accession | Score | Mass | L/(L + H) | SD(geo) | # |
|---|---|---|---|---|---|---|
| 200 | P32802 | 20 | 75914 | 0.9962 | | 1 |

TMN1_YEAST Transmembrane 9 superfamily member 1 OS = *Saccharomyces cerevisiae* GN = EMP70 PE = 1 SV = 2

| z | Sequence | Incl. | L/(L + H) | Std. Err. | Fraction | Correlation | Intensity | Modifications |
|---|---|---|---|---|---|---|---|---|
| 1 | 2 KIYSSIK | X | 0.9962 | 0.02516 | 0.03919 | 0.9666 | 1.24E+04 | |

| Hit | Accession | Score | Mass | L/(L + H) | SD(geo) | # |
|---|---|---|---|---|---|---|
| 201 | P53295 | 20 | 40980 | 0.9333 | | 1 |

YG3Y_YEAST Uncharacterized GTP-binding protein YGR173W OS = *Saccharomyces cerevisiae* GN = YGR173W PE = 1 SV = 1

| z | Sequence | Incl. | L/(L + H) | Std. Err. | Fraction | Correlation | Intensity | Modifications |
|---|---|---|---|---|---|---|---|---|
| 1 | 3 CLYVYNKIDAVSLEEVDK | X | 0.9333 | 0.01137 | 0.1522 | 0.9687 | 5.58E+05 | |

| Hit | Accession | Score | Mass | L/(L + H) | SD(geo) | # |
|---|---|---|---|---|---|---|
| 202 | P53244 | 20 | 65724 | 0.03843 | | 1 |

ART5_YEAST Arrestin-related trafficking adapter 5 OS = *Saccharomyces cerevisiae* GN = ART5 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 GRLVLFDK | | 0.03843 | 0.07779 | 0.03009 | 0.8963 | 8.52E+05 | |

| Hit | Accession | Score | Mass | L/(L + H) | SD(geo) | # |
|---|---|---|---|---|---|---|
| 203 | P53598 | 20 | 35010 | 0.9917 | | 1 |

SUCA_YEAST Succinyl-CoA ligase [ADP-forming] subunit alpha, mitochondrial OS = *Saccharomyces cerevisiae* GN = LSC1 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 ESIPYDK | X | 0.9917 | 0.001 | 0.4495 | 0.9852 | 2.95E+06 | |

| Hit | Accession | Score | Mass | L/(L + H) | SD(geo) | # |
|---|---|---|---|---|---|---|
| 204 | P48524 | 19 | 109107.00 | | | 0 |

BUL1_YEAST Ubiquitin ligase-binding protein BUL1 OS = *Saccharomyces cerevisiae* GN = BUL1 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 SPSLHSPK | | 0.5209 | 0.06221 | 0.06108 | 0.3577 | 1.00E+05 | |

TABLE 2-continued

Proteins identified by Mascot Distiller from ChAP-MS analysis of GAL1 chromatin isolated from cells grown in galactose.
Mascot Distiller
Quantitation Report

| Hit | Accession | Score | Mass | L/(L + H) | SD (geo) | # |
|---|---|---|---|---|---|---|
| 205 | P35172 | 19 | 89623 | | | 0 |

TREB_YEAST Probable trehalase OS = *Saccharomyces cerevisiae*
GN = NTH2 PE = 1 SV = 1

| z | Sequence | Incl. | L/(L + H) | Std. Err. | Fraction | Correlation | Intensity | Modifications |
|---|---|---|---|---|---|---|---|---|
| 1 | 2 RAFRAAIK | | 0.05024 | 0.1466 | 0.00365 | 0.2201 | 1.25E+04 | |

| Hit | Accession | Score | Mass | L/(L + H) | SD (geo) | # |
|---|---|---|---|---|---|---|
| 206 | P10963 | 18 | 61201 | | | 0 |

PCKA_YEAST Phosphoenolpyruvate carboxykinase [ATP]
OS = *Saccharomyces cerevisiae* GN = PCK1 PE = 1 SV = 2

| z | Sequence | Incl. | L/(L + H) | Std. Err. | Fraction | Correlation | Intensity | Modifications |
|---|---|---|---|---|---|---|---|---|

| Hit | Accession | Score | Mass | L/(L + H) | SD (geo) | # |
|---|---|---|---|---|---|---|
| 207 | P53133 | 18 | 30896 | 0.8643 | | 1 |

YGL7_YEAST Uncharacterized protein YGL117W OS = *Saccharomyces cerevisiae* GN = YGL117W PE = 1 SV = 1

| z | Sequence | Incl. | L/(L + H) | Std. Err. | Fraction | Correlation | Intensity | Modifications |
|---|---|---|---|---|---|---|---|---|
| 1 | 2 TSLKITHRR | X | 0.8643 | 0.01604 | 0.0279 | 0.7852 | 9.11E+04 | |

| Hit | Accession | Score | Mass | L/(L + H) | SD (geo) | # |
|---|---|---|---|---|---|---|
| 208 | Q07913 | 17 | 38310 | | | 0 |

NSE1_YEAST Non-structural maintenance of chromosomes element 1
OS = *Saccharomyces cerevisiae* GN = NSE1 PE = 1 SV = 1

TABLE 3

Ribosomal proteins used to establish the non-specifically associating baseline for ChAP-MS analyses. The percentage light and standard deviation are listed for each ribosomal protein.

| Ribosomal Proteins | Glucose | Stdev Glucose | Galactose | Stdev Galactose |
|---|---|---|---|---|
| 40S ribosomal protein S10-A OS = *Saccharomyces cerevisiae* GN = RPS10A PE = 1 SV = 1 | 48.01% | 1.14% | 65.47% | 0.00% |
| 40S ribosomal protein S17-A OS = *Saccharomyces cerevisiae* GN = RPS17A PE = 1 SV = 1 | 47.77% | 0.00% | 70.60% | 4.47% |
| 40S ribosomal protein S21-A OS = *Saccharomyces cerevisiae* GN = RPS21A PE = 1 SV = 1 | 53.30% | 1.79% | 56.17% | 1.13% |
| 60S ribosomal protein L14-B OS = *Saccharomyces cerevisiae* GN = RPL14B PE = 1 SV = 1 | 52.21% | 4.40% | 77.37% | 10.01% |
| 60S ribosomal protein L19 OS = *Saccharomyces cerevisiae* GN = RPL19A PE = 1 SV = 5 | 50.26% | 1.25% | 71.05% | 5.03% |
| 60S ribosomal protein L26-A OS = *Saccharomyces cerevisiae* GN = RPL26A PE = 1 SV = 3 | 51.09% | 0.00% | 70.20% | 0.00% |
| 60S ribosomal protein L3 OS = *Saccharomyces cerevisiae* GN = RPL3 PE = 1 SV = 4 | 49.39% | 5.09% | 66.83% | 7.02% |
| 60S ribosomal protein L30 OS = *Saccharomyces cerevisiae* GN = RPL30 PE = 1 SV = 3 | 48.85% | 4.03% | 62.85% | 4.95% |
| 40S ribosomal protein S12 OS = *Saccharomyces cerevisiae* GN = RPS12 PE = 1 SV = 1 | 50.92% | 13.06% | 78.21% | 1.50% |
| 40S ribosomal protein S19-A OS = *Saccharomyces cerevisiae* GN = RPS19A PE = 1 SV = 2 | 49.03% | 1.43% | 59.47% | 1.64% |
| 40S ribosomal protein S26-A OS = *Saccharomyces cerevisiae* GN = RPS26A PE = 1 SV = 1 | 50.63% | 2.36% | 71.70% | 4.02% |
| 40S ribosomal protein S4 OS = *Saccharomyces cerevisiae* GN = RPS4A PE = 1 SV = 3 | 44.54% | 11.51% | 54.31% | 4.61% |
| 40S ribosomal protein S7-A OS = *Saccharomyces cerevisiae* GN = RPS7A PE = 1 SV = 4 | 51.87% | 2.38% | 75.86% | 6.19% |
| 40S ribosomal protein S11 OS = *Saccharomyces cerevisiae* GN = RPS11A PE = 1 SV = 3 | 49.48% | 3.94% | 74.42% | 3.71% |
| 60S acidic ribosomal protein P0 OS = *Saccharomyces cerevisiae* GN = RPP0 PE = 1 SV = 1 | 50.01% | 2.91% | 62.25% | 3.64% |

TABLE 3-continued

Ribosomal proteins used to establish the non-specifically associating baseline for ChAP-MS analyses. The percentage light and standard deviation are listed for each ribosomal protein.

| Ribosomal Proteins | Glucose | Stdev Glucose | Galactose | Stdev Galactose |
|---|---|---|---|---|
| 60S ribosomal protein L10 OS = Saccharomyces cerevisiae GN = RPL10 PE = 1 SV = 1 | 53.45% | 2.89% | 63.81% | 2.66% |
| 60S ribosomal protein L12 OS = Saccharomyces cerevisiae GN = RPL12A PE = 1 SV = 1 | 51.79% | 1.15% | 66.76% | 2.02% |
| 60S ribosomal protein L30 OS = Saccharomyces cerevisiae GN = RPL30 PE = 1 SV = 3 | 48.85% | 4.03% | 63.49% | 4.82% |
| 60S ribosomal protein L9-A OS = Saccharomyces cerevisiae GN = RPL9A PE = 1 SV = 2 | 49.58% | 3.07% | 58.70% | 2.73% |
| 40S ribosomal protein S1-B OS = Saccharomyces cerevisiae (strain YJM789) GN = RPS1B PE = 3 SV = 1 | 47.63% | 4.27% | 75.33% | 9.16% |

TABLE 4

Proteins and PTMs specifically associating with GAL1 chromatin isolated from cells cultured in galactose. Proteins and histone posttranslational modifications listed are greater than two standard deviations from the non-specific threshold (80.9% Light).

| Protein Name | % Light Glucose | Stdev Glucose |
|---|---|---|
| DNA-directed RNA polymerase II 140 kDa polypeptide (EC 2.7.7.6) (B150) - S cerevisiae | 100.00% | 0.00% |
| Histone H3K18acK23ac | 100.00% | 0.00% |
| Histone H2A.1 OS = Saccharomyces cerevisiae GN = HTA1 PE = 1 SV = 2 | 97.10% | 6.02% |
| NAD-specific glutamate dehydrogenase OS = Saccharomyces cerevisiae GN = GDH2 PE = 1 SV = 1 | 96.09% | 2.70% |
| Histone H4K5acK8ac | 95.89% | 0.00% |
| DNA-directed RNA polymerase II largest subunit (EC 2.7.7.6) (RNA polymerase II subunit 1) (B220) - S cerevisiae | 94.36% | 4.99% |
| Histone H3K9acK14ac | 93.62% | 0.00% |
| Histone H4K12acK16ac | 90.56% | 3.00% |
| Histone H2B.1 OS = Saccharomyces cerevisiae GN = HTB1 PE = 1 SV = 2 | 89.59% | 9.51% |
| Acetyl-CoA carboxylase OS = Saccharomyces cerevisiae GN = FAS3 PE = 1 SV = 2 | 89.04% | 3.39% |
| 6-phosphogluconate dehydrogenase, decarboxylating 1 OS = Saccharomyces cerevisiae GN = GND1 PE = 1 SV = 1 | 87.74% | 3.05% |
| Probable inosine-5'-monophosphate dehydrogenase IMD3 OS = Saccharomyces cerevisiae GN = IMD3 PE = 1 SV = 1 | 87.19% | 14.00% |
| Eukaryotic translation initiation factor 3 subunit A OS = Saccharomyces cerevisiae GN = TIF32 PE = 1 SV = 1 | 86.97% | 7.61% |
| Histone H3K14ac | 85.83% | 4.48% |
| Histone H3 OS = Saccharomyces cerevisiae GN = HHT1 PE = 1 SV = 2 | 85.83% | 4.48% |
| Zuotin OS = Saccharomyces cerevisiae GN = ZUO1 PE = 1 SV = 1 | 85.33% | 5.43% |
| Protein GCY OS = Saccharomyces cerevisiae GN = GCY1 PE = 1 SV = 1 | 85.18% | 7.02% |
| Histone H4 OS = Saccharomyces cerevisiae GN = HHF1 PE = 1 SV = 2 | 90.42% | 8.84% |
| Actin-related protein 2/3 complex subunit 4 OS = Saccharomyces cerevisiae GN = ARC19 PE = 1 SV = 2 | 84.74% | 4.60% |
| Translationally-controlled tumor protein homolog OS = Saccharomyces cerevisiae GN = TMA19 PE = 1 SV = 1 | 84.64% | 1.50% |
| Suppressor protein STM1 OS = Saccharomyces cerevisiae GN = STM1 PE = 1 SV = 3 | 84.58% | 5.36% |
| FACT complex subunit SPT16 OS = Saccharomyces cerevisiae GN = SPT16 PE = 1 SV = 1 | 84.24% | 3.60% |
| Hexokinase-2 OS = Saccharomyces cerevisiae GN = HXK2 PE = 1 SV = 4 | 84.22% | 5.92% |
| Alcohol dehydrogenase 1 OS = Saccharomyces cerevisiae GN = ADH1 PE = 1 SV = 4 | 83.55% | 11.23% |
| Pyruvate carboxylase 1 OS = Saccharomyces cerevisiae GN = PYC1 PE = 1 SV = 2 | 82.51% | 7.74% |
| Protein GAL3 OS = Saccharomyces cerevisiae GN = GAL3 PE = 1 SV = 2 | 81.95% | 8.37% |
| Cell division control protein 48 OS = Saccharomyces cerevisiae GN = CDC48 PE = 1 SV = 3 | 80.99% | 2.13% |

TABLE 5

Proteins and PTMs specifically associating with GAL1 chromatin isolated from cells cultured in glucose. Proteins and histone posttranslational modifications listed are greater than two standard deviations from the non-specific threshold (56.18% Light).

| Protein Name | % Light Glucose | Stdev Glucose |
|---|---|---|
| Histone H3K36me3 | 100.00% | 0.00% |
| Glucose-6-phosphate isomerase OS = Saccharomyces cerevisiae GN = PGI1 PE = 1 SV = 3 | 66.33% | 12.98% |
| Magnesium-activated aldehyde dehydrogenase, cytosolic OS = Saccharomyces cerevisiae GN = ALD6 PE = 1 SV = 4 | 58.78% | 9.50% |
| Phosphoglycerate mutase 1 OS = Saccharomyces cerevisiae GN = GPM1 PE = 1 SV = 3 | 58.62% | 6.39% |
| Plasma membrane ATPase 1 OS = Saccharomyces cerevisiae GN = PMA1 PE = 1 SV = 2 | 58.47% | 6.81% |
| Cystathionine gamma-lyase OS = Saccharomyces cerevisiae GN = CYS3 PE = 1 SV = 2 | 58.10% | 3.72% |
| Enolase 1 OS = Saccharomyces cerevisiae GN = ENO1 PE = 1 SV = 2 | 57.88% | 2.93% |
| Enolase 2 OS = Saccharomyces cerevisiae GN = ENO2 PE = 1 SV = 2 | 57.40% | 2.33% |

TABLE 5-continued

Proteins and PTMs specifically associating with GAL1 chromatin isolated from cells cultured in glucose. Proteins and histone posttranslational modifications listed are greater than two standard deviations from the non-specific threshold (56.18% Light).

| Protein Name | % Light Glucose | Stdev Glucose |
|---|---|---|
| Heat shock protein SSA4 OS = *Saccharomyces cerevisiae* GN = SSA4 PE = 1 SV = 3 | 56.99% | 4.82% |
| Cell division control protein 48 OS = *Saccharomyces cerevisiae* GN = CDC48 PE = 1 SV = 3 | 56.59% | 4.13% |
| Hexokinase-2 OS = *Saccharomyces cerevisiae* GN = HXK2 PE = 1 SV = 4 | 56.50% | 3.43% |
| Fatty acid synthase subunit alpha OS = *Saccharomyces cerevisiae* GN = FAS2 PE = 1 SV = 2 | 56.19% | 6.29% |

TABLE 6

TAL protein DNA-binding specificity. ChIP was performed for the TAL-PrA used in this study and relative genomic binding was measured with qPCR at each sequence listed below.
Real time qPCR primers were used to amplify regions containing the indicated sequences and enrichment of each was measured relative to ACT1. The standard error of three analyses is shown. The first listed DNA sequence at GAL1 (highlighted gray) was used to design the TAL protein. A BLAST search was used to identify the next five closest binding sites in the *S. cerevisiae* genome. Mismatches of these five sequences relative to the GAL1 sequence are shown in bold.

| Sequence | Chromosome | Coordinates | Closest Gene | Locus tag | ChIP-qPCR for TAL-PrA binding Relative to Actin |
|---|---|---|---|---|---|
| GGGGTAATTAATCAGCGA | ChrII | 278829-278846 | GAL1 | YBR020W, promoter region | 6.14 ± 0.28 |
| GGGGTAATTAATCATTTT | ChrIV | 823079-823066 | SCC2 | YDR180W | 0.65 ± 0.06 |
| TTATACATTAATCAGCGA | ChrXV | 18844-18855 | ENB1 | between YOL159C and YOL158C | 1.34 ± 0.13 |
| GGGGTAATTAATGTAAAT | ChrXIV | 614716-614705 | IDP3 | YNL009W, promoter region | 0.94 ± 0.46 |
| AAATTAATCAGCGGTGAC | ChrIX | 88064-88053 | REV7 | YIL139C | 0.77 ± 0.27 |
| GGGGTAATTAAAATTTCT | ChrXVI | 94211-94221 | IQG1 | YPL242C | 0.76 ± 0.10 |

TABLE 7

Significant proteins (>2-fold enriched) identified with GAL1 promoter chromatin from cells grown in galactose-containing media. The top 10% of proteins that are >15-fold enriched are highlighted in gray.

| Proteins | | Molecular Weight | Spectral Counts TAL-PrA | Spectral Counts Wild type |
|---|---|---|---|---|
| Plasma membrane ATPase 1 OS = *Saccharomyces cerevisiae* GN = PMA1 PE = 1 SM = 2 | PMA1_YEAST | 99,621.60 | 558 | 0 |
| Transposon Ty1-H Gag-Pol polyprotein OS = *Saccharomyces cerevisiae* GN = TY1B-H PE = 1 SV = 1 | YH11B_YEAST (+2) | 202,825.20 | 273 | 0 |
| ATP-dependent RNA helicase DED1 OS = *Saccharomyces cerevisiae* (strain YJM789) GN = DED1 PE = 3 SV = 1 | DED1_YEAS7 (+1) | 65,554.50 | 261 | 0 |
| Protein TIF31 OS = *Saccharomyces cerevisiae* GN = TIF31 PE = 1 SV = 1 | TIF31 YEAST | 145,171.10 | 226 | 0 |
| Protein URA1 OS = *Saccharomyces cerevisiae* GN = URA2 PE = 1 SM = 4 | PYR1_YEAST | 245,129.90 | 1356 | 3 |
| Elongation factor 3B OS = *Saccharomyces cerevisiae* GN = HEF3 PE = 1 SV = 2 | EF3B_YEAST | 115,871.60 | 220 | 0 |
| Transposon Ty1-OL Gag polyprotein OS = *Saccharomyces cerevisiae* GN = TY1A-OL PE = 1 SV = 1 | YO11A_YEAST | 49,006.10 | 216 | 0 |

TABLE 7-continued

| Description | ID | MW | Score | — |
|---|---|---|---|---|
| 40S ribosomal protein S1-B OS = *Saccharomyces cerevisiae* (strain RM11-1a) GN = RPS1B PE = 3 SV = 1 | RS3A2_YEAS1 (+3) | 28,812.90 | 204 | 0 |
| 40S ribosomal protein S1-A OS = *Saccharomyces cerevisiae* (strain RM11-1a) GN = RPS1B PE = 3 SV = 1 | RS3A1_YEAS1 (+4) | 28,743.60 | 189 | 0 |
| Transposon Ty1-DR3 Gag polyprotein OS = *Saccharomyces cerevisiae* GN = TY1A-DR3 PE = 1 SV = 1 | YD12A_YEAST | 49,187.40 | 188 | 0 |
| Galactose transporter OS = *Saccharomyces cerevisiae* GN = GAL2 PE = 1 SV = 3 | GAL2_YEAST | 63,627.00 | 183 | 0 |
| Argininosuccinate synthase OS = *Saccharomyces cerevisiae* GN = ARG1 PE = 1 SV = 2 | ASSY_YEAST | 46,941.00 | 177 | 0 |
| Pleiotropic ABC efflux transporter of multiple drugs OS = *Saccharomyces cerevisiae* GN = PDR5 PE = 1 SV = 1 | PDR5_YEAST | 170,444.10 | 152 | 0 |
| 1,3-beta-glucan synthase component FKS1 OS = *Saccharomyces cerevisiae* GN = FKS1 PE = 1 SV = 2 | FKS1_YEAST | 214,859.40 | 151 | 0 |
| Heat shock protein SSC3, mitochondrial OS = *Saccharomyces cerevisiae* GN = ECM10 PE = 1 SV = 1 | HSP7E_YEAST | 70,086.90 | 150 | 0 |
| Pyruvate decarboxylase isozyme 3 OS = *Saccharomyces cerevisiae* GN = PDC6 PE = 1 SV = 3 | PDC6_YEAST | 61,582.40 | 150 | 0 |
| Nuclear segregation protein BFR1 OS = *Saccharomyces cerevisiae* GN = BFR1 PE = 1 SV = 1 | BFR1_YEAST | 54,641.70 | 137 | 0 |
| 60S ribosomal protein L18 OS = *Saccharomyces cerevisiae* GN = RPL18A PE = 1 SV = 1 | RL18_YEAST | 20,563.70 | 129 | 0 |
| 40S ribosomal protein S2 OS = *Saccharomyces cerevisiae* GN = RPS2 PE = 1 SV = 3 | RS2_YEAST | 27,450.20 | 126 | 0 |
| 1,3-beta-glucan synthase component GSC2 OS = *Saccharomyces cerevisiae* GN = GSC2 PE = 1 SV = 2 | FKS2_YEAST | 216,998.10 | 126 | 0 |
| 6-phosphogluconate dehydrogenase, decarboxylating 2 OS = *Saccharomyces cerevisiae* GN = GND2 PE = 1 SV = 1 | 6PGD2_YEAST | 53,925.30 | 118 | 0 |
| High-affinity hexose transporter HXT6 OS = *Saccharomyces cerevisiae* GN = HXT7 PE = 1 SV = 1 | HXT7_YEAST | 62,736.00 | 108 | 0 |
| Protein GAL3 OS = *Saccharomyces cerevisiae* GN = GAL3 PE = 1 SV = 2 | GAL3_YEAST | 58,130.40 | 107 | 0 |
| ATP-dependent RNA helicase MSS116, mitochondrial OS = *Saccharomyces cerevisiae* GN = MSS116 PE = 1 SV = 1 | MS116_YEAST | 76,272.50 | 105 | 0 |
| Probable cation-transporting ATPase 1 OS = *Saccharomyces cerevisiae* GN = SPF1 PE = 1 SV = 1 | ATC6_YEAST | 135,274.80 | 98 | 0 |
| High-affinity hexose transporter HXT6 OS = *Saccharomyces cerevisiae* GN = HXT6 PE = 1 SV = 2 | HXT6_YEAST | 62,706.00 | 98 | 0 |
| Eukaryotic translation initiation factor 5B OS = *Saccharomyces cerevisiae* GN = FUN12 PE = 1 SV = 2 | IF2P_YEAST | 112,271.50 | 98 | 0 |

TABLE 7-continued

| | | | | |
|---|---|---|---|---|
| DNA-directed RNA polymerase II subunit RPB1 OS = Saccharomyces cerevisiae GN = RPB1 PE = 1 SV = 2 | RPB1_YEAST | 191,615.10 | 96 | 0 |
| 1,3-beta-glucanosyltransferase GAS1 OS = Saccharomyces cerevisiae GN = GAS1 PE = 1 SV = 2 | GAS1_YEAST | 59,583.20 | 94 | 0 |
| Eukaryotic translation initiation factor 3 subunit B OS = Saccharomyces cerevisiae (strain YJM789) GN = PRT1 PE = 3 SV = 1 | EIF3B_YEAS7 | 88,131.50 | 93 | 0 |
| Phosphoglucomutase-1 OS = Saccharomyces cerevisiae GN = PGM1 PE = 1 SV = 1 | PGM1_YEAST | 63,114.70 | 91 | 0 |
| T-complex protein 1 subunit gamma OS = Saccharomyces cerevisiae GN = CCT3 PE = 1 SV = 2 | TCPG_YEAST | 58,814.70 | 90 | 0 |
| FACT complex subunit SPT16 OS = Saccharomyces cerevisiae GN = SPT16 PE = 1 SV = 1 | SPT16_YEAST | 118,636.00 | 88 | 0 |
| ATP-dependent RNA helicase DBP1 OS = Saccharomyces cerevisiae (strain YJM789) GN = DBP1 PE = 3 SV = 1 | DBP1_YEAS7 (+1) | 67,992.10 | 87 | 0 |
| Dihydrolipoyllysine-residue acetyltransferase component of pyruvate dehydrogenase complex, mitochondrial OS = Saccharomyces cerevisiae GN = PDA2 PE = 1 SV = 1 | ODP2_YEAST | 51,819.70 | 87 | 0 |
| Clathrin heavy chain OS = Saccharomyces cerevisiae GN = CHC1 PE = 1 SV = 1 | CLH_YEAST | 187,243.20 | 173 | 1 |
| 40S ribosomal protein S8 OS = Saccharomyces cerevisiae GN = RPS8A PE = 1 SV = 3 | RS8_YEAST | 22,490.40 | 86 | 0 |
| DNA-directed RNA polymerase II subunit RPB2 OS = Saccharomyces cerevisiae GN = RPB2 PE = 1 SV = 2 | RPB2_YEAST | 138,757.20 | 85 | 0 |
| Glutamine synthetase OS = Saccharomyces cerevisiae GN = GLN1 PE = 1 SV = 2 | GLNA_YEAST | 41,767.10 | 80 | 0 |
| Mitochondrial import receptor subunit TOM40 OS = Saccharomyces cerevisiae GN = TOM40 PE = 1 SV = 1 | TOM40_YEAST | 42,039.40 | 79 | 0 |
| C-1-tetrahydrofolate synthase, cytoplasmic OS = Saccharomyces cerevisiae GN = ADE3 PE = 1 SV = 1 | C1TC_YEAST | 102,207.30 | 76 | 0 |
| rNA 2'-O-methyltransferase fibrillarin OS = Saccharomyces cerevisiae GN = NOP1 PE = 1 SV = 1 | FBRL_YEAST | 34,365.50 | 75 | 0 |
| Protein SCP160 OS = Saccharomyces cerevisiae GN = SCP160 PE = 1 SV = 3 | SC160_YEAST | 134,813.70 | 300 | 2 |
| Protein transport protein SEC23 OS = Saccharomyces cerevisiae GN = SEC23 PE = 1 SV = 1 | SEC23_YEAST | 85,387.60 | 73 | 0 |
| Nucleolar protein 56 OS = Saccharomyces cerevisiae GN = NOP56 PE = 1 SV = 1 | NOP56_YEAST | 56,867.30 | 73 | 0 |
| Orotidine 5'-phosphate decarboxylase OS = Saccharomyces cerevisiae GN = URA3 PE = 1 SV = 2 | PYRF_YEAST | 29,240.40 | 71 | 0 |
| Homocitrate synthase, cytosolic isozyme OS = Saccharomyces cerevisiae GN = LYS20 PE = 1 SV = 1 | HOSC_YEAST | 47,100.30 | 68 | 0 |

TABLE 7-continued

| | | | | |
|---|---|---|---|---|
| External NADH-ubiquinone oxidoreductase 1, mitochondrial OS = Saccharomyces cerevisiae GN = NDE1 PE = 1 SV = 1 | NDH1_YEAST | 62,776.50 | 67 | 0 |
| Eukaryotic translation initiation factor 3 subunit C OS = Saccharomyces cerevisiae (strain YJM789) GN = NIP1 PE = 3 SV = 1 | EIF3C_YEAS7 | 93,225.20 | 67 | 0 |
| Zuotin OS = Saccharomyces cerevisiae GN = ZUO1 PE = 1 SV = 1 | ZUO1_YEAST | 49,021.50 | 66 | 0 |
| Trehalose-phosphatase OS = Saccharomyces cerevisiae GN = TPS2 PE = 1 SV = 3 | TPS2_YEAST | 102,978.90 | 63 | 0 |
| Saccharopepsin OS = Saccharomyces cerevisiae GN = PEP4 PE = 1 SV = 1 | RRP5_YEAST | 193,141.40 | 63 | 0 |
| rRNA biogenesis protein RRP5 OS = Saccharomyces cerevisiae GN = RRP5 PE = 1 SV = 1 | RRP5_YEAST | 193,141.40 | 63 | 0 |
| cAMP-dependent protein kinase regulatory subunit OS = Saccharomyces cerevisiae GN = BCY1 PE = 1 SV = 4 | KAPR_YEAST | 47,220.30 | 62 | 0 |
| Galactokinase OS = Saccharomyces cerevisiae GN = GAL1 PE = 1 SV = 4 | GAL1_YEAST | 57,945.00 | 1350 | 11 |
| Probable 2-methylcitrate dehydratase OS = Saccharomyces cerevisiae GN = PDH1 PE = SV = 1 | PRPD_YEAST | 57,685.70 | 61 | 0 |
| 2-isopropylmalate synthase 2, mitochondrial OS = Saccharomyces cerevisiae GN = LEU9 PE = SV = 1 | LEU9_YEAST | 67,201.00 | 61 | 0 |
| NADH-cytochrome b5 reductase 2 OS = Saccharomyces cerevisiae (strain YJM789) GN = MCR1 PE = 2 SV = 1 | MCR1_YEAS7 (+1) | 34,109.10 | 61 | 0 |
| 6,7-dimethyl-8-ribitylumazine synthase OS = Saccharomyces cerevisiae GN = RIB4 PE = 1 SV = 2 | RIB4_YEAST | 18,555.70 | 60 | 0 |
| N-(5'-phosphoribosyl)anthranilate isomerase OS = Saccharomyces cerevisiae GN = TRP1 PE = 1 SV = 2 | TRPF_YEAST | 24,144.90 | 60 | 0 |
| Glutamate synthase [NADH] OS = Saccharomyces cerevisiae GN = GLT1 PE = 1 SV = 2 | GLT1_YEAST | 238,108.30 | 58 | 0 |
| Nuclear localization sequence-binding protein OS = Saccharomyces cerevisiae GN = NSR1 PE = 1 SV = 1 | NSR1_YEAST | 44,536.10 | 55 | 0 |
| V-type proton ATPase subunit a, vacuolar isoform OS = Saccharomyces cerevisiae GN = VPH1 PE = 1 SV = 3 | VPH1_YEAST | 95,533.10 | 55 | 0 |
| 4-aminobutyrate aminotransferase OS = Saccharomyces cerevisiae GN = UGA1 PE = 1 SV = 2 | GATA_YEAST | 52,948.60 | 55 | 0 |
| Dihydroorotate dehydrogenase OS = Saccharomyces cerevisiae GN = URA1 PE = 1 SV = 1 | PYRD_YEAST | 34,802.70 | 54 | 0 |
| Eukaryotic translation initiation factor 2A OS = Saccharomyces cerevisiae GN = YGR054W PE = 1 SV = 1 | EIF2A_YEAST | 71,307.10 | 54 | 0 |
| 60S ribosomal protein L32 OS = Saccharomyces cerevisiae GN = RPL32 PE = SV = 1 | RL32_YEAST | 14,771.80 | 53 | 0 |
| 60S ribosomal protein L15-A OS = Saccharomyces cerevisiae GN = RPL15A PE = 1 SV = 3 | RL15A_YEAST | 24,422.60 | 105 | 1 |
| Mitochondrial import receptor subunit TOM70 OS = Saccharomyces cerevisiae (strain YJM789) GN = TOM70 PE = 3 SV = 1 | TOM70_YEAS7 (+1) | 70,127.70 | 51 | 0 |
| Mitochondrial acidic protein MAM33 OS = Saccharomyces cerevisiae GN = MAM33 PE = 1 SV = 1 | MAM33_YEAST | 30,132.70 | 51 | 0 |
| H/ACA ribonucleoprotein complex subunit 4 OS = Saccharomyces cerevisiae GN = CBF5 PE = 1 SV = 1 | CBF5_YEAST | 54,706.30 | 51 | 0 |
| 60S ribosomal protein L8-A OS = Saccharomyces cerevisiae GN = RPL8A PE = 1 SV = 4 | RL8A_YEAST | 28,125.50 | 201 | 2 |
| Eukaryotic translation initiation factor 2 subunit alpha OS = Saccharomyces cerevisiae GN = SUI2 PE = SV = 1 | IF2A_YEAST | 34,718.70 | 50 | 0 |
| NADPH--cytochrome P450 reductase OS = Saccharomyces cerevisiae GN = NCP1 PE = 1 SV = 3 | NCPR_YEAST | 76,774.20 | 50 | 0 |
| Nucleolar protein 58 OS = Saccharomyces cerevisiae (strain YJM789) GN = NOP58 PE = 3 SV = 1 | NOP58_YEAS7 (+1) | 56,959.80 | 98 | 1 |
| 60S ribosomal protein L14-B OS = Saccharomyces cerevisiae GN = RPL14B PE = 1 SV = 1 | RL148B_YEAST | 15,153.20 | 97 | 1 |
| Pentafunctional AROM polypeptide OS = Saccharomyces cerevisiae GN = ARO1 PE = 1 SV = 1 | ARO1_YEAST | 174,758.00 | 97 | 1 |
| 60S ribosomal protein L8-B OS = Saccharomyces cerevisiae GN = RPL8B PE = 1 SV = 3 | RL8B_YEAST | 28,112.80 | 193 | 2 |
| GTP-binding protein RHO1 OS = Saccharomyces cerevisiae GN = RHO1 PE = 1 SV = 3 | RHO1_YEAST | 23,152.00 | 48 | 0 |
| Invertase 2 OS = Saccharomyces cerevisiae GN = SUC2 PE = 1 SV = 1 | INV2_YEAST (+1) | 60,641.00 | 48 | 0 |
| Squalene synthase OS = Saccharomyces cerevisiae GN = ERG9 PE = 1 SV = 2 | FDFT_YEAST | 51,722.50 | 48 | 0 |

TABLE 7-continued

| Description | ID | Value | Count | Flag |
|---|---|---|---|---|
| Eukaryotic translation initiation factor 3 subunit B OS = Saccharomyces cerevisiae GN = PRT1 PE = 1 SV = 1 | EIF3B_YEAST | 88,131.50 | 95 | 1 |
| Cytochrome c iso-2 OS = Saccharomyces cerevisiae GN = CYC7 PE-1 SV = 1 | CYC7_YEAST | 12,532.80 | 47 | 0 |
| ATP-dependent permease PDR15 OS = Saccharomyces cerevisiae GN = PDR15 PE = 1 SV = 1 | PDR15_YEAST | 172,261.80 | 47 | 0 |
| 60S ribosomal protein L28 OS = Saccharomyces cerevisiae GN = RPL28 PE = 1 SV = 2 | RL28_YEAST | 16,722.90 | 46 | 0 |
| Methionyl-tRNA synthetase, cytoplasmic OS = Saccharomyces cerevisiae GN = MES1 PE = 1 SV = 4 | SYMC_YEAST | 85,680.90 | 46 | 0 |
| Eukaryotic translation initiation factor 3 subunit G OS = Saccharomyces cerevisiae GN = TIF35 PE = 1 SV = 1 | EIF3G_YEAST | 30,501.60 | 45 | 0 |
| General transcriptional corepressor TUP1 OS = Saccharomyces cerevisiae GN = TUP1 PE = 1 SV-2 | TUP1_YEAST | 78,307.20 | 45 | 0 |
| Heat shock protein 42 OS = Saccharomyces cerevisiae GN = HSP42 PE = 1 SV = 1 | HSP42_YEAST | 42,817.50 | 44 | 0 |
| 60S ribosomal protein L15-B OS = Saccharomyces cerevisiae GN = RPL15B PE = 1 SV = 2 | RL15B_YEAST | 24,422.60 | 84 | 1 |
| 40S ribosomal protein S23 OS = Saccharomyces cerevisiae GN = RPS23A PE = 1 SV = 1 | RS23_YEAST | 16,038.30 | 42 | 0 |
| T-complex protein 1 subunit theta OS = Saccharomyces cerevisiae GN = CCT8 PE = 1 SV = 1 | TCPQ_YEAST | 61,663.60 | 42 | 0 |
| 26S protease regulatory subunit 8 homolog OS = Saccharomyces cerevisiae GN = RPT6 PE = 1 SV = 4 | PRS8_YEAST | 45,272.60 | 41 | 0 |
| SDO1-like protein YHR087W OS = Saccharomyces cerevisiae GN = YHR087W PE = 1 SV = 1 | SDO1L_YEAST | 12,009.80 | 41 | 0 |
| Mitochondrial escape protein 2 OS = Saccharomyces cerevisiae GN = YME2 PE = 1 SV = 1 | YME2_YEAST | 96,692.20 | 40 | 0 |
| Alpha-soluble NSF attachment protein SEC63 OS = Saccharomyces cerevisiae GN = SEC17 PE = 1 SV = 4 | SEC17_YEAST | 32,804.40 | 40 | 0 |
| Protein translocation protein SEC63 OS = Saccharomyces cerevisiae GN = SEC63 PE = 1 SV = 2 | SEC63_YEAST | 75,348.10 | 40 | 0 |
| Delta-1-pyrroline-5-carboxylate dehydrogenase, mitochondrial OS = Saccharomyces cerevisiae GN = PUT2 PE = 1 SV = 2 | PUT2_YEAST | 64,437.50 | 40 | 0 |
| Polyamine N-acetyltransferase 1 OS = Saccharomyces cerevisiae GN = PAA1 PE = 1 SV = 1 | PAA1_YEAST | 21,948.70 | 79 | 1 |
| 40S ribosomal protein S22-B OS = Saccharomyces cerevisiae GN = RPS22B PE = 1 SV = 3 | RS22B_YEAST | 14,626.50 | 79 | 1 |
| Phosphoinositide phosphatase SAC1 OS = Saccharomyces cerevisiae GN = SAC1 PE = 1 SV = 1 | SAC1_YEAST | 71,125.90 | 38 | 0 |
| 40S ribosomal protein S26-A OS = Saccharomyces cerevisiae GN = RPS26A PE = 1 SV = 1 | RS26A_YEAST | 13,505.00 | 38 | 0 |
| 26S proteasome regulatory subunit RPN2 OS = Saccharomyces cerevisiae GN = RPN2 PE = 1 SV = 4 | RPN2_YEAST | 104,237.00 | 76 | 1 |
| Translational activator GCN1 OS = Saccharomyces cerevisiae GN = GCN1 PE = 1 SV = 1 | GCN1_YEAST | 296,710.20 | 38 | 0 |
| Dolichyl-diphosphooligosaccharide--protein glycosyltransferase subunit STT3 OS = Saccharomyces cerevisiae GN = STT3 PE = 1 SV = 2 | STT3_YEAST | 81,532.90 | 38 | 0 |
| 1,3-beta-glucanosyltransferase GAS5 OS = Saccharomyces cerevisiae GN = GAS5 PE = 1 SV = 1 | GAS5_YEAST | 51,870.70 | 38 | 0 |
| Acyl-CoA-binding protein OS = Saccharomyces cerevisiae GN = ACB1 PE = 1 SV = 3 | ACBP_YEAST | 10,061.80 | 38 | 0 |
| Tricalbin-1 OS = Saccharomyces cerevisiae GN = TCB1 PE = 1 SV = 1 | TCB1_YEAST | 133,581.30 | 37 | 0 |
| NADP-specific glutamate dehydrogenase 2 OS = Saccharomyces cerevisiae GN = GDH3 PE = 1 SV = 1 | DHE5_YEAST | 49,627.60 | 37 | 0 |
| Dolichyl-phosphate-mannose--protein mannosyltransferase 1 OS = Saccharomyces cerevisiae GN = PMT1 PE = 1 SV = 1 | PMT1_YEAST | 92,678.00 | 37 | 0 |
| Mitochondrial import inner membrane translocase subunit TIM10 OS = Saccharomyces cerevisiae GN = MRS11 PE = 1 SV = 1 | TIM10_YEAST | 10,304.60 | 37 | 0 |
| Ornithine carbamoyltransferase OS = Saccharomyces cerevisiae GN = ARG3 PE = 1 SV = 1 | OTC_YEAST | 37,846.40 | 37 | 0 |
| Putative magnesium-dependent phosphatase YER134C OS = Saccharomyces cerevisiae GN = YER134C PE = 1 SV = 1 | MGDP1_YEAST | 20,442.40 | 36 | 0 |
| Eukaryotic translation initiation factor 4B OS = Saccharomyces cerevisiae GN = TIF3 PE = 1 SV = 1 | IF4B_YEAST | 48,522.50 | 36 | 0 |
| Mitochondrial escape protein 2 OS = Saccharomyces cerevisiae (strain YJM789) GN = YME2 PE = 3 SV = 1 | YME2_YEAS7 | 96,662.30 | 36 | 0 |
| Vesicle-associated membrane protein-associated protein SCS2 OS = Saccharomyces cerevisiae GN = SCS2 PE = 1 SV = 3 | SCS2_YEAST | 26,924.80 | 36 | 0 |
| Importin beta SMX1 OS = Saccharomyces cerevisiae GN = SXM1 PE = 1 SV = 1 | SXM1_YEAST | 108,410.90 | 36 | 0 |
| Inorganic phosphate transport protein PHO88 OS = Saccharomyces cerevisiae GN = PHO88 PE = 1 SV = 1 | PHO88_YEAST | 21,138.00 | 36 | 0 |
| Transcription elongation factor SPT6 OS = Saccharomyces cerevisiae GN = SPT6 PE = 1 SV = 2 | SPT6_YEAST | 168,298.50 | 71 | 1 |
| T-complex protein 1 subunit delta OS = Saccharomyces cerevisiae GN = CCT4 PE = 1 SV = 2 | TCPD_YEAST | 57,605.60 | 35 | 0 |
| 5'-3' exoribonuclease 1 OS = Saccharomyces cerevisiae GN = KEM1 PE = 1 SV = 1 | XRN1_YEAST | 175,468.00 | 70 | 1 |

TABLE 7-continued

| Description | ID | MW | Col4 | Col5 |
|---|---|---|---|---|
| Fumarate reductase OS = Saccharomyces cerevisiae GN = YEL047C PE = 1 SV = 1 | FRDS_YEAST | 50,845.00 | 35 | 0 |
| 3-hydroxy-3-methylglutaryl-coenzyme A reductase 1 OS = Saccharomyces cerevisiae GN = HMG1 PE = 1 SV = 1 | HMDH1_YEAST | 115,629.10 | 34 | 0 |
| 26S proteasome regulatory subunit RPN9 OS = Saccharomyces cerevisiae GN = RPN9 PE = 1 SV = 1 | RPN9_YEAST | 45,785.80 | 34 | 0 |
| Dolichyl-phosphate-mannose--protein mannosyltransferase 2 OS = Saccharomyces cerevisiae GN = PMT2 PE = 1 SV = 2 | PMT2_YEAST | 86,872.80 | 34 | 0 |
| Bifunctional protein GAL10 OS = Saccharomyces cerevisiae GN = GAL10 PE = 1 SV = 2 | GAL10_YEAST | 78,197.30 | 939 | 14 |
| ATP-dependent bile acid permease OS = Saccharomyces cerevisiae GN = YBT1 PE = 1 SV = 2 | YBT1_YEAST | 189,172.20 | 33 | 0 |
| Saccharopine dehydrogenase [NAD+, L-lysine-forming] OS = Saccharomyces cerevisiae GN = LYS1 PE = 1 SV = 3 | LYS1_YEAST | 41,466.20 | 33 | 0 |
| Coatomer subunit gamma OS = Saccharomyces cerevisiae GN = SEC21 PE = 1 SV = 2 | COPG_YEAST | 104,836.20 | 32 | 0 |
| Cell division control protein 53 OS = Saccharomyces cerevisiae GN = CDC53 PE = 1 SV = 1 | CDC53_YEAST | 93,949.60 | 32 | 0 |
| Rotenone-insensitive NADH-ubiquinone oxidoreductase, mitochondrial OS = Saccharomyces cerevisiae GN = NDI1 PE = 1 SV = 1 | NDI1_YEAST | 57,252.80 | 32 | 0 |
| Argininosuccinate lyase OS = Saccharomyces cerevisiae GN = ARG4 PE = 1 SV = 2 | ARLY_YEAST | 51,991.40 | 32 | 0 |
| Zinc finger protein GIS2 OS = Saccharomyces cerevisiae GN = GIS2 PE = 1 SV = 1 | GIS2_YEAST | 17,102.60 | 31 | 0 |
| Protein kinase MCK1 OS = Saccharomyces cerevisiae GN = MCK1 PE = 1 SV = 1 | MCK1_YEAST | 43,137.90 | 31 | 0 |
| Malate dehydrogenase, peroxisomal OS = Saccharomyces cerevisiae GN = MDH3 PE = 1 SV = 3 | MDHP_YEAST | 37,187.20 | 31 | 0 |
| T-complex protein 1 subunit zeta OS = Saccharomyces cerevisiae GN = CCT6 PE = 1 SV = 1 | TCPZ_YEAST | 59,925.90 | 31 | 0 |
| ATP-dependent RNA helicase DBP2 OS = Saccharomyces cerevisiae GN = DBP2 PE = 1 SV = 1 | DBP2_YEAST | 61,001.20 | 30 | 0 |
| Cytochrome B pre-mRNA-processing protein 6 OS = Saccharomyces cerevisiae GN = CBP6 PE = 1 SV = 1 | CBP6_YEAST | 18,679.70 | 30 | 0 |
| Protein DCS2 OS = Saccharomyces cerevisiae GN = DCS2 PE = 1 SV = 3 | DCS2_YEAST | 40,941.80 | 30 | 0 |
| Eukaryotic translation initiation factor 3 subunit A OS = Saccharomyces cerevisiae GN = TIF32 PE = 1 SV = 1 | EIF3A_YEAST | 110,348.50 | 176 | 3 |
| Glucose-signaling factor 2 OS = Saccharomyces cerevisiae GN = GSF2 PE = 1 SV = 1 | GSF2_YEAST | 45,872.50 | 58 | 1 |
| Glycerol-3-phosphate dehydrogenase [NAD+] 2, mitochondrial OS = Saccharomyces cerevisiae GN = GPD2 PE = 1 SV = 2 | GPD2_YEAST | 49,422.10 | 29 | 0 |
| Prohibitin-2 OS = Saccharomyces cerevisiae GN = PHB2 PE = 1 SV = 2 | PHB2_YEAST | 34,407.20 | 29 | 0 |
| 40S ribosomal protein S29-A OS = Saccharomyces cerevisiae GN = RPS29A PE = 1 SV = 3 | RS29A_YEAST | 6,660.70 | 29 | 0 |
| DNA-directed RNA polymerase I subunit RPA1 OS = Saccharomyces cerevisiae GN = RPA1 PE = 1 SV = 2 | RPA1_YEAST | 186,435.30 | 29 | 0 |
| Protein transport protein SEC24 OS = Saccharomyces cerevisiae GN = SEC24 PE = 1 SV = 1 | SEC24_YEAST | 103,638.70 | 29 | 0 |
| Carboxypeptidase Y OS = Saccharomyces cerevisiae GN = PRC1 PE = 1 SV = 1 | CBPY_YEAST | 59,803.60 | 28 | 0 |
| V-type proton ATPase subunit d OS = Saccharomyces cerevisiae GN = VMA6 PE = 1 SV = 2 | VAOD_YEAST | 39,792.40 | 28 | 0 |
| Uncharacterized protein YJL171C OS = Saccharomyces cerevisiae GN = YJL171C PE = 1 SV = 1 | YJR1_YEAST | 43,014.50 | 28 | 0 |
| Vacuolar protein sorting/targeting protein PEP1 OS = Saccharomyces cerevisiae GN = PEP1 PE = 1 SV = 1 | PEP1_YEAST | 177,783.50 | 28 | 0 |
| FACT complex subunit POB3 OS = Saccharomyces cerevisiae GN = POB3 PE = 1 SV = 1 | POB3_YEAST | 62,995.20 | 28 | 0 |
| Uncharacterized mitochondrial membrane protein FMP10 OS = Saccharomyces cerevisiae GN = FMP10 PE = 1 SV = 1 | FMP10_YEAST | 27,698.90 | 28 | 0 |
| RNA annealing protein YRA1 OS = Saccharomyces cerevisiae GN = YRA1 PE = 1 SV = 2 | YRA1_YEAST | 24,956.30 | 27 | 0 |
| Mitochondrial outer membrane protein OM45 OS = Saccharomyces cerevisiae GN = OM45 PE = 1 SV = 2 | OM45_YEAST | 44,582.00 | 27 | 0 |
| Mitochondrial import receptor subunit TOM5 OS = Saccharomyces cerevisiae GN = TOM5 PE = 1 SV = 1 | TOM5_YEAST | 5,984.70 | 27 | 0 |
| T-complex protein 1 subunit alpha OS = Saccharomyces cerevisiae GN = TCP1 PE = 1 SV = 2 | TCPA_YEAST | 60,482.30 | 27 | 0 |
| Eukaryotic translation initiation factor 1A OS = Saccharomyces cerevisiae GN = TIF11 PE = 1 SV = 1 | IF1A_YEAST | 17,435.70 | 26 | 0 |
| Protein MSN5 OS = Saccharomyces cerevisiae GN = MSN5 PE = 1 SV = 1 | MSN5_YEAST | 142,126.30 | 26 | 0 |
| Putative fatty aldehyde dehydrogenase HFD1 OS = Saccharomyces cerevisiae GN = HFD1 PE = 1 SV = 1 | HFD1_YEAST | 59,981.90 | 26 | 0 |
| Ergosterol biosynthetic protein 28 OS = Saccharomyces cerevisiae GN = ERG28 PE = 1 SV = 1 | ERG28_YEAST | 17,135.80 | 26 | 0 |
| Protein YRO2 OS = Saccharomyces cerevisiae GN = YRO2 PE = 1 SV = 1 | YRO2_YEAST | 38,721.30 | 26 | 0 |
| Methylene-fatty-acyl-phospholipid synthase OS = Saccharomyces cerevisiae GN = PEM2 PE = 1 SV = 1 | PEM2_YEAST | 23,151.10 | 26 | 0 |
| Protein MKT1 OS = Saccharomyces cerevisiae GN = MKT1 PE = 1 SV = 2 | MKT1_YEAST | 94,499.40 | 25 | 0 |
| Protein MRH1 OS = Saccharomyces cerevisiae GN = MRH1 PE = 1 SV = 1 | MRH1_YEAST | 36,192.40 | 25 | 0 |

TABLE 7-continued

| Description | ID | Mass | Col4 | Col5 |
|---|---|---|---|---|
| Eukaryotic translation initiation factor 2 subunit beta OS = *Saccharomyces cerevisiae* GN = SUI3 PE = 1 SV = 2 | IF2B_YEAST | 31,575.70 | 25 | 0 |
| Peroxiredoxin TSA2 OS = *Saccharomyces cerevisiae* GN = TSA2 PE = 1 SV = 3 | TSA2_YEAST | 21,615.40 | 24 | 0 |
| Endoplasmic reticulum vesicle protein 25 OS = *Saccharomyces cerevisiae* GN = ERV25 PE = 1 SV = 1 | TMEDA_YEAST | 24,106.40 | 24 | 0 |
| PKHD-type hydroxylase TPA1 OS = *Saccharomyces cerevisiae* GN = TPA1 PE = 1 SV = 1 | TPA1_YEAST | 74,044.60 | 24 | 0 |
| SED5-binding protein 3 OS = *Saccharomyces cerevisiae* GN = SFB3 PE = 1 SV = 1 | SFB3_YEAST | 103,953.30 | 24 | 0 |
| D-lactate dehydrogenase [cytochrome] 3 OS = *Saccharomyces cerevisiae* GN = DLD3 PE = 1 SV = 1 | DLD3_YEAST | 55,226.80 | 24 | 0 |
| Single-stranded nucleic acid-binding protein OS = *Saccharomyces cerevisiae* GN = DLD3 PE = 1 SV = 1 | SSBP1_YEAST | 32,989.90 | 47 | 1 |
| Protein CWH43 OS = *Saccharomyces cerevisiae* GN = CWH43 PE = 1 SV = 2 | CWH43_YEAST | 107,887.70 | 23 | 0 |
| T-complex protein 1 subunit eta OS = *Saccharomyces cerevisiae* GN = CCT7 PE = 1 SV = 1 | TCPH_YEAST | 59,737.10 | 23 | 0 |
| 26S protease regulatory subunit 6B homolog OS = *Saccharomyces cerevisiae* GN = RPT3 PE = 1 SV = 1 | PRS6B_YEAST | 47,971.50 | 23 | 0 |
| NADH-cytochrome b5 reductase 1 OS = *Saccharomyces cerevisiae* GN = CBR1 PE = 1 SV = 1 | NCB5R_YEAST | 31,494.80 | 23 | 0 |
| Glycogen debranching enzyme OS = *Saccharomyces cerevisiae* GN = GDB1 PE = 1 SV = 1 | GDE_YEAST | 174,978.70 | 46 | 1 |
| C-5 sterol desaturase OS = *Saccharomyces cerevisiae* GN = ERG3 PE = 1 SV = 1 | ERG3_YEAST | 42,731.70 | 23 | 0 |
| 13 kDa ribonucleoprotein-associated protein OS = *Saccharomyces cerevisiae* GN = SNU13 PE = 1 SV = 1 | SNU13_YEAST | 13,569.40 | 23 | 0 |
| UPF0202 protein KRE33 OS = *Saccharomyces cerevisiae* GN = KRE33 PE = 1 SV = 1 | KRE33_YEAST | 119,353.80 | 23 | 0 |
| Protein phosphatase PP2A regulatory subunit A OS = *Saccharomyces cerevisiae* GN = TPD3 PE = 1 SV = 2 | 2AAA_YEAST | 79,954.70 | 23 | 0 |
| Eukaryotic translation initiation factor 2 subunit gamma OS = *Saccharomyces cerevisiae* GN = GCD11 PE = 1 SV = 1 | IF2G_YEAST | 57,857.20 | 23 | 0 |
| Midasin OS = *Saccharomyces cerevisiae* GN = MDN1 PE = 1 SV = 1 | MDN1_YEAST | 559,323.50 | 23 | 0 |
| Galactose-1-phosphate uridyltransferase OS = *Saccharomyces cerevisiae* GN = GAL7 PE = 1 SV = 4 | GAL7_YEAST | 42,386.00 | 459 | 10 |
| UPF0121 membrane protein YLL023C OS = *Saccharomyces cerevisiae* GN = YLL0232C PE = 1 SV = 1 | YL023_YEAST | 32,187.70 | 22 | 0 |
| Phosphatidylinositol transfer protein PDR16 OS = *Saccharomyces cerevisiae* GN = PDR16 PE = 1 SV = 1 | PDR16_YEAST | 40,715.80 | 22 | 0 |
| 60S ribosomal protein L43 OS = *Saccharomyces cerevisiae* GN = RPL43A PE = 1 SV = 2 | RL43_YEAST | 10,090.80 | 22 | 0 |
| Arginine biosynthesis bifunctional protein ARG7, mitochondrial OS = *Saccharomyces cerevisiae* GN = ARG7 PE = 1 SV = 1 | ARGJ_YEAST | 47,850.20 | 22 | 0 |
| Probable family 17 glucosidase SCW4 OS = *Saccharomyces cerevisiae* GN = SCW4 PE = 1 SV = 1 | SCW4_YEAST | 40,172.20 | 22 | 0 |
| 26S protease subunit RPT4 OS = *Saccharomyces cerevisiae* GN = RPT4 PE = 1 SV = 4 | PRS10_YEAST | 49,410.10 | 22 | 0 |
| 60S ribosomal protein L3 OS = *Saccharomyces cerevisiae* GN = RPL3 PE = 1 SV = 4 | RL3_YEAST | 43,757.90 | 219 | 5 |
| Phosphoglucomutase-2 OS = *Saccharomyces cerevisiae* GN = PGM2 PE = 1 SV = 1 | PGM2_YEAST | 63,091.20 | 345 | 8 |
| Uncharacterized phosphatase YNL010W OS = *Saccharomyces cerevisiae* GN = YNL010W PE = 1 SV = 1 | YNB0_YEAST | 27,481.40 | 43 | 1 |
| Elongation factor 3A OS = *Saccharomyces cerevisiae* GN = YEF3 PE = 1 SV = 3 | EF3A_YEAST | 115,996.20 | 892 | 21 |
| Casein kinase II subunit alpha' OS = *Saccharomyces cerevisiae* GN = CKA2 PE = 1 SV = 2 | CSK22_YEAST | 39,405.00 | 21 | 0 |
| 54S ribosomal protein L12, mitochondrial OS = *Saccharomyces cerevisiae* GN = MNP1 PE = 1 SV = 1 | MNP1_YEAST | 20,650.80 | 21 | 0 |
| Nuclear protein SNF4 OS = *Saccharomyces cerevisiae* GN = SNF4 PE = 1 SV = 1 | SNF4_YEAST | 36,402.50 | 21 | 0 |
| Eukaryotic initiation factor 4F subunit p150 OS = *Saccharomyces cerevisiae* GN = TIF4631 PE = 1 SV = 2 | IF4F1_YEAST | 107,103.80 | 21 | 0 |
| Medium-chain fatty acid ethyl ester synthase/esterase 2 OS = *Saccharomyces cerevisiae* GN = EHT1 PE = 1 SV = 1 | MCFS2_YEAST | 51,256.90 | 21 | 0 |
| ABC transporter ATP-binding protein ARB1 OS = *Saccharomyces cerevisiae* GN = ARB1 PE = 1 SV = 1 | ARB1_YEAST | 68,379.50 | 21 | 0 |
| Cysteinyl-tRNA synthetase OS = *Saccharomyces cerevisiae* GN = YNL247W PE = 1 SV = 1 | SYC_YEAST | 87,533.90 | 21 | 0 |
| Protein TTP1 OS = *Saccharomyces cerevisiae* GN = TTP1 PE = 1 SV = 1 | TTP1_YEAST | 67,777.60 | 21 | 0 |
| 26S proteasome regulatory subunit RPN8 OS = *Saccharomyces cerevisiae* GN = RPN8 PE = 1 SV = 3 | RPN8_YEAST | 38,313.90 | 21 | 0 |
| NADH-cytochrome b5 reductase 1 OS = *Saccharomyces cerevisiae* (strain YJM789) GN = CBR1 PE = 2 SV = 2 | NCB5R_YEAS7 | 31,422.60 | 21 | 0 |
| ER membrane protein complex subunit 1 OS = *Saccharomyces cerevisiae* GN = EMC1 PE = 1 SV = 1 | EMC1_YEAST | 87,185.00 | 21 | 0 |
| Heat shock protein 78, mitochondrial OS = *Saccharomyces cerevisiae* GN = HSP78 PE = 1 SV = 2 | HSP78_YEAST | 91,340.80 | 292 | 7 |

TABLE 7-continued

| | | | | |
|---|---|---|---|---|
| Nuclear protein STH1/NPS1 OS = Saccharomyces cerevisiae GN = STH1 PE = 1 SV = 1 | STH1_YEAST | 156,750.60 | 20 | 0 |
| mRNA-binding protein PUF3 OS = Saccharomyces cerevisiae GN = PUF3 PE = 1 SV = 1 | PUF3_YEAST | 98,070.00 | 20 | 0 |
| Actin-interacting protein 1 OS = Saccharomyces cerevisiae GN = AIP1 PE = 1 SV = 1 | AIP1_YEAST | 67,326.00 | 20 | 0 |
| Cytochrome c iso-1 OS = Saccharomyces cerevisiae GN = CYC1 PE = 1 SV = 2 | CYC1_YEAST | 12,182.50 | 80 | 2 |
| CTP synthase 1 OS = Saccharomyces cerevisiae GN = URA7 PE = 1 SV = 2 | URA7_YEAST | 64,711.50 | 20 | 0 |
| Squalene monooxygenase OS = Saccharomyces cerevisiae GN = ERG1 PE = 1 SV = 2 | ERG1_YEAST | 55,127.20 | 20 | 0 |
| Putative aldehyde dehydrogenase-like protein YHR039C OS = Saccharomyces cerevisiae GN = MSC7 PE = 1 SV = 1 | MSC7_YEAST | 71,322.60 | 20 | 0 |
| Glucosamine-fructose-6-phosphate aminotransferase [isomerizing] OS = Saccharomyces cerevisiae GN = GFA1 PE = 1 SV = 4 | GFA1_YEAST | 80,048.70 | 78 | 2 |
| Uncharacterized GTP-binding protein OLA1 OS = Saccharomyces cerevisiae GN = OLA1 PE = 1 SV = 1 | OLA1_YEAST | 44,175.90 | 155 | 4 |
| Probable 1-acyl-sn-glycerol-3-phosphate acyltransferase OS = Saccharomyces cerevisiae GN = SLC1 PE = 1 SV = 1 | PLSC_YEAST | 33,887.80 | 19 | 0 |
| Sporulation-specific protein 21 OS = Saccharomyces cerevisiae GN = SPO21 PE = 1 SV = 1 | MPC70_YEAST | 69,881.80 | 19 | 0 |
| Cell division control protein 42 OS = Saccharomyces cerevisiae GN = CDC42 PE = 1 SV = 2 | CDC42_YEAST | 21,322.60 | 19 | 0 |
| Serine/threonine-protein phosphatase PP-Z2 OS = Saccharomyces cerevisiae GN = PPZ2 PE = 1 SV = 4 | PPZ2_YEAST | 78,494.20 | 19 | 0 |
| Putative mitochondrial carrier protein YHM1/SHM1 OS = Saccharomyces cerevisiae GN = YHM1 PE = 1 SV = 1 | YHM1_YEAST | 33,217.70 | 19 | 0 |
| 60S ribosomal protein L24-A OS = Saccharomyces cerevisiae GN = RPL24A PE = 1 SV = 1 | RL24A_YEAST | 17,614.40 | 38 | 1 |
| 60S ribosomal protein L35 OS = Saccharomyces cerevisiae GN = RPL35A PE = 1 SV = 1 | RL35_YEAST | 13,910.20 | 38 | 1 |
| Mitochondrial respiratory chain complexes assembly protein RCA1 OS = Saccharomyces cerevisiae GN = RCA1 PE = 1 SV = 1 | RCA1_YEAST | 93,280.10 | 19 | 0 |
| Prohibitin-1 OS = Saccharomyces cerevisiae GN = PHB1 PE = 1 SV = 2 | PHB1_YEAST | 31,427.90 | 38 | 1 |
| T-complex protein 1 subunit epsilon OS = Saccharomyces cerevisiae GN = CCT5 PE = 1 SV = 3 | TCPE_YEAST | 61,916.50 | 19 | 0 |
| Translation machinery-associated protein 22 OS = Saccharomyces cerevisiae (strain YJM789) GN = TMA22 PE = 3 SV = 1 | DENR_YEAS7 (+1) | 22,495.70 | 19 | 0 |
| DnaJ homolog 1, mitochondrial OS = Saccharomyces cerevisiae GN = MDJ1 PE = 1 SV = 1 | MDJ1_YEAST | 55,562.00 | 19 | 0 |
| Alpha, alpha-trehalose-phosphate synthase [UDP-forming] 56 kDa subunit OS = Saccharomyces cerevisiae GN = TPS1 PE = 1 SV = 2 | TPS1_YEAST | 56,148.30 | 76 | 2 |
| Acetyl-coenzyme A synthetase 2 OS = Saccharomyces cerevisiae GN = ACS2 PE = 1 SV = 1 | ACS2_YEAST | 75,492.20 | 228 | 6 |
| 60S ribosomal protein L24-B OS = Saccharomyces cerevisiae GN = RPL24B PE = 1 SB = 1 | RL24B_YEAST | 17,548.10 | 38 | 1 |
| Protein YGP1 OS = Saccharomyces cerevisiae GN = YGP1 PE = 1 SV = 2 | YGP1_YEAST | 37,328.10 | 19 | 0 |
| Actin-related protein 2/3 complex subunit 3 OS = Saccharomyces cerevisiae GN = ARC18 PE = 1 SV = 1 | ARPC3_YEAST | 20,579.60 | 19 | 0 |
| Isoleucyl-tRNA synthetase, cytoplasmic OS = Saccharomyces cerevisiae GN = ILS1 PE = 1 SV = 1 | SYIC_YEAST | 122,988.30 | 262 | 7 |
| Eukaryotic translation initiation factor 3 subunit I OS = Saccharomyces cerevisiae (strain YJM789) GN = TIF34 PE = 3 SV = 1 | EIF3I_YEAS7 (+1) | 38,756.20 | 37 | 1 |
| Dolichol-phosphate mannosyltransferase OS = Saccharomyces cerevisiae GN = DPM1 PE = 1 SV = 3 | DPM1_YEAST | 30,363.40 | 73 | 2 |
| 40S ribosomal protein S29-B OS = Saccharomyces cerevisiae GN = RPS29B PE = 1 SV = 3 | RS29B_YEAST | 6,727.60 | 18 | 0 |
| Pre-mRNA-splicing factor ATP-dependent RNA helicase PRP43 OS = Saccharomyces cerevisiae GN = PRP43 PE = 1 SV = 1 | PRP43_YEAST | 87,564.80 | 18 | 0 |
| Translocation protein SEC72 OS = Saccharomyces cerevisiae GN = SEC72 PE = 1 SV = 3 | SEC72_YEAST | 21,608.40 | 18 | 0 |
| Transcription elongation factor SPT5 OS = Saccharomyces cerevisiae GN = SPT5 PE = 1 SV = 1 | SPT5_YEAST | 115,651.40 | 36 | 1 |
| Endoplasmic reticulum transmembrane protein 1 OS = Saccharomyces cerevisiae GN = YET1 PE = 1 SV = 1 | YET1_YEAST | 23,428.60 | 18 | 0 |
| Ferrochelatase, mitochondrial OS = Saccharomyces cerevisiae GN = HEM15 PE = 1 SV = 1 | HEMH_YEAST | 44,597.70 | 18 | 0 |
| Protein CBP3, mitochondrial OS = Saccharomyces cerevisiae GN = CBP3 PE = 1 SV = 1 | CBP3_YEAST | 39,085.40 | 18 | 0 |
| Putative protein disulfide-isomerase YIL005W OS = Saccharomyces cerevisiae GN = YIL005W PE = 1 SV = 1 | YIA5_YEAST | 81,223.80 | 18 | 0 |
| Mitochondrial protein import protein MA65 OS = Saccharomyces cerevisiae GN = YDJ1 PE = 1 SV = 1 | MAS5_YEAST | 44,671.70 | 72 | 2 |
| Peroxisomal-coenzyme A synthetase OS = Saccharomyces cerevisiae GN = FAT2 PE = 1 SV = 1 | FAT2_YEAST | 60,489.90 | 18 | 0 |
| Nuclear cap-binding protein complex subunit 1 OS = Saccharomyces cerevisiae GN = STO1 PE = 1 SV = 2 | NCBP1_YEAST | 100,023.30 | 36 | 1 |
| Proteasome component Y13 OS = Saccharomyces cerevisiae GN = PRE9 PE = 1 SV = 1 | PSA4_YEAST | 28,715.80 | 18 | 0 |

TABLE 7-continued

| | | | | |
|---|---|---|---|---|
| Trehalose synthase complex regulatory subunit TSL1 OS = Saccharomyces cerevisiae GN = TSL1 PE = 1 SV = 1 | TSL1_YEAST | 123,021.70 | 70 | 2 |
| Ribosomal RNA-processing protein 12 OS = Saccharomyces cerevisiae GN = RRP12 PE = SV = 1 | RRP12_YEAST | 137,515.10 | 17 | 0 |
| U3 small nucleolar RNA-associated protein 22 OS = Saccharomyces cerevisiae GN = UTP22 PE = 1 SV = 1 | UTP22_YEAST | 140,492.90 | 17 | 0 |
| 40S ribosomal protein S26-B OS = Saccharomyces cerevisiae GN = RPS26B PE = 1 SV = 1 | RS26B_YEAST | 13,447.00 | 34 | 1 |
| Elongator complex protein 1 OS = Saccharomyces cerevisiae GN = IKI3 PE = 1 SV = 1 | ELP1_YEAST | 152,994.20 | 17 | 0 |
| Probable 1,3-beta-glucanosyltransferase GAS3 OS = Saccharomyces cerevisiae GN = GAS3 PE = 1 SV = 1 | GAS3_YEAST | 56,796.00 | 17 | 0 |
| Dynamin-related protein DNM1 OS = Saccharomyces cerevisiae GN = DNM1 PE = 1 SV = 1 | DNM1_YEAST | 84,976.60 | 68 | 2 |
| Pyruvate dehydrogenase complex protein X component, mitochondrial OS = Saccharomyces cerevisiae GN = PDX1 PE = 1 SV = 1 | ODPX_YEAST | 45,363.80 | 34 | 1 |
| GTP-binding protein RHO3 OS = Saccharomyces cerevisiae GN = RHO3 PE = 1 SV = 2 | RHO3_YEAST | 25,312.80 | 17 | 0 |
| DNA-directed RNA polymerase I subunit RPA2 OS = Saccharomyces cerevisiae GN = RPA2 PE = 1 SV = 1 | RPA2_YEAST | 135,745.40 | 33 | 1 |
| 54S ribosomal protein YmL6, mitochondrial OS = Saccharomyces cerevisiae GN = YML6 PE = 1 SV = 1 | RL4P_YEAST | 31,970.50 | 16 | 0 |
| ER-derived vesicles protein ERV29 OS = Saccharomyces cerevisiae GN = ERV29 PE = 1 SV = 1 | ERV29_YEAST | 35,014.90 | 16 | 0 |
| 54S ribosomal protein L3, mitochondrial OS = Saccharomyces cerevisiae GN = MRPL3 PE = 1 SV = 2 | RM03_YEAST | 44,001.20 | 16 | 0 |
| Pyrroline-5-carboxylate reductase OS = Saccharomyces cerevisiae GN = PRO3 PE = 1 SV = 1 | P5CR_YEAST | 30,131.40 | 16 | 0 |
| 60S ribosomal protein L34-A PS = Saccharomyces cerevisiae GN = RPL34A PE = 1 SV = 1 | RL34A_YEAST (+1) | 13,639.20 | 16 | 0 |
| Serine/threonin-protein kinase YPK1 OS = Saccharomyces cerevisiae GN = YPK1 PE = 1 SV = 2 | YPK1_YEAST | 76,483.80 | 16 | 0 |
| 60S ribosomal protein L19 OS = Saccharomyces cerevisiae GN = RPL19A PE = 1 SV = 5 | RL19_YEAST | 21,704.60 | 32 | 1 |
| CDP-diacylglycerol-inositol 3-phosphatidyltransferase OS = Saccharomyces cerevisiae GN = PIS1 PE = 1 SV = 1 | PIS_YEAST | 24,824.30 | 16 | 0 |
| 60S ribosome subunit biogenesis protein NIP7OS = Saccharomyces cerevisiae GN = NIP7 PE = 1 SV = 1 | NIP7_YEAST | 20,381.10 | 16 | 0 |
| Cell division control protein 10 OS = Saccharomyces cerevisiae GN = CDC10 PE = 1 SV = 1 | CDC10_YEAST | 37,026.30 | 16 | 0 |
| E3 ubiquitin-protein ligase RSP5 OS = Saccharomyces cerevisiae GN = RSP5 PE = 1 SV = 1 | RSP5_YEAST | 91,817.40 | 16 | 0 |
| Glucan 1,3-beta-glucosidase I/II OS = Saccharomyces cerevisiae GN = EXG1 PE = 1 SV = 1 | EXG1_YEAST | 51,312.30 | 16 | 0 |
| Eukaryotic translation initiation factor 5A-2 OS = Saccharomyces cerevisiae GN = HYP2 PE = 1 SV = 3 | IF5A2_YEAST | 17,114.60 | 346 | 11 |
| 1,4-alpha-glucan-branching enzyme OS = Saccharomyces cerevisiae GN = GLC3 PE = 1 SV = 2 | GLGB_YEAST | 81,118.50 | 31 | 1 |
| Polyadenylate-binding protein, cytoplasmic and nuclear OS = Saccharomyces cerevisiae GN = PAB1 PE = 1 SV = 4 | PABP_YEAST | 64,345.40 | 183 | 6 |
| Protein GCY OS = Saccharomyces cerevisiae GN = GCY1 PE = 1 SV = 1 | GCY_YEAST | 35,079.90 | 272 | 9 |
| Putative thiosulfate sulfurtransferase YOR285W OS = Saccharomyces cerevisiae GN = YOR285W PE = 1 SV = 1 | YO285_YEAST | 15,413.30 | 30 | 1 |
| DNA topoisomerase 2-associated protein PAT1 OS = Saccharomyces cerevisiae GN = PAT1 PE = 1 SV = 3 | PAT1_YEAST | 88,499.40 | 15 | 0 |
| CAAX prenyl protease 1 OS = Saccharomyces cerevisiae GN = STE24 PE = 1 SV = 1 | STE24_YEAST | 52,327.50 | 15 | 0 |
| Endoplasmic reticulum transmembrane protein 3 OS = Saccharomyces cerevisiae GN = YET3 PE = 1 SV = 1 | YET3_YEAST | 22,904.20 | 15 | 0 |
| ATP-dependent RNA helicase DOB1 OS = Saccharomyces cerevisiae GN = MTR4 PE = 1 SV = 1 | MTR4_YEAST | 122,058.70 | 15 | 0 |
| Translation machinery-associated protein 17 OS = Saccharomyces cerevisiae GN = SNF1 PE = 1 SV = 1 | TMA17_YEAST | 16,771.90 | 15 | 0 |
| Carbon catabolite-derepressing protein kinase OS = Saccharomyces cerevisiae GN = SNF1 PE = 1 SV = 1 | SNF1_YEAST | 72,047.90 | 15 | 0 |
| tRNA (cytosine-5-)-methyltransferase NCL1 OS = Saccharomyces cerevisiae GN = NCL1 PE = 1 SV = 1 | NCL1_YEAST | 77,879.60 | 15 | 0 |
| Protein transport protein SEC61 OS = Saccharomyces cerevisiae GN = SEC61 PE = 1 SV = 1 | SC61A_YEAST | 52,940.20 | 15 | 0 |
| Calcineurin subunit B OS = Saccharomyces cerevisiae GN = CNB1 PE = 1 SV = 3 | CANB_YEAST | 19,640.10 | 15 | 0 |
| Lysophospholipase 1 OS = Saccharomyces cerevisiae GN = PLB1 PE = 1 SV = 2 | PLB1_YEAST | 71,670.00 | 15 | 0 |
| Proteasome component Y7 OS = Saccharomyces cerevisiae GN = PRE8 PE = 1 SV = 1 | PSA2_YEAST | 27,163.10 | 15 | 0 |
| Metal resistance protein YCF1 OS = Saccharomyces cerevisiae GN = YCF1 PE = 1 SV = 2 | YCF1_YEAST | 171,129.30 | 15 | 0 |
| Ran GTPase-activating protein 1 OS = Saccharomyces cerevisiae GN = RNA1 PE = SV = 2 | RNA1_YEAST | 45,817.80 | 15 | 0 |

TABLE 7-continued

| | | | | |
|---|---|---|---|---|
| L-aminoadipate-semialdehyde dehydrogenase OS = Saccharomyces cerevisiae GN = LYS2 PE = 1 SV = 2 | LYS2_YEAST | 155,350.80 | 30 | 1 |
| Serine hydroxymethyltransferase, mitochondrial OS = Saccharomyces cerevisiae GN = SHM1 PE = 1 SV = 2 | GLYM_YEAST | 53,688.00 | 30 | 1 |
| Coatomer subunit slpha OS = Saccharomyces cerevisiae GN = RET1 PE = 1 SV = 2 | COPA_YEAST | 135,611.20 | 89 | 3 |
| 40S ribosomal protein S10-B OS = Saccharomyces cerevisiae GN = RPS10B PE = 1 SV = 1 | RS10B_YEAST | 12,738.70 | 89 | 3 |
| 40S ribosomal protein S10-A OS = Saccharomyces cerevisiae GN = RPS10A PE = 1 SV = 1 | RS10A_YEAST | 12,739.70 | 89 | 3 |
| Tryptophan synthase OS = Saccharomyces cerevisiae GN - TRP5 PE = 1 SV = 1 | TRP_YEAST | 76,626.60 | 59 | 2 |
| Serine/threonine-protein phosphatase PP-1-2 OS = Saccharomyces cerevisiae GN = GLC7 PE = 1 SV = 1 | PP12_YEAST | 35,909.00 | 58 | 2 |
| Aminopeptidase Y OS = Saccharomyces cerevisiae GN = APE3 PE = 1 SV = 1 | APE3_YEAST | 60,139.20 | 29 | 1 |
| Glycerol-3-phosphate dehydrogenase [NAD+] 1 OS = Saccharomyces cerevisiae GN = GPD1 PE = 1 SV = 4 | GPD1_YEAST | 42,868.60 | 115 | 4 |
| Valyl-tRNA synthetase, mitochondrial OS = Saccharomyces cerevisiae GN = VAS1 PE = 1 SV = 2 | SYV_YEAST | 125,774.70 | 172 | 6 |
| Aconitate hydratase, mitochondrial OS = Saccharomyces cerevisiae GN = ACO1 PE = 1 SV = 2 | ACON_YEAST | 85,371.60 | 688 | 24 |
| Elongation factor Tu, mitochondrial OS = Saccharomyces cerevisiae GN = TUF1 PE = 1 SV = 1 | EFTU_YEAST | 47,972.90 | 57 | 2 |
| Glycerol-3-phosphate O-actyltransferase 2 OS = Saccharomyces cerevisiae GN = GPT2 PE = 1 SV = 1 | GPT2_YEAST | 83,648.60 | 14 | 0 |
| Putative ribosomal RNA methyltransferase Nop2 OS = Saccharomyces cerevisiae GN = NOP2 PE = 1 SV = 1 | NOP2_YEAST | 69,814.30 | 14 | 0 |
| Serine/threonine-protein kinase YPK2/YKR2 OS = Saccharomyces cerevisiae GN = YPK2 PE = 1 SV = 1 | YPK2_YEAST | 76,669.00 | 14 | 0 |
| Xanthine phosphoribosyltransferase 1 OS = Saccharomyces cerevisiae GN = XPT1 PE = 1 SV = 1 | XPT1_YEAST | 23,672.00 | 14 | 0 |
| 3-hydroxy-3-methylglutaryl-coenzyme A reductase 2 OS = Saccharomyces cerevisiae GN = HMG2 PE = 1 SV = 1 | HMDH2_YEAST | 115,696.90 | 14 | 0 |
| 3-keto-steroid reductase OS = Saccharomyces cerevisiae GN = ERG27 PE = 1 SV = 1 | ERG27_YEAST | 39,726.60 | 14 | 0 |
| Ras-like protein 2 OS = Saccharomyces cerevisiae GN = RAS2 PE = 1 SV = 4 | RAS2_YEAST | 34,705.00 | 14 | 0 |
| Protein phosphatase 1 regulatory subunit SDS22 OS = Saccharomyces cerevisiae GN = SDS22 PE = 1 SV = 1 | SDS22_YEAST | 38,890.20 | 14 | 0 |
| Ubiquitin-like protein SMT3 OS = Saccharomyces cerevisiae GN = SMT3 PE = 1 SV = 1 | SMT3_YEAST | 11,597.50 | 28 | 1 |
| Sphingosine-1-phosphate lyase OS = Saccharomyces cerevisiae GN = DPL1 PE = 1 SV = 1 | SGPL_YEAST | 65,567.50 | 14 | 0 |
| Protein transport protein SSS1 OS = Saccharomyces cerevisiae GN = SSS1 PE = 1 SV = 2 | SC61G_YEAST | 8,943.80 | 14 | 0 |
| UPF0675 endoplasmic reticulum membrane protein YNR021W OS = Saccharomyces cerevisiae GN = YNR021W PE = 1 SV = 3 | YN8B_YEAST | 47,095.10 | 14 | 0 |
| Non-classical export protein 2 OS = Saccharomyces cerevisiae GN = NCE102 PE = 1 SV = 1 | NCE2_YEAST | 18,967.70 | 14 | 0 |
| Reduced viability upon starvation protein 161 OS = Saccharmomyces cerevisiae GN = RVS161 PE = 1 SV = 1 | RV161_YEAST | 30,251.90 | 14 | 0 |
| Cytochrome b5 OS = Saccharomyces cerevisiae GN = CYB5 PE = 1 SV = 2 | CYB5_YEAST | 13,297.10 | 14 | 0 |
| 60S ribosomal protein L37-A OS = Saccharomyces cerevisiae GN = RPL37A PE = 1 SV = 2 | RL37A_YEAST | 9,850.40 | 14 | 0 |
| Calmodulin OS = Saccharomyces cerevisiae GN = CMD1 PE = 1 SV = 1 | CALM_YEAST | 16,135.50 | 14 | 0 |
| Actin-related protein 2/3 complex subunit 5 OS = Saccharomyces cerevisiae GN = ARC15 PE = 1 SV = 1 | ARPC5_YEAST | 17,134.60 | 14 | 0 |
| Mitochondrial outer membrane protein SCY_3392 OS = Saccharomyces cerevisiae (strain YJM789) GN = SCY_3392 PE = 3 SV = 1 | YKR18_YEAS7 (+1) | 81,773.40 | 14 | 0 |
| tRNA pseudouridine synthase 1 OS = Saccharomyces cerevisiae GN = PUS1 PE = 1 SV = 1 | PUS1_YEAST | 62,145.30 | 14 | 0 |
| Heterotrimeric G protein gamma subunit GPG1 OS = Saccharomyces cerevisiae GN = GPG1 PE = 1 SV = 1 | GPG1_YEAST | 14,922.30 | 14 | 0 |
| Anthranilate synthase component 1 OS = Saccharomyces cerevisiae GN = TRP2 PE = 1 SV = 4 | TRPE_YEAST | 56,769.50 | 14 | 0 |
| UPF0662 protein YPL260W OS = Saccharomyces cerevisiae GN = YPL260W PE = 1 SV = 1 | YP260_YEAST | 62,782.70 | 27 | 1 |
| NADPH-dependent 1-acyldihydroxyactone phosphate reductase OS = Saccharomyces cerevisiae GN = AYR1 PE = 1 SV = 1 | AYR1_YEAST | 32,815.30 | 27 | 1 |
| Long-chain-fatty-acid--CoA ligase 1 OS = Saccharomyces cerevisiae GN = FAA1 PE = 1 SV = 1 | LCF1_YEAST | 77,868.10 | 81 | 3 |
| Small COPII coat GTPase SAR1 OS = Saccharomyces cerevisiae GN = SAR1 PE = 1 SV = 1 | SAR1_YEAST | 21,451.50 | 53 | 2 |
| GMP synthase [glutamine-hydrolyzing] OS = Saccharomyces cerevisiae GN = GUA1 PE = 1 SV = 4 | GUAA_YEAST | 58,483.40 | 53 | 2 |
| Mitochondrial outer membrane protein porin 1 OS = Saccharomyces cerevisiae GN = POR1 PE = 1 SV = 4 | VDAC1_YEAST | 30,429.50 | 185 | 7 |

TABLE 7-continued

| Description | ID | MW | Col4 | Col5 |
|---|---|---|---|---|
| ATP-dependent helicase NAM7 OS = Saccharomyces cerevisiae GN = NAM7 PE = 1 SV = 1 | NAM7_YEAST | 109,432.60 | 13 | 0 |
| Proteasome component PRE2 OS = Saccharomyces cerevisiae GN = PRE2 PE = 1 SM = 3 | PSB5_YEAST | 31,636.90 | 13 | 0 |
| Homocitrate synthase, mitochondrial OS = Saccharomyces cerevisiae GN = LYL21 PE = 1 SV = 1 | HOSM_YEAST | 48,595.50 | 78 | 3 |
| Nucleolar complex protein 2 OS = Saccharomyces cerevisiae GN = NOC2 PE = 1 SV = 2 | NOC2_YEAST | 81,605.10 | 13 | 0 |
| Transcriptional regulatory protein SIN3 OS = Saccharomyces cerevisiae GN = SIN3 PE = 1 SV = 2 | SIN3_YEAST | 174,843.10 | 13 | 0 |
| Ribosome biogenesis protein ERB1 OS = Saccharomyces cerevisiae (strain YJM789) GN = ERB1 PE = 3 SV = 1 | ERB1_YEAS7 (+1) | 91,706.30 | 13 | 0 |
| Dihydroxy-acid dehydratase, mitochondrial OS = Saccharomyces cerevisiae GN = ILV3 PE = 1 SV = 2 | ILV3_YEAST | 62,862.80 | 78 | 3 |
| Uncharacterized protein YKL054C OS = Saccharomyces cerevisiae GN = YKL054C PE = 1 SV = 1 | YKF4_YEAST | 83,968.30 | 13 | 0 |
| DNA-directed RNA polymerases I, II, and III subunit RPABC5 OS = Saccharomyces cerevisiae GN = RPB10 PE = 1 SV = 2 | RPAB5_YEAST | 8,278.00 | 13 | 0 |
| Mitochondrial presequence protease OS = Saccharomyces cerevisiae GN = CYM1 PE = 1 SV = 2 | CYM1_YEAST | 112,185.50 | 26 | 1 |
| Amidophosphoribosyltransferase OS = Saccharomyces cerevisiae GN = ADE4 PE = 1 SV = 2 | PUR1_YEAST | 56,720.30 | 13 | 0 |
| Protein ERP1 OS = Saccharomyces cerevisiae GN = ERP1 PE = 1 SV = 1 | ERP1_YEAST | 24,724.00 | 13 | 0 |
| Hsp90 co-chaperone HCH1 OS = Saccharomyces cerevisiae GN = HCH1 PE = 1 SV = 1 | HCH1_YEAST | 17,246.80 | 13 | 0 |
| Acetyl-CoA carboxylase OS = Saccharomyces cerevisiae GN = FAS3 PE = 1 SV = 2 | ACAC_YEAST | 250,359.50 | 572 | 22 |
| Mitochondrial outer membrane protein IML2 OS = Saccharomyces cerevisiae (strain YJM789) GN = IML2 PE = 3 SV = 1 | IML2_YEAS7 (+89) | 82,553.00 | 13 | 0 |
| Choline-phosphate cytidyltransferase OS = Saccharomyces cerevisiae GN = PCT1 PE = 1 SV = 2 | PCY1_YEAST | 49,408.40 | 13 | 0 |
| Nucleosome assembly protein OS = Saccharomyces cerevisiae GN = NAP1 PE = 1 SV = 2 | NAP1_YEAST | 47,886.10 | 13 | 0 |
| THO complex subunit 2 OS = Saccharomyces cerevisiae GN = THO2 PE = 1 SV = 1 | THO2_YEAST | 183,940.50 | 13 | 0 |
| Sec sixty-one protein homolog OS = Saccharomyces cerevisiae GN = SSH1 PE = 1 SV = 1 | SSH1_YEAST | 53,314.50 | 13 | 0 |
| Cytochrome c heme lyase OS = Saccharomyces cerevisiae GN = CYC3 PE = 1 SV = 1 | CCHL_YEAST | 30,080.70 | 13 | 0 |
| Prefoldin subunit 4 OS = Saccharomyces cerevisiae GN = GIM3 PE = 1 SV = 1 | PFD4_YEAST | 15,181.00 | 13 | 0 |
| Gamma-glutamyl phosphate reductase OS = Saccharomyces cerevisiae GN = PRO2 PE = 1 SV = 1 | PROA_YEAST | 49,742.20 | 13 | 0 |
| 60S ribosomal protein L37-B OS = Saccharomyces cerevisiae GN = RPL378B PE = 1 SV = 2 | RL37B_YEAST | 9,868.30 | 13 | 0 |
| UPF0368 protein YPL225W OS = Saccharomyces cerevisiae GN = YPL225W PE = 1 SV = 1 | YP225_YEAST | 17,445.20 | 26 | 1 |
| Dolichyl-phosphate-mannose--protein mannosyltransferase 4 OS = Saccharomyces cerevisiae GN = PMT4 PE = 1 SV = 1 | PMT4_YEAST | 87,968.60 | 13 | 0 |
| Increased sodium tolerance protein 2 OS = Saccharomyces cerevisiae GN = IST2 PE = 1 SV = 1 | IST2_YEAST | 105,908.10 | 13 | 0 |
| Glucokinase-1 OS = Saccharomyces cerevisiae GN = GLK1 PE = 1 SV = 1 | HXKG_YEAST | 55,379.10 | 231 | 9 |
| Suppressor protein STM1 OS = Saccharomyces cerevisiae GN = STM1 PE = 1 SV = 3 | STM1_YEAST | 29,995.40 | 202 | 8 |
| Uridylate kinase OS = Saccharomyces cerevisiae GN = URA6 PE = 1 SV = 1 | UMPK_YEAST | 22,933.90 | 12 | 0 |
| Myosin light chain 1 OS = Saccharomyces cerevisiae GN = MLC1 PE = 1 SV = 1 | MLC1_YEAST | 16,445.30 | 24 | 1 |
| Glucose-repressible alcohol dehydrogenase transcriptional effector OS = Saccharomyces cerevisiae GN = CCR4 PE = 1 SV = 1 | CCR4_YEAST | 94,702.70 | 12 | 0 |
| 54S ribosomal protein L1, mitochondrial OS = Saccharomyces cerevisiae GN = MRPL1 PE = 1 SV = 1 | RM01_YEAST | 30,997.30 | 12 | 0 |
| Nuclear polyadenylated RNA-binding protein 3 OS = Saccharomyces cerevisiae GN = NAB3 PE = 1 SV = 1 | NAB3_YEAST | 90,438.50 | 12 | 0 |
| Phosphoglycerate mutase 2 OS = saccharomyces cerevisiae GN = GPM2 PE = 1 SV = 1 | PMG2_YEAST | 36,074.50 | 12 | 0 |
| 3'(2'),5'-bisphosphate nucleotidase OS = Saccharomyces cerevisiae GN = HAL2 PE = 1 SV = 1 | HAL2_YEAST | 39,150.30 | 12 | 0 |
| Protein SEY1 OS = Saccharomyces cerevisiae (strain AWRI1631) GN = SEY1 PE = 3 SV = 1 | SEQY1_YEAS6 (+2) | 89,425.20 | 12 | 0 |
| Thiamine metabolism regulatory protein THI3 OS = Saccharomyces cerevisiae GN = THI3 PE = 1 SV = 1 | THI3_YEAST | 68,367.90 | 12 | 0 |
| Alpha-mannosidase OS = Saccharomyces cerevisiae GN = AMS1 PE = 1 SV = 2 | MAN1_YEAST | 124,503.20 | 24 | 1 |
| [NU+] prion formation protein 1 OS = Saccharomyces cerevisiae GN = NEW1 PE = 1 SV = 1 | NEW1_YEAST | 134,335.50 | 12 | 0 |
| T-complex protein 1 subunit beta OS = Saccharomyces cerevisiae GN = CCT2 PE = 1 SV = 1 | TCPB_YEAST | 57,205.70 | 12 | 0 |
| Putative zinc metalloproteinase YIL108W OS = Saccharomyces cerevisiae GN = YIL108W PE = 1 SV = 1 | YIK8_YEAST | 77,416.50 | 12 | 0 |

TABLE 7-continued

| Description | ID | Mass | Col4 | Col5 |
|---|---|---|---|---|
| Prefoldin subunit 5 OS = Saccharomyces cerevisiae GN = GIM5 PE = 1 SV = 1 | PFD5_YEAST | 18,356.30 | 12 | 0 |
| Probable glycosidase CRH2 OS = Saccharomyces cerevisiae GN = UTR2 PE = 1 SV = 3 | CRH2_YEAST | 49,906.20 | 12 | 0 |
| Coatomer subunit epsilon OS = Saccharomyces cerevisiae GN = SEC28 PE = 1 SV = 2 | COPE_YEAST | 33,830.60 | 12 | 0 |
| 26S proteasome regulatory subunit RPN13 OS = Saccharomyces cerevisiae GN = RPN13 PE = 1 SV = 1 | RPN13_YEAST | 17,902.50 | 12 | 0 |
| 40S ribosomal protein S28-A OS = Saccharomyces cerevisiae GN = RPS28A PE = 1 SV = 1 | RS28A_YEAST | 7,591.70 | 24 | 1 |
| D-3-phosphoglycerate dehydrogenase 1 OS = Saccharomyces cerevisiae GN = SER3 PE = 1 SV = 1 | SERA_YEAST | 51,194.10 | 12 | 0 |
| Adenylosuccinate synthetase OS = Saccharomyces cerevisiae GN = ADE12 PE = 1 SV = 3 | PURA_YEAST | 48,280.40 | 12 | 0 |
| CTP synthase 2 OS = Saccharomyces cerevisiae (strain YJM789) GN = URA8 PE = 3 SV = 1 | URA8_YEAS7 (+1) | 64,497.40 | 12 | 0 |
| ATP-dependent RNA helicase HAS1 OS = Saccharomyces cerevisiae GN = HAS1 PE = 1 SV = 1 | HAS1_YEAST | 56,720.20 | 12 | 0 |
| Zinc finger protein ZPR1 OS = Saccharomyces cerevisiae GN = ZPR1 PE = 1 SV = 1 | ZPR1_YEAST | 55,072.70 | 12 | 0 |
| 26S proteasome regulatory subunit RPN3 OS = Saccharomyces cerevisiae GN = RPN3 PE = 1 SV = 4 | RPN3_YEAST | 60,426.30 | 12 | 0 |
| Peroxisomal membrane protein PMP27 OS = Saccharomyces cerevisiae GN = PEX11 PE = 1 SV = 2 | PEX11_YEAST | 26,876.20 | 12 | 0 |
| Ribose-phosphate pyrophosphokinase 5 OS = Saccharomyces cerevisiae GN = PRS5 PE = 1 SV = 1 | KPR5_YEAST | 53,506.20 | 12 | 0 |
| U6 snRNA-associated Sm-like protein LSm6 OS = Saccharomyces cereviaiae (strain YJM789) GN = LSM6 PE = 3 SV = 1 | LSM6_YEAS7 (+1) | 9,398.00 | 12 | 0 |
| Protein HMF1 OS = Saccharomyces cerevisiae GN = HMF1 PE = 1 SV = 1 | HMF1_YEAST | 13,905.90 | 12 | 0 |
| General negative regulator of transcription subunit 1 OS = Saccharomyces cerevisiae GN = NOT1 PE = 1 SV = 2 | NOT1_YEAST | 240,344.80 | 12 | 0 |
| Putative glucokinase-2 OS = Saccharomyces cerevisiae GN = EMI2 PE = 1 SV = 1 | EMI2_YEAST | 55,923.00 | 92 | 4 |
| 26S protease regulatory subunit 4 homolog OS = Saccharomyces cerevisiae GN = RPT2 PE = 1 SV = 3 | PRS4_YEAST | 48,830.50 | 23 | 1 |
| Sphingolipid long chain base-responsive protein LSP1 OS = Saccharomyces cerevisiae GN = LSP1 PE = 1 SV = 1 | LSP1_YEAST | 38,071.60 | 113 | 5 |
| UPF0001 protein YBL036C OS = Saccharomyces cerevisiae GN = YBL036C PE = 1 SV = 1 | YBD6_YEAST | 29,124.20 | 11 | 0 |
| Galactose/lactose metabolism regulatory protein GAL80 OS = Saccharomyces cerevisiae GN = GAL80 PE = 1 SV = 2 | GAL80_YEAST | 48,325.40 | 11 | 0 |
| U3 small nucleolar ribonucleoprotein protein IMP3 OS = Saccharomyces cerevisiae GN = IMP3 PE = 1 SV = 1 | IMP3_YEAST | 21,886.10 | 11 | 0 |
| U3 small nucleolar RNA-associated protein 21 OS = Saccharomyces cerevisiae GN = UPT21 PE = 1 SV = 1 | UPT21_YEAST | 104,794.60 | 11 | 0 |
| DNA polymerase alpha catalytic subunit A OS = Saccharomyces cerevisiae GN = POL1 PE = 1 SV = 2 | DPOA_YEAST | 166,815.30 | 11 | 0 |
| Probable glycerophosphodiester phosphodiesterase YPL206C OS = Saccharomyces cerevisiae GN = YPL206C PE = 1 SV = 1 | YP206_YEAST | 37,071.30 | 11 | 0 |
| Cytochrome c oxidase assembly protein COX15 OS = Saccharomyces cerevisiae GN = COX15 PE = 1 SV = 1 | COX15_YEAST | 54,660.50 | 11 | 0 |
| U6 snRNA-associated Sm-like protein LSm5 OS = Saccharomyces cerevisiae GN = LSM5 PE = 1 SV = 1 | LSM5_YEAST | 10,423.20 | 11 | 0 |
| 60S ribosomal protein L29 OS = Saccharomyces cerevisiae GN = RPL29 PE = 1 SV = 3 | RL29_YEAST | 6,669.10 | 11 | 0 |
| Tricalbin-3 OS = Saccharomyces cerevisiae GN = TCB3 PE = 1 SV = 1 | TCB3_YEAST | 171,081.40 | 22 | 1 |
| Peroxiredoxin HYR1 OS = Saccharomyces cerevisiae GN = HYR1 PE = 1 SV = 1 | GPX3_YEAST | 18,642.20 | 22 | 1 |
| Glucose-6-phosphate 1 dehydrogenase OS = Saccharomyces cerevisiae GN = ZWF1 PE = 1 SV = 4 | G6PD_YEAST | 57,523.60 | 44 | 2 |
| Endosomal protein P24B OS = Saccharomyces cerevisiae GN = EMP24 PE = 1 SV = 1 | EMP24_YEAST | 23,332.70 | 11 | 0 |
| Proteasome component C1 OS = Saccharomyces cerevisiae GN = PRE10 PE = 1 SV = 2 | PSA3_YEAST | 31,536.40 | 11 | 0 |
| 26S proteasome regulatory subunit RPN6 OS = Saccharomyces cerevisiae GN = RPN6 PE = 1 SV = 3 | RPN6_YEAST | 49,776.20 | 11 | 0 |
| Monothiol glutaredoxin-3 OS = Saccharomyces cerevisiae GN = GRX3 PE = 1 SV = 1 | GLRX3_YEAST | 32,481.70 | 11 | 0 |
| C-8 sterol isomerase OS = Saccharomyces cerevisiae GN = ERG2 PE = 1 SV = 1 | ERG2_YEAST | 24,896.60 | 11 | 0 |
| Uncharacterized membrane glycoprotein YNR065C OS = Saccharomyces cerevisiae GN = YNR065C PE = 1 SV = 1 | YN94_YEAST | 125,204.80 | 11 | 0 |
| Ubiquitin carboxyl-terminal hydrolase 6 OS = Saccharomyces cerevisiae GN = UBP6 PE = 1 SV = 1 | UBP6_YEAST | 57,112.50 | 11 | 0 |
| Histone chaperaone ASF1 OS = Saccharomyces cerevisiae GN = ASF1 PE = 1 SV = 1 | ASF1_YEAST | 31,603.10 | 11 | 0 |
| Pumilio homology domain family member 6 OS = Saccharomyces cerevisiae GN = PUF6 PE = 1 SV = 1 | PUF6_YEAST | 75,109.00 | 22 | 1 |
| Mitochondrial outer membrane protein OM14 OS = Saccharomyces cerevisiae (strain YJM789) GN = OM14 PE = 3 SV = 1 | OM14_YEAS7 (+1) | 14,609.90 | 11 | 0 |

TABLE 7-continued

| | | | | |
|---|---|---|---|---|
| AP-1 complex subunit gamma-1 OS = Saccharomyces cerevisiae GN = APL4 PE = 1 SV = 1 | AP1G1_YEAST | 93,631.50 | 11 | 0 |
| Signal recognition particle subunit SRP72 OS = Saccharomyces cerevisiae GN = SRP72 PE = 1 SV = 2 | SRP72_YEAST | 73,544.80 | 11 | 0 |
| Protein transport protein SEC31 OS = Saccharomyces cerevisiae GN = SEC31 PE = 1 SV = 2 | SEC31_YEAST | 138,706.80 | 11 | 0 |
| Phosphatidylethanolamine N-methyltransferase OS = Saccharomyces cerevisiae GN = PEM1 PE = 1 SV = 1 | PEM1_YEAST | 101,208.50 | 11 | 0 |
| Mitochondrial import inner membrane translocase subunit TIM16 OS = Saccharomyces cerevisiae GN = PAM16 PE = 1 SV = 1 | TIM16_YEAST | 16,216.50 | 11 | 0 |
| Phosphatidate cytidylyltransferase OS = Saccharomyces cerevisiae GN = CDS1 PE = 1 SV = 1 | CDS1_YEAST | 51,825.70 | 11 | 0 |
| 26S proteasome regulatory subunit RPN12 OS = Saccharomyces cerevisiae GN = RPN12 PE = 1 SV = 3 | RPN12_YEAST | 31,922.00 | 11 | 0 |
| N-terminal acetyltransferase A complex subunit NAT1 OS = Saccharomyces cerevisiae GN = NAT1 PE = 1 SV = 2 | NAT1_YEAST | 98,912.00 | 11 | 0 |
| Nucleolar pre-ribosomal-associated protein 1 OS = Saccharomyces cerevisiae GN = URB1 PE = 1 SV = 2 | URB1_YEAST | 203,200.10 | 11 | 0 |
| GU4 nucleic-binding protein 1 OS = Saccharomyces cerevisiae GN = ARC1 PE = 1 SV = 2 | G4P1_YEAST | 42,084.50 | 87 | 4 |
| Mitochondrial peculiar membrane protein 1 OS = Saccharomyces cerevisiae GN = MPM1 PE = 1 SV = 1 | MPM1_YEAST | 28,471.40 | 43 | 2 |
| 6-phosphogluconate dehydrogenase, decarboxylating 1 OS = Saccharomyces cerevisiae GN = GND1 PE = 1 SV = 1 | 6PGD1_YEAST | 53,545.30 | 494 | 23 |
| Transcription-associated protein 1 OS = Saccharomyces cerevisiae GN = TRA1 PE = 1 SV = 1 | TRA1_YEAST | 433,195.70 | 21 | 1 |
| RNA polymerase-associated protein CTR9 OS = Saccharomyces cerevisiae GN = CTR9 PE = 1 SV = 2 | CTR9_YEAST | 124,663.10 | 42 | 2 |
| DNA-directed RNA polymerases I, II, and III subunit RPABC3 OS = Saccharomyces cerevisiae GN = RPB8 PE = 1 SV = 1 | RPAB3_YEAST | 16,512.10 | 21 | 1 |
| Ribonucleoside-diphosphate reductase large chain 1 OS = Saccharomyces cerevisiae GN = RNR1 PE = 1 SV = 2 | RIR1_YEAST | 99,564.50 | 21 | 1 |
| 60S ribosomal protein L10 OS = Saccharomyces cerevisiae GN = RPL10 PE = 1 SV = 1 | RL10_YEAST | 25,362.10 | 168 | 8 |
| Sphingolipid long chain base-responsive protein PIL1 OS = Saccharomyces cerevisiae GN = PIL1 PE = 1 SV = 1 | PIL1_YEAST | 38,350.30 | 166 | 8 |
| Ribosome-associated complex subunit SSZ1 OS = Saccharomyces cerevisiae GN = SSZ1 PE = 1 SV = 2 | SSZ1_YEAST | 58,239.50 | 145 | 7 |
| Golgin IMH1 OS = Saccharomyces cerevisiae GN = IMH1 PE = 1 SV = 1 | IMH1_YEAST | 105,231.40 | 10 | 0 |
| Protein SCO2, mitochondrial OS = Saccharomyces cerevisiae GN = SCO2 PE = 1 SV = 1 | SCO2_YEAST | 34,890.60 | 10 | 0 |
| 3-ketoacyl-CoA reductase OS = Saccharomyces cerevisiae GN = IFA38 PE = 1 SV = 1 | MKAR_YEAST | 38,709.70 | 10 | 0 |
| Iron transport multicopper oxidase FET5 OS = Saccharomyces cerevisiae GN = FET5 PE = 1 SV = 1 | FET5_YEAST | 70,880.90 | 10 | 0 |
| Protein ISD11 OS = Saccharomyces cerevisiae GN = ISD11 PE = 1 SV = 1 | ISD11_YEAST | 11,266.40 | 10 | 0 |
| Mitochondrial distribution and morphology protein 38 OS = Saccharomyces cerevisiae GN = MDM38 PE = 1 SV = 1 | MDM38_YEAST | 65,008.10 | 10 | 0 |
| Elongation of fatty acids protein 3 OS = Saccharomyces cerevisiae GN = ELO3 PE = 1 SV = 1 | ELO3_YEAST | 39,467.00 | 10 | 0 |
| Nucleolar GTP-binding protein 1 OS = Saccharomyces cerevisiae GN = NOG1 PE = 1 SV = 1 | NOG1_YEAST | 74,412.80 | 10 | 0 |
| Peptidyl-prolyl cis-trans isomerase ESS1 OS = Saccharomyces cerevisiae GN = ESS1 PE = 1 SV = 3 | ESS1_YEAST | 19,404.90 | 10 | 0 |
| ATPase GET3 OS = Saccharomyces cerevisiae (strain RM11-1a) GN = GET3 PE = 3 SV = 1 | GET3_YEAS1 (+2) | 39,355.10 | 10 | 0 |
| Protein APA1 OS = Saccharomyces cerevisiae GN = APA1 PE = 1 SV = 4 | APA1_YEAST | 36,494.20 | 10 | 0 |
| Mitochondrial respiratory chain complexes assembly protein AFG3 OS = Saccharomyces cerevisiae GN = AFG3 PE = 1 SV = 1 | AFG3_YEAST | 84,547.40 | 10 | 0 |
| Calcium-transporting ATPase 2 OS = Saccharomyces cerevisiae GN = PMC1 PE = 1 SV = 1 | ATC2_YEAST | 130,866.40 | 10 | 0 |
| Probable intramembrane protease YKL100C OS = Saccharomyces cerevisiae GN = YKL100C PE = 1 SV = 1 | YKK0_YEAST | 67,528.20 | 10 | 0 |
| KH domain-containing protein YBL032W OS = Saccharomyces cerevisiae GN = YBL032W PE = 1 SV = 1 | YBD2_YEAST | 41,684.60 | 10 | 0 |
| Mitochondrial import receptor subunit TOM22 OS = Saccharomyces cerevisiae GN = TOM22 PE = 1 SV = 3 | TOM22_YEAST | 16,790.90 | 10 | 0 |
| Protein MSP1 OS = Saccharomyces cerevisiae GN = MSP1 PE = 1 SV = 2 | MSP1_YEAST | 40,346.50 | 10 | 0 |
| UPF0364 protein YMR027W OS = Saccharomyces cerevisiae GN = YMR027W PE = 1 SV = 1 | YMR7_YEAST | 54,130.90 | 10 | 0 |
| Uncharacterized protein YJL217W OS = Saccharomyces cerevisiae GN = YJL217W PE = 1 SV = 1 | YJV7_YEAST | 21,966.80 | 10 | 0 |
| ER membrane protein complex subunit 4 OS = Saccharomyces cerevisiae GN = EMC4 PE = 1 SV = 1 | EMC4_YEAST | 21,460.70 | 10 | 0 |
| Sm-like protein LSm1 OS = Saccharomyces cerevisiae GN = LSM1 PE = 1 SV = 1 | LSM1_YEAST | 20,307.60 | 10 | 0 |
| Probable alpha-1,6-mannosyltransferase MNN10 OS = Saccharomyces cerevisiae GN = MNN10 PE = 1 SV = 1 | MNN10_YEAST | 46,750.50 | 10 | 0 |
| Protein HAM1 OS = Saccharomyces cerevisiae GN = HAM1 PE = 1 SV = 1 | HAM1_YEAST | 22,093.90 | 10 | 0 |

TABLE 7-continued

| Description | ID | Mass | Col4 | Col5 |
|---|---|---|---|---|
| NADPH-dependent methylglyoxal reductase GRE2 OS = *Saccharomyces cerevisiae* GN = GRE2 PE = 1 SV = 1 | GRE2_YEAST | 38,170.30 | 10 | 0 |
| Alpha-1,2-mannosyltransferase KTR1 OS = *Saccharomyces cerevisiae* GN = KTR1 PE = 1 SV = 1 | KTR1_YEAST | 46,023.70 | 10 | 0 |
| Protein VTH1 OS = *Saccharomyces cerevisiae* GN = VTH1 PE = 1 SV = 1 | VTH1_YEAST (+1) | 174,434.90 | 10 | 0 |
| Trehalose synthase complex regulatory subunit TPS3 OS = *Saccharomyces cerevisiae* GN = TPS3 PE = 1 SV = 3 | TPS3_YEAST | 118,837.50 | 10 | 0 |
| Heat shock protein 60, mitochondrial OS = *Saccharomyces cerevisiae* GN = HSP60 PE = 1 SV = 1 | HSP60_YEAST | 60,7553.00 | 743 | 38 |
| Pyruvate dehydrogenase E1 component subunit beta, mitochondrial OS = *Saccharomyces cerevisiae* GN = PDB1 PE = 1 SV = 2 | ODPB_YEAST | 40,054.20 | 77 | 4 |
| Pyruvate dehydrogenase E1 component subunit alpha, mitochondrial OS = *Saccharomyces cerevisiae* GN = PDA1 PE = 1 SV = 2 | ODPA_YEAST | 46,344.40 | 96 | 5 |
| Actin-related protein 3 OS = *Saccharomyces cerevisiae* GN = ARP3 PE = 1 SV = 1 | ARP3_YEAST | 49,542.70 | 19 | 1 |
| AMP deaminase OS = *Saccharomyces cerevisiae* GN = AMD1 PE = 1 SV = 2 | AMPD_YEAST | 93,304.30 | 19 | 1 |
| Lon protease homolog, mitochondrial OS = *Saccharomyces cerevisiae* GN = PIM1 PE = 1 SV = 2 | LONM_YEAST | 127,116.80 | 56 | 3 |
| Isocitrate dehydrogenase [NAD] subunit 1, mitochondrial OS = *Saccharomyces cerevisiae* GN = IDH1 PE = 1 SV = 2 | IDH1_YEAST | 39,325.30 | 223 | 12 |
| Serine hydroxymethyltransferase, cytosolic OS = *Saccharomyces cerevisiae* GN = SHM2 PE = 1 SV = 2 | GLYC_YEAST | 52,219.70 | 110 | 6 |
| Rab proteins geranylgeranyltransferase component A OS = *Saccharomyces cerevisiae* GN = MRS6 PE = 1 SV = 2 | RAEP_YEAST | 67,374.90 | 9 | 0 |
| 37S ribosomal protein MRP1, mitochondrial OS = *Saccharomyces cerevisiae* GN = MRP1 PE = 1 SV = 2 | RT01_YEAST | 36,730.90 | 9 | 0 |
| Carboxypeptidase S OS = *Saccharomyces cerevisiae* GN = CPS1 PE = 1 SV = 2 | CBPS_YEAST | 64,599.30 | 9 | 0 |
| Probable glucose transporter HXT5 OS = *Saccharomyces cerevisiae* GN = HXT5 PE = 1 SV = 1 | HXT5_YEAST | 66,252.90 | 9 | 0 |
| Glycerol-3-phosphate dehydrogenase, mitochondrial OS = *Saccharomyces cerevisiae* GN = GUT2 PE = 1 SV = 2 | GPDM_YEAST | 72,390.60 | 90 | 5 |
| Cytochrome b2, mitochondrial OS = *Saccharomyces cerevisiae* GN = CYB2 PE = 1 SV = 1 | CYB2_YEAST | 65,541.20 | 9 | 0 |
| Translation machinery-associated protein 20 OS = *Saccharomyces cerevisiae* GN = TMA20 PE = 1 SV = 1 | TMA20_YEAST | 20,278.30 | 9 | 0 |
| D-arabinono-1,4-lactone oxidase OS = *Saccharomyces cerevisiae* GN = ALO1 PE = 1 SV = 1 | ALO_YEAST | 59,494.80 | 9 | 0 |
| Protein phosphatase 2C homolog 3 OS = *Saccharomyces cerevisiae* GN = PTC3 PE = 1 SV = 3 | PP2C3_YEAST | 51,391.60 | 9 | 0 |
| DNA-directed RNA polymerase II subunit RPB9 OS = *Saccharomyces cerevisiae* GN = RPB9 PE = 1 SV = 1 | RPB9_YEAST | 14,288.00 | 9 | 0 |
| Casein kinase II subunit alpha OS = *Saccharomyces cerevisiae* GN = CKA1 PE = SV = 1 | CSK21_YEAST | 44,669.80 | 9 | 0 |
| 26S protease regulatory subunit 6A OS = *Saccharomyces cerevisiae* GN = RPT5 PE ==0 SV = 3 | PRS6A_YEAST | 48,257.20 | 9 | 0 |
| Enoyl reductase TSC13 OS = *Saccharomyces cerevisiae* GN = TSC13 PE = 1 SV = 1 | TSC13_YEAST | 36,770.00 | 9 | 0 |
| H/ACA ribonucleoprotein complex subunit 2 OS = *Saccharomyces cerevisiae* GN = NHP2 PE = 1 SV = 2 | NHP2_YEAST | 17,122.10 | 9 | 0 |
| Retrograde regulation protein 2 OS = *Saccharomyces cerevisiae* GN = RTG2 PE = 1 SV = 2 | RTG2_YEAST | 65,573.60 | 9 | 0 |
| Uncharacterized protein YDR476C OS = *Saccharomyces cerevisiae* GN = YDR476C PE = 1 SV = 1 | YD476_YEAST | 25,266.70 | 9 | 0 |
| DNA-directed RNA polymerases I and III subunit RPAC2 OS = *Saccharomyces cerevisiae* GN = RPC19 PE = 1 SV = 1 | RPAC2_YEAST | 16,150.90 | 9 | 0 |
| GPI transamidase component GPI16 OS = *Saccharomyces cerevisiae* GN = GPI16 PE = 1 SV = 2 | GPI16_YEAST | 68,775.10 | 9 | 0 |
| V-type proton ATPase subunit e OS = *Saccharomyces cerevisiae* GN = VMA9 PE = 1 SV = 1 | VA0E_YEAST | 8,381.10 | 9 | 0 |
| Cell division control protein 28 OS = *Saccharomyces cerevisiae* GN = CDC28 PE = 1 SV = 1 | CDC28_YEAST | 34,063.40 | 18 | 1 |
| Serine/threonine-protein phosphatase 2B catalytic subunit A2 OS = *Saccharomyces cerevisiae* GN = CNA2 PE = 1 SV = 2 | PP2B2_YEAST | 68,529.90 | 9 | 0 |
| GTP-binding protein YPT31/YPT8 OS = *Saccharomyces cerevisiae* GN = YPT31 PE = 1 SV = 3 | YPT31_YEAST (+1) | 24,469.90 | 9 | 0 |
| FK506-binding nuclear protein OS = *Saccharomyces cerevisiae* GN = FPR3 PE = 1 SV = 2 | FKBP3_YEAST | 46,554.20 | 9 | 0 |
| D-3-phosphoglycerate dehydrogenase 2 OS = *Saccharomyces cerevisiae* GN = SER33 PE = 1 SV = 1 | SER33_YEAST | 51,189.50 | 9 | 0 |
| Coatomer subunit beta OS = *Saccharomyces cerevisiae* GN = SEC26 PE = 1 SV = 2 | COPB_YEAST | 109,023.60 | 9 | 0 |
| Dipeptidyl aminopeptidase B OS = *Saccharomyces cerevisiae* GN = DAP2 PE = 2 SV = 2 | DAP2_YEAST | 93,406.70 | 9 | 0 |
| Protein UTH1 OS = *Saccharomyces cerevisiae* (strain RM11-1a) GN = UTH1 PE = 3 SV = 1 | UTH1_YEAS1 (+3) | 36,735.90 | 9 | 0 |
| Uncharacterized oxidoreductase YML125C OS = *Saccharomyces cerevisiae* GN = YML125C PE = 1 SV = 1 | YMM5_YEAST | 35,388.60 | 9 | 0 |

TABLE 7-continued

| | | | | |
|---|---|---|---|---|
| Long-chain-fatty-acid-CoA ligase 3 OS = Saccharomyces cerevisiae GN = FAA3 PE = 1 SV = 1 | LCF3_YEAST | 77,948.60 | 9 | 0 |
| Actin-related protein 2/3 complex subunit 2 OS = Saccharomyces cerevisiae GN = ARC35 PE = 1 SV = 1 | ARPC2_YEAST | 39,567.70 | 18 | 1 |
| Ceramide very long chain fatty acid hydroxylase SCS7 OS = Saccharomyces cerevisiae GN = SCS7 PE = 1 SV = 1 | SCS7_YEAST | 44,882.80 | 9 | 0 |
| Protein SDS24 OS = Saccharomyces cerevisiae (strain YJM789) GN = SDS24 PE = 3 SV = 1 | SDS24_YEAS7 (+1) | 57,188.20 | 9 | 0 |
| Cytochrome c oxidase assembly protein COX14 OS = Saccharomyces cerevisiae GN = COX14 PE = 1 SV = 1 | COX14_YEAST | 7,959.10 | 9 | 0 |
| Signal recognition particle subunit SRP14 OS = Saccharomyces cerevisiae GN = SRP14 PE = 1 SV = 1 | SRP14_YEAST | 16,430.30 | 9 | 0 |
| Putative guanine nucleotide-exchange factor SED4 OS = Saccharomyces cerevisiae GN = SED4 PE = 1 SV = 1 | SED4_YEAST | 114,081.60 | 9 | 0 |
| Cytochrome b-c1 complex subunit 1, mitochondrial OS = Saccharomyces cerevisiae GN = COR1 PE = 1 SV = 1 | QCR1_YEAST | 50,229.00 | 71 | 4 |
| Lysyl-tRNA synthetase, cytoplasmic OS = Saccharomyces cerevisiae GN = KRS1 PE = 1 SV = 2 | SYKC_YEAST | 67,960.50 | 88 | 5 |
| Glutamyl-tRNA synthetase, cytoplasmic OS = Saccharomyces cerevisiae GN = GUS1 PE = 1 SV = 3 | SYEC_YEAST | 80,846.20 | 246 | 14 |
| Protein transport protein SEC13 OS = Saccharomyces cerevisiae GN = SEC13 PE = 1 SV = 1 | SEC13_YEAST | 33,042.60 | 35 | 2 |
| Threonyl-tRNA synthetase, cytoplasmic OS = Saccharomyces cerevisiae GN = THS1 PE = 1 SV = 2 | SYTC_YEAST | 84,522.60 | 121 | 7 |
| Uncharacterized protein YMR178W OS = Saccharomyces cerevisiae GN = YMR178W PE = 1 SV = 1 | YM44_YEAST | 31,145.60 | 51 | 3 |
| 40S ribosomal protein S25-A OS = Saccharomyces cerevisiae GN = RPS25A PE = 1 SV = 1 | RS25A_YEAST (+1) | 12,039.90 | 68 | 4 |
| Transposon TY2-LR2 Gag-Pol polyprotein OS = Saccharomyces cerevisiae GN = TY2B-LR1 PE = 3 SV = 1 | YL21B_YEAST | 202,130.30 | 17 | 1 |
| Farnesyl pyrophosphate synthase OS = Saccharomyces cerevisiae GN = FPP1 PE = 1 SV = 2 | FPPS_YEAST | 40,485.30 | 135 | 8 |
| Isocitrate dehydrogenase [NAD] subunit 2, mitochondrial OS = Saccharomyces cerevisiae GN = IDH2 PE = 1 SV = 1 | IDH2_YEAST | 39,740.60 | 151 | 9 |
| Nascent polypeptide-associated complex subunit beta-1 OS = Saccharomyces cerevisiae (strain YJM789) GN = EGD1 PE = 3 SV = 1 | NACB1_YEAS7 (+1) | 17,020.50 | 33 | 2 |
| 40S ribosomal protein S3 OS = Saccharomyces cerevisiae GN = RPS3 PE = 1 SV = 5 | RS3_YEAST | 26,503.00 | 296 | 18 |
| ATP-dependent RNA helicase SUB2 OS = Saccharomyces cerevisiae (strain YJM789) GN = SUB2 PE = 3 SV = 1 | SUB2_YEAS7 (+1) | 50,280.10 | 49 | 3 |
| Elongation factor 1-gamma 2 OS = Saccharomyces cerevisiae GN = TEF4 PE = 1 SV = 1 | EF1G2_YEAST | 46,521.90 | 98 | 6 |

| Protein | NSAF TAL-PrA | NSAF Wild type | Fold enriched TAL-PrA/WT | Rank | Rank/N |
|---|---|---|---|---|---|
| Plasma membrane ATPase 1 OS = Saccharomyces cerevisiae GN = PMA1 PE = 1 SV = 2 | 0.00300044 | 2.19206E-05 | 136.8778684 | 1 | 0.001956947 |
| Transposon Ty1-H Gag-Pol polyprotein OS = Saccharomyces cerevisiae GN = TY1B-H PE = 1 SV = 1 | 0.000721016 | 1.07667E-05 | 66.96712916 | 2 | 0.003913894 |
| ATP-dependent RNA helicase DED1 OS = Saccharomyces cerevisiae (strain YJM789) GN = DED1 PE = 3 SV = 1 | 0.002132761 | 3.33122E-05 | 64.02351908 | 3 | 0.005870841 |
| Protein TIF31 OS = Saccharomyces cerevisiae GN = TIF31 PE = 1 SV = 1 | 0.000833936 | 1.50427E-05 | 55.43798971 | 4 | 0.007827789 |
| Protein URA1 OS = Saccharomyces cerevisiae GN = URA2 PE = 1 SV = 4 | 0.002963245 | 5.34515E-05 | 55.43798971 | 5 | 0.009784736 |
| Elongation factor 3B OS = Saccharomyces cerevisiae GN = HEF3 PE = 1 SV = 2 | 0.001017068 | 1.88464E-05 | 53.96618467 | 6 | 0.011741683 |
| Transposon Ty1-OL Gag polyprotein OS = Saccharomyces cerevisiae GN = TY1A-OL PE = 1 SV = 1 | 0.002361064 | 4.4561E-05 | 52.98498131 | 7 | 0.01369863 |
| 40S ribosomal protein S1-B OS = Saccharomyces cerevisiae (strain RM11-1a) GN = RPS1B PE = 3 SV = 1 | 0.003792691 | 7.57911E-05 | 50.04137124 | 8 | 0.015655577 |
| 40S ribosomal protein S1-A OS = Saccharomyces cerevisiae (strain RM11-1a) GN = RPS1A PE = 3 SV = 1 | 0.003522263 | 7.59733E-05 | 46.36185865 | 9 | 0.017612524 |
| Transposon Ty1-DR3 Gag polyprotein OS = Saccharomyces cerevisiae GN = TY1A-DR3 PE = 1 SV = 1 | 0.002047426 | 4.43968E-05 | 46.11655781 | 10 | 0.019569472 |
| Galactose transporter OS = Saccharomyces cerevisiae GN = GAL2 PE = 1 SV = 3 | 0.001540685 | 3.43213E-05 | 44.89005361 | 11 | 0.021526419 |
| Argininosuccinate synthase OS = Saccharomyces cerevisiae GN = ARG1 PE = 1 SV = 2 | 0.002019878 | 4.65214E-05 | 43.41824857 | 12 | 0.023483366 |
| Pleiotropic ABC efflux transporter of multiple drugs OS = Saccharomyces cerevisiae GN = PDR5 PE = 1 SV = 1 | 0.000477712 | 1.28122E-05 | 37.28572759 | 13 | 0.025440313 |
| 1,3-beta-glucan synthase compnent FKS1 OS = Saccharomyces cerevisiae GN = FKS1 PE = 1 SV = 2 | 0.000376467 | 1.01637E-05 | 37.04042675 | 14 | 0.02739726 |

TABLE 7-continued

| | | | | | |
|---|---|---|---|---|---|
| Heat shock protein SSC3, mitochondrial OS = *Saccharomyces cerevisiae* GN = ECM10 PE = 1 SV = 1 | 0.001146459 | 3.11579E-05 | 36.79512591 | 15 | 0.029354207 |
| Pyruvate decarboxylase isozyme 3 OS = *Saccharomyces cerevisiae* GN = PDC6 PE = 1 SV = 3 | 0.001304785 | 3.54608E-05 | 36.79512591 | 16 | 0.031311155 |
| Nuclear segregation protein BFR1 OS = *Saccharomyces cerevisiae* GN = BFR1 PE = SV = 1 | 0.001343076 | 3.99651E-05 | 33.606215 | 17 | 0.033268102 |
| 60S ribosomal protein L18 OS = *Saccharomyces cerevisiae* GN = RPL18A PE = 1 SV = 1 | 0.003360413 | 0.000106195 | 31.64380828 | 18 | 0.035225049 |
| 40S ribosomal protein S2 OS = *Saccharomyces cerevisiae* GN = RPS2 PE = 1 SV = 3 | 0.002458834 | 7.95536E-05 | 30.90790577 | 19 | 0.037181996 |
| 1,3-beta-glucan synthase component GSC2 OS = *Saccharomyces cerevisiae* GN = GSC2 PE = 1 SV = 2 | 0.000311042 | 1.00635E-05 | 30.90790577 | 20 | 0.039138943 |
| 6-phosphogluconate dehydrogenase, decarboxylating 2 OS = *Saccharomyces cerevisiae* GN = GND2 PE = 1 SV = 1 | 0.001172178 | 4.0496E-05 | 28.94549905 | 21 | 0.04109589 |
| High-affinity hexose transporter HXT6 OS = *Saccharomyces cerevisiae* GN = HXT7 PE = 1 SV = 1 | 0.00092217 | 3.48087E-05 | 26.49249066 | 22 | 0.043052838 |
| Protein GAL3 OS = *Saccharomyces cerevisiae* GN = GAL3 PE = 1 SV = 2 | 0.000986018 | 3.75666E-05 | 26.24718982 | 23 | 0.056009785 |
| ATP-dependent RNA halicase MSS116, mitochondrial OS = *Saccharomyces cerevisiae* GN = MSS116 PE = 1 SV = 1 | 0.000737438 | 2.8631E-05 | 25.75658814 | 24 | 0.046966732 |
| Probable cation-transporting ATPase 1 OS = *Saccharomyces cerevisiae* GN = SPF1 PE = 1 SV = 1 | 0.000388073 | 1.61431E-05 | 24.03948226 | 25 | 0.048923679 |
| High-affinity hexose transporter HXT6 OS = *Saccharomyces cerevisiae* GN = HXT6 PE = 1 SV = 2 | 0.000837185 | 3.48254E-05 | 24.03948226 | 26 | 0.050880626 |
| Eukaryotic translation initiation factor 5B OS = *Saccharomyces cerevisiae* GN = FUN12 PE = 1 SV = 2 | 0.000467585 | 1.94507E-05 | 24.03948226 | 26 | 0.050880626 |
| DNA-directed RNA polymerase II subunit RPB1 OS = *Saccharomyces cerevisiae* GN = RPB1 PE = 1 SV = 2 | 0.000268377 | 1.13966E-05 | 23.54888058 | 28 | 0.054794521 |
| 1,3-beta-glucanosyltransferase GAS1 OS = *Saccharomyces cerevisiae* GN = GAS1 PE = 1 SV = 2 | 0.0008451 | 3.66506E-05 | 23.0582789 | 29 | 0.056761468 |
| Eukaryotic translation initiation factor 3 subunit B OS = *Saccharomyces cerevisiae* (strain YJM789) GN = PRT1 PE = 3 SV = 1 | 0.00056527 | 2.47784E-05 | 22.81297806 | 30 | 0.058708415 |
| Phosphoglucomutase-1 OS = *Saccharomyces cerevisiae* GN = PGM1 PE = 1 SV = 1 | 0.000772352 | 3.45999E-05 | 22.32237639 | 31 | 0.060665362 |
| T-complex protein 1 subunit gamma OS = *Saccharomyces cerevisiae* GN = CCT3 PE = 1 SV = 2 | 0.000819711 | 3.71295E-05 | 22.07707555 | 32 | 0.062622309 |
| FACT complex subunit SPT16 OS = *Saccharomyces cerevisiae* GN = SPT16 PE = 1 SV = 1 | 0.000397347 | 1.84072E-05 | 21.58647387 | 33 | 0.64579256 |
| ATP-dependent RNA helicase DBP1 OS = *Saccharomyces cerevisiae* (strain YJM789) GN = DBP1 PE = 3 SV = 1 | 0.000685433 | 3.21179E-05 | 21.34117303 | 34 | 0.066536204 |
| Dihydrolipoyllysine-residue acetyltransferase component of pyruvate dehydrogenase complex, mitochondrial OS = *Saccharomyces cerevisiae* GN = PDA2 PE = 1 SV = 1 | 0.00089935 | 4.21415E-05 | 21.34117303 | 34 | 0.066536204 |
| Clathrin heave chain OS = *Saccharomyces cerevisiae* GN = CHC1 PE = 1 SV = 1 | 0.000494931 | 2.33254E-05 | 21.21852261 | 36 | 0.070450098 |
| 40S ribosomal protein S8 OS = *Saccharomyces cerevisiae* GN = RPS8A PE = 1 SV = 3 | 0.002048356 | 9.70975E-05 | 21.98587219 | 37 | 0.072407045 |
| DNA-directed RNA polymerase II subunit RPB2 OS = *Saccharomyces cerevisiae* GN = RPB2 PE = 1 SV = 2 | 0.000328146 | 1.5738E-05 | 20.85057135 | 38 | 0.074363992 |
| Glutamine synthetase OS = *Saccharomyces cerevisiae* GN = GLN1 PE = 1 SV = 2 | 0.00102603 | 5.22842E-05 | 19.62406715 | 39 | 0.076320939 |
| Mitochondrial import receptor subunit TOM40 OS = *Saccharomyces cerevisiae* GN = TOM40 PE = 1 SV = 1 | 0.001006641 | 5.19456E-05 | 19.37876631 | 40 | 0.078277886 |
| C-1-tetrahydrofolate synthase, cytoplasmic OS = *Saccharomyces cerevisiae* GN = ADE3 PE = 1 SV = 1 | 0.000398323 | 2.1366E-05 | 18.64286379 | 41 | 0.080234834 |
| rRNA 2'-O-methyltransferase fibrillarin OS = *Saccharomyces cerevisiae* GN = NOP1 PE = 1 SV = 1 | 0.001165684 | 6.33608E-05 | 18.39756296 | 42 | 0.082191781 |
| Protein SCP160 OS = *Saccharomyces cerevisiae* GN = SCP160 PE = 1 SV = 3 | 0.001192042 | 6.47935E-05 | 18.39756296 | 42 | 0.082191781 |
| Protein transport protein 56 OS = *Saccharomyces cerevisiae* GN = SEC23 PE = 1 SV = 1 | 0.000687645 | 3.8401E-05 | 17.90696128 | 44 | 0.086105675 |
| Nucleolar protein 56 OS = *Saccharomyces cerevisiae* GN = NOP56 PE = 1 SV = 1 | 0.000687645 | 3.8401E-05 | 17.90696128 | 45 | 0.088062622 |
| Orotidine 5'-phosphate decarboxylase OS = *Saccharomyces cerevisiae* GN = URA3 PE = 1 SV = 2 | 0.001300706 | 7.4683E-05 | 17.4163596 | 46 | 0.090019569 |
| Homocitrate synthase, cytosolic isozyme OS = *Saccharomyces cerevisiae* GN = LYS20 PE = 1 SV = 1 | 0.000773374 | 4.63641E-05 | 16.68045708 | 47 | 0.091976517 |
| External NADH-ubiquinone oxidoreductase 1, mitochondrial OS = *Saccharomyces cerevisiae* GN = NDE1 PE = 1 SV = 1 | 0.000571718 | 3.47863E-05 | 16.43515624 | 48 | 0.093933464 |
| Eukaryotic translation initiation factor 3 subunit C OS = *Saccharomyces cerevisiae* (strain YJM789) GN = NIP1 PE = 3 SV = 1 | 0.000384987 | 2.34246E-05 | 16.43515624 | 49 | 0.095890411 |
| Zuotin OS = *Saccharomyces cerevisiae* GN = ZUO1 PE = 1 SV = 1 | 0.00072121 | 4.4547E-05 | 16.1898554 | 50 | 0.097847358 |
| Trehalose-phosphatase OS = *Saccharomyces cerevisiae* GN = TPS2 PE = 1 SV = 3 | 0.000327715 | 2.12059E-05 | 15.45395288 | 51 | 0.099804305 |

TABLE 7-continued

| | | | | | |
|---|---|---|---|---|---|
| Saccharopepsin OS = Saccharomyces cerevisiae GN = PEP4 PE = 1 SV = 1 | 0.000758359 | 4.90722E-05 | 15.45395288 | 51 | 0.99804305 |
| rRNA biogenesis protein RRP5 OS = Saccharomyces cerevisiae GN = RRP5 PE = 1 SV = 1 | 0.000174731 | 1.13065E-05 | 15.45395288 | 53 | 0.1037182 |
| cAMP-dependent protein kinase regulatory subunit OS = Saccharomyces cerevisiae GN = BCY1 PE = 1 SV = 4 | 0.000703343 | 4.62462E-05 | 15.20865204 | 54 | 0.105675147 |
| Galactokinase OS = Saccharomyces cerevisiae GN = GAL1 PE = 1 SV = 4 | 0.012480213 | 0.000829109 | 15.05255151 | 55 | 0.107632094 |
| Probable 2-methylcitrate dehydratase OS = Saccharmyces cerevisiae GN = PDH1 PE = 1 SV = 1 | 0.000566456 | 3.78562E-05 | 14.9633512 | 56 | 0.109589041 |
| 2-isopropylmalate synthase 2, mitochondrial OS = Saccharomyces cerevisiae GN = LEU9 PE = 1 SV = 1 | 0.000486249 | 3.2496E-05 | 14.9633512 | 57 | 0.11545988 |
| NADH-cytochrome b5 reductase 2 OS = Saccharomyces cerevisiae (strain YJM789) GN = MCR1 PE = 2 SV = 1 | 0.000957996 | 6.40228E-05 | 14.9633512 | 58 | 0.113502935 |
| 6,7-dimethyl-8-ribityllumazine synthase OS = Saccharomyces cerevisiae GN = RIB4 PE = 1 SV = 2 | 0.00017321121 | 0.00117687 | 14.71805036 | 59 | 0.115459883 |
| N-(5'-phosphoribosyl)anthranilate isomerase OS = Saccharomyces cerevisiae GN = TRP1 PE = 1 SV = 2 | 0.001331159 | 9.0444E-05 | 14.71805036 | 59 | 0.115459883 |
| Glutamate synthase [NADH] OS = Saccharomyces cerevisiae GN = GLT1 PE = 1 SV = 2 | 0.000130484 | 9.17129E-06 | 14.22744869 | 61 | 0.119373777 |
| Nuclear localization sequence-binding protein OS = Saccharomyces cerevisiae GN = NSR1 PE = 1 SV = 1 | 0.000661538 | 4.90335E-05 | 13.49154617 | 62 | 0.121330724 |
| V-type proton ATPase subunit a, vacuolar isoform OS = Saccharomyces cerevisiae GN = VPH1 PE = 1 SV = 3 | 0.000308399 | 2.28587E-05 | 13.49154617 | 62 | 0.121330724 |
| 4-aminobutyrate aminotransferase OS = Saccharomyces cerevisiae GN = UGA1 PE = 1 SV = 2 | 0.000556432 | 4.1243E-05 | 13.49154617 | 64 | 0.125244618 |
| Dihydroorotate dehydrogenase OS = Saccharomyces cerevisiae GN = URA1 PE = 1 SV = 1 | 0.000831161 | 6.27469E-05 | 13.24624533 | 65 | 0.127201566 |
| Eukaryotic translation initiation factor 2A OS = Saccharomyces cerevisiae GN = YGR054W PE = 1 SV = 1 | 0.000405663 | 3.06247E-05 | 13.24624533 | 66 | 0.129158513 |
| 60S ribosomal protein L32 OS = Saccharomyces cerevisiae GN = RPL32 PE = 1 SV = 1 | 0.00192197 | 0.000147833 | 13.00094449 | 67 | 0.13111546 |
| 60S ribosomal protein L15-A OS = Saccharomyces cerevisiae GN = RPL15A PE = 1 SV = 3 | 0.002303041 | 0.000178831 | 12.87829407 | 68 | 0.133072407 |
| Mitochondrial import receptor subunit TOM70 OS = Saccharomyces cerevisiae (strain YJM789) GN = TOM70 PE = 3 SV = 1 | 0.000389459 | 3.11398E-05 | 12.51034281 | 69 | 0.135029354 |
| Mitochondrial acidic protein MAM33 OS = Saccharomyces cerevisiae FN = MAM33 PE = 1 SV = 1 | 0.000906643 | 7.24715E-05 | 12.51034281 | 70 | 0.136986301 |
| H/ACA ribonucleoprotein complex subunit 4 OS = Saccharomyces cerevisiae GN = CBF5 PE = 1 SV = 1 | 0.000499387 | 3.99179E-05 | 12.51034281 | 70 | 0.136986301 |
| 60S ribosomal protein L8-A OS = Saccharomyces cerevisiae GN = RPL8A PE = 1 SV = 4 | 0.003828248 | 0.000310574 | 12.32636718 | 72 | 0.140900196 |
| Eukaryotic translation initiation factor 2 subunit alpha OS = Saccharomyces cerevisiae GN = SUI2 PE = 1 SV = 1 | 0.000771455 | 6.28987E-05 | 12.26504197 | 73 | 0.142857143 |
| NADPH--cytochrome P450 reductasse OS = Saccharomyces cerevisiae GN = NCP1 PE = 1 SV = 3 | 0.000348866 | 2.84439E-05 | 12.26504197 | 74 | 0.14481409 |
| Nucleolar protein 58 OS = Saccharomyces cerevisiae (strain YJM789) GN = NOP58 PE = 3 SV = 1 | 0.000921641 | 7.66773E-05 | 12.01974113 | 75 | 0.146771037 |
| 60S ribosomal protein L14-B OS = Saccharomyces cerevisiae GN = RPL14B PE = 1 SV = 1 | 0.003429032 | 0.000288224 | 11.89709071 | 76 | 0.148727984 |
| Pentafunctional AROM polypeptide OS = Saccharomyces cerevisiae GN = ARO1 PE = 1 SV = 1 | 0.00029733 | 2.49918E-05 | 11.89709071 | 76 | 0.148727984 |
| 60S ribosomal protein L8-B OS = Saccharomyces cerevisiae GN = RPL8B PE = 1 SV = 3 | 0.00367754 | 0.000310714 | 11.8357655 | 78 | 0.152641879 |
| GTP-binding protein RHO1 OS = Saccharomyces cerevisiae GN = RHO1 PE = 1 SV = 3 | 0.001110598 | 9.43228E-05 | 11.77444029 | 79 | 0.154598826 |
| Invertase 2 OS = Saccharomyces cerevisiae GN = SUC2 PE = 1 SV = 1 | 0.000424013 | 3.60113E-05 | 11.77444029 | 80 | 0.156555773 |
| Squalene synthase OS = Saccharomyces cerevisiae GN = ERG9 PE = 1 SV = 2 | 0.000497125 | 4.22207E-05 | 11.77444029 | 80 | 0.156555773 |
| Eukaryotic translation initiation factor 3 subunit B OS = Saccharomyces cerevisiae GN = PRT1 PE = 1 SV = 1 | 0.000577426 | 4.95569E-05 | 11.65178987 | 82 | 0.160469667 |
| Cytochrome c iso-2 OS = Saccharomyces cerevisiae GN = CYC7 PE = 1 SV = 1 | 0.00200888 | 0.000174244 | 11.52913945 | 83 | 0.162426614 |
| ATP-dependent permease PDR15 OS = Saccharomyces cerevisiae GN = PDR15 PE = 1 SV = 1 | 0.000146155 | 1.2677E-05 | 11.52913945 | 84 | 0.164383562 |
| 60S ribosomal protein L28 OS = Saccharomyces cerevisiae GN = RPL28 PE = 1 SV = 2 | 0.001473501 | 0.000130585 | 11.28383861 | 85 | 0.166340509 |
| Methionyl-tRNA synthetase, cytoplasmic OS = Saccharomyces cerevisiae GN = MES1 PE = 1 SV = 4 | 0.000287593 | 2.54871E-05 | 11.28383861 | 86 | 0.1628297456 |
| Eukaryotic translation initiation factor 3 subunit G OS = Saccharomyces cerevisiae GN = TIF35 PE = 1 SV = 1 | 0.000790304 | 7.1595E-05 | 11.03853777 | 87 | 0.170254403 |
| General transcriptional corepressor TUP1 OS = Saccharomyces cerevisiae GN = TUP1 PE = 1 SV = 2 | 0.000307833 | 2.78871E-05 | 11.03853777 | 88 | 0.17221135 |
| Heat shock protein 42 OS = Saccharomyces cerevisiae GN = HSP42 PE = 1 SV = 1 | 0.000550472 | 5.10016E-05 | 10.79323693 | 89 | 0.174168297 |

TABLE 7-continued

| | | | | | |
|---|---|---|---|---|---|
| 60S ribosomal protein L15-B OS = *Saccharomyces cerevisiae* GN = RPL15B PE = 1 SV = 2 | 0.001842433 | 0.000178831 | 10.30263526 | 90 | 0.176125245 |
| 40S ribosomal protein S23 OS = *Saccharomyces cerevisiae* GN = RPS23A PE = 1 SV = 1 | 0.001402798 | 0.000136159 | 10.30263526 | 90 | 0.176125245 |
| T-complex protein 1 subunit theta OS = *Saccharomyces cerevisiae* GN = CCT8 PE = 1 SV = 1 | 0.000364859 | 3.54141E-05 | 10.30263526 | 92 | 0.180039139 |
| 26S protease regulatory subunit 8 homolog OS = *Saccharomyces cerevisiae* GN = RPT6 PE = 1 SV = 4 | 0.000485124 | 4.82358E-05 | 10.05733442 | 93 | 0.181996086 |
| SDO1-like protein YHR087W OS = *Saccharomyces cerevisiae* GN = YHR087W PE = 1 SV = 1 | 0.001828741 | 0.000181832 | 10.05733442 | 94 | 0.183953033 |
| Mitochondrial escape protein 2 OS = *Saccharomyces cerevisiae* GN = YME2 PE = 1 SV = 1 | 0.000221602 | 2.25847E-05 | 9.812033576 | 95 | 0.18590998 |
| Alpha-soluble NSF attachment protein OS = *Saccharomyces cerevisiae* GN = SEC17 PE = 1 SV = 4 | 0.000653179 | 6.65692E-05 | 9.812033676 | 95 | 0.18590998 |
| Protein translocation protein SEC63 OS = *Saccharomyces cerevisiae* GN = SEC63 PE = 1 SV = 2 | 0.000284375 | 2.89823E-05 | 9.812033576 | 95 | 0.18590998 |
| Delta-1-pyrroline-5-carboxylate dehydrogenase, mitochondrial OS = *Saccharomyces cerevisiae* GN = PUT2 PE = 1 SV = 2 | 0.000332526 | 3.38896E-05 | 9.812033576 | 98 | 0.191780822 |
| Polyamine N-acetyltransferase 1 OS = *Saccharomyces cerevisiae* GN = PAA1 PE = 1 SV = 1 | 0.001928069 | 0.000198988 | 9.689383157 | 99 | 0.193737769 |
| 40S ribosomal protein S22-B OS = *Saccharomyces cerevisiae* GN = RPS22B PE = 1 SV = 3 | 0.002893283 | 0.000298603 | 9.689383157 | 99 | 0.193737789 |
| Phosphoinositide phosphatase SAC1 OS = *Saccharomyces cerevisiae* GN = SAC1 PE = 1 SV = 1 | 0.000286194 | 3.07028E-05 | 9.321431897 | 101 | 0.197651663 |
| 40S ribosomal protein S26-A OS = *Saccharomyces cerevisiae* GN = RPS26A PE = 1 SV = 1 | 0.001507278 | 0.0001617 | 9.321431897 | 101 | 0.197651663 |
| 26S proteasome regulatory subunit RPN2 OS = *Saccharomyces cerevisiae* GN = RPN2 PE = 1 SV = 4 | 0.000390567 | 4.18999E-05 | 9.321431897 | 101 | 0.197651663 |
| Translational activator GCN1 OS = *Saccharomyces cerevisiae* GN = GCN1 PE = 1 SV = 1 | 6.86049E-05 | 7.35991E-06 | 9.321431897 | 101 | 0.197651663 |
| Dolichyl-diphosphooligosaccharide--protein glycosyltransferase subunit STT3 OS = *Saccharomyces cerevisiae* GN = STT3 PE = 1 SV = 2 | 0.000249663 | 2.67838E-05 | 9.321431897 | 105 | 0.205479452 |
| 1,3-beta-glucanosyltransferase GAS5 OS = *Saccharomyces cerevisiae* GN = GAS5 PE = 1 SV = 1 | 0.000392433 | 4.21001E-05 | 9.321431897 | 105 | 0.205479452 |
| Acyl-CoA-binding protein OS = *Saccharomyces cerevisiae* GN = ACB1 PE = 1 SV = 3 | 0.002023076 | 0.000217035 | 9.321431897 | 107 | 0.209393346 |
| Tricalbin-1 OS = *Saccharomyces cerevisiae* GN = TCB1 PE = 1 SV = 1 | 0.000148375 | 1.63478E-05 | 9.076131058 | 108 | 0.211350294 |
| NADP-specific glutamate dehydrogenase 2 OS = *Saccharomyces cerevisiae* GN = GDH3 PE = 1 SV = 1 | 0.000399377 | 4.4003E-05 | 9.076131058 | 108 | 0.211350294 |
| Dolichyl-phosphate-mannose--protein mannosyltransferase 1 OS = *Saccharomyces cerevisiae* GN = PMT1 PE = 1 SV = 1 | 0.00021386 | 2.35629E-05 | 9.076131058 | 110 | 0.215264188 |
| Mitochondrial import inner membrane translocase subunit TIM10 OS = *Saccharomyces cerevisiae* GN = MRS11 PE = 1 SV = 1 | 0.001923423 | 0.000211921 | 9.076131058 | 110 | 0.215264188 |
| Ornithine carbamoyltransferase OS = *Saccharomyces cerevisiae* GN = ARG3 PE = 1 SV = 1 | 0.000523699 | 5.77006E-05 | 9.076131058 | 110 | 0.215264188 |
| Putative magnesium-dependent phosphatase YER134C OS = *Saccharomyces cerevisiae* GN = YER134C PE = 1 SV = 1 | 0.000943354 | 0.000106825 | 8.830830219 | 113 | 0.221135029 |
| Eukaryotic translation initiation factor 4B OS = *Saccharomyces cerevisiae* GN = TIF3 PE = 1 SV = 1 | 0.000397433 | 4.50051E-05 | 8.830830219 | 113 | 0.221135029 |
| Mitochondrial escape protein 2 OS = *Saccharomyces cerevisiae* (strain YJM789) GN = YME2 PE = 3 SV = 1 | 0.000199503 | 2.25917E-05 | 8.830830219 | 115 | 0.225048924 |
| Vesicle-associated membrane protein-associated protein SCS2 OS = *Saccharomyces cerevisiae* GN = SCS2 PE = 1 SV = 3 | 0.000716233 | 8.11059E-05 | 8.830830219 | 115 | 0.225048924 |
| Importin beta SMX1 OS = *Saccharomyces cerevisiae* GN = SXM1 PE = 1 SV = 1 | 0.000177883 | 2.01434E-05 | 8.830830219 | 115 | 0.225048924 |
| Inorganic phosphate transport protein PHO88 OS = *Saccharomyces cerevisiae* GN = PHO88 PE = 1 SV = 1 | 0.000912311 | 0.00010331 | 8.830830219 | 115 | 0.225048924 |
| Transcription elongation factor SPT6 OS = *Saccharomyces cerevisiae* GN = SPT6 PE = 1 SV = 1 | 0.000225986 | 2.5951E-05 | 8.708179799 | 119 | 0.232876712 |
| T-complex protein 1 subunit delta OS = *Saccharomyces cerevisiae* GN = CCT4 PE = 1 SV = 2 | 0.000325467 | 3.79088E-05 | 8.585529379 | 120 | 0.234833659 |
| 5'-3' exoribonuclease 1 OS = *Saccharomyces cerevisiae* GN = KEM1 PE = 1 SV = 1 | 0.0002137 | 2.48907E-05 | 8.585529379 | 120 | 0.234833659 |
| Fumarate reductase OS = *Saccharomyces cerevisiae* GN = YEL047C PE = 1 SV = 1 | 0.000368743 | 4.29494E-05 | 8.585529379 | 122 | 0.238747554 |
| 3-hydroxy-3-methylglutaryl-coenzyme A reductase 1 OS = *Saccharomyces cerevisiae* GN = HMG1 PE = 1 SV = 1 | 0.000157513 | 1.88859E-05 | 8.34022854 | 123 | 0.240704501 |
| 26S proteasome regulatory subunit RPN9 OS = *Saccharomyces cerevisiae* GN = RPN9 PE = 1 SV = 1 | 0.000397789 | 4.76952E-05 | 8.34022854 | 123 | 0.240704501 |
| Dolichyl-phosphate-mannose--protein mannosyltransferase 2 OS = *Saccharomyces cerevisiae* GN = PMT2 PE = 1 SV = 2 | 0.000209652 | 2.51375E-05 | 8.34022854 | 123 | 0.240704501 |

TABLE 7-continued

| | | | | | |
|---|---|---|---|---|---|
| Bifunctional protein GAL10 OS = *Saccharomyces cerevisiae* GN = GAL10 PE = 1 SV = 2 | 0.006432474 | 0.000781936 | 8.226338864 | 126 | 0.246575342 |
| ATP-dependent bile acid permease OS = *Saccharomyces cerevisiae* GN = YBT1 PE = 1 SV = 2 | 9.3446E-05 | 1.15438E-05 | 8.0949277 | 127 | 0.24853229 |
| Saccharopine dehydrogenase [NAD+, L-lysine-forming] OS = *Saccharomyces cerevisiae* GN = LYS1 PE = 1 SV = 3 | 0.000426308 | 5.26636E-05 | 8.0949277 | 127 | 0.24853229 |
| Coatomer subunit gamma OS = *Saccharomyces cerevisiae* GN = SEC21 PE = 1 SV = 2 | 0.000163509 | 2.08302E-05 | 7.849626861 | 129 | 0.252446184 |
| Cell division control protein 53 OS = *Saccharomyces cerevisiae* GN = CDC53 PE = 1 SV = 1 | 0.000182456 | 2.3244E-05 | 7.849626861 | 129 | 0.252446184 |
| Rotenone-insensitive NADH-ubiquinone oxidoreductase, mitochondrial OS = *Saccharomyces cerevisiae* GN = NDI1 PE = 1 SV = 1 | 0.000299404 | 3.81424E-05 | 7.849626861 | 131 | 0.256360078 |
| Argininosuccinate lyase OS = *Saccharomyces cerevisiae* GN = ARG4 PE = 1 SV = 2 | 0.000329703 | 4.20024E-05 | 7.849626861 | 131 | 0.256360078 |
| Zinc finger protein GIS2 OS = *Saccharomyces cerevisiae* GN = GIS2 PE = 1 SV = 1 | 0.000970965 | 0.000127686 | 7.604326022 | 133 | 0.260273973 |
| Protein kinase MCK1 OS = *Saccharomyces cerevisiae* GN = MCK1 PE = 1 SV = 1 | 0.000384952 | 5.06228E-05 | 7.604326022 | 133 | 0.260273973 |
| Malate dehydrogenase, peroxisomal OS = *Saccharomyces cerevisiae* GN = MDH3 PE = 1 SV = 3 | 0.000446552 | 5.87235E-05 | 7.604326022 | 135 | 0.264187867 |
| T-complex protein 1 subunit zeta OS = *Saccharomyces cerevisiae* GN = CCT6 PE = 1 SV = 1 | 0.000277109 | 3.6441E-05 | 7.604326022 | 136 | 0.266144814 |
| ATP-dependent RNA helicase DBP2 OS = *Saccharomyces cerevisiae* GN = DBP2 PE = 1 SV = 1 | 0.000263443 | 3.57987E-05 | 7.359025182 | 137 | 0.268101761 |
| Cytochrome B pre-mRNA-processing protein 6 OS = *Saccharomyces cerevisiae* GN = CBP6 PE = 1 SV = 1 | 0.000860311 | 0.000116906 | 7.359025182 | 138 | 0.270058708 |
| Protein DCS2 OS = *Saccharomyces cerevisiae* GN = DCS2 PE = 1 SV = 3 | 0.000392517 | 5.33382E-05 | 7.359025182 | 138 | 0.270058708 |
| Eukaryotic translation initiation factor 3 subunit A OS = *Saccharomyces cerevisiae* GN = TIF32 PE = 1 SV = 1 | 0.000854379 | 0.000118738 | 7.195491289 | 140 | 0.273972603 |
| Glucose-signaling factor 2 OS = *Saccharomyces cerevisiae* GN = GSF2 PE = 1 SV = 1 | 0.000677298 | 9.521E-05 | 7.11374343 | 141 | 0.27592955 |
| Glycerol-3-phosphate dehydrogenase [NAD+] 2, mitochondrial OS = *Saccharomyces cerevisiae* GN = GPD2 PE = 1 SV = 2 | 0.000314327 | 4.41859E-05 | 7.113724343 | 142 | 0.277886497 |
| Prohibitin-2 OS = *Saccharomyces cerevisiae* GN = PHB2 PE = 1 SV = 2 | 0.000451495 | 6.34682E-05 | 7.113724343 | 142 | 0.277886497 |
| 40S ribosomal protein S29-A OS = *Saccharomyces cerevisiae* GN = RPS29A PE = 1 SV = 3 | 0.002332289 | 0.000327858 | 7.113724343 | 142 | 0.277886497 |
| DNA-directed RNA polymerase I subunit RPA1 OS = *Saccharomyces cerevisiae* GN = RPA1 PE = 1 SV = 2 | 8.33248E-05 | 1.17132E-05 | 7.113724343 | 145 | 0.283757339 |
| Protein transport protein SEC24 OS = *Saccharomyces cerevisiae* GN = SEC24 PE = 1 SV = 1 | 0.000149893 | 2.10709E-05 | 7.113724343 | 145 | 0.283757339 |
| Carboxypeptidase Y OS = *Saccharomyces cerevisiae* GN = PRC1 PE = 1 SV = 1 | 0.000250804 | 3.65156E-05 | 6.868423503 | 147 | 0.287671233 |
| V-type proton ATPase subunit d OS = *Saccharomyces cerevisiae* GN = VMA6 PE = 1 SV = 2 | 0.000376931 | 5.48789E-05 | 6.868423503 | 148 | 0.28962818 |
| Uncharacterized protein YJL171C OS = *Saccharomyces cerevisiae* GN = YJL171C PE = 1 SV = 1 | 0.000348696 | 5.0768E-05 | 6.868423503 | 148 | 0.28962818 |
| Vacuolar protein sorting/targeting protein PEP1 OS = *Saccharomyces cerevisiae* GN = PEP1 PE = 1 SV = 1 | 8.43666E-04 | 1.22833E-05 | 6.868423503 | 148 | 0.28962818 |
| FACT complex subunit POB3 OS = *Saccharomyces cerevisiae* GN = POB3 PE = 1 SV = 1 | 0.000238097 | 3.46655E-05 | 6.868423503 | 151 | 0.295499022 |
| Uncharacterized mitochondrial membrane protein FMP10 OS = *Saccharomyces cerevisiae* GN = FMP10 PE = 1 SV = 1 | 0.000541502 | 7.88393E-05 | 6.868423503 | 151 | 0.295499022 |
| RNA annealing protein YRA1 OS = *Saccharomyces cerevisiae* GN = YRA2 PE = 1 SV = 2 | 0.000579546 | 8.75034E-05 | 6.623122664 | 153 | 0.299412916 |
| Mitochondrial outer membrane protein OM45 OS = *Saccharomyces cerevisiae* GN = OM45 PE = 1 SV = 2 | 0.000324421 | 4.8983E-05 | 6.623122664 | 154 | 0.301369863 |
| Mitochondrial import receptor subunit TOM5 OS = *Saccharomyces cerevisiae* GN = TOM5 PE = 1 SV = 1 | 0.002416716 | 0.000364891 | 6.623122664 | 154 | 0.301369863 |
| T-complex protein 1 subunit alpha OS = *Saccharomyces cerevisiae* GN = TCP1 PE = 1 SV = 2 | 0.000239133 | 3.61058E-05 | 6.623122664 | 156 | 0.305283757 |
| Eukaryotic translation initiation factor 1A OS = *Saccharomyces cerevisiae* GN = TIF11 PE = 1 SV = 1 | 0.0007988 | 0.000125247 | 6.377821825 | 157 | 0.307240705 |
| Protein MSN5 OS = *Saccharomyces cerevisiae* GN = MSN5 PE = 1 SV = 1 | 9.79948E-05 | 1.53649E-05 | 6.377821825 | 158 | 0.309197652 |
| Putative fatty aldehyde dehydrogenase HFD1 OS = *Saccharomyces cerevisiae* GN = HFD1 PE = 1 SV = 1 | 0.000232197 | 3.6407E-05 | 6.377821825 | 158 | 0.309197652 |
| Ergosterol biosynthetic protein 28 OS = *Saccharomyces cerevisiae* GN = ERG28 PE = 1 SV = 1 | 0.00081278 | 0.000127439 | 6.377821825 | 158 | 0.309197652 |
| Protein YRO2 OS = *Saccharomyces cerevisiae* GN = YRO2 PE = 1 SV = 1 | 0.000359689 | 5.63969E-05 | 6.377821825 | 158 | 0.309197652 |
| Methylene-fatty acyl-phospholipid synthase OS = *Saccharomyces cerevisiae* GN = PEM2 PE = 1 SV = 1 | 0.000601597 | 9.43265E-05 | 6.377821825 | 162 | 0.31702544 |
| Protein MKT1 OS = *Saccharomyces cerevisiae* GN = MKT1 PE = 1 SV = 1 | 0.000141715 | 2.31087E-05 | 6.132520985 | 163 | 0.318982387 |

TABLE 7-continued

| | | | | |
|---|---|---|---|---|
| Protein MRH1 OS = Saccharomyces cerevisiae GN = MRH1 PE = 1 SV = 1 | 0.000370021 | 6.03376E-05 | 6.132520985 | 163 | 0.318982387 |
| Eukaryotic translation initiation factor 2 subunit beta OS = Saccharomyces cerevisiae GN = SUI3 PE = 1 SV = 2 | 0.000424122 | 6.91596E-05 | 6.132520985 | 165 | 0.322896282 |
| Peroxiredoxin TSA2 OS = Saccharomyces cerevisiae GN = TSA2 PE = 1 SV = 3 | 0.000594774 | 0.000101028 | 5.887220146 | 166 | 0.324853229 |
| Endoplasmic reticulum veriscle protein 25 OS = Saccharomyces cerevisiae GN = ERV25 PE = 1 SV = 1 | 0.000533314 | 9.05884E-05 | 5.887220146 | 166 | 0.324853229 |
| PKHD-type hydroxylase TPA1 OS = Saccharomyces cerevisiae GN = TPA1 PE = 1 SV = 1 | 0.000173629 | 2.94925E-05 | 5.887220146 | 166 | 0.324853229 |
| SED5-binding protein 3 OS = Saccharomyces cerevisiae GN = SFB3 PE = 1 SV = 1 | 0.000123674 | 2.10071E-05 | 5.887220146 | 169 | 0.33072407 |
| D-lactate dehydrogenase [cytochrome] 3 OS = Saccharomyces cerevisiae GN = DLD3 PE = 1 SV = 1 | 0.000232791 | 3.95417E-05 | 5.887220146 | 169 | 0.33072407 |
| Single-stranded nucleic acid-binding protein OS = Saccharomyces cerevisiae GN = SBP1 PE = 1 SV = 2 | 0.00076317 | 0.00013239 | 5.764569726 | 171 | 0.334637965 |
| Protein CWH43 OS = Saccharomyces cerevisiae GN = CWH43 PE = 1 SV = 2 | 0.000114198 | 2.02411E-05 | 5.641919306 | 172 | 0.336594912 |
| T-complex protein 1 subunit eta OS = Saccharomyces cerevisiae GN = CCT7 PE = 1 SV = 1 | 0.000206247 | 3.65562E-05 | 5.641919306 | 172 | 0.336594912 |
| 26S protease regulatory subunit 6B homolog OS = Saccharomyces cerevisiae GN = RPT3 PE = 1 SV = 1 | 0.000256832 | 4.55221E-05 | 5.641919306 | 172 | 0.336594912 |
| NADH-cytochrome b5 reductase 1 OS = Saccharomyces cerevisiae GN = CBR1 PE = 1 SV = 2 | 0.000391195 | 6.93372E-05 | 5.641919306 | 172 | 0.336594912 |
| Glycogen debranching enzyme OS = Saccharomyces cerevisiae GN = GDB1 PE = 1 SV = 1 | 0.000140824 | 2.49603E-05 | 5.641919306 | 176 | 0.344422701 |
| C-5 sterol desaturase OS = Saccharomyces cerevisiae GN = ERG3 PE = 1 SV = 1 | 0.000288325 | 5.1104E-05 | 5.641919306 | 176 | 0.344422701 |
| 13 kDa ribonucleoprotein-associated protein OS = Saccharomyces cerevisiae GN = SNU13 PE = 1 SV = 1 | 0.00090797 | 0.000160933 | 5.641919306 | 176 | 0.344422701 |
| UPF0202 protein KRE33 OS = Saccharomyces cerevisiae GN = KRE33 PE = 1 SV = 1 | 0.000103228 | 1.82965E-04 | 5.641919306 | 176 | 0.344422701 |
| Protein phosphatase PP2A regulatory subunit A OS = Saccharomyces cerevisiae GN = TPD3 PE = 1 SV = 2 | 0.00017364 | 3.07768E-05 | 5.641919306 | 176 | 0.344422701 |
| Eukaryotic translation initiation factor 2 subunit gamma OS = Saccharomyces cerevisiae GN = GCD11 PE = 1 SV = 1 | 0.000212912 | 3.77375E-05 | 5.641919306 | 176 | 0.344422701 |
| Midasin OS = Saccharomyces cerevisiae GN = MDN1 PE = 1 SV = 1 | 2.20277E-05 | 3.90429E-06 | 5.641919306 | 182 | 0.356164384 |
| Galactose-1-phosphate uridylyltransferase OS = Saccharomyces cerevisiae GN = GAL7 PE = 1 SV = 4 | 0.005800888 | 0.001030416 | 5.629654264 | 183 | 0.358121331 |
| UPF0121 membrane protein YLL023C OS = Saccharomyces cerevisiae GN = YLL023C PE = 1 SV = 1 | 0.000366131 | 6.778446E-05 | 5.396618467 | 184 | 0.360078278 |
| Phosphatidylinositol transfer protein PDR16 OS = Saccharomyces cerevisiae GN = PDR16 PE = 1 SV = 1 | 0.000289444 | 5.36342E-05 | 5.396618467 | 184 | 0.360078278 |
| 60S ribosomal protein L43 OS = Saccharomyces cerevisiae GN = RPL43A PE = 1 SV = 2 | 0.001167888 | 0.000216411 | 5.396618467 | 186 | 0.363992172 |
| Arginine biosynthesis bifunctional protein ARG7, mitochondrial OS = Saccharomyces cerevisiae GN = ARG7 PE = 1 SV = 1 | 0.000246288 | 4.456375E-05 | 5.396618467 | 186 | 0.363992172 |
| Probable family 17 glucosidase SCW4 OS = Saccharomyces cerevisiae GN = SCW4 PE = 1 SV = 1 | 0.00029336 | 5.436E-05 | 5.396618467 | 186 | 0.363992172 |
| 26S protease subunit RPT4 OS = Saccharomyces cerevisiae GN = RPT4 PE = 1 SV = 4 | 0.000238513 | 4.41967E-05 | 5.396618467 | 189 | 0.369863014 |
| 60S ribosomal protein L3 OS = Saccharomyces cerevisiae GN = RPL3 PR = 1 SV = 4 | 0.002680969 | 0.000499055 | 5.372088383 | 190 | 0.371819961 |
| Phosphoglucomutase-2 OS = Saccharomyces cerevisiae GN = PGM2 PE = 1 SV = 1 | 0.002929237 | 0.000553804 | 5.28929935 | 191 | 0.373776908 |
| Uncharacterized phosphatase YNL010W OS = Saccharomyces cerevisiae GN = YNL010W PE = 1 SV = 1 | 0.000838173 | 0.000158927 | 5.273968047 | 192 | 0.375733855 |
| Elongation factor 3A OS = Saccharomyces cerevisiae GN = YEF3 PE = 1 SV = 3 | 0.004119318 | 0.000790698 | 5.209722589 | 193 | 0.377690802 |
| Casein kinase II subunit alpha' OS = Saccharomyces cerevisiae GN = CKA2 PE = 1 SV = 2 | 0.000285478 | 5.54184E-05 | 5.151317628 | 194 | 0.37964775 |
| 54S ribosomal protein L12, mitochondrial OS = Saccharomyces cerevisiae GN = MNP1 PE = 1 SV = 1 | 0.000544737 | 0.000105747 | 5.151317628 | 194 | 0.37964775 |
| Nuclear protein SNF4 OS = Saccharomyces cerevisiae GN = SNF4 PE = 1 SV = 1 | 0.000309024 | 5.99893E-05 | 5.151317628 | 194 | 0.37964775 |
| Eukaryotic initiation factor 4F subunit p150 OS = Saccharomyces cerevisiae GN = TIF4631 PE = 1 SV = 2 | 0.000105031 | 2.03892E-05 | 5.151317628 | 194 | 0.37964775 |
| Medium-chain fatty acid ethyl ester synthase/esterase 2 OS = Saccharomyces cerevisiae GN = EHT1 PE = 1 SV = 1 | 0.000219468 | 4.26042E-05 | 5.151317628 | 194 | 0.37964775 |
| ABC transporter ATP-binding protein ARB1 OS = Saccharomyces cerevisiae GN = ARB1 PE = 1 SV = 1 | 0.000164512 | 3.19359E-05 | 5.151317628 | 194 | 0.37964775 |
| Cysteinyl-tRNA synthetase OS = Saccharomyces cereviaie GN = YNL247W PE = 1 SV = 1 | 0.000128513 | 2.49476E-05 | 5.151317628 | 194 | 0.37964775 |
| Protein TTP1 OS = Saccharomyces cerevisiae GN = TTP1 PE = 1 SV = 1 | 0.000165973 | 3.22195E-05 | 5.151317628 | 194 | 0.37964775 |

TABLE 7-continued

| | | | | | |
|---|---|---|---|---|---|
| 26S proteasome regulatory subunit RPN8 OS = Saccharomyces cerevisiae GN = RPN8 PE = 1 SV = 3 | 0.000293607 | 5.69966E-05 | 5.151317628 | 194 | 0.37964775 |
| NADH-cytochrome b5 reductase 1 OS = Saccharomyces cerevisiae (strain YJM789) GN = CBR1 PE = 2 SV = 2 | 0.000357999 | 6.94965E-05 | 5.151317628 | 194 | 0.37964775 |
| ER membrane protein complex subunit 1 OS = Saccharomyces cerevisiae GN = EMC1 PE = 1 SV = 1 | 0.000129027 | 2.50474E-05 | 5.151317628 | 204 | 0.399217221 |
| Heat shock protein 78, mitochondrial OS = Saccharomyces cerevisiae GN = HSP78 PE = 1 SV = 2 | 0.001712467 | 0.00033471 | 5.11627465 | 205 | 0.401174168 |
| Nuclear protein STH1/NPS1 OS = Saccharomyces cerevisiae GN = STH1 PE = 1 SV = 1 | 6.83479E-05 | 1.39314E-05 | 4.906016788 | 206 | 0.403131115 |
| mRNA-binding protein PUF3 OS = Saccharomyces cerevisiae GN = PUF3 PE = 1 SV = 1 | 0.000109244 | 2.22674E-05 | 4.906016788 | 206 | 0.403131115 |
| Actin-interacting protein 1 OS = Saccharomyces cerevisiae GN = AIP1 PE = 1 SV = 1 | 0.00015913 | 3.24356E-05 | 4.906016788 | 206 | 0.403131115 |
| Cytochrome c iso-1 OS = Saccharomyces cerevisiae GN = CYC1 PE = 1 SV = 2 | 0.003517692 | 0.000717016 | 4.906016788 | 206 | 0.403131115 |
| CTP synthase 1 OS = Saccharomyces cerevisiae GN = URA7 PE = 1 SV = 2 | 0.000165559 | 3.37461E-05 | 4.906016788 | 206 | 0.403131115 |
| Squalene monooxygenase OS = Saccharomyces cerevisiae GN = ERG1 PE = 1 SV = 2 | 0.000194343 | 3.96131E-05 | 4.906016788 | 206 | 0.403131115 |
| Putative aldehyde dehydrogenase-like protein YHR039C OS = Saccharomyces cerevisiae GN = MSC7 PE = 1 SV = 1 | 0.000150213 | 3.06181E-05 | 4.906016788 | 212 | 0.414872798 |
| Glucosamine--fructose-6-phosphate aminotransferase [isomerizing] OS = Saccharomyces cerevisiae GN = GFA1 PE = 1 SV = 4 | 0.000521969 | 0.000109122 | 4.783366368 | 213 | 0.416829746 |
| Uncharacterized GTP-binding protein OLA1 OS = Saccharomyces cerevisiae GN = OLA1 PE = 1 SV = 1 | 0.001879535 | 0.000395467 | 4.752703763 | 214 | 0.418786693 |
| Probable 1-acyl-sn-glycerol-3-phosphate acyltransferase OS = Saccharomyces cerevisiae GN = SLC1 PE = 1 SV = 1 | 0.000300341 | 6.44409E-05 | 4.660715949 | 215 | 0.42074364 |
| Sporulation-specific protein 21 OS = Saccharomyces cerevisiae GN = SPO21 PE = 1 SV = 1 | 0.000145644 | 3.12494E-05 | 4.660715949 | 216 | 0.422700587 |
| Cell division control protein 42 OS = Saccharomyces cerevisiae GN = CDC42 PE = 1 SV = 2 | 0.000477329 | 0.000102415 | 4.660715949 | 216 | 0.422700587 |
| Serine/threonine-protein phosphatase PP-Z2 OS = Saccharomyces cerevisiae GN = PPZ2 PE = 1 SV = 4 | 0.000129664 | 2.78207E-05 | 4.660715949 | 216 | 0.422700587 |
| Putative mitochondrial carrier protein YHM1/SHM1 OS = Saccharomyces cerevisiae GN = YHM1 PE = 1 SV = 1 | 0.0003064 | 6.57409E-05 | 4.660715949 | 216 | 0.422700587 |
| 60S ribosomal protein L24-A OS = Saccharomyces cerevisiae GN = RPL24A PE = 1 SV = 1 | 0.001155633 | 0.000247952 | 4.660715949 | 216 | 0.422700587 |
| 60S ribosomal protein L35 OS = Saccharomyces cerevisiae GN = RPL35A PE = 1 SV = 1 | 0.001463371 | 0.00031398 | 4.660715949 | 216 | 0.422700587 |
| Mitochondrial respiratory chain complexes assembly protein RCA1 OS = Saccharomyces cerevisiae GN = RCA1 PE = 1 SV = 2 | 0.000109111 | 2.34108E-05 | 4.660715949 | 222 | 0.43444227 |
| Prohibitin-1 OS = Saccharomyces cerevisiae GN = PHB1 PE = 1 SV = 2 | 0.000647698 | 0.00013897 | 4.660715949 | 222 | 0.43444227 |
| T-complex protein 1 subunit epsilon OS = Saccharomyces cerevisiae GN = CCT5 PE = 1 SV = 3 | 0.000164381 | 3.52695E-05 | 4.660715949 | 222 | 0.43444227 |
| Translation machinery-associated protein 22 OS = Saccharomyces cerevisiae (strain YJM789) GN = TMA22 PE = 3 SV = 1 | 0.000452437 | 9.70746E-05 | 4.660715949 | 222 | 0.43444227 |
| DnaJ homolog 1, mitochondrial OS = Saccharomyces cerevisiae GN = MDJ1 PE = 1 SV = 1 | 0.000183181 | 3.93031E-05 | 4.660715949 | 222 | 0.43444227 |
| Alpha, alpha-trehalose-phosphate synthase [UDP-forming] 56 kDa subunit OS = Saccharomyces cerevisiae GN = TPS1 PE = 1 SV = 2 | 0.000725072 | 0.000155571 | 4.660715949 | 222 | 0.43444227 |
| Acetyl-coenzyme A synthetase 2 OS = Saccharomyces cerevisiae GN = ACS2 PE = 1 SV = 1 | 0.001617845 | 0.000347124 | 4.660715949 | 222 | 0.43444227 |
| 60S ribosomal protein L24-B OS = Saccharomyces cerevisiae GN = RPL24B PE = 1 SV = 1 | 0.001159999 | 0.000248889 | 4.660715949 | 222 | 0.43444227 |
| Protein YGP1 OS = Saccharomyces cerevisiae GN = YGP1 PE = 1 SV = 2 | 0.00027266 | 5.85018E-05 | 4.660715949 | 222 | 0.43444227 |
| Actin-related protein 2/3 complex subunit 3 OS = Saccharomyces cerevisiae GN = ARC18 PE = 1 SV = 1 | 0.000494562 | 0.000106113 | 4.660715949 | 231 | 0.452054795 |
| Isoleucyl-tRNA synthetase, cytoplasmic OS = Saccharomyces cerevisiae GN = ILS1 PE = 1 SV = 1 | 0.001141147 | 0.000248582 | 4.590629995 | 232 | 0.454011742 |
| Eukaryotic translation initiation factor 3 subunit I OS = Saccharomyces cerevisiae (strain YJM789) GN = TIF34 PE = 3 SV = 1 | 0.000511405 | 0.000112692 | 4.538065529 | 233 | 0.455968689 |
| Dolichol-phosphate mannosyltransferase OS = Saccharomyces cerevisiae GN = DPM1 PE = 1 SV = 3 | 0.001287884 | 0.000287683 | 4.476740319 | 234 | 0.457925636 |
| 40S ribosomal protein S29-B OS = Saccharomyces cerevisiae GN = RPS29B PE = 1 SV = 3 | 0.001433232 | 0.000324597 | 4.415415109 | 235 | 0.459882583 |
| Pre-mRNA-splicing factor ATP-dependent RNA helicase PRP43 OS = Saccharomyces cerevisiae GN = PRP43 PE = 1 SV = 1 | 0.000110115 | 2.49388E-05 | 4.415415109 | 236 | 0.46183953 |
| Translocation protein SEC72 OS = Saccharomyces cerevisiae GN = SEC72 PE = 1 SV = 3 | 0.000446225 | 0.000101061 | 4.415415109 | 236 | 0.46183953 |
| Transcription elongation factor SPT5 OS = Saccharomyces cerevisiae GN = SPT5 PE = 1 SV = 1 | 0.000166746 | 3.77645E-05 | 4.415415109 | 236 | 0.46183953 |

TABLE 7-continued

| | | | | | |
|---|---|---|---|---|---|
| Endoplasmic reticulum transmembrane protein 1 OS = Saccharomyces cerevisiae GN = YET1 PE = 1 SV = 1 | 0.000411557 | 9.32092E-05 | 4.415415109 | 236 | 0.46183953 |
| Ferrochelatase, mitochondrial OS = Saccharomyces cerevisiae GN = HEM15 PE = 1 SV = 1 | 0.000216204 | 4.89658E-05 | 4.415415109 | 236 | 0.46183953 |
| Protein CBP3, mitochondrial OS = Saccharomyces cerevisiae GN = CBP3 PE = 1 SV = 1 | 0.000246696 | 5.58715E-05 | 4.415415109 | 236 | 0.46183953 |
| Putative protein disulfide-isomerase YIL005W OS = Saccharomyces cerevisiae GN = YIL005W PE = 1 SV = 1 | 0.000118712 | 2.68857E-05 | 4.415415109 | 236 | 0.46183953 |
| Mitochondrial protein import protein MAS5 OS = Saccharomyces cerevisiae GN = YDJ1 PE = 1 SV = 1 | 0.000863384 | 0.000195539 | 4.415415109 | 236 | 0.46183953 |
| Peroxisomal-coenzyme A synthetase OS = Saccharomyces cerevisiae GN = FAT2 PE = 1 SV = 1 | 0.000159402 | 3.61013E-05 | 4.415415109 | 236 | 0.46183953 |
| Nuclear cap-binding protein complex subunit 1 OS = Saccharomyces cerevisiae GN = STO1 PE = 1 SV = 2 | 0.000192799 | 4.36651E-05 | 4.415415109 | 245 | 0.479452055 |
| Proteasome component Y13 OS = Saccharomyces cerevisiae GN = PRE9 PE = 1 SV = 1 | 0.000335781 | 7.60474E-05 | 4.415415109 | 245 | 0.479452055 |
| Trehalose synthase complex regulatory subunit TSL1 OS = Saccharomyces cerevisiae GN = TSL1 PE = 1 SV = 1 | 0.000304804 | 7.10041E-05 | 4.29276469 | 247 | 0.483365949 |
| Ribosomal RNA-processing protein 12 OS = Saccharomyces cerevisiae GN = RRP12 PE = 1 SV = 1 | 6.62221E-05 | 1.58802E-05 | 4.17011427 | 248 | 0.485322896 |
| U3 small nucleolar RNA-associated protein 22 OS = Saccharomyces cerevisiae GN = UTP22 PE = 1 SV = 1 | 6.48185E-05 | 1.55436E-05 | 4.17011427 | 248 | 0.485322896 |
| 40S ribosomal protein S26-B OS = Saccharomyces cerevisiae GN = RPS26B PE = 1 SV = 1 | 0.001354434 | 0.000324795 | 4.17011427 | 248 | 0.485322896 |
| Elongator complex protein 1 OS = Saccharomyces cerevisiae GN = IKI3 PE = 1 SV = 1 | 5.95221E-05 | 1.42735E-05 | 4.17011427 | 248 | 0.485322896 |
| Probable 1,3-beta-glucanosyltransferase GAS3 OS = Saccharomyces cerevisiae GN = GAS3 PE = 1 SV = 1 | 0.0001603338 | 3.84492E-05 | 4.17011427 | 252 | 0.493150685 |
| Dynamin-related protein DNM1 OS = Saccharomyces cerevisiae GN = DNM1 PE = 1 SV = 1 | 0.000428661 | 0.000102794 | 4.17011427 | 252 | 0.493150685 |
| Pyruvate dehydrogenase complexs protein X component, mitochondrial OS = Saccharomyces cerevisiae GN = PDX1 PE = 1 SV = 1 | 0.000401489 | 9.62777E-05 | 4.17011427 | 252 | 0.493150685 |
| GTP-binding protein RHO3 OS = Saccharomyces cerevisiae GN = RHO3 PE = 1 SV = 2 | 0.00035976 | 8.6271E-05 | 4.17011427 | 252 | 0.493150685 |
| DNA-directed RNA polymerase I subunit RPA2 OS = Saccharomyces cerevisiae GN = RPA2 PE = 1 SV = 1 | 0.000130225 | 3.21744E-05 | 4.04746385 | 256 | 0.500978474 |
| 54S ribosomal protein YmL6, mitochondrial OS = Saccharomyces cerevisiae GN = YML6 PE = 1 SV = 2 | 0.000268086 | 6.83055E-05 | 3.92481343 | 257 | 0.502935421 |
| ER-derived vesicles protein ERV29 OS = Saccharomyces cerevisiae GN = ERV29 PE = 1 SV = 1 | 0.000244777 | 6.23666E-05 | 3.92481343 | 257 | 0.502935421 |
| 54S ribosomal protein L3, mitochondrial OS = Saccharomyces cerevisiae GN = MRPL3 PE = 1 SV = 2 | 0.000194787 | 4.96296E-05 | 3.92481343 | 257 | 0.502935421 |
| Pyrroline-5-carboxylate reductase OS = Saccharomyces cerevisiae GN = PRO3 PE = 1 SV = 1 | 0.000284449 | 7.24746E-05 | 3.92481343 | 257 | 0.502935421 |
| 60S ribosomal protein L34-A OS = Saccharomyces cerevisiae GN = RPL34A PE = 1 SV = 1 | 0.000628399 | 0.000160109 | 3.92481343 | 257 | 0.502935421 |
| Serine/threonine-protein kinase YPK1 OS = Saccharomyces cerevisiae GN = YPK1 PE = 1 SV = 2 | 0.000112061 | 2.85519E-05 | 3.92481343 | 257 | 0.502935421 |
| 60S ribosomal protein L19 OS = Saccharomyces cerevisiae GN = RPL19A PE = 1 SV = 5 | 0.000789773 | 0.000201226 | 3.92481343 | 257 | 0.502935421 |
| CDP-diacylglycerol--inositol 3-phosphatidyltransferase OS = Saccharomyces cerevisiae GN = PIS1 PE = 1 SV = 1 | 0.000345261 | 8.79687E-05 | 3.92481343 | 264 | 0.516634051 |
| 60S ribosome subunit biogeneses protein NIP7 OS = Saccharomyces cerevisiae GN = NIP7 PE = 1 SV = 1 | 0.00042053 | 0.000107146 | 3.92481343 | 264 | 0.516634051 |
| Cell division control protein 10 OS = Saccharomyces cerevisiae GN = CDC10 PE = 1 SV = 1 | 0.00023148 | 5.89787E-05 | 3.92481343 | 264 | 0.516634051 |
| E3 ubiquitin-protein ligase RSP5 OS = Saccharomyces cerevisiae GN = RSP5 PE = 1 SV = 1 | 9.33468E-05 | 2.37837E-05 | 3.92481343 | 264 | 0.516634051 |
| Glucan 1,3-beta-glucosidase I/II OS = Saccharomyces cerevisiae GN = EXG1 PE = 1 SV = 1 | 0.000167033 | 4.25582E-05 | 3.92481343 | 264 | 0.516634051 |
| Eukaryotic translation initiation factor 5A-2 OS = Saccharomyces cerevisiae GN = HYP2 PE = 1 SV = 3 | 0.010829628 | 0.002807121 | 3.857913202 | 269 | 0.526418787 |
| 1,4-alpha-glucan-branching enzyme OS = Saccharomyces cerevisiae GN = GLC3 PE = 1 SV = 2 | 0.000204713 | 5.38413E-05 | 3.802163011 | 270 | 0.52875734 |
| Polyadenylate-binding protein, cytoplasmic and nuclear OS = Saccharomyces cerevisiae GN = PAB1 PE = 1 SV = 4 | 0.001523484 | 0.000407257 | 3.740837801 | 271 | 0.530332681 |
| Protein GCY OS = Saccharomyces cerevisiae GN = GCY1 PE = 1 SV = 1 | 0.004153505 | 0.001120519 | 3.70676824 | 272 | 0.532289628 |
| Putative thiosulfate sulfurtransferase YOR285W OS = Saccharomyces cerevisiae GN = YOR285W PE = 1 SV = 1 | 0.001042629 | 0.000283361 | 3.679512591 | 273 | 0.534246575 |
| DNA topoisomerase 2-associated protein PAT1 OS = Saccharomyces cerevisiae GN = PAT1 PE = 1 SV = 3 | 9.07936E-05 | 2.46754E-05 | 3.679512591 | 274 | 0.536203523 |
| CAAX prenyl protease 1 OS = Saccharomyces cerevisiae GN = STE24 PE = 1 SV = 1 | 0.000153556 | 4.17326E-05 | 3.679512591 | 274 | 0.536203523 |
| Endoplasmic reticulum transmembrane protein 3 OS = Saccharomyces cerevisiae GN = YET3 PE = 1 SV = 1 | 0.000350817 | 9.53433E-05 | 3.679512591 | 274 | 0.536203523 |

TABLE 7-continued

| | | | | | |
|---|---|---|---|---|---|
| ATP-dependent RNA helicase DOB1 OS = Saccharomyces cerevisiae GN = MTR4 PE = 1 SV = 1 | 6.58304E-05 | 1.78911E-05 | 3.679512591 | 277 | 0.542074364 |
| Translation machinery-associated protein 17 OS = Saccharomyces cerevisiae GN = TMA17 PE = 1 SV = 1 | 0.000479086 | 0.000130204 | 3.679512591 | 277 | 0.542074364 |
| Carbon catabolite-derepressing protein kinase OS = Saccharomyces cerevisiae GN = SNF1 PE = 1 SV = 1 | 0.000111525 | 3.03099E-05 | 3.679512591 | 277 | 0.542074364 |
| tRNA (cytosinw-5-)-methyltransferase NCL1 OS = Saccharomyces cerevisiae GN = NCL1 PE = 1 SV = 1 | 0.000103174 | 2.80402E-05 | 3.679512591 | 277 | 0.542074364 |
| Protein transport protein SEC61 OS = Saccharomyces cerevisiae GN = SEC61 PE = 1 SV = 1 | 0.000151778 | 4.12496E-05 | 3.679512591 | 277 | 0.542074364 |
| Calcineurin subunit B OS = Saccharomyces cerevisiae GN = CNB1 PE = 1 SV = 3 | 0.000409121 | 0.000111189 | 3.679512591 | 277 | 0.542074364 |
| Lysophospholipase 1 OS = Saccharomyces cerevisiae GN = PLB1 PE = 1 SV = 2 | 0.000112114 | 3.04697E-05 | 3.679512591 | 277 | 0.542074364 |
| Proteasome component Y7 OS = Saccharomyces cerevisiae GN = PRE8 PE = 1 SV = 1 | 0.000295812 | 8.03944E-05 | 3.679512591 | 277 | 0.542074364 |
| Metal resistance protein YCF1 OS = Saccharomyces cerevisiae GN = YCF1 PE = 1 SV = 2 | 4.69538E-05 | 1.27609E-05 | 3.679512591 | 277 | 0.542074364 |
| Ran GTPase-activating protein 1 OS = Saccharomyces cerevisiae GN = RNA1 PE = 1 SV = 2 | 0.000175372 | 4.76619E-05 | 3.679512591 | 277 | 0.542074364 |
| L-aminoadipate-semialdehyde dehydrogenase OS = Saccharomyces cerevisiae GN = LYS2 PE = 1 SV = 2 | 0.000103446 | 2.81139E-05 | 3.679512591 | 277 | 0.542074364 |
| Serine hydroxymethyltransferase, mitochondrial OS = Saccharomyces cerevisiae GN = SHM1 PE = 1 SV = 2 | 0.000299329 | 8.13501E-05 | 3.679512591 | 288 | 0.563600783 |
| Coatomer subunit alpha OS = Saccharomyces cerevisiae GN = RET1 PE = 1 SV = 2 | 0.000351559 | 9.66186E-05 | 3.638629118 | 289 | 0.56555773 |
| 40S ribosomal protein S10-B OS = Saccharomyces cerevisiae GN = RPS10B PE = 1 SV = 1 | 0.003742563 | 0.001028564 | 3.638629118 | 289 | 0.56555773 |
| 40S ribosomal protein S10-A OS = Saccharomyces cerevisiae GN = RPS10A PE = 1 SV = 1 | 0.003742269 | 0.001028483 | 3.638629118 | 289 | 0.56555773 |
| Tryptophan synthase OS = Saccharomyces cerevisiae GN = TRP5 PE = 1 SV = 1 | 0.000412455 | 0.000113995 | 3.618187381 | 292 | 0.571428571 |
| Serine/threonine-protein phosphatase PP1-2 OS = Saccharomyces cerevisiae GN = GLC7 PE = 1 SV = 1 | 0.000865225 | 0.000243255 | 3.556862171 | 293 | 0.573385519 |
| Aminopeptidase Y OS = Saccharomyces cerevisiae GN = APE3 PE = 1 SV = 1 | 0.000258312 | 7.26236E-05 | 3.556862171 | 293 | 0.573385519 |
| Glycerol-3-phosphate dehydrogenase [NAD+] 1 OS = Saccharomyces cerevisiae GN = GPD1 PE = 1 SV = 4 | 0.00143702 | 0.000407527 | 3.526199566 | 295 | 0.577299413 |
| Valyl-tRNA synthetase, mitochondrial OS = Saccharomyces cerevisiae GN = VAS1 PE = 1 SV = 2 | 0.000732554 | 0.00020835 | 3.515978698 | 296 | 0.57925636 |
| Aconitrate hydratase, mitochondrial OS = Saccharomyces cerevisiae GN = ACO1 PE = 1 SV = 2 | 0.004316972 | 0.001227815 | 3.515978698 | 297 | 0.581213307 |
| Elongation factor Tu, mitochondrial OS = Saccharomyces cerevisiae GN = TUF1 PE = 1 SV = 1 | 0.000636478 | 0.000182083 | 3.495536962 | 298 | 0.583170254 |
| Glycerol-3-phosphate O-acyltransferase 2 OS = Saccharomyces cerevisiae GN = GPT2 PE = 1 SV = 1 | 8.96548E-05 | 2.61064E-05 | 3.434211752 | 299 | 0.585127202 |
| Putative ribosomal RNA methyltransferase Nop2 OS = Saccharomyces cerevisiae GN = NOP2 PE = 1 SV = 1 | 0.000107421 | 3.12796E-05 | 3.434211752 | 299 | 0.585127202 |
| Serine/threonine-protein kinase YPK2/YKR2 OS = Saccharomyces cerevisiae GN = YPK2 PE = 1 SV = 1 | 9.78166E-05 | 2.8483E-05 | 3.434211752 | 299 | 0.585127202 |
| Xanthine phosphoribosyltransferase 1 OS = Saccharomyces cerevisiae GN = XPT1 PE = 1 SV = 1 | 0.000316809 | 9.22508E-05 | 3.434211752 | 302 | 0.590998043 |
| 3-hydroxy-3-methylgutaryl-coenzyme A reductase 2 OS = Saccharomyces cerevisiae GN = HMG2 PE = 1 SV = 1 | 6.48202E-05 | 1.88748E-05 | 3.434211752 | 302 | 0.590998043 |
| 3-keto-steroid reductase OS = Saccharomyces cerevisiae GN = ERG27 PE = 1 SV = 1 | 0.000188778 | 5.49698E-05 | 3.434211752 | 302 | 0.590998043 |
| Ras-like protein 2 OS = Saccharomyces cerevisiae GN = RAS2 PE = 1 SV = 4 | 0.000216093 | 6.29235E-05 | 3.434211752 | 302 | 0.590998043 |
| Protein phosphatase 1 regulatory subunit SDS22 OS = Saccharomyces cerevisiae GN = SDS22 PE = 1 SV = 1 | 0.000192838 | 5.6152E-05 | 3.434211752 | 302 | 0.590998043 |
| Ubiquitin-like protein SMT3 OS = Saccharomyces cerevisiae GN = SMT3 PE = 1 SV = 1 | 0.001293296 | 0.00376592 | 3.434211752 | 302 | 0.590998043 |
| Sphingosine-1-phosphate lyase OS = Saccharomyces cerevisiae GN = DPL1 PE = 1 SV = 1 | 0.000114378 | 3.33055E-05 | 3.434211752 | 302 | 0.590998043 |
| Protein transport protein SSS1 OS = Saccharomyces cerevisiae GN = SSS1 PE = 1 SV = 2 | 0.000838514 | 0.000244165 | 3.434211752 | 302 | 0.590998043 |
| UPF0674 endoplasmic reticulum membrane protein YNR021W OS = Saccharomyces cerevisiae GN = YNR021W PE = 1 SV = 3 | 0.000159242 | 4.63692E-05 | 3.434211752 | 302 | 0.590998043 |
| Non-classical export protein 2 OS = Saccharomyces cerevisiae GN = NCE102 PE = 1 SV = 1 | 0.000395383 | 0.000115131 | 3.434211752 | 302 | 0.590998043 |
| Reduced viability upon starvation protein 161 OS = Saccharomyces cerevisiae GN = RVS161 PE = 1 SV = 1 | 0.000247902 | 7.21859E-05 | 3.434211752 | 302 | 0.590998043 |
| Cytochrome b5 OS = Saccharomyces cerevisiae GN = CYB5 PE = 1 SV = 2 | 0.000563995 | 0.000164228 | 3.434211752 | 302 | 0.590998043 |
| 60S ribosomal protein L37-A OS = Saccharomyces cerevisiae GN = RPL37A PE = 1 SV = 2 | 0.00076134 | 0.000221693 | 3.434211752 | 302 | 0.590998043 |
| Calmodulin OS = Saccharoyces cerevisiae GN = CMD1 PE = 1 SV = 1 | 0.000464783 | 0.000135339 | 3.434211752 | 302 | 0.590998043 |

TABLE 7-continued

| | | | | | |
|---|---|---|---|---|---|
| Actin-related protein 2/3 complex subunit 5 OS = Saccharomyces cerevisiae GN = ARC15 PE = 1 SV = 1 | 0.000437682 | 0.000127447 | 3.434211752 | 302 | 0.590998043 |
| Mitochondrial outer membrane protein SCY_3392 OS = Saccharomyces cerevisiae (strain YJM789) GN = SCY_3392 PE = 3 SV = 1 | 9.17107E-05 | 2.6705E-05 | 3.434211752 | 317 | 0.62035225 |
| tRNA pseudouridine synthase 1 OS = Saccharomyces cerevisiae GN = PUS1 PE = 1 SV = 1 | 0.000120677 | 3.51396E-05 | 3.434211752 | 317 | 0.62035225 |
| Heterotrimeric G protein gamma subunit GPG1 OS = Saccharomyces cerevisiae GN = GPG1 PE = SV = 1 | 0.00050257 | 0.000146342 | 3.434211752 | 317 | 0.62035225 |
| Anthranilate synthase component 1 OS = Saccharomyces cerevisiae GN = TRP2 PE = 1 SV = 4 | 0.000132104 | 3.84672E-05 | 3.434211752 | 320 | 0.626223092 |
| UPF0662 protein YPL260W OS = Saccharomyces cerevisiae GN = YPL260W PE = 1 SV = 1 | 0.000230371 | 6.95657E-05 | 3.311561332 | 321 | 0.628180039 |
| NADPH-dependent 1-acyldihydroxyacetone phosphate reductase OS = Saccharomyces cerevisiae GN = AYR1 PE = 1 SV = 1 | 0.000440749 | 0.000133094 | 3.311561332 | 321 | 0.6218180039 |
| Long-chain-fatty-acid--CoA ligase 1 OS = Saccharomyces cerevisiae GN = FAA1 PE = 1 SV = 1 | 0.000557224 | 0.000168266 | 3.311561332 | 323 | 0.632093933 |
| Small COPII coat GTPase SAR1 OS = Saccharomyces cerevisiae GN = SAR1 PE = 1 SV = 1 | 0.001323495 | 0.0004072 | 3.250236122 | 324 | 0.634050881 |
| GMP synthase [glutamine-hydrolyzing] OS = Saccharomyces cerevisiae GN = GUA1 PE = 1 SV = 4 | 0.000485453 | 0.000149359 | 3.250236122 | 325 | 0.636007828 |
| Mitochondrial outer membrane protein porin 1 OS = Saccharomyces cerevisiae GN = POR1 PE = 1 SV = 4 | 0.003256725 | 0.001004705 | 3.241475378 | 326 | 0.637964775 |
| ATP-dependent helicase NAM7 OS = Saccharomyces cerevisiae GN = NAM7 PE = 1 SV = 1 | 6.36357E-05 | 1.99553E-05 | 3.188910912 | 327 | 0.639921722 |
| Proteasome component PRE2 OS = Saccharomyces cerevisiae GN = PRE2 PE = 1 SV = 3 | 0.000220117 | 6.90258E-05 | 3.188910912 | 327 | 0.639921722 |
| Homocitrate synthase, mitochondrial OS = Saccharomyces cerevisiae GN = LYS21 PE = 1 SV = 1 | 0.000859811 | 0.000269625 | 3.188910912 | 327 | 0.639921722 |
| Nucleolar complex protein 2 OS = Saccharomyces cerevisiae GN = NOC2 PE = 1 SV = 2 | 8.53356E-05 | 2.67601E-05 | 3.188910912 | 330 | 0.645792564 |
| Transcriptional regulatory protein SIN3 OS = Saccharomyces cerevisiae GN = SIN3 PE = 1 SV = 2 | 3.9829E-05 | 1.24898E-05 | 3.188910912 | 330 | 0.645792564 |
| Ribosome biogenesis protein ERB1 OS = Saccharomyces cerevisiae (strain YJM789) GN = ERB1 PE = 3 SV = 1 | 7.59361E-05 | 2.38126E-05 | 3.188910912 | 330 | 0.645792564 |
| Dihydroxy-acid dehydratase, mitochondrial OS = Saccharomyces cerevisiae GN = ILV3 PE = 1 SV = 2 | 0.000664668 | 0.000208431 | 3.188910912 | 330 | 0.645792564 |
| Uncharacterized protein YKL054C OS = Saccharomyces cerevisiae GN = YKL054C PE = 1 SV = 1 | 8.29339E-05 | 2.6007E-05 | 3.188910912 | 330 | 0.645792564 |
| DNA-directed RNA polymerases I, II, and III subunit RPABC5 OS = Saccharomyces cerevisiae GN = RPB10 PE = 1 SV = 2 | 0.000841244 | 0.000263803 | 3.188910912 | 330 | 0.645792564 |
| Mitochondrial presequence protease OS = Saccharomyces cerevisiae GN = CYM1 PE = 1 SV = 2 | 0.000124148 | 3.89313E-05 | 3.188910912 | 330 | 0.645792564 |
| Amidophosphoribosyltranferase OS = Saccharomyces cerevisiae GN = ADE4 PE = 1 SV = 1 | 0.000122775 | 3.85005E-05 | 3.188910912 | 330 | 0.645792564 |
| Protein ERP1 OS = Saccharomyces cerevisiae GN = ERP1 PE = 1 SV = 1 | 0.000281662 | 8.83256E-05 | 3.188910912 | 330 | 0.645792564 |
| Hsp90 co-chaperone HCH1 OS = Saccharomyces cerevisiae GN = HCH1 PE = SV = 1 | 0.000403775 | 0.000126618 | 3.188910912 | 330 | 0.645792564 |
| Acetyl-CoA carboxylase OS = Saccharomyces cerevisiae GN = FAS3 PE = 1 SV = 2 | 0.001223872 | 0.00038379 | 3.188910912 | 330 | 0.645792564 |
| Mitochondrial outer membrane protein IML2 OS = Saccharomyces cerevisiae (strain YJM789) GN = IML2 PE = 3 SV = 1 | 8.435558E-05 | 2.64528E-05 | 3.188910912 | 330 | 0.645792564 |
| Choline-phosphate cytidylyltransferase OS = Saccharomyces cerevisiae GN = PCT1 PE = 1 SV = 2 | 0.000140944 | 4.41982E-05 | 3.188910912 | 342 | 0.66927593 |
| Nucleosome assembly protein OS = Saccharomyces cerevisiae GN = NAP1 PE = 1 SV = 2 | 0.000145425 | 4.56032E-05 | 3.188910912 | 342 | 0.68927593 |
| THO complex subunit 2 OS = Saccharomyces cerevisiae GN = THO2 PE = 1 SV = 1 | 3.78591E-05 | 1.18721E-05 | 3.188910912 | 342 | 0.66927593 |
| Sec sixty-one protein homolog OS = Saccharomyces cerevisiae GN = SSH1 PE = 1 SV = 1 | 0.000130618 | 4.096E-05 | 3.188910912 | 342 | 0.66927593 |
| Cytochrome c heme lyase OS = Saccharomyces cerevisiae GN = CYC3 PE = 1 SV = 1 | 0.000231505 | 7.25968E-05 | 3.188910912 | 342 | 0.66927593 |
| Prefoldin subunit 4 OS = Saccharomyces cerevisiae GN = GIM3 PE = 1 SV = 1 | 0.000458719 | 0.000143848 | 3.188910912 | 342 | 0.66927593 |
| Gamma-glutamyl phosphate reductase OS = Saccharomyces cerevisiae GN = PRO2 PE = 1 SV = 1 | 0.000139998 | 4.39016E-05 | 3.188910912 | 342 | 0.66927593 |
| 60S ribosomal protein L37-B OS = Saccharomyces cerevisiae GN = RPL37B PE = 1 SV = 2 | 0.000705676 | 0.000221291 | 3.188910912 | 342 | 0.66927593 |
| UPF0368 protein YPL225W OS = Saccharomyces cerevisiae GN = YPL225W PE = 1 SV = 1 | 0.000798365 | 0.000250357 | 3.118910912 | 342 | 0.66927593 |
| Dolichyl-phosphate-mannose--protein mannosyltransferase 4 OS = Saccharomyces cerevisiae GN = PMT4 PE = 1 SV = 1 | 7.91626E-05 | 2.48243E-05 | 3.188910912 | 351 | 0.686888454 |
| Increased sodium tolerance protein 2 OS = Saccharomyces cerevisiae GN = IST2 PE = 1 SV = 1 | 6.57534E-05 | 2.06194E-05 | 3.188910912 | 351 | 0.686888454 |

TABLE 7-continued

| | | | | | |
|---|---|---|---|---|---|
| Glucokinase-1 OS = *Saccharomyces cerevisiae* GN = GLK1 PE = 1 SV = 1 | 0.002234448 | 0.000709793 | 3.148027439 | 353 | 0.690802348 |
| Suppressor protein STM1 OS = *Saccharomyces cerevisiae* GN = STM1 PE = 1 SV = 3 | 0.003607455 | 0.001164851 | 3.096923097 | 354 | 0.692759295 |
| Uridylate kinase OS = *Saccharomyces cerevisiae* GN = URA6 PE = 1 SV = 1 | 0.00028029 | 9.52198E-05 | 2.943610073 | 355 | 0.694716243 |
| Myosin light chain 1 OS = *Saccharomyces cerevisiae* GN = MLC1 PE = 1 SV = 1 | 0.00078176 | 0.000265579 | 2.943610073 | 355 | 0.694716243 |
| Glucose-repressible alcohol dehydrogenase transcriptional effector OS = *Saccharomyces cerevisiae* GN = CCR4 PE = 1 SV = 1 | 6.78771E-05 | 2.30591E-05 | 2.943610073 | 357 | 0.698630137 |
| 54S ribosomal protein L1, mitochondrial OS = *Saccharomyces cerevisiae* GN = MRPL1 PE = 1 SV = 1 | 0.000207377 | 7.04501E-05 | 2.943610073 | 357 | 0.698630137 |
| Nuclear polyadenylated RNA-binding protein 3 OS = *Saccharomyces cerevisiae* GN = NAB3 PE = 1 SV = 1 | 7.10775E-05 | 2.41464E-05 | 2.943610073 | 357 | 0.698630137 |
| Phosphoglycerate mutase 2 OS = *Saccharomyces cerevisiae* GN = GPM2 PE = 1 SV = 1 | 0.000178191 | 6.05348E-05 | 2.943610073 | 357 | 0.698630137 |
| 3'(2'),5'-bisphosphate nucleotidase OS = *Saccharomyces cerevisiae* GN = HAL2 PE = 1 SV = 1 | 0.000164191 | 5.57789E-05 | 2.943610073 | 357 | 0.698630137 |
| Protein SEY1 OS = *Saccharomyces cerevisiae* (strain AWRI1631) GN = SEY1 PE = 3 SV = 1 | 7.18829E-05 | 2.442E-05 | 2.943610073 | 357 | 0.698630137 |
| Thiamine metabolism regulatory protein THI3 OS = *Saccharomyces cerevisiae* GN = THI3 PE = 1 SV = 1 | 9.40228E-05 | 3.19413E-05 | 2.943610073 | 357 | 0.698630137 |
| Alpha-mannosidase OS = *Saccharomyces cerevisiae* GN = AMS1 PE = 1 SV = 2 | 0.000103261 | 3.57096E-05 | 2.943610073 | 357 | 0.698630137 |
| [NU+] prion formation protein 1 OS = *Saccharomyces cerevisiae* GN = NEW1 PE = 1 SV = 1 | 4.78514E-05 | 1.6256E-05 | 2.943610073 | 357 | 0.698630137 |
| T-complex protein 1 subunit beta OS = *Saccharomyces cerevisiae* GN = CCT2 PE = 1 SV = 1 | 0.000112369 | 3.81738E-05 | 2.943610073 | 357 | 0.698630137 |
| Putative zinc metalloproteinase YIL108W OS = *Saccharomyces cerevisiae* GN = YIL108W PE = 1 SV = 1 | 8.30332E-05 | 2.8208E-05 | 2.943610073 | 357 | 0.698630137 |
| Prefoldin suunit 5 OS = *Saccharomyces cerevisiae* GN = GIM5 PE = 1 SV = 1 | 0.000350187 | 0.000118965 | 2.943610073 | 357 | 0.698630137 |
| Probable glycosidase CRH2 OS = *Saccharomyces cerevisiae* GN = UTR2 PE = 1 SV = 3 | 0.000128804 | 4.37573E-05 | 2.943610073 | 357 | 0.698630137 |
| Coatomer subunit epsilon OS = *Saccharomyces cerevisiae* GN = SEC28 PE = 1 SV = 3 | 0.00019001 | 6.45499E-05 | 2.943610073 | 357 | 0.698630137 |
| 26S proteasome regulatory subunit RPN13 OS = *Saccharomyces cerevisiae* GN = RPN13 PE = 1 SV = 1 | 0.000359064 | 0.000121981 | 2.943610073 | 357 | 0.698630137 |
| 40S ribosomal protein S28-A OS = *Saccharomyces cerevisiae* GN = RPS28A PE = 1 SV = 1 | 0.001693466 | 0.000575302 | 2.943610073 | 357 | 0.698630137 |
| D-3-phosphoglycerate dehydrogenase 1 OS = *Saccharomyces cerevisiae* GN = SER3 PE = 1 SV = 1 | 0.000125564 | 4.26565E-05 | 2.943610073 | 357 | 0.698630137 |
| Adenylosuccinate synthetase OS = *Saccharomyces cerevisiae* GN = ADE12 PE = 1 SV = 3 | 0.000133142 | 4.52308E-05 | 2.943610073 | 357 | 0.698630137 |
| CTP synthase 2 OS = *Saccharomyces cerevisiae* (strain YJM789) GN = URA8 PE = 3 SV = 1 | 9.96651E-05 | 3.38581E-05 | 2.943610073 | 375 | 0.733855186 |
| ATP-dependent RNA helicase HAS1 OS = *Saccharomyces cerevisiae* GN = HAS1 PE = 1 SV = 1 | 0.000113331 | 3.85006E-05 | 2.943610073 | 375 | 0.733855186 |
| Zinc finger protein ZPR1 OS = *Saccharomyces cerevisiae* GN = ZPR1 PE = 1 SV = 1 | 0.000116721 | 3.96523E-05 | 2.943610073 | 375 | 0.733855186 |
| 26S proteasome regulatory subunit RPN3 OS = *Saccharomyces cerevisiae* GN = RPN3 PE = 1 SV = 4 | 0.00010638 | 3.61393E-05 | 2.943610073 | 375 | 0.733855186 |
| Peroxisomal membrane protein PMP27 OS = *Saccharomyces cerevisiae* GN = PEX11 PE = 1 SV = 2 | 0.000239176 | 8.12526E-05 | 2.943610073 | 375 | 0.733855186 |
| Ribose-phosphate pyrophoskinase 5 OS = *Saccharomyces cerevisiae* GN = PRS5 PE = 1 SV = 1 | 0.000120138 | 4.08132E-05 | 2.943610073 | 375 | 0.733855186 |
| U6 snRNA-associated Sm-like protein LSm6 OS = *Saccharomyces cerevisiae* (strain YJM789) GN = LSM6 PE = 3 SV = 1 | 0.00068399 | 0.000232364 | 2.943610073 | 375 | 0.733855186 |
| Protein HMF1 OS = *Saccharomyces cerevisiae* GN = HMF1 PE = 1 SV = 1 | 0.00046226 | 0.000157038 | 2.943610073 | 375 | 0.733855186 |
| General negative regulator of transcription subunit 1 OS = *Saccharomyces cerevisiae* GN = NOT1 PE = 1 SV = 2 | 2.67455E-05 | 9.08595E-06 | 2.943610073 | 375 | 0.733855186 |
| Putative glucokinase-2 OS = *Saccharomyces cerevisiae* GN = EMI2 PE = 1 SV = 1 | 0.000881255 | 0.000312395 | 2.820959653 | 384 | 0.75146771 |
| 26S protease regulatory subunit 4 homolog OS = *Saccharomyces cerevisiae* GN = RPT2 PE = SV = 3 | 0.000252314 | 8.94425E-05 | 2.820959653 | 385 | 0.753424658 |
| Sphingolipid long chain base-responsive protein LSP1 OS = *Saccharomyces cerevisiae* GN = LSP1 PE = 1 SV = 1 | 0.001589943 | 0.000573593 | 2.771899485 | 386 | 0.755381605 |
| UPF0001 protein YBL036C OS = *Saccharomyces cerevisiae* GN = YBL036C PE = 1 SV = 1 | 0.000202322 | 7.4981E-05 | 2.698309233 | 387 | 0.757338552 |
| Galactose/lactose metabolism regulatory protein GAL80 OS = *Saccharomyces cerevisiae* GN = GAL80 PE = 1 SV = 2 | 0.000121933 | 4.51887E-05 | 2.698309233 | 388 | 0.759295499 |
| U3 small nucleolar ribonucleoprotein protein IMP3 OS = *Saccharomyces cerevisiae* GN = IMP3 PE = 1 SV = 1 | 0.000269233 | 9.97785E-05 | 2.698309233 | 388 | 0.759295499 |
| U3 small nucleolar RNA-associated protein 21 OS = *Saccharomyces cerevisiae* GN = UTP21 PE = 1 SV = 1 | 5.62287E-05 | 2.08385E-05 | 2.698309233 | 388 | 0.759295499 |

TABLE 7-continued

| | | | | | |
|---|---|---|---|---|---|
| DNA polymerase alpha catalytic subunit A OS = Saccharomyces cerevisiae GN = POL1 PE = 1 SV = 2 | 3.53233E-05 | 1.30909E-05 | 2.698309233 | 388 | 0.759295499 |
| Probable glycerophosphodiester phosphodiesterase YPL206C OS = Saccharomyces cerevisiae GN = YPL206C PE = 1 SV = 1 | 0.000158949 | 5.89071E-05 | 2.698309233 | 388 | 0.759295499 |
| Cytochrome c oxidase assembly protein COX15 OS = Saccharomyces cerevisiae GN = COX15 PE = 1 SV = 1 | 0.000107801 | 3.99514E-05 | 2.698309233 | 388 | 0.759295499 |
| U6 snRNA-associated Sm-like protein LSm5 OS = Saccharomyces cerevisiae GN = LSM5 PE = 1 SV = 1 | 0.000565322 | 0.00020951 | 2.698309233 | 388 | 0.759295499 |
| 60S ribosomal protein L29 OS = Saccharomyces cerevisiae GN = RPL29 PE = 1 SV = 3 | 0.000883547 | 0.000327445 | 2.698309233 | 388 | 0.759295499 |
| Tricalbin-3 OS = Saccharomyces cerevisiae GN = TCB3 PE = 1 SV = 1 | 6.88849E-05 | 2.55289E-05 | 2.698309233 | 388 | 0.759295499 |
| Peroxiredoxin HYR1 OS = Saccharomyces cerevisiae GN = HYR1 PE = 1 SV = 1 | 0.000632164 | 0.000234282 | 2.698309233 | 388 | 0.759295499 |
| Glucose-6-phosphate 1-dehydrogenase OS = Saccharomyces cerevisiae GN = ZWF1 PE = 1 SV = 4 | 0.000409742 | 0.000151852 | 2.698309233 | 388 | 0.759295499 |
| Endosomal protein P24B OS = Saccharomyces cerevisiae GN = EMP24 PE = 1 SV = 1 | 0.000252541 | 9.35923E-05 | 2.698309233 | 388 | 0.759295499 |
| Proteasome component C1 OS = Saccharomyces cerevisiae GN = PRE10 PE = 1 SV = 2 | 0.000186846 | 6.92457E-05 | 2.698309233 | 388 | 0.759295499 |
| 26S proteasome regulatory subunit RPN6 OS = Saccharomyces cerevisiae GN = RPN6 PE = 1 SV = 3 | 0.000118379 | 4.38716E-05 | 2.698309233 | 388 | 0.759295499 |
| Monothiol glutaredoxin-3 OS = Saccharomyces cerevisiae GN = GRX3 PE = 1 SV = 1 | 0.000181409 | 6.72305E-05 | 2.698309233 | 388 | 0.759295499 |
| C-8 sterol isomerase OS = Saccharomyces cerevisiae GN = ERG2 PE = 1 SV = 1 | 0.000236677 | 8.77132E-05 | 2.698309233 | 388 | 0.759295499 |
| Uncharacterized membrane glycoprotein YNR065C OS = Saccharomyces cerevisiae GN = YNR065C PE = 1 SV = 1 | 4.70626E-05 | 1.74415E-05 | 2.698309233 | 388 | 0.759295499 |
| Ubiquitin carboxyl-terminal hydrolase 6 OS = Saccharomyces cerevisiae GN = UBP6 PE = 1 SV = 1 | 0.000103173 | 3.82361E-05 | 2.698309233 | 405 | 0.792563601 |
| Histone chaperone ASF1 OS = Saccharomyces cerevisiae GN = ASF1 PE = 1 SV = 1 | 0.000186452 | 6.90996E-05 | 2.698309233 | 405 | 0.72563601 |
| Pumilio homology domain family member 6 OS = Saccharomyces cerevisiae GN = PUF6 PE = 1 SV = 1 | 0.000156904 | 5.81491E-05 | 2.698309233 | 405 | 0.792563601 |
| Mitochondrial outer membrane protein OM14 OS = Saccharomyces cerevisiae (strain YJM789) GN = OM14 PE = 3 SV = 1 | 0.00040332 | 0.000149471 | 2.698309233 | 405 | 0.792563601 |
| AP-1 complex subunit gamma-1 OS = Saccharomyces cerevisiae GN = APL4 PE = 1 SV = 1 | 6.29325E-05 | 2.332295E-05 | 2.698309233 | 405 | 0.792563601 |
| Signal recognition particle subunit SRP72 OS = Saccharomyces cerevisiae GN = SRP72 PE = 1 SV = 2 | 8.01207E-05 | 2.96929E-05 | 2.698309233 | 405 | 0.792563601 |
| Protein transport protein SEC31 OS = Saccharomyces cerevisiae GN = SEC31 PE = 1 SV = 2 | 4.24814E-05 | 1.57437E-05 | 2.698309233 | 405 | 0.792563601 |
| Phosphatidylethanolamine N-methyltransferase OS = Saccharomyces cerevisiae GN = PEM1 PE = 1 SV = 1 | 5.8221E-05 | 2.15769E-05 | 2.698309233 | 405 | 0.792563601 |
| Mitochondrial import inner membrane translocase subunit TIM16 OS = Saccharomyces cerevisiae GN = PAM16 PE = 1 SV = 1 | 0.000363362 | 0.000134663 | 2.698309233 | 405 | 0.792563601 |
| Phosphatidate cytidylyltransferase OS = Saccharomyces cerevisiae GN = CDS1 PE = 1 SV = 1 | 0.000113698 | 4.21366E-05 | 2.698309233 | 405 | 0.792563601 |
| 26S proteasome regulatory subunit RPN12 OS = Saccharomyces cerevisiae GN = RPN12 PE = 1 SV = 3 | 0.000184589 | 6.84093E-05 | 2.698309233 | 405 | 0.792563601 |
| N-terminal acetyltransferase A complex subunit NAT1 OS = Saccharomyces cerevisiae GN = NAT1 PE = 1 SV = 2 | 5.95728E-05 | 2.20778E-05 | 2.698309233 | 405 | 0.792563601 |
| Nucleolar pre-ribosomal-associated protein 1 OS = Saccharomyces cerevisiae GN = URB1 PE = 1 SV = 2 | 2.89842E-05 | 1.07416E-05 | 2.698309233 | 405 | 0.792563601 |
| GU4 nucleic-binding protein 1 OS = Saccharomyces cerevisiae GN = ARC1 PE = 1 SV = 2 | 0.001107392 | 0.000415119 | 2.667646629 | 418 | 0.818003914 |
| Mitochondrial peculiar membrane protein 1 OS = Saccharomyces cerevisiae GN = MPM1 PE = 1 SV = 1 | 0.000809029 | 0.000306801 | 2.636984024 | 419 | 0.819960861 |
| 6-phosphogluconate dehydrogenase, decarboxylating 1 OS = Saccharomyces cerevisiae GN = GND1 PE = 1 SV = 1 | 0.00494208 | 0.001876038 | 2.63431771 | 420 | 0.821917808 |
| Transcription-associated protein 1 OS = Saccharomyces cerevisiae GN = TRA1 PE = 1 SV = 1 | 2.59681E-05 | 1.00821E-05 | 2.575658814 | 421 | 0.823874755 |
| RNA polymerase-associated protein CTR9 OS = Saccharomyces cerevisiae GN = CTR9 PE = 1 SV = 2 | 0.000180474 | 7.00692E-05 | 2.575658814 | 421 | 0.823874755 |
| DNA-directed RNA polymerases I, II, and III subunit RPABC3 OS = Saccharomyces cerevisiae GN = RPB8 PE = 1 SV = 1 | 0.000681273 | 0.000264504 | 2.575658814 | 423 | 0.82778865 |
| Ribonucleoside-diphosphate reductase large chain 1 OS = Saccharomyces cerevisiae GN = RNR1 PE = 1 SV = 2 | 0.000112985 | 4.38663E-05 | 2.575658814 | 423 | 0.82778865 |
| 60S ribosomal protein L10 OS = Saccharomyces cerevisiae GN = RPL10 PE = 1 SV = 1 | 0.003548365 | 0.001377653 | 2.575658814 | 423 | 0.82778866 |
| Sphingolipid long chain base-responsive protein PIL1 OS = Saccharomyces cerevisiae GN = PIL1 PE = 1 SV = 1 | 0.002318695 | 0.00091108 | 2.544996209 | 426 | 0.833659491 |
| Ribosome-associated complex subunit SSZ1 OS = Saccharomyces cerevisiae GN = SSZ1 PE = 1 SV = 2 | 0.001333689 | 0.000524947 | 2.540615837 | 427 | 0.835616438 |

TABLE 7-continued

| Protein | Col2 | Col3 | Col4 | Col5 | Col6 |
|---|---|---|---|---|---|
| Golgin IMH1 OS = Saccharomyces cerevisiae GN = IMH1 PE = 1 SV = 1 | 5.09048E-05 | 2.0752E-05 | 2.453008394 | 428 | 0.837573386 |
| Protein SCO2, mitochondrial OS = Saccharomyces cerevisiae GN = SCO2 PE = 1 SV = 1 | 0.000153531 | 6.25888E-05 | 2.453008394 | 428 | 0.837573386 |
| 3-ketoacyl-CoA reductase OS = Saccharomyces cerevisiae GN = IFA38 PE = 1 SV = 1 | 0.000138384 | 5.64138E-05 | 2.453008394 | 428 | 0.837573386 |
| Iron transport multicopper oxidase FET5 OS = Saccharomyces cerevisiae GN = FET5 PE = 1 SV = 1 | 7.55744E-05 | 3.08089E-05 | 2.453008394 | 428 | 0.837573386 |
| Protein ISD11 OS = Saccharomyces cerevisiae GN = ISD11 PE = 1 SV = 1 | 0.000475466 | 0.00019383 | 2.453008394 | 428 | 0.837573386 |
| Mitochondrial distribution and morphology protein 38 OS = Saccharomyces cerevisiae GN = MDM38 PE = 1 SV = 1 | 8.24018E-05 | 3.35921E-05 | 2.453008394 | 428 | 0.837573386 |
| Elongation of fatty acids protein 3 OS = Saccharomyces cerevisiae GN = ELO3 PE = 1 SV = 1 | 0.000135728 | 5.53313E-05 | 2.453008394 | 428 | 0.837573386 |
| Nucleolar GTP-binding protein 1 OS = Saccharomyces cerevisiae GN = NOG1 PE = 1 SV = 1 | 7.19874E-05 | 2.93466E-05 | 2.453008394 | 428 | 0.837573386 |
| Peptidyl-prolyl cis-trans isomerase ESS1 OS = Saccharomyces cerevisiae GN = ESS1 PE = 1 SV = 3 | 0.000276053 | 0.000112537 | 2.453008394 | 428 | 0.837573386 |
| ATPase GET3 OS = Saccharomyces cerevisiae (strain RM11-1a) GN = GET3 PE = 3 SV = 1 | 0.000136114 | 5.54886E-05 | 2.453008394 | 428 | 0.837573386 |
| Protein APA1 OS = Saccharomyces cerevisiae GN = APA1 PE = 1 SV = 4 | 0.000146785 | 5.98386E-05 | 2.453008394 | 428 | 0.837573386 |
| Mitochondrial respiratory chain complexes assembly protein AFG3 OS = Saccharomyces cerevisiae GN = AFG3 PE = 1 SV = 1 | 6.33584E-05 | 2.58288E-05 | 2.453008394 | 439 | 0.859099804 |
| Calcium-transporting ATPase 2 OS = Saccharomyces cereviiae GN = PMC1 PE = 1 SV = 1 | 4.09332E-05 | 1.6687E-05 | 2.453008394 | 439 | 0.859099804 |
| Probable intramembrane protease YKL100C OS = Saccharomyces cerevisiae GN = YKL100C PE = 1 SV = 1 | 7.93266E-05 | 3.23385E-05 | 2.453008394 | 439 | 0.859099804 |
| KH domain-containing protein YBL032W OS = Saccharomyces cerevisiae GN = YBL032W PE = 1 SV = 1 | 0.000128508 | 5.23877E-05 | 2.453008394 | 439 | 0.859099804 |
| Mitochondrial import receptor subunit TOM22 OS = Saccharomyces cerevisiae GN = TOM22 PE = 1 SV = 3 | 0.000319029 | 0.000130056 | 2.453008394 | 439 | 0.859099804 |
| Protein MSP1 OS = Saccharomyces cerevisiae GN = MSP1 PE = 1 SV = 2 | 0.00013277 | 5.41252E-05 | 2.453008394 | 439 | 0.859099804 |
| UPF0364 protein YMR027W OS = Saccharomyces cerevisiae GN = YMR027W PE = 1 SV = 1 | 9.89598E-05 | 4.03422E-05 | 2.453008394 | 439 | 0.859099804 |
| Uncharacterized protein YJL217W OS = Saccharomyces cerevisiae GN = YJL217W PE = 1 SV = 1 | 0.000243858 | 9.94119E-0 | 2.453008394 | 439 | 0.859099804 |
| ER membrane protein complex subunit 4 OS = Saccharomyces cerevisiae GN = EMC4 PE = 1 SV = 1 | 0.000249609 | 0.000101756 | 2.453008394 | 439 | 0.859099804 |
| Sm-like protein LSm1 OS = Saccharomyces cerevisiae GN = LSM1 PE = 1 SV = 1 | 0.000263782 | 0.000107534 | 2.453008394 | 439 | 0.859099804 |
| Probable alphs-1,6-mannosyltransferase MNN10 OS = Saccharomyces cerevisiae GN = MNN10 PE = 1 SV = 1 | 0.000114582 | 4.6711E-05 | 2.453008394 | 439 | 0.859099804 |
| Protein HAM1 OS = Saccharomyces cerevisiae GN = HAM1 PE = 1 SV = 1 | 0.000242455 | 9.884E-05 | 2.453008394 | 439 | 0.859099804 |
| NADPH-dependent methylglyoxal reductase GRE2 OS = Saccharomyces cerevisiae GN = GRE2 PE = 1 SV = 1 | 0.000140339 | 5.7211E-05 | 2.453008394 | 439 | 0.859099804 |
| Alpha-1,2 mannosyltransferase KTR1 OS = Saccharomyces cerevisiae GN = KTR1 PE = 1 SV = 1 | 0.000116392 | 4.74486E-05 | 2.453008394 | 439 | 0.859099804 |
| Protein VTH1 OS = Saccharomyces cerevisiae GN = VTH1 PE = 1 SV = 1 | 3.07094E-05 | 1.25191E-05 | 2.453008394 | 453 | 0.886497065 |
| Trehalose synthase complex regulatory subunit TPS3 OS = Saccharomyces cerevisiae GN = TPS3 PE = 1 SV = 3 | 4.50766E-05 | 1.8376E-05 | 2.453008394 | 453 | 0.886497065 |
| Heat shock protein 60, mitochondrial OS = Saccharomyces cerevisiae GN = HSP60 PE = 1 SV = 1 | 0.006551267 | 0.002731813 | 2.398138469 | 455 | 0.890410959 |
| Pyruvate dehydrogenase E1 component subunit alphs, mitochondrial OS = Saccharomyces cerevisiae GN = PDB1 PE = 1 SV = 2 | 0.001029786 | 0.000436161 | 2.361020579 | 456 | 0.892367906 |
| Pyruvate dehydrogenase E1 component subunit alpha, mitochondrial OS = Saccharomyces cerevisiae GN = PDA1 PE = 1 SV = 2 | 0.00110963 | 0.000471203 | 2.354888058 | 457 | 0.894324853 |
| Actin-related protein 3 OS = Saccharomyces cerevisiae GN = ARP3 PE = 1 SV = 1 | 0.000205437 | 8.81567E-05 | 2.330357974 | 458 | 0.8962818 |
| AMP deaminase OS = Saccharomyces cerevisiae GN = AMD1 PE = 1 SV = 2 | 0.000109083 | 4.68094E-05 | 2.330357974 | 458 | 0.8962818 |
| Lon protease homolog, mitochondrial OS = Saccharomyces cerevisiae GN = PIM1 PE = 1 SV = 2 | 0.000235988 | 0.000103075 | 2.289474501 | 460 | 0.900195695 |
| Isocitrate dehydrogenase [NAD] subunit 1, mitochondrial OS = Saccharomyces cerevisiae GN = IDH1 PE = 1 SV = 2 | 0.003037645 | 0.001332737 | 2.279253633 | 461 | 0.902152642 |
| Serine hydroxymethyltransferase, cytosolic OS = Saccharomyces cerevisiae GN = SHM2 PE = 1 SV = 2 | 0.001128399 | 0.00501825 | 2.248591028 | 462 | 0.904109589 |
| Rab proteins geranylgeranyltransferase component A OS = Saccharomyces cerevisiae GN = MRS6 PE = 1 SV = 2 | 7.15564E-05 | 3.24121E-05 | 2.207707555 | 463 | 0.906066536 |
| 37S ribosomal protein MRP1, mitochondrial OS = Saccharomyces cerevisiae GN = MRP1 PE = 1 SV = 2 | 0.000131255 | 5.9453E-05 | 2.207707555 | 463 | 0.906066536 |

TABLE 7-continued

| | | | | | |
|---|---|---|---|---|---|
| Carboxypeptidase S OS = Saccharomyces cerevisiae GN = CPS1 PE = 1 SV = 2 | 7.46309E-05 | 3.38047E-05 | 2.207707555 | 463 | 0.906066536 |
| Probable glucose transporter HXT5 OS = Saccharomyces cerevisiae GN = HXT5 PE = 1 SV = 1 | 7.27682E-05 | 3.2961E-05 | 2.207707555 | 466 | 0.911937378 |
| Glycerol-3-phosphate dehydrogenase, mitochondrial OS = Saccharomyces cerevisiae GN = GUT2 PE = 1 SV = 2 | 0.000665985 | 0.000301664 | 2.207707555 | 466 | 0.9119378378 |
| Cytochrome b2, mitochondrial OS = Saccharomyces cerevisiae GN = CYB2 PE = 1 SV = 1 | 7.35584E-05 | 3.33189E-05 | 2.207707555 | 466 | 0.911937378 |
| Translation machinery-associated protein 20 OS = Saccharomyces cerevisiae GN = TMA20 PE = 1 SV = 1 | 0.000237747 | 0.00010769 | 2.207707555 | 466 | 0.911937378 |
| D-arabinono-1,4-lactone oxidase OS = Saccharomyces cerevisiae GN = ALO1 PE = 1 SV = 1 | 8.10341E-05 | 3.67051E-05 | 2.207707555 | 466 | 0.911937378 |
| Protein phosphatase 2C homolog 3 OS = Saccharomyces cerevisiae GN = PTC3 PE = 1 SV = 3 | 9.38112E-05 | 4.24926E-05 | 2.207707555 | 466 | 0.911937378 |
| DNA-directed RNA polymerase II subunit RPB9 OS = Saccharomyces cerevisiae GN = RPB9 PE = 1 SV = 1 | 0.000337423 | 0.000152839 | 2.207707555 | 466 | 0.911937378 |
| Casein kinase II subunit alpha OS = Saccharomyces cerevisiae GN = CKA1 PE = 1 SV = 1 | 0.000107928 | 4.88868E-05 | 2.207707555 | 466 | 0.911937378 |
| 26S protease regulatory subunit 6A OS = Saccharomyces cerevisiae GN = RPT5 PE = 1 SV = 3 | 9.99044E-05 | 4.52526E-05 | 2.207707555 | 466 | 0.911937378 |
| Enoyl reductase TSC13 OS = Saccharomyces cerevisiae GN = TSC13 PE = 1 SV = 1 | 0.000131115 | 5.93898E-05 | 2.207707555 | 466 | 0.911937378 |
| H/ACA ribonucleoprotein complex subunit 2 OS = Saccharomyces cerevisiae GN = NHP2 PE = 1 SV = 2 | 0.000281572 | 0.000127541 | 2.207707555 | 466 | 0.911937378 |
| Retrograde regulation protein 2 OS = Saccharomyces cerevisiae GN = RTG2 PE = 1 SV = 2 | 7.35221E-05 | 3.33024E-05 | 2.207707555 | 466 | 0.911937378 |
| Uncharacterized protein YDR476C OS = Saccharomyces cerevisiae GN = YDR476C PE = 1 SV = 1 | 0.000190809 | 8.64284E-05 | 2.207707555 | 466 | 0.911937378 |
| DNA-directed RNA polymerases I and III subunit RPAC2 OS = Saccharomyces cerevisiae GN = RPC19 PE = 1 SV = 1 | 0.000298504 | 0.00013521 | 2.207707555 | 466 | 0.911937378 |
| GPI transamidase omponent GPI16 OS = Saccharomyces cerevisiae GN = GPI16 PE = 1 SV = 2 | 7.00996E-05 | 3.17522E-05 | 2.207707555 | 466 | 0.911937378 |
| V-type proton ATPase subunit e OS = Saccharomyces cerevisiae GN = VMA9 PE = 1 SV = 1 | 0.000575236 | 0.000260558 | 2.207707555 | 466 | 0.911937378 |
| Cell division control protein 28 OS = Saccharomyces cerevisiae GN = CDC28 PE = 1 SV = 1 | 0.000283067 | 0.000128217 | 2.207707555 | 466 | 0.911937378 |
| Serine/threonine-protein phosphatase 2B catalytic subunit A2 OS = Saccharomyces cerevisiae GN = CNA2 PE = 1 SV = 2 | 7.03504E-05 | 3.18658E-05 | 2.207707555 | 466 | 0.911937378 |
| GTP-binding protein YPT31/YPT8 OS = Saccharomyces cerevisiae GN = YPT31 PE = 1 SV = 3 | 0.000197022 | 8.92428E-05 | 2.207707555 | 466 | 0.911937378 |
| FK506-binding nuclear protein OS = Saccharomyces cerevisiae GN = FPR3 PE = 1 SV = 2 | 0.000103559 | 4.69079E-05 | 2.207707555 | 466 | 0.911937378 |
| D-3-phosphoglycerate dehydrogenase 2 OS = Saccharomyces cerevisiae GN = SER33 PE = 1 SV = 1 | 9.41815E-05 | 4.26603E-05 | 2.207707555 | 466 | 0.911937378 |
| Coatomer subunit beta OS = Saccharomyces cerevisiae BN = SEC26 PE = 1 SV = 2 | 4.42208E-05 | 2.00302E-05 | 2.207707555 | 466 | 0.911937378 |
| Dipeptidyl aminopeptidase B OS = Saccharomyces cerevisiae GN = DAP2 PE = 2 SV = 2 | 5.16141E-05 | 2.33791E-05 | 2.207707555 | 466 | 0.911937378 |
| Protein UTH1 OS = Saccharomyces cerevisiae (strain RM11-1a) GN = UTH1 PE = 3 SV = 1 | 0.000131237 | 5.94449E-05 | 2.207707555 | 466 | 0.911937378 |
| Uncharacterized oxidoreductase YML125C OS = Saccharomyces cerevisiae GN = YML125C PE = 1 SV = 1 | 0.000136619 | 6.18829E-05 | 2.207707555 | 490 | 0.95890411 |
| Long-chain-fatty-acid--CoA ligase 3 OS = Saccharomyces cerevisiae GN = FAA3 PE = 1 SV = 1 | 6.18498E-05 | 2.80154E-05 | 2.207707555 | 490 | 0.95890411 |
| Actin-related protein 2/3 complex subunit 2 OS = Saccharomyces cerevisiae GN = ARC35 PE = 1 SV = 1 | 0.000243689 | 0.000110381 | 2.207707555 | 490 | 0.95890411 |
| Ceramide very long chain fatty acid hydroxylase SCS7 OS = Saccharomyces cerevisiae GN = SCS7 PE = 1 SV = 1 | 0.000107415 | 4.86547E-05 | 2.207707555 | 490 | 0.95890411 |
| Protein SDS24 OS = Saccharomyces cerevisiae (strain YJM789) GN = SDS24 PE = 3 SV = 1 | 8.43025E-05 | 3.81855E-05 | 2.207707555 | 490 | 0.95890411 |
| Cytochrome c oxidase assembly protein COX14 OS = Saccharomyces cerevisiae GN = COX14 PE = 1 SV = 1 | 0.000605735 | 0.000274373 | 2.207707555 | 490 | 0.95890411 |
| Signal recognition particle subunit SRP14 OS = Saccharomyces cerevisiae GN = SRP14 PE = 1 SV = 1 | 0.000293428 | 0.000132911 | 2.207707555 | 490 | 0.95890411 |
| Putative guanine nucleotide-exchange factor SED4 OS = Saccharomyces cerevisiae GN = SED4 PE = 1 SV = 1 | 4.22602E-05 | 1.91421E-05 | 2.207707555 | 497 | 0.97260274 |
| Cytochrome b-c1 complex subunit 1, mitochondrial OS = Saccharomyces cerevisiae GN = COR1 PE = 1 SV = 1 | 0.000757196 | 0.000347809 | 2.17704495 | 498 | 0.974559687 |
| Lysyl-tRNA synthetase, cytoplasmic OS = Saccharomyces cerevisiae GN = KRS1 PE = 1 SV = 2 | 0.000693634 | 0.000321328 | 2.158647387 | 499 | 0.976516634 |
| Glutamyl-tRNA synthetase, cytoplasmic OS = Saccharomyces cerevisiae GN = GUS1 PE = 1 SV = 3 | 0.00162997 | 0.000756317 | 2.155143089 | 500 | 0.978473581 |
| Protein transport protein SEC13 OS = Saccharomyces cerevisiae GN = SEC13 PE = 1 SV = 1 | 0.000567411 | 0.000264357 | 2.146382345 | 501 | 0.980430528 |
| Threonyl-tRNA synthetase, cytoplasmic OS = Saccharomyces cerevisiae GN = THS1 PE = 1 SV = 2 | 0.000766861 | 0.00036171 | 2.120100112 | 502 | 0.982387476 |
| Uncharacterized protein YMR178W OS = Saccharomyces cerevisiae GN = YMR178W PE = 1 SV = 1 | 0.000877158 | 0.000420688 | 2.085057135 | 503 | 0.984344423 |

TABLE 7-continued

| | | | | | |
|---|---|---|---|---|---|
| 40S ribosomal protein S25-A OS = *Saccharomyces cerevisiae* GN = RPS25A PE = 1 SV = 1 | 0.003025452 | 0.001451016 | 2.085057135 | 503 | 0.984344423 |
| Transposon Ty2-LR1 Gag-Pol polyprotein OS = *Saccharomyces cerevisiae* GN = TY2B-LR1 PE = 3 SV = 1 | 4.50528E-05 | 2.16075E-05 | 2.085057135 | 503 | 0.984344423 |
| Farnesyl pyrophosphate synthase OS = *Saccharomyces cerevisiae* GN = FPP1 PE = 1 SV = 2 | 0.001786243 | 0.000863034 | 2.069725832 | 506 | 0.990215264 |
| Isocitrate dehydrogenase [NAD] subunit 2, mitochondrial OS = *Saccharomyces cerevisiae* GN = IDH2 PE = 1 SV = 1 | 0.002035386 | 0.000989107 | 2.057801486 | 507 | 0.992172211 |
| Nascent polypeptide-associated complex subunit beta-1 OS = *Saccharomyces cerevisiae* (strain YJM789) GN = EGD1 PE = 3 SV = 1 | 0.001038594 | 0.000513207 | 2.023731925 | 508 | 0.994129159 |
| 40S ribosomal protein S3 OS = *Saccharomyces cerevisiae* GN = RPS3 PE = 1 SV = 5 | 0.00598275 | 0.002966283 | 2.016918013 | 509 | 0.996086106 |
| ATP-dependent RNA helicase SUB2 OS = *Saccharomyces cerevisiae* (strain YJM789) GN = SUB2 PE = 3 SV = 1 | 0.00052204 | 0.000260592 | 2.003290188 | 510 | 0.998043053 |
| Elongation factor 1-gamma 2 OS = *Saccharomyces cerevisiae* GN = TEF4 PE = 1 SV = 1 | 0.001128425 | 0.000563286 | 2.003290188 | 510 | 0.998043053 |

TABLE 8

Histone PTMs identified from GAL1 promoter chromatin isolated from cells grown in galactose-containing media.

| Protein | Sequence | Modifications | PTM |
|---|---|---|---|
| Histone H3 | (R)EIAQDFkTDLR(F) | Trimethyl (+42) | K79me3 |
| | (R)EIAQDFkTDLR(F) | Dimethyl (+28) | K79me2 |
| | (R)EIAQDFkTDLR(F) | Methyl (+14) | K79me |
| | (R)FQkSTELLIR(K) | Acetyl (+42) | K56ac |
| | (R)KQLASkAAR(K) | Acetyl (+42) | K23ac |
| | (R)kQLASkAAR(K) | Acetyl (+42), Acetyl (+42) | K18ac K23ac |
| | (R)KSTGGkAPR(K) | Acetyl (+42) | K14ac |
| | (R)kSTGGkAPR(K) | Acetyl (+42), Acetyl (+42) | K9ac K14ac |
| Histone H2B | (K)AEkKPASkAPAEK(K) | Acetyl (+42), Acetyl (+42) | K6ac K11ac |
| | (K)KPASkAPAEKkPAAK(K) | Acetyl (+42), Acetyl (+42) | K11ac K17ac |
| | (K)APAEKkPAAK(K) | Acetyl (+42) | K17ac |
| Histone H2A | (K)GGkAGSAAK(A) | Acetyl (+42) | K7ac |
| Histone H4 | | None | |

| Histone H3 Sequence | Modifications | PTM | Spectrum ID |
|---|---|---|---|
| (R)EIAQDFkTDLR(F) | Trimethyl (+42) | K79me3 | Tackett_051413_L1_21.3892.3892.3.dta |
| (R)EIAQDFkTDLR(F) | Trimethyl (+42) | | Tackett_051413_L1_19.3763.3763.2.dta |
| (R)EIAQDFkTDLR(F) | Dimethyl (+28) | K79me2 | Tackett_051413_L1_21.3948.3948.3.dta |
| (R)EIAQDFkTDLR(F) | Dimethyl (+28) | | Tackett_051413_L1_19.3877.3877.3.dta |
| (R)EIAQDFkTDLR(F) | Methyl (+14) | K79me | Tackett_051413_L1_19.3827.3827.3.dta |
| (R)EIAQDFkTDLR(F) | Acetyl (+42) | K79ac | Tackett_051413_L1_19.3776.3776.3.dta |
| (R)EIAQDFkTDLR(F) | Methyl (+14) | | Tackett_051413_L1_19.3815.3815.3.dta |
| (R)EIAQDFkTDLR(F) | Methyl (+14) | | Tackett_051413_L1_19.3832.3832.2.dta |
| (R)FQkSTELLIR(K) | Acetyl (+42) | K56ac | Tackett_051413_L1_20.5345.5345.2.dta |
| (R)FQkSTELLIR(K) | Acetyl (+42) | | Tackett_051413_L1_19.5128.5128.2.dta |
| (R)FQkSTELLIR(K) | Acetyl (+42) | | Tackett_051413_L1_19.5114.5114.2.dta |
| (R)KQLASkAAR(K) | Acetyl (+42) | K23ac | Tackett_051413_L1_16.1239.1239.2.dta |
| (R)KQLASkAAR(K) | Acetyl (+42) | | Tackett_051413_L1_01.1032.1032.2.dta |
| (R)KQLASkAAR(K) | Acetyl (+42) | | Tackett_051413_L1_20.1311.1311.2.dta |
| (R)KQLASkAAR(K) | Acetyl (+42) | | Tackett_051413_L1_20.1316.1316.2.dta |
| (R)kQLASkAAR(K) | Acetyl (+42), Acetyl (+42) | K18ac K23ac | Tackett_051413_L1_19.2100.2100.2.dta |
| (R)KQLASkAAR(K) | Acetyl (+42) | | Tackett_051413_L1_19.1327.1327.2.dta |
| (R)KQLASkAAR(K) | Acetyl (+42) | | Tackett_051413_L1_19.1340.1340.2.dta |
| (R)kQLASkAAR(K) | Acetyl (+42), Acetyl (+42) | | Tackett_051413_L1_20.2166.2166.2.dta |
| (R)kQLASkAAR(K) | Acetyl (+42), Acetyl (+42) | | Tackett_051413_L1_20.2178.2178.2.dta |
| (R)KSTGGkAPR(K) | Acetyl (+42) | K14ac | Tackett_051413_L1_20.549.549.2.dta |
| (R)KSTGGkAPR(K) | Acetyl (+42) | | Tackett_051413_L1_23.698.698.2.dta |
| (R)KSTGGkAPR(K) | Acetyl (+42) | | Tackett_051413_L1_22.552.552.2.dta |
| (R)kSTGGkAPR(K) | Acetyl (+42), Acetyl (+42) | K9ac K14ac | Tackett_051413_L1_12.1197.1197.2.dta |
| (R)kSTGGkAPR(K) | Acetyl (+42) | | Tackett_051413_L1_19.506.506.2.dta |
| (R)kSTGGkAPR(K) | Acetyl (+42), Acetyl (+42) | | Tackett_051413_L1_13.1112.1112.2.dta |

TABLE 8-continued

Histone PTMs identified from GAL1 promoter chromatin isolated from cells grown in galactose-containing media.

| | | |
|---|---|---|
| (R)KSTGGkAPR(K) | Acetyl (+42) | Tackett_051413_L1_20.438.438.2.dta |
| (R)KSTGGkAPR(K) | Acetyl (+42) | Tackett_051413_L1_22.555.555.2.dta |
| (R)KSTGGkAPR(K) | Acetyl (+42) | Tackett_051413_L1_19.623.623.2.dta |
| (R)KSTGGkAPR(K) | Acetyl (+42) | Tackett_051413_L1_19.627.627.2.dta |
| (K)STGGkAPR(K) | Acetyl (+42) | Tackett_051413_L1_20.734.734.2.dta |
| (K)STGGkAPR(K) | Acetyl (+42) | Tackett_051413_L1_19.715.715.2.dta |
| (K)STGGkAPR(K) | Acetyl (+42) | Tackett_051413_L1_19.720.720.2.dta |
| (K)STGGkAPR(K) | Acetyl (+42) | Tackett_051413_L1_20.744.744.2.dta |
| (K)STELLIR(K) | | Tackett_051413_L1_16.3348.3348.2.dta |
| (K)STELLIR(K) | | Tackett_051413_L1_19.3325.3325.2.dta |
| (K)STELLIR(K) | | Tackett_051413_L1_20.3349.3349.2.dta |

What is claimed is:

1. A method of identifying proteins, including proteins comprising posttranslational modifications, specifically associated with a target chromatin in a cell, the method comprising:
   (a) providing:
      i) a first cell sample comprising nucleic acid binding proteins and the target chromatin, wherein the target chromatin is tagged by contacting the target chromatin with a tag capable of specifically recognizing and binding one or more portions of the target chromatin and wherein the tag comprises an affinity handle, and
      ii) a second cell sample comprising nucleic acid binding proteins and the target chromatin, where in the target chromatin is not tagged,
      wherein the first cell sample and the second cell sample are lysed;
   (b) performing affinity purification on each lysed cell sample in (a) using a substrate capable of binding the affinity handle, wherein affinity purification of the first cell sample results in isolation of affinity handle bound to tagged target chromatin bound to nucleic acid binding proteins and affinity purification of the second cell sample results in isolation of nucleic acid binding proteins non-specifically bound to the substrate, wherein isolating the affinity handle isolates proteins associated with the tagged target chromatin, (c) identifying bound proteins from (b), (d) determining the amount of each bound protein in each sample from (b), wherein bound proteins that are enriched in the first cell sample as compared to the second cell sample are specifically associated with the tagged chromatin in the first cell sample.

2. The method of claim 1, wherein the first cell sample is lysed before tagging the target chromatin.

3. The method of claim 1, wherein the first cell sample is lysed after tagging the target chromatin.

4. The method of claim 3, wherein a target chromatin is tagged by expressing in a cell protein A tagged TAL protein engineered to have binding specificity for a nucleic acid sequence component of the target chromatin.

5. The method of claim 1, wherein the proteins in the first cell sample and the second cell sample are crosslinked before lysis.

6. The method of claim 1, wherein the chromatin in the lysed cell sample from step (a) is fragmented before isolating the tagged target nucleic acid sequence.

7. The method of claim 6, wherein the chromatin in the lysed cell sample is fragmented to comprise nucleic acid sections comprising 500 to 1500 base pairs.

8. The method of claim 1, wherein proteins or protein fragments associated with the target chromatin are identified using mass spectrometry.

9. The method of claim 8, wherein the proteins or protein fragments identified using mass spectrometry are quantified and identified as enriched in the sample containing the tagged target chromatin compared to the sample containing the untagged target chromatin using label-free proteomics.

10. The method of claim 9, wherein the label-free proteomics technique is spectral counting.

11. The method of claim 9, wherein proteins enriched in the sample containing the tagged target chromatin compared to the sample containing the untagged target chromatin are enriched by at least 2 fold.

* * * * *